(12) United States Patent
Green et al.

(10) Patent No.: US 12,193,994 B2
(45) Date of Patent: Jan. 14, 2025

(54) COMBINATION OF A CELL THERAPY AND A GAMMA SECRETASE INHIBITOR

(71) Applicants: Juno Therapeutics, Inc., Seattle, WA (US); Fred Hutchinson Cancer Center, Seattle, WA (US)

(72) Inventors: Damian J. Green, Seattle, WA (US); Stanley R. Riddell, Seattle, WA (US); Melissa Works, Seattle, WA (US)

(73) Assignees: Juno Therapeutics, Inc., Seattle, WA (US); Fred Hutchinson Cancer Center, Seattle, WA (US)

( * ) Notice: Subject to any disclaimer, the term of this patent is extended or adjusted under 35 U.S.C. 154(b) by 1206 days.

(21) Appl. No.: 16/761,770

(22) PCT Filed: Nov. 6, 2018

(86) PCT No.: PCT/US2018/059510
§ 371 (c)(1),
(2) Date: May 5, 2020

(87) PCT Pub. No.: WO2019/090364
PCT Pub. Date: May 9, 2019

(65) Prior Publication Data
US 2020/0289565 A1    Sep. 17, 2020

Related U.S. Application Data

(60) Provisional application No. 62/665,450, filed on May 1, 2018, provisional application No. 62/582,937, filed on Nov. 7, 2017, provisional application No. 62/582,308, filed on Nov. 6, 2017.

(51) Int. Cl.
| | | |
|---|---|---|
| *A61K 31/55* | (2006.01) | |
| *A61K 38/17* | (2006.01) | |
| *A61K 39/00* | (2006.01) | |
| *A61P 35/00* | (2006.01) | |
| *C07K 14/705* | (2006.01) | |
| *C07K 14/715* | (2006.01) | |
| *C07K 14/725* | (2006.01) | |
| *C07K 16/28* | (2006.01) | |
| *C12N 5/0783* | (2010.01) | |

(52) U.S. Cl.
CPC ............ *A61K 31/55* (2013.01); *A61K 38/177* (2013.01); *A61K 39/4611* (2023.05); *A61K 39/4631* (2023.05); *A61K 39/464417* (2023.05); *A61P 35/00* (2018.01); *C07K 14/7051* (2013.01); *C07K 14/70521* (2013.01); *C07K 14/70578* (2013.01); *C07K 14/7151* (2013.01); *C07K 16/2878* (2013.01); *C12N 5/0636* (2013.01); *A61K 2239/31* (2023.05); *A61K 2239/38* (2023.05); *A61K 2239/48* (2023.05); *C07K 2317/622* (2013.01); *C07K 2319/03* (2013.01)

(58) Field of Classification Search
CPC ..................................................... A61K 31/55
See application file for complete search history.

(56) References Cited

U.S. PATENT DOCUMENTS

| | | | |
|---|---|---|---|
| 4,452,773 | A | 6/1984 | Molday |
| 4,690,915 | A | 9/1987 | Rosenberg |
| 4,795,698 | A | 1/1989 | Owen et al. |
| 5,200,084 | A | 4/1993 | Liberti et al. |
| 5,219,740 | A | 6/1993 | Miller et al. |
| 5,283,173 | A | 2/1994 | Fields et al. |
| 5,468,614 | A | 11/1995 | Fields et al. |
| 6,040,177 | A | 3/2000 | Riddell et al. |
| 6,207,453 | B1 | 3/2001 | Maass et al. |
| 6,410,319 | B1 | 6/2002 | Raubitschek et al. |
| 6,451,995 | B1 | 9/2002 | Cheung et al. |
| 7,070,995 | B2 | 7/2006 | Jensen |
| 7,265,209 | B2 | 9/2007 | Jensen |
| 7,354,762 | B2 | 4/2008 | Jensen |
| 7,446,179 | B2 | 11/2008 | Jensen et al. |
| 7,446,190 | B2 | 11/2008 | Sadelain et al. |
| 7,446,191 | B2 | 11/2008 | Jensen |
| 7,605,236 | B2 | 10/2009 | Ruben et al. |
| 8,324,353 | B2 | 12/2012 | Jensen |
| 8,389,282 | B2 | 3/2013 | Sadelain et al. |
| 8,399,645 | B2 | 3/2013 | Campana et al. |
| 8,497,118 | B2 | 7/2013 | Jensen |
| 8,569,286 | B2 | 10/2013 | Hipskind et al. |

(Continued)

FOREIGN PATENT DOCUMENTS

| | | |
|---|---|---|
| AU | 2012327200 | 5/2013 |
| CN | 102 085 372 | 6/2011 |

(Continued)

OTHER PUBLICATIONS

US 8,252,592 B2, 08/2012, Sadelain (withdrawn)
Abbott. "Inhibiting γ-secretase in myeloma tumor cells to improve killing by chimeric antigen receptor T cells." (2017).
Anson et al., "An improved β-galactosidase reporter gene," Journal of Biotechnology (2004) 108:17-30.
Gacerez et al., "How Chimeric Antigen Receptor Design Affects Adoptive T Cell Therapy," J Cell Physiol. (2016) 231(12): 2590-2598.
Jena et al. "Redirecting T-cell specificity by introducing a tumor-specific chimeric antigen receptor." *Blood, The Journal of the American Society of Hematology* 116.7 (2010): 1035-1044.

(Continued)

*Primary Examiner* — Rei Tsang Shiao
(74) *Attorney, Agent, or Firm* — Morrison & Foerster LLP

(57) ABSTRACT

Provided herein are combination therapies involving administration of an immunotherapy involving a cell therapy, such as a T cell therapy, and an inhibitor of gamma secretase. Also provided are methods for engineering, preparing, and producing the cells, compositions containing the cells and/or gamma secretase inhibitor, and kits and devices containing and for using, producing and administering the cells and/or gamma secretase inhibitor, such as in accord with the provided combination therapy methods.

32 Claims, 23 Drawing Sheets

Specification includes a Sequence Listing.

(56) References Cited

U.S. PATENT DOCUMENTS

| | | | |
|---|---|---|---|
| 8,629,136 B2 | 1/2014 | Gavai et al. |
| 8,802,374 B2 | 8/2014 | Jensen |
| 8,822,647 B2 | 9/2014 | Jensen |
| 8,911,993 B2 | 12/2014 | June et al. |
| 9,034,324 B2 | 5/2015 | Kalled et al. |
| 9,243,058 B2 | 1/2016 | Armitage et al. |
| 9,650,430 B2 | 5/2017 | Browning et al. |
| 9,765,342 B2 | 9/2017 | Kochenderfer |
| 10,126,301 B2 | 11/2018 | Berenson et al. |
| 10,174,095 B2 | 1/2019 | Brogdon et al. |
| 10,555,951 B2 | 2/2020 | Benhadji |
| 10,562,972 B2 | 2/2020 | Brentjens et al. |
| 10,688,104 B2 | 6/2020 | Bender et al. |
| 10,821,135 B2 | 11/2020 | Brentjens et al. |
| 10,918,665 B2 | 2/2021 | Brentjens et al. |
| 10,947,314 B2 | 3/2021 | Brentjens et al. |
| 10,968,275 B2 | 4/2021 | Balakrishnan et al. |
| 11,000,549 B2 | 5/2021 | Brentjens et al. |
| 11,066,475 B2 | 7/2021 | Sather et al. |
| 11,298,362 B2 | 4/2022 | Beckmann et al. |
| 11,376,259 B2 | 7/2022 | Benhadji et al. |
| 11,458,167 B2 | 10/2022 | Jensen |
| 11,564,929 B2 | 1/2023 | Patel et al. |
| 11,623,961 B2 | 4/2023 | Sather et al. |
| 11,725,059 B2 | 8/2023 | Brentjens et al. |
| 11,826,317 B2 | 11/2023 | Bender et al. |
| 2002/0131960 A1 | 9/2002 | Sadelain et al. |
| 2002/0150914 A1 | 10/2002 | Andersen et al. |
| 2003/0170238 A1 | 9/2003 | Gruenberg et al. |
| 2003/0223994 A1 | 12/2003 | Hoogenboom et al. |
| 2004/0191260 A1 | 9/2004 | Reiter et al. |
| 2005/0187179 A1 | 8/2005 | Miele et al. |
| 2006/0034850 A1 | 2/2006 | Weidanz et al. |
| 2006/0084055 A1 | 4/2006 | Gaiger et al. |
| 2007/0092530 A1 | 4/2007 | Weidanz et al. |
| 2007/0116690 A1 | 5/2007 | Yang et al. |
| 2008/0058316 A1 | 3/2008 | Eberhart et al. |
| 2009/0169562 A1 | 7/2009 | Throsby et al. |
| 2009/0226474 A1 | 9/2009 | Weidanz et al. |
| 2009/0304679 A1 | 12/2009 | Weidanz et al. |
| 2010/0041074 A1 | 2/2010 | Kimura |
| 2011/0003380 A1 | 1/2011 | Miltenyi et al. |
| 2011/0117093 A1 | 5/2011 | Ruben et al. |
| 2011/0129478 A1 | 6/2011 | Okano et al. |
| 2012/0082661 A1 | 4/2012 | Kalled et al. |
| 2012/0213029 A1 | 8/2012 | Villiger |
| 2013/0029972 A1 | 1/2013 | Hipskind |
| 2013/0149337 A1 | 6/2013 | Cooper et al. |
| 2013/0287748 A1 | 10/2013 | June et al. |
| 2013/0336964 A1 | 12/2013 | Rovati et al. |
| 2014/0161828 A1 | 6/2014 | Armitage et al. |
| 2014/0193433 A1 | 7/2014 | Borges et al. |
| 2014/0234893 A1 | 8/2014 | Enenkel |
| 2014/0271635 A1 | 9/2014 | Brogdon |
| 2014/0294841 A1 | 10/2014 | Scheinberg et al. |
| 2015/0051266 A1 | 2/2015 | Kochenderfer |
| 2015/0125460 A1 | 5/2015 | Kalled et al. |
| 2016/0046724 A1 | 2/2016 | Brogdon et al. |
| 2016/0237139 A1 | 8/2016 | Pule et al. |
| 2016/0164580 A1 | 10/2016 | El-Najjar et al. |
| 2016/0297884 A1 | 10/2016 | Kuo et al. |
| 2017/0051035 A1 | 2/2017 | Payne et al. |
| 2017/0226216 A1 | 8/2017 | Morgan et al. |
| 2017/0281766 A1 | 10/2017 | Wiltzius |
| 2017/0283504 A1 | 10/2017 | Wiltzius |
| 2018/0104254 A1 | 4/2018 | Karim et al. |
| 2018/0118842 A1 | 5/2018 | Brentjens et al. |
| 2018/0214553 A1 | 8/2018 | Berenson |
| 2018/0334653 A1 | 11/2018 | O'Neill |
| 2018/0360880 A1 | 12/2018 | Brentjens et al. |
| 2019/0040132 A1 | 2/2019 | Balakrishnan et al. |
| 2019/0107541 A1 | 4/2019 | Berenson et al. |
| 2019/0161553 A1 | 5/2019 | Sather et al. |
| 2019/0185559 A1 | 6/2019 | Russell et al. |
| 2019/0192531 A1 | 6/2019 | Bender et al. |
| 2019/0209581 A1 | 7/2019 | Benhadji et al. |
| 2019/0231794 A1 | 8/2019 | Benhadji et al. |
| 2019/0359727 A1 | 11/2019 | Riddell et al. |
| 2020/0123266 A1 | 4/2020 | Brentjens et al. |
| 2020/0276239 A1 | 9/2020 | Brentjens et al. |
| 2020/0276240 A1 | 9/2020 | Brentjens et al. |
| 2020/0392236 A1 | 12/2020 | Blythe et al. |
| 2021/0177859 A1* | 6/2021 | Patel .................... A61P 43/00 |
| 2021/0324100 A1 | 10/2021 | Sather et al. |
| 2021/0346432 A1 | 11/2021 | Brentjens et al. |
| 2021/0393690 A1 | 12/2021 | Blythe et al. |
| 2022/0008432 A1 | 1/2022 | Bender et al. |
| 2022/0096651 A1 | 3/2022 | Costa et al. |
| 2022/0296607 A1 | 9/2022 | Benhadji et al. |
| 2022/0315660 A1 | 10/2022 | Brentjens et al. |
| 2023/0220059 A1* | 7/2023 | Terrett ................. A61K 35/17 |
| | | | 424/130.1 |
| 2023/0346734 A1 | 11/2023 | Hudecek et al. |
| 2023/0365699 A1 | 11/2023 | Sather et al. |

FOREIGN PATENT DOCUMENTS

| | | |
|---|---|---|
| CN | 103 492 406 | 1/2014 |
| CN | 105777911 | 7/2016 |
| CN | 107 827 989 | 3/2018 |
| EP | 0452342 | 10/1991 |
| EP | 2537416 | 12/2012 |
| JP | 2011-178691 | 9/2011 |
| RU | 2009138932 A | 10/2013 |
| WO | WO 1992/008796 | 5/1992 |
| WO | WO 1994/028143 | 12/1994 |
| WO | WO 1996/013593 | 5/1996 |
| WO | WO 1996/018105 | 6/1996 |
| WO | WO 1998/28268 | 7/1998 |
| WO | WO 1999/18129 | 4/1999 |
| WO | WO 1999/60120 | 11/1999 |
| WO | WO 2000/014257 | 3/2000 |
| WO | WO 2003/020763 | 3/2003 |
| WO | WO 2003/068201 | 8/2003 |
| WO | WO 2004/033685 | 4/2004 |
| WO | WO 2006/000830 | 1/2006 |
| WO | WO 2006/001956 | 1/2006 |
| WO | WO 2007/004743 | 1/2007 |
| WO | WO 2007/005874 | 1/2007 |
| WO | WO 2007/100895 | 9/2007 |
| WO | WO 2008/112249 | 9/2008 |
| WO | WO 2008/116149 | 9/2008 |
| WO | WO 2008/121742 | 10/2008 |
| WO | WO 2009/023453 | 2/2009 |
| WO | WO 2009/072003 | 6/2009 |
| WO | WO 2009/087130 | 7/2009 |
| WO | WO 2010/033140 | 3/2010 |
| WO | WO 2010/054007 | 5/2010 |
| WO | WO 2010/075074 | 7/2010 |
| WO | WO 2010/104949 | 9/2010 |
| WO | WO 2011/044186 | 4/2011 |
| WO | WO 2011/060051 | 5/2011 |
| WO | WO 2011/085103 | 7/2011 |
| WO | WO 2011/159877 | 12/2011 |
| WO | WO 2012/066058 | 5/2012 |
| WO | WO 2012/079000 | 6/2012 |
| WO | WO 2012/097039 | 7/2012 |
| WO | WO 2012/129514 | 9/2012 |
| WO | WO 2012/143498 | 10/2012 |
| WO | WO 2012/163805 | 12/2012 |
| WO | WO 2013/016081 | 1/2013 |
| WO | WO 2013/019906 | 2/2013 |
| WO | WO 2013/026837 | 2/2013 |
| WO | WO 2013/071154 | 5/2013 |
| WO | WO 2013/072406 | 5/2013 |
| WO | WO 2013/072415 | 5/2013 |
| WO | WO 2013/123061 | 8/2013 |
| WO | WO 2013/124726 | 8/2013 |
| WO | WO 2013/154760 | 10/2013 |
| WO | WO 2013/166321 | 11/2013 |
| WO | WO 2014/031687 | 2/2014 |
| WO | WO 2014/055668 | 4/2014 |
| WO | WO 2014/068079 | 5/2014 |
| WO | WO 2014/087010 | 6/2014 |

(56) References Cited

FOREIGN PATENT DOCUMENTS

| | | |
|---|---|---|
| WO | WO 2014/089335 | 6/2014 |
| WO | WO 2014/100385 | 6/2014 |
| WO | WO 2014/124280 | 8/2014 |
| WO | WO 2014/134165 | 9/2014 |
| WO | WO 2014/144039 | 9/2014 |
| WO | WO 2014/191128 | 12/2014 |
| WO | WO 2014/193898 | 12/2014 |
| WO | WO 2015/026634 | 2/2015 |
| WO | WO 2015/052538 | 4/2015 |
| WO | WO 2015/095895 | 6/2015 |
| WO | WO 2015/142675 | 9/2015 |
| WO | WO 2015/157391 | 10/2015 |
| WO | WO 2015/158671 | 10/2015 |
| WO | WO 2015/193352 | 12/2015 |
| WO | WO 2016/014565 | 1/2016 |
| WO | WO 2016/014789 | 1/2016 |
| WO | WO 2016/040880 | 3/2016 |
| WO | WO 2016/070051 | 5/2016 |
| WO | WO 2016/090320 | 6/2016 |
| WO | WO 2016/090327 | 6/2016 |
| WO | WO 2016/094304 | 6/2016 |
| WO | WO 2016/130598 | 8/2016 |
| WO | WO 2016/154628 | 9/2016 |
| WO | WO 2016/164580 | 10/2016 |
| WO | WO2016168014 * | 10/2016 |
| WO | WO 2017/019496 | 2/2017 |
| WO | WO 2017/025038 | 2/2017 |
| WO | WO 2017/027291 | 2/2017 |
| WO | WO 2017/031104 | 2/2017 |
| WO | WO 2017/040930 | 3/2017 |
| WO | WO 2017/041143 | 3/2017 |
| WO | WO 2017/064084 | 4/2017 |
| WO | WO 2017/087547 | 5/2017 |
| WO | WO 2017/096329 | 6/2017 |
| WO | WO 2017/130223 | 8/2017 |
| WO | WO 2017/136607 | 8/2017 |
| WO | WO 2017/157825 | 9/2017 |
| WO | WO 2017/173256 | 10/2017 |
| WO | WO 2017/180385 | 10/2017 |
| WO | WO 2017/180389 | 10/2017 |
| WO | WO 2017/180993 | 10/2017 |
| WO | WO 2017/181119 | 10/2017 |
| WO | WO 2017/200969 | 11/2017 |
| WO | WO 2018/044662 | 3/2018 |
| WO | WO 2018/071307 | 4/2018 |
| WO | WO 2018/085690 | 5/2018 |
| WO | WO 2018/151836 | 8/2018 |
| WO | WO 2018/175988 | 9/2018 |
| WO | WO 2018/197675 | 11/2018 |
| WO | WO 2018/201056 | 11/2018 |
| WO | WO 2018/204427 | 11/2018 |
| WO | WO 2019/089969 | 5/2019 |
| WO | WO 2019/090003 | 5/2019 |
| WO | WO 2020/092848 | 5/2020 |

OTHER PUBLICATIONS

Millrine et al., "A brighter side to thalidomide: It's potential use in immunological Disorders," Trends in Mol Medicine (2017) 23(4):348-364.
Olsaukas-Kuprys et al. "Gamma secretase inhibitors of Notch signaling." *Onco Targets and therapy* 6 (2013): 943.
Ormhoj et al., "CARs in the lead against Multiple Myeloma," Curr Hematol Malig Rep. (2017) 12(2): 119-125.
Pant et al., Journal of Clinical Oncology, 2012; 30(15_suppl):3008-3008) (Year: 2012).
Parkman, "Clonal analysis of murine graft-vs-host disease. I. Phenotypic and functional analysis of T lymphocyte clones," J. Immunol. (1986) 136(10):3543-3548.
Presnyak et al., "Codon optimality is a major determinant of mRNA stability," Cell (2015) 160(6):1111-1124.
Shepherd et al., "PI3K/mTOR inhibition upregulates NOTCH-MYC signalling leading to an impaired cytotoxic response," Leukemia. Mar. 2013;27(3):650-60.
Van Arsdale et al., "Molecular Pathways: Targeting the Cyclin D-CDK4/6 Axis for Cancer Treatment," Clinical Cancer Research, 2015 , 21, 2905-2910.
Yanagi, et al., "Transcripts from a single full-length cDNA clone of hepatitis C virus are infectious when directly transfected into the liver of achimpanzee," PNAS, vol. 94(16), Aug. 5, 1997, p. 8738-8743.
Zhao et al., "Structural Design of Engineered Costimulation Determines Tumor Rejection Kinetics and Persistence of CAR T Cells," Cancer Cell (2015) 28(4):415-428.
Clinical Trial Identifier NCT04855136, "Safety and Efficacy of bb2121 (Ide-cel) Combinations in Multiple Myeloma (KarMMa-7)," Retrieved on https://clinicaltrials.gov/ct2/show/study/NCT04855136. Retrieved on Feb. 24, 2022.
Huang et al., "Genetic Engineering Antibody," South China University of Technology Press (Dec. 1997): p. 63. English translation provided.
Jonnalagadda et al., "Chimeric antigen receptors with mutated IgG4 Fc spacer avoid fc receptor binding and improve T cell persistence and antitumor efficacy," Mol Ther. (2015) 23(4):757-68.
Murray R. et al., "Human Biochemistry," Moscow, Mir (1993) vol. 1, p. 34. English translation provided.
NCBI-GENE—TNFRSF17 TNF receptorsuperfamily member 17 [*Homo sapiens* (human)] pp. 1-6 (Sep. 25, 2023, 10:06 AM).
Qian et al., "Progress of Engineering Chimeric Antigen Receptor in Tumor Therapy," Letters in Biotechnology. (2017) 28(2):188-195. (Article in Chinese) English abstract provided.
Qin et al., "Incorporation of a hinge domain improves the expansion of chimeric antigen receptor T cells," J Hematol Oncol. (2017) 10(1):68.
U.S. Appl. No. 16/760,411, filed Nov. 1, 2018, by Blythe et al. (Copy not provided). (Copy not submitted herewith pursuant to the waiver of 37 C.F. R. § 1.98(a)(2)(iii) issued by the Office on Sep. 21, 2004).
U.S. Appl. No. 16/844,610, filed Apr. 9, 2020, by Brentjens et al. (Copy not provided). (Copy not submitted herewith pursuant to the waiver of 37 C.F. R. § 1.98(a)(2)(iii) issued by the Office on Sep. 21, 2004).
U.S. Appl. No. 16/844,759, filed Apr. 9, 2020, by Brentjens et al. (Copy not provided). (Copy not submitted herewith pursuant to the waiver of 37 C.F. R. § 1.98(a)(2)(iii) issued by the Office on Sep. 21, 2004).
U.S. Appl. No. 16/093,117, filed Oct. 11, 2018, by Patel et al. (Copy not provided). (Copy not submitted herewith pursuant to the waiver of 37 C.F. R. § 1.98(a)(2)(iii) issued by the Office on Sep. 21, 2004).
U.S. Appl. No. 16/093,123, filed Oct. 11, 2018, by Beckmann et al. (Copy not provided). (Copy not submitted herewith pursuant to the waiver of 37 C.F. R. § 1.98(a)(2)(iii) issued by the Office on Sep. 21, 2004).
"Chemotherapy of Neoplastic Diseases," in Goodmann & Gilman's Manual of Pharmacology and Therapeutics (2008) Chapter 51.
Adams et al., "Development of KITE-585 A fully human BCMA CAR T-cell therapy for the treatment of multiple myeloma," AACR Annual Meeting 2017. Abstract 4979. Presented on Apr. 4, 2017.
Adams et al., "Selectivity and specificity of engineered T cells expressing KITE-585 a chimeric anitgen receptor targeting B-cell maturation antigen BCMA," AACR Annual Meeting 2017. Abstract 2135. Presented on Apr. 3, 2017.
Al-Hujaily et al., "Development of novel immunotherapies for multiple myeloma," Int J Mol Sci 2016;17:1506.
Ali et al., "T cells expressing an anti-B-cell maturation antigen chimeric antigen receptor cause remissions of multiple myeloma," Blood (2016) 128(13):1688-1700.
Al-Lazikani et al., "Standard conformations for the canonical structures of immunoglobulins," JMB (1997) 273:927-948.
Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.
Alyea et al., "Toxicity and efficacy of defined doses of CD4(+) donor lymphocytes for treatment of relapse after allogeneic bone marrow transplant," Blood (1998) 91(10):3671-3680.

(56) References Cited

OTHER PUBLICATIONS

Anderson, "Oncogenomics to target myeloma in the bone marrow microenvironment," Clin Cancer Res (2011)17(6):1225-1233.
Anderson, "Progress and paradigms in multiple myeloma" Clin Cancer Res (2016); 22(22); 5419-27.
Andersson, E., Lendahl, U. Therapeutic modulation of Notch signalling—are we there yet?. Nat Rev Drug Discov 13, 357-378 (2014).
Anonymous, "A ROR1 antibody (Receptor Tyrosine Kinase-Like Orphan Receptor 1) (C-Term) Antigen: Receptor Tyrosine Kinase-Like Orphan Receptor 1(ROR1)" retrieved from the internet www.antibodies-online.com [retrieved Sep. 10, 2019].
Anonymous, "FS25 Peripheral T-Cell Lymphoma Facts I p. 1 Revised," Leukemia & Lymphoma Society (2014) Retrieved on https://www.lls.org/sites/default/files/file_assets/peripheraltcell-lymphomafacts.pdf.
Anonymous, "Notch Inhibitor Shows Modest Efficacy," Cancer Discovery (2016) pp. 1-3. Retrieved on URL:http://cancerdiscovery.aacrjournals.org/content/early/2016/12/13/2159-8290.CD-NB2016-159.
Anonymous, "Product Data sheet:ARP63925 P050—RORI Antibody—C-terminal region (ARP63925 P050)—Aviva Systems Biology" Retrieved from the internet: URL:http://www.avivasysbio.com/sd/tds/html_datasheet.php?sku=ARP63925_P050 [retrieved on Sep. 9, 2019].
Barret, D.M. et al. (2014, e-pub. Nov. 20, 2013). "Chimeric Antigen Receptor Therapy for Cancer," Annu Rev Med. (2014);65:333-347.
Bender et al., "Novel inhibitor of Notch signaling for the treatment of cancer," Cancer Res (2013) 73:1131.
Berdeja et al., "First-in-human multicenter study of bb2121 anti-BCMA CAR T cell therapy for relapsed/refractory multiple myeloma: updated results," ASCO 2017. Abstract 3010. Presented Jun. 5, 2017.
Bluebirdbio Corporate Overview Oct. 2017.
Boris-Lawrie et al., "Recent advances in retrovirus vector technology," Cur. Opin. Genet. Develop. (1993) 3:102-109.
Brentjens et al., "CD19-targeted T cells rapidly induce molecular remissions in adults with chemotherapy-refractory acute lymphoblastic leukemia," Sci Transl Med. (2013) 5(177).
Brentjens et al., "Safety and persistence of adoptively transferred autologous CD19-targeted T cells in patients with relapsed or chemotherapy refractory B-cell leukemias," Blood (2011) 118(18):4817-4828.
Brown et al., "Tolerance of single, but not multiple, amino acid replacements in antibody VH CDR2: a means of minimizing B cells wastage from somatic hypermutation?" J. Immunol. (1996) 156(9):3285-3291.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.
Carlens et al., "Ex vivo T lymphocyte expansion for retroviral transduction: influence of serum-free media on variations in cell expansion rates and lymphocyte subset distribution," Exp Hematol (2000) 28(10): 1137-46.
Caron et al., "Engineered Humanized Dimeric Forms of IgG are More Effective Antibodies," J Exp. Med 176: 1191-1195 (1992).
Carpenter et al., "B-cell maturation antigen is a promising target for adoptive T-cell therapy of multiple myeloma," Clin Cancer Res (2013) 19(8):2048-2060.
Carrillo et al., "The Multiple Sequence Alignment Problem in Biology," SIAM J Applied Math (1988) 48: 1073.
Casset et al."A peptide mimetic of an anti-CD4 monoclonal antibody by rational design." BBRC, 307: 198-205 (2003).
Cavalieri et al., "Human T lymphocytes transduced by lentiviral vectors in the absence of TCR activation maintain an intact immune competence," Blood (2003) 102(2): 497-505.
Challita et al., "Multiple modifications in cis elements of the long terminal repeat of retroviral vectors lead to increased expression and decreased DNA methylation in embryonic carcinoma cells," J Virol. (1995) 69(2): 748-55.
Cheadle et al., "Chimeric antigen receptors for T-cell based therapy," Methods Mol Biol. (2012);907:645-66.
Cheever et al., "The Prioritization of Cancer Antigens: A National Cancer Institute Pilot Project for the Acceleration of Translational Research." Clin Cancer Res 2009; 15(17) 5323-5337.
Chekmasova et al., "A Novel and Highly Potent CAR T Cell Drug Product for Treatment of BCMA-Expressing Hematological Malignances," ASH 2015 Abstract.
Chen et al. J. Mol. Bio. (1999) 293, 865-881.
Chervin et al., "Engineering higher affinity T cell receptors using a T cell display system," (2008) J Immunol Methods, 339, 175-84.
Chicaybam et al., "An efficient low cost method for gene transfer to T lymphocytes," PLoS ONE (2013) 8(3): e60298.
Cho et al., "Human mammalian cell sorting using a highly integrated micro-fabricated fluorescence-activated cell sorter (microFACS)," Lab Chip (2010) 10: 1567-1573.
Chothia et al. "The outline structure of the T-cell alpha beta receptor," (1988) EMBO J. 7:3745.
Chung, "Role of Immunotherapy in Targeting the Bone Marrow Microenvironment in Multiple Myeloma: An Evolving Therapeutic Strategy," Pharmacotherapy (2017) 37(1):129-143.
Clackson et al., "Making antibody fragments using phage display libraries," Nature (1991) 352:624-628.
Claudio et al., "A molecular compendium of genes expressed in multiple myeloma," Blood (2002) 100(6):2175-2186.
Clinical Trial Identifier NCT/02079636. Updated Feb. 3, 2016. Retrieved from https://clinicaltrials.gov/archive/NCT02079636/2016_02_03.
Clinical Trial Identifier NCT02215967, "Study of T Cells Targeting B-Cell Maturation Antigen for Previously Treated Multiple Myeloma," Retrieved on https://clinicaltrials.gov/ct2/show/NCT02215967. Retrieved on Feb. 8, 2019.
Clinical Trial Identifier NCT02546167, "CART-BCMA Cells for Multiple Myeloma," Retrieved on https://clinicaltrials.gov/ct2/show/NCT02546167. Retrieved on Oct. 22, 2018.
Clinical Trial Identifier NCT02658929, "Study of bb2121 in Multiple Myeloma," Retrieved on https://clinicaltrials.gov/ct2/show/NCT02658929. Retrieved on Oct. 22, 2018.
Clinical Trial Identifier NCT02784795. "A Study of LY3039478 in Participants with Advanced or Metastatic Solid Tumors". Updated May 26, 2016. Retrieved from https://clinicaltrials.gov/archive/NCT02784795/2016_05_26.
Clinical Trial Identifier NCT03070327, "BCMA Targeted CAR T Cells With or Without Lenalidomide for the Treatment of Multiple Myeloma," Retrieved on https://clinicaltrials.gov/ct2/show/NCT03070327. Retrieved on Feb. 8, 2019.
Clinical Trial Identifier NCT03430011, "Study Evaluating the Safety and Efficacy of JCARH125 in Subjects With Relapsed and/or Refractory Multiple Myeloma (EVOLVE)," Retrieved on https://clinicaltrials.gov/ct2/show/NCT03430011. Retrieved on Oct. 30, 2018.
Clinical Trial Identifier NCT03436771, "Long-term Follow-up Study for Patients Previously Treated With a Juno CAR T-Cell Product," Retrieved on https://clinicaltrials.gov/ct2/show/NCT03436771. Retrieved on Feb. 7, 2019.
Clinical Trial Identifier NCT03502577, "BCMA-Specific CAR T-Cells Combined With a Gamma Secretase Inhibitor (JSMD194) to Treat Relapsed or Persistent Multiple Myeloma," Retrieved on https://clinicaltrials.gov/ct2/show/NCT03502577. Retrieved on Apr. 16, 2019.
Cohen et al. "Recombinant antibodies with MHC-restricted, peptide-specific, T-cell receptor-like specificity: new tools to study antigen presentation and TCR-peptide-MHC interactions," (2003) J Mol. Recogn. 16:324-332.
Cohen et al., "B-cell Maturation Antigen (BMCA)-specific chimeric antigen receptor T cells (CART-BCMA) for multiple myeloma (MM): initial safety and efficacy from a phase I study," Blood (2016) 128:1147.

(56) References Cited

OTHER PUBLICATIONS

Cohen et al., "CAR-T Cell Therapy for Myeloma: State of the Art and Perspective on a Possible Cure," Lymphoma and Myeloma 2018. Presentation. Presented on Oct. 18, 2018.
Cohen et al., "Safety and efficacy of B-Cell maturation antigen (BCMA)-specific chimeric antigen receptor T cells (CART-BCMA) with Cyclosphamide conditioning for refractory multiple myeloma (MM)" Blood (2017) 130 (supplement I):505; pp. 1-3.
Cohen, C.J. (Nov. 1, 2005). "Recognition of Fresh Human Tumor by Human Peripheral Blood Lymphocytes Transduced with a Bicistronic Retroviral Vector Encoding a Murine Anti-p53 TCR", *J. Immunol.* 175(9):5799-5808.
Cooper et al., "T-cell clones can be rendered specific for CD19: toward the selective augmentation of the graft-versus-B-lineage leukemia effect," Blood. (2003) 101:1637-1644.
Coquery et al., "Regulatory roles of the tumor necrosis factor receptor BCMA," Crit Rev Immunol (2012) 32(4):287-305.
Cornell et al., "Evolving paradigms in the treatment of relapsed/refractory multiple myeloma: increased options and increased complexity," Bone Marrow Transplant (2016) 51(4):479-491.
Cowan, A. "Gamma secretase inhibitor improves responses to BCMA CAR T cells in myeloma." Jan. 14, 2020.
Creative Biomart, Anti-Human TNFRSFI 7 scFv Stable Cell Line-CHO. (Aug. 30, 2013) [according to the properties of the posted document] (Retrieved from the Internet Mar. 23, 2016: <http://www.creativebiomart.net/pdf/CSC-P0544,TNFRSF17.pdt>); p. 1.
Cullion et al., "Targeting the Notch1 and mTOR pathways in a mouse T-ALL model," Blood (2009) 113:6172-6181.
Daneshmanesh et al., "Ror1, a cell surface receptor tyrosine kinase is expressed in chronic lymphocytic leukemia and may serve as a putative target for therapy," International Journal of Cancer (2008) 123:1190-1195.
Database WPI, Week 201156, Thomas Scientific, London, GB; AN 2011-J01934, XP002771616, CN 102 085 372 (Inst Basic Medical Sci Chinese Acad Medi), Jun. 8, 2011 abstract.
Davila et al., "CD19 CAR-targeted T cells induce long-term remission and B Cell Aplasia in an immunocompetent mouse model of B cell acute lymphoblastic leukemia," PLoS ONE (2013) 8(4): e61338.
Davila et al., "How do CARs work?: Early insights from recent clinical studies targeting CD19," Oncoimmunology (2012) 1(9):1577-1583.
De Felipe et al., "Skipping the co-expression problem: the new 2A "Chysel" technology," Genetics Vaccines and Therapy (2004) 2:13.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology 169:3076-3084 (2002).
Dimopoulos et al. "Current treatment landscape for relapsed and/or refractory multiple myeloma," Nat Rev Clin Oncol (2015) 12:42-54.
Dondelinger et a., "Understanding the Significance and Implications of Antibody Numbering and Antigen-Binding Surface/Residue Definition," Fronts. Immunol. 9 (2018):1-15.
Dudley et al., "Cancer regression and autoimmunity in patients after clonal repopulation with antitumor lymphocytes," Science (2002) 298, 850-54.
Fan et al., "Durable remissions with BCMA specific chimeric antigen receptor (CAR)-modified T cells in patients with refractory/relapsed multiple myeloma," ASCO 2017. Abstract LBA3001. Presented Jun. 5, 2017.
Fedorov et al., "PD-1- and CTLA-4-based inhibitory chimeric antigen receptors (iCARs) divert off-target immunotherapy responses," Sci. Transl. Medicine (2013) 5(215).
Fonseca et al., "International Myeloma Working Group molecular classification of multiple myeloma: spotlight review," Leukemia (2009) 23(12):2210-2221.
Food and Drug Administration, "Guidance for Industry: Considerations for the Design of Early-Phase Clinical Trials of Cellular and Gene Therapy Products," Dated Jun. 2015.
Frigyesi et al., "Robust isolation of malignant plasma cells in multiple myeloma," Blood (2014) vol. 123, No. 9.
Gadducci et al., "Pharmacological treatment for uterine leiomyosarcomas", Expert Opin Pharmacother (2014) 16(3):335-346.
Gantke et al., "AFM26 is a novel and highly potent Bcma CD16A directed bispecfic antibody for high affinity NK-cell engagement in multiple myeloma," ASCO 2017. Abstract 8045. Presented Jun. 5, 2017.
Garfall et al., "Immunotherapy with chimeric antigen receptors for multiple myeloma," Discov Med (2014) 17(91):37-46.
Gerecke et al., "The Diagnosis and Treatment of Multiple Myeloma," Dtsch Arztebl Int (2016) 113(27-28):470-476.
Gershoni et al., "Epitope mapping—The first step in developing epitope-based vaccines," Biod, Adis International Ltd, 21 (3 ): 145-156 (2007).
Geyer et al., "Review: Current clinical applications of chimeric antigen receptor (CAR) modified T cells," Cytotherapy (2016) 18:1393-1409.
Ghermezi et al., "Serum B-cell maturation antigen: a novel biomarker to predict outcomes for multiple myeloma patients," Haematologica (2017) 102(4):785-95.
Gieseler et al., "Cellular resistance mechanisms with impact on the therapy of multiple myeloma," Leukemia (1998) 12(7):1009-1012.
Godin et al., "Microfluidics and photonics for Bio-System-on-a-Chip: a review of advancements in technology towards a microfluidic flow cytometry chip," J Biophoton. (2008) 1(5):355-376.
Grabher et al., "Notch 1 activation in the molecular pathogenesis of T-cell acute lymphoblastic leukaemia," Nature Review Cancer, (2006) (6):347-359.
Granell et al., "Prognostic impact of circulating plasma cells in patients with multiple myeloma: implications for plasma cell leukemia definition," Haematologica (2017) 102(6):1099-1104.
Green et al., "Fully Human BCMA Targeted CAR T cells Administered in a Defined Composition: First-in Human Treatment Demonstrates Clinical Potency at Low Doses in Advanced Stage High Risk Multiple Myeloma," ASH 2018. Abstract 1011. Presented on Dec. 3.
Green et al., "Fully Human BCMA Targeted Car T cells Administered in a Defined Composition: First-in Human Treatment Demonstrates Clinical Potency at Low Doses in Advanced Stage High Risk Multiple Myeloma," ASH 2018. Presentation. Presented on Dec. 3, 2018.
Han et al., "Chimeric antigen receptor-engineered T cells for cancer immunotherapy: progress and challenges," Journal of Hematology & Oncology (2013) 6:47.
Harrington et al., "Development of JCARH125: Optimization of a Fully Human Anti-BCMA CAR for Use in the Treatment of Multiple Myeloma," Blood (2017) 130:1813.
Harrington et al., "JCARH125: Development of an Optimized Fully Human Anti-BCMA CAR for the Treatment of Multiple Myeloma," ASH 2017. Poster 1813. Presented on Dec. 9-12.
Hermans et al., "The VITAL assay: a versatile fluorometric technique for assessing CTL- and NKT-mediated cytotoxicity against multiple targets in vitro and in vivo," J. Immunological Methods (2004) 285(1): 25-40.
Hill et al., "Gamma secretase inhibition increase recognition of multiple myeloma by BCMA-specific chimeric antigen receptor modified T cells," J Immunotherapy of Cancer (2017) 5(S2):010.
Holler et al., "In vitro evolution of a T cell receptor with high affinity for peptide/MHC," PNAS (2000) 97(10):5387-5392.
Holler et al., "TCRs with high affinity for foreign pMHC show self-reactivity," Nat Immunol (2003) 4(1):55-62.
Holliger et al., "Specific killing of lymphoma cells by cytotoxic T-cells mediated by a bispecific diabody," Protein Engineering (1996) 9(3):299-305.
Honegger A and Plückthun A, "Yet another numbering scheme for immunoglobulin variable domains: an automatic modeling and analysis tool," J Mol Biol, (2001) 8;309(3):657-70.
Huang et al., "DNA transposons for modification of human primary T lymphocytes," Methods Mol Biol (2009) 506: 115-126.

(56) References Cited

OTHER PUBLICATIONS

Hudecek et al., "Receptor affinity and extracellular domain modifications affect tumor recognition by ROR1-specific chimeric antigen receptor T cells," Clin. Cancer Res. (2013) 19:3153.

Hudecek et al., "The nonsignaling extracellular spacer domain of chimeric antigen receptors is decisive for in vivo antitumor activity," Cancer Immunol Res (2015) 3(2):125-135.

Janeway et al. "Structure of the Antibody Molecule and Immunoglobulin genes," Immunology 3rd Edition p. 3:1-3:11.

Jensen et al, "Antitransgene Rejection Responses Contribute to Attenuated Persistence of Adoptively Transferred CD20/CD19-specific Chimeric Antigen Receptor Redirected T Cells in Humans," Biol Blood Marrow Transplant (2010) 16 (9); 1245-1256.

Jensen et al., "Design and implementation of adoptive therapy with chimeric antigen receptor-modified T cells," Immunological reviews (2014) 257(1):127-144.

Jiang et al., "T-cell exhaustion in the tumor microenvironment," Cell Death & Disease (2015) 6:e1792.

Johnston, et al., "Biolistic transformation: microbes to mice," Nature (1990) 346: 776-777.

Jores et al., "Resolution of hypervariable regions in T-cell receptor beta chains by a modified Wu-Kabat index of amino acid diversity.," PNAS (1990) 87(23):9138-9142.

Jundt et al., "Activated Notch 1 signaling promotes tumor cell proliferation and survival in Hodgkin and anaplastic large cell lymphoma," Blood (2002) 99:3398-3403.

Juno Corporate Presentation. Retrieved on http://ir.junotherapeutics.com. Retrieved on Jan. 2018.

Juno Corporate Presentation. Retrieved on http://ir.junotherapeutics.com. Retrieved on Sep. 2017.

Kalos et al., "T cells with chimeric antigen receptors have potent antitumor effects and can establish memory in patients with advanced leukemia," Sci Transl Med (2011) 3(95):95ra73.

Kandoth et al., "Mutational landscape and significance across 12 major cancer types," Nature (2013) 502(7471):333-339.

Kapustin et al., "Cryptic splice sites and split genes," Nucleic Acids Res. (2011) 39(14):5837-5844.

Kindt et al., Kuby Immunology 6th ed., W.H. Freeman and Co. (2007) p. 91.

Kipriyanov et al., "Bispecific tandem diabody for tumor therapy with improved antigen binding and pharmacokinetics," J Mol Biol (1999) 293(1):41-56.

Klebanoff et al., "Sorting through subsets: which T-cell populations mediate highly effective adoptive immunotherapy?," J Immunother. (2012) 35(9): 651-660.

Kochenderfer et al., "Adoptive transfer of syngeneic T cells transduced with a chimeric antigen receptor that recognizes murine CD19 can eradicate lymphoma and normal B cells", Blood (2010) 116(19):3875-3886.

Kochenderfer et al., "B cell depletion and remissions of malignancy a long with cytokine associated toxicity in a clinical trial of anti-CD 19 chimeric-antigen receptor-transduced T cells," Blood (2012) 119(12):2709-2720.

Kochenderfer et al., "Chemotherapy-refractory diffuse large B-cell lymphoma and indolent B-cell malignancies can be effectively treated with autologous T cells expressing an anti-CD19 chimeric antigen receptor," J Clin Oncol. Feb. 20, 2015;33(6):540-9.

Kochenderfer et al., "Construction and preclinical evaluation of an anti-CD19 chimeric antigen receptor," J. Immunotherapy (2009) 32(7): 689-702.

Kochenderfer et al., "Treating B-cell cancer with T cells expressing anti-CD19 chimeric antigen receptors," Nature Reviews Clinical Oncology (2013) 10, 267-276.

Koste et al., "T-cell receptor transfer into human T cells with ecotropic retroviral vectors," Gene Therapy (2014) 21: 533-538.

Kotb et al., "Bacterial pyrogenic exotoxins as superantigens," Clinical Microbiology Reviews (1995) 8:411-426.

Koyko et al., "Immunology," translation from English, edited by N.B. Serebryanaya, Mosow, "Akademiya," 2008, p. 37 (in Russian).

Kramer et al., "Lenalidomide enhances myeloma-specific T-cell responses in vivo and in vitro." Oncoimmunologu 2016, vol. 5, No. 5. e1139662.

Kurucz et al., "A bacterially expressed single-chain Fv construct from the 2B4 T-cell receptor," PNAS (1993) 90(9):3830-3834.

Lamers et al., "Immune Responses to Transgene and Retroviral Vector in Patients Treated With Ex Vivo-Engineered T Cells," Blood (2011) 117 (1); 72-82.

Lamminmaki et al. "Crystal Structure of a Recombinant Anti-estradiol Fab Fragment in Complex with 17β-Estradiol" JBC 276:36687-36694 (2001).

Laurent et al., "γ-Secretase directly sheds the survival receptor BCMA from plasma cells," Nat Commun (2015) 6:7333.

Lee et al., "Evaluation of B cell maturation antigen as a target for antibody drug conjugate mediated cytotoxicity in multiple myeloma." BJH, 2016, 174, 911-922.

Lee et al., "T cells expressing CD19 chimeric antigen receptors for acute lymphoblastic leukaemia in children and yound adults: a phase 1 dose escalation trial," The Lancet (2015) 385(9967): 517-528.

Lefranc et al., "IMGT unique numbering for immunoglobulin and T cell receptor variable domains and Ig superfamily V-like domains," Dev Comp Immunol (2003) 27(1):55-77.

Lewis et al., "Catalytic site-directed gamma-secretase complex inhibitors do not discriminate pharmacologically between Notch S3 and beta-APP cleavages," Biochemistry (2003) 42(24):7580-7586.

Li et al., "Directed evolution of human T-cell receptors with picomolar affinities by phage display," Nature Biotechnology (2005) 23:349-354.

Lin et al., "EORTC-NCI-AACR Molecular targets and cancer therapies symposium." Dec. 1, 2016 Presentation.

Lipson et al., "Durable cancer regression off-treatment and effective reinduction therapy with an anti-PD-1 antibody," Clin Cancer Res (2013) 19(2):462-468.

Liu et al., "Inclusion of Strep-tag II in design of antigen receptors for T-cell immunotherapy," Nat Biotechnol (2016) 34(4):430-434.

Liu et al., "Silencing of Receptor Tyrosine Kinase ROR1 Inhibits Tumor-Cell Proliferation via PI3K/AKT/mTOR Signaling Pathway in Lung Adenocarcinoma," PLoS One (2015) 10(5):e0127092.

Lupton S. D. et al., "Dominant positive and negative selection using a hygromycin phosphotransferase-thymidine kinase fusion gene," Mol. and Cell Biol. (1991) 11:6.

MacCallum et al., "Antibody-antigen interactions: Contact analysis and binding site topography," J. Mol. Biol. (1996) 262, 732-745.

Mailankody et al., "JCARH125, Anti-BCMA CAR T-cell Therapy for Relapsed/Refractory Multiple Myeloma_ Initial Proof of Concept Results from a Phase 1/2 Multicenter Study (Evolve)," ASH 2018 Presentation. Presented on Dec. 3, 2018.

Mailankody et al., "JCARH125, Anti-BCMA CAR T-cell Therapy for Relapsed/Refractory Multiple Myeloma_ Initial Proof of Concept Results from a Phase 1/2 Multicenter Study (EVOLVE)," ASH 2018. Abstract 957. Presented on Dec. 3, 2018.

Manuri et al., "piggyBac transposon/transposase system to generate CD19-specific T cells for the treatment of B-lineage malignancies," Hum Gene Ther (2010) 21(4): 427-437.

Martin et al., "Modeling antibody hypervariable loops: a combined algorithm," Proc Natl Acad Sci U S A. Dec. 1989;86(23):9268-72.

Martin-Liberal, "Leiomyosarcoma: Principles of management, intractable & rare disease research," (2013) 2(4):127-129.

Massard et al., "First-in-human study of LY3039478, a Notch signaling inhibitor in advanced or metastatic cancer," J Clin Oncol (2015) 33(15_suppl):2533.

Mathieu et al., "Notch signaling regulates PD-1 expression during CD8+ T-cell activation," Immunology and Cell Biology, (2013) 91: 82-88.

Maude et al., "Chimeric Antigen Receptor T Cells for Sustained Remissions in Leukemia," N Engl J Med. (2014) 371(16): 1507-1517.

Maus et al., "Zoom: racing CARs for multiple myeloma," Clinical cancer research (2013) 19(8):1917-1919.

Meibohm (Keuester), Pharmacokinetics and Pharmacodynamics of Biotech Drugs, Wiley-VHC (2006) Chapter 3:45-91.

(56) References Cited

OTHER PUBLICATIONS

Miller et al., "Improved retroviral vectors for gene transfer and expression," BioTechniques (1989) 7:980-990.
Miller et al., "Retrovirus packaging cells," Human Gene Therapy (1990) 1:5-14.
Mullen et al., "Transfer of the bacterial gene for cytosine deaminase to mammalian cells confers lethal sensitivity to 5-fluorocytosine: a negative selection system," Proc. Natl. Acad. Sci. USA (1992) 89:33.
Muranski et al., "Increased intensity lymphodepletion and adoptive immunotherapy—how far can we go?," Nat Clin Pract Oncol. (2006) 3(12): 668-681.
Nagoresen et al., "Immunomodulatory therapy of cancer with T cell-engaging BiTE antibody blinatumomab," Exp Cell Res (2011) 317(9): 1255-1260.
Nasonov et al., "Belimumab: progress in treatment systemic lupus erythematosus", Nauch-praktich revmatol, 2012, 54(5), pp. 13-19.
Naymagon et al., "Novel agents in the treatment of multiple myeloma: a review about the future," J Hematol Oncol (2016) 9(1):52.
Neelapu SS, Tummala S, Kebriaei P, et al. Chimeric antigen receptor T-cell therapy—assessment and management of toxicities. Nat Rev Clin Oncol (2018)15(1):47-62.
Novak et al., "Expression of BCMA, TACI, and BAFF-R in multiple myeloma: a mechanism for growth and survival," Blood (2004) 103(2):689-694.
Ozhegov et al. "Dictionary of a Russian Language: 80,000 words and phraseological expressions," 4th ed. Supplemented, Mosow, "OOO 'A TEMP'" 2006, p. 375.
Padlan et al. "Structure of an antibody-antigen complex: crystal structure of the HyHEL-10 Fab-lysozyme complex" PNAS 86:5938-5942 (1989).
Paiva B, van Dongen JJ, Orfao A. New criteria for response assessment: role of minimal residual disease in multiple myeloma. Blood. 2015;125(20):3059-3068. doi:10.1182/blood-2014-11-568907.
Palumbo et al., "Multiple myeloma," N Engl J Med (2011) 364(11):1046-1060.
Pardoll, "The blockade of immune checkpoints in cancer immunotherapy," Nature (2012) 12:252-264.
Park et al., "Adoptive transfer of chimeric antigen receptor re-directed cytolytic T lymphocyte clones in patients with neuroblastoma," Molecular Therapy (2007) 15(4):825-833.
Park et al., "Treating cancer with genetically engineered T cells," Trends Biotechnol. (2011) 29(11): 550-557.
Parkhurst, M.R. et al. (Jan.1, 2009). "Characterization of Genetically Modified T-Cell Receptors that Recognize the CEA:691-699 Peptide in the Context of HLA-A2.1 on Human Colorectal Cancer Cells", Clin. Cancer Res. 15(1):169-180.
Porter et al., "Chimeric antigen receptor T cells persist and induce sustained remissions in relapsed refractory chronic lymphocytic leukemia," Sci Trans. Med. (2015) 7(303): 303ra139.
Portolano et al., "Lack of promiscuity in autoantigen-specific H and L chain combinations as revealed by human H and L chain "roulette"," J. Immunol. (1993) 150:880-887.
Rajkumar et al., "Multiple myeloma: 2012 update on diagnosis, risk-stratification, and management," Am J Hematol (2012) 87(1):78-88.
Rajkumar et al., "Guidelines for determination of the number of prior lines of therapy in multiple myeloma," Blood (2015) 126(7):921-922.
Rajkumar SV. "Updated Diagnostic criteria and staging for multiple myeloma," ASCO Educational Book (2016) e418.
Ramadoss et al., "An Anti-B Cell Maturation Antigen Bispecific Antibody for Multiple Myeloma," J. Am. Chem. Soc., 137:5288-5291 (2015).
Raza et al., "Optimizing current and emerging therapies in multiple myeloma: a guide for the hematologist," Ther Adv Hematol (2017) 8(2):55-70.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.
Rosenberg et al., "Durable complete responses in heavily pretreated patients with metastatic melanoma using T-cell transfer immunotherapy," Clin Cancer Res (2011) 17(13):4550-4557.
Rosenberg, et al., "Cell transfer immunotherapy for metastatic solid cancer—what clinicians need to know," Nat Rev Clin Oncol. (2011) 8(10):577-85).
Rudikoff et al., "Single amino acid substitution altering antigen-binding specificity," ONAS (1982) 79(6):1979-1983.
Ryan et al., "Antibody targeting of B-cell maturation antigen on malignant plasma cells," Molecular Cancer Therapeutics, American Association for Cancer Research (2007) 69(11):3009-3018.
Sadelain et al., "The basic principles of chimeric antigen receptor design," Cancer Discov. (2013) 3(4): 388-398.
Sahebjam et al., "A Phase I study of the combination of ro4929097 and cediranib in patients with advanced solid tumors (PJC-004/NCI 8503)" Brit J of Cancer (2013) 109:943-949.
Sanchez et al. "Serum B-cell maturation antigen is elevated in multiple myeloma and correlates with disease status and survival," Br J Haematol (2012) 158(6):727-38.
Sanchez et al., "Soluble BCMA in myeloma serum binds its ligands BAFF and prevents normal antibody production in multiple myeloma patients," Blood (2015) 126:1799.
Savoldo et al., "CD28 costimulation improves expansion and persistence of chimeric antigen receptor-modified T cells in lymphoma patients," JCI (2011) 121(5):1822-1826.
Scarpa et al., "Characterization of recombinant helper retroviruses from Moloney-based vectors in ecotropic and amphotropic packaging cell lines," Virology (1991) 180:849-852.
Scatchard, "The attractions of proteins for small molecules and ions," Annals of the New York Academy of Sciences (1949) 51(4):660-672.
Schlueter et al. "Specificity and Binding Properties of a Single-chain T Cell Receptor," J. Mol. Biol. (1996) 256(5):859.
Schuler et al. SYFPEITHI, Database for Searching and T-Cell Epitope Prediction. in Immunoinformatics Methods in Molecular Biology, vol. 409(1): 75-93 2007.
Seckinger et al. "Target Expression, Generation, Preclinical Activity, and Pharmacokinetics of the BCMA-T Cell Bispecific Antibody EM801 for Multiple Myeloma Treatment," Cancer Cell (2017) 31(3):396-410.
Seimetz et al., "Development and approval of the trifunctional antibody catumaxomab (anti-EpCAM x anti-CD3) as a targeted cancer immunotherapy," Cancer Treat Rev (2010) 36(6):458-467.
Seow et al., "Advances in Targeted and Immunobased Therapies for Colorectal Cancer in the Genomic Era," Onco Targets Ther. (2016) 9: 1899-1920.
Sharma et al., "Efficient sleeping beauty DNA transposition from DNA minicircles," Molec Ther Nucl Acids (2013) 2, e74.
Singh et al., "ProPred: prediction of HLA-DR binding sites," Bioinformatics (2001) 17(12):1236-1237.
Smith et al., "A phase I dose escalation and expansion study of the anticancer stem cell agent demcizumab (Anti-DLL4) in patients with previously treated solid tumors," Clin Cancer Re (2014) 20(24):6295-303.
Smith et al., "Development and Evaluation of a Human scFv Derived BCMA Targeted CAR T Cell Vector Leads to a High Objective Response Rate in Patients with Advanced MM," Presented at 2017 ASH annual meeting. Presentation [23 pages].
Smith et al., "Development and Evaluation of a Human Single Chain Variable Fragment (scFv) Derived BCMA Targeted CAR T Cell Vector Leads to a High Objective Response Rate in Patients with Advanced MM," Blood (2017) 130:742.
Sonneveld et al., "Treatment of multiple myeloma with high-risk cytogenetics: a consensus of the International Myeloma Working Group," Blood (2016) 127(24):2955-2962.
Soo Hoo et al., "Characterization of a single-chain T-cell receptor expressed in *Escherichia coli*," Proc Natl Acad Sci U S A. (1992) 89(10):4759-4763.

(56) References Cited

OTHER PUBLICATIONS

Stewart et al., "Carfilzomib, Lenalidomide, and Dexamethasone vs Lenalidomide and Dexamethasone in Patients (Pts) with Relapsed Multiple Myeloma: Interim Results from ASPIRE, a Randomized, Open-Label, Multicenter Phase 3 Study." Blood (2014) 124(21):79.
Tai et al., "Novel anti-B-cell maturation antigen antibody-drug conjugate (GSK2857916) selectively induces killing of multiple myeloma," Blood (2014) 123(20):3128-3138.
Tai et al., "Targeting B-cell maturation antigen in multiple myeloma," Immunotherapy (2015) 7(11):1187-1199.
Takebe et al., "Targeting Notch signaling pathway in cancer: Clinical development advances and challenges," Pharmacol Ther (2014) 141(2):140-149.
Tejada et al., "The challenge of targeting Notch in hematologic malignancies," Frontiers in Pediatrics (2014) 2:1-8.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
Tsukahara et al., "CD19 target-engineered T-cells accumulate at tumor lesions in human B-cell lymphoma xenograft mouse models," Biochem Biophys Res Commun (2013) 438(1): 84-9.
Turtle et al., "Engineered T cells for anti-cancer therapy," Curr. Opin. Immunol. (2012) 24(5): 633-39.
Vajdos et al. "Comprehensive functional maps of the antigen-binding site of an anti-ErbB2 antibody obtained with shotgun scanning mutagenesis." J. Mol. Biol. 320, 415-428 (2002).
Van Tendeloo et al., "High-level transgene expression in primary human T lymphocytes and adult bone marrow CD34+ cells via electroporation-mediated gene delivery," Gene Therapy (2000) 7(16): 1431-1437.
Varela-Rohena, A. et al. (Dec. 2008). "Control of HIV-1 immune escape by CD8 T-cells expressing enhanced T-cell receptor", Nat. Med. 14(12):1390-1395.
Verhoeyen et al., "Lentiviral vector gene transfer into human T cells," Methods Mol Biol. (2009) 506: 97-114.
Wang et al., "Phenotypic and functional attributes of lentivirus-modified CD19-specific human CD8+ central memory T cells manufactured at clinical scale," J Immunother. (2012) 35(9):689-701.
Weng et al., "Activating mutations of NOTCH1 in human T cell acute lymphoblastic leukemia," Science, (2004) 306(5694):269-271.
White et al. "Antibody-Targeted Immunotherapy for Treatment of Malignancy" Ann. Rev. Med. 52:125-145 (2001).
Wigler et al., "Transfer of purified herpes virus thymidine kinase gene to cultured mouse cells," Cell (1997) 11: 223-232.
Wilson, "Tech.Sight. Analyzing biomolecular interactions," Science (2002) 295(5562):2103-2105.
Wolff et al., "Monoclonal Antibody Homodimers: Enhanced Antitumor Activity in Nude Mice," Can Res (1993) 53:2560-2565.
Wooldridge et al., "Corticosteroids in Advanced Cancer," Oncology (2001) 15 (2):225-236.
Worcester, "Gsi inhibition may boost BCMA CAR T-cell therapy efficacy in myeloma," Hematology News. Published on Nov. 27, 2017. Retrieved on https://www.mdedge.com/hematology-oncology/article/152733/multiple-myeloma/gsi-inhibition-may-boost-bcma-car-t-cell-therapy.
Works et al., "Lenalidomide Enhances Anti-BCMA Chimeric Antigen Receptor T Cell Function Against Multiple Myeloma" ASH 2017 (Presentation).
Works et al., "Lenalidomide Enhances Anti-BCMA Chimeric Antigen Receptor T Cell Function Against Multiple Myeloma," Blood (2017) 130:1794.
Wu et al. "Humanization of a murine monoclonal antibody by simultaneous optimization of framework and CDR residues." J. Mol. Biol. 294, 151-162 (1999).
Wu et al., "Adoptive T-cell therapy using autologous tumor-infiltrating lymphocytes for metastatic melanoma: current status and future outlook," Cancer (2012) 18(2): 160-75.
Wulfing et al., "Correctly Folded T-cell Receptor Fragments in the Periplasm of *Escherichia coli*: Influence of Folding Catalysts," J. Mol. Biol. (1994) 242(5): 655-669.
Yong et al., "Evaluation of BCMA as a Therapeutic Target in Multiple Myeloma Using an Antibody-Drug Conjugate." Blood (2013) 122(21):4447.
Yuen et al., "Abstract CT048: Population pharmacokinetics and pharmacodynamics for an oral Notch inhibitor, LY3039478, in the first-in-man study," Cancer Research (2016) 76(14):CT048.
Zhang et al., "ROR1 expression correlated with poor clinical outcome in human ovarian cancer," Scientific Reports (2014) 4:5811.
Zhang et al., "ROR1 Is Expressed in Human Breast Cancer and Associated with Enhanced Tumor-Cell Growth," PloS One (2012) 7(3): e31127.
Zhang et al., "The onco-embryonic antigen ROR1 is expressed by a variety of human cancers," The American Journal of Pathology. (2012) 181(6):1903-1910.
Anonymous "Small molecule versus biological drugs," Generics and Biosimilar Initiatve, https://www.gabionline.net/biosimilars/research/Small-molecule-versus-b, Jun. 29, 2012, 5 pages.
Azaro et al., "Phase 1 study of 2 high dose intensity schedules of the pan-Notch inhibitor crenigacestat (LY3039478) in combination with prednisone in patients with advanced or metastatic cancer," Investigational New Drugs (2021) 39(1):193-201, 9 pages.
Beckman et al., "Antibody constructs in cancer therapy: protein engineering strategies to improve exposure in solid tumors," Cancer (2007) 109(2):170-179.
Boursier et al., "Evidence for an Extended Structure of the T-cell Co-receptor CD5 as Deduced from the Hydrodynamic Properties of Soluble Forms of the Extracellular Region," The Journal of Biological Chemistry 268(3):2013-2020, Jan. 25, 1993.
Buvailo, "Will Biologics Surpass Small Molecules in the Pharma Race?," Bio Pharma Trend, Nov. 3, 2023. (11 pages).
Camacho et al., "Biosimilars 101: considerations for U.S. oncologists in clinical practice," Cancer Medicine 3(4):889-899, Aug. 2014. (11 pages).
Cespedes et al., "Mouse models in oncogenesis and cancer therapy," Clin Transl Oncol (2006) 8(5):318-329.
Chen et al., "Gene Expression of Gamma Secretase (GS) Complex-Related Proteins, the Enzyme That Sheds B-Cell Maturation Antigen (BCMA), Among Patients with Multiple Myeloma (MM) and Effects of the GS Inhibitor LSN424354 on Solubilized Berna in MM and Chronic Lymphocytic Leukemia," Blood 128(22):5641, 2016. (3 pages).
Debeb et al., "Pre-Clinical studies of Notch Signaling Inhibitor RO4929097 in Inflammatory Breast Cancer Cells," Breast Cancer Res. Treat. 134(2):495-510, Jul. 2012. (26 pages).
Dennis, "Off by a whisker," Nature (2006) 442:739-741.
Downing et al., "Regulatory Review of Novel Therapeutics—Comparison of Three Regulatory Agencies," The New England Journal of Medicine 366(24):2284-93, Jun. 14, 2012. (Published Online May 16, 2012) (10 pages).
Eagar et al., "Notch 1 Signaling Regulates Peripheral T Cell Activation," Immunity 20:407-415, Apr. 2004.
Filipovic et al., "Anti-nicastrin monoclonal antibodies elicit pleiotropic anti-tumour pharmacological effects in invasive breast cancer cells," Breast Cancer Res Treat 148:455-462, 2014 [Published Online Sep. 24, 2014] (8 pages).
Fujimori et al., "A Modeling Analysis of Monoclonal Antibody Percolation Through Tumors: A Binding-Site Barrier," J Nucl Med (1990) 31(7):1191-1198.
Giannis et al., "Peptidomimetics for Receptor Ligands-Discovery, Development, and Medical Perspectives," Angewandte Chemie International Edition in English 32(9):1244-1267, Sep. 1993. (Abstract Only) (2 pages).
Golde et al., "γ-Secretase inhibitors and modulators," Biochim. Biophys. Acta. 1828(12):2898-2907, Dec. 2013.
Hayashi et al., "Neutralization of the γ-secretase activity by monoclonal antibody against extracellular domain of nicastrin," Oncogene 31(6):787-798, Feb. 9, 2012 (21 pages).

(56) References Cited

OTHER PUBLICATIONS

Huang et al., "Recombinant immunotherapeutics: current state and perspectives regarding the feasibility of the market," Appl. Microbiol. Biotechnol. (2010) 87:401-410.

Juno Therapeutics, "Juno Therapeutics Signs Licensing Agreements with Lilly, OncoTracker, and Fred Hutchinson Cancer Research Center to Advance Its BCMA- Directed Engineered T Cell Program in Multiple Myeloma with Gamma Secretase Inhibition," Business Wire, Dec. 6, 2017, 3 pages.

Luistro et al., "Preclinical Profile of a Potent γ-Secretase Inhibitor Targeting Notch Signaling with In vivo Efficacy and Pharmacodynamic Properties," Cancer Res 69(19):7672-7680, Oct. 1, 2009. (Published Online Sep. 22, 2009) (19 pages).

Melkova et al., "Classification of Conditioning Regimens for Bone Marrow Transplantation: Historical Background and Current Perspectives," Clinical oncohematology (2017) 10(4):494-500, 7 pages. (English Abstract provided).

Nagle et al., "The Promise of Chimeric Antigen Receptor Engineered T cells in the Treatment of Hematologic Malignancies," Cancer J. 22(1):27-33, 2016. (16 pages).

National Cancer Institute dictionary entry for RO4929097, excerpt of what is available at URL: <https://www.cancer.gov/publications/dictionaries/cancer-terms/def/ro4929097>, generated May 2, 2024 (1 page).

Pelay-Gimeno et al., "Structure-Based Design of Inhibitors of Protein-Protein Interactions: Mimicking Peptide Binding Epitopes," Angew. Chem. Int. Ed. 54:8896-8927, 2015. (Published Online Jun. 26, 2015) (32 pages).

Pont et al., "γ-Secretase inhibition increases efficacy of BCMA-specific chimeric antigen receptor T cells in multiple myeloma," Blood 134(19):1585-1597, Nov. 7, 2019.

Porter et al., "Discovery of a Novel Notch Inhibitor", Retrieved from the Internet: https://www.rsc.org/images/Warren_Porter_tcm18-237088.pdf, Apr. 16, 2013, (Apr. 16, 2013), 18 pages.

PubChem CID 9843750, Semagacestat, URL: <https://pubchem.ncbi.nlm.nih.gov/compound/Semagacestat>, Oct. 25, 2006, generated May 2, 2024 (32 pages).

PubChem Compound Summary for CID 11754711, Cbz-leucinyl-leucinyl-norleucinal, created Oct. 26, 2006. (17 pages) https://pubchem.ncbi.nlm.nih.gov/compound/Cbz-leucinyl-leucinyl-norleucinal.

Purow, "Notch inhibition as a promising new approach to cancer therapy," Adv Exp Med Biol. (2012) 727:305-19, 16 pages.

Rudnick et al., "Affinity and Avidity in Antibody-Based Tumor Targeting." Cancer Biother Radiopharm (2009) 24(2):155-161.

Sato et al., "Discovery of a Biomarker That Predicts Increased Sensitivity to Immumne Checkpoint Blocking Agents," Journal of St. Marianna University. (2016) 43: 237-243 (English Abstract Included).

Shearman et al., "L-685,458, an aspartyl protease transition state mimic, is a potent inhibitor of amyloid beta-protein precursor gamma-secretase activity," Biochemistry 39:8698-8704, 2000. (7 pages).

Shih et al., "Notch Signaling, γ-Secretase Inhibitors, and Cancer Therapy," Cancer Research, (2007) 67(5):1879-1882.

Talmadge et al., "Murine Models to Evaluate Novel and Conventional Therapeutic Strategies for Cancer," Am J Pathol (2007) 170(3):793-804.

Thachil et al., "Haematological Diseases in the Tropics, " Manson's Tropical Infectious Diseases 65:894-932.e7, 2014. (46 pages).

Thurber et al., "Antibody tumor penetration: transport opposed by systemic and antigen-mediated clearance," Adv Drug Deliv Rev (2008) 60(12):1421-1434.

Vagner et al., "Peptidomimetics, a synthetic tool of drug discovery," Curr Opin Chem Biol. 12(3):292-296, Jun. 2008. (10 pages).

Voskoglou-Nomikos et al., "Clinical Predictive Value of the in Vitro Cell Line, Human Xenograft, and Mouse Allograft Preclinical Cancer Models1," Clin Can Res (2003) 9:4227-4239.

Zhang et al., "A Synthetic Antibody Fragment Targeting Nicastrin Affects Assembly and Trafficking of γ-Secretase," The Journal of Biological Chemistry 289(50):34851-34861, Dec. 12, 2014.

* cited by examiner

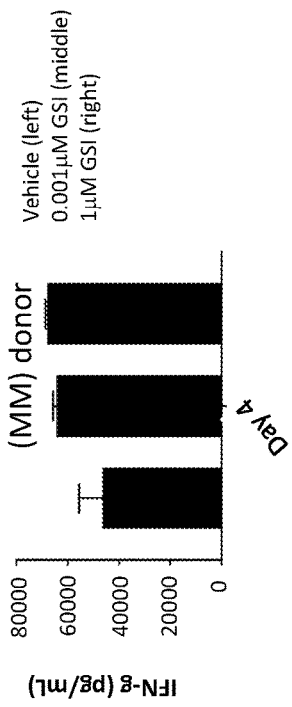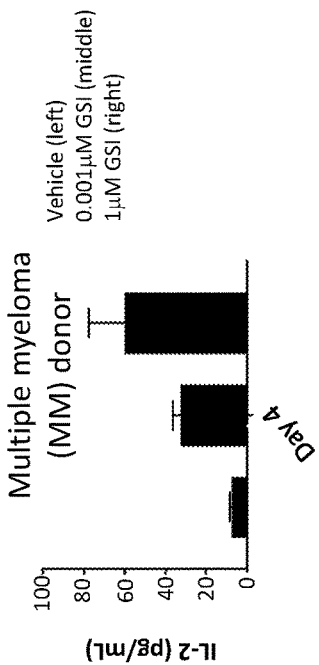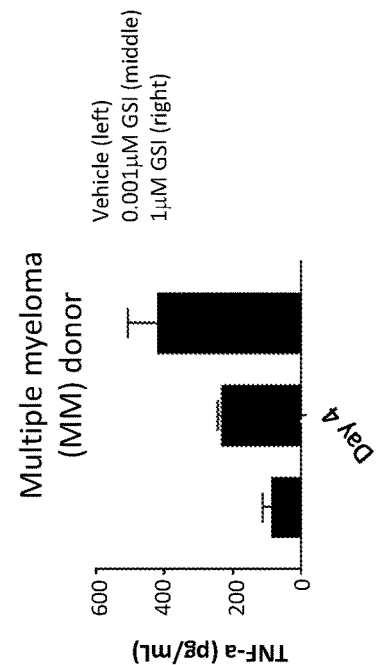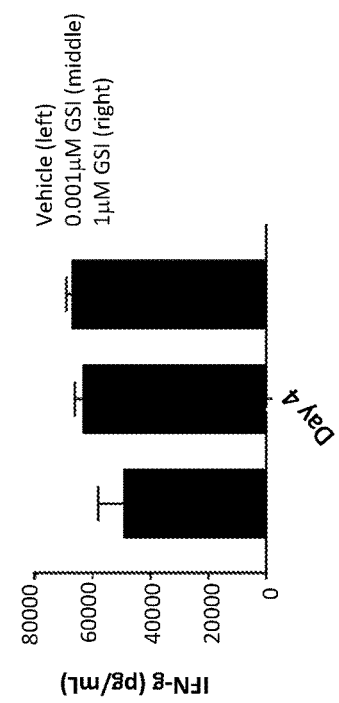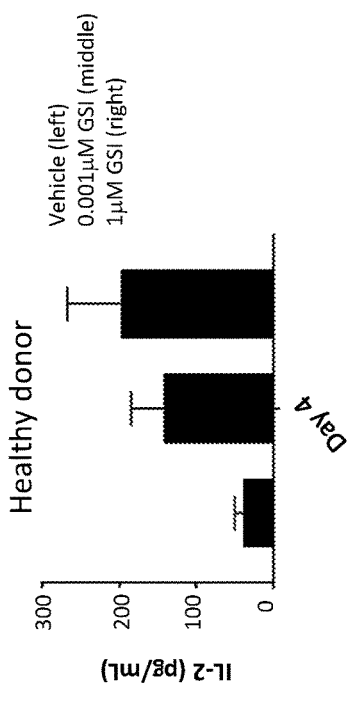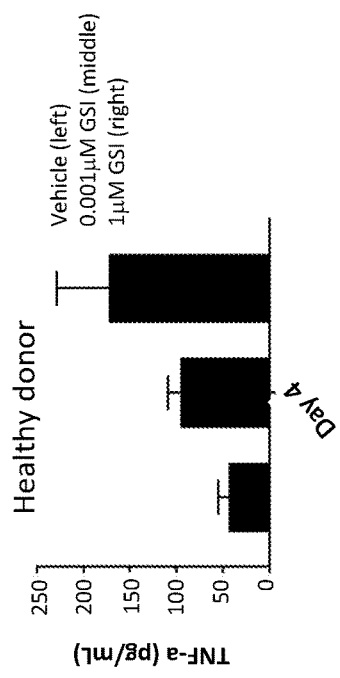
FIG. 5A
FIG. 5B

SEQUENCE LISTING

<160> NUMBER OF SEQ ID NOS: 188

<210> SEQ ID NO 1
<211> LENGTH: 12
<212> TYPE: PRT
<213> ORGANISM: Homo sapiens
<220> FEATURE:
<223> OTHER INFORMATION: Spacer (IgG4hinge) (aa)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Homo sapiens
<220> FEATURE:
<223> OTHER INFORMATION: Spacer (IgG4hinge) (nt)

<400> SEQUENCE: 2
gaatctaagt acggaccgcc ctgcccccct tgccct                                36

<210> SEQ ID NO 3
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
                20                  25                  30

Asn Gln Val Ser Leu Thr Cys Leu Val Lys Gly Phe Tyr Pro Ser Asp
            35                  40                  45

Ile Ala Val Glu Trp Glu Ser Asn Gly Gln Pro Glu Asn Asn Tyr Lys
        50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

```
<210> SEQ ID NO 4
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 4

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 5
<211> LENGTH: 282
<212> TYPE: PRT
<213> ORGANISM: Homo sapiens
<220> FEATURE:
<223> OTHER INFORMATION: IgD-hinge-Fc

<400> SEQUENCE: 5

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80
```

Asp Leu Trp Leu Arg Asp Lys Ala Thr Phe Thr Cys Phe Val Val Gly
                85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

Ala Gly Thr Ser Val Thr Cys Thr Leu Asn His Pro Ser Leu Pro Pro
145                 150                 155                 160

Gln Arg Leu Met Ala Leu Arg Glu Pro Ala Ala Gln Ala Pro Val Lys
                165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
        195                 200                 205

Met Trp Leu Glu Asp Gln Arg Glu Val Asn Thr Ser Gly Phe Ala Pro
    210                 215                 220

Ala Arg Pro Pro Gln Pro Gly Ser Thr Thr Phe Trp Ala Trp Ser
225                 230                 235                 240

Val Leu Arg Val Pro Ala Pro Ser Pro Gln Pro Ala Thr Tyr Thr
                245                 250                 255

Cys Val Val Ser His Glu Asp Ser Arg Thr Leu Leu Asn Ala Ser Arg
            260                 265                 270

Ser Leu Glu Val Ser Tyr Val Thr Asp His
        275                 280

<210> SEQ ID NO 6
<211> LENGTH: 24
<212> TYPE: PRT
<213> ORGANISM: Artificial Sequence
<220> FEATURE:
<223> OTHER INFORMATION: T2A

<400> SEQUENCE: 6

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 7
<211> LENGTH: 335
<212> TYPE: PRT
<213> ORGANISM: Artificial Sequence
<220> FEATURE:
<223> OTHER INFORMATION: tEGFR

<400> SEQUENCE: 7

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

```
Arg Thr Asp Leu His Ala Phe Glu Asn Leu Glu Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335

<210> SEQ ID NO 8
<211> LENGTH: 27
<212> TYPE: PRT
<213> ORGANISM: Homo sapiens
<220> FEATURE:
<223> OTHER INFORMATION: CD28 (amino acids 153-179 of Accession No.
      P10747)

<400> SEQUENCE: 8

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 9
<211> LENGTH: 66
<212> TYPE: PRT
<213> ORGANISM: Homo sapiens
<220> FEATURE:
<223> OTHER INFORMATION: CD28 (amino acids 114-179 of Accession No.
      P10747)

<400> SEQUENCE: 9

Ile Glu Val Met Tyr Pro Pro Pro Tyr Leu Asp Asn Glu Lys Ser Asn
1               5                   10                  15
```

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
            35                  40                  45

Val Leu Ala Cys Tyr Ser Leu Leu Val Thr Val Ala Phe Ile Ile Phe
    50                  55                  60

Trp Val
65

<210> SEQ ID NO 10
<211> LENGTH: 41
<212> TYPE: PRT
<213> ORGANISM: Homo sapiens
<220> FEATURE:
<223> OTHER INFORMATION: CD28 (amino acids 180-220 of P10747)

<400> SEQUENCE: 10

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 11
<211> LENGTH: 41
<212> TYPE: PRT
<213> ORGANISM: Homo sapiens
<220> FEATURE:
<223> OTHER INFORMATION: CD28 (LL to GG)
      Homo sapiens

<400> SEQUENCE: 11

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 12
<211> LENGTH: 42
<212> TYPE: PRT
<213> ORGANISM: Homo sapiens
<220> FEATURE:
<223> OTHER INFORMATION: 4-1BB (amino acids 214-255 of Q07011.1)

<400> SEQUENCE: 12

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 13
<211> LENGTH: 112
<212> TYPE: PRT
<213> ORGANISM: Homo sapiens
<220> FEATURE:
<223> OTHER INFORMATION: CD3 zeta

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 112
<212> TYPE: PRT
<213> ORGANISM: Homo sapiens
<220> FEATURE:
<223> OTHER INFORMATION: CD3 zeta

<400> SEQUENCE: 14

Arg Val Lys Phe Ser Arg Ser Ala Glu Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 15
<211> LENGTH: 112
<212> TYPE: PRT
<213> ORGANISM: Homo sapiens
<220> FEATURE:
<223> OTHER INFORMATION: CD3 zeta

<400> SEQUENCE: 15

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

```
Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 16
<211> LENGTH: 10
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (5)...(9)
<223> OTHER INFORMATION: SGGGG is repeated 5 times

<400> SEQUENCE: 16

```
Pro Gly Gly Gly Ser Gly Gly Gly Gly Pro
1               5                   10
```

<210> SEQ ID NO 17
<211> LENGTH: 17
<212> TYPE: PRT
<213> ORGANISM: Artificial Sequence
<220> FEATURE:
<223> OTHER INFORMATION: Linker

<400> SEQUENCE: 17

```
Gly Ser Ala Asp Asp Ala Lys Lys Asp Ala Ala Lys Lys Asp Gly Lys
1               5                   10                  15

Ser
```

<210> SEQ ID NO 18
<211> LENGTH: 117
<212> TYPE: PRT
<213> ORGANISM: Artificial Sequence
<220> FEATURE:
<223> OTHER INFORMATION: Variable heavy (VH) Anti-BCMA

<400> SEQUENCE: 18

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser
        115
```

<210> SEQ ID NO 19
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 19

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110

<210> SEQ ID NO 20
<211> LENGTH: 122
<212> TYPE: PRT
<213> ORGANISM: Artificial Sequence
<220> FEATURE:
<223> OTHER INFORMATION: Variable heavy (VH) Anti-BCMA

<400> SEQUENCE: 20

Gln Ile Gln Leu Val Gln Ser Gly Pro Asp Leu Lys Lys Pro Gly Glu
1               5                   10                  15

Thr Val Lys Leu Ser Cys Lys Ala Ser Gly Tyr Thr Phe Thr Asn Phe
            20                  25                  30

Gly Met Asn Trp Val Lys Gln Ala Pro Gly Lys Gly Phe Lys Trp Met
        35                  40                  45

Ala Trp Ile Asn Thr Tyr Thr Gly Glu Ser Tyr Phe Ala Asp Asp Phe
    50                  55                  60

Lys Gly Arg Phe Ala Phe Ser Val Glu Thr Ser Ala Thr Thr Ala Tyr
65                  70                  75                  80

Leu Gln Ile Asn Asn Leu Lys Thr Glu Asp Thr Ala Thr Tyr Phe Cys
                85                  90                  95

Ala Arg Gly Glu Ile Tyr Tyr Gly Tyr Asp Gly Gly Phe Ala Tyr Trp
            100                 105                 110

Gly Gln Gly Thr Leu Val Thr Val Ser Ala
        115                 120

<210> SEQ ID NO 21
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 21

Asp Val Val Met Thr Gln Ser His Arg Phe Met Ser Thr Ser Val Gly
1               5                   10                  15

Asp Arg Val Ser Ile Thr Cys Arg Ala Ser Gly Asp Val Asn Thr Ala
            20                  25                  30

Val Ser Trp Tyr Gln Gln Lys Pro Gly Gln Ser Pro Lys Leu Leu Ile
        35                  40                  45

Phe Ser Ala Ser Tyr Arg Tyr Thr Gly Val Pro Asp Arg Phe Thr Gly
    50                  55                  60

```
Ser Gly Ser Gly Ala Asp Phe Thr Leu Thr Ile Ser Ser Val Gln Ala
 65                  70                  75                  80

Glu Asp Leu Ala Val Tyr Tyr Cys Gln Gln His Tyr Ser Thr Pro Trp
                 85                  90                  95

Thr Phe Gly Gly Gly Thr Lys Leu Asp Ile Lys
            100                 105

<210> SEQ ID NO 22
<211> LENGTH: 116
<212> TYPE: PRT
<213> ORGANISM: Artificial Sequence
<220> FEATURE:
<223> OTHER INFORMATION: Variable heavy (VH) Anti-BCMA

<400> SEQUENCE: 22

Glu Val Gln Leu Val Gln Ser Gly Ala Glu Val Lys Lys Pro Gly Glu
 1               5                  10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
 50                  55                  60

Gln Gly His Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Tyr Ser Gly Ser Phe Asp Asn Trp Gly Gln Gly Thr Leu Val
            100                 105                 110

Thr Val Ser Ser
        115

<210> SEQ ID NO 23
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 23

Ser Tyr Glu Leu Thr Gln Pro Pro Ser Ala Ser Gly Thr Pro Gly Gln
 1               5                  10                  15

Arg Val Thr Met Ser Cys Ser Gly Thr Ser Ser Asn Ile Gly Ser His
                20                  25                  30

Ser Val Asn Trp Tyr Gln Gln Leu Pro Gly Thr Ala Pro Lys Leu Leu
            35                  40                  45

Ile Tyr Thr Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Gly Ser Leu
                85                  90                  95

Asn Gly Leu Val Phe Gly Gly Gly Thr Lys Leu Thr Val Leu Gly
            100                 105                 110

<210> SEQ ID NO 24
<211> LENGTH: 118
<212> TYPE: PRT
```

<213> ORGANISM: Artificial Sequence
<220> FEATURE:
<223> OTHER INFORMATION: Variable heavy (VH) Anti-BCMA

<400> SEQUENCE: 24

```
Glu Val Gln Leu Val Gln Ser Gly Ala Glu Met Lys Lys Pro Gly Ala
1               5                   10                  15

Ser Leu Lys Leu Ser Cys Lys Ala Ser Gly Tyr Thr Phe Ile Asp Tyr
            20                  25                  30

Tyr Val Tyr Trp Met Arg Gln Ala Pro Gly Gln Gly Leu Glu Ser Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Met Tyr Tyr Cys
                85                  90                  95

Ala Arg Ser Gln Arg Asp Gly Tyr Met Asp Tyr Trp Gly Gln Gly Thr
            100                 105                 110

Leu Val Thr Val Ser Ser
        115
```

<210> SEQ ID NO 25
<211> LENGTH: 105
<212> TYPE: PRT
<213> ORGANISM: Artificial Sequence
<220> FEATURE:
<223> OTHER INFORMATION: Variable light (VL) Anti-BCMA

<400> SEQUENCE: 25

```
Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly
            100                 105
```

<210> SEQ ID NO 26
<211> LENGTH: 5
<212> TYPE: PRT
<213> ORGANISM: Artificial Sequence
<220> FEATURE:
<223> OTHER INFORMATION: Linker

<400> SEQUENCE: 26

```
Gly Gly Gly Gly Ser
1               5
```

<210> SEQ ID NO 27
<211> LENGTH: 4
<212> TYPE: PRT
<213> ORGANISM: Artificial Sequence -continued

```
<220> FEATURE:
<223> OTHER INFORMATION: Linker

<400> SEQUENCE: 27

Gly Gly Gly Ser
1

<210> SEQ ID NO 28
<211> LENGTH: 15
<212> TYPE: PRT
<213> ORGANISM: Artificial Sequence
<220> FEATURE:
<223> OTHER INFORMATION: Linker

<400> SEQUENCE: 28

Gly Gly Gly Gly Ser Gly Gly Gly Ser Gly Gly Gly Gly Ser
1               5                   10                  15

<210> SEQ ID NO 29
<211> LENGTH: 18
<212> TYPE: PRT
<213> ORGANISM: Artificial Sequence
<220> FEATURE:
<223> OTHER INFORMATION: Linker

<400> SEQUENCE: 29

Gly Ser Thr Ser Gly Ser Gly Lys Pro Gly Ser Gly Glu Gly Ser Thr
1               5                   10                  15

Lys Gly

<210> SEQ ID NO 30
<211> LENGTH: 21
<212> TYPE: PRT
<213> ORGANISM: Artificial Sequence
<220> FEATURE:
<223> OTHER INFORMATION: Linker

<400> SEQUENCE: 30

Ser Arg Gly Gly Gly Gly Ser Gly Gly Gly Gly Ser Gly Gly Gly Gly
1               5                   10                  15

Ser Leu Glu Met Ala
            20

<210> SEQ ID NO 31
<211> LENGTH: 228
<212> TYPE: PRT
<213> ORGANISM: Homo sapiens
<220> FEATURE:
<223> OTHER INFORMATION: Hinge-CH2-CH3 spacer

<400> SEQUENCE: 31

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95
```

Gly Lys Glu Tyr Lys Cys Lys Val Ser Asn Lys Gly Leu Pro Ser Ser
                100                 105                 110

Ile Glu Lys Thr Ile Ser Lys Ala Lys Gly Gln Pro Arg Glu Pro Gln
                115                 120                 125

Val Tyr Thr Leu Pro Pro Ser Gln Glu Glu Met Thr Lys Asn Gln Val
            130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
                195                 200                 205

Met His Glu Ala Leu His Asn His Tyr Thr Gln Lys Ser Leu Ser Leu
            210                 215                 220

Ser Leu Gly Lys
225

<210> SEQ ID NO 32
<211> LENGTH: 122
<212> TYPE: PRT
<213> ORGANISM: Artificial Sequence
<220> FEATURE:
<223> OTHER INFORMATION: Variable heavy (VH) Anti-BCMA

<400> SEQUENCE: 32

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
        50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Ser Lys Ser Ile Val Ser Tyr Met Asp Tyr Trp
                100                 105                 110

Gly Gln Gly Thr Leu Val Thr Val Ser Ser
            115                 120

<210> SEQ ID NO 33
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 33

Leu Pro Val Leu Thr Gln Pro Pro Ser Thr Ser Gly Thr Pro Gly Gln
1               5                   10                  15

Arg Val Thr Val Ser Cys Ser Gly Ser Ser Ser Asn Ile Gly Ser Asn
                20                  25                  30

Val Val Phe Trp Tyr Gln Gln Leu Pro Gly Thr Ala Pro Lys Leu Val

```
                35                  40                  45
Ile Tyr Arg Asn Asn Gln Arg Pro Ser Gly Val Pro Asp Arg Phe Ser
 50                  55                  60
Val Ser Lys Ser Gly Thr Ser Ala Ser Leu Ala Ile Ser Gly Leu Arg
 65                  70                  75                  80
Ser Glu Asp Glu Ala Asp Tyr Tyr Cys Ala Ala Trp Asp Asp Ser Leu
                 85                  90                  95
Ser Gly Tyr Val Phe Gly Thr Gly Thr Lys Val Thr Val Leu Gly
                100                 105                 110

<210> SEQ ID NO 34
<211> LENGTH: 120
<212> TYPE: PRT
<213> ORGANISM: Artificial Sequence
<220> FEATURE:
<223> OTHER INFORMATION: Variable heavy (VH) Anti-BCMA

<400> SEQUENCE: 34

Gln Val Gln Leu Val Gln Ser Gly Ala Glu Val Lys Lys Pro Gly Ser
 1               5                  10                  15
Ser Val Lys Val Ser Cys Lys Ala Ser Gly Gly Thr Phe Ser Ser Tyr
                20                  25                  30
Ala Ile Ser Trp Val Arg Gln Ala Pro Gly Gln Gly Leu Glu Trp Met
             35                  40                  45
Gly Arg Ile Ile Pro Ile Leu Gly Thr Ala Asn Tyr Ala Gln Lys Phe
 50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Ser Gly Tyr Gly Ser Tyr Arg Trp Glu Asp Ser Trp Gly Gln
                100                 105                 110
Gly Thr Leu Val Thr Val Ser Ser
            115                 120

<210> SEQ ID NO 35
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 35

Gln Ala Val Leu Thr Gln Pro Ser Ala Ser Gly Thr Pro Gly Gln
 1               5                  10                  15
Arg Val Thr Ile Ser Cys Ser Gly Ser Ser Asn Ile Gly Ser Asn
                20                  25                  30
Tyr Val Phe Trp Tyr Gln Gln Leu Pro Gly Thr Ala Pro Lys Leu Leu
             35                  40                  45
Ile Tyr Ser Asn Asn Gln Arg Pro Ser Gly Val Pro Asp Arg Phe Ser
 50                  55                  60
Gly Ser Lys Ser Gly Thr Ser Ala Ser Leu Ala Ile Ser Gly Leu Arg
 65                  70                  75                  80
Ser Glu Asp Glu Ala Asp Tyr Tyr Cys Ala Ala Trp Asp Asp Ser Leu
                 85                  90                  95
Ser Ala Ser Tyr Val Phe Gly Thr Gly Thr Lys Val Thr Val Leu Gly
                100                 105                 110
```

```
<210> SEQ ID NO 36
<211> LENGTH: 118
<212> TYPE: PRT
<213> ORGANISM: Artificial Sequence
<220> FEATURE:
<223> OTHER INFORMATION: Variable heavy (VH) Anti-BCMA

<400> SEQUENCE: 36
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Arg Leu Glu Trp Met
        35                  40                  45

Gly Trp Ile Asn Pro Asn Ser Gly Gly Thr Asn Tyr Ala Gln Lys Phe
    50                  55                  60

Gln Asp Arg Ile Thr Val Thr Arg Asp Thr Ser Asn Thr Gly Tyr
65                  70                  75                  80

Met Glu Leu Thr Arg Leu Arg Ser Asp Asp Thr Ala Val Tyr Tyr Cys
                85                  90                  95

Ala Arg Ser Pro Tyr Ser Gly Val Leu Asp Lys Trp Gly Gln Gly Thr
            100                 105                 110

Leu Val Thr Val Ser Ser
            115

```
<210> SEQ ID NO 37
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 37
```

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

```
<210> SEQ ID NO 38
<211> LENGTH: 17
<212> TYPE: PRT
<213> ORGANISM: Artificial Sequence
<220> FEATURE:
<223> OTHER INFORMATION: Linker

<400> SEQUENCE: 38
```

Ala Ser Gly Gly Gly Gly Ser Gly Gly Arg Ala Ser Gly Gly Gly Gly
1               5                   10                  15

Ser

<210> SEQ ID NO 39
<211> LENGTH: 21
<212> TYPE: PRT
<213> ORGANISM: Artificial Sequence
<220> FEATURE:
<223> OTHER INFORMATION: CD8a signal peptide

<400> SEQUENCE: 39

Met Ala Leu Pro Val Thr Ala Leu Leu Pro Leu Ala Leu Leu Leu
1               5                   10                  15

His Ala Ala Arg Pro
            20

<210> SEQ ID NO 40
<211> LENGTH: 20
<212> TYPE: PRT
<213> ORGANISM: Artificial Sequence
<220> FEATURE:
<223> OTHER INFORMATION: Signal peptide

<400> SEQUENCE: 40

Met Glu Thr Asp Thr Leu Leu Leu Trp Val Leu Leu Leu Trp Val Pro
1               5                   10                  15

Gly Ser Thr Gly
            20

<210> SEQ ID NO 41
<211> LENGTH: 118
<212> TYPE: PRT
<213> ORGANISM: Artificial Sequence
<220> FEATURE:
<223> OTHER INFORMATION: Variable heavy (VH) Anti-BCMA

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Glu Met Gly Ala Val Phe Asp Ile Trp Gly Gln Gly Thr
            100                 105                 110

Met Val Thr Val Ser Ser
        115

<210> SEQ ID NO 42
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 42

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ile Ser Trp Pro Phe
                85                  90                  95

Thr Phe Gly Gly Gly Thr Lys Val Glu Ile Lys
            100                 105

<210> SEQ ID NO 43
<211> LENGTH: 122
<212> TYPE: PRT
<213> ORGANISM: Artificial Sequence
<220> FEATURE:
<223> OTHER INFORMATION: Variable heavy (VH) Anti-BCMA

<400> SEQUENCE: 43

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Tyr Leu Gly Gly Leu Trp Tyr Phe Asp Leu Trp
            100                 105                 110

Gly Arg Gly Thr Leu Val Thr Val Ser Ser
            115                 120

<210> SEQ ID NO 44
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 44

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly

```
                    85                  90                  95

Leu Gly Leu Pro Leu Thr Phe Gly Gly Gly Thr Lys Val Glu Ile Lys
                100                 105                 110

<210> SEQ ID NO 45
<211> LENGTH: 116
<212> TYPE: PRT
<213> ORGANISM: Artificial Sequence
<220> FEATURE:
<223> OTHER INFORMATION: Variable heavy (VH) Anti-BCMA

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Pro Met Asp Val Trp Gly Gln Gly Thr Thr Val
                100                 105                 110

Thr Val Ser Ser
        115

<210> SEQ ID NO 46
<211> LENGTH: 106
<212> TYPE: PRT
<213> ORGANISM: Artificial Sequence
<220> FEATURE:
<223> OTHER INFORMATION: Variable light (VL) Anti-BCMA

<400> SEQUENCE: 46

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ala Ala Tyr Pro Thr
                85                  90                  95

Phe Gly Gly Gly Thr Lys Val Glu Ile Lys
                100                 105

<210> SEQ ID NO 47
<211> LENGTH: 122
<212> TYPE: PRT
<213> ORGANISM: Artificial Sequence
<220> FEATURE:
<223> OTHER INFORMATION: Variable heavy (VH) Anti-BCMA

<400> SEQUENCE: 47
```

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
        35                  40                  45

Trp Ile Gly Ser Ile Ser Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Arg Gly Tyr Ala Thr Ser Leu Ala Phe Asp Ile Trp
            100                 105                 110

Gly Gln Gly Thr Met Val Thr Val Ser Ser
            115                 120

<210> SEQ ID NO 48
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg His Val Trp Pro Pro
                85                  90                  95

Thr Phe Gly Gly Gly Thr Lys Val Glu Ile Lys
            100                 105

<210> SEQ ID NO 49
<211> LENGTH: 119
<212> TYPE: PRT
<213> ORGANISM: Artificial Sequence
<220> FEATURE:
<223> OTHER INFORMATION: Variable heavy (VH) Anti-BCMA

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
        35                  40                  45

Ser Thr Ile Ser Ser Ser Ser Thr Ile Tyr Tyr Ala Asp Ser Val
50                  55                  60

Lys Gly Arg Phe Thr Ile Ser Arg Asp Asn Ala Lys Asn Ser Leu Tyr
```

65                  70                  75                  80
Leu Gln Met Asn Ser Leu Arg Ala Glu Asp Thr Ala Val Tyr Tyr Cys
                    85                  90                  95

Ala Arg Gly Ser Gln Glu His Leu Ile Phe Asp Tyr Trp Gly Gln Gly
                100                 105                 110

Thr Leu Val Thr Val Ser Ser
            115

<210> SEQ ID NO 50
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 50

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Phe Tyr Tyr Pro Trp
                85                  90                  95

Thr Phe Gly Gly Gly Thr Lys Val Glu Ile Lys
            100                 105

<210> SEQ ID NO 51
<211> LENGTH: 122
<212> TYPE: PRT
<213> ORGANISM: Artificial Sequence
<220> FEATURE:
<223> OTHER INFORMATION: Variable heavy (VH) Anti-BCMA

<400> SEQUENCE: 51

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Asp Phe Trp Ser Gly Ser Pro Pro Gly Leu Asp Tyr Trp
                100                 105                 110

Gly Gln Gly Thr Leu Val Thr Val Ser Ser
            115                 120

<210> SEQ ID NO 52
<211> LENGTH: 107

<212> TYPE: PRT
<213> ORGANISM: Artificial Sequence
<220> FEATURE:
<223> OTHER INFORMATION: Variable light (VL) Anti-BCMA

<400> SEQUENCE: 52

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Tyr Thr Phe Pro Phe
                85                  90                  95

Thr Phe Gly Gly Gly Thr Lys Val Glu Ile Lys
            100                 105

<210> SEQ ID NO 53
<211> LENGTH: 126
<212> TYPE: PRT
<213> ORGANISM: Artificial Sequence
<220> FEATURE:
<223> OTHER INFORMATION: Variable heavy (VH) Anti-BCMA

<400> SEQUENCE: 53

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Pro Glu Tyr Ser Ser Ile Trp His Tyr Tyr Tyr Gly
            100                 105                 110

Met Asp Val Trp Gly Gln Gly Thr Thr Val Thr Val Ser Ser
        115                 120                 125

<210> SEQ ID NO 54
<211> LENGTH: 113
<212> TYPE: PRT
<213> ORGANISM: Artificial Sequence
<220> FEATURE:
<223> OTHER INFORMATION: Variable light (VL) Anti-BCMA

<400> SEQUENCE: 54

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln

```
                35                  40                  45
Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Phe Ala His Thr Pro Phe Thr Phe Gly Gly Gly Thr Lys Val Glu Ile
                100                 105                 110

Lys

<210> SEQ ID NO 55
<211> LENGTH: 123
<212> TYPE: PRT
<213> ORGANISM: Artificial Sequence
<220> FEATURE:
<223> OTHER INFORMATION: Variable heavy (VH) Anti-BCMA

<400> SEQUENCE: 55

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Val Lys Gly Pro Leu Gln Glu Pro Pro Tyr Asp Tyr Gly Met Asp Val
                100                 105                 110

Trp Gly Gln Gly Thr Thr Val Thr Val Ser Ser
            115                 120

<210> SEQ ID NO 56
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 56

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
             35                  40                  45

Tyr Ser Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln His His Val Trp Pro Leu
                 85                  90                  95

Thr Phe Gly Gly Gly Thr Lys Val Glu Ile Lys
```

<210> SEQ ID NO 57
<211> LENGTH: 121
<212> TYPE: PRT
<213> ORGANISM: Artificial Sequence
<220> FEATURE:
<223> OTHER INFORMATION: Variable heavy (VH) Anti-BCMA

<400> SEQUENCE: 57

```
Gln Val Gln Leu Val Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
Ala Ile Ser Trp Val Arg Gln Ala Pro Gly Gln Gly Leu Glu Trp Met
        35                  40                  45
Gly Arg Ile Ile Pro Ile Leu Gly Ile Ala Asn Tyr Ala Gln Lys Phe
    50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Gly Tyr Tyr Ser His Asp Met Trp Ser Glu Asp Trp Gly
            100                 105                 110
Gln Gly Thr Leu Val Thr Val Ser Ser
        115                 120
```

<210> SEQ ID NO 58
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 58

```
Leu Pro Val Leu Thr Gln Pro Pro Ser Ala Ser Gly Thr Pro Gly Gln
1               5                   10                  15
Arg Val Thr Ile Ser Cys Ser Gly Arg Ser Ser Asn Ile Gly Ser Asn
            20                  25                  30
Ser Val Asn Trp Tyr Arg Gln Leu Pro Gly Ala Ala Pro Lys Leu Leu
        35                  40                  45
Ile Tyr Ser Asn Asn Gln Arg Pro Pro Gly Val Pro Val Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Thr Tyr Tyr Cys Ala Thr Trp Asp Asp Asn Leu
                85                  90                  95
Asn Val His Tyr Val Phe Gly Thr Gly Thr Lys Val Thr Val Leu Gly
            100                 105                 110
```

<210> SEQ ID NO 59
<211> LENGTH: 117
<212> TYPE: PRT
<213> ORGANISM: Artificial Sequence
<220> FEATURE:
<223> OTHER INFORMATION: Variable heavy (VH) Anti-BCMA

<400> SEQUENCE: 59

```
Gln Val Gln Leu Val Gln Ser Gly Ser Glu Leu Lys Lys Pro Gly Ala
1               5                   10                  15
```

-continued

Ser Val Lys Val Ser Cys Lys Ala Ser Gly Tyr Thr Phe Thr Asp Tyr
            20                  25                  30

Ser Ile Asn Trp Val Arg Gln Ala Pro Gly Gln Gly Leu Glu Trp Met
        35                  40                  45

Gly Trp Ile Asn Thr Glu Thr Arg Glu Pro Ala Tyr Ala Tyr Asp Phe
50                  55                  60

Arg Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Tyr Ser Tyr Ala Met Asp Tyr Trp Gly Gln Gly Thr Leu
            100                 105                 110

Val Thr Val Ser Ser
            115

<210> SEQ ID NO 60
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 60

Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Tyr Cys Leu Gln Ser Arg
                85                  90                  95

Ile Phe Pro Arg Thr Phe Gly Gln Gly Thr Lys Leu Glu Ile Lys
            100                 105                 110

<210> SEQ ID NO 61
<211> LENGTH: 115
<212> TYPE: PRT
<213> ORGANISM: Artificial Sequence
<220> FEATURE:
<223> OTHER INFORMATION: Variable heavy (VH) Anti-BCMA

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser

```
                    85                  90                  95
Ala His Gly Gly Glu Ser Asp Val Trp Gly Gln Gly Thr Thr Val Thr
                100                 105                 110

Val Ser Ser
        115

<210> SEQ ID NO 62
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 62

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105

<210> SEQ ID NO 63
<211> LENGTH: 120
<212> TYPE: PRT
<213> ORGANISM: Artificial Sequence
<220> FEATURE:
<223> OTHER INFORMATION: Variable heavy (VH) Anti-BCMA

<400> SEQUENCE: 63

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Gly Trp Val
        35                  40                  45

Ser Gly Ile Ser Arg Ser Gly Glu Asn Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Asp Glu Asp Thr Ala Val Tyr Tyr Cys
                85                  90                  95

Ala Arg Ser Pro Ala His Tyr Tyr Gly Gly Met Asp Val Trp Gly Gln
            100                 105                 110

Gly Thr Thr Val Thr Val Ser Ser
        115                 120

<210> SEQ ID NO 64
<211> LENGTH: 109
<212> TYPE: PRT
<213> ORGANISM: Artificial Sequence
<220> FEATURE:
```

<223> OTHER INFORMATION: Variable light (VL) Anti-BCMA

<400> SEQUENCE: 64

```
Asp Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Phe Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Ser Ala Val Tyr Tyr Cys Gln Gln Tyr His Ser Ser Pro
                85                  90                  95

Ser Trp Thr Phe Gly Gln Gly Thr Lys Leu Glu Ile Lys
            100                 105
```

<210> SEQ ID NO 65
<211> LENGTH: 115
<212> TYPE: PRT
<213> ORGANISM: Artificial Sequence
<220> FEATURE:
<223> OTHER INFORMATION: Variable heavy (VH) Anti-BCMA

<400> SEQUENCE: 65

```
Gln Val Gln Leu Val Glu Ser Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser
        115
```

<210> SEQ ID NO 66
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 66

```
Asp Ile Arg Leu Thr Gln Ser Pro Ser Pro Leu Ser Ala Ser Val Gly
1               5                   10                  15

Asp Arg Val Thr Ile Thr Cys Gln Ala Ser Glu Asp Ile Asn Lys Phe
            20                  25                  30

Leu Asn Trp Tyr His Gln Thr Pro Gly Lys Ala Pro Lys Leu Leu Ile
        35                  40                  45

Tyr Asp Ala Ser Thr Leu Gln Thr Gly Val Pro Ser Arg Phe Ser Gly
```

-continued

```
                50                  55                  60
Ser Gly Ser Gly Thr Asp Phe Thr Leu Thr Ile Asn Ser Leu Gln Pro
 65                  70                  75                  80

Glu Asp Ile Gly Thr Tyr Tyr Cys Gln Gln Tyr Glu Ser Leu Pro Leu
                 85                  90                  95

Thr Phe Gly Gly Gly Thr Lys Val Glu Ile Lys
            100                 105

<210> SEQ ID NO 67
<211> LENGTH: 115
<212> TYPE: PRT
<213> ORGANISM: Artificial Sequence
<220> FEATURE:
<223> OTHER INFORMATION: Variable  heavy (VH) Anti-BCMA

<400> SEQUENCE: 67

Glu Val Gln Leu Val Glu Ser Gly Gly Gly Leu Val Gln Pro Gly Gly
  1               5                  10                  15

Ser Leu Arg Leu Ser Cys Ala Val Ser Gly Phe Ala Leu Ser Asn His
                 20                  25                  30

Gly Met Ser Trp Val Arg Arg Ala Pro Gly Lys Gly Leu Glu Trp Val
             35                  40                  45

Ser Gly Ile Val Tyr Ser Gly Ser Thr Tyr Tyr Ala Ala Ser Val Lys
         50                  55                  60

Gly Arg Phe Thr Ile Ser Arg Asp Asn Ser Arg Asn Thr Leu Tyr Leu
 65                  70                  75                  80

Gln Met Asn Ser Leu Arg Pro Glu Asp Thr Ala Ile Tyr Tyr Cys Ser
                 85                  90                  95

Ala His Gly Gly Glu Ser Asp Val Trp Gly Gln Gly Thr Thr Val Thr
            100                 105                 110

Val Ser Ser
        115

<210> SEQ ID NO 68
<211> LENGTH: 109
<212> TYPE: PRT
<213> ORGANISM: Artificial Sequence
<220> FEATURE:
<223> OTHER INFORMATION: Variable light (VL) Anti-BCMA

<400> SEQUENCE: 68

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Ile Gly Ser Ser
                 20                  25                  30

Ser Leu Ala Trp Tyr Gln Gln Lys Pro Gly Gln Ala Pro Arg Leu Leu
             35                  40                  45

Met Tyr Gly Ala Ser Ser Arg Ala Ser Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Ala Gly Ser Pro
                 85                  90                  95

Pro Phe Thr Phe Gly Gln Gly Thr Lys Val Glu Ile Lys
            100                 105

<210> SEQ ID NO 69
<211> LENGTH: 117
```

```
<212> TYPE: PRT
<213> ORGANISM: Artificial Sequence
<220> FEATURE:
<223> OTHER INFORMATION: Variable heavy (VH) Anti-BCMA

<400> SEQUENCE: 69

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Arg His Tyr
            20                  25                  30

Ser Met Asn Trp Val Lys Gln Ala Pro Gly Lys Gly Leu Lys Trp Met
        35                  40                  45

Gly Arg Ile Asn Thr Glu Ser Gly Val Pro Ile Tyr Ala Asp Asp Phe
    50                  55                  60

Lys Gly Arg Phe Ala Phe Ser Val Glu Thr Ser Ala Ser Thr Ala Tyr
65                  70                  75                  80

Leu Val Ile Asn Asn Leu Lys Asp Glu Asp Thr Ala Ser Tyr Phe Cys
                85                  90                  95

Ser Asn Asp Tyr Leu Tyr Ser Leu Asp Phe Trp Gly Gln Gly Thr Ala
            100                 105                 110

Leu Thr Val Ser Ser
            115

<210> SEQ ID NO 70
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 70

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile Tyr Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110

<210> SEQ ID NO 71
<211> LENGTH: 117
<212> TYPE: PRT
<213> ORGANISM: Artificial Sequence
<220> FEATURE:
<223> OTHER INFORMATION: Variable heavy (VH) Anti-BCMA

<400> SEQUENCE: 71

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr His Tyr
            20                  25                  30

Ser Met Asn Trp Val Lys Gln Ala Pro Gly Lys Gly Leu Lys Trp Met
```

```
                35                  40                  45

Gly Arg Ile Asn Thr Glu Thr Gly Glu Pro Leu Tyr Ala Asp Asp Phe
            50                  55                  60

Lys Gly Arg Phe Ala Phe Ser Leu Glu Thr Ser Ala Ser Thr Ala Tyr
 65                  70                  75                  80

Leu Val Ile Asn Asn Leu Lys Asn Glu Asp Thr Ala Thr Phe Phe Cys
                85                  90                  95

Ser Asn Asp Tyr Leu Tyr Ser Cys Asp Tyr Trp Gly Gln Gly Thr Thr
                100                 105                 110

Leu Thr Val Ser Ser
            115

<210> SEQ ID NO 72
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 72

Asp Ile Val Leu Thr Gln Ser Pro Ala Ser Leu Ala Met Ser Leu Gly
 1               5                  10                  15

Lys Arg Ala Thr Ile Ser Cys Arg Ala Ser Glu Ser Val Ser Val Ile
                20                  25                  30

Gly Ala His Leu Ile His Trp Tyr Gln Gln Lys Pro Gly Gln Pro Pro
            35                  40                  45

Lys Leu Leu Ile Tyr Leu Ala Ser Asn Leu Glu Thr Gly Val Pro Ala
 50                  55                  60

Arg Phe Ser Gly Ser Gly Ser Gly Thr Asp Phe Thr Leu Thr Ile Asp
 65                  70                  75                  80

Pro Val Glu Glu Asp Asp Val Ala Ile Tyr Ser Cys Leu Gln Ser Arg
                85                  90                  95

Ile Phe Pro Arg Thr Phe Gly Gly Gly Thr Lys Leu Glu Ile Lys
                100                 105                 110

<210> SEQ ID NO 73
<211> LENGTH: 119
<212> TYPE: PRT
<213> ORGANISM: Artificial Sequence
<220> FEATURE:
<223> OTHER INFORMATION: Variable heavy (VH) Anti-BCMA

<400> SEQUENCE: 73

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ser Phe Pro Asp Tyr
                20                  25                  30

Tyr Ile Asn Trp Val Arg Gln Ala Pro Gly Gln Gly Leu Glu Trp Met
            35                  40                  45

Gly Trp Ile Tyr Phe Ala Ser Gly Asn Ser Glu Tyr Asn Gln Lys Phe
 50                  55                  60

Thr Gly Arg Val Thr Met Thr Arg Asp Thr Ser Ile Asn Thr Ala Tyr
 65                  70                  75                  80

Met Glu Leu Ser Ser Leu Thr Ser Glu Asp Thr Ala Val Tyr Phe Cys
                85                  90                  95

Ala Ser Leu Tyr Asp Tyr Asp Tyr Phe Asp Val Trp Gly Gln Gly
                100                 105                 110
```

```
Thr Met Val Thr Val Ser Ser
            115

<210> SEQ ID NO 74
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 74

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Ser Gln Ser
                85                  90                  95

Ser Ile Tyr Pro Trp Thr Phe Gly Gln Gly Thr Lys Leu Glu Ile Lys
            100                 105                 110

<210> SEQ ID NO 75
<211> LENGTH: 119
<212> TYPE: PRT
<213> ORGANISM: Artificial Sequence
<220> FEATURE:
<223> OTHER INFORMATION: Variable heavy (VH) Anti-BCMA

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
            20                  25                  30

Tyr Ile Asn Trp Val Arg Gln Ala Pro Gly Gln Gly Leu Glu Trp Met
        35                  40                  45

Gly Trp Ile Tyr Phe Ala Ser Gly Asn Ser Glu Tyr Asn Gln Lys Phe
    50                  55                  60

Thr Gly Arg Val Thr Met Thr Arg Asp Thr Ser Ser Thr Ala Tyr
65                  70                  75                  80

Met Glu Leu Ser Ser Leu Arg Ser Glu Asp Thr Ala Val Tyr Phe Cys
                85                  90                  95

Ala Ser Leu Tyr Asp Tyr Asp Tyr Phe Asp Val Trp Gly Gln Gly
            100                 105                 110

Thr Met Val Thr Val Ser Ser
            115

<210> SEQ ID NO 76
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 76

Asp Ile Val Met Thr Gln Thr Pro Leu Ser Leu Ser Val Thr Pro Gly
```

```
                1               5                  10                 15
            Glu Pro Ala Ser Ile Ser Cys Lys Ser Ser Gln Ser Leu Val His Ser
                            20                  25                  30

Asn Gly Asn Thr Tyr Leu His Trp Tyr Leu Gln Lys Pro Gly Gln Ser
                        35                  40                  45

Pro Gln Leu Leu Ile Tyr Lys Val Ser Asn Arg Phe Ser Gly Val Pro
                50                  55                  60

Asp Arg Phe Ser Gly Ser Gly Ser Gly Ala Asp Phe Thr Leu Lys Ile
            65                  70                  75                  80

Ser Arg Val Glu Ala Glu Asp Val Gly Val Tyr Tyr Cys Ala Glu Thr
                            85                  90                  95

Ser His Val Pro Trp Thr Phe Gly Gln Gly Thr Lys Leu Glu Ile Lys
                        100                 105                 110
```

<210> SEQ ID NO 77
<211> LENGTH: 122
<212> TYPE: PRT
<213> ORGANISM: Artificial Sequence
<220> FEATURE:
<223> OTHER INFORMATION: Anti-BCMA sdAb

<400> SEQUENCE: 77

```
            Gln Val Gln Leu Val Glu Ser Gly Gly Gly Leu Val Gln Pro Gly Gly
            1               5                   10                  15

Ser Leu Arg Leu Ser Cys Glu Ala Ser Gly Phe Thr Leu Asp Tyr Tyr
                            20                  25                  30

Ala Ile Gly Trp Phe Arg Gln Ala Pro Gly Lys Glu Arg Glu Gly Val
                        35                  40                  45

Ile Cys Ile Ser Arg Ser Asp Gly Ser Thr Tyr Tyr Ala Asp Ser Val
                50                  55                  60

Lys Gly Arg Phe Thr Ile Ser Arg Asp Asn Ala Lys Lys Thr Val Tyr
            65                  70                  75                  80

Leu Gln Met Ile Ser Leu Lys Pro Glu Asp Thr Ala Ala Tyr Tyr Cys
                            85                  90                  95

Ala Ala Gly Ala Asp Cys Ser Gly Tyr Leu Arg Asp Tyr Glu Phe Arg
                        100                 105                 110

Gly Gln Gly Thr Gln Val Thr Val Ser Ser
                        115                 120
```

<210> SEQ ID NO 78
<211> LENGTH: 39
<212> TYPE: PRT
<213> ORGANISM: Artificial Sequence
<220> FEATURE:
<223> OTHER INFORMATION: CD28 spacer

<400> SEQUENCE: 78

```
            Ile Glu Val Met Tyr Pro Pro Pro Tyr Leu Asp Asn Glu Lys Ser Asn
            1               5                   10                  15

Gly Thr Ile Ile His Val Lys Gly Lys His Leu Cys Pro Ser Pro Leu
                            20                  25                  30

Phe Pro Gly Pro Ser Lys Pro
                        35
```

<210> SEQ ID NO 79
<211> LENGTH: 25
<212> TYPE: PRT
<213> ORGANISM: Artificial Sequence
<220> FEATURE:

<223> OTHER INFORMATION: CD8a TM

<400> SEQUENCE: 79

Ile Tyr Ile Trp Ala Pro Leu Ala Gly Thr Cys Gly Val Leu Leu Leu
1               5                   10                  15

Ser Leu Val Ile Thr Leu Tyr Cys Asn
            20                  25

<210> SEQ ID NO 80
<211> LENGTH: 30
<212> TYPE: PRT
<213> ORGANISM: Artificial Sequence
<220> FEATURE:
<223> OTHER INFORMATION: CD28 spacer (truncated)

<400> SEQUENCE: 80

Leu Asp Asn Glu Lys Ser Asn Gly Thr Ile Ile His Val Lys Gly Lys
1               5                   10                  15

His Leu Cys Pro Ser Pro Leu Phe Pro Gly Pro Ser Lys Pro
            20                  25                  30

<210> SEQ ID NO 81
<211> LENGTH: 46
<212> TYPE: PRT
<213> ORGANISM: Artificial Sequence
<220> FEATURE:
<223> OTHER INFORMATION: CD8a hinge

<400> SEQUENCE: 81

Pro Thr Thr Thr Pro Ala Pro Arg Pro Pro Thr Pro Ala Pro Thr Ile
1               5                   10                  15

Ala Ser Gln Pro Leu Ser Leu Arg Pro Glu Ala Cys Arg Pro Ala Ala
            20                  25                  30

Gly Gly Ala Val His Thr Arg Gly Leu Asp Phe Ala Cys Asp
        35                  40                  45

<210> SEQ ID NO 82
<211> LENGTH: 45
<212> TYPE: PRT
<213> ORGANISM: Artificial Sequence
<220> FEATURE:
<223> OTHER INFORMATION: CD8a hinge

<400> SEQUENCE: 82

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 83
<211> LENGTH: 55
<212> TYPE: PRT
<213> ORGANISM: Artificial Sequence
<220> FEATURE:
<223> OTHER INFORMATION: CD8a hinge

<400> SEQUENCE: 83

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

-continued

Arg Pro Glu Ala Cys Arg Pro Ala Gly Gly Ala Val His Thr Arg
         35                  40                  45

Gly Leu Asp Phe Ala Cys Asp
         50                  55

<210> SEQ ID NO 84
<211> LENGTH: 39
<212> TYPE: PRT
<213> ORGANISM: Artificial Sequence
<220> FEATURE:
<223> OTHER INFORMATION: CTLA4 hinge

<400> SEQUENCE: 84

Asp Thr Gly Leu Tyr Ile Cys Lys Val Glu Leu Met Tyr Pro Pro Pro
1               5                   10                  15

Tyr Tyr Leu Gly Ile Gly Asn Gly Thr Gln Ile Tyr Val Ile Asp Pro
            20                  25                  30

Glu Pro Cys Pro Asp Ser Asp
        35

<210> SEQ ID NO 85
<211> LENGTH: 24
<212> TYPE: PRT
<213> ORGANISM: Artificial Sequence
<220> FEATURE:
<223> OTHER INFORMATION: CTLA4 TM

<400> SEQUENCE: 85

Phe Leu Leu Trp Ile Leu Ala Ala Val Ser Ser Gly Leu Phe Phe Tyr
1               5                   10                  15

Ser Phe Leu Leu Thr Ala Val Ser
            20

<210> SEQ ID NO 86
<211> LENGTH: 38
<212> TYPE: PRT
<213> ORGANISM: Artificial Sequence
<220> FEATURE:
<223> OTHER INFORMATION: PD-1 hinge

<400> SEQUENCE: 86

Gln Ile Lys Glu Ser Leu Arg Ala Glu Leu Arg Val Thr Glu Arg Arg
1               5                   10                  15

Ala Glu Val Pro Thr Ala His Pro Ser Pro Ser Pro Arg Pro Ala Gly
            20                  25                  30

Gln Phe Gln Thr Leu Val
        35

<210> SEQ ID NO 87
<211> LENGTH: 21
<212> TYPE: PRT
<213> ORGANISM: Artificial Sequence
<220> FEATURE:
<223> OTHER INFORMATION: PD-1 TM

<400> SEQUENCE: 87

Val Gly Val Val Gly Gly Leu Leu Gly Ser Leu Val Leu Leu Val Trp
1               5                   10                  15

Val Leu Ala Val Ile
            20

<210> SEQ ID NO 88

```
<211> LENGTH: 16
<212> TYPE: PRT
<213> ORGANISM: Artificial Sequence
<220> FEATURE:
<223> OTHER INFORMATION: Fc(gamma)RIIIa hinge

<400> SEQUENCE: 88

Gly Leu Ala Val Ser Thr Ile Ser Ser Phe Phe Pro Pro Gly Tyr Gln
1               5                   10                  15

<210> SEQ ID NO 89
<211> LENGTH: 231
<212> TYPE: PRT
<213> ORGANISM: Artificial Sequence
<220> FEATURE:
<223> OTHER INFORMATION: IgG1 hinge

<400> SEQUENCE: 89

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ala Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 90
<211> LENGTH: 457
<212> TYPE: PRT
<213> ORGANISM: Artificial Sequence
<220> FEATURE:
<223> OTHER INFORMATION: anti-BCMA CAR

<400> SEQUENCE: 90

Glu Val Gln Leu Leu Glu Ser Gly Gly Gly Leu Val Gln Pro Gly Gly
1               5                   10                  15
```

-continued

Ser Leu Arg Leu Ser Cys Ala Ala Ser Gly Phe Thr Phe Ser Ser Tyr
              20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Glu Met Gly Ala Val Phe Asp Ile Trp Gly Gln Gly Thr
                100                 105                 110

Met Val Thr Val Ser Ser Gly Ser Thr Ser Gly Ser Gly Lys Pro Gly
            115                 120                 125

Ser Gly Glu Gly Ser Thr Lys Gly Glu Ile Val Leu Thr Gln Ser Pro
        130                 135                 140

Ala Thr Leu Ser Leu Ser Pro Gly Glu Arg Ala Thr Leu Ser Cys Arg
145                 150                 155                 160

Ala Ser Gln Ser Val Ser Arg Tyr Leu Ala Trp Tyr Gln Gln Lys Pro
                165                 170                 175

Gly Gln Ala Pro Arg Leu Leu Ile Tyr Asp Ala Ser Asn Arg Ala Thr
                180                 185                 190

Gly Ile Pro Ala Arg Phe Ser Gly Ser Gly Ser Gly Thr Asp Phe Thr
            195                 200                 205

Leu Thr Ile Ser Ser Leu Glu Pro Glu Asp Phe Ala Val Tyr Tyr Cys
        210                 215                 220

Gln Gln Arg Ile Ser Trp Pro Phe Thr Phe Gly Gly Gly Thr Lys Val
225                 230                 235                 240

Glu Ile Lys Arg Ala Ala Ala Leu Asp Asn Glu Lys Ser Asn Gly Thr
                245                 250                 255

Ile Ile His Val Lys Gly Lys His Leu Cys Pro Ser Pro Leu Phe Pro
                260                 265                 270

Gly Pro Ser Lys Pro Phe Trp Val Leu Val Val Val Gly Gly Val Leu
            275                 280                 285

Ala Cys Tyr Ser Leu Leu Val Thr Val Ala Phe Ile Ile Phe Trp Val
        290                 295                 300

Arg Ser Lys Arg Ser Arg Leu Leu His Ser Asp Tyr Met Asn Met Thr
305                 310                 315                 320

Pro Arg Arg Pro Gly Pro Thr Arg Lys His Tyr Gln Pro Tyr Ala Pro
                325                 330                 335

Pro Arg Asp Phe Ala Ala Tyr Arg Ser Arg Val Lys Phe Ser Arg Ser
            340                 345                 350

Ala Asp Ala Pro Ala Tyr Gln Gln Gly Gln Asn Gln Leu Tyr Asn Glu
        355                 360                 365

Leu Asn Leu Gly Arg Arg Glu Glu Tyr Asp Val Leu Asp Lys Arg Arg
    370                 375                 380

Gly Arg Asp Pro Glu Met Gly Gly Lys Pro Arg Arg Lys Asn Pro Gln
385                 390                 395                 400

Glu Gly Leu Tyr Asn Glu Leu Gln Lys Asp Lys Met Ala Glu Ala Tyr
                405                 410                 415

Ser Glu Ile Gly Met Lys Gly Glu Arg Arg Arg Gly Lys Gly His Asp
            420                 425                 430

Gly Leu Tyr Gln Gly Leu Ser Thr Ala Thr Lys Asp Thr Tyr Asp Ala

```
                435                 440                 445
Leu His Met Gln Ala Leu Pro Pro Arg
    450                 455

<210> SEQ ID NO 91
<211> LENGTH: 457
<212> TYPE: PRT
<213> ORGANISM: Artificial Sequence
<220> FEATURE:
<223> OTHER INFORMATION: anti-BCMA CAR

<400> SEQUENCE: 91

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ile Ser Trp Pro Phe
                85                  90                  95

Thr Phe Gly Gly Gly Thr Lys Val Glu Ile Lys Arg Gly Ser Thr Ser
            100                 105                 110

Gly Ser Gly Lys Pro Gly Ser Gly Glu Gly Ser Thr Lys Gly Glu Val
        115                 120                 125

Gln Leu Leu Glu Ser Gly Gly Gly Leu Val Gln Pro Gly Gly Ser Leu
    130                 135                 140

Arg Leu Ser Cys Ala Ala Ser Gly Phe Thr Phe Ser Ser Tyr Ala Met
145                 150                 155                 160

Ser Trp Val Arg Gln Ala Pro Gly Lys Gly Leu Glu Trp Val Ser Ala
                165                 170                 175

Ile Ser Gly Ser Gly Gly Ser Thr Tyr Tyr Ala Asp Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Ala Val Tyr Tyr Cys Ala Arg
    210                 215                 220

Ala Glu Met Gly Ala Val Phe Asp Ile Trp Gly Gln Gly Thr Met Val
225                 230                 235                 240

Thr Val Ser Ser Ala Ala Ala Leu Asp Asn Glu Lys Ser Asn Gly Thr
                245                 250                 255

Ile Ile His Val Lys Gly Lys His Leu Cys Pro Ser Pro Leu Phe Pro
            260                 265                 270

Gly Pro Ser Lys Pro Phe Trp Val Leu Val Val Val Gly Gly Val Leu
        275                 280                 285

Ala Cys Tyr Ser Leu Leu Val Thr Val Ala Phe Ile Ile Phe Trp Val
    290                 295                 300

Arg Ser Lys Arg Ser Arg Leu Leu His Ser Asp Tyr Met Asn Met Thr
305                 310                 315                 320

Pro Arg Arg Pro Gly Pro Thr Arg Lys His Tyr Gln Pro Tyr Ala Pro
                325                 330                 335

Pro Arg Asp Phe Ala Ala Tyr Arg Ser Arg Val Lys Phe Ser Arg Ser
```

```
              340                 345                 350
Ala Asp Ala Pro Ala Tyr Gln Gln Gly Gln Asn Gln Leu Tyr Asn Glu
            355                 360                 365

Leu Asn Leu Gly Arg Arg Glu Glu Tyr Asp Val Leu Asp Lys Arg Arg
        370                 375                 380

Gly Arg Asp Pro Glu Met Gly Gly Lys Pro Arg Arg Lys Asn Pro Gln
385                 390                 395                 400

Glu Gly Leu Tyr Asn Glu Leu Gln Lys Asp Lys Met Ala Glu Ala Tyr
                405                 410                 415

Ser Glu Ile Gly Met Lys Gly Glu Arg Arg Arg Gly Lys Gly His Asp
            420                 425                 430

Gly Leu Tyr Gln Gly Leu Ser Thr Ala Thr Lys Asp Thr Tyr Asp Ala
        435                 440                 445

Leu His Met Gln Ala Leu Pro Pro Arg
    450                 455

<210> SEQ ID NO 92
<211> LENGTH: 466
<212> TYPE: PRT
<213> ORGANISM: Artificial Sequence
<220> FEATURE:
<223> OTHER INFORMATION: anti-BCMA CAR

<400> SEQUENCE: 92

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Tyr Leu Gly Gly Leu Trp Tyr Phe Asp Leu Trp
            100                 105                 110

Gly Arg Gly Thr Leu Val Thr Val Ser Ser Gly Ser Thr Ser Gly Ser
        115                 120                 125

Gly Lys Pro Gly Ser Gly Glu Gly Ser Thr Lys Gly Asp Ile Val Met
    130                 135                 140

Thr Gln Ser Pro Leu Ser Leu Pro Val Thr Pro Gly Glu Pro Ala Ser
145                 150                 155                 160

Ile Ser Cys Arg Ser Ser Gln Ser Leu Leu His Ser Asn Gly Tyr Asn
                165                 170                 175

Tyr Leu Asp Trp Tyr Leu Gln Lys Pro Gly Gln Ser Pro Gln Leu Leu
            180                 185                 190

Ile Tyr Leu Gly Ser Asn Arg Ala Ser Gly Val Pro Asp Arg Phe Ser
        195                 200                 205

Gly Ser Gly Ser Gly Thr Asp Phe Thr Leu Lys Ile Ser Arg Val Glu
    210                 215                 220

Ala Glu Asp Val Gly Val Tyr Tyr Cys Met Gln Gly Leu Gly Leu Pro
225                 230                 235                 240

Leu Thr Phe Gly Gly Gly Thr Lys Val Glu Ile Lys Arg Ala Ala Ala
```

```
                    245                 250                 255
Leu Asp Asn Glu Lys Ser Asn Gly Thr Ile Ile His Val Lys Gly Lys
            260                 265                 270

His Leu Cys Pro Ser Pro Leu Phe Pro Gly Pro Ser Lys Pro Phe Trp
        275                 280                 285

Val Leu Val Val Val Gly Gly Val Leu Ala Cys Tyr Ser Leu Leu Val
    290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Arg Val Lys Phe Ser Arg Ser Ala Asp Ala Pro Ala Tyr Gln
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg
465

<210> SEQ ID NO 93
<211> LENGTH: 466
<212> TYPE: PRT
<213> ORGANISM: Artificial Sequence
<220> FEATURE:
<223> OTHER INFORMATION: anti-BCMA CAR

<400> SEQUENCE: 93

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gly Leu Pro Leu Thr Phe Gly Gly Gly Thr Lys Val Glu Ile Lys
            100                 105                 110

Arg Gly Ser Thr Ser Gly Ser Gly Lys Pro Gly Ser Gly Glu Gly Ser
        115                 120                 125

Thr Lys Gly Gln Val Gln Leu Val Glu Ser Gly Gly Gly Val Val Gln
```

```
                130                 135                 140
Pro Gly Arg Ser Leu Arg Leu Ser Cys Ala Ala Ser Gly Phe Thr Phe
145                 150                 155                 160

Ser Ser Tyr Gly Met His Trp Val Arg Gln Ala Pro Gly Lys Gly Leu
                165                 170                 175

Glu Trp Val Ala Val Ile Ser Tyr Asp Gly Ser Asn Lys Tyr Tyr Ala
                180                 185                 190

Asp Ser Val Lys Gly Arg Phe Thr Ile Ser Arg Asp Asn Ser Lys Asn
                195                 200                 205

Thr Leu Tyr Leu Gln Met Asn Ser Leu Arg Ala Glu Asp Thr Ala Val
                210                 215                 220

Tyr Tyr Cys Ala Arg Asp Gly Thr Tyr Leu Gly Leu Trp Tyr Phe
225                 230                 235                 240

Asp Leu Trp Gly Arg Gly Thr Leu Val Thr Val Ser Ser Ala Ala Ala
                245                 250                 255

Leu Asp Asn Glu Lys Ser Asn Gly Thr Ile Ile His Val Lys Gly Lys
                260                 265                 270

His Leu Cys Pro Ser Pro Leu Phe Pro Gly Pro Ser Lys Pro Phe Trp
                275                 280                 285

Val Leu Val Val Gly Gly Val Leu Ala Cys Tyr Ser Leu Leu Val
                290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
                340                 345                 350

Arg Ser Arg Val Lys Phe Ser Arg Ser Ala Asp Ala Pro Ala Tyr Gln
                355                 360                 365

Gln Gly Gln Asn Gln Leu Tyr Asn Glu Leu Asn Leu Gly Arg Arg Glu
                370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
                420                 425                 430

Glu Arg Arg Arg Gly Lys Gly His Asp Gly Leu Tyr Gln Gly Leu Ser
                435                 440                 445

Thr Ala Thr Lys Asp Thr Tyr Asp Ala Leu His Met Gln Ala Leu Pro
        450                 455                 460

Pro Arg
465

<210> SEQ ID NO 94
<211> LENGTH: 454
<212> TYPE: PRT
<213> ORGANISM: Artificial Sequence
<220> FEATURE:
<223> OTHER INFORMATION: anti-BCMA CAR

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
              20                  25                  30
Tyr Met His Trp Val Arg Gln Ala Pro Gly Gln Gly Leu Glu Trp Met
                35                  40                  45
Gly Ile Ile Asn Pro Gly Gly Ser Thr Ser Tyr Ala Gln Lys Phe
 50                  55                  60
Gln Gly Arg Val Thr Met Thr Arg Asp Thr Ser Thr Ser Thr Val Tyr
 65                  70                  75                  80
Met Glu Leu Ser Ser Leu Arg Ser Glu Asp Thr Ala Val Tyr Tyr Cys
                85                  90                  95
Ala Arg Glu Ser Trp Pro Met Asp Val Trp Gly Gln Gly Thr Thr Val
                100                 105                 110
Thr Val Ser Ser Gly Ser Thr Ser Gly Ser Gly Lys Pro Gly Ser Gly
                115                 120                 125
Glu Gly Ser Thr Lys Gly Glu Ile Val Met Thr Gln Ser Pro Ala Thr
                130                 135                 140
Leu Ser Val Ser Pro Gly Glu Arg Ala Thr Leu Ser Cys Arg Ala Ser
145                 150                 155                 160
Gln Ser Val Ser Ser Asn Leu Ala Trp Tyr Gln Gln Lys Pro Gly Gln
                165                 170                 175
Ala Pro Arg Leu Leu Ile Tyr Gly Ala Ser Thr Arg Ala Thr Gly Ile
                180                 185                 190
Pro Ala Arg Phe Ser Gly Ser Gly Ser Gly Thr Glu Phe Thr Leu Thr
                195                 200                 205
Ile Ser Ser Leu Gln Ser Glu Asp Phe Ala Val Tyr Tyr Cys Gln Gln
                210                 215                 220
Tyr Ala Ala Tyr Pro Thr Phe Gly Gly Gly Thr Lys Val Glu Ile Lys
225                 230                 235                 240
Arg Ala Ala Ala Leu Asp Asn Glu Lys Ser Asn Gly Thr Ile Ile His
                245                 250                 255
Val Lys Gly Lys His Leu Cys Pro Ser Pro Leu Phe Pro Gly Pro Ser
                260                 265                 270
Lys Pro Phe Trp Val Leu Val Val Val Gly Gly Val Leu Ala Cys Tyr
                275                 280                 285
Ser Leu Leu Val Thr Val Ala Phe Ile Ile Phe Trp Val Arg Ser Lys
                290                 295                 300
Arg Ser Arg Leu Leu His Ser Asp Tyr Met Asn Met Thr Pro Arg Arg
305                 310                 315                 320
Pro Gly Pro Thr Arg Lys His Tyr Gln Pro Tyr Ala Pro Pro Arg Asp
                325                 330                 335
Phe Ala Ala Tyr Arg Ser Arg Val Lys Phe Ser Arg Ser Ala Asp Ala
                340                 345                 350
Pro Ala Tyr Gln Gln Gly Gln Asn Gln Leu Tyr Asn Glu Leu Asn Leu
                355                 360                 365
Gly Arg Arg Glu Glu Tyr Asp Val Leu Asp Lys Arg Arg Gly Arg Asp
                370                 375                 380
Pro Glu Met Gly Gly Lys Pro Arg Arg Lys Asn Pro Gln Glu Gly Leu
385                 390                 395                 400
Tyr Asn Glu Leu Gln Lys Asp Lys Met Ala Glu Ala Tyr Ser Glu Ile
                405                 410                 415
Gly Met Lys Gly Glu Arg Arg Gly Lys Gly His Asp Gly Leu Tyr
                420                 425                 430
Gln Gly Leu Ser Thr Ala Thr Lys Asp Thr Tyr Asp Ala Leu His Met
                435                 440                 445
```

Gln Ala Leu Pro Pro Arg
    450

<210> SEQ ID NO 95
<211> LENGTH: 454
<212> TYPE: PRT
<213> ORGANISM: Artificial Sequence
<220> FEATURE:
<223> OTHER INFORMATION: anti-BCMA CAR

<400> SEQUENCE: 95

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Ala Ala Tyr Pro Thr
                85                  90                  95

Phe Gly Gly Gly Thr Lys Val Glu Ile Lys Arg Gly Ser Thr Ser Gly
            100                 105                 110

Ser Gly Lys Pro Gly Ser Gly Glu Ser Thr Lys Gly Gln Val Gln
        115                 120                 125

Leu Val Gln Ser Gly Ala Glu Val Lys Lys Pro Gly Ala Ser Val Lys
    130                 135                 140

Val Ser Cys Lys Ala Ser Gly Tyr Thr Phe Thr Ser Tyr Tyr Met His
145                 150                 155                 160

Trp Val Arg Gln Ala Pro Gly Gln Gly Leu Glu Trp Met Gly Ile Ile
                165                 170                 175

Asn Pro Gly Gly Gly Ser Thr Ser Tyr Ala Gln Lys Phe Gln Gly Arg
            180                 185                 190

Val Thr Met Thr Arg Asp Thr Ser Thr Ser Thr Val Tyr Met Glu Leu
        195                 200                 205

Ser Ser Leu Arg Ser Glu Asp Thr Ala Val Tyr Tyr Cys Ala Arg Glu
    210                 215                 220

Ser Trp Pro Met Asp Val Trp Gly Gln Gly Thr Thr Val Thr Val Ser
225                 230                 235                 240

Ser Ala Ala Ala Leu Asp Asn Glu Lys Ser Asn Gly Thr Ile Ile His
                245                 250                 255

Val Lys Gly Lys His Leu Cys Pro Ser Pro Leu Phe Pro Gly Pro Ser
            260                 265                 270

Lys Pro Phe Trp Val Leu Val Val Gly Gly Val Leu Ala Cys Tyr
        275                 280                 285

Ser Leu Leu Val Thr Val Ala Phe Ile Ile Phe Trp Val Arg Ser Lys
    290                 295                 300

Arg Ser Arg Leu Leu His Ser Asp Tyr Met Asn Met Thr Pro Arg Arg
305                 310                 315                 320

Pro Gly Pro Thr Arg Lys His Tyr Gln Pro Tyr Ala Pro Pro Arg Asp
                325                 330                 335

Phe Ala Ala Tyr Arg Ser Arg Val Lys Phe Ser Arg Ser Ala Asp Ala
            340                 345                 350

```
Pro Ala Tyr Gln Gln Gly Gln Asn Gln Leu Tyr Asn Glu Leu Asn Leu
        355                 360                 365

Gly Arg Arg Glu Glu Tyr Asp Val Leu Asp Lys Arg Gly Arg Asp
    370                 375                 380

Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
                405                 410                 415

Gly Met Lys Gly Glu Arg Arg Arg Gly Lys Gly His Asp Gly Leu Tyr
            420                 425                 430

Gln Gly Leu Ser Thr Ala Thr Lys Asp Thr Tyr Asp Ala Leu His Met
        435                 440                 445

Gln Ala Leu Pro Pro Arg
    450

<210> SEQ ID NO 96
<211> LENGTH: 461
<212> TYPE: PRT
<213> ORGANISM: Artificial Sequence
<220> FEATURE:
<223> OTHER INFORMATION: anti-BCMA CAR

<400> SEQUENCE: 96

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Ser Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Arg Gly Tyr Ala Thr Ser Leu Ala Phe Asp Ile Trp
            100                 105                 110

Gly Gln Gly Thr Met Val Thr Val Ser Ser Gly Ser Thr Ser Gly Ser
        115                 120                 125

Gly Lys Pro Gly Ser Gly Glu Gly Ser Thr Lys Gly Glu Ile Val Leu
    130                 135                 140

Thr Gln Ser Pro Ala Thr Leu Ser Leu Ser Pro Gly Glu Arg Ala Thr
145                 150                 155                 160

Leu Ser Cys Arg Ala Ser Gln Ser Val Ser Ser Tyr Leu Ala Trp Tyr
                165                 170                 175

Gln Gln Lys Pro Gly Gln Ala Pro Arg Leu Leu Ile Tyr Asp Ala Ser
            180                 185                 190

Asn Arg Ala Thr Gly Ile Pro Ala Arg Phe Ser Gly Ser Gly Ser Gly
        195                 200                 205

Thr Asp Phe Thr Leu Thr Ile Ser Ser Leu Glu Pro Glu Asp Phe Ala
    210                 215                 220

Val Tyr Tyr Cys Gln Gln Arg His Val Trp Pro Pro Thr Phe Gly Gly
225                 230                 235                 240

Gly Thr Lys Val Glu Ile Lys Arg Ala Ala Ala Leu Asp Asn Glu Lys
                245                 250                 255
```

```
Ser Asn Gly Thr Ile Ile His Val Lys Gly Lys His Leu Cys Pro Ser
            260                 265                 270

Pro Leu Phe Pro Gly Pro Ser Lys Pro Phe Trp Val Leu Val Val Val
        275                 280                 285

Gly Gly Val Leu Ala Cys Tyr Ser Leu Leu Val Thr Val Ala Phe Ile
    290                 295                 300

Ile Phe Trp Val Arg Ser Lys Arg Ser Arg Leu Leu His Ser Asp Tyr
305                 310                 315                 320

Met Asn Met Thr Pro Arg Arg Pro Gly Pro Thr Arg Lys His Tyr Gln
                325                 330                 335

Pro Tyr Ala Pro Pro Arg Asp Phe Ala Ala Tyr Arg Ser Arg Val Lys
            340                 345                 350

Phe Ser Arg Ser Ala Asp Ala Pro Ala Tyr Gln Gln Gly Gln Asn Gln
        355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg
    450                 455                 460

<210> SEQ ID NO 97
<211> LENGTH: 461
<212> TYPE: PRT
<213> ORGANISM: Artificial Sequence
<220> FEATURE:
<223> OTHER INFORMATION: anti-BCMA CAR

<400> SEQUENCE: 97

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg His Val Trp Pro Pro
                85                  90                  95

Thr Phe Gly Gly Gly Thr Lys Val Glu Ile Lys Arg Gly Ser Thr Ser
            100                 105                 110

Gly Ser Gly Lys Pro Gly Ser Gly Glu Gly Ser Thr Lys Gly Gln Leu
        115                 120                 125

Gln Leu Gln Glu Ser Gly Pro Gly Leu Val Lys Pro Ser Glu Thr Leu
    130                 135                 140

Ser Leu Thr Cys Thr Val Ser Gly Gly Ser Ile Ser Ser Ser Ser Tyr
145                 150                 155                 160
```

```
Tyr Trp Gly Trp Ile Arg Gln Pro Pro Gly Lys Gly Leu Glu Trp Ile
                165                 170                 175

Gly Ser Ile Ser Tyr Ser Gly Ser Thr Tyr Tyr Asn Pro Ser Leu Lys
            180                 185                 190

Ser Arg Val Thr Ile Ser Val Asp Thr Ser Lys Asn Gln Phe Ser Leu
        195                 200                 205

Lys Leu Ser Ser Val Thr Ala Ala Asp Thr Ala Val Tyr Tyr Cys Ala
    210                 215                 220

Arg Gly Arg Gly Tyr Ala Thr Ser Leu Ala Phe Asp Ile Trp Gly Gln
225                 230                 235                 240

Gly Thr Met Val Thr Val Ser Ser Ala Ala Ala Leu Asp Asn Glu Lys
                245                 250                 255

Ser Asn Gly Thr Ile Ile His Val Lys Gly Lys His Leu Cys Pro Ser
            260                 265                 270

Pro Leu Phe Pro Gly Pro Ser Lys Pro Phe Trp Val Leu Val Val Val
        275                 280                 285

Gly Gly Val Leu Ala Cys Tyr Ser Leu Leu Val Thr Val Ala Phe Ile
    290                 295                 300

Ile Phe Trp Val Arg Ser Lys Arg Ser Arg Leu Leu His Ser Asp Tyr
305                 310                 315                 320

Met Asn Met Thr Pro Arg Arg Pro Gly Pro Thr Arg Lys His Tyr Gln
                325                 330                 335

Pro Tyr Ala Pro Pro Arg Asp Phe Ala Ala Tyr Arg Ser Arg Val Lys
            340                 345                 350

Phe Ser Arg Ser Ala Asp Ala Pro Ala Tyr Gln Gln Gly Gln Asn Gln
        355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
        435                 440                 445

Thr Tyr Asp Ala Leu His Met Gln Ala Leu Pro Pro Arg
    450                 455                 460

<210> SEQ ID NO 98
<211> LENGTH: 458
<212> TYPE: PRT
<213> ORGANISM: Artificial Sequence
<220> FEATURE:
<223> OTHER INFORMATION: anti-BCMA CAR

<400> SEQUENCE: 98

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Thr Ile Ser Ser Ser Ser Thr Ile Tyr Tyr Ala Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg Gly Ser Gln Glu His Leu Ile Phe Asp Tyr Trp Gly Gln Gly
            100                 105                 110

Thr Leu Val Thr Val Ser Ser Gly Ser Thr Ser Gly Ser Gly Lys Pro
                115                 120                 125

Gly Ser Gly Glu Gly Ser Thr Lys Gly Glu Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Arg Tyr Leu Ala Trp Tyr Gln Gln Lys
                165                 170                 175

Pro Gly Gln Ala Pro Arg Leu Leu Ile Tyr Asp Ala Ser Asn Arg Ala
            180                 185                 190

Thr Gly Ile Pro Ala Arg Phe Ser Gly Ser Gly Ser Gly Thr Asp Phe
            195                 200                 205

Thr Leu Thr Ile Ser Ser Leu Glu Pro Glu Asp Phe Ala Val Tyr Tyr
    210                 215                 220

Cys Gln Gln Arg Phe Tyr Tyr Pro Trp Thr Phe Gly Gly Gly Thr Lys
225                 230                 235                 240

Val Glu Ile Lys Arg Ala Ala Ala Leu Asp Asn Glu Lys Ser Asn Gly
                245                 250                 255

Thr Ile Ile His Val Lys Gly Lys His Leu Cys Pro Ser Pro Leu Phe
            260                 265                 270

Pro Gly Pro Ser Lys Pro Phe Trp Val Leu Val Val Val Gly Gly Val
            275                 280                 285

Leu Ala Cys Tyr Ser Leu Leu Val Thr Val Ala Phe Ile Ile Phe Trp
    290                 295                 300

Val Arg Ser Lys Arg Ser Arg Leu Leu His Ser Asp Tyr Met Asn Met
305                 310                 315                 320

Thr Pro Arg Arg Pro Gly Pro Thr Arg Lys His Tyr Gln Pro Tyr Ala
                325                 330                 335

Pro Pro Arg Asp Phe Ala Ala Tyr Arg Ser Arg Val Lys Phe Ser Arg
            340                 345                 350

Ser Ala Asp Ala Pro Ala Tyr Gln Gln Gly Gln Asn Gln Leu Tyr Asn
            355                 360                 365

Glu Leu Asn Leu Gly Arg Arg Glu Glu Tyr Asp Val Leu Asp Lys Arg
    370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
            420                 425                 430

Asp Gly Leu Tyr Gln Gly Leu Ser Thr Ala Thr Lys Asp Thr Tyr Asp
            435                 440                 445

Ala Leu His Met Gln Ala Leu Pro Pro Arg
    450                 455

<210> SEQ ID NO 99
<211> LENGTH: 458
```

```
<212> TYPE: PRT
<213> ORGANISM: Artificial Sequence
<220> FEATURE:
<223> OTHER INFORMATION: anti-BCMA CAR

<400> SEQUENCE: 99
```

| | | | | | | | | | | | | | | |
|---|---|---|---|---|---|---|---|---|---|---|---|---|---|---|
| Glu | Ile | Val | Leu | Thr | Gln | Ser | Pro | Ala | Thr | Leu | Ser | Leu | Ser | Pro | Gly |
| 1 | | | | 5 | | | | | 10 | | | | | 15 | |
| Glu | Arg | Ala | Thr | Leu | Ser | Cys | Arg | Ala | Ser | Gln | Ser | Val | Ser | Arg | Tyr |
| | | | 20 | | | | | 25 | | | | | 30 | | |
| Leu | Ala | Trp | Tyr | Gln | Gln | Lys | Pro | Gly | Gln | Ala | Pro | Arg | Leu | Leu | Ile |
| | | | 35 | | | | | 40 | | | | | 45 | | |
| Tyr | Asp | Ala | Ser | Asn | Arg | Ala | Thr | Gly | Ile | Pro | Ala | Arg | Phe | Ser | Gly |
| | | 50 | | | | | 55 | | | | | 60 | | | |
| Ser | Gly | Ser | Gly | Thr | Asp | Phe | Thr | Leu | Thr | Ile | Ser | Ser | Leu | Glu | Pro |
| 65 | | | | | 70 | | | | | 75 | | | | | 80 |
| Glu | Asp | Phe | Ala | Val | Tyr | Tyr | Cys | Gln | Gln | Arg | Phe | Tyr | Tyr | Pro | Trp |
| | | | | 85 | | | | | 90 | | | | | 95 | |
| Thr | Phe | Gly | Gly | Gly | Thr | Lys | Val | Glu | Ile | Lys | Arg | Gly | Ser | Thr | Ser |
| | | | 100 | | | | | 105 | | | | | 110 | | |
| Gly | Ser | Gly | Lys | Pro | Gly | Ser | Gly | Glu | Gly | Ser | Thr | Lys | Gly | Glu | Val |
| | | 115 | | | | | 120 | | | | | 125 | | | |
| Gln | Leu | Val | Glu | Ser | Gly | Gly | Gly | Leu | Val | Gln | Pro | Gly | Gly | Ser | Leu |
| | 130 | | | | | 135 | | | | | 140 | | | | |
| Arg | Leu | Ser | Cys | Ala | Ala | Ser | Gly | Phe | Thr | Phe | Ser | Ser | Tyr | Ser | Met |
| 145 | | | | | 150 | | | | | 155 | | | | | 160 |
| Asn | Trp | Val | Arg | Gln | Ala | Pro | Gly | Lys | Gly | Leu | Glu | Trp | Val | Ser | Thr |
| | | | | 165 | | | | | 170 | | | | | 175 | |
| Ile | Ser | Ser | Ser | Ser | Ser | Thr | Ile | Tyr | Tyr | Ala | Asp | Ser | Val | Lys | Gly |
| | | | 180 | | | | | 185 | | | | | 190 | | |
| Arg | Phe | Thr | Ile | Ser | Arg | Asp | Asn | Ala | Lys | Asn | Ser | Leu | Tyr | Leu | Gln |
| | | 195 | | | | | 200 | | | | | 205 | | | |
| Met | Asn | Ser | Leu | Arg | Ala | Glu | Asp | Thr | Ala | Val | Tyr | Tyr | Cys | Ala | Arg |
| 210 | | | | | 215 | | | | | 220 | | | | | |
| Gly | Ser | Gln | Glu | His | Leu | Ile | Phe | Asp | Tyr | Trp | Gly | Gln | Gly | Thr | Leu |
| 225 | | | | | 230 | | | | | 235 | | | | | 240 |
| Val | Thr | Val | Ser | Ser | Ala | Ala | Ala | Leu | Asp | Asn | Glu | Lys | Ser | Asn | Gly |
| | | | | 245 | | | | | 250 | | | | | 255 | |
| Thr | Ile | Ile | His | Val | Lys | Gly | Lys | His | Leu | Cys | Pro | Ser | Pro | Leu | Phe |
| | | | 260 | | | | | 265 | | | | | 270 | | |
| Pro | Gly | Pro | Ser | Lys | Pro | Phe | Trp | Val | Leu | Val | Val | Val | Gly | Gly | Val |
| | | 275 | | | | | 280 | | | | | 285 | | | |
| Leu | Ala | Cys | Tyr | Ser | Leu | Leu | Val | Thr | Val | Ala | Phe | Ile | Ile | Phe | Trp |
| | 290 | | | | | 295 | | | | | 300 | | | | |
| Val | Arg | Ser | Lys | Arg | Ser | Arg | Leu | Leu | His | Ser | Asp | Tyr | Met | Asn | Met |
| 305 | | | | | 310 | | | | | 315 | | | | | 320 |
| Thr | Pro | Arg | Arg | Pro | Gly | Pro | Thr | Arg | Lys | His | Tyr | Gln | Pro | Tyr | Ala |
| | | | | 325 | | | | | 330 | | | | | 335 | |
| Pro | Pro | Arg | Asp | Phe | Ala | Ala | Tyr | Arg | Ser | Arg | Val | Lys | Phe | Ser | Arg |
| | | | 340 | | | | | 345 | | | | | 350 | | |
| Ser | Ala | Asp | Ala | Pro | Ala | Tyr | Gln | Gln | Gly | Gln | Asn | Gln | Leu | Tyr | Asn |
| | | 355 | | | | | 360 | | | | | 365 | | | |
| Glu | Leu | Asn | Leu | Gly | Arg | Arg | Glu | Glu | Tyr | Asp | Val | Leu | Asp | Lys | Arg |
| | 370 | | | | | 375 | | | | | 380 | | | | |

```
Arg Gly Arg Asp Pro Glu Met Gly Gly Lys Pro Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
                420                 425                 430

Asp Gly Leu Tyr Gln Gly Leu Ser Thr Ala Thr Lys Asp Thr Tyr Asp
            435                 440                 445

Ala Leu His Met Gln Ala Leu Pro Pro Arg
        450                 455

<210> SEQ ID NO 100
<211> LENGTH: 461
<212> TYPE: PRT
<213> ORGANISM: Artificial Sequence
<220> FEATURE:
<223> OTHER INFORMATION: anti-BCMA CAR

<400> SEQUENCE: 100

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Asp Phe Trp Ser Gly Ser Pro Pro Gly Leu Asp Tyr Trp
            100                 105                 110

Gly Gln Gly Thr Leu Val Thr Val Ser Ser Gly Ser Thr Ser Gly Ser
        115                 120                 125

Gly Lys Pro Gly Ser Gly Glu Gly Ser Thr Lys Gly Asp Ile Gln Leu
    130                 135                 140

Thr Gln Ser Pro Ser Ser Val Ser Ala Ser Val Gly Asp Arg Val Thr
145                 150                 155                 160

Ile Thr Cys Arg Ala Ser Gln Gly Ile Ser Ser Trp Leu Ala Trp Tyr
                165                 170                 175

Gln Gln Lys Pro Gly Lys Ala Pro Lys Leu Leu Ile Tyr Gly Ala Ser
            180                 185                 190

Ser Leu Gln Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln Ile Tyr Thr Phe Pro Phe Thr Phe Gly Gly
225                 230                 235                 240

Gly Thr Lys Val Glu Ile Lys Arg Ala Ala Ala Leu Asp Asn Glu Lys
                245                 250                 255

Ser Asn Gly Thr Ile Ile His Val Lys Gly Lys His Leu Cys Pro Ser
            260                 265                 270

Pro Leu Phe Pro Gly Pro Ser Lys Pro Phe Trp Val Leu Val Val Val
        275                 280                 285
```

```
Gly Gly Val Leu Ala Cys Tyr Ser Leu Leu Val Thr Val Ala Phe Ile
            290                 295                 300

Ile Phe Trp Val Arg Ser Lys Arg Ser Arg Leu Leu His Ser Asp Tyr
305                 310                 315                 320

Met Asn Met Thr Pro Arg Arg Pro Gly Pro Thr Arg Lys His Tyr Gln
                325                 330                 335

Pro Tyr Ala Pro Pro Arg Asp Phe Ala Ala Tyr Arg Ser Arg Val Lys
                340                 345                 350

Phe Ser Arg Ser Ala Asp Ala Pro Ala Tyr Gln Gln Gly Gln Asn Gln
            355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
            435                 440                 445

Thr Tyr Asp Ala Leu His Met Gln Ala Leu Pro Pro Arg
    450                 455                 460

<210> SEQ ID NO 101
<211> LENGTH: 461
<212> TYPE: PRT
<213> ORGANISM: Artificial Sequence
<220> FEATURE:
<223> OTHER INFORMATION: anti-BCMA CAR

<400> SEQUENCE: 101

Asp Ile Gln Leu Thr Gln Ser Pro Ser Val Ser Ala Ser Val Gly
1               5                   10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Gly Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Tyr Thr Phe Pro Phe
                85                  90                  95

Thr Phe Gly Gly Gly Thr Lys Val Glu Ile Lys Arg Gly Ser Thr Ser
            100                 105                 110

Gly Ser Gly Lys Pro Gly Ser Gly Glu Gly Ser Thr Lys Gly Gln Val
        115                 120                 125

Gln Leu Val Glu Ser Gly Gly Gly Val Val Gln Pro Gly Arg Ser Leu
    130                 135                 140

Arg Leu Ser Cys Ala Ala Ser Gly Phe Thr Phe Ser Ser Tyr Gly Met
145                 150                 155                 160

His Trp Val Arg Gln Ala Pro Gly Lys Gly Leu Glu Trp Val Ala Val
                165                 170                 175

Ile Ser Tyr Asp Gly Ser Asn Lys Tyr Tyr Ala Asp Ser Val Lys Gly
            180                 185                 190
```

```
Arg Phe Thr Ile Ser Arg Asp Asn Ser Lys Asn Thr Leu Tyr Leu Gln
            195                 200                 205

Met Asn Ser Leu Arg Ala Glu Asp Thr Ala Val Tyr Tyr Cys Ala Arg
    210                 215                 220

Thr Asp Phe Trp Ser Gly Ser Pro Pro Gly Leu Asp Tyr Trp Gly Gln
225                 230                 235                 240

Gly Thr Leu Val Thr Val Ser Ser Ala Ala Ala Leu Asp Asn Glu Lys
                245                 250                 255

Ser Asn Gly Thr Ile Ile His Val Lys Gly Lys His Leu Cys Pro Ser
            260                 265                 270

Pro Leu Phe Pro Gly Pro Ser Lys Pro Phe Trp Val Leu Val Val Val
            275                 280                 285

Gly Gly Val Leu Ala Cys Tyr Ser Leu Leu Val Thr Val Ala Phe Ile
290                 295                 300

Ile Phe Trp Val Arg Ser Lys Arg Ser Arg Leu Leu His Ser Asp Tyr
305                 310                 315                 320

Met Asn Met Thr Pro Arg Arg Pro Gly Pro Thr Arg Lys His Tyr Gln
            325                 330                 335

Pro Tyr Ala Pro Pro Arg Asp Phe Ala Ala Tyr Arg Ser Arg Val Lys
            340                 345                 350

Phe Ser Arg Ser Ala Asp Ala Pro Ala Tyr Gln Gln Gly Gln Asn Gln
    355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
            435                 440                 445

Thr Tyr Asp Ala Leu His Met Gln Ala Leu Pro Pro Arg
    450                 455                 460

<210> SEQ ID NO 102
<211> LENGTH: 471
<212> TYPE: PRT
<213> ORGANISM: Artificial Sequence
<220> FEATURE:
<223> OTHER INFORMATION: anti-BCMA CAR

<400> SEQUENCE: 102

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Thr Pro Glu Tyr Ser Ser Ile Trp His Tyr Tyr Gly
            100                 105                 110

Met Asp Val Trp Gly Gln Gly Thr Thr Val Thr Val Ser Ser Gly Ser
            115                 120                 125

Thr Ser Gly Ser Gly Lys Pro Gly Ser Gly Glu Gly Ser Thr Lys Gly
            130                 135                 140

Asp Ile Val Met Thr Gln Ser Pro Asp Ser Leu Ala Val Ser Leu Gly
145                 150                 155                 160

Glu Arg Ala Thr Ile Asn Cys Lys Ser Ser Gln Ser Val Leu Tyr Ser
                165                 170                 175

Ser Asn Asn Lys Asn Tyr Leu Ala Trp Tyr Gln Gln Lys Pro Gly Gln
            180                 185                 190

Pro Pro Lys Leu Leu Ile Tyr Trp Ala Ser Thr Arg Glu Ser Gly Val
            195                 200                 205

Pro Asp Arg Phe Ser Gly Ser Gly Ser Gly Thr Asp Phe Thr Leu Thr
            210                 215                 220

Ile Ser Ser Leu Gln Ala Glu Asp Val Ala Val Tyr Tyr Cys Gln Gln
225                 230                 235                 240

Phe Ala His Thr Pro Phe Thr Phe Gly Gly Gly Thr Lys Val Glu Ile
            245                 250                 255

Lys Arg Ala Ala Ala Leu Asp Asn Glu Lys Ser Asn Gly Thr Ile Ile
            260                 265                 270

His Val Lys Gly Lys His Leu Cys Pro Ser Pro Leu Phe Pro Gly Pro
            275                 280                 285

Ser Lys Pro Phe Trp Val Leu Val Val Val Gly Gly Val Leu Ala Cys
            290                 295                 300

Tyr Ser Leu Leu Val Thr Val Ala Phe Ile Ile Phe Trp Val Arg Ser
305                 310                 315                 320

Lys Arg Ser Arg Leu Leu His Ser Asp Tyr Met Asn Met Thr Pro Arg
                325                 330                 335

Arg Pro Gly Pro Thr Arg Lys His Tyr Gln Pro Tyr Ala Pro Pro Arg
            340                 345                 350

Asp Phe Ala Ala Tyr Arg Ser Arg Val Lys Phe Ser Arg Ser Ala Asp
            355                 360                 365

Ala Pro Ala Tyr Gln Gln Gly Gln Asn Gln Leu Tyr Asn Glu Leu Asn
            370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
            405                 410                 415

Leu Tyr Asn Glu Leu Gln Lys Asp Lys Met Ala Glu Ala Tyr Ser Glu
            420                 425                 430

Ile Gly Met Lys Gly Glu Arg Arg Arg Gly Lys Gly His Asp Gly Leu
            435                 440                 445

Tyr Gln Gly Leu Ser Thr Ala Thr Lys Asp Thr Tyr Asp Ala Leu His
            450                 455                 460

Met Gln Ala Leu Pro Pro Arg
465                 470

<210> SEQ ID NO 103
<211> LENGTH: 471
<212> TYPE: PRT
<213> ORGANISM: Artificial Sequence
<220> FEATURE:
<223> OTHER INFORMATION: anti-BCMA CAR
```

<400> SEQUENCE: 103

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Ala His Thr Pro Phe Thr Phe Gly Gly Gly Thr Lys Val Glu Ile
            100                 105                 110

Lys Arg Gly Ser Thr Ser Gly Ser Gly Lys Pro Gly Ser Gly Glu Gly
            115                 120                 125

Ser Thr Lys Gly Gln Val Gln Leu Val Gln Ser Gly Ala Glu Val Lys
130                 135                 140

Lys Pro Gly Ser Ser Val Lys Val Ser Cys Lys Ala Ser Gly Gly Thr
145                 150                 155                 160

Phe Ser Ser Tyr Ala Ile Ser Trp Val Arg Gln Ala Pro Gly Gln Gly
                165                 170                 175

Leu Glu Trp Met Gly Gly Ile Ile Pro Ile Phe Gly Thr Ala Asn Tyr
            180                 185                 190

Ala Gln Lys Phe Gln Gly Arg Val Thr Ile Thr Ala Asp Glu Ser Thr
            195                 200                 205

Ser Thr Ala Tyr Met Glu Leu Ser Ser Leu Arg Ser Glu Asp Thr Ala
210                 215                 220

Val Tyr Tyr Cys Ala Arg Thr Pro Glu Tyr Ser Ser Ile Trp His
225                 230                 235                 240

Tyr Tyr Tyr Gly Met Asp Val Trp Gly Gln Gly Thr Thr Val Thr Val
                245                 250                 255

Ser Ser Ala Ala Ala Leu Asp Asn Glu Lys Ser Asn Gly Thr Ile Ile
            260                 265                 270

His Val Lys Gly Lys His Leu Cys Pro Ser Pro Leu Phe Pro Gly Pro
            275                 280                 285

Ser Lys Pro Phe Trp Val Leu Val Val Val Gly Gly Val Leu Ala Cys
            290                 295                 300

Tyr Ser Leu Leu Val Thr Val Ala Phe Ile Ile Phe Trp Val Arg Ser
305                 310                 315                 320

Lys Arg Ser Arg Leu Leu His Ser Asp Tyr Met Asn Met Thr Pro Arg
                325                 330                 335

Arg Pro Gly Pro Thr Arg Lys His Tyr Gln Pro Tyr Ala Pro Pro Arg
            340                 345                 350

Asp Phe Ala Ala Tyr Arg Ser Arg Val Lys Phe Ser Arg Ser Ala Asp
            355                 360                 365

Ala Pro Ala Tyr Gln Gln Gly Gln Asn Gln Leu Tyr Asn Glu Leu Asn
            370                 375                 380

Leu Gly Arg Arg Glu Glu Tyr Asp Val Leu Asp Lys Arg Arg Gly Arg
385                 390                 395                 400

Asp Pro Glu Met Gly Gly Lys Pro Arg Arg Lys Asn Pro Gln Glu Gly
```

```
                    405                 410                 415
Leu Tyr Asn Glu Leu Gln Lys Asp Lys Met Ala Glu Ala Tyr Ser Glu
            420                 425                 430

Ile Gly Met Lys Gly Glu Arg Arg Gly Lys Gly His Asp Gly Leu
        435                 440                 445

Tyr Gln Gly Leu Ser Thr Ala Thr Lys Asp Thr Tyr Asp Ala Leu His
    450                 455                 460

Met Gln Ala Leu Pro Pro Arg
465             470

<210> SEQ ID NO 104
<211> LENGTH: 462
<212> TYPE: PRT
<213> ORGANISM: Artificial Sequence
<220> FEATURE:
<223> OTHER INFORMATION: anti-BCMA CAR

<400> SEQUENCE: 104

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Pro Leu Gln Glu Pro Pro Tyr Asp Tyr Gly Met Asp Val
            100                 105                 110

Trp Gly Gln Gly Thr Thr Val Thr Val Ser Ser Gly Ser Thr Ser Gly
        115                 120                 125

Ser Gly Lys Pro Gly Ser Gly Glu Gly Ser Thr Lys Gly Glu Ile Val
    130                 135                 140

Met Thr Gln Ser Pro Ala Thr Leu Ser Val Ser Pro Gly Glu Arg Ala
145                 150                 155                 160

Thr Leu Ser Cys Arg Ala Ser Gln Ser Val Ser Ser Asn Leu Ala Trp
                165                 170                 175

Tyr Gln Gln Lys Pro Gly Gln Ala Pro Arg Leu Leu Ile Tyr Ser Ala
            180                 185                 190

Ser Thr Arg Ala Thr Gly Ile Pro Ala Arg Phe Ser Gly Ser Gly Ser
        195                 200                 205

Gly Thr Glu Phe Thr Leu Thr Ile Ser Ser Leu Gln Ser Glu Asp Phe
    210                 215                 220

Ala Val Tyr Tyr Cys Gln Gln His His Val Trp Pro Leu Thr Phe Gly
225                 230                 235                 240

Gly Gly Thr Lys Val Glu Ile Lys Arg Ala Ala Ala Leu Asp Asn Glu
                245                 250                 255

Lys Ser Asn Gly Thr Ile Ile His Val Lys Gly Lys His Leu Cys Pro
            260                 265                 270

Ser Pro Leu Phe Pro Gly Pro Ser Lys Pro Phe Trp Val Leu Val Val
        275                 280                 285

Val Gly Gly Val Leu Ala Cys Tyr Ser Leu Leu Val Thr Val Ala Phe
```

```
                    290                 295                 300
Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Arg Val
                340                 345                 350

Lys Phe Ser Arg Ser Ala Asp Ala Pro Ala Tyr Gln Gln Gly Gln Asn
                355                 360                 365

Gln Leu Tyr Asn Glu Leu Asn Leu Gly Arg Arg Glu Glu Tyr Asp Val
            370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
                420                 425                 430

Gly Lys Gly His Asp Gly Leu Tyr Gln Gly Leu Ser Thr Ala Thr Lys
            435                 440                 445

Asp Thr Tyr Asp Ala Leu His Met Gln Ala Leu Pro Pro Arg
        450                 455                 460

<210> SEQ ID NO 105
<211> LENGTH: 462
<212> TYPE: PRT
<213> ORGANISM: Artificial Sequence
<220> FEATURE:
<223> OTHER INFORMATION: anti-BCMA CAR

<400> SEQUENCE: 105

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His His Val Trp Pro Leu
                85                  90                  95

Thr Phe Gly Gly Gly Thr Lys Val Glu Ile Lys Arg Gly Ser Thr Ser
                100                 105                 110

Gly Ser Gly Lys Pro Gly Ser Gly Glu Gly Ser Thr Lys Gly Gln Val
            115                 120                 125

Gln Leu Val Glu Ser Gly Gly Val Val Gln Pro Gly Arg Ser Leu
        130                 135                 140

Arg Leu Ser Cys Ala Ala Ser Gly Phe Thr Phe Ser Ser Tyr Gly Met
145                 150                 155                 160

His Trp Val Arg Gln Ala Pro Gly Lys Gly Leu Glu Trp Val Ala Val
                165                 170                 175

Ile Ser Tyr Asp Gly Ser Asn Lys Tyr Tyr Ala Asp Ser Val Lys Gly
            180                 185                 190

Arg Phe Thr Ile Ser Arg Asp Asn Ser Lys Asn Thr Leu Tyr Leu Gln
```

```
                195                 200                 205
Met Asn Ser Leu Arg Ala Glu Asp Thr Ala Val Tyr Tyr Cys Val Lys
    210                 215                 220

Gly Pro Leu Gln Glu Pro Pro Tyr Asp Tyr Gly Met Asp Val Trp Gly
225                 230                 235                 240

Gln Gly Thr Thr Val Thr Val Ser Ser Ala Ala Ala Leu Asp Asn Glu
                245                 250                 255

Lys Ser Asn Gly Thr Ile Ile His Val Lys Gly Lys His Leu Cys Pro
            260                 265                 270

Ser Pro Leu Phe Pro Gly Pro Ser Lys Pro Phe Trp Val Leu Val Val
        275                 280                 285

Val Gly Gly Val Leu Ala Cys Tyr Ser Leu Leu Val Thr Val Ala Phe
    290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Arg Val
            340                 345                 350

Lys Phe Ser Arg Ser Ala Asp Ala Pro Ala Tyr Gln Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460

<210> SEQ ID NO 106
<211> LENGTH: 466
<212> TYPE: PRT
<213> ORGANISM: Artificial Sequence
<220> FEATURE:
<223> OTHER INFORMATION: anti-BCMA CAR

<400> SEQUENCE: 106

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly Ser Arg Gly Gly Gly Gly Ser
```

```
                100             105             110
Gly Gly Gly Gly Ser Gly Gly Gly Ser Leu Glu Met Ala Glu Val
            115             120             125
Gln Leu Val Gln Ser Gly Ala Glu Met Lys Lys Pro Gly Ala Ser Leu
        130             135             140
Lys Leu Ser Cys Lys Ala Ser Gly Tyr Thr Phe Ile Asp Tyr Tyr Val
145             150             155             160
Tyr Trp Met Arg Gln Ala Pro Gly Gln Gly Leu Glu Ser Met Gly Trp
                165             170             175
Ile Asn Pro Asn Ser Gly Gly Thr Asn Tyr Ala Gln Lys Phe Gln Gly
            180             185             190
Arg Val Thr Met Thr Arg Asp Thr Ser Ile Ser Thr Ala Tyr Met Glu
        195             200             205
Leu Ser Arg Leu Arg Ser Asp Asp Thr Ala Met Tyr Tyr Cys Ala Arg
    210             215             220
Ser Gln Arg Asp Gly Tyr Met Asp Tyr Trp Gly Gln Gly Thr Leu Val
225             230             235             240
Thr Val Ser Ser Ala Ala Ala Ile Glu Val Met Tyr Pro Pro Pro Tyr
                245             250             255
Leu Asp Asn Glu Lys Ser Asn Gly Thr Ile Ile His Val Lys Gly Lys
            260             265             270
His Leu Cys Pro Ser Pro Leu Phe Pro Gly Pro Ser Lys Pro Phe Trp
        275             280             285
Val Leu Val Val Val Gly Gly Val Leu Ala Cys Tyr Ser Leu Leu Val
    290             295             300
Thr Val Ala Phe Ile Ile Phe Trp Val Arg Ser Lys Arg Ser Arg Leu
305             310             315             320
Leu His Ser Asp Tyr Met Asn Met Thr Pro Arg Arg Pro Gly Pro Thr
                325             330             335
Arg Lys His Tyr Gln Pro Tyr Ala Pro Pro Arg Asp Phe Ala Ala Tyr
            340             345             350
Arg Ser Arg Val Lys Phe Ser Arg Ser Ala Asp Ala Pro Ala Tyr Gln
        355             360             365
Gln Gly Gln Asn Gln Leu Tyr Asn Glu Leu Asn Leu Gly Arg Arg Glu
    370             375             380
Glu Tyr Asp Val Leu Asp Lys Arg Arg Gly Arg Asp Pro Glu Met Gly
385             390             395             400
Gly Lys Pro Arg Arg Lys Asn Pro Gln Glu Gly Leu Tyr Asn Glu Leu
                405             410             415
Gln Lys Asp Lys Met Ala Glu Ala Tyr Ser Glu Ile Gly Met Lys Gly
            420             425             430
Glu Arg Arg Arg Gly Lys Gly His Asp Gly Leu Tyr Gln Gly Leu Ser
        435             440             445
Thr Ala Thr Lys Asp Thr Tyr Asp Ala Leu His Met Gln Ala Leu Pro
    450             455             460

Pro Arg
465

<210> SEQ ID NO 107
<211> LENGTH: 473
<212> TYPE: PRT
<213> ORGANISM: Artificial Sequence
<220> FEATURE:
<223> OTHER INFORMATION: anti-BCMA CAR
```

-continued

```
<400> SEQUENCE: 107

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
            20                  25                  30

Phe Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Gln Val Gln Leu Val Gln Ser Gly Ala Glu Val
130                 135                 140

Lys Lys Pro Gly Ala Ser Val Lys Val Ser Cys Lys Ala Ser Gly Tyr
145                 150                 155                 160

Thr Phe Thr Asp Tyr Tyr Met His Trp Val Arg Gln Ala Pro Gly Gln
                165                 170                 175

Arg Leu Glu Trp Met Gly Trp Ile Asn Pro Asn Ser Gly Gly Thr Asn
            180                 185                 190

Tyr Ala Gln Lys Phe Gln Asp Arg Ile Thr Val Thr Arg Asp Thr Ser
        195                 200                 205

Ser Asn Thr Gly Tyr Met Glu Leu Thr Arg Leu Arg Ser Asp Asp Thr
210                 215                 220

Ala Val Tyr Tyr Cys Ala Arg Ser Pro Tyr Ser Gly Val Leu Asp Lys
225                 230                 235                 240

Trp Gly Gln Gly Thr Leu Val Thr Val Ser Ser Ala Ala Ile Glu
                245                 250                 255

Val Met Tyr Pro Pro Pro Tyr Leu Asp Asn Glu Lys Ser Asn Gly Thr
            260                 265                 270

Ile Ile His Val Lys Gly Lys His Leu Cys Pro Ser Pro Leu Phe Pro
        275                 280                 285

Gly Pro Ser Lys Pro Phe Trp Val Leu Val Val Val Gly Gly Val Leu
290                 295                 300

Ala Cys Tyr Ser Leu Leu Val Thr Val Ala Phe Ile Ile Phe Trp Val
305                 310                 315                 320

Arg Ser Lys Arg Ser Arg Leu Leu His Ser Asp Tyr Met Asn Met Thr
                325                 330                 335

Pro Arg Arg Pro Gly Pro Thr Arg Lys His Tyr Gln Pro Tyr Ala Pro
            340                 345                 350

Pro Arg Asp Phe Ala Ala Tyr Arg Ser Arg Val Lys Phe Ser Arg Ser
        355                 360                 365

Ala Asp Ala Pro Ala Tyr Gln Gln Gly Gln Asn Gln Leu Tyr Asn Glu
370                 375                 380

Leu Asn Leu Gly Arg Arg Glu Glu Tyr Asp Val Leu Asp Lys Arg Arg
385                 390                 395                 400

Gly Arg Asp Pro Glu Met Gly Gly Lys Pro Arg Arg Lys Asn Pro Gln
                405                 410                 415
```

```
Glu Gly Leu Tyr Asn Glu Leu Gln Lys Asp Lys Met Ala Glu Ala Tyr
            420                 425                 430

Ser Glu Ile Gly Met Lys Gly Glu Arg Arg Gly Lys Gly His Asp
            435                 440                 445

Gly Leu Tyr Gln Gly Leu Ser Thr Ala Thr Lys Asp Thr Tyr Asp Ala
450                 455                 460

Leu His Met Gln Ala Leu Pro Pro Arg
465                 470

<210> SEQ ID NO 108
<211> LENGTH: 470
<212> TYPE: PRT
<213> ORGANISM: Artificial Sequence
<220> FEATURE:
<223> OTHER INFORMATION: anti-BCMA CAR

<400> SEQUENCE: 108

Ser Tyr Glu Leu Thr Gln Pro Pro Ser Ala Ser Gly Thr Pro Gly Gln
1               5                   10                  15

Arg Val Thr Met Ser Cys Ser Gly Thr Ser Ser Asn Ile Gly Ser His
            20                  25                  30

Ser Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asn Gly Leu Val Phe Gly Gly Thr Lys Leu Thr Val Leu Gly Ser
            100                 105                 110

Arg Gly Gly Gly Gly Ser Gly Gly Gly Ser Gly Gly Gly Ser
            115                 120                 125

Leu Glu Met Ala Glu Val Gln Leu Val Gln Ser Gly Ala Glu Val Lys
        130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly His Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Tyr Ser Gly Ser Phe Asp Asn Trp Gly Gln
225                 230                 235                 240

Gly Thr Leu Val Thr Val Ser Ser Ala Ala Ile Glu Val Met Tyr
            245                 250                 255

Pro Pro Pro Tyr Leu Asp Asn Glu Lys Ser Asn Gly Thr Ile Ile His
            260                 265                 270

Val Lys Gly Lys His Leu Cys Pro Ser Pro Leu Phe Pro Gly Pro Ser
        275                 280                 285

Lys Pro Phe Trp Val Leu Val Val Val Gly Gly Val Leu Ala Cys Tyr
            290                 295                 300
```

```
Ser Leu Leu Val Thr Val Ala Phe Ile Ile Phe Trp Val Arg Ser Lys
305                 310                 315                 320

Arg Ser Arg Leu Leu His Ser Asp Tyr Met Asn Met Thr Pro Arg Arg
            325                 330                 335

Pro Gly Pro Thr Arg Lys His Tyr Gln Pro Tyr Ala Pro Pro Arg Asp
            340                 345                 350

Phe Ala Ala Tyr Arg Ser Arg Val Lys Phe Ser Arg Ser Ala Asp Ala
            355                 360                 365

Pro Ala Tyr Gln Gln Gly Gln Asn Gln Leu Tyr Asn Glu Leu Asn Leu
370                 375                 380

Gly Arg Arg Glu Glu Tyr Asp Val Leu Asp Lys Arg Arg Gly Arg Asp
385                 390                 395                 400

Pro Glu Met Gly Gly Lys Pro Arg Arg Lys Asn Pro Gln Glu Gly Leu
            405                 410                 415

Tyr Asn Glu Leu Gln Lys Asp Lys Met Ala Glu Ala Tyr Ser Glu Ile
            420                 425                 430

Gly Met Lys Gly Glu Arg Arg Gly Lys Gly His Asp Gly Leu Tyr
            435                 440                 445

Gln Gly Leu Ser Thr Ala Thr Lys Asp Thr Tyr Asp Ala Leu His Met
450                 455                 460

Gln Ala Leu Pro Pro Arg
465                 470

<210> SEQ ID NO 109
<211> LENGTH: 476
<212> TYPE: PRT
<213> ORGANISM: Artificial Sequence
<220> FEATURE:
<223> OTHER INFORMATION: anti-BCMA CAR

<400> SEQUENCE: 109

Leu Pro Val Leu Thr Gln Pro Pro Ser Ala Ser Gly Thr Pro Gly Gln
1               5                   10                  15

Arg Val Thr Ile Ser Cys Ser Gly Arg Ser Ser Asn Ile Gly Ser Asn
            20                  25                  30

Ser Val Asn Trp Tyr Arg Gln Leu Pro Gly Ala Ala Pro Lys Leu Leu
        35                  40                  45

Ile Tyr Ser Asn Asn Gln Arg Pro Pro Gly Val Pro Val Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Thr Tyr Tyr Cys Ala Thr Trp Asp Asp Asn Leu
                85                  90                  95

Asn Val His Tyr Val Phe Gly Thr Gly Thr Lys Val Thr Val Leu Gly
            100                 105                 110

Ser Arg Gly Gly Gly Gly Ser Gly Gly Gly Gly Ser Gly Gly Gly Gly
        115                 120                 125

Ser Leu Glu Met Ala Gln Val Gln Leu Val Gln Ser Gly Ala Glu Val
130                 135                 140

Lys Lys Pro Gly Ser Ser Val Lys Val Ser Cys Lys Ala Ser Gly Gly
145                 150                 155                 160

Thr Phe Ser Ser Tyr Ala Ile Ser Trp Val Arg Gln Ala Pro Gly Gln
                165                 170                 175

Gly Leu Glu Trp Met Gly Arg Ile Ile Pro Ile Leu Gly Ile Ala Asn
            180                 185                 190
```

```
Tyr Ala Gln Lys Phe Gln Gly Arg Val Thr Ile Thr Ala Asp Lys Ser
                195                 200                 205

Thr Ser Thr Ala Tyr Met Glu Leu Ser Ser Leu Arg Ser Glu Asp Thr
            210                 215                 220

Ala Val Tyr Tyr Cys Ala Arg Gly Gly Tyr Tyr Ser His Asp Met Trp
225                 230                 235                 240

Ser Glu Asp Trp Gly Gln Gly Thr Leu Val Thr Val Ser Ser Ala Ala
                245                 250                 255

Ala Ile Glu Val Met Tyr Pro Pro Tyr Leu Asp Asn Glu Lys Ser
                260                 265                 270

Asn Gly Thr Ile Ile His Val Lys Gly Lys His Leu Cys Pro Ser Pro
            275                 280                 285

Leu Phe Pro Gly Pro Ser Lys Pro Phe Trp Val Leu Val Val Val Gly
            290                 295                 300

Gly Val Leu Ala Cys Tyr Ser Leu Leu Val Thr Val Ala Phe Ile Ile
305                 310                 315                 320

Phe Trp Val Arg Ser Lys Arg Ser Arg Leu Leu His Ser Asp Tyr Met
                325                 330                 335

Asn Met Thr Pro Arg Arg Pro Gly Pro Thr Arg Lys His Tyr Gln Pro
            340                 345                 350

Tyr Ala Pro Pro Arg Asp Phe Ala Ala Tyr Arg Ser Arg Val Lys Phe
            355                 360                 365

Ser Arg Ser Ala Asp Ala Pro Ala Tyr Gln Gln Gly Gln Asn Gln Leu
        370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
            420                 425                 430

Glu Ala Tyr Ser Glu Ile Gly Met Lys Gly Glu Arg Arg Arg Gly Lys
            435                 440                 445

Gly His Asp Gly Leu Tyr Gln Gly Leu Ser Thr Ala Thr Lys Asp Thr
        450                 455                 460

Tyr Asp Ala Leu His Met Gln Ala Leu Pro Pro Arg
465                 470                 475

<210> SEQ ID NO 110
<211> LENGTH: 475
<212> TYPE: PRT
<213> ORGANISM: Artificial Sequence
<220> FEATURE:
<223> OTHER INFORMATION: anti-BCMA CAR

<400> SEQUENCE: 110

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Tyr Val Phe Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80
```

Ser Glu Asp Glu Ala Asp Tyr Tyr Cys Ala Ala Trp Asp Asp Ser Leu
                85                  90                  95

Ser Ala Ser Tyr Val Phe Gly Thr Gly Thr Lys Val Thr Val Leu Gly
            100                 105                 110

Ser Arg Gly Gly Gly Ser Gly Gly Gly Ser Gly Gly Gly Gly
        115                 120                 125

Ser Leu Glu Met Ala Gln Val Gln Leu Val Gln Ser Gly Ala Glu Val
130                 135                 140

Lys Lys Pro Gly Ser Ser Val Lys Val Ser Cys Lys Ala Ser Gly Gly
145                 150                 155                 160

Thr Phe Ser Ser Tyr Ala Ile Ser Trp Val Arg Gln Ala Pro Gly Gln
                165                 170                 175

Gly Leu Glu Trp Met Gly Arg Ile Ile Pro Ile Leu Gly Thr Ala Asn
            180                 185                 190

Tyr Ala Gln Lys Phe Gln Gly Arg Val Thr Ile Thr Ala Asp Glu Ser
        195                 200                 205

Thr Ser Thr Ala Tyr Met Glu Leu Ser Ser Leu Arg Ser Glu Asp Thr
210                 215                 220

Ala Val Tyr Tyr Cys Ala Arg Ser Gly Tyr Gly Ser Tyr Arg Trp Glu
225                 230                 235                 240

Asp Ser Trp Gly Gln Gly Thr Leu Val Thr Val Ser Ser Ala Ala Ala
                245                 250                 255

Ile Glu Val Met Tyr Pro Pro Tyr Leu Asp Asn Glu Lys Ser Asn
            260                 265                 270

Gly Thr Ile Ile His Val Lys Gly Lys His Leu Cys Pro Ser Pro Leu
        275                 280                 285

Phe Pro Gly Pro Ser Lys Pro Phe Trp Val Leu Val Val Val Gly Gly
290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
                325                 330                 335

Met Thr Pro Arg Arg Pro Gly Pro Thr Arg Lys His Tyr Gln Pro Tyr
            340                 345                 350

Ala Pro Pro Arg Asp Phe Ala Ala Tyr Arg Ser Arg Val Lys Phe Ser
        355                 360                 365

Arg Ser Ala Asp Ala Pro Ala Tyr Gln Gln Gly Gln Asn Gln Leu Tyr
370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
450                 455                 460

Asp Ala Leu His Met Gln Ala Leu Pro Pro Arg
465                 470                 475

<210> SEQ ID NO 111
<211> LENGTH: 482

```
<212> TYPE: PRT
<213> ORGANISM: Artificial Sequence
<220> FEATURE:
<223> OTHER INFORMATION: anti-BCMA CAR

<400> SEQUENCE: 111

Leu Pro Val Leu Thr Gln Pro Pro Ser Ala Ser Gly Thr Pro Gly Gln
1               5                   10                  15

Arg Val Thr Ile Ser Cys Ser Gly Arg Ser Ser Asn Ile Gly Ser Asn
            20                  25                  30

Ser Val Asn Trp Tyr Arg Gln Leu Pro Gly Ala Ala Pro Lys Leu Leu
        35                  40                  45

Ile Tyr Ser Asn Asn Gln Arg Pro Pro Gly Val Pro Val Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Thr Tyr Tyr Cys Ala Thr Trp Asp Asp Asn Leu
                85                  90                  95

Asn Val His Tyr Val Phe Gly Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Gln Val Gln Leu Val Gln Ser Gly Ala Glu Val
    130                 135                 140

Lys Lys Pro Gly Ser Ser Val Lys Val Ser Cys Lys Ala Ser Gly Gly
145                 150                 155                 160

Thr Phe Ser Ser Tyr Ala Ile Ser Trp Val Arg Gln Ala Pro Gly Gln
                165                 170                 175

Gly Leu Glu Trp Met Gly Arg Ile Ile Pro Ile Leu Gly Ile Ala Asn
            180                 185                 190

Tyr Ala Gln Lys Phe Gln Gly Arg Val Thr Ile Thr Ala Asp Lys Ser
        195                 200                 205

Thr Ser Thr Ala Tyr Met Glu Leu Ser Ser Leu Arg Ser Glu Asp Thr
    210                 215                 220

Ala Val Tyr Tyr Cys Ala Arg Gly Gly Tyr Tyr Ser His Asp Met Trp
225                 230                 235                 240

Ser Glu Asp Trp Gly Gln Gly Thr Leu Val Thr Val Ser Ser Ala Ala
                245                 250                 255

Ala Pro Thr Thr Thr Pro Ala Pro Arg Pro Pro Thr Pro Ala Pro Thr
            260                 265                 270

Ile Ala Ser Gln Pro Leu Ser Leu Arg Pro Glu Ala Cys Arg Pro Ala
        275                 280                 285

Ala Gly Gly Ala Val His Thr Arg Gly Leu Asp Phe Ala Cys Asp Ile
    290                 295                 300

Tyr Ile Trp Ala Pro Leu Ala Gly Thr Cys Gly Val Leu Leu Leu Ser
305                 310                 315                 320

Leu Val Ile Thr Leu Tyr Cys Asn Lys Arg Gly Arg Lys Lys Leu Leu
                325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
        355                 360                 365

Glu Leu Arg Val Lys Phe Ser Arg Ser Ala Glu Pro Pro Ala Tyr Gln
    370                 375                 380
```

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
            405                 410                 415

Gly Lys Pro Arg Arg Lys Asn Pro Gln Glu Gly Leu Tyr Asn Glu Leu
        420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg

<210> SEQ ID NO 112
<211> LENGTH: 476
<212> TYPE: PRT
<213> ORGANISM: Artificial Sequence
<220> FEATURE:
<223> OTHER INFORMATION: anti-BCMA CAR

<400> SEQUENCE: 112

Ser Tyr Glu Leu Thr Gln Pro Pro Ser Ala Ser Gly Thr Pro Gly Gln
1               5                   10                  15

Arg Val Thr Met Ser Cys Ser Gly Thr Ser Ser Asn Ile Gly Ser His
            20                  25                  30

Ser Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Ser Ser Leu
                85                  90                  95

Asn Gly Leu Val Phe Gly Gly Gly Thr Lys Leu Thr Val Leu Gly Ser
            100                 105                 110

Arg Gly Gly Gly Gly Ser Gly Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
            180                 185                 190

Ser Pro Ser Phe Gln Gly His Val Thr Ile Ser Ala Asp Lys Ser Ile
        195                 200                 205

Ser Thr Ala Tyr Leu Gln Trp Ser Ser Leu Lys Ala Ser Asp Thr Ala
    210                 215                 220

Met Tyr Tyr Cys Ala Arg Tyr Ser Gly Ser Phe Asp Asn Trp Gly Gln
225                 230                 235                 240

Gly Thr Leu Val Thr Val Ser Ser Ala Ala Ala Pro Thr Thr Thr Pro
                245                 250                 255

Ala Pro Arg Pro Pro Thr Pro Ala Pro Thr Ile Ala Ser Gln Pro Leu

-continued

```
                260                 265                 270
Ser Leu Arg Pro Glu Ala Cys Arg Pro Ala Gly Gly Ala Val His
                275                 280                 285

Thr Arg Gly Leu Asp Phe Ala Cys Asp Ile Tyr Ile Trp Ala Pro Leu
            290                 295                 300

Ala Gly Thr Cys Gly Val Leu Leu Leu Ser Leu Val Ile Thr Leu Tyr
305                 310                 315                 320

Cys Asn Lys Arg Gly Arg Lys Lys Leu Leu Tyr Ile Phe Lys Gln Pro
                325                 330                 335

Phe Met Arg Pro Val Gln Thr Thr Gln Glu Glu Asp Gly Cys Ser Cys
                340                 345                 350

Arg Phe Pro Glu Glu Glu Glu Gly Gly Cys Glu Leu Arg Val Lys Phe
            355                 360                 365

Ser Arg Ser Ala Glu Pro Pro Ala Tyr Gln Gln Gly Gln Asn Gln Leu
            370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
                420                 425                 430

Glu Ala Tyr Ser Glu Ile Gly Met Lys Gly Glu Arg Arg Arg Gly Lys
            435                 440                 445

Gly His Asp Gly Leu Tyr Gln Gly Leu Ser Thr Ala Thr Lys Asp Thr
            450                 455                 460

Tyr Asp Ala Leu His Met Gln Ala Leu Pro Pro Arg
465                 470                 475

<210> SEQ ID NO 113
<211> LENGTH: 481
<212> TYPE: PRT
<213> ORGANISM: Artificial Sequence
<220> FEATURE:
<223> OTHER INFORMATION: anti-BCMA CAR

<400> SEQUENCE: 113

Gln Ala Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Phe Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Ala Ser Tyr Val Phe Gly Thr Gly Thr Lys Val Thr Val Leu Gly
                100                 105                 110

Ser Arg Gly Gly Gly Gly Ser Gly Gly Gly Gly Ser Gly Gly Gly Gly
            115                 120                 125

Ser Leu Glu Met Ala Gln Val Gln Leu Val Gln Ser Gly Ala Glu Val
130                 135                 140

Lys Lys Pro Gly Ser Ser Val Lys Val Ser Cys Lys Ala Ser Gly Gly
```

```
            145                 150                 155                 160
        Thr Phe Ser Ser Tyr Ala Ile Ser Trp Val Arg Gln Ala Pro Gly Gln
                        165                 170                 175

Gly Leu Glu Trp Met Gly Arg Ile Ile Pro Ile Leu Gly Thr Ala Asn
                        180                 185                 190

Tyr Ala Gln Lys Phe Gln Gly Arg Val Thr Ile Thr Ala Asp Glu Ser
                        195                 200                 205

Thr Ser Thr Ala Tyr Met Glu Leu Ser Ser Leu Arg Ser Glu Asp Thr
                        210                 215                 220

Ala Val Tyr Tyr Cys Ala Arg Ser Gly Tyr Gly Ser Tyr Arg Trp Glu
        225                 230                 235                 240

Asp Ser Trp Gly Gln Gly Thr Leu Val Thr Val Ser Ser Ala Ala Ala
                        245                 250                 255

Pro Thr Thr Thr Pro Ala Pro Arg Pro Pro Thr Pro Ala Pro Thr Ile
                        260                 265                 270

Ala Ser Gln Pro Leu Ser Leu Arg Pro Glu Ala Cys Arg Pro Ala Ala
                        275                 280                 285

Gly Gly Ala Val His Thr Arg Gly Leu Asp Phe Ala Cys Asp Ile Tyr
                        290                 295                 300

Ile Trp Ala Pro Leu Ala Gly Thr Cys Gly Val Leu Leu Leu Ser Leu
        305                 310                 315                 320

Val Ile Thr Leu Tyr Cys Asn Lys Arg Gly Arg Lys Lys Leu Leu Tyr
                        325                 330                 335

Ile Phe Lys Gln Pro Phe Met Arg Pro Val Gln Thr Thr Gln Glu Glu
                        340                 345                 350

Asp Gly Cys Ser Cys Arg Phe Pro Glu Glu Glu Glu Gly Gly Cys Glu
                        355                 360                 365

Leu Arg Val Lys Phe Ser Arg Ser Ala Glu Pro Pro Ala Tyr Gln Gln
                        370                 375                 380

Gly Gln Asn Gln Leu Tyr Asn Glu Leu Asn Leu Gly Arg Arg Glu Glu
        385                 390                 395                 400

Tyr Asp Val Leu Asp Lys Arg Arg Gly Arg Asp Pro Glu Met Gly Gly
                        405                 410                 415

Lys Pro Arg Arg Lys Asn Pro Gln Glu Gly Leu Tyr Asn Glu Leu Gln
                        420                 425                 430

Lys Asp Lys Met Ala Glu Ala Tyr Ser Glu Ile Gly Met Lys Gly Glu
                        435                 440                 445

Arg Arg Arg Gly Lys Gly His Asp Gly Leu Tyr Gln Gly Leu Ser Thr
        450                 455                 460

Ala Thr Lys Asp Thr Tyr Asp Ala Leu His Met Gln Ala Leu Pro Pro
        465                 470                 475                 480

Arg

<210> SEQ ID NO 114
<211> LENGTH: 479
<212> TYPE: PRT
<213> ORGANISM: Artificial Sequence
<220> FEATURE:
<223> OTHER INFORMATION: anti-BCMA CAR

<400> SEQUENCE: 114

Gln Ser Val Leu Thr Gln Pro Pro Ser Val Ser Gly Ala Pro Gly Gln
        1               5                   10                  15

Arg Val Thr Ile Ser Cys Thr Gly Ser Ser Ser Asn Ile Gly Ala Gly
                        20                  25                  30
```

-continued

```
Phe Asp Val His Trp Tyr Gln Gln Leu Pro Gly Thr Ala Pro Lys Leu
         35                  40                  45
Leu Ile Tyr Gly Asn Ser Asn Arg Pro Ser Gly Val Pro Asp Arg Phe
 50                  55                  60
Ser Gly Ser Lys Ser Gly Thr Ser Ala Ser Leu Ala Ile Thr Gly Leu
 65                  70                  75                  80
Gln Ala Glu Asp Glu Ala Asp Tyr Tyr Cys Gln Ser Tyr Asp Ser Ser
                 85                  90                  95
Leu Ser Gly Tyr Val Phe Gly Thr Gly Thr Lys Val Thr Val Leu Gly
                100                 105                 110
Ser Arg Gly Gly Gly Gly Ser Gly Gly Gly Ser Gly Gly Gly Gly
                115                 120                 125
Ser Leu Glu Met Ala Gln Val Gln Leu Val Gln Ser Gly Ala Glu Val
            130                 135                 140
Lys Lys Pro Gly Ala Ser Val Lys Val Ser Cys Lys Ala Ser Gly Tyr
145                 150                 155                 160
Thr Phe Thr Asp Tyr Tyr Met His Trp Val Arg Gln Ala Pro Gly Gln
                165                 170                 175
Arg Leu Glu Trp Met Gly Trp Ile Asn Pro Asn Ser Gly Gly Thr Asn
            180                 185                 190
Tyr Ala Gln Lys Phe Gln Asp Arg Ile Thr Val Thr Arg Asp Thr Ser
        195                 200                 205
Ser Asn Thr Gly Tyr Met Glu Leu Thr Arg Leu Arg Ser Asp Asp Thr
    210                 215                 220
Ala Val Tyr Tyr Cys Ala Arg Ser Pro Tyr Ser Gly Val Leu Asp Lys
225                 230                 235                 240
Trp Gly Gln Gly Thr Leu Val Thr Val Ser Ser Ala Ala Ala Pro Thr
                245                 250                 255
Thr Thr Pro Ala Pro Arg Pro Pro Thr Pro Ala Pro Thr Ile Ala Ser
            260                 265                 270
Gln Pro Leu Ser Leu Arg Pro Glu Ala Cys Arg Pro Ala Ala Gly Gly
        275                 280                 285
Ala Val His Thr Arg Gly Leu Asp Phe Ala Cys Asp Ile Tyr Ile Trp
    290                 295                 300
Ala Pro Leu Ala Gly Thr Cys Gly Val Leu Leu Leu Ser Leu Val Ile
305                 310                 315                 320
Thr Leu Tyr Cys Asn Lys Arg Gly Arg Lys Lys Leu Leu Tyr Ile Phe
                325                 330                 335
Lys Gln Pro Phe Met Arg Pro Val Gln Thr Thr Gln Glu Glu Asp Gly
            340                 345                 350
Cys Ser Cys Arg Phe Pro Glu Glu Glu Glu Gly Gly Cys Glu Leu Arg
        355                 360                 365
Val Lys Phe Ser Arg Ser Ala Glu Pro Pro Ala Tyr Gln Gln Gly Gln
    370                 375                 380
Asn Gln Leu Tyr Asn Glu Leu Asn Leu Gly Arg Arg Glu Glu Tyr Asp
385                 390                 395                 400
Val Leu Asp Lys Arg Arg Gly Arg Asp Pro Glu Met Gly Gly Lys Pro
                405                 410                 415
Arg Arg Lys Asn Pro Gln Glu Gly Leu Tyr Asn Glu Leu Gln Lys Asp
            420                 425                 430
Lys Met Ala Glu Ala Tyr Ser Glu Ile Gly Met Lys Gly Glu Arg Arg
        435                 440                 445
```

Arg Gly Lys Gly His Asp Gly Leu Tyr Gln Gly Leu Ser Thr Ala Thr
450                 455                 460

Lys Asp Thr Tyr Asp Ala Leu His Met Gln Ala Leu Pro Pro Arg
465                 470                 475

<210> SEQ ID NO 115
<211> LENGTH: 472
<212> TYPE: PRT
<213> ORGANISM: Artificial Sequence
<220> FEATURE:
<223> OTHER INFORMATION: anti-BCMA CAR

<400> SEQUENCE: 115

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly Ser Arg Gly Gly Gly Gly Ser
            100                 105                 110

Gly Gly Gly Gly Ser Gly Gly Gly Ser Leu Glu Met Ala Glu Val
            115                 120                 125

Gln Leu Val Gln Ser Gly Ala Glu Met Lys Lys Pro Gly Ala Ser Leu
130                 135                 140

Lys Leu Ser Cys Lys Ala Ser Gly Tyr Thr Phe Ile Asp Tyr Tyr Val
145                 150                 155                 160

Tyr Trp Met Arg Gln Ala Pro Gly Gln Gly Leu Glu Ser Met Gly Trp
                165                 170                 175

Ile Asn Pro Asn Ser Gly Gly Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Met Tyr Tyr Cys Ala Arg
    210                 215                 220

Ser Gln Arg Asp Gly Tyr Met Asp Tyr Trp Gly Gln Gly Thr Leu Val
225                 230                 235                 240

Thr Val Ser Ser Ala Ala Ala Pro Thr Thr Pro Ala Pro Arg Pro
                245                 250                 255

Pro Thr Pro Ala Pro Thr Ile Ala Ser Gln Pro Leu Ser Leu Arg Pro
            260                 265                 270

Glu Ala Cys Arg Pro Ala Ala Gly Ala Val His Thr Arg Gly Leu
        275                 280                 285

Asp Phe Ala Cys Asp Ile Tyr Ile Trp Ala Pro Leu Ala Gly Thr Cys
290                 295                 300

Gly Val Leu Leu Leu Ser Leu Val Ile Thr Leu Tyr Cys Asn Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Asp Gly Cys Ser Cys Arg Phe Pro Glu
            340                 345                 350

Glu Glu Glu Gly Gly Cys Glu Leu Arg Val Lys Phe Ser Arg Ser Ala
            355                 360                 365

Glu Pro Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
            435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470

<210> SEQ ID NO 116
<211> LENGTH: 472
<212> TYPE: PRT
<213> ORGANISM: Artificial Sequence
<220> FEATURE:
<223> OTHER INFORMATION: anti-BCMA CAR

<400> SEQUENCE: 116

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Ile Gln Leu Val Gln Ser Gly Pro Glu Leu Lys Lys Pro Gly
    130                 135                 140

Glu Thr Val Lys Ile Ser Cys Lys Ala Ser Gly Tyr Thr Phe Thr Asp
145                 150                 155                 160

Tyr Ser Ile Asn Trp Val Lys Arg Ala Pro Gly Lys Gly Leu Lys Trp
                165                 170                 175

Met Gly Trp Ile Asn Thr Glu Thr Arg Glu Pro Ala Tyr Ala Tyr Asp
            180                 185                 190

Phe Arg Gly Arg Phe Ala Phe Ser Leu Glu Thr Ser Ala Ser Thr Ala
        195                 200                 205

Tyr Leu Gln Ile Asn Asn Leu Lys Tyr Glu Asp Thr Ala Thr Tyr Phe
    210                 215                 220

```
Cys Ala Leu Asp Tyr Ser Tyr Ala Met Asp Tyr Trp Gly Gln Gly Thr
225                 230                 235                 240

Ser Val Thr Val Ser Ser Ala Ala Thr Thr Thr Pro Ala Pro Arg
                245                 250                 255

Pro Pro Thr Pro Ala Pro Thr Ile Ala Ser Gln Pro Leu Ser Leu Arg
                260                 265                 270

Pro Glu Ala Cys Arg Pro Ala Ala Gly Gly Ala Val His Thr Arg Gly
                275                 280                 285

Leu Asp Phe Ala Cys Asp Ile Tyr Ile Trp Ala Pro Leu Ala Gly Thr
                290                 295                 300

Cys Gly Val Leu Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
                340                 345                 350

Glu Glu Glu Gly Gly Cys Glu Leu Arg Val Lys Phe Ser Arg Ser Ala
                355                 360                 365

Asp Ala Pro Ala Tyr Gln Gln Gly Gln Asn Gln Leu Tyr Asn Glu Leu
                370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
                420                 425                 430

Glu Ile Gly Met Lys Gly Glu Arg Arg Arg Gly Lys Gly His Asp Gly
                435                 440                 445

Leu Tyr Gln Gly Leu Ser Thr Ala Thr Lys Asp Thr Tyr Asp Ala Leu
                450                 455                 460

His Met Gln Ala Leu Pro Pro Arg
465                 470

<210> SEQ ID NO 117
<211> LENGTH: 472
<212> TYPE: PRT
<213> ORGANISM: Artificial Sequence
<220> FEATURE:
<223> OTHER INFORMATION: anti-BCMA CAR

<400> SEQUENCE: 117

Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
                20                  25                  30

Gly Ala His Leu Ile His Trp Tyr Gln Gln Lys Pro Gly Gln Pro Pro
                35                  40                  45

Lys Leu Leu Ile Tyr Leu Ala Ser Asn Leu Glu Thr Gly Val Pro Ala
            50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Tyr Cys Leu Gln Ser Arg
                85                  90                  95

Ile Phe Pro Arg Thr Phe Gly Gln Gly Thr Lys Leu Glu Ile Lys Gly
                100                 105                 110
```

Ser Thr Ser Gly Ser Gly Lys Pro Gly Ser Gly Glu Gly Ser Thr Lys
        115                 120                 125

Gly Gln Val Gln Leu Val Gln Ser Gly Ser Glu Leu Lys Lys Pro Gly
    130                 135                 140

Ala Ser Val Lys Val Ser Cys Lys Ala Ser Gly Tyr Thr Phe Thr Asp
145                 150                 155                 160

Tyr Ser Ile Asn Trp Val Arg Gln Ala Pro Gly Gln Gly Leu Glu Trp
                165                 170                 175

Met Gly Trp Ile Asn Thr Glu Thr Arg Glu Pro Ala Tyr Ala Tyr Asp
            180                 185                 190

Phe Arg Gly Arg Phe Val Phe Ser Leu Asp Thr Ser Val Ser Thr Ala
        195                 200                 205

Tyr Leu Gln Ile Ser Ser Leu Lys Ala Glu Asp Thr Ala Val Tyr Tyr
    210                 215                 220

Cys Ala Arg Asp Tyr Ser Tyr Ala Met Asp Tyr Trp Gly Gln Gly Thr
225                 230                 235                 240

Leu Val Thr Val Ser Ser Ala Ala Ala Thr Thr Thr Pro Ala Pro Arg
                245                 250                 255

Pro Pro Thr Pro Ala Pro Thr Ile Ala Ser Gln Pro Leu Ser Leu Arg
            260                 265                 270

Pro Glu Ala Cys Arg Pro Ala Ala Gly Gly Ala Val His Thr Arg Gly
        275                 280                 285

Leu Asp Phe Ala Cys Asp Ile Tyr Ile Trp Ala Pro Leu Ala Gly Thr
    290                 295                 300

Cys Gly Val Leu Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
            340                 345                 350

Glu Glu Glu Gly Gly Cys Glu Leu Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470

<210> SEQ ID NO 118
<211> LENGTH: 466
<212> TYPE: PRT
<213> ORGANISM: Artificial Sequence
<220> FEATURE:
<223> OTHER INFORMATION: anti-BCMA CAR

<400> SEQUENCE: 118

-continued

```
Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Tyr Cys Leu Gln Ser Arg
                85                  90                  95

Ile Phe Pro Arg Thr Phe Gly Gln Gly Thr Lys Leu Glu Ile Lys Gly
            100                 105                 110

Ser Thr Ser Gly Ser Gly Lys Pro Gly Ser Gly Glu Gly Ser Thr Lys
            115                 120                 125

Gly Gln Val Gln Leu Val Gln Ser Gly Ser Glu Leu Lys Lys Pro Gly
        130                 135                 140

Ala Ser Val Lys Val Ser Cys Lys Ala Ser Gly Tyr Thr Phe Thr Asp
145                 150                 155                 160

Tyr Ser Ile Asn Trp Val Arg Gln Ala Pro Gly Gln Gly Leu Glu Trp
                165                 170                 175

Met Gly Trp Ile Asn Thr Glu Thr Arg Glu Pro Ala Tyr Ala Tyr Asp
            180                 185                 190

Phe Arg Gly Arg Phe Val Phe Ser Leu Asp Thr Ser Val Ser Thr Ala
        195                 200                 205

Tyr Leu Gln Ile Ser Ser Leu Lys Ala Glu Asp Thr Ala Val Tyr Tyr
    210                 215                 220

Cys Ala Arg Asp Tyr Ser Tyr Ala Met Asp Tyr Trp Gly Gln Gly Thr
225                 230                 235                 240

Leu Val Thr Val Ser Ser Ala Ala Asp Thr Gly Leu Tyr Ile Cys
                245                 250                 255

Lys Val Glu Leu Met Tyr Pro Pro Pro Tyr Tyr Leu Gly Ile Gly Asn
            260                 265                 270

Gly Thr Gln Ile Tyr Val Ile Asp Pro Glu Pro Cys Pro Asp Ser Asp
        275                 280                 285

Phe Leu Leu Trp Ile Leu Ala Ala Val Ser Ser Gly Leu Phe Phe Tyr
    290                 295                 300

Ser Phe Leu Leu Thr Ala Val Ser Lys Arg Gly Arg Lys Lys Leu Leu
305                 310                 315                 320

Tyr Ile Phe Lys Gln Pro Phe Met Arg Pro Val Gln Thr Thr Gln Glu
            325                 330                 335

Glu Asp Gly Cys Ser Cys Arg Phe Pro Glu Glu Glu Gly Gly Cys
        340                 345                 350

Glu Leu Arg Val Lys Phe Ser Arg Ser Ala Asp Ala Pro Ala Tyr Gln
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
            405                 410                 415

Gln Lys Asp Lys Met Ala Glu Ala Tyr Ser Glu Ile Gly Met Lys Gly
```

```
                    420                 425                 430
Glu Arg Arg Arg Gly Lys Gly His Asp Gly Leu Tyr Gln Gly Leu Ser
                435                 440                 445

Thr Ala Thr Lys Asp Thr Tyr Asp Ala Leu His Met Gln Ala Leu Pro
            450                 455                 460

Pro Arg
465

<210> SEQ ID NO 119
<211> LENGTH: 464
<212> TYPE: PRT
<213> ORGANISM: Artificial Sequence
<220> FEATURE:
<223> OTHER INFORMATION: anti-BCMA CAR

<400> SEQUENCE: 119

Asp Ile Val Leu Thr Gln Ser Pro Ala Ser Leu Ala Val Ser Leu Gly
1               5                   10                  15

Glu Arg Ala Thr Ile Asn Cys Arg Ala Ser Glu Ser Val Ser Val Ile
            20                  25                  30

Gly Ala His Leu Ile His Trp Tyr Gln Gln Lys Pro Gly Gln Pro Pro
        35                  40                  45

Lys Leu Leu Ile Tyr Leu Ala Ser Asn Leu Glu Thr Gly Val Pro Ala
    50                  55                  60

Arg Phe Ser Gly Ser Gly Ser Gly Thr Asp Phe Thr Leu Thr Ile Ser
65                  70                  75                  80

Ser Leu Gln Ala Glu Asp Ala Ala Ile Tyr Tyr Cys Leu Gln Ser Arg
                85                  90                  95

Ile Phe Pro Arg Thr Phe Gly Gln Gly Thr Lys Leu Glu Ile Lys Gly
            100                 105                 110

Ser Thr Ser Gly Ser Gly Lys Pro Gly Ser Gly Glu Gly Ser Thr Lys
        115                 120                 125

Gly Gln Val Gln Leu Val Gln Ser Gly Ser Glu Leu Lys Lys Pro Gly
    130                 135                 140

Ala Ser Val Lys Val Ser Cys Lys Ala Ser Gly Tyr Thr Phe Thr Asp
145                 150                 155                 160

Tyr Ser Ile Asn Trp Val Arg Gln Ala Pro Gly Gln Gly Leu Glu Trp
                165                 170                 175

Met Gly Trp Ile Asn Thr Glu Thr Arg Glu Pro Ala Tyr Ala Tyr Asp
            180                 185                 190

Phe Arg Gly Arg Phe Val Phe Ser Leu Asp Thr Ser Val Ser Thr Ala
        195                 200                 205

Tyr Leu Gln Ile Ser Ser Leu Lys Ala Glu Asp Thr Ala Val Tyr Tyr
    210                 215                 220

Cys Ala Arg Asp Tyr Ser Tyr Ala Met Asp Tyr Trp Gly Gln Gly Thr
225                 230                 235                 240

Leu Val Thr Val Ser Ser Ala Ala Ala Gln Ile Lys Glu Ser Leu Arg
                245                 250                 255

Ala Glu Leu Arg Val Thr Glu Arg Arg Ala Glu Val Pro Thr Ala His
            260                 265                 270

Pro Ser Pro Ser Pro Arg Pro Ala Gly Gln Phe Gln Thr Leu Val Val
        275                 280                 285

Gly Val Val Gly Gly Leu Leu Gly Ser Leu Val Leu Leu Val Trp Val
    290                 295                 300

Leu Ala Val Ile Cys Ser Lys Arg Gly Arg Lys Lys Leu Leu Tyr Ile
```

```
                        305                 310                 315                 320
                Phe Lys Gln Pro Phe Met Arg Pro Val Gln Thr Thr Gln Glu Glu Asp
                                    325                 330                 335

Gly Cys Ser Cys Arg Phe Pro Glu Glu Glu Gly Gly Cys Glu Leu
                                340                 345                 350

Arg Val Lys Phe Ser Arg Ser Ala Asp Ala Pro Ala Tyr Gln Gln Gly
                                355                 360                 365

Gln Asn Gln Leu Tyr Asn Glu Leu Asn Leu Gly Arg Arg Glu Glu Tyr
                    370                 375                 380

Asp Val Leu Asp Lys Arg Arg Gly Arg Asp Pro Glu Met Gly Gly Lys
                385                 390                 395                 400

Pro Arg Arg Lys Asn Pro Gln Glu Gly Leu Tyr Asn Glu Leu Gln Lys
                                405                 410                 415

Asp Lys Met Ala Glu Ala Tyr Ser Glu Ile Gly Met Lys Gly Glu Arg
                                420                 425                 430

Arg Arg Gly Lys Gly His Asp Gly Leu Tyr Gln Gly Leu Ser Thr Ala
                                435                 440                 445

Thr Lys Asp Thr Tyr Asp Ala Leu His Met Gln Ala Leu Pro Pro Arg
                    450                 455                 460

<210> SEQ ID NO 120
<211> LENGTH: 653
<212> TYPE: PRT
<213> ORGANISM: Artificial Sequence
<220> FEATURE:
<223> OTHER INFORMATION: anti-BCMA CAR

<400> SEQUENCE: 120

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Asp Tyr Glu Asp Tyr Trp Gly Gln Gly Thr
                100                 105                 110

Leu Val Thr Val Ser Ser Gly Gly Gly Ser Gly Gly Gly Gly Ser
                115                 120                 125

Gly Gly Gly Gly Ser Gln Ser Ala Leu Thr Gln Pro Ala Ser Val Ser
                130                 135                 140

Gly Ser Pro Gly Gln Ser Ile Thr Ile Ser Cys Thr Gly Ser Ser Ser
145                 150                 155                 160

Asp Val Gly Lys Tyr Asn Leu Val Ser Trp Tyr Gln Gln Pro Pro Gly
                165                 170                 175

Lys Ala Pro Lys Leu Ile Ile Tyr Asp Val Asn Lys Arg Pro Ser Gly
                180                 185                 190

Val Ser Asn Arg Phe Ser Gly Ser Lys Ser Gly Asn Thr Ala Thr Leu
                195                 200                 205

Thr Ile Ser Gly Leu Gln Gly Asp Asp Glu Ala Asp Tyr Tyr Cys Ser
```

```
              210                 215                 220
Ser Tyr Gly Gly Ser Arg Ser Tyr Val Phe Gly Thr Gly Thr Lys Val
225                 230                 235                 240

Thr Val Leu Glu Ser Lys Tyr Gly Pro Pro Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser Gln Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Gln Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Gly Leu
            340                 345                 350

Pro Ser Ser Ile Glu Lys Thr Ile Ser Lys Ala Lys Gly Gln Pro Arg
        355                 360                 365

Glu Pro Gln Val Tyr Thr Leu Pro Pro Ser Gln Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Arg Leu Thr Val Asp Lys Ser Arg Trp Gln Glu Gly Asn Val Phe Ser
        435                 440                 445

Cys Ser Val Met His Glu Ala Leu His Asn His Tyr Thr Gln Lys Ser
    450                 455                 460

Leu Ser Leu Ser Leu Gly Lys Met Phe Trp Val Leu Val Val Val Gly
465                 470                 475                 480

Gly Val Leu Ala Cys Tyr Ser Leu Leu Val Thr Val Ala Phe Ile Ile
                485                 490                 495

Phe Trp Val Lys Arg Gly Arg Lys Lys Leu Leu Tyr Ile Phe Lys Gln
            500                 505                 510

Pro Phe Met Arg Pro Val Gln Thr Thr Gln Glu Glu Asp Gly Cys Ser
        515                 520                 525

Cys Arg Phe Pro Glu Glu Glu Glu Gly Gly Cys Glu Leu Arg Val Lys
    530                 535                 540

Phe Ser Arg Ser Ala Asp Ala Pro Ala Tyr Gln Gln Gly Gln Asn Gln
545                 550                 555                 560

Leu Tyr Asn Glu Leu Asn Leu Gly Arg Arg Glu Glu Tyr Asp Val Leu
                565                 570                 575

Asp Lys Arg Arg Gly Arg Asp Pro Glu Met Gly Gly Lys Pro Arg Arg
            580                 585                 590

Lys Asn Pro Gln Glu Gly Leu Tyr Asn Glu Leu Gln Lys Asp Lys Met
        595                 600                 605

Ala Glu Ala Tyr Ser Glu Ile Gly Met Lys Gly Glu Arg Arg Arg Gly
    610                 615                 620

Lys Gly His Asp Gly Leu Tyr Gln Gly Leu Ser Thr Ala Thr Lys Asp
625                 630                 635                 640
```

Thr Tyr Asp Ala Leu His Met Gln Ala Leu Pro Pro Arg
            645                 650

<210> SEQ ID NO 121
<211> LENGTH: 650
<212> TYPE: PRT
<213> ORGANISM: Artificial Sequence
<220> FEATURE:
<223> OTHER INFORMATION: anti-BCMA CAR

<400> SEQUENCE: 121

Glu Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Lys Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Gln Met Thr Gln Ser Pro Ala Phe Leu
    130                 135                 140

Ser Ala Ser Val Gly Asp Arg Val Thr Val Thr Cys Arg Ala Ser Gln
145                 150                 155                 160

Gly Ile Ser Asn Tyr Leu Ala Trp Tyr Gln Gln Lys Pro Gly Asn Ala
                165                 170                 175

Pro Arg Leu Leu Ile Tyr Ser Ala Ser Thr Leu Gln Ser Gly Val Pro
            180                 185                 190

Ser Arg Phe Arg Gly Thr Gly Tyr Gly Thr Glu Phe Ser Leu Thr Ile
        195                 200                 205

Asp Ser Leu Gln Pro Glu Asp Phe Ala Thr Tyr Tyr Cys Gln Gln Ser
    210                 215                 220

Tyr Thr Ser Arg Gln Thr Phe Gly Pro Gly Thr Arg Leu Asp Ile Lys
225                 230                 235                 240

Glu Ser Lys Tyr Gly Pro Pro Cys Pro Pro Cys Pro Ala Pro Pro Val
                245                 250                 255

Ala Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Gln Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

```
Ile Glu Lys Thr Ile Ser Lys Ala Lys Gly Gln Pro Arg Glu Pro Gln
            355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Gln Gly Asn Val Phe Ser Cys Ser Val
    435                 440                 445

Met His Glu Ala Leu His Asn His Tyr Thr Gln Lys Ser Leu Ser Leu
450                 455                 460

Ser Leu Gly Lys Met Phe Trp Val Leu Val Val Val Gly Gly Val Leu
465                 470                 475                 480

Ala Cys Tyr Ser Leu Leu Val Thr Val Ala Phe Ile Ile Phe Trp Val
                485                 490                 495

Lys Arg Gly Arg Lys Lys Leu Leu Tyr Ile Phe Lys Gln Pro Phe Met
            500                 505                 510

Arg Pro Val Gln Thr Thr Gln Glu Glu Asp Gly Cys Ser Cys Arg Phe
    515                 520                 525

Pro Glu Glu Glu Glu Gly Gly Cys Glu Leu Arg Val Lys Phe Ser Arg
530                 535                 540

Ser Ala Asp Ala Pro Ala Tyr Gln Gln Gly Gln Asn Gln Leu Tyr Asn
545                 550                 555                 560

Glu Leu Asn Leu Gly Arg Arg Glu Glu Tyr Asp Val Leu Asp Lys Arg
                565                 570                 575

Arg Gly Arg Asp Pro Glu Met Gly Gly Lys Pro Arg Arg Lys Asn Pro
            580                 585                 590

Gln Glu Gly Leu Tyr Asn Glu Leu Gln Lys Asp Lys Met Ala Glu Ala
    595                 600                 605

Tyr Ser Glu Ile Gly Met Lys Gly Glu Arg Arg Arg Gly Lys Gly His
610                 615                 620

Asp Gly Leu Tyr Gln Gly Leu Ser Thr Ala Thr Lys Asp Thr Tyr Asp
625                 630                 635                 640

Ala Leu His Met Gln Ala Leu Pro Pro Arg
                645                 650

<210> SEQ ID NO 122
<211> LENGTH: 651
<212> TYPE: PRT
<213> ORGANISM: Artificial Sequence
<220> FEATURE:
<223> OTHER INFORMATION: anti-BCMA CAR

<400> SEQUENCE: 122

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Asp Gly Pro Pro Ser Phe Asp Ile Trp Gly Gln Gly Thr
            100                 105                 110

Met Val Thr Val Ser Ser Gly Gly Gly Ser Gly Gly Gly Gly Ser
        115                 120                 125

Gly Gly Gly Gly Ser Ser Tyr Val Leu Thr Gln Pro Pro Ser Val Ser
        130                 135                 140

Val Ala Pro Gly Gln Thr Ala Arg Ile Thr Cys Gly Ala Asn Asn Ile
145                 150                 155                 160

Gly Ser Lys Ser Val His Trp Tyr Gln Gln Lys Pro Gly Gln Ala Pro
            165                 170                 175

Met Leu Val Val Tyr Asp Asp Asp Arg Pro Ser Gly Ile Pro Glu
        180                 185                 190

Arg Phe Ser Gly Ser Asn Ser Gly Asn Thr Ala Thr Leu Thr Ile Ser
        195                 200                 205

Gly Val Glu Ala Gly Asp Glu Ala Asp Tyr Phe Cys His Leu Trp Asp
210                 215                 220

Arg Ser Arg Asp His Tyr Val Phe Gly Thr Gly Thr Lys Leu Thr Val
225                 230                 235                 240

Leu Glu Ser Lys Tyr Gly Pro Pro Cys Pro Pro Cys Pro Ala Pro Pro
            245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser Gln Glu Asp Pro Glu Val Gln Phe Asn Trp Tyr Val Asp Gly Val
290                 295                 300

Glu Val His Asn Ala Lys Thr Lys Pro Arg Glu Glu Gln Phe Gln Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Gly Leu Pro Ser
            340                 345                 350

Ser Ile Glu Lys Thr Ile Ser Lys Ala Lys Gly Gln Pro Arg Glu Pro
        355                 360                 365

Gln Val Tyr Thr Leu Pro Pro Ser Gln Glu Glu Met Thr Lys Asn Gln
        370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Arg Leu
            420                 425                 430

Thr Val Asp Lys Ser Arg Trp Gln Glu Gly Asn Val Phe Ser Cys Ser
        435                 440                 445

Val Met His Glu Ala Leu His Asn His Tyr Thr Gln Lys Ser Leu Ser
        450                 455                 460

Leu Ser Leu Gly Lys Met Phe Trp Val Leu Val Val Val Gly Gly Val
465                 470                 475                 480
```

```
Leu Ala Cys Tyr Ser Leu Leu Val Thr Val Ala Phe Ile Ile Phe Trp
                485                 490                 495
Val Lys Arg Gly Arg Lys Lys Leu Leu Tyr Ile Phe Lys Gln Pro Phe
            500                 505                 510
Met Arg Pro Val Gln Thr Thr Gln Glu Glu Asp Gly Cys Ser Cys Arg
            515                 520                 525
Phe Pro Glu Glu Glu Glu Gly Gly Cys Glu Leu Arg Val Lys Phe Ser
530                 535                 540
Arg Ser Ala Asp Ala Pro Ala Tyr Gln Gln Gly Gln Asn Gln Leu Tyr
545                 550                 555                 560
Asn Glu Leu Asn Leu Gly Arg Arg Glu Glu Tyr Asp Val Leu Asp Lys
                565                 570                 575
Arg Arg Gly Arg Asp Pro Glu Met Gly Gly Lys Pro Arg Arg Lys Asn
            580                 585                 590
Pro Gln Glu Gly Leu Tyr Asn Glu Leu Gln Lys Asp Lys Met Ala Glu
            595                 600                 605
Ala Tyr Ser Glu Ile Gly Met Lys Gly Glu Arg Arg Arg Gly Lys Gly
            610                 615                 620
His Asp Gly Leu Tyr Gln Gly Leu Ser Thr Ala Thr Lys Asp Thr Tyr
625                 630                 635                 640
Asp Ala Leu His Met Gln Ala Leu Pro Pro Arg
                645                 650

<210> SEQ ID NO 123
<211> LENGTH: 658
<212> TYPE: PRT
<213> ORGANISM: Artificial Sequence
<220> FEATURE:
<223> OTHER INFORMATION: anti-BCMA CAR

<400> SEQUENCE: 123

Ser Tyr Glu Leu Thr Gln Pro Pro Ser Ala Ser Gly Thr Pro Gly Gln
1               5                   10                  15
Arg Val Thr Met Ser Cys Ser Gly Thr Ser Ser Asn Ile Gly Ser His
            20                  25                  30
Ser Val Asn Trp Tyr Gln Gln Leu Pro Gly Thr Ala Pro Lys Leu Leu
        35                  40                  45
Ile Tyr Thr Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Gly Ser Leu
                85                  90                  95
Asn Gly Leu Val Phe Gly Gly Gly Thr Lys Leu Thr Val Leu Gly Ser
            100                 105                 110
Arg Gly Gly Gly Ser Gly Gly Gly Ser Gly Gly Gly Gly Ser
            115                 120                 125
Leu Glu Met Ala Glu Val Gln Leu Val Gln Ser Gly Ala Glu Val Lys
            130                 135                 140
Lys Pro Gly Glu Ser Leu Lys Ile Ser Cys Lys Gly Ser Gly Tyr Ser
145                 150                 155                 160
Phe Thr Ser Tyr Trp Ile Gly Trp Val Arg Gln Met Pro Gly Lys Gly
                165                 170                 175
Leu Glu Trp Met Gly Ile Ile Tyr Pro Gly Asp Ser Asp Thr Arg Tyr
            180                 185                 190
```

-continued

```
Ser Pro Ser Phe Gln Gly His Val Thr Ile Ser Ala Asp Lys Ser Ile
            195                 200                 205
Ser Thr Ala Tyr Leu Gln Trp Ser Ser Leu Lys Ala Ser Asp Thr Ala
            210                 215                 220
Met Tyr Tyr Cys Ala Arg Tyr Ser Gly Ser Phe Asp Asn Trp Gly Gln
225                 230                 235                 240
Gly Thr Leu Val Thr Val Ser Ser Glu Ser Lys Tyr Gly Pro Pro Cys
            245                 250                 255
Pro Pro Cys Pro Ala Pro Pro Val Ala Gly Pro Ser Val Phe Leu Phe
            260                 265                 270
Pro Pro Lys Pro Lys Asp Thr Leu Met Ile Ser Arg Thr Pro Glu Val
            275                 280                 285
Thr Cys Val Val Val Asp Val Ser Gln Glu Asp Pro Glu Val Gln Phe
290                 295                 300
Asn Trp Tyr Val Asp Gly Val Glu Val His Asn Ala Lys Thr Lys Pro
305                 310                 315                 320
Arg Glu Glu Gln Phe Gln Ser Thr Tyr Arg Val Val Ser Val Leu Thr
            325                 330                 335
Val Leu His Gln Asp Trp Leu Asn Gly Lys Glu Tyr Lys Cys Lys Val
            340                 345                 350
Ser Asn Lys Gly Leu Pro Ser Ser Ile Glu Lys Thr Ile Ser Lys Ala
            355                 360                 365
Lys Gly Gln Pro Arg Glu Pro Gln Val Tyr Thr Leu Pro Pro Ser Gln
            370                 375                 380
Glu Glu Met Thr Lys Asn Gln Val Ser Leu Thr Cys Leu Val Lys Gly
385                 390                 395                 400
Phe Tyr Pro Ser Asp Ile Ala Val Glu Trp Glu Ser Asn Gly Gln Pro
            405                 410                 415
Glu Asn Asn Tyr Lys Thr Thr Pro Pro Val Leu Asp Ser Asp Gly Ser
            420                 425                 430
Phe Phe Leu Tyr Ser Arg Leu Thr Val Asp Lys Ser Arg Trp Gln Glu
            435                 440                 445
Gly Asn Val Phe Ser Cys Ser Val Met His Glu Ala Leu His Asn His
450                 455                 460
Tyr Thr Gln Lys Ser Leu Ser Leu Ser Leu Gly Lys Met Phe Trp Val
465                 470                 475                 480
Leu Val Val Val Gly Val Leu Ala Cys Tyr Ser Leu Leu Val Thr
            485                 490                 495
Val Ala Phe Ile Ile Phe Trp Val Lys Arg Gly Arg Lys Lys Leu Leu
            500                 505                 510
Tyr Ile Phe Lys Gln Pro Phe Met Arg Pro Val Gln Thr Thr Gln Glu
            515                 520                 525
Glu Asp Gly Cys Ser Cys Arg Phe Pro Glu Glu Glu Glu Gly Gly Cys
            530                 535                 540
Glu Leu Arg Val Lys Phe Ser Arg Ser Ala Asp Ala Pro Ala Tyr Gln
545                 550                 555                 560
Gln Gly Gln Asn Gln Leu Tyr Asn Glu Leu Asn Leu Gly Arg Arg Glu
            565                 570                 575
Glu Tyr Asp Val Leu Asp Lys Arg Arg Gly Arg Asp Pro Glu Met Gly
            580                 585                 590
Gly Lys Pro Arg Arg Lys Asn Pro Gln Glu Gly Leu Tyr Asn Glu Leu
            595                 600                 605
Gln Lys Asp Lys Met Ala Glu Ala Tyr Ser Glu Ile Gly Met Lys Gly
```

Glu Arg Arg Arg Gly Lys Gly His Asp Gly Leu Tyr Gln Gly Leu Ser
625                 630                 635                 640

Thr Ala Thr Lys Asp Thr Tyr Asp Ala Leu His Met Gln Ala Leu Pro
            645                 650                 655

Pro Arg

<210> SEQ ID NO 124
<211> LENGTH: 654
<212> TYPE: PRT
<213> ORGANISM: Artificial Sequence
<220> FEATURE:
<223> OTHER INFORMATION: anti-BCMA CAR

<400> SEQUENCE: 124

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly Ser Arg Gly Gly Gly Gly Ser
            100                 105                 110

Gly Gly Gly Gly Ser Gly Gly Gly Ser Leu Glu Met Ala Glu Val
            115                 120                 125

Gln Leu Val Gln Ser Gly Ala Glu Met Lys Lys Pro Gly Ala Ser Leu
        130                 135                 140

Lys Leu Ser Cys Lys Ala Ser Gly Tyr Thr Phe Ile Asp Tyr Tyr Val
145                 150                 155                 160

Tyr Trp Met Arg Gln Ala Pro Gly Gln Gly Leu Glu Ser Met Gly Trp
                165                 170                 175

Ile Asn Pro Asn Ser Gly Gly Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Met Tyr Tyr Cys Ala Arg
210                 215                 220

Ser Gln Arg Asp Gly Tyr Met Asp Tyr Trp Gly Gln Gly Thr Leu Val
225                 230                 235                 240

Thr Val Ser Ser Glu Ser Lys Tyr Gly Pro Pro Cys Pro Pro Cys Pro
                245                 250                 255

Ala Pro Pro Val Ala Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser Gln Glu Asp Pro Glu Val Gln Phe Asn Trp Tyr Val
    290                 295                 300

Asp Gly Val Glu Val His Asn Ala Lys Thr Lys Pro Arg Glu Glu Gln
305                 310                 315                 320

```
Phe Gln Ser Thr Tyr Arg Val Ser Val Leu Thr Val Leu His Gln
                325                 330                 335

Asp Trp Leu Asn Gly Lys Glu Tyr Lys Cys Lys Val Ser Asn Lys Gly
            340                 345                 350

Leu Pro Ser Ser Ile Glu Lys Thr Ile Ser Lys Ala Lys Gly Gln Pro
        355                 360                 365

Arg Glu Pro Gln Val Tyr Thr Leu Pro Pro Ser Gln Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Arg Leu Thr Val Asp Lys Ser Arg Trp Gln Glu Gly Asn Val Phe
        435                 440                 445

Ser Cys Ser Val Met His Glu Ala Leu His Asn His Tyr Thr Gln Lys
    450                 455                 460

Ser Leu Ser Leu Ser Leu Gly Lys Met Phe Trp Val Leu Val Val Val
465                 470                 475                 480

Gly Gly Val Leu Ala Cys Tyr Ser Leu Leu Val Thr Val Ala Phe Ile
                485                 490                 495

Ile Phe Trp Val Lys Arg Gly Arg Lys Lys Leu Leu Tyr Ile Phe Lys
            500                 505                 510

Gln Pro Phe Met Arg Pro Val Gln Thr Thr Gln Glu Glu Asp Gly Cys
        515                 520                 525

Ser Cys Arg Phe Pro Glu Glu Glu Glu Gly Gly Cys Glu Leu Arg Val
    530                 535                 540

Lys Phe Ser Arg Ser Ala Asp Ala Pro Ala Tyr Gln Gln Gly Gln Asn
545                 550                 555                 560

Gln Leu Tyr Asn Glu Leu Asn Leu Gly Arg Arg Glu Glu Tyr Asp Val
                565                 570                 575

Leu Asp Lys Arg Arg Gly Arg Asp Pro Glu Met Gly Gly Lys Pro Arg
            580                 585                 590

Arg Lys Asn Pro Gln Glu Gly Leu Tyr Asn Glu Leu Gln Lys Asp Lys
        595                 600                 605

Met Ala Glu Ala Tyr Ser Glu Ile Gly Met Lys Gly Glu Arg Arg Arg
    610                 615                 620

Gly Lys Gly His Asp Gly Leu Tyr Gln Gly Leu Ser Thr Ala Thr Lys
625                 630                 635                 640

Asp Thr Tyr Asp Ala Leu His Met Gln Ala Leu Pro Pro Arg
                645                 650

<210> SEQ ID NO 125
<211> LENGTH: 653
<212> TYPE: PRT
<213> ORGANISM: Artificial Sequence
<220> FEATURE:
<223> OTHER INFORMATION: anti-BCMA CAR

<400> SEQUENCE: 125

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
                20                  25                  30
```

```
Gln Gln His Pro Gly Lys Ala Pro Lys Leu Met Ile Tyr Glu Asp Ser
         35                  40                  45

Lys Arg Pro Ser Gly Val Ser Asn Arg Phe Ser Gly Ser Lys Ser Gly
 50                  55                  60

Asn Thr Ala Ser Leu Thr Ile Ser Gly Leu Gln Ala Glu Asp Glu Ala
 65                  70                  75                  80

Asp Tyr Tyr Cys Ser Ser Asn Thr Arg Ser Ser Thr Leu Val Phe Gly
                 85                  90                  95

Gly Gly Thr Lys Leu Thr Val Leu Gly Ser Arg Gly Gly Gly Gly Ser
             100                 105                 110

Gly Gly Gly Gly Ser Gly Gly Gly Ser Leu Glu Met Ala Glu Val
         115                 120                 125

Gln Leu Val Gln Ser Gly Ala Glu Met Lys Lys Pro Gly Ala Ser Leu
130                 135                 140

Lys Leu Ser Cys Lys Ala Ser Gly Tyr Thr Phe Ile Asp Tyr Tyr Val
145                 150                 155                 160

Tyr Trp Met Arg Gln Ala Pro Gly Gln Gly Leu Glu Ser Met Gly Trp
                 165                 170                 175

Ile Asn Pro Asn Ser Gly Gly Thr Asn Tyr Ala Gln Lys Phe Gln Gly
             180                 185                 190

Arg Val Thr Met Thr Arg Asp Thr Ser Ile Ser Thr Ala Tyr Met Glu
             195                 200                 205

Leu Ser Arg Leu Arg Ser Asp Asp Thr Ala Met Tyr Tyr Cys Ala Arg
210                 215                 220

Ser Gln Arg Asp Gly Tyr Met Asp Tyr Trp Gly Gln Gly Thr Leu Val
225                 230                 235                 240

Thr Val Ser Ser Glu Ser Lys Tyr Gly Pro Pro Cys Pro Pro Cys Pro
                 245                 250                 255

Ala Pro Pro Val Ala Gly Pro Ser Val Phe Leu Phe Pro Pro Lys Pro
             260                 265                 270

Lys Asp Thr Leu Met Ile Ser Arg Thr Pro Glu Val Thr Cys Val Val
             275                 280                 285

Val Asp Val Ser Gln Glu Asp Pro Glu Val Gln Phe Asn Trp Tyr Val
290                 295                 300

Asp Gly Val Glu Val His Asn Ala Lys Thr Lys Pro Arg Glu Glu Gln
305                 310                 315                 320

Phe Gln Ser Thr Tyr Arg Val Val Ser Val Leu Thr Val Leu His Gln
                 325                 330                 335

Asp Trp Leu Asn Gly Lys Glu Tyr Lys Cys Lys Val Ser Asn Lys Gly
             340                 345                 350

Leu Pro Ser Ser Ile Glu Lys Thr Ile Ser Lys Ala Lys Gly Gln Pro
             355                 360                 365

Arg Glu Pro Gln Val Tyr Thr Leu Pro Pro Ser Gln Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                 405                 410                 415

Lys Thr Thr Pro Pro Val Leu Asp Ser Asp Gly Ser Phe Phe Leu Tyr
             420                 425                 430

Ser Arg Leu Thr Val Asp Lys Ser Arg Trp Gln Glu Gly Asn Val Phe
             435                 440                 445
```

```
Ser Cys Ser Val Met His Glu Ala Leu His Asn His Tyr Thr Gln Lys
    450                 455                 460

Ser Leu Ser Leu Ser Leu Gly Lys Met Phe Trp Val Leu Val Val
465                 470                 475                 480

Gly Gly Val Leu Ala Cys Tyr Ser Leu Leu Val Thr Val Ala Phe Ile
                485                 490                 495

Ile Phe Trp Val Arg Ser Lys Arg Ser Arg Leu Leu His Ser Asp Tyr
            500                 505                 510

Met Asn Met Thr Pro Arg Arg Pro Gly Pro Thr Arg Lys His Tyr Gln
        515                 520                 525

Pro Tyr Ala Pro Pro Arg Asp Phe Ala Ala Tyr Arg Ser Arg Val Lys
530                 535                 540

Phe Ser Arg Ser Ala Asp Ala Pro Ala Tyr Gln Gln Gly Gln Asn Gln
545                 550                 555                 560

Leu Tyr Asn Glu Leu Asn Leu Gly Arg Arg Glu Glu Tyr Asp Val Leu
                565                 570                 575

Asp Lys Arg Arg Gly Arg Asp Pro Glu Met Gly Gly Lys Pro Arg Arg
                580                 585                 590

Lys Asn Pro Gln Glu Gly Leu Tyr Asn Glu Leu Gln Lys Asp Lys Met
            595                 600                 605

Ala Glu Ala Tyr Ser Glu Ile Gly Met Lys Gly Glu Arg Arg Arg Gly
        610                 615                 620

Lys Gly His Asp Gly Leu Tyr Gln Gly Leu Ser Thr Ala Thr Lys Asp
625                 630                 635                 640

Thr Tyr Asp Ala Leu His Met Gln Ala Leu Pro Pro Arg
                645                 650

<210> SEQ ID NO 126
<211> LENGTH: 462
<212> TYPE: PRT
<213> ORGANISM: Artificial Sequence
<220> FEATURE:
<223> OTHER INFORMATION: anti-BCMA CAR

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ala Leu Ser Asn His
            20                  25                  30

Gly Met Ser Trp Val Arg Arg Ala Pro Gly Lys Gly Leu Glu Trp Val
        35                  40                  45

Ser Gly Ile Val Tyr Ser Gly Ser Thr Tyr Tyr Ala Ala Ser Val Lys
    50                  55                  60

Gly Arg Phe Thr Ile Ser Arg Asp Asn Ser Arg Asn Thr Leu Tyr Leu
65                  70                  75                  80

Gln Met Asn Ser Leu Arg Pro Glu Asp Thr Ala Ile Tyr Tyr Cys Ser
                85                  90                  95

Ala His Gly Gly Glu Ser Asp Val Trp Gly Gln Gly Thr Thr Val Thr
            100                 105                 110

Val Ser Ser Ala Ser Gly Gly Gly Gly Ser Gly Gly Arg Ala Ser Gly
        115                 120                 125

Gly Gly Gly Ser Asp Ile Gln Leu Thr Gln Ser Pro Ser Ser Leu Ser
130                 135                 140

Ala Ser Val Gly Asp Arg Val Thr Ile Thr Cys Arg Ala Ser Gln Ser
145                 150                 155                 160
```

```
Ile Ser Ser Tyr Leu Asn Trp Tyr Gln Gln Lys Pro Gly Lys Ala Pro
            165                 170                 175

Lys Leu Leu Ile Tyr Ala Ala Ser Ser Leu Gln Ser Gly Val Pro Ser
        180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Tyr Thr Phe Gly Gln Gly Thr Lys Val Glu Ile Lys Thr
225                 230                 235                 240

Thr Thr Pro Ala Pro Arg Pro Pro Thr Pro Ala Pro Thr Ile Ala Ser
                245                 250                 255

Gln Pro Leu Ser Leu Arg Pro Glu Ala Cys Arg Pro Ala Ala Gly Gly
        260                 265                 270

Ala Val His Thr Arg Gly Leu Asp Phe Ala Cys Asp Ile Tyr Ile Trp
        275                 280                 285

Ala Pro Leu Ala Gly Thr Cys Gly Val Leu Leu Leu Ser Leu Val Ile
        290                 295                 300

Thr Leu Tyr Cys Lys Arg Gly Arg Lys Lys Leu Leu Tyr Ile Phe Lys
305                 310                 315                 320

Gln Pro Phe Met Arg Pro Val Gln Thr Thr Gln Glu Glu Asp Gly Cys
                325                 330                 335

Ser Cys Arg Phe Pro Glu Glu Glu Glu Gly Gly Cys Glu Leu Arg Val
        340                 345                 350

Lys Phe Ser Arg Ser Ala Asp Ala Pro Ala Tyr Lys Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
        420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460

<210> SEQ ID NO 127
<211> LENGTH: 469
<212> TYPE: PRT
<213> ORGANISM: Artificial Sequence
<220> FEATURE:
<223> OTHER INFORMATION: anti-BCMA CAR

<400> SEQUENCE: 127

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Gly Trp Val
        35                  40                  45

Ser Gly Ile Ser Arg Ser Gly Glu Asn Thr Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Asp Glu Asp Thr Ala Val Tyr Tyr Cys
                 85                  90                  95

Ala Arg Ser Pro Ala His Tyr Tyr Gly Gly Met Asp Val Trp Gly Gln
            100                 105                 110

Gly Thr Thr Val Thr Val Ser Ser Ala Ser Gly Gly Gly Gly Ser Gly
            115                 120                 125

Gly Arg Ala Ser Gly Gly Gly Ser Asp Ile Val Leu Thr Gln Ser
            130                 135                 140

Pro Gly Thr Leu Ser Leu Ser Pro Gly Glu Arg Ala Thr Leu Ser Cys
145                 150                 155                 160

Arg Ala Ser Gln Ser Ile Ser Ser Ser Phe Leu Ala Trp Tyr Gln Gln
                165                 170                 175

Lys Pro Gly Gln Ala Pro Arg Leu Leu Ile Tyr Gly Ala Ser Arg Arg
            180                 185                 190

Ala Thr Gly Ile Pro Asp Arg Phe Ser Gly Ser Gly Ser Gly Thr Asp
            195                 200                 205

Phe Thr Leu Thr Ile Ser Arg Leu Glu Pro Glu Asp Ser Ala Val Tyr
            210                 215                 220

Tyr Cys Gln Gln Tyr His Ser Ser Pro Ser Trp Thr Phe Gly Gln Gly
225                 230                 235                 240

Thr Lys Leu Glu Ile Lys Thr Thr Thr Pro Ala Pro Arg Pro Pro Thr
                245                 250                 255

Pro Ala Pro Thr Ile Ala Ser Gln Pro Leu Ser Leu Arg Pro Glu Ala
            260                 265                 270

Cys Arg Pro Ala Ala Gly Gly Ala Val His Thr Arg Gly Leu Asp Phe
            275                 280                 285

Ala Cys Asp Ile Tyr Ile Trp Ala Pro Leu Ala Gly Thr Cys Gly Val
            290                 295                 300

Leu Leu Leu Ser Leu Val Ile Thr Leu Tyr Cys Lys Arg Gly Arg Lys
305                 310                 315                 320

Lys Leu Leu Tyr Ile Phe Lys Gln Pro Phe Met Arg Pro Val Gln Thr
                325                 330                 335

Thr Gln Glu Glu Asp Gly Cys Ser Cys Arg Phe Pro Glu Glu Glu Glu
            340                 345                 350

Gly Gly Cys Glu Leu Arg Val Lys Phe Ser Arg Ser Ala Asp Ala Pro
            355                 360                 365

Ala Tyr Lys Gln Gly Gln Asn Gln Leu Tyr Asn Glu Leu Asn Leu Gly
            370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
            420                 425                 430

Met Lys Gly Glu Arg Arg Arg Gly Lys Gly His Asp Gly Leu Tyr Gln
            435                 440                 445

Gly Leu Ser Thr Ala Thr Lys Asp Thr Tyr Asp Ala Leu His Met Gln
            450                 455                 460

Ala Leu Pro Pro Arg
465
```

```
<210> SEQ ID NO 128
<211> LENGTH: 462
<212> TYPE: PRT
<213> ORGANISM: Artificial Sequence
<220> FEATURE:
<223> OTHER INFORMATION: anti-BCMA CAR

<400> SEQUENCE: 128
```

| | | | | | | | | | | | | | | | |
|---|---|---|---|---|---|---|---|---|---|---|---|---|---|---|---|
| Gln | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Val | Ser | Gly | Phe | Ala | Leu | Ser | Asn | His |
| | | | 20 | | | | | 25 | | | | | 30 | | |
| Gly | Met | Ser | Trp | Val | Arg | Arg | Ala | Pro | Gly | Lys | Gly | Leu | Glu | Trp | Val |
| | | 35 | | | | | 40 | | | | | 45 | | | |
| Ser | Gly | Ile | Val | Tyr | Ser | Gly | Ser | Thr | Tyr | Tyr | Ala | Ala | Ser | Val | Lys |
| 50 | | | | | 55 | | | | | 60 | | | | | |
| Gly | Arg | Phe | Thr | Ile | Ser | Arg | Asp | Asn | Ser | Arg | Asn | Thr | Leu | Tyr | Leu |
| 65 | | | | 70 | | | | | 75 | | | | | 80 | |
| Gln | Met | Asn | Ser | Leu | Arg | Pro | Glu | Asp | Thr | Ala | Ile | Tyr | Tyr | Cys | Ser |
| | | | | 85 | | | | | 90 | | | | | 95 | |
| Ala | His | Gly | Gly | Glu | Ser | Asp | Val | Trp | Gly | Gln | Gly | Thr | Thr | Val | Thr |
| | | | 100 | | | | | 105 | | | | | 110 | | |
| Val | Ser | Ser | Ala | Ser | Gly | Gly | Gly | Gly | Ser | Gly | Gly | Arg | Ala | Ser | Gly |
| | | 115 | | | | | 120 | | | | | 125 | | | |
| Gly | Gly | Gly | Ser | Asp | Ile | Arg | Leu | Thr | Gln | Ser | Pro | Ser | Pro | Leu | Ser |
| 130 | | | | | 135 | | | | | 140 | | | | | |
| Ala | Ser | Val | Gly | Asp | Arg | Val | Thr | Ile | Thr | Cys | Gln | Ala | Ser | Glu | Asp |
| 145 | | | | | 150 | | | | | 155 | | | | | 160 |
| Ile | Asn | Lys | Phe | Leu | Asn | Trp | Tyr | His | Gln | Thr | Pro | Gly | Lys | Ala | Pro |
| | | | | 165 | | | | | 170 | | | | | 175 | |
| Lys | Leu | Leu | Ile | Tyr | Asp | Ala | Ser | Thr | Leu | Gln | Thr | Gly | Val | Pro | Ser |
| | | | 180 | | | | | 185 | | | | | 190 | | |
| Arg | Phe | Ser | Gly | Ser | Gly | Ser | Gly | Thr | Asp | Phe | Thr | Leu | Thr | Ile | Asn |
| | | 195 | | | | | 200 | | | | | 205 | | | |
| Ser | Leu | Gln | Pro | Glu | Asp | Ile | Gly | Thr | Tyr | Tyr | Cys | Gln | Gln | Tyr | Glu |
| 210 | | | | | 215 | | | | | 220 | | | | | |
| Ser | Leu | Pro | Leu | Thr | Phe | Gly | Gly | Gly | Thr | Lys | Val | Glu | Ile | Lys | Thr |
| 225 | | | | | 230 | | | | | 235 | | | | | 240 |
| Thr | Thr | Pro | Ala | Pro | Arg | Pro | Pro | Thr | Pro | Ala | Pro | Thr | Ile | Ala | Ser |
| | | | | 245 | | | | | 250 | | | | | 255 | |
| Gln | Pro | Leu | Ser | Leu | Arg | Pro | Glu | Ala | Cys | Arg | Pro | Ala | Ala | Gly | Gly |
| | | | 260 | | | | | 265 | | | | | 270 | | |
| Ala | Val | His | Thr | Arg | Gly | Leu | Asp | Phe | Ala | Cys | Asp | Ile | Tyr | Ile | Trp |
| | | 275 | | | | | 280 | | | | | 285 | | | |
| Ala | Pro | Leu | Ala | Gly | Thr | Cys | Gly | Val | Leu | Leu | Leu | Ser | Leu | Val | Ile |
| 290 | | | | | 295 | | | | | 300 | | | | | |
| Thr | Leu | Tyr | Cys | Lys | Arg | Gly | Arg | Lys | Lys | Leu | Leu | Tyr | Ile | Phe | Lys |
| 305 | | | | | 310 | | | | | 315 | | | | | 320 |
| Gln | Pro | Phe | Met | Arg | Pro | Val | Gln | Thr | Thr | Gln | Glu | Glu | Asp | Gly | Cys |
| | | | | 325 | | | | | 330 | | | | | 335 | |
| Ser | Cys | Arg | Phe | Pro | Glu | Glu | Glu | Gly | Gly | Cys | Glu | Leu | Arg | Val |
| | | | 340 | | | | | 345 | | | | | 350 | | |
| Lys | Phe | Ser | Arg | Ser | Ala | Asp | Ala | Pro | Ala | Tyr | Lys | Gln | Gly | Gln | Asn |
| | | 355 | | | | | 360 | | | | | 365 | | | |
| Gln | Leu | Tyr | Asn | Glu | Leu | Asn | Leu | Gly | Arg | Arg | Glu | Glu | Tyr | Asp | Val |

```
    370             375             380
Leu Asp Lys Arg Arg Gly Arg Asp Pro Glu Met Gly Gly Lys Pro Arg
385             390             395             400

Arg Lys Asn Pro Gln Glu Gly Leu Tyr Asn Glu Leu Gln Lys Asp Lys
                405             410             415

Met Ala Glu Ala Tyr Ser Glu Ile Gly Met Lys Gly Glu Arg Arg Arg
            420             425             430

Gly Lys Gly His Asp Gly Leu Tyr Gln Gly Leu Ser Thr Ala Thr Lys
        435             440             445

Asp Thr Tyr Asp Ala Leu His Met Gln Ala Leu Pro Pro Arg
450             455             460
```

<210> SEQ ID NO 129
<211> LENGTH: 464
<212> TYPE: PRT
<213> ORGANISM: Artificial Sequence
<220> FEATURE:
<223> OTHER INFORMATION: anti-BCMA CAR

<400> SEQUENCE: 129

```
Glu Val Gln Leu Val Glu Ser Gly Gly Gly Leu Val Gln Pro Gly Gly
1               5               10              15

Ser Leu Arg Leu Ser Cys Ala Val Ser Gly Phe Ala Leu Ser Asn His
            20              25              30

Gly Met Ser Trp Val Arg Arg Ala Pro Gly Lys Gly Leu Glu Trp Val
        35              40              45

Ser Gly Ile Val Tyr Ser Gly Ser Thr Tyr Tyr Ala Ala Ser Val Lys
    50              55              60

Gly Arg Phe Thr Ile Ser Arg Asp Asn Ser Arg Asn Thr Leu Tyr Leu
65              70              75              80

Gln Met Asn Ser Leu Arg Pro Glu Asp Thr Ala Ile Tyr Tyr Cys Ser
            85              90              95

Ala His Gly Gly Glu Ser Asp Val Trp Gly Gln Gly Thr Thr Val Thr
        100             105             110

Val Ser Ser Ala Ser Gly Gly Gly Gly Ser Gly Gly Arg Ala Ser Gly
    115             120             125

Gly Gly Gly Ser Glu Ile Val Leu Thr Gln Ser Pro Gly Thr Leu Ser
130             135             140

Leu Ser Pro Gly Glu Arg Ala Thr Leu Ser Cys Arg Ala Ser Gln Ser
145             150             155             160

Ile Gly Ser Ser Ser Leu Ala Trp Tyr Gln Gln Lys Pro Gly Gln Ala
            165             170             175

Pro Arg Leu Leu Met Tyr Gly Ala Ser Ser Arg Ala Ser Gly Ile Pro
        180             185             190

Asp Arg Phe Ser Gly Ser Gly Ser Gly Thr Asp Phe Thr Leu Thr Ile
    195             200             205

Ser Arg Leu Glu Pro Glu Asp Phe Ala Val Tyr Tyr Cys Gln Gln Tyr
    210             215             220

Ala Gly Ser Pro Pro Phe Thr Phe Gly Gln Gly Thr Lys Val Glu Ile
225             230             235             240

Lys Thr Thr Thr Pro Ala Pro Arg Pro Pro Thr Pro Ala Pro Thr Ile
            245             250             255

Ala Ser Gln Pro Leu Ser Leu Arg Pro Glu Ala Cys Arg Pro Ala Ala
        260             265             270

Gly Gly Ala Val His Thr Arg Gly Leu Asp Phe Ala Cys Asp Ile Tyr
```

```
                   275                 280                 285
Ile Trp Ala Pro Leu Ala Gly Thr Cys Gly Val Leu Leu Ser Leu
            290                 295                 300

Val Ile Thr Leu Tyr Cys Lys Arg Gly Arg Lys Lys Leu Leu Tyr Ile
305                 310                 315                 320

Phe Lys Gln Pro Phe Met Arg Pro Val Gln Thr Thr Gln Glu Glu Asp
                325                 330                 335

Gly Cys Ser Cys Arg Phe Pro Glu Glu Glu Glu Gly Gly Cys Glu Leu
            340                 345                 350

Arg Val Lys Phe Ser Arg Ser Ala Asp Ala Pro Ala Tyr Lys Gln Gly
                355                 360                 365

Gln Asn Gln Leu Tyr Asn Glu Leu Asn Leu Gly Arg Arg Glu Glu Tyr
            370                 375                 380

Asp Val Leu Asp Lys Arg Arg Gly Arg Asp Pro Glu Met Gly Gly Lys
385                 390                 395                 400

Pro Arg Arg Lys Asn Pro Gln Glu Gly Leu Tyr Asn Glu Leu Gln Lys
                405                 410                 415

Asp Lys Met Ala Glu Ala Tyr Ser Glu Ile Gly Met Lys Gly Glu Arg
            420                 425                 430

Arg Arg Gly Lys Gly His Asp Gly Leu Tyr Gln Gly Leu Ser Thr Ala
                435                 440                 445

Thr Lys Asp Thr Tyr Asp Ala Leu His Met Gln Ala Leu Pro Pro Arg
            450                 455                 460

<210> SEQ ID NO 130
<211> LENGTH: 467
<212> TYPE: PRT
<213> ORGANISM: Artificial Sequence
<220> FEATURE:
<223> OTHER INFORMATION: anti-BCMA CAR

<400> SEQUENCE: 130

Gln Ile Gln Leu Val Gln Ser Gly Pro Asp Leu Lys Lys Pro Gly Glu
1               5                   10                  15

Thr Val Lys Leu Ser Cys Lys Ala Ser Gly Tyr Thr Phe Thr Asn Phe
            20                  25                  30

Gly Met Asn Trp Val Lys Gln Ala Pro Gly Lys Gly Phe Lys Trp Met
        35                  40                  45

Ala Trp Ile Asn Thr Tyr Thr Gly Glu Ser Tyr Phe Ala Asp Asp Phe
    50                  55                  60

Lys Gly Arg Phe Ala Phe Ser Val Glu Thr Ser Ala Thr Thr Ala Tyr
65                  70                  75                  80

Leu Gln Ile Asn Asn Leu Lys Thr Glu Asp Thr Ala Thr Tyr Phe Cys
                85                  90                  95

Ala Arg Gly Glu Ile Tyr Tyr Gly Tyr Asp Gly Gly Phe Ala Tyr Trp
            100                 105                 110

Gly Gln Gly Thr Leu Val Thr Val Ser Ala Gly Gly Gly Gly Ser Gly
        115                 120                 125

Gly Gly Gly Ser Gly Gly Gly Gly Ser Asp Val Val Met Thr Gln Ser
    130                 135                 140

His Arg Phe Met Ser Thr Ser Val Gly Asp Arg Val Ser Ile Thr Cys
145                 150                 155                 160

Arg Ala Ser Gln Asp Val Asn Thr Ala Val Ser Trp Tyr Gln Gln Lys
                165                 170                 175

Pro Gly Gln Ser Pro Lys Leu Leu Ile Phe Ser Ala Ser Tyr Arg Tyr
```

```
                 180                 185                 190

Thr Gly Val Pro Asp Arg Phe Thr Gly Ser Gly Ser Gly Ala Asp Phe
            195                 200                 205

Thr Leu Thr Ile Ser Ser Val Gln Ala Glu Asp Leu Ala Val Tyr Tyr
        210                 215                 220

Cys Gln Gln His Tyr Ser Thr Pro Trp Thr Phe Gly Gly Gly Thr Lys
225                 230                 235                 240

Leu Asp Ile Lys Thr Thr Thr Pro Ala Pro Arg Pro Pro Thr Pro Ala
                245                 250                 255

Pro Thr Ile Ala Ser Gln Pro Leu Ser Leu Arg Pro Glu Ala Cys Arg
            260                 265                 270

Pro Ala Ala Gly Gly Ala Val His Thr Arg Gly Leu Asp Phe Ala Cys
        275                 280                 285

Asp Ile Tyr Ile Trp Ala Pro Leu Ala Gly Thr Cys Gly Val Leu Leu
    290                 295                 300

Leu Ser Leu Val Ile Thr Leu Tyr Cys Lys Arg Gly Arg Lys Lys Leu
305                 310                 315                 320

Leu Tyr Ile Phe Lys Gln Pro Phe Met Arg Pro Val Gln Thr Thr Gln
                325                 330                 335

Glu Glu Asp Gly Cys Ser Cys Arg Phe Pro Glu Glu Glu Glu Gly Gly
            340                 345                 350

Cys Glu Leu Arg Val Lys Phe Ser Arg Ser Ala Asp Ala Pro Ala Tyr
        355                 360                 365

Lys Gln Gly Gln Asn Gln Leu Tyr Asn Glu Leu Asn Leu Gly Arg Arg
    370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
                405                 410                 415

Leu Gln Lys Asp Lys Met Ala Glu Ala Tyr Ser Glu Ile Gly Met Lys
            420                 425                 430

Gly Glu Arg Arg Arg Gly Lys Gly His Asp Gly Leu Tyr Gln Gly Leu
        435                 440                 445

Ser Thr Ala Thr Lys Asp Thr Tyr Asp Ala Leu His Met Gln Ala Leu
    450                 455                 460

Pro Pro Arg
465

<210> SEQ ID NO 131
<211> LENGTH: 472
<212> TYPE: PRT
<213> ORGANISM: Artificial Sequence
<220> FEATURE:
<223> OTHER INFORMATION: anti-BCMA CAR

<400> SEQUENCE: 131

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
```

```
                65                  70                  75                  80
Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
               100                 105                 110

Val Thr Val Ser Ser Gly Gly Gly Gly Ser Gly Gly Gly Gly Ser Gly
               115                 120                 125

Gly Gly Ser Gln Ile Gln Leu Val Gln Ser Gly Pro Glu Leu Lys
130                 135                 140

Lys Pro Gly Glu Thr Val Lys Ile Ser Cys Lys Ala Ser Gly Tyr Thr
145                 150                 155                 160

Phe Thr Asp Tyr Ser Ile Asn Trp Val Lys Arg Ala Pro Gly Lys Gly
               165                 170                 175

Leu Lys Trp Met Gly Trp Ile Asn Thr Glu Thr Arg Glu Pro Ala Tyr
               180                 185                 190

Ala Tyr Asp Phe Arg Gly Arg Phe Ala Phe Ser Leu Glu Thr Ser Ala
               195                 200                 205

Ser Thr Ala Tyr Leu Gln Ile Asn Asn Leu Lys Tyr Glu Asp Thr Ala
               210                 215                 220

Thr Tyr Phe Cys Ala Leu Asp Tyr Ser Tyr Ala Met Asp Tyr Trp Gly
225                 230                 235                 240

Gln Gly Thr Ser Val Thr Val Ser Ser Thr Thr Thr Pro Ala Pro Arg
               245                 250                 255

Pro Pro Thr Pro Ala Pro Thr Ile Ala Ser Gln Pro Leu Ser Leu Arg
               260                 265                 270

Pro Glu Ala Cys Arg Pro Ala Ala Gly Gly Ala Val His Thr Arg Gly
               275                 280                 285

Leu Asp Phe Ala Cys Asp Ile Tyr Ile Trp Ala Pro Leu Ala Gly Thr
               290                 295                 300

Cys Gly Val Leu Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
               325                 330                 335

Val Gln Thr Thr Gln Glu Glu Asp Gly Cys Ser Cys Arg Phe Pro Glu
               340                 345                 350

Glu Glu Glu Gly Gly Cys Glu Leu Arg Val Lys Phe Ser Arg Ser Ala
               355                 360                 365

Asp Ala Pro Ala Tyr Lys Gln Gly Gln Asn Gln Leu Tyr Asn Glu Leu
370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
               405                 410                 415

Gly Leu Tyr Asn Glu Leu Gln Lys Asp Lys Met Ala Glu Ala Tyr Ser
               420                 425                 430

Glu Ile Gly Met Lys Gly Glu Arg Arg Arg Gly Lys Gly His Asp Gly
               435                 440                 445

Leu Tyr Gln Gly Leu Ser Thr Ala Thr Lys Asp Thr Tyr Asp Ala Leu
               450                 455                 460

His Met Gln Ala Leu Pro Pro Arg
465                 470

<210> SEQ ID NO 132
```

<211> LENGTH: 466
<212> TYPE: PRT
<213> ORGANISM: Artificial Sequence
<220> FEATURE:
<223> OTHER INFORMATION: anti-BCMA CAR

<400> SEQUENCE: 132

```
Gln Ile Gln Leu Val Gln Ser Gly Pro Glu Leu Lys Lys Pro Gly Glu
1               5                   10                  15
Thr Val Lys Ile Ser Cys Lys Ala Ser Gly Tyr Thr Phe Thr Asp Tyr
            20                  25                  30
Ser Ile Asn Trp Val Lys Arg Ala Pro Gly Lys Gly Leu Lys Trp Met
        35                  40                  45
Gly Trp Ile Asn Thr Glu Thr Arg Glu Pro Ala Tyr Ala Tyr Asp Phe
    50                  55                  60
Arg Gly Arg Phe Ala Phe Ser Leu Glu Thr Ser Ala Ser Thr Ala Tyr
65                  70                  75                  80
Leu Gln Ile Asn Asn Leu Lys Tyr Glu Asp Thr Ala Thr Tyr Phe Cys
                85                  90                  95
Ala Leu Asp Tyr Ser Tyr Ala Met Asp Tyr Trp Gly Gln Gly Thr Ser
            100                 105                 110
Val Thr Val Ser Ser Gly Gly Gly Ser Gly Gly Gly Gly Ser Gly
        115                 120                 125
Gly Gly Gly Ser Asp Ile Val Leu Thr Gln Ser Pro Ala Ser Leu Ala
    130                 135                 140
Met Ser Leu Gly Lys Arg Ala Thr Ile Ser Cys Arg Ala Ser Glu Ser
145                 150                 155                 160
Val Ser Val Ile Gly Ala His Leu Ile His Trp Tyr Gln Gln Lys Pro
                165                 170                 175
Gly Gln Pro Pro Lys Leu Leu Ile Tyr Leu Ala Ser Asn Leu Glu Thr
            180                 185                 190
Gly Val Pro Ala Arg Phe Ser Gly Ser Gly Ser Gly Thr Asp Phe Thr
        195                 200                 205
Leu Thr Ile Asp Pro Val Glu Glu Asp Asp Val Ala Ile Tyr Ser Cys
    210                 215                 220
Leu Gln Ser Arg Ile Phe Pro Arg Thr Phe Gly Gly Gly Thr Lys Leu
225                 230                 235                 240
Glu Ile Lys Thr Thr Thr Pro Ala Pro Arg Pro Pro Thr Pro Ala Pro
                245                 250                 255
Thr Ile Ala Ser Gln Pro Leu Ser Leu Arg Pro Glu Ala Cys Arg Pro
            260                 265                 270
Ala Ala Gly Gly Ala Val His Thr Arg Gly Leu Asp Phe Ala Cys Asp
        275                 280                 285
Ile Tyr Ile Trp Ala Pro Leu Ala Gly Thr Cys Gly Val Leu Leu Leu
    290                 295                 300
Ser Leu Val Ile Thr Leu Tyr Cys Lys Arg Gly Arg Lys Lys Leu Leu
305                 310                 315                 320
Tyr Ile Phe Lys Gln Pro Phe Met Arg Pro Val Gln Thr Thr Gln Glu
                325                 330                 335
Glu Asp Gly Cys Ser Cys Arg Phe Pro Glu Glu Glu Glu Gly Gly Cys
            340                 345                 350
Glu Leu Arg Val Lys Phe Ser Arg Ser Ala Asp Ala Pro Ala Tyr Lys
        355                 360                 365
Gln Gly Gln Asn Gln Leu Tyr Asn Glu Leu Asn Leu Gly Arg Arg Glu
    370                 375                 380
```

```
Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg
465

<210> SEQ ID NO 133
<211> LENGTH: 466
<212> TYPE: PRT
<213> ORGANISM: Artificial Sequence
<220> FEATURE:
<223> OTHER INFORMATION: anti-BCMA CAR

<400> SEQUENCE: 133

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Arg His Tyr
            20                  25                  30

Ser Met Asn Trp Val Lys Gln Ala Pro Gly Lys Gly Leu Lys Trp Met
        35                  40                  45

Gly Arg Ile Asn Thr Glu Ser Gly Val Pro Ile Tyr Ala Asp Asp Phe
    50                  55                  60

Lys Gly Arg Phe Ala Phe Ser Val Glu Thr Ser Ala Ser Thr Ala Tyr
65                  70                  75                  80

Leu Val Ile Asn Asn Leu Lys Asp Glu Asp Thr Ala Ser Tyr Phe Cys
                85                  90                  95

Ser Asn Asp Tyr Leu Tyr Ser Leu Asp Phe Trp Gly Gln Gly Thr Ala
            100                 105                 110

Leu Thr Val Ser Ser Gly Gly Gly Gly Ser Gly Gly Gly Gly Ser Gly
        115                 120                 125

Gly Gly Gly Ser Asp Ile Val Leu Thr Gln Ser Pro Pro Ser Leu Ala
    130                 135                 140

Met Ser Leu Gly Lys Arg Ala Thr Ile Ser Cys Arg Ala Ser Glu Ser
145                 150                 155                 160

Val Thr Ile Leu Gly Ser His Leu Ile Tyr Trp Tyr Gln Gln Lys Pro
                165                 170                 175

Gly Gln Pro Pro Thr Leu Leu Ile Gln Leu Ala Ser Asn Val Gln Thr
            180                 185                 190

Gly Val Pro Ala Arg Phe Ser Gly Ser Gly Ser Arg Thr Asp Phe Thr
        195                 200                 205

Leu Thr Ile Asp Pro Val Glu Glu Asp Asp Val Ala Val Tyr Tyr Cys
    210                 215                 220

Leu Gln Ser Arg Thr Ile Pro Arg Thr Phe Gly Gly Gly Thr Lys Leu
225                 230                 235                 240

Glu Ile Lys Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270
```

```
Ala Ala Gly Gly Ala Val His Thr Arg Gly Leu Asp Phe Ala Cys Asp
            275                 280                 285

Ile Tyr Ile Trp Ala Pro Leu Ala Gly Thr Cys Gly Val Leu Leu Leu
        290                 295                 300

Ser Leu Val Ile Thr Leu Tyr Cys Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Glu Gly Gly Cys
            340                 345                 350

Glu Leu Arg Val Lys Phe Ser Arg Ser Ala Asp Ala Pro Ala Tyr Lys
        355                 360                 365

Gln Gly Gln Asn Gln Leu Tyr Asn Glu Leu Asn Leu Gly Arg Arg Glu
    370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
        435                 440                 445

Thr Ala Thr Lys Asp Thr Tyr Asp Ala Leu His Met Gln Ala Leu Pro
    450                 455                 460

Pro Arg
465

<210> SEQ ID NO 134
<211> LENGTH: 466
<212> TYPE: PRT
<213> ORGANISM: Artificial Sequence
<220> FEATURE:
<223> OTHER INFORMATION: anti-BCMA CAR

<400> SEQUENCE: 134

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr His Tyr
            20                  25                  30

Ser Met Asn Trp Val Lys Gln Ala Pro Gly Lys Gly Leu Lys Trp Met
        35                  40                  45

Gly Arg Ile Asn Thr Glu Thr Gly Glu Pro Leu Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Val Ile Asn Asn Leu Lys Asn Glu Asp Thr Ala Thr Phe Phe Cys
                85                  90                  95

Ser Asn Asp Tyr Leu Tyr Ser Cys Asp Tyr Trp Gly Gln Gly Thr Thr
            100                 105                 110

Leu Thr Val Ser Ser Gly Gly Gly Gly Ser Gly Gly Gly Gly Ser Gly
        115                 120                 125

Gly Gly Gly Ser Asp Ile Val Leu Thr Gln Ser Pro Pro Ser Leu Ala
    130                 135                 140

Met Ser Leu Gly Lys Arg Ala Thr Ile Ser Cys Arg Ala Ser Glu Ser
145                 150                 155                 160
```

Val Thr Ile Leu Gly Ser His Leu Ile Tyr Trp Tyr Gln Lys Pro
              165                 170                 175

Gly Gln Pro Pro Thr Leu Leu Ile Gln Leu Ala Ser Asn Val Gln Thr
            180                 185                 190

Gly Val Pro Ala Arg Phe Ser Gly Ser Gly Ser Arg Thr Asp Phe Thr
            195                 200                 205

Leu Thr Ile Asp Pro Val Glu Glu Asp Val Ala Val Tyr Tyr Cys
        210                 215                 220

Leu Gln Ser Arg Thr Ile Pro Arg Thr Phe Gly Gly Gly Thr Lys Leu
225                 230                 235                 240

Glu Ile Lys Thr Thr Thr Pro Ala Pro Arg Pro Pro Thr Pro Ala Pro
                245                 250                 255

Thr Ile Ala Ser Gln Pro Leu Ser Leu Arg Pro Glu Ala Cys Arg Pro
            260                 265                 270

Ala Ala Gly Gly Ala Val His Thr Arg Gly Leu Asp Phe Ala Cys Asp
        275                 280                 285

Ile Tyr Ile Trp Ala Pro Leu Ala Gly Thr Cys Gly Val Leu Leu Leu
        290                 295                 300

Ser Leu Val Ile Thr Leu Tyr Cys Lys Arg Gly Arg Lys Lys Leu Leu
305                 310                 315                 320

Tyr Ile Phe Lys Gln Pro Phe Met Arg Pro Val Gln Thr Thr Gln Glu
                325                 330                 335

Glu Asp Gly Cys Ser Cys Arg Phe Pro Glu Glu Glu Glu Gly Gly Cys
            340                 345                 350

Glu Leu Arg Val Lys Phe Ser Arg Ser Ala Asp Ala Pro Ala Tyr Lys
            355                 360                 365

Gln Gly Gln Asn Gln Leu Tyr Asn Glu Leu Asn Leu Gly Arg Arg Glu
        370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
            435                 440                 445

Thr Ala Thr Lys Asp Thr Tyr Asp Ala Leu His Met Gln Ala Leu Pro
        450                 455                 460

Pro Arg
465

<210> SEQ ID NO 135
<211> LENGTH: 482
<212> TYPE: PRT
<213> ORGANISM: Artificial Sequence
<220> FEATURE:
<223> OTHER INFORMATION: anti-BCMA CAR

<400> SEQUENCE: 135

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
 50                  55                  60

Arg Phe Ser Gly Ser Gly Ser Arg Thr Asp Phe Thr Leu Thr Ile Asp
 65                  70                  75                  80

Pro Val Glu Glu Asp Asp Val Ala Val Tyr Tyr Cys Leu Gln Ser Arg
                 85                  90                  95

Thr Ile Pro Arg Thr Phe Gly Gly Thr Lys Leu Glu Ile Lys Gly
            100                 105                 110

Ser Thr Ser Gly Ser Gly Lys Pro Gly Ser Gly Glu Gly Ser Thr Lys
            115                 120                 125

Gly Gln Ile Gln Leu Val Gln Ser Gly Pro Glu Leu Lys Lys Pro Gly
130                 135                 140

Glu Thr Val Lys Ile Ser Cys Lys Ala Ser Gly Tyr Thr Phe Thr Asp
145                 150                 155                 160

Tyr Ser Ile Asn Trp Val Lys Arg Ala Pro Gly Lys Gly Leu Lys Trp
                165                 170                 175

Met Gly Trp Ile Asn Thr Glu Thr Arg Glu Pro Ala Tyr Ala Tyr Asp
            180                 185                 190

Phe Arg Gly Arg Phe Ala Phe Ser Leu Glu Thr Ser Ala Ser Thr Ala
        195                 200                 205

Tyr Leu Gln Ile Asn Asn Leu Lys Tyr Glu Asp Thr Ala Thr Tyr Phe
    210                 215                 220

Cys Ala Leu Asp Tyr Ser Tyr Ala Met Asp Tyr Trp Gly Gln Gly Thr
225                 230                 235                 240

Ser Val Thr Val Ser Ser Phe Val Pro Val Phe Leu Pro Ala Lys Pro
                245                 250                 255

Thr Thr Thr Pro Ala Pro Arg Pro Pro Thr Pro Ala Pro Thr Ile Ala
            260                 265                 270

Ser Gln Pro Leu Ser Leu Arg Pro Glu Ala Cys Arg Pro Ala Ala Gly
        275                 280                 285

Gly Ala Val His Thr Arg Gly Leu Asp Phe Ala Cys Asp Ile Tyr Ile
    290                 295                 300

Trp Ala Pro Leu Ala Gly Thr Cys Gly Val Leu Leu Leu Ser Leu Val
305                 310                 315                 320

Ile Thr Leu Tyr Cys Asn His Arg Asn Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
450                 455                 460

```
Thr Ala Thr Lys Asp Thr Tyr Asp Ala Leu His Met Gln Ala Leu Pro
465                 470                 475                 480

Pro Arg

<210> SEQ ID NO 136
<211> LENGTH: 440
<212> TYPE: PRT
<213> ORGANISM: Artificial Sequence
<220> FEATURE:
<223> OTHER INFORMATION: anti-BCMA CAR

<400> SEQUENCE: 136

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
                20                  25                  30

Tyr Ile Asn Trp Val Arg Gln Ala Pro Gly Gln Gly Leu Glu Trp Met
            35                  40                  45

Gly Trp Ile Tyr Phe Ala Ser Gly Asn Ser Glu Tyr Asn Gln Lys Phe
    50                  55                  60

Thr Gly Arg Val Thr Met Thr Arg Asp Thr Ser Ile Asn Thr Ala Tyr
65                  70                  75                  80

Met Glu Leu Ser Ser Leu Thr Ser Glu Asp Thr Ala Val Tyr Phe Cys
                85                  90                  95

Ala Ser Leu Tyr Asp Tyr Asp Trp Tyr Phe Asp Val Trp Gly Gln Gly
                100                 105                 110

Thr Met Val Thr Val Ser Ser Gly Gly Gly Gly Ser Gly Gly Gly Gly
            115                 120                 125

Ser Gly Gly Gly Gly Ser Asp Ile Val Met Thr Gln Thr Pro Leu Ser
    130                 135                 140

Leu Ser Val Thr Pro Gly Gln Pro Ala Ser Ile Ser Cys Lys Ser Ser
145                 150                 155                 160

Gln Ser Leu Val His Ser Asn Gly Asn Thr Tyr Leu His Trp Tyr Leu
                165                 170                 175

Gln Lys Pro Gly Gln Ser Pro Gln Leu Leu Ile Tyr Lys Val Ser Asn
            180                 185                 190

Arg Phe Ser Gly Val Pro Asp Arg Phe Ser Gly Ser Gly Ser Gly Thr
        195                 200                 205

Asp Phe Thr Leu Lys Ile Ser Arg Val Glu Ala Glu Asp Val Gly Ile
    210                 215                 220

Tyr Tyr Cys Ser Gln Ser Ser Ile Tyr Pro Trp Thr Phe Gly Gln Gly
225                 230                 235                 240

Thr Lys Leu Glu Ile Lys Gly Leu Ala Val Ser Thr Ile Ser Ser Phe
                245                 250                 255

Phe Pro Pro Gly Tyr Gln Ile Tyr Ile Trp Ala Pro Leu Ala Gly Thr
            260                 265                 270

Cys Gly Val Leu Leu Leu Ser Leu Val Ile Thr Leu Tyr Cys Lys Arg
        275                 280                 285

Gly Arg Lys Lys Leu Leu Tyr Ile Phe Lys Gln Pro Phe Met Arg Pro
    290                 295                 300

Val Gln Thr Thr Gln Glu Asp Gly Cys Ser Cys Arg Phe Pro Glu
305                 310                 315                 320

Glu Glu Glu Gly Gly Cys Glu Leu Arg Val Lys Phe Ser Arg Ser Ala
                325                 330                 335

Asp Ala Pro Ala Tyr Gln Gln Gly Gln Asn Gln Leu Tyr Asn Glu Leu
```

```
                340                 345                 350
Asn Leu Gly Arg Arg Glu Glu Tyr Asp Val Leu Asp Lys Arg Arg Gly
            355                 360                 365

Arg Asp Pro Glu Met Gly Gly Lys Pro Arg Arg Lys Asn Pro Gln Glu
    370                 375                 380

Gly Leu Tyr Asn Glu Leu Gln Lys Asp Lys Met Ala Glu Ala Tyr Ser
385                 390                 395                 400

Glu Ile Gly Met Lys Gly Glu Arg Arg Arg Gly Lys Gly His Asp Gly
                405                 410                 415

Leu Tyr Gln Gly Leu Ser Thr Ala Thr Lys Asp Thr Tyr Asp Ala Leu
            420                 425                 430

His Met Gln Ala Leu Pro Pro Arg
            435                 440

<210> SEQ ID NO 137
<211> LENGTH: 469
<212> TYPE: PRT
<213> ORGANISM: Artificial Sequence
<220> FEATURE:
<223> OTHER INFORMATION: anti-BCMA CAR

<400> SEQUENCE: 137

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
            20                  25                  30

Tyr Ile Asn Trp Val Arg Gln Ala Pro Gly Gln Gly Leu Glu Trp Met
        35                  40                  45

Gly Trp Ile Tyr Phe Ala Ser Gly Asn Ser Glu Tyr Asn Gln Lys Phe
    50                  55                  60

Thr Gly Arg Val Thr Met Thr Arg Asp Thr Ser Ile Asn Thr Ala Tyr
65                  70                  75                  80

Met Glu Leu Ser Ser Leu Thr Ser Glu Asp Thr Ala Val Tyr Phe Cys
                85                  90                  95

Ala Ser Leu Tyr Asp Tyr Asp Trp Tyr Phe Asp Val Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Asp Ile Val Met Thr Gln Thr Pro Leu Ser
    130                 135                 140

Leu Ser Val Thr Pro Gly Gln Pro Ala Ser Ile Ser Cys Lys Ser Ser
145                 150                 155                 160

Gln Ser Leu Val His Ser Asn Gly Asn Thr Tyr Leu His Trp Tyr Leu
                165                 170                 175

Gln Lys Pro Gly Gln Ser Pro Gln Leu Leu Ile Tyr Lys Val Ser Asn
            180                 185                 190

Arg Phe Ser Gly Val Pro Asp Arg Phe Ser Gly Ser Gly Ser Gly Thr
        195                 200                 205

Asp Phe Thr Leu Lys Ile Ser Arg Val Glu Ala Glu Asp Val Gly Ile
    210                 215                 220

Tyr Tyr Cys Ser Gln Ser Ser Ile Tyr Pro Trp Thr Phe Gly Gln Gly
225                 230                 235                 240

Thr Lys Leu Glu Ile Lys Thr Thr Thr Pro Ala Pro Arg Pro Pro Thr
                245                 250                 255

Pro Ala Pro Thr Ile Ala Ser Gln Pro Leu Ser Leu Arg Pro Glu Ala
```

```
                260                 265                 270
Cys Arg Pro Ala Ala Gly Gly Ala Val His Thr Arg Gly Leu Asp Phe
            275                 280                 285
Ala Cys Asp Ile Tyr Ile Trp Ala Pro Leu Ala Gly Thr Cys Gly Val
            290                 295                 300
Leu Leu Leu Ser Leu Val Ile Thr Leu Tyr Cys Lys Arg Gly Arg Lys
305                 310                 315                 320
Lys Leu Leu Tyr Ile Phe Lys Gln Pro Phe Met Arg Pro Val Gln Thr
                325                 330                 335
Thr Gln Glu Glu Asp Gly Cys Ser Cys Arg Phe Pro Glu Glu Glu Glu
            340                 345                 350
Gly Gly Cys Glu Leu Arg Val Lys Phe Ser Arg Ser Ala Asp Ala Pro
            355                 360                 365
Ala Tyr Gln Gln Gly Gln Asn Gln Leu Tyr Asn Glu Leu Asn Leu Gly
            370                 375                 380
Arg Arg Glu Glu Tyr Asp Val Leu Asp Lys Arg Arg Gly Arg Asp Pro
385                 390                 395                 400
Glu Met Gly Gly Lys Pro Arg Arg Lys Asn Pro Gln Glu Gly Leu Tyr
                405                 410                 415
Asn Glu Leu Gln Lys Asp Lys Met Ala Glu Ala Tyr Ser Glu Ile Gly
                420                 425                 430
Met Lys Gly Glu Arg Arg Arg Gly Lys Gly His Asp Gly Leu Tyr Gln
            435                 440                 445
Gly Leu Ser Thr Ala Thr Lys Asp Thr Tyr Asp Ala Leu His Met Gln
450                 455                 460
Ala Leu Pro Pro Arg
465

<210> SEQ ID NO 138
<211> LENGTH: 655
<212> TYPE: PRT
<213> ORGANISM: Artificial Sequence
<220> FEATURE:
<223> OTHER INFORMATION: anti-BCMA CAR

<400> SEQUENCE: 138

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ser Phe Pro Asp Tyr
                20                  25                  30
Tyr Ile Asn Trp Val Arg Gln Ala Pro Gly Gln Gly Leu Glu Trp Met
            35                  40                  45
Gly Trp Ile Tyr Phe Ala Ser Gly Asn Ser Glu Tyr Asn Gln Lys Phe
        50                  55                  60
Thr Gly Arg Val Thr Met Thr Arg Asp Thr Ser Ile Asn Thr Ala Tyr
65                  70                  75                  80
Met Glu Leu Ser Ser Leu Thr Ser Glu Asp Thr Ala Val Tyr Phe Cys
                85                  90                  95
Ala Ser Leu Tyr Asp Tyr Asp Trp Tyr Phe Asp Val Trp Gly Gln Gly
                100                 105                 110
Thr Met Val Thr Val Ser Ser Gly Gly Gly Gly Ser Gly Gly Gly Gly
            115                 120                 125
Ser Gly Gly Gly Gly Ser Asp Ile Val Met Thr Gln Thr Pro Leu Ser
        130                 135                 140
Leu Ser Val Thr Pro Gly Gln Pro Ala Ser Ile Ser Cys Lys Ser Ser
```

```
                145                 150                 155                 160
        Gln Ser Leu Val His Ser Asn Gly Asn Thr Tyr Leu His Trp Tyr Leu
                        165                 170                 175
        Gln Lys Pro Gly Gln Ser Pro Gln Leu Leu Ile Tyr Lys Val Ser Asn
                        180                 185                 190
        Arg Phe Ser Gly Val Pro Asp Arg Phe Ser Gly Ser Gly Ser Gly Thr
                        195                 200                 205
        Asp Phe Thr Leu Lys Ile Ser Arg Val Glu Ala Glu Asp Val Gly Ile
                        210                 215                 220
        Tyr Tyr Cys Ser Gln Ser Ser Ile Tyr Pro Trp Thr Phe Gly Gln Gly
        225                 230                 235                 240
        Thr Lys Leu Glu Ile Lys Glu Pro Lys Ser Pro Asp Lys Thr His Thr
                        245                 250                 255
        Cys Pro Pro Cys Pro Ala Pro Val Ala Gly Pro Ser Val Phe Leu
                        260                 265                 270
        Phe Pro Pro Lys Pro Lys Asp Thr Leu Met Ile Ala Arg Thr Pro Glu
                        275                 280                 285
        Val Thr Cys Val Val Val Asp Val Ser His Glu Asp Pro Glu Val Lys
                        290                 295                 300
        Phe Asn Trp Tyr Val Asp Gly Val Glu Val His Asn Ala Lys Thr Lys
        305                 310                 315                 320
        Pro Arg Glu Glu Gln Tyr Asn Ser Thr Tyr Arg Val Val Ser Val Leu
                        325                 330                 335
        Thr Val Leu His Gln Asp Trp Leu Asn Gly Lys Glu Tyr Lys Cys Lys
                        340                 345                 350
        Val Ser Asn Lys Ala Leu Pro Ala Pro Ile Glu Lys Thr Ile Ser Lys
                        355                 360                 365
        Ala Lys Gly Gln Pro Arg Glu Pro Gln Val Tyr Thr Leu Pro Pro Ser
                        370                 375                 380
        Arg Asp Glu Leu Thr Lys Asn Gln Val Ser Leu Thr Cys Leu Val Lys
        385                 390                 395                 400
        Gly Phe Tyr Pro Ser Asp Ile Ala Val Glu Trp Glu Ser Asn Gly Gln
                        405                 410                 415
        Pro Glu Asn Asn Tyr Lys Thr Thr Pro Pro Val Leu Asp Ser Asp Gly
                        420                 425                 430
        Ser Phe Phe Leu Tyr Ser Lys Leu Thr Val Asp Lys Ser Arg Trp Gln
                        435                 440                 445
        Gln Gly Asn Val Phe Ser Cys Ser Val Met His Glu Ala Leu His Asn
                        450                 455                 460
        His Tyr Thr Gln Lys Ser Leu Ser Leu Ser Pro Gly Lys Ile Tyr Ile
        465                 470                 475                 480
        Trp Ala Pro Leu Ala Gly Thr Cys Gly Val Leu Leu Leu Ser Leu Val
                        485                 490                 495
        Ile Thr Leu Tyr Cys Lys Arg Gly Arg Lys Lys Leu Leu Tyr Ile Phe
                        500                 505                 510
        Lys Gln Pro Phe Met Arg Pro Val Gln Thr Thr Gln Glu Glu Asp Gly
                        515                 520                 525
        Cys Ser Cys Arg Phe Pro Glu Glu Glu Glu Gly Gly Cys Glu Leu Arg
                        530                 535                 540
        Val Lys Phe Ser Arg Ser Ala Asp Ala Pro Ala Tyr Gln Gln Gly Gln
        545                 550                 555                 560
        Asn Gln Leu Tyr Asn Glu Leu Asn Leu Gly Arg Arg Glu Glu Tyr Asp
                        565                 570                 575
```

```
Val Leu Asp Lys Arg Gly Arg Asp Pro Glu Met Gly Gly Lys Pro
            580                 585                 590

Arg Arg Lys Asn Pro Gln Glu Gly Leu Tyr Asn Glu Leu Gln Lys Asp
        595                 600                 605

Lys Met Ala Glu Ala Tyr Ser Glu Ile Gly Met Lys Gly Glu Arg Arg
    610                 615                 620

Arg Gly Lys Gly His Asp Gly Leu Tyr Gln Gly Leu Ser Thr Ala Thr
625                 630                 635                 640

Lys Asp Thr Tyr Asp Ala Leu His Met Gln Ala Leu Pro Pro Arg
            645                 650                 655

<210> SEQ ID NO 139
<211> LENGTH: 440
<212> TYPE: PRT
<213> ORGANISM: Artificial Sequence
<220> FEATURE:
<223> OTHER INFORMATION: anti-BCMA CAR

<400> SEQUENCE: 139

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
            20                  25                  30

Tyr Ile Asn Trp Val Arg Gln Ala Pro Gly Gln Gly Leu Glu Trp Met
        35                  40                  45

Gly Trp Ile Tyr Phe Ala Ser Gly Asn Ser Glu Tyr Asn Gln Lys Phe
    50                  55                  60

Thr Gly Arg Val Thr Met Thr Arg Asp Thr Ser Ser Thr Ala Tyr
65                  70                  75                  80

Met Glu Leu Ser Ser Leu Arg Ser Glu Asp Thr Ala Val Tyr Phe Cys
                85                  90                  95

Ala Ser Leu Tyr Asp Tyr Asp Trp Tyr Phe Asp Val Trp Gly Gln Gly
            100                 105                 110

Thr Met Val Thr Val Ser Ser Gly Gly Gly Ser Gly Gly Gly Gly
        115                 120                 125

Ser Gly Gly Gly Gly Ser Asp Ile Val Met Thr Gln Thr Pro Leu Ser
130                 135                 140

Leu Ser Val Thr Pro Gly Glu Pro Ala Ser Ile Ser Cys Lys Ser Ser
145                 150                 155                 160

Gln Ser Leu Val His Ser Asn Gly Asn Thr Tyr Leu His Trp Tyr Leu
                165                 170                 175

Gln Lys Pro Gly Gln Ser Pro Gln Leu Leu Ile Tyr Lys Val Ser Asn
            180                 185                 190

Arg Phe Ser Gly Val Pro Asp Arg Phe Ser Gly Ser Gly Ser Gly Ala
        195                 200                 205

Asp Phe Thr Leu Lys Ile Ser Arg Val Glu Ala Glu Asp Val Gly Val
    210                 215                 220

Tyr Tyr Cys Ala Glu Thr Ser His Val Pro Trp Thr Phe Gly Gln Gly
225                 230                 235                 240

Thr Lys Leu Glu Ile Lys Gly Leu Ala Val Ser Thr Ile Ser Ser Phe
                245                 250                 255

Phe Pro Pro Gly Tyr Gln Ile Tyr Ile Trp Ala Pro Leu Ala Gly Thr
            260                 265                 270

Cys Gly Val Leu Leu Leu Ser Leu Val Ile Thr Leu Tyr Cys Lys Arg
        275                 280                 285
```

```
Gly Arg Lys Lys Leu Leu Tyr Ile Phe Lys Gln Pro Phe Met Arg Pro
            290                 295                 300

Val Gln Thr Thr Gln Glu Asp Gly Cys Ser Cys Arg Phe Pro Glu
305                 310                 315                 320

Glu Glu Glu Gly Gly Cys Glu Leu Arg Val Lys Phe Ser Arg Ser Ala
                    325                 330                 335

Asp Ala Pro Ala Tyr Gln Gln Gly Gln Asn Gln Leu Tyr Asn Glu Leu
                340                 345                 350

Asn Leu Gly Arg Arg Glu Glu Tyr Asp Val Leu Asp Lys Arg Arg Gly
            355                 360                 365

Arg Asp Pro Glu Met Gly Gly Lys Pro Arg Arg Lys Asn Pro Gln Glu
            370                 375                 380

Gly Leu Tyr Asn Glu Leu Gln Lys Asp Lys Met Ala Glu Ala Tyr Ser
385                 390                 395                 400

Glu Ile Gly Met Lys Gly Glu Arg Arg Arg Gly Lys Gly His Asp Gly
                    405                 410                 415

Leu Tyr Gln Gly Leu Ser Thr Ala Thr Lys Asp Thr Tyr Asp Ala Leu
                420                 425                 430

His Met Gln Ala Leu Pro Pro Arg
            435                 440

<210> SEQ ID NO 140
<211> LENGTH: 469
<212> TYPE: PRT
<213> ORGANISM: Artificial Sequence
<220> FEATURE:
<223> OTHER INFORMATION: anti-BCMA CAR

<400> SEQUENCE: 140

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
                20                  25                  30

Tyr Ile Asn Trp Val Arg Gln Ala Pro Gly Gln Gly Leu Glu Trp Met
            35                  40                  45

Gly Trp Ile Tyr Phe Ala Ser Gly Asn Ser Glu Tyr Asn Gln Lys Phe
50                  55                  60

Thr Gly Arg Val Thr Met Thr Arg Asp Thr Ser Ser Thr Ala Tyr
65                  70                  75              80

Met Glu Leu Ser Ser Leu Arg Ser Glu Asp Thr Ala Val Tyr Phe Cys
                85                  90                  95

Ala Ser Leu Tyr Asp Tyr Asp Trp Tyr Phe Asp Val Trp Gly Gln Gly
                100                 105                 110

Thr Met Val Thr Val Ser Gly Gly Gly Gly Ser Gly Gly Gly Gly
            115                 120                 125

Ser Gly Gly Gly Ser Asp Ile Val Met Thr Gln Thr Pro Leu Ser
            130                 135                 140

Leu Ser Val Thr Pro Gly Glu Pro Ala Ser Ile Ser Cys Lys Ser Ser
145                 150                 155                 160

Gln Ser Leu Val His Ser Asn Gly Asn Thr Tyr Leu His Trp Tyr Leu
                165                 170                 175

Gln Lys Pro Gly Gln Ser Pro Gln Leu Leu Ile Tyr Lys Val Ser Asn
            180                 185                 190

Arg Phe Ser Gly Val Pro Asp Arg Phe Ser Gly Ser Gly Ser Gly Ala
            195                 200                 205
```

```
Asp Phe Thr Leu Lys Ile Ser Arg Val Glu Ala Glu Asp Val Gly Val
    210                 215                 220

Tyr Tyr Cys Ala Glu Thr Ser His Val Pro Trp Thr Phe Gly Gln Gly
225                 230                 235                 240

Thr Lys Leu Glu Ile Lys Thr Thr Thr Pro Ala Pro Arg Pro Pro Thr
                245                 250                 255

Pro Ala Pro Thr Ile Ala Ser Gln Pro Leu Ser Leu Arg Pro Glu Ala
                260                 265                 270

Cys Arg Pro Ala Ala Gly Gly Ala Val His Thr Arg Gly Leu Asp Phe
            275                 280                 285

Ala Cys Asp Ile Tyr Ile Trp Ala Pro Leu Ala Gly Thr Cys Gly Val
    290                 295                 300

Leu Leu Leu Ser Leu Val Ile Thr Leu Tyr Cys Lys Arg Gly Arg Lys
305                 310                 315                 320

Lys Leu Leu Tyr Ile Phe Lys Gln Pro Phe Met Arg Pro Val Gln Thr
                325                 330                 335

Thr Gln Glu Glu Asp Gly Cys Ser Cys Arg Phe Pro Glu Glu Glu Glu
                340                 345                 350

Gly Gly Cys Glu Leu Arg Val Lys Phe Ser Arg Ser Ala Asp Ala Pro
            355                 360                 365

Ala Tyr Gln Gln Gly Gln Asn Gln Leu Tyr Asn Glu Leu Asn Leu Gly
    370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
                420                 425                 430

Met Lys Gly Glu Arg Arg Arg Gly Lys Gly His Asp Gly Leu Tyr Gln
            435                 440                 445

Gly Leu Ser Thr Ala Thr Lys Asp Thr Tyr Asp Ala Leu His Met Gln
    450                 455                 460

Ala Leu Pro Pro Arg
465

<210> SEQ ID NO 141
<211> LENGTH: 655
<212> TYPE: PRT
<213> ORGANISM: Artificial Sequence
<220> FEATURE:
<223> OTHER INFORMATION: anti-BCMA CAR

<400> SEQUENCE: 141

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
                20                  25                  30

Tyr Ile Asn Trp Val Arg Gln Ala Pro Gly Gln Gly Leu Glu Trp Met
            35                  40                  45

Gly Trp Ile Tyr Phe Ala Ser Gly Asn Ser Glu Tyr Asn Gln Lys Phe
    50                  55                  60

Thr Gly Arg Val Thr Met Thr Arg Asp Thr Ser Ser Ser Thr Ala Tyr
65                  70                  75                  80

Met Glu Leu Ser Ser Leu Arg Ser Glu Asp Thr Ala Val Tyr Phe Cys
                85                  90                  95
```

```
Ala Ser Leu Tyr Asp Tyr Asp Trp Tyr Phe Asp Val Trp Gly Gln Gly
            100                 105                 110

Thr Met Val Thr Val Ser Ser Gly Gly Gly Ser Gly Gly Gly
            115                 120                 125

Ser Gly Gly Gly Ser Asp Ile Val Met Thr Gln Thr Pro Leu Ser
130                 135                 140

Leu Ser Val Thr Pro Gly Glu Pro Ala Ser Ile Ser Cys Lys Ser Ser
145                 150                 155                 160

Gln Ser Leu Val His Ser Asn Gly Asn Thr Tyr Leu His Trp Tyr Leu
            165                 170                 175

Gln Lys Pro Gly Gln Ser Pro Gln Leu Leu Ile Tyr Lys Val Ser Asn
            180                 185                 190

Arg Phe Ser Gly Val Pro Asp Arg Phe Ser Gly Ser Gly Ser Gly Ala
            195                 200                 205

Asp Phe Thr Leu Lys Ile Ser Arg Val Glu Ala Glu Asp Val Gly Val
            210                 215                 220

Tyr Tyr Cys Ala Glu Thr Ser His Val Pro Trp Thr Phe Gly Gln Gly
225                 230                 235                 240

Thr Lys Leu Glu Ile Lys Glu Pro Lys Ser Pro Asp Lys Thr His Thr
            245                 250                 255

Cys Pro Pro Cys Pro Ala Pro Pro Val Ala Gly Pro Ser Val Phe Leu
            260                 265                 270

Phe Pro Pro Lys Pro Lys Asp Thr Leu Met Ile Ala Arg Thr Pro Glu
            275                 280                 285

Val Thr Cys Val Val Val Asp Val Ser His Glu Asp Pro Glu Val Lys
            290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
            325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
            355                 360                 365

Ala Lys Gly Gln Pro Arg Glu Pro Gln Val Tyr Thr Leu Pro Pro Ser
            370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
            405                 410                 415

Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
            435                 440                 445

Gln Gly Asn Val Phe Ser Cys Ser Val Met His Glu Ala Leu His Asn
            450                 455                 460

His Tyr Thr Gln Lys Ser Leu Ser Leu Ser Pro Gly Lys Ile Tyr Ile
465                 470                 475                 480

Trp Ala Pro Leu Ala Gly Thr Cys Gly Val Leu Leu Leu Ser Leu Val
            485                 490                 495

Ile Thr Leu Tyr Cys Lys Arg Gly Arg Lys Lys Leu Leu Tyr Ile Phe
            500                 505                 510
```

```
Lys Gln Pro Phe Met Arg Pro Val Gln Thr Thr Gln Glu Glu Asp Gly
            515                 520                 525

Cys Ser Cys Arg Phe Pro Glu Glu Glu Glu Gly Gly Cys Glu Leu Arg
        530                 535                 540

Val Lys Phe Ser Arg Ser Ala Asp Ala Pro Ala Tyr Gln Gln Gly Gln
545                 550                 555                 560

Asn Gln Leu Tyr Asn Glu Leu Asn Leu Gly Arg Arg Glu Glu Tyr Asp
                565                 570                 575

Val Leu Asp Lys Arg Arg Gly Arg Asp Pro Glu Met Gly Gly Lys Pro
            580                 585                 590

Arg Arg Lys Asn Pro Gln Glu Gly Leu Tyr Asn Glu Leu Gln Lys Asp
        595                 600                 605

Lys Met Ala Glu Ala Tyr Ser Glu Ile Gly Met Lys Gly Glu Arg Arg
    610                 615                 620

Arg Gly Lys Gly His Asp Gly Leu Tyr Gln Gly Leu Ser Thr Ala Thr
625                 630                 635                 640

Lys Asp Thr Tyr Asp Ala Leu His Met Gln Ala Leu Pro Pro Arg
                645                 650                 655

<210> SEQ ID NO 142
<211> LENGTH: 28
<212> TYPE: PRT
<213> ORGANISM: Artificial Sequence
<220> FEATURE:
<223> OTHER INFORMATION: CD8a TM

<400> SEQUENCE: 142

Ile Tyr Ile Trp Ala Pro Leu Ala Gly Thr Cys Gly Val Leu Leu Leu
1               5                   10                  15

Ser Leu Val Ile Thr Leu Tyr Cys Asn His Arg Asn
            20                  25

<210> SEQ ID NO 143
<211> LENGTH: 21
<212> TYPE: PRT
<213> ORGANISM: Artificial Sequence
<220> FEATURE:
<223> OTHER INFORMATION: CD8a TM

<400> SEQUENCE: 143

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 144
<211> LENGTH: 4
<212> TYPE: PRT
<213> ORGANISM: Artificial Sequence
<220> FEATURE:
<223> OTHER INFORMATION: Linking peptide

<400> SEQUENCE: 144

Arg Ala Ala Ala
1

<210> SEQ ID NO 145
<211> LENGTH: 118
<212> TYPE: PRT
<213> ORGANISM: Artificial Sequence
<220> FEATURE:
<223> OTHER INFORMATION: Variable heavy (VH) Anti-BCMA
```

<400> SEQUENCE: 145

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Asp Tyr Thr Glu Asp Tyr Trp Gly Gln Gly Thr
            100                 105                 110

Leu Val Thr Val Ser Ser
            115

<210> SEQ ID NO 146
<211> LENGTH: 110
<212> TYPE: PRT
<213> ORGANISM: Artificial Sequence
<220> FEATURE:
<223> OTHER INFORMATION: Variable light (VL) Anti-BCMA

<400> SEQUENCE: 146

Gln Ser Ala Leu Thr Gln Pro Ala Ser Val Ser Gly Ser Pro Gly Gln
1               5                   10                  15

Ser Ile Thr Ile Ser Cys Thr Gly Ser Ser Ser Asp Val Gly Lys Tyr
            20                  25                  30

Asn Leu Val Ser Trp Tyr Gln Gln Pro Pro Gly Lys Ala Pro Lys Leu
        35                  40                  45

Ile Ile Tyr Asp Val Asn Lys Arg Pro Ser Gly Val Ser Asn Arg Phe
50                  55                  60

Ser Gly Ser Lys Ser Gly Asn Thr Ala Thr Leu Thr Ile Ser Gly Leu
65                  70                  75                  80

Gln Gly Asp Asp Glu Ala Asp Tyr Tyr Cys Ser Ser Tyr Gly Gly Ser
                85                  90                  95

Arg Ser Tyr Val Phe Gly Thr Gly Thr Lys Val Thr Val Leu
            100                 105                 110

<210> SEQ ID NO 147
<211> LENGTH: 118
<212> TYPE: PRT
<213> ORGANISM: Artificial Sequence
<220> FEATURE:
<223> OTHER INFORMATION: Variable heavy (VH) Anti-BCMA

<400> SEQUENCE: 147

Glu Val Gln Leu Val Gln Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Ala Ala Trp Ser Ala Pro Thr Asp Tyr Trp Gly Gln Gly Thr
            100                 105                 110

Leu Val Thr Val Ser Ser
            115

<210> SEQ ID NO 148
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 148

Asp Ile Gln Met Thr Gln Ser Pro Ala Phe Leu Ser Ala Ser Val Gly
1               5                   10                  15

Asp Arg Val Thr Val Thr Cys Arg Ala Ser Gln Gly Ile Ser Asn Tyr
            20                  25                  30

Leu Ala Trp Tyr Gln Gln Lys Pro Gly Asn Ala Pro Arg Leu Leu Ile
        35                  40                  45

Tyr Ser Ala Ser Thr Leu Gln Ser Gly Val Pro Ser Arg Phe Arg Gly
50                  55                  60

Thr Gly Tyr Gly Thr Glu Phe Ser Leu Thr Ile Asp Ser Leu Gln Pro
65                  70                  75                  80

Glu Asp Phe Ala Thr Tyr Tyr Cys Gln Gln Ser Tyr Thr Ser Arg Gln
                85                  90                  95

Thr Phe Gly Pro Gly Thr Arg Leu Asp Ile Lys
            100                 105

<210> SEQ ID NO 149
<211> LENGTH: 118
<212> TYPE: PRT
<213> ORGANISM: Artificial Sequence
<220> FEATURE:
<223> OTHER INFORMATION: Variable heavy (VH) Anti-BCMA

<400> SEQUENCE: 149

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Asp Gly Pro Pro Ser Phe Asp Ile Trp Gly Gln Gly Thr
            100                 105                 110

Met Val Thr Val Ser Ser
            115

```
<210> SEQ ID NO 150
<211> LENGTH: 108
<212> TYPE: PRT
<213> ORGANISM: Artificial Sequence
<220> FEATURE:
<223> OTHER INFORMATION: Variable light (VL) Anti-BCMA

<400> SEQUENCE: 150

Ser Tyr Val Leu Thr Gln Pro Pro Ser Val Ser Val Ala Pro Gly Gln
1               5                   10                  15

Thr Ala Arg Ile Thr Cys Gly Ala Asn Asn Ile Gly Ser Lys Ser Val
            20                  25                  30

His Trp Tyr Gln Gln Lys Pro Gly Gln Ala Pro Met Leu Val Val Tyr
        35                  40                  45

Asp Asp Asp Asp Arg Pro Ser Gly Ile Pro Glu Arg Phe Ser Gly Ser
    50                  55                  60

Asn Ser Gly Asn Thr Ala Thr Leu Thr Ile Ser Gly Val Glu Ala Gly
65                  70                  75                  80

Asp Glu Ala Asp Tyr Phe Cys His Leu Trp Asp Arg Ser Arg Asp His
                85                  90                  95

Tyr Val Phe Gly Thr Gly Thr Lys Leu Thr Val Leu
            100                 105

<210> SEQ ID NO 151
<211> LENGTH: 122
<212> TYPE: PRT
<213> ORGANISM: Artificial Sequence
<220> FEATURE:
<223> OTHER INFORMATION: Variable heavy (VH) Anti-BCMA

<400> SEQUENCE: 151

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Ser Lys Ser Ile Val Ser Tyr Met Asp Tyr Trp
            100                 105                 110

Gly Gln Gly Thr Leu Val Thr Val Ser Ser
        115                 120

<210> SEQ ID NO 152
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 152

Leu Pro Val Leu Thr Gln Pro Pro Ser Thr Ser Gly Thr Pro Gly Gln
1               5                   10                  15

Arg Val Thr Val Ser Cys Ser Gly Ser Ser Ser Asn Ile Gly Ser Asn
            20                  25                  30
```

```
Val Val Phe Trp Tyr Gln Gln Leu Pro Gly Thr Ala Pro Lys Leu Val
         35                  40                  45

Ile Tyr Arg Asn Asn Gln Arg Pro Ser Gly Val Pro Asp Arg Phe Ser
 50                  55                  60

Val Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Ser Gly Tyr Val Phe Gly Thr Gly Thr Lys Val Thr Val Leu Gly
            100                 105                 110

<210> SEQ ID NO 153
<211> LENGTH: 16
<212> TYPE: PRT
<213> ORGANISM: Artificial Sequence
<220> FEATURE:
<223> OTHER INFORMATION: CD33 Signal peptide

<400> SEQUENCE: 153

Met Pro Leu Leu Leu Leu Leu Pro Leu Leu Trp Ala Gly Ala Leu Ala
 1               5                   10                  15

<210> SEQ ID NO 154
<211> LENGTH: 18
<212> TYPE: PRT
<213> ORGANISM: Artificial Sequence
<220> FEATURE:
<223> OTHER INFORMATION: CD8 alpha signal peptide

<400> SEQUENCE: 154

Met Ala Leu Pro Val Thr Ala Leu Leu Leu Pro Leu Ala Leu Leu Leu
 1               5                   10                  15

His Ala

<210> SEQ ID NO 155
<211> LENGTH: 66
<212> TYPE: DNA
<213> ORGANISM: Artificial Sequence
<220> FEATURE:
<223> OTHER INFORMATION: GMCSFR alpha chain signal sequence

<400> SEQUENCE: 155
atgcttctcc tggtgacaag ccttctgctc tgtgagttac acacccagc attcctcctg    60 atccca                                                              66

<210> SEQ ID NO 156
<211> LENGTH: 22
<212> TYPE: PRT
<213> ORGANISM: Artificial Sequence
<220> FEATURE:
<223> OTHER INFORMATION: GMCSFR alpha chain signal sequence

<400> SEQUENCE: 156

Met Leu Leu Leu Val Thr Ser Leu Leu Leu Cys Glu Leu Pro His Pro
 1               5                   10                  15

Ala Phe Leu Leu Ile Pro
            20

<210> SEQ ID NO 157
<211> LENGTH: 14
<212> TYPE: PRT
<213> ORGANISM: Artificial Sequence
```

```
<220> FEATURE:
<223> OTHER INFORMATION: Exemplary IgG Hinge

<400> SEQUENCE: 157

Glu Val Val Val Lys Tyr Gly Pro Pro Cys Pro Pro Cys Pro
1               5                   10

<210> SEQ ID NO 158
<211> LENGTH: 5
<212> TYPE: PRT
<213> ORGANISM: Artificial Sequence
<220> FEATURE:
<223> OTHER INFORMATION: Exemplary IgG Hinge
<220> FEATURE:
<221> NAME/KEY: VARIANT
<222> LOCATION: (1)...(1)
<223> OTHER INFORMATION: Xaa is glycine, cysteine or arginine
<220> FEATURE:
<221> NAME/KEY: VARIANT
<222> LOCATION: (4)...(4)
<223> OTHER INFORMATION: Xaa is cysteine or threonine

<400> SEQUENCE: 158

Xaa Pro Pro Xaa Pro
1               5

<210> SEQ ID NO 159
<211> LENGTH: 15
<212> TYPE: PRT
<213> ORGANISM: Artificial Sequence
<220> FEATURE:
<223> OTHER INFORMATION: Exemplary IgG Hinge

<400> SEQUENCE: 159

Glu Pro Lys Ser Cys Asp Lys Thr His Thr Cys Pro Pro Cys Pro
1               5                   10                  15

<210> SEQ ID NO 160
<211> LENGTH: 12
<212> TYPE: PRT
<213> ORGANISM: Artificial Sequence
<220> FEATURE:
<223> OTHER INFORMATION: Exemplary IgG Hinge

<400> SEQUENCE: 160

Glu Arg Lys Cys Cys Val Glu Cys Pro Pro Cys Pro
1               5                   10

<210> SEQ ID NO 161
<211> LENGTH: 61
<212> TYPE: PRT
<213> ORGANISM: Artificial Sequence
<220> FEATURE:
<223> OTHER INFORMATION: Exemplary IgG Hinge

<400> SEQUENCE: 161

Glu Leu Lys Thr Pro Leu Gly Asp Thr His Thr Cys Pro Arg Cys Pro
1               5                   10                  15

Glu Pro Lys Ser Cys Asp Thr Pro Pro Cys Pro Arg Cys Pro Glu
                20                  25                  30

Pro Lys Ser Cys Asp Thr Pro Pro Cys Pro Arg Cys Pro Glu Pro
            35                  40                  45

Lys Ser Cys Asp Thr Pro Pro Cys Pro Arg Cys Pro
        50                  55                  60

<210> SEQ ID NO 162
```

```
<211> LENGTH: 12
<212> TYPE: PRT
<213> ORGANISM: Artificial Sequence
<220> FEATURE:
<223> OTHER INFORMATION: Exemplary IgG Hinge

<400> SEQUENCE: 162

Glu Ser Lys Tyr Gly Pro Pro Cys Pro Ser Cys Pro
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Exemplary IgG Hinge

<400> SEQUENCE: 163

Glu Ser Lys Tyr Gly Pro Pro Cys Pro Pro Cys Pro
1               5                   10

<210> SEQ ID NO 164
<211> LENGTH: 9
<212> TYPE: PRT
<213> ORGANISM: Artificial Sequence
<220> FEATURE:
<223> OTHER INFORMATION: Exemplary IgG Hinge

<400> SEQUENCE: 164

Tyr Gly Pro Pro Cys Pro Pro Cys Pro
1               5

<210> SEQ ID NO 165
<211> LENGTH: 10
<212> TYPE: PRT
<213> ORGANISM: Artificial Sequence
<220> FEATURE:
<223> OTHER INFORMATION: Exemplary IgG Hinge

<400> SEQUENCE: 165

Lys Tyr Gly Pro Pro Cys Pro Pro Cys Pro
1               5                   10

<210> SEQ ID NO 166
<211> LENGTH: 357
<212> TYPE: PRT
<213> ORGANISM: Artificial Sequence
<220> FEATURE:
<223> OTHER INFORMATION: tEGFR

<400> SEQUENCE: 166

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
                20                  25                  30

Glu Phe Lys Asp Ser Leu Ser Ile Asn Ala Thr Asn Ile Lys His Phe
            35                  40                  45

Lys Asn Cys Thr Ser Ile Ser Gly Asp Leu His Ile Leu Pro Val Ala
        50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
```

```
                100                 105                 110
Glu Ile Ile Arg Gly Arg Thr Lys Gln His Gly Gln Phe Ser Leu Ala
                115                 120                 125
Val Val Ser Leu Asn Ile Thr Ser Leu Gly Leu Arg Ser Leu Lys Glu
                130                 135                 140
Ile Ser Asp Gly Asp Val Ile Ile Ser Gly Asn Lys Asn Leu Cys Tyr
145                 150                 155                 160
Ala Asn Thr Ile Asn Trp Lys Lys Leu Phe Gly Thr Ser Gly Gln Lys
                165                 170                 175
Thr Lys Ile Ile Ser Asn Arg Gly Glu Asn Ser Cys Lys Ala Thr Gly
                180                 185                 190
Gln Val Cys His Ala Leu Cys Ser Pro Glu Gly Cys Trp Gly Pro Glu
                195                 200                 205
Pro Arg Asp Cys Val Ser Cys Arg Asn Val Ser Arg Gly Arg Glu Cys
                210                 215                 220
Val Asp Lys Cys Asn Leu Leu Glu Gly Glu Pro Arg Glu Phe Val Glu
225                 230                 235                 240
Asn Ser Glu Cys Ile Gln Cys His Pro Glu Cys Leu Pro Gln Ala Met
                245                 250                 255
Asn Ile Thr Cys Thr Gly Arg Gly Pro Asp Asn Cys Ile Gln Cys Ala
                260                 265                 270
His Tyr Ile Asp Gly Pro His Cys Val Lys Thr Cys Pro Ala Gly Val
                275                 280                 285
Met Gly Glu Asn Asn Thr Leu Val Trp Lys Tyr Ala Asp Ala Gly His
                290                 295                 300
Val Cys His Leu Cys His Pro Asn Cys Thr Tyr Gly Cys Thr Gly Pro
305                 310                 315                 320
Gly Leu Glu Gly Cys Pro Thr Asn Gly Pro Lys Ile Pro Ser Ile Ala
                325                 330                 335
Thr Gly Met Val Gly Ala Leu Leu Leu Leu Val Val Ala Leu Gly
                340                 345                 350
Ile Gly Leu Phe Met
                355

<210> SEQ ID NO 167
<211> LENGTH: 18
<212> TYPE: PRT
<213> ORGANISM: Artificial Sequence
<220> FEATURE:
<223> OTHER INFORMATION: T2A

<400> SEQUENCE: 167

Glu Gly Arg Gly Ser Leu Leu Thr Cys Gly Asp Val Glu Glu Asn Pro
1               5                   10                  15

Gly Pro

<210> SEQ ID NO 168
<211> LENGTH: 22
<212> TYPE: PRT
<213> ORGANISM: Artificial Sequence
<220> FEATURE:
<223> OTHER INFORMATION: P2A

<400> SEQUENCE: 168

Gly Ser Gly Ala Thr Asn Phe Ser Leu Leu Lys Gln Ala Gly Asp Val
1               5                   10                  15

Glu Glu Asn Pro Gly Pro
```

```
<210> SEQ ID NO 169
<211> LENGTH: 19
<212> TYPE: PRT
<213> ORGANISM: Artificial Sequence
<220> FEATURE:
<223> OTHER INFORMATION: P2A

<400> SEQUENCE: 169

Ala Thr Asn Phe Ser Leu Leu Lys Gln Ala Gly Asp Val Glu Glu Asn
1               5                   10                  15

Pro Gly Pro

<210> SEQ ID NO 170
<211> LENGTH: 20
<212> TYPE: PRT
<213> ORGANISM: Artificial Sequence
<220> FEATURE:
<223> OTHER INFORMATION: E2A

<400> SEQUENCE: 170

Gln Cys Thr Asn Tyr Ala Leu Leu Lys Leu Ala Gly Asp Val Glu Ser
1               5                   10                  15

Asn Pro Gly Pro
            20

<210> SEQ ID NO 171
<211> LENGTH: 22
<212> TYPE: PRT
<213> ORGANISM: Artificial Sequence
<220> FEATURE:
<223> OTHER INFORMATION: F2A

<400> SEQUENCE: 171

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 172
<211> LENGTH: 290
<212> TYPE: PRT
<213> ORGANISM: Artificial Sequence
<220> FEATURE:
<223> OTHER INFORMATION: BCMA-Fc fusion polypeptide

<400> SEQUENCE: 172

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Gly Gly Gly Gly Ser Pro Lys Ser Ser Asp
        50                  55                  60

Lys Thr His Thr Cys Pro Pro Cys Pro Ala Pro Glu Ala Glu Gly Ala
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Val Asp Val Ser His Glu
            100                 105                 110
```

-continued

Asp Pro Glu Val Lys Phe Asn Trp Tyr Val Asp Gly Val Glu Val His
            115                 120                 125

Asn Ala Lys Thr Lys Pro Arg Glu Glu Gln Tyr Asn Ser Thr Tyr Arg
        130                 135                 140

Val Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ser Ser Ile Glu
                165                 170                 175

Lys Thr Ile Ser Lys Ala Lys Gly Gln Pro Arg Glu Pro Gln Val Tyr
            180                 185                 190

Thr Leu Pro Pro Ser Arg Asp Glu Leu Thr Lys Asn Gln Val Ser Leu
        195                 200                 205

Thr Cys Leu Val Lys Gly Phe Tyr Pro Ser Asp Ile Ala Val Glu Trp
    210                 215                 220

Glu Ser Asn Gly Gln Pro Glu Asn Asn Tyr Lys Thr Thr Pro Pro Val
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Val Phe Ser Cys Ser Val Met His
            260                 265                 270

Glu Ala Leu His Asn His Tyr Thr Gln Lys Ser Leu Ser Leu Ser Pro
        275                 280                 285

Gly Lys
    290

<210> SEQ ID NO 173
<211> LENGTH: 5
<212> TYPE: PRT
<213> ORGANISM: Artificial Sequence
<220> FEATURE:
<223> OTHER INFORMATION: CDR-H1

<400> SEQUENCE: 173

Asp Tyr Tyr Val Tyr
1               5

<210> SEQ ID NO 174
<211> LENGTH: 17
<212> TYPE: PRT
<213> ORGANISM: Artificial Sequence
<220> FEATURE:
<223> OTHER INFORMATION: CDR-H2

<400> SEQUENCE: 174

Trp Ile Asn Pro Asn Ser Gly Gly Thr Asn Tyr Ala Gln Lys Phe Gln
1               5                   10                  15

Gly

<210> SEQ ID NO 175
<211> LENGTH: 9
<212> TYPE: PRT
<213> ORGANISM: Artificial Sequence
<220> FEATURE:
<223> OTHER INFORMATION: CDR-H3

<400> SEQUENCE: 175

Ser Gln Arg Asp Gly Tyr Met Asp Tyr
1               5

```
<210> SEQ ID NO 176
<211> LENGTH: 7
<212> TYPE: PRT
<213> ORGANISM: Artificial Sequence
<220> FEATURE:
<223> OTHER INFORMATION: CDR-H1

<400> SEQUENCE: 176

Gly Tyr Thr Phe Ile Asp Tyr
1               5

<210> SEQ ID NO 177
<211> LENGTH: 6
<212> TYPE: PRT
<213> ORGANISM: Artificial Sequence
<220> FEATURE:
<223> OTHER INFORMATION: CDR-H2

<400> SEQUENCE: 177

Asn Pro Asn Ser Gly Gly
1               5

<210> SEQ ID NO 178
<211> LENGTH: 10
<212> TYPE: PRT
<213> ORGANISM: Artificial Sequence
<220> FEATURE:
<223> OTHER INFORMATION: CDR-H1

<400> SEQUENCE: 178

Gly Tyr Thr Phe Ile Asp Tyr Tyr Val Tyr
1               5                   10

<210> SEQ ID NO 179
<211> LENGTH: 10
<212> TYPE: PRT
<213> ORGANISM: Artificial Sequence
<220> FEATURE:
<223> OTHER INFORMATION: CDR-H2

<400> SEQUENCE: 179

Trp Ile Asn Pro Asn Ser Gly Gly Thr Asn
1               5                   10

<210> SEQ ID NO 180
<211> LENGTH: 8
<212> TYPE: PRT
<213> ORGANISM: Artificial Sequence
<220> FEATURE:
<223> OTHER INFORMATION: CDR-H1

<400> SEQUENCE: 180

Gly Tyr Thr Phe Ile Asp Tyr Tyr
1               5

<210> SEQ ID NO 181
<211> LENGTH: 8
<212> TYPE: PRT
<213> ORGANISM: Artificial Sequence
<220> FEATURE:
<223> OTHER INFORMATION: CDR-H2

<400> SEQUENCE: 181

Ile Asn Pro Asn Ser Gly Gly Thr
1               5

<210> SEQ ID NO 182
```

```
<211> LENGTH: 11
<212> TYPE: PRT
<213> ORGANISM: Artificial Sequence
<220> FEATURE:
<223> OTHER INFORMATION: CDR-H3

<400> SEQUENCE: 182

Ala Arg Ser Gln Arg Asp Gly Tyr Met Asp Tyr
1               5                   10

<210> SEQ ID NO 183
<211> LENGTH: 8
<212> TYPE: PRT
<213> ORGANISM: Artificial Sequence
<220> FEATURE:
<223> OTHER INFORMATION: CDR-L1

<400> SEQUENCE: 183

Thr Gly Thr Ser Ser Asp Val Gly
1               5

<210> SEQ ID NO 184
<211> LENGTH: 7
<212> TYPE: PRT
<213> ORGANISM: Artificial Sequence
<220> FEATURE:
<223> OTHER INFORMATION: CDR-L2

<400> SEQUENCE: 184

Glu Asp Ser Lys Arg Pro Ser
1               5

<210> SEQ ID NO 185
<211> LENGTH: 10
<212> TYPE: PRT
<213> ORGANISM: Artificial Sequence
<220> FEATURE:
<223> OTHER INFORMATION: CDR-L3

<400> SEQUENCE: 185

Ser Ser Asn Thr Arg Ser Ser Thr Leu Val
1               5                   10

<210> SEQ ID NO 186
<211> LENGTH: 9
<212> TYPE: PRT
<213> ORGANISM: Artificial Sequence
<220> FEATURE:
<223> OTHER INFORMATION: CDR-L1

<400> SEQUENCE: 186

Ile Ser Cys Thr Gly Thr Ser Ser Asp
1               5

<210> SEQ ID NO 187
<211> LENGTH: 3
<212> TYPE: PRT
<213> ORGANISM: Artificial Sequence
<220> FEATURE:
<223> OTHER INFORMATION: CDR-L2
```

<400> SEQUENCE: 187

Glu Asp Ser
1

<210> SEQ ID NO 188
<211> LENGTH: 244
<212> TYPE: PRT
<213> ORGANISM: Artificial Sequence
<220> FEATURE:
<223> OTHER INFORMATION: anti-BCMA scFv

<400> SEQUENCE: 188

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly Ser Arg Gly Gly Gly Gly Ser
            100                 105                 110

Gly Gly Gly Gly Ser Gly Gly Gly Ser Leu Glu Met Ala Glu Val
        115                 120                 125

Gln Leu Val Gln Ser Gly Ala Glu Met Lys Lys Pro Gly Ala Ser Leu
    130                 135                 140

Lys Leu Ser Cys Lys Ala Ser Gly Tyr Thr Phe Ile Asp Tyr Tyr Val
145                 150                 155                 160

Tyr Trp Met Arg Gln Ala Pro Gly Gln Gly Leu Glu Ser Met Gly Trp
                165                 170                 175

Ile Asn Pro Asn Ser Gly Gly Thr Asn Tyr Ala Gln Lys Phe Gln Gly
            180                 185                 190

Arg Val Thr Met Thr Arg Asp Thr Ser Ile Ser Thr Ala Tyr Met Glu
        195                 200                 205

Leu Ser Arg Leu Arg Ser Asp Asp Thr Ala Met Tyr Tyr Cys Ala Arg
    210                 215                 220

Ser Gln Arg Asp Gly Tyr Met Asp Tyr Trp Gly Gln Gly Thr Leu Val
225                 230                 235                 240

Thr Val Ser Ser

COMBINATION OF A CELL THERAPY AND A GAMMA SECRETASE INHIBITOR

CROSS-REFERENCE TO RELATED APPLICATIONS

This application is a national stage application under 35 U.S.C. § 371 of International Application No. PCT/US2018/059510, filed internationally on Nov. 6, 2018, which claims the benefit of priority to U.S. provisional patent application 62/582,308, entitled "COMBINATION OF A CELL THERAPY AND A GAMMA SECRETASE INHIBITOR" filed on Nov. 6, 2017; U.S. provisional patent application 62/582,937, entitled "COMBINATION OF A CELL THERAPY AND A GAMMA SECRETASE INHIBITOR" filed on Nov. 7, 2017; and U.S. provisional patent application 62/665,450, entitled "COMBINATION OF A CELL THERAPY AND A GAMMA SECRETASE INHIBITOR" filed on May 1, 2018, the contents of which are incorporated by reference in their entirety.

INCORPORATION BY REFERENCE OF SEQUENCE LISTING

The present application is being filed along with a Sequence Listing in electronic format. The Sequence Listing is provided as a file entitled 735042014200SeqList.txt, created Apr. 30, 2020, which is 320,079 bytes in size. The information in the electronic format of the Sequence Listing is incorporated by reference in its entirety.

FIELD

The present disclosure relates in some aspects to methods, compositions and uses involving immunotherapies, such as adoptive cell therapy, e.g., T cell therapy, and a gamma secretase inhibitor. The provided methods, compositions and uses include those for combination therapies involving the administration or use of a gamma secretase inhibitor in conjunction with a T cell therapy, such as a genetically engineered T cell therapy involving cells engineered with a recombinant receptor, such as chimeric antigen receptor (CAR)-expressing T cells, such as anti-BCMA chimeric antigen receptor (CAR)-expressing T cells. Also provided are compositions, methods of administration to subjects, articles of manufacture and kits for use in the methods. In some aspects, features of the methods and cells provide for increased or improved activity, efficacy, persistence, expansion and/or proliferation of T cells for adoptive cell therapy or endogenous T cells recruited by immunotherapeutic agents.

BACKGROUND

Various strategies are available for immunotherapy, for example administering engineered T cells for adoptive therapy. For example, strategies are available for engineering T cells expressing genetically engineered antigen receptors, such as CARs, and administering compositions containing such cells to subjects. Improved strategies are needed to improve efficacy of the cells, for example, improving the persistence, activity and/or proliferation of the cells upon administration to subjects. Provided are methods, compositions, kits, and systems that meet such needs.

SUMMARY

Provided herein are combination therapies involving administration of an immunotherapy involving a cell therapy, such as a T cell therapy, and an inhibitor of gamma secretase. In some aspects, the provided methods of treating a subject having a disease or disorder involve administration of an immunotherapy or immunotherapeutic agent, such as a composition including cells for adoptive cell therapy, e.g., such as a T cell therapy (e.g. CAR-expressing T cells), and administration of a gamma secretase inhibitor. In some embodiments, the cell therapy, such as CAR-expressing T cells, comprises an antigen-binding domain that binds to a B Cell Maturation Antigen (BCMA), such as surface BCMA. In some embodiments, the method further comprises selecting a subject for treatment, wherein the subject has a low expression of surface BCMA on a cell (such as a tumor/cancer cell). In some embodiments, the cell therapy comprises a recombinant receptor, such as a receptor that does not bind to BCMA. In some embodiments, the gamma secretase inhibitor prohibits intramembrane cleavage of a receptor on a cell (such as a tumor/cancer cell), wherein the cell therapy specifically targets the receptor. In some embodiments, the combination therapy generally involves administration of a gamma secretase inhibitor and administration of a cell therapy, such as a composition including cells for adoptive cell therapy, e.g., such as a T cell therapy (e.g. CAR-expressing T cells), wherein the gamma secretase administration is subsequent to the administration of cell therapy. In some embodiments, the therapy modulates activity of a cell therapy.

Provided herein are methods of treatment that involve: (a) administering a cell therapy to a subject having a disease or disorder, said cell therapy comprising a dose of genetically engineered cells expressing a chimeric antigen receptor (CAR) comprising an antigen-binding domain that specifically binds to surface B cell maturation antigen (BCMA); and (b) administering to the subject an inhibitor of gamma secretase, wherein binding of the CAR to surface BCMA, or a measure indicative of function or activity following exposure to cells expressing surface BCMA, is not reduced or blocked or is not substantially reduced or blocked in the presence of a soluble or shed form of the BCMA. In some embodiments, the binding of the CAR to surface BCMA, or a measure indicative of function or activity following exposure to cells expressing surface BCMA, is not reduced or blocked or is not substantially reduced or blocked in the presence of a soluble or shed form of the BCMA at a concentration or amount of the soluble or shed form of the BCMA corresponding to a concentration or amount present in serum or blood or plasma of the subject or of a multiple myeloma patient or on average in a patient population for the disease or disorder, or at a concentration or amount of the soluble or shed BCMA at which the binding or measure is reduced or blocked, or is substantially reduced or blocked, for cells expressing a reference anti-BCMA CAR in the same assay.

Provided here are methods of treatment that involve: administering a cell therapy to a subject having a disease or disorder, said cell therapy comprising a dose of genetically engineered cells expressing a chimeric antigen receptor comprising an antigen-binding domain that binds to surface B cell maturation antigen (BCMA), wherein binding of the CAR to surface BCMA or a measure indicative of function or activity, following exposure to cells expressing surface BCMA, is not reduced or blocked or is not substantially reduced or blocked in the presence of a soluble or shed form of the BCMA, optionally at a concentration or amount of the soluble or shed form of the BCMA corresponding to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA CAR in the same assay, wherein, at the time of initiation of the administration of the cell therapy, the subject has been previously administered, and/or is undergoing treatment with, an inhibitor of gamma secretase.

Provided here are methods of treatment that involve: administering an inhibitor of gamma secretase to a subject having a disease or disorder, wherein, at the time of initiation of the administration of the inhibitor, the subject has been previously administered, and/or is undergoing treatment with, a cell therapy, said cell therapy comprising a dose of genetically engineered cells expressing a chimeric antigen receptor comprising an antigen-binding domain that specifically binds surface B cell maturation antigen (BCMA), wherein binding of the CAR to surface BCMA or a measure indicative of function or activity, following exposure to cells expressing surface BCMA, is not reduced or blocked or is not substantially reduced or blocked in the presence of a soluble or shed form of the BCMA, optionally at a concentration or amount of the soluble or shed form of the BCMA corresponding to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA CAR in the same assay.

Provided here are methods of treatment that involve: (a) selecting a subject having a cancer in which cells of the cancer in the subject (i) express surface CD138, surface CD38 or a surface plasma cell marker or are derived from plasma cells and (ii) comprise low expression of surface B cell maturation antigen (BCMA) and/or a level of expression of surface BCMA below a threshold level; (b) administering a cell therapy to the subject selected in (a), said cell therapy comprising a dose of genetically engineered cells expressing a chimeric antigen receptor comprising an antigen-binding domain that binds to B cell maturation antigen (BCMA); and (c) administering to the subject an inhibitor of gamma secretase.

Provided here are methods of treatment that involve: (a) administering an inhibitor of gamma secretase to a subject having a cancer, said subject selected as having plasma cells comprising low expression of surface B cell maturation antigen (BCMA) and/or a level of expression of surface BCMA below a threshold level; and (b) administering to the subject a cell therapy for treating the cancer, said cell therapy comprising a dose of genetically engineered cells expressing a chimeric antigen receptor comprising an antigen-binding domain that specifically binds to B cell maturation antigen (BCMA).

In some embodiments of any one of the methods provided herein, the threshold level of expression of surface BCMA is lower than the average or median expression or level of surface BCMA on plasma cells in a plurality of control subjects, optionally wherein the control subjects are a group of healthy or normal subjects.

In some embodiments of any one of the methods provided herein, the low expression of surface BCMA is present when less than or less than about 60%, less than or less than about 50%, less than or less than about 40%, less than or less than about 30%, less than or less than about 20% or less than or less than about 10% of the plasma cells, or cells with a plasma cell marker or phenotype or the cancer cells, in the subject express surface BCMA; or the threshold level of surface BCMA is less than or less than about 60%, less than or less than about 50%, less than or less than about 40%, less than or less than about 30%, less than or less than about 20% or less than or less than about 10% of the plasma cells, or cells with a plasma cell marker or phenotype or the cancer cells, in the subject that express surface BCMA.

In some embodiments of any one of the methods provided herein, the expression of surface BCMA is determined by flow cytometry and/or an immunoassay.

In some embodiments of any one of the embodiments provided herein, binding of the CAR to surface BCMA or a measure indicative of function or activity, following exposure to cells expressing surface BCMA, is not reduced or blocked or is not substantially reduced or blocked in the presence of a soluble or shed form of the BCMA, optionally at a concentration or amount of the soluble or shed form of the BCMA corresponding to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA CAR in the same assay.

In some embodiments of any one of the methods provided herein, the antigen-binding domain does not bind soluble BCMA or binds to soluble BCMA with an affinity lower than the affinity of said antigen-binding domain binding to surface BCMA. In some embodiments, the affinity of the antigen-binding domain to the surface B cell maturation antigen (BCMA) is at least 1-fold, 2-fold, 3-fold, 4-fold, 5-fold, 6-fold, 7-fold, 8-fold, 9-fold, or 10-fold higher than the affinity to the soluble BCMA.

In some of any of the provided embodiments, the anti-BCMA CAR is an anti-BCMA CAR as described herein. Among a provided anti-BCMA CAR for use in the methods and uses herein is a CAR in which the antibody or antigen-binding fragment contains a $V_H$ region comprising the sequence set forth in SEQ ID NO: 24 or an amino acid sequence having at least at or about 90%, at or about 91%, at or about 92%, at or about 93%, at or about 94%, at or about 95%, at or about 96%, at or about 97%, at or about 98%, or at or about 99% identity to SEQ ID NO:24; and contains a $V_L$ region comprising the sequence set forth in SEQ ID NO:25 or an amino acid sequence having at least at or about 90%, at or about 91%, at or about 92%, at or about 93%, at or about 94%, at or about 95%, at or about 96%, at or about 97%, at or about 98%, or at or about 99% identity to SEQ ID NO:25. In some embodiments, the antibody or antigen-binding fragment of the provided CAR contains a $V_H$ region that has a CDRH1, a CDRH2 and a CDRH3 comprising the amino acid sequence of SEQ ID NOS: 173, 174 and 175, respectively and a $V_L$ region that has a CDRL1, a CDRL2 and a CDRL3 comprising the amino acid sequence of SEQ ID NOS: 183, 184 and 185, respectively. In some embodiments, the antibody or antigen-binding fragment of the provided CAR contains a $V_H$ region that has a CDRH1, a CDRH2 and a CDRH3 comprising the amino acid sequence of SEQ ID NOS: 176, 177 and 175, respectively and a $V_L$ region that has a CDRL1, a CDRL2 and a CDRL3 comprising the amino acid sequence of SEQ ID NOS: 183, 184 and 185, respectively. In some embodiments, the antibody or antigen-binding fragment of the provided CAR contains a $V_H$ region that has a CDRH1, a CDRH2 and a CDRH3 comprising the amino acid sequence of SEQ ID NOS: 178, 179 and 175, respectively and a $V_L$ region that has a CDRL1, a CDRL2 and a CDRL3 comprising the amino acid sequence of SEQ ID NOS: 183, 184 and 185, respectively. In some embodiments, the antibody or antigen-binding fragment of the provided CAR contains a $V_H$ region that has a CDRH1, a CDRH2 and a CDRH3 comprising the amino acid sequence of SEQ ID NOS: 180, 181 and 182, respectively and a $V_L$ region that has a CDRL1, a CDRL2 and a CDRL3 comprising the amino acid sequence of SEQ ID NOS: 186, 187 and 185, respectively. In some embodiments, the $V_H$ region comprises the sequence set forth in SEQ ID NO:24 and the $V_L$ region comprises the sequence set forth in SEQ ID NO:25. In some embodiments, the antibody or antigen-binding fragment is a single-chain antibody fragment, such as an scFv. In some embodiments, the scFv comprises the sequence of amino acids set forth in SEQ ID NO:188 or a sequence of amino acids at least at or about 90%, at or about 91%, at or about 92%, at or about 93%, at or about 94%, at or about 95%, at or about 96%, at or about 97%, at or about 98%, or at or about 99% identity to SEQ ID NO:188. In some embodiments, the anti-BCMA CAR has the sequence of amino acids set forth in SEQ NO: 124 or a sequence of amino acids at least at or about 90%, at or about 91%, at or about 92%, at or about 93%, at or about 94%, at or about 95%, at or about 96%, at or about 97%, at or about 98%, or at or about 99% identity to SEQ ID NO:124. In some embodiments, the anti-BCMA CAR has the sequence of amino acids set forth in SEQ NO: 125 or a sequence of amino acids at least at or about 90%, at or about 91%, at or about 92%, at or about 93%, at or about 94%, at or about 95%, at or about 96%, at or about 97%, at or about 98%, or at or about 99% identity to SEQ ID NO:125.

In some embodiments of any one of the methods provided herein, the gamma secretase inhibitor inhibits intramembrane cleavage of BCMA.

In some embodiments of any one of the methods provided herein, the gamma secretase inhibitor inhibits intramembrane cleavage of BCMA with a half-maximal inhibitory concentration ($IC_{50}$) of 0.01 nM to 10 nM, 0.01 nM to 5 nM, 0.01 nM to 1 nM, 0.01 nM to 0.5 nM, 0.01 nM to 0.35 nM, 0.01 nM to 0.25 nM, 0.01 nM to 0.1 nM, 0.01 nM to 0.05 nM, 0.05 nM to 10 nM, 0.05 nM to 5 nM, 0.05 nM to 1 nM, 0.05 nM to 0.5 nM, 0.05 nM to 0.35 nM, 0.05 nM to 0.25 nM, 0.05 nM to 0.1 nM, 0.1 nM to 10 nM, 0.1 nM to 5 nM, 0.1 nM to 1 nM, 0.1 nM, to 0.5 nM, 0.1 nM to 0.35 nM, 0.1 nM to 0.25 nM, 0.25 nM to 10 nM, 0.25 nM to 5 nM, 0.25 nM to 1 nM, 0.25 nM to 0.5 nM, 0.25 nM to 0.35 nM, 0.35 nM to 10 nM, 0.35 nM to 5 nM, 0.35 nM to 1 nM, 0.35 nM to 0.5 nM, 0.5 nM to 10 nM, 0.5 nM to 5 nM, 0.5 nM to 1 nM, 1 nM to 10 nM, 1 nM to 5 nM or 5 nM to 10 nM.

In some embodiments of any one of the methods provided herein, the gamma secretase inhibitor inhibits intramembrane cleavage of BCMA with a half-maximal inhibitory concentration ($IC_{50}$) of less than or less than about 10 nM, 5 nM, 1 nM, 0.5 nM, 0.35 nM, 0.25 nM, 0.1 nM, 0.05 nM or 0.01 nM or less.

Provided herein are methods of treatment that involve: (a) administering a cell therapy to a subject having a disease or disorder, said cell therapy comprising a dose of genetically engineered cells expressing a recombinant receptor, wherein the recombinant receptor does not specifically bind to surface B cell maturation antigen (BCMA); and (b) administering an inhibitor of gamma secretase.

Provided herein are methods of treatment that involve: administering a cell therapy to a subject having a disease or disorder, said cell therapy comprising a dose of genetically engineered cells expressing a recombinant receptor, wherein the recombinant receptor does not specifically bind to surface B cell maturation antigen (BCMA), wherein, at the time of initiation of the administration of the cell therapy, the subject has been previously administered, and/or is undergoing treatment with, an inhibitor of gamma secretase.

Provided herein are methods of treatment that involve: administering an inhibitor of gamma secretase to a subject having a disease or disorder, wherein, at the time of initiation of the administration of the inhibitor, the subject has been previously administered, and/or is undergoing treatment with, a cell therapy, said cell therapy comprising a dose of genetically engineered cells expressing a recombinant receptor, wherein the recombinant receptor does not specifically bind to surface B cell maturation antigen (BCMA).

In some embodiments of any one of the methods provided herein, the recombinant receptor specifically binds to a target antigen associated with the disease or disorder.

In some embodiments of any one of the methods provided herein, the target antigen is selected from among, carbonic anhydrase 9 (CAIX), Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR viii, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag.

Provided herein are methods of treatment that involve: (a) administering a cell therapy to a subject having a disease or disorder, said cell therapy comprising a dose of genetically engineered cells expressing a recombinant receptor; and (b) subsequent to the administration in (a) administering to the subject an inhibitor of gamma secretase.

Provided herein are methods of treatment that involve: administering an inhibitor of gamma secretase to a subject having a disease or disorder, wherein, at the time of initiation of the administration of the inhibitor, the subject has been previously administered, and/or is undergoing treatment with, a cell therapy, said cell therapy comprising a dose of genetically engineered cells expressing recombinant receptor.

In some embodiments of any one of the methods provided herein, the recombinant receptor specifically binds to a target antigen associated with the disease or disorder.

In some embodiments of any one of the methods provided herein, the target antigen is selected from among, B cell maturation antigen (BCMA), carbonic anhydrase 9 (CAIX), Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag. In some embodiments, the target antigen is Muc1. In some embodiments of any one of the methods provided herein, the target antigen is BCMA. In some embodiments, wherein the BCMA is surface BCMA.

In some embodiments of any one of the methods provided herein, the gamma secretase inhibitor inhibits or reduces or is capable of inhibiting or reducing cleavage of one or more targets selected from BCMA, Notch 1, Notch 2, Notch 3, Notch 4, Muc1, Ephrin B2, Betaglycan (TGFBR3), CD43, CD44, CSF1R, CXCR1, CXCL16, Delta1, E-cadherin, N-cadherin, HLA-A2, IFNaR2, IL1R1, IL1R2, IL6R or ameloid precursor protein (APP). In some embodiments, the one or more targets the cleavage of which is reduced or inhibited comprises Muc1. In some embodiments, the one or more targets the cleavage of which is reduced or inhibited comprises BCMA.

In some embodiments of any one of the methods provided herein, cleavage of one or more targets selected from BCMA, Notch 1, Notch 2, Notch 3, Notch 4, Muc1, Ephrin B2, Betaglycan (TGFBR3), CD43, CD44, CSF1R, CXCR1, CXCL16, Delta1, E-cadherin, N-cadherin, HLA-A2, IFNaR2, IL1R1, IL1R2, IL6R or ameloid precursor protein (APP) is inhibited or reduced or can be inhibited or reduced by the gamma secretase inhibitor. In some embodiments, the one or more targets the cleavage of which is reduced or inhibited comprises Muc1. In some embodiments, the one or more targets the cleavage of which is reduced or inhibited comprises BCMA.

In some embodiments of any one of the methods provided herein, the gamma secretase inhibitor inhibits the target with a half-maximal inhibitory concentration ($IC_{50}$) of 0.01 nM to 1 µM, 0.01 nM to 100 nM, 0.01 nM to 10 nM, 0.01 nM to 5 nM, 0.01 nM to 1 nM, 0.01 nM to 0.5 nM, 0.01 nM to 0.25 nM, 0.01 nM to 0.1 nM, 0.01 nM to 0.05 nM, 0.05 nM to 1 µM, 0.05 nM to 100 nM, 0.05 nM to 10 nM, 0.05 nM to 5 nM, 0.05 nM to 1 nM, 0.05 nM to 0.5 nM, 0.05 nM to 0.25 nM, 0.05 nM to 0.1 nM, 0.1 nM to 1 µM, 0.1 nM to 100 nM, 0.1 nM to 10 nM, 0.1 nM to 5 nM, 0.1 nM to 1 nM, 0.1 nM to 0.5 nM, 0.1 nM to 0.25 nM, 0.25 nM to 1 µM, 0.25 nM to 100 nM, 0.25 nM to 10 nM, 0.25 nM to 5 nM, 0.25 nM to 1 nM, 0.25 nM to 0.5 nM, 0.5 nM to 1 µM, 0.5 nM to 100 nM, 0.5 nM to 10 nM, 0.5 nM to 5 nM, 0.5 nM to 1 nM, 1 nM to 1 µM, 1 nM to 100 nM, 1 nM to 10 nM, 1 nM to 5 nM, 5 nM to 1 µM, 5 nM to 100 nM, 5 nM to 10 nM, 10 nM to 1 µM, 10 nM to 100 nM or 100 nM to 1 µM.

In some embodiments of any one of the methods provided herein, the gamma secretase inhibitor inhibits the target with a half-maximal inhibitory concentration ($IC_{50}$) of less than or less than about 1 µM, 100 nM, 10 nM, 5 nM, 1 nM, 0.5 nM, 0.35 nM, 0.25 nM, 0.1 nM, 0.05 nM or 0.01 nM or less.

In some embodiments of any one of the methods provided herein, the gamma secretase inhibitor is a peptide inhibitor or non-peptide inhibitor. In some embodiments, the gamma secretase inhibitor is a peptide inhibitor and the peptide inhibitor is selected from among peptide aldehydes derivatives, difluoroketones derivatives, hydroxyethylene dipeptide isotere derivatives, alpha-helical peptide derivatives and dipeptide analogs. In some embodiments, the gamma secretase inhibitor is a non-peptide inhibitor and the non-peptide inhibitor is a benzodiazepines derivative or a sulfonamides derivative.

In some embodiments of any one of the methods provided herein, the gamma secretase inhibitor is a transition state inhibitor or non-transition state inhibitor.

In some embodiments of any one of the methods provided herein, the gamma secretase inhibitor is a nonsteroidal anti-inflammatory drug.

In some embodiments of any one of the methods provided herein, the gamma secretase inhibitor is selected from LY3039478, secretase inhibitor I (GSI I) Z-Leu-Leu-Norleucine; γ-secretase inhibitor II (GSI II); γ-secretase inhibitor III (GSI III), N-Benzyloxycarbonyl-Leu-leucinal, N-(2-Naphthoyl)-Val-phenylalaninal; γ-secretase inhibitor III (GSI IV); γ-secretase inhibitor III (GSI V), N-Benzyloxycarbonyl-Leu-phenylalaninal; γ-secretase inhibitor III (GSI VI), 1-(S)-endo-N-(1,3,3)-Trimethylbicyclo[2.2.1]hept-2-yl)-4-fluorophenyl Sulfonamide; γ-secretase inhibitor III (GSI VII), Menthyloxycarbonyl-LL-CHO; γ-secretase inhibitor III (GSI IX), (DAPT), N-[N-(3,5-Difluorophenacetyl-L-alanyl)]-S-phenylglycine t-Butyl Ester; γ-secretase inhibitor X (GSI X), {1 S-Benzyl-4R-[1-(1S-carbamoyl-2-phenethylcarbamoyl)-1S-3-methylbutylcarb-amoyl]-2R-hydroxy-5-phenylpentyl}carbamic Acid tert-butyl Ester; γ-secretase inhibitor XI (GSI XI), 7-Amino-4-chloro-3-methoxyisocoumarin; γ-secretase inhibitor XII (GSI XII), Z-Ile-Leu-CHO; γ-secretase inhibitor XIII (GSI XIII), Z-Tyr-Ile-Leu-CHO; γ-secretase inhibitor XIV (GSI XIV), Z-Cys(t-Bu)-Ile-Leu-CHO; γ-secretase inhibitor XVI (GSI XVI), N-[N-3,5-Difluorophenacetyl]-L-alanyl-S-phenylglycine Methyl Ester; γ-secretase inhibitor XVII (GSI XVII); γ-secretase inhibitor XIX (GSI XIX), benzo[e][1,4]diazepin-3-yl)-butyramide; γ-secretase inhibitor XX (GSI XX), (S,S)-2-[2-(3,5-Difluorophenyl)acetylamino]-N-(5-methyl-6-oxo-6,7-dihydro-5H-dibenzo[b,d]azepin-7-yl)propionamide; γ-secretase inhibitor XXI (GSI XXI), (S,S)-2-[2-(3,5-Difluorophenyl)-acetylamino]-N-(1-methyl-2-oxo-5-phenyl-2-,3-dihydro-1H-benzo[e][1,4]diazepin-3-yl)-propionamide; Gamma40 secretase inhibitor I, N-trans-3,5-Dimethoxycinnamoyl-Ile-leucinal; Gamma40 secretase inhibitor II, N-tert-Butyloxycarbonyl-Gly-Val-Valinal Isovaleryl-V V-Sta-A-Sta-OCH3; MK-0752; MRK-003 (Merck); semagacestat/LY450139; RO4929097; PF-03084, 014; BMS-708163; MPC-7869 (γ-secretase modifier), YO-01027 (Dibenzazepine), Compound E ([(2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide], LY411575, L-685,458, BMS-289948 (4-chloro-N-(2, 5-difluorophenyl)-N-((1R)-{4-fluoro-2-[3-(1H-imidazol-1-yl)propyl]phenyl}ethyl)benzenesulfonamide hydrochloride) and BMS-299897 (4-[2-((1R)-1-{[(4-chlorophenyl)sulfonyl]-2,5-difluoroanilino}ethyl)-5-fluorophenyl]butanoic acid).

In some embodiments of any one of the methods provided herein, the gamma secretase inhibitor is a compound of the structure:

Compound 1

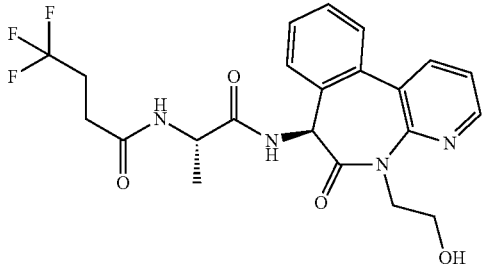

or a pharmaceutically acceptable salt of hydrate thereof.

Provided herein are methods of treatment that involve: (a) administering a cell therapy to a subject having a disease or disorder, said cell therapy comprising a dose of genetically engineered cells expressing a recombinant receptor; and (b) administering to the subject a compound of the structure:

Compound 1

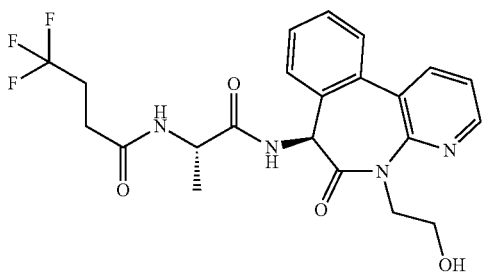

or a pharmaceutically acceptable salt of hydrate thereof.

Provided herein are methods of treatment that involve: administering a cell therapy to a subject having a disease or disorder, said cell therapy comprising a dose of genetically engineered cells expressing a recombinant receptor, wherein, at the time of initiation of the administration of the cell therapy, the subject has been previously administered, and/or is undergoing treatment with, a compound of the structure:

Compound 1

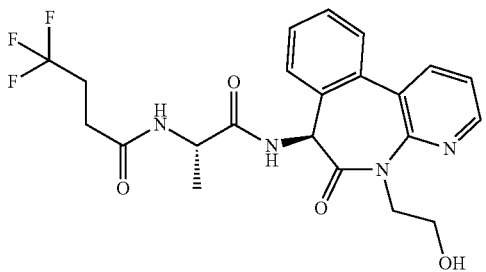

or a pharmaceutically acceptable salt of hydrate thereof.

Provided herein are methods of treatment that involve: administering to a subject having a disease or disorder a compound of the structure:

Compound 1

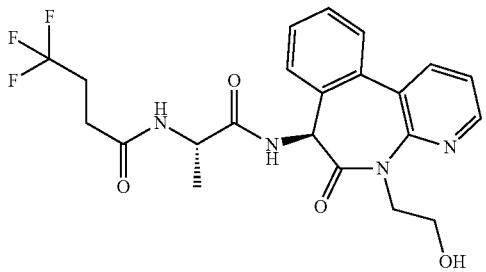

or a pharmaceutically acceptable salt of hydrate thereof, wherein, at the time of initiation of the administration, the subject has been previously administered, and/or is undergoing treatment with a cell therapy, said cell therapy comprising a dose of genetically engineered cells expressing a recombinant receptor.

In some embodiments of any one of the methods provided herein, the recombinant receptor specifically binds to a target antigen associated with the disease or disorder. In some embodiments, the target antigen is selected from among, B cell maturation antigen (BCMA), carbonic anhydrase 9 (CAIX), Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag. In some embodiments, the target antigen is Muc1. In some embodiments, the target antigen is BCMA. In some embodiments, the BCMA is surface BCMA. In some embodiments, the recombinant receptor does not bind soluble BCMA or binds to soluble BCMA with an affinity lower than the affinity of said recombinant receptor for binding to surface BCMA. In some embodiments, the affinity of the antigen-binding domain to the surface B cell maturation antigen (BCMA) is at least 1-fold, 2-fold, 3-fold, 4-fold, 5-fold, 6-fold, 7-fold, 8-fold, 9-fold, or 10-fold higher than the affinity to the soluble BCMA.

In some embodiments of anyone of the methods provided herein, the subject comprises plasma cells, or cancer cells or myeloma cells or cells expressing plasma cell markers, expressing surface BCMA.

In some embodiments of any one of the methods provided herein, the subject is selected as having cells comprising low expression of surface B cell maturation antigen (BCMA); and/or selecting a subject for administration of the cell therapy and/or the inhibitor based on having plasma cells comprising low expression of surface BCMA.

In some embodiments of any one of the methods provided herein, the target of the gamma secretase inhibitor is the target antigen and the gamma secretase inhibitor inhibits cleavage of the target antigen.

In some embodiments of any one of the methods provided herein, administration of the inhibitor: decreases BCMA cleavage or shedding from cells, optionally plasma cells, by greater than or greater than about 5%, 10%, 20%, 30%, 40%, 50%, 60%, 70%, 80%, 90% or more compared to the level of BCMA cleavage or shedding from cells in the subject prior to administration of the inhibitor; decreases the level or amount of BCMA detected in the serum of a subject by greater than or greater than about 5%, 10%, 20%, 30%, 40%, 50%, 60%, 70%, 80%, 90% or more compared to the level or amount of BCMA in the serum of the subject prior to administration of the inhibitor; and/or increases expression of surface BCMA on cells, optionally plasma cells by greater than or greater than about 5%, 10%, 20%, 30%, 40%, 50%, 60%, 70%, 80%, 90% or more compared to the level of surface BCMA on the cells in the subject prior to administration of the inhibitor.

In some embodiments of any one of the methods provided herein, administration of the inhibitor: decreases cleavage or shedding of the target or the target antigen, optionally BCMA or Muc1, from cells, optionally plasma cells, by greater than or greater than about 5%, 10%, 20%, 30%, 40%, 50%, 60%, 70%, 80%, 90% or more compared to the level of cleavage or shedding of the target or target antigen from cells in the subject prior to administration of the inhibitor; decreases the level or amount of the target or target antigen, optionally BCMA or Muc1, detected in the serum of a subject by greater than or greater than about 5%, 10%, 20%, 30%, 40%, 50%, 60%, 70%, 80%, 90% or more compared to the level or amount of the target or target antigen in the serum of the subject prior to administration of the inhibitor; and/or increases expression of surface target or target antigen, optionally BCMA or Muc1, on cells, optionally plasma cells, by greater than or greater than about 5%, 10%, 20%, 30%, 40%, 50%, 60%, 70%, 80%, 90% or more compared to the level of surface target or target antigen on the cells in the subject prior to administration of the inhibitor.

In some embodiments of any one of the methods provided herein, the disease or disorder is a cancer. In some embodiments, the cancer is a B cell malignancy. In some embodiments, the cancer is multiple myeloma, plasmacytoma, a cancer of plasma cell origin and/or a cancer of B cell origin.

In some embodiments of any one of the methods provided herein, the inhibitor is administered orally, subcutaneously or intravenously. In some embodiments, the inhibitor is administered orally.

In some embodiments of any one of the methods provided herein, the inhibitor is administered at least or is administered six times daily, five times daily, four times daily, three times daily, twice daily, once daily, every other day, three times a week, at least once a week, or only one time. In some embodiments, the inhibitor is administered three times a week.

In some embodiments of any one of the methods provided herein, the administration of the inhibitor is carried out in a treatment cycle that is at least or at least about or 14 days, at least or at least about or 21 days or at least or at least about or 28 days.

In some embodiments of any one of the methods provided herein, the inhibitor is administered, or each administration of the inhibitor is independently administered, in an amount of 0.5 mg to 500 mg, 0.5 mg to 250 mg, 0.5 mg to 100 mg, 0.5 mg to 50 mg, 0.5 mg to 25 mg, 0.5 mg to 10 mg, 0.5 mg to 5.0 mg, 0.5 mg to 2.5 mg, 0.5 mg to 1.0 mg, 1.0 mg to 500 mg, 1.0 mg to 250 mg, 1.0 mg to 100 mg, 1.0 mg to 50 mg, 1.0 mg to 25 mg, 1.0 mg to 10 mg, 1.0 mg to 5.0 mg, 1.0 mg to 2.5 mg, 2.5 mg to 500 mg, 2.5 mg to 250 mg, 2.5 mg to 100 mg, 2.5 mg to 50 mg, 2.5 mg to 25 mg, 2.5 mg to 10 mg, 2.5 mg to 5.0 mg, 5.0 mg to 500 mg, 5.0 mg to 250 mg, 5.0 mg to 100 mg, 5.0 mg to 50 mg, 5.0 mg to 25 mg, 5.0 mg to 10 mg, 10 mg to 500 mg, 10 mg to 250 mg, 10 mg to 100 mg, 10 mg to 50 mg, 10 mg to 25 mg, 25 mg to 500 mg, 25 mg to 250 mg, 25 mg to 100 mg, 25 mg to 50 mg, 50 mg to 500 mg, 50 mg to 250 mg, 50 mg to 100 mg, 100 mg to 500 mg, 100 mg to 250 mg or 250 mg to 500 mg. In some embodiments, the inhibitor is administered, or each administration of the inhibitor is independently administered, in an amount that is at least or at least about or is or is about 0.5 mg, 1.0 mg, 2.5 mg, 5.0 mg, 10.0 mg, 25 mg, 50 mg, 100 mg, 250 mg or 500 mg.

In some embodiments of any one of the methods provided herein, the recombinant receptor is a transgenic T cell receptor (TCR) or a functional non-T cell receptor. In some embodiments, the recombinant receptor is a chimeric receptor, which optionally is a chimeric antigen receptor (CAR). In some embodiments, the chimeric antigen receptor (CAR) comprises an extracellular antigen-recognition domain that specifically binds to the antigen and an intracellular signaling domain comprising an ITAM. In some embodiments, the intracellular signaling domain comprises and intracellular domain of a CD3-zeta (CD3) chain. In some embodiments, the chimeric antigen receptor (CAR) further comprises a costimulatory signaling region. In some embodiments, the costimulatory signaling region comprises a signaling domain derived from CD28 or 4-1BB, optionally human CD28 or human 4-1BB. In some embodiments, the costimulatory signaling region is a domain derived from 4-1BB, optionally human 4-1BB.

In some embodiments of any one of the methods provided herein, the subject is a human.

In some embodiments of any one of the methods provided herein, the BCMA is human BCMA or the target antigen is a human antigen.

In some embodiments of any one of the methods provided herein, the genetically engineered cells comprise T cells or NK cells. In some embodiments, the cell therapy is a T cell therapy and the dose of genetically engineered cells comprises T cells. In some embodiments, the T cells are CD4+ and/or CD8+. In some embodiments, the T cells are primary T cells obtained from a subject.

In some embodiments of any one of the methods provided herein, the cell therapy comprises cells that are autologous to the subject.

In some embodiments of any one of the methods provided herein, the cell therapy comprises cells that are allogeneic to the subject.

In some embodiments of any one of the methods provided herein, the cell therapy comprises the administration of from or from about $1 \times 10^5$ to $5 \times 10^8$ total recombinant receptor-expressing cells, total T cells, or total peripheral blood mononuclear cells (PBMCs); the cell therapy comprises the administration of from or from about $1 \times 10^5$ to $1 \times 10^8$ total recombinant receptor-expressing cells, total T cells, or total PBMCs; from or from about $5 \times 10^5$ to $1 \times 10^7$ total recombinant receptor-expressing cells, total T cells, or total PBMCs; or from or from about $1 \times 10^6$ to $1 \times 10^7$ total recombinant receptor-expressing cells, total T cells, or total PBMCs, each inclusive.

In some embodiments of any one of the methods provided herein, the cell therapy comprises the administration of no more than $5 \times 10^8$ total recombinant receptor-expressing cells, total T cells, or total peripheral blood mononuclear cells (PBMCs); no more than $2.5 \times 10^8$ total recombinant receptor-expressing cells, total T cells, or total PBMCs; no more than $1 \times 10^8$ total recombinant receptor-expressing cells, total T cells, or total PBMCs; no more than $1 \times 10^7$ total recombinant receptor-expressing cells, total T cells, or total PBMCs; no more than $0.5 \times 10^7$ total recombinant receptor-expressing cells, total T cells, or total PBMCs; no more than $1 \times 10^6$ total recombinant receptor-expressing cells, total T cells, or total PBMCs; no more than $0.5 \times 10^6$ total recombinant receptor-expressing cells, total T cells, or total PBMCs.

In some embodiments of any one of the methods provided herein, the initiation of administration of the inhibitor is prior to, concurrently with or subsequently to initiation of administration of the cell therapy. In some embodiments, the inhibitor is administered prior to initiation of administration of the cell therapy. In some embodiments, initiation of administration of the inhibitor is within, or within about, 1 hours, 2 hour, 6 hours, 12 hours, 24 hours, 48 hours, 72 hours, 96 hours or 1 week prior to the initiation of the administration of the cell therapy. In some embodiments, the inhibitor is administered subsequently to initiation of administration of the cell therapy. In some embodiments, initiation of administration of the inhibitor is within, or within about, 1 hours, 2 hour, 6 hours, 12 hours, 24 hours, 48 hours, 72 hours, 96 hours, 1 week, 14 days, 21 days, 28 days or more after the initiation of the administration of the cell therapy. In some embodiments, the inhibitor is administered up to 7 days, 14 days, 21 days, 28 days or more after initiation of the administration of the cells.

In some embodiments of any one of the methods provided herein, the inhibitor is administered at a time in which: the number of cells of the cell therapy detectable in the blood from the subject is decreased compared to in the subject at a preceding time point after initiation of the administration of the cells; the number of cells of the cell therapy detectable in the blood is less than or less than about 1.5-fold, 2-fold, 3-fold, 4-fold, 5-fold, 10-fold, 50-fold or 100-fold or less the peak or maximum number of the cells of the cell therapy detectable in the blood of the subject after initiation of administration of the administration of the cells; and/or at a time after a peak or maximum level of the cells of the cell therapy are detectable in the blood of the subject, the number of cells of or derived from the cells detectable in the blood from the subject is less than less than 10%, less than 5%, less than 1% or less than 0.1% of total peripheral blood mononuclear cells (PBMCs) in the blood of the subject.

In some embodiments of any one of the methods provided herein, the method further comprises administering a lymphodepleting chemotherapy prior to administration of the cell therapy and/or wherein the subject has received a lymphodepleting chemotherapy prior to administration of the cells. In some embodiments, the lymphodepleting chemotherapy comprises administering fludarabine and/or cyclophosphamide to the subject.

In some embodiments of any one of the methods provided herein, the method further comprises administering a steroid, optionally wherein the steroid is administered prior to, concurrently with and/or subsequently to initiation of administration of the inhibitor, optionally wherein the steroid is administered during the cycle of treatment with the inhibitor. In some embodiments, the steroid is or comprises dexamethasone.

In some embodiments of any one of the methods provided herein, the cell therapy exhibits increased or prolonged expansion and/or persistence in the subject as compared to a method in which the cell therapy is administered to the subject in the absence of the gamma secretase inhibitor.

In some embodiments of any one of the methods provided herein, the method thereby prevents, reduces or ameliorates one or more symptoms or outcomes of the disease or disorder.

Provided herein are methods of treatment that involve: (a) administering to a subject having a disease or disorder, a therapeutic agent or therapy that targets or is specific for B cell maturation antigen (BCMA); and (b) administering a gamma secretase inhibitor to the subject.

In some embodiments of any one of the methods provided herein, the therapeutic agent or therapy is or comprises an antibody or antigen-binding fragment thereof, optionally a bispecific antibody. In some embodiments, therapeutic agent or therapy is a bispecific antibody that further targets or specifically binds to a T cell antigen, optionally CD2 or CD3. In some embodiments, the therapeutic agent or therapy is a bispecific antibody that further targets a second antigen, optionally wherein the second antigen is selected from CD19, CD20, CD22, CD33, CD38, CS1, ROR1, GPC3, CD123, IL-13R, CD138, c-Met, EGFRvIII, GD-2, NY-ESO-1, MAGE A3, and glycolipid F77.

In some embodiments of any one of the methods provided herein, the gamma secretase inhibitor is selected from LY3039478, secretase inhibitor I (GSI I) Z-Leu-Leu-Norleucine; γ-secretase inhibitor II (GSI II); γ-secretase inhibitor III (GSI III), N-Benzyloxycarbonyl-Leu-leucinal, N-(2-Naphthoyl)-Val-phenylalaninal; γ-secretase inhibitor III (GSI IV); γ-secretase inhibitor III (GSI V), N-Benzyloxycarbonyl-Leu-phenylalaninal; γ-secretase inhibitor III (GSI VI), 1-(S)-endo-N-(1,3,3)-Trimethylbicyclo[2.2.1]hept-2-yl)-4-fluorophenyl Sulfonamide; γ-secretase inhibitor III (GSI VII), Menthyloxycarbonyl-LL-CHO; γ-secretase inhibitor III (GSI IX), (DAPT), N-[N-(3,5-Difluorophenacetyl-L-alanyl)]-S-phenylglycine t-Butyl Ester; γ-secretase inhibitor X (GSI X), {1 S-Benzyl-4R-[1-(1S-carbamoyl-2-phenethylcarbamoyl)-1S-3-methylbutylcarb-amoyl]-2R-hydroxy-5-phenylpentyl}carbamic Acid tert-butyl Ester; γ-secretase inhibitor XI (GSI XI), 7-Amino-4-chloro-3-methoxyisocoumarin; γ-secretase inhibitor XII (GSI XII), Z-Ile-Leu-CHO; γ-secretase inhibitor XIII (GSI XIII), Z-Tyr-Ile-Leu-CHO; γ-secretase inhibitor XIV (GSI XIV), Z-Cys(t-Bu)-Ile-Leu-CHO; γ-secretase inhibitor XVI (GSI XVI), N-[N-3,5-Difluorophenacetyl]-L-alanyl-S-phenylglycine Methyl Ester; γ-secretase inhibitor XVII (GSI XVII); γ-secretase inhibitor XIX (GSI XIX), benzo[e][1,4]diazepin-3-yl)-butyramide; γ-secretase inhibitor XX (GSI XX), (S,S)-2-[2-(3,5-Difluorophenyl)acetylamino]-N-(5-methyl-6-oxo-6,7-dihydro-5H-dibenzo[b,d]azepin-7-yl)propionamide; γ-secretase inhibitor XXI (GSI XXI), (S,S)-2-[2-(3,5-Difluorophenyl)-acetylamino]-N-(1-methyl-2-oxo-5-phenyl-2-,3-dihydro-1H-benzo[e][1,4]diazepin-3-yl)-propionamide; Gamma40 secretase inhibitor I, N-trans-3,5-Dimethoxycinnamoyl-Ile-leucinal; Gamma40 secretase inhibitor II, N-tert-Butyloxycarbonyl-Gly-Val-Valinal Isovaleryl-V V-Sta-A-Sta-OCH3; MK-0752; MRK-003 (Merck); semagacestat/LY450139; RO4929097; PF-03084, 014; BMS-708163; MPC-7869 (γ-secretase modifier), YO-01027 (Dibenzazepine), Compound E ([(2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide], LY411575, L-685,458, BMS-289948 (4-chloro-N-(2,5-difluorophenyl)-N-((1R)-{4-fluoro-2-[3-(1H-imidazol-1-yl)propyl]phenyl}ethyl)benzenesulfonamide hydrochloride) and BMS-299897 (4-[2-((1R)-1-{[(4-chlorophenyl)sulfonyl]-2,5-difluoroanilino}ethyl)-5-fluorophenyl}butanoic acid).

In some embodiments of any one of the methods provided herein, the gamma secretase inhibitor is a compound of the structure:

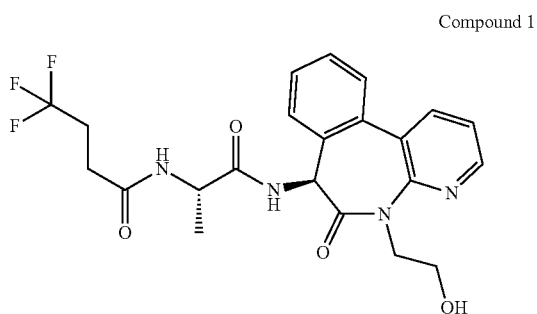 [SMILES: C[C@H](NC(=O)CCC(F)(F)F)C(=O)N[C@@H]1C(=O)N(CCO)c2ncccc2-c2ccccc21]

Compound 1 or a pharmaceutically acceptable salt of hydrate thereof.

Provided herein are combinations that include: (a) genetically engineered cells expressing a chimeric receptor comprising an antigen binding domain that binds to surface B cell maturation antigen (BCMA); (b) an inhibitor of gamma secretase, wherein binding of the CAR to surface BCMA or a measure indicative of function or activity, following exposure to cells expressing surface BCMA, is not reduced or blocked or is not substantially reduced or blocked in the presence of a soluble or shed form of the BCMA, optionally at a concentration or amount of the soluble or shed form of the BCMA corresponding to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA CAR in the same assay.

In some embodiments of any one of the combinations provided herein, the gamma secretase inhibitor inhibits intramembrane cleavage of BCMA.

In some embodiments of any one of the combinations provided herein, the gamma secretase inhibitor inhibits intramembrane cleavage of BCMA with a half-maximal inhibitory concentration ($IC_{50}$) of 0.01 nM to 10 nM, 0.01 nM to 5 nM, 0.01 nM to 1 nM, 0.01 nM to 0.5 nM, 0.01 nM to 0.35 nM, 0.01 nM to 0.25 nM, 0.01 nM to 0.1 nM, 0.01 nM to 0.05 nM, 0.05 nM to 10 nM, 0.05 nM to 5 nM, 0.05 nM to 1 nM, 0.05 nM to 0.5 nM, 0.05 nM to 0.35 nM, 0.05 nM to 0.25 nM, 0.05 nM to 0.1 nM, 0.1 nM to 10 nM, 0.1 nM to 5 nM, 0.1 nM to 1 nM, 0.1 nM, to 0.5 nM, 0.1 nM to 0.35 nM, 0.1 nM to 0.25 nM, 0.25 nM to 10 nM, 0.25 nM to 5 nM, 0.25 nM to 1 nM, 0.25 nM to 0.5 nM, 0.25 nM to 0.35 nM, 0.35 nM to 10 nM, 0.35 nM to 5 nM, 0.35 nM to 1 nM, 0.35 nM to 0.5 nM, 0.5 nM to 10 nM, 0.5 nM to 5 nM, 0.5 nM to 1 nM, 1 nM to 10 nM, 1 nM to 5 nM or 5 nM to 10 nM. In some embodiments, the gamma secretase inhibitor inhibits intramembrane cleavage of BCMA with a half-maximal inhibitory concentration ($IC_{50}$) of less than or less than about 10 nM, 5 nM, 1 nM, 0.5 nM, 0.35 nM, 0.25 nM, 0.1 nM, 0.05 nM or 0.01 nM or less.

Provided herein are combinations that include: (a) genetically engineered cells expressing a recombinant receptor, wherein the recombinant receptor does not specifically bind to surface B cell maturation antigen (BCMA); and (b) an inhibitor of gamma secretase.

Provided herein are combinations that include: (a) genetically engineered cells expressing a recombinant receptor, wherein the recombinant receptor does not specifically bind to surface B cell maturation antigen (BCMA); and (b) an inhibitor of gamma secretase, wherein binding of the CAR to surface BCMA or a measure indicative of function or activity, following exposure to cells expressing surface BCMA, is not reduced or blocked or is not substantially reduced or blocked in the presence of a soluble or shed form of the BCMA, optionally at a concentration or amount of the soluble or shed form of the BCMA corresponding to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA CAR in the same assay.

In some embodiments of any one of the combinations provided herein, the recombinant receptor specifically binds to a target antigen associated with the disease or disorder. In some embodiments, the target antigen is selected from among, carbonic anhydrase 9 (CAIX), Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag. In some embodiments, the target antigen is Muc1.

In some embodiments of any one of the combinations provided herein, the gamma secretase inhibitor inhibits or reduces or is capable of inhibiting or reducing cleavage of one or more targets selected from BCMA, Notch 1, Notch 2, Notch 3, Notch 4, Muc1, Ephrin B2, Betaglycan (TGFBR3), CD43, CD44, CSF1R, CXCR1, CXCL16, Delta1, E-cadherein, N-cadherin, HLA-A2, IFNaR2, IL1R1, IL1R2, IL6R or ameloid precursor protein (APP). In some embodiments, the one or more targets the cleavage of which is reduced or inhibited comprises Muc1. In some embodiments, the one or more targets the cleavage of which is reduced or inhibited comprises BCMA.

In some embodiments of any one of the combinations provided herein, cleavage of one or more targets selected from BCMA, Notch 1, Notch 2, Notch 3, Notch 4, Muc1, Ephrin B2, Betaglycan (TGFBR3), CD43, CD44, CSF1R, CXCR1, CXCL16, Delta1, E-cadherein, N-cadherin, HLA-A2, IFNaR2, IL1R1, IL1R2, IL6R or ameloid precursor protein (APP) is inhibited or reduced or can be inhibited or reduced by the gamma secretase inhibitor. In some embodiments, the one or more targets the cleavage of which is inhibited or reduced comprises Muc1. In some embodiments, the one or more targets the cleavage of which is reduced or inhibited comprises BCMA.

In some embodiments of any one of the combinations provided herein, the gamma secretase inhibitor inhibits the target with a half-maximal inhibitory concentration ($IC_{50}$) of 0.01 nM to 1 µM, 0.01 nM to 100 nM, 0.01 nM to 10 nM, 0.01 nM to 5 nM, 0.01 nM to 1 nM, 0.01 nM to 0.5 nM, 0.01 nM to 0.25 nM, 0.01 nM to 0.1 nM, 0.01 nM to 0.05 nM, 0.05 nM to 1 µM, 0.05 nM to 100 nM, 0.05 nM to 10 nM, 0.05 nM to 5 nM, 0.05 nM to 1 nM, 0.05 nM to 0.5 nM, 0.05 nM to 0.25 nM, 0.05 nM to 0.1 nM, 0.1 nM to 1 µM, 0.1 nM to 100 nM, 0.1 nM to 10 nM, 0.1 nM to 5 nM, 0.1 nM to 1 nM, 0.1 nM to 0.5 nM, 0.1 nM to 0.25 nM, 0.25 nM to 1 µM, 0.25 nM to 100 nM, 0.25 nM to 10 nM, 0.25 nM to 5 nM, 0.25 nM to 1 nM, 0.25 nM to 0.5 nM, 0.5 nM to 1 µM, 0.5 nM to 100 nM, 0.5 nM to 10 nM, 0.5 nM to 5 nM, 0.5 nM to 1 nM, 1 nM to 1 µM, 1 nM to 100 nM, 1 nM to 10 nM, 1 nM to 5 nM, 5 nM to 1 µM, 5 nM to 100 nM, 5 nM to 10 nM, 10 nM to 1 µM, 10 nM to 100 nM or 100 nM to 1 µM. In some embodiments, the gamma secretase inhibitor inhibits the target with a half-maximal inhibitory concentration ($IC_{50}$) of less than or less than about 1 µM, 100 nM, 10 nM, 5 nM, 1 nM, 0.5 nM, 0.35 nM, 0.25 nM, 0.1 nM, 0.05 nM or 0.01 nM or less.

In some embodiments of any one of the combinations provided herein, the gamma secretase inhibitor is a peptide inhibitor or non-peptide inhibitor. In some embodiments, the gamma secretase inhibitor is a peptide inhibitor and the peptide inhibitor is selected from among peptide aldehydes derivatives, difluoroketones derivatives, hydroxyethylene dipeptide isotere derivatives, alpha-helical peptide derivatives and dipeptide analogs. In some embodiments, the gamma secretase inhibitor is a non-peptide inhibitor and the non-peptide inhibitor is a benzodiazepines derivative or a sulfonamides derivative.

In some embodiments of any one of the combinations provided herein, the gamma secretase inhibitor is a transition state inhibitor or non-transition state inhibitor.

In some embodiments of any one of the combinations provided herein, the gamma secretase inhibitor is a non-steroidal anti-inflammatory drug.

In some embodiments of any one of the combinations provided herein, the gamma secretase inhibitor is selected from LY3039478, secretase inhibitor I (GSI I) Z-Leu-Leu-Norleucine; γ-secretase inhibitor II (GSI II); γ-secretase inhibitor III (GSI III), N-Benzyloxycarbonyl-Leu-leucinal, N-(2-Naphthoyl)-Val-phenylalaninal; γ-secretase inhibitor III (GSI IV); γ-secretase inhibitor III (GSI V), N-Benzyloxycarbonyl-Leu-phenylalaninal; γ-secretase inhibitor III (GSI VI), 1-(S)-endo-N-(1,3,3)-Trimethylbicyclo[2.2.1]hept-2-yl)-4-fluorophenyl Sulfonamide; γ-secretase inhibitor III (GSI VII), Menthyloxycarbonyl-LL-CHO; γ-secretase inhibitor III (GSI IX), (DAPT), N-[N-(3,5-Difluorophenacetyl-L-alanyl)]-S-phenylglycine t-Butyl Ester; γ-secretase inhibitor X (GSI X), {1S-Benzyl-4R-[1-(1S-carbamoyl-2-phenethylcarbamoyl)-1S-3-methylbutylcarbamoyl]-2R-hydroxy-5-phenylpentyl}carbamic Acid tert-butyl Ester; γ-secretase inhibitor XI (GSI XI), 7-Amino-4-chloro-3-methoxyisocoumarin; γ-secretase inhibitor XII (GSI XII), Z-Ile-Leu-CHO; γ-secretase inhibitor XIII (GSI XIII), Z-Tyr-Ile-Leu-CHO; γ-secretase inhibitor XIV (GSI XIV), Z-Cys(t-Bu)-Ile-Leu-CHO; γ-secretase inhibitor XVI (GSI XVI), N-[N-3,5-Difluorophenacetyl]-L-alanyl-S-phenylglycine Methyl Ester; γ-secretase inhibitor XVII (GSI XVII); γ-secretase inhibitor XIX (GSI XIX), benzo[e][1,4]diazepin-3-yl)-butyramide; γ-secretase inhibitor XX (GSI XX), (S,S)-2-[2-(3,5-Difluorophenyl)acetylamino]-N-(5-methyl-6-oxo-6,7-dihydro-5H-dibenzo[b,d]azepin-7-yl)propionamide; γ-secretase inhibitor XXI (GSI XXI), (S,S)-2-[2-(3,5-Difluorophenyl)-acetylamino]-N-(1-methyl-2-oxo-5-phenyl-2-,3-dihydro-1H-benzo[e][1,4]diazepin-3-yl)-propionamide; Gamma40 secretase inhibitor I, N-trans-3,5-Dimethoxycinnamoyl-Ile-leucinal; Gamma40 secretase inhibitor II, N-tert-Butyloxycarbonyl-Gly-Val-Valinal Isovaleryl-V V-Sta-A-Sta-OCH3; MK-0752; MRK-003 (Merck); semagacestat/LY450139; RO4929097; PF-03084, 014; BMS-708163; MPC-7869 (γ-secretase modifier), YO-01027 (Dibenzazepine), Compound E ([(2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide], LY411575, L-685,458, BMS-289948 (4-chloro-N-(2,5-difluorophenyl)-N-((1R)-{4-fluoro-2-[3-(1H-imidazol-1-yl)propyl]phenyl}ethyl)benzenesulfonamide hydrochloride) and BMS-299897 (4-[2-((1R)-1-{[(4-chlorophenyl)sulfonyl]-2,5-difluoroanilino}ethyl)-5-fluorophenyl]butanoic acid).

In some embodiments of any one of the combinations provided herein, the gamma secretase inhibitor is a compound of the structure:

Compound 1

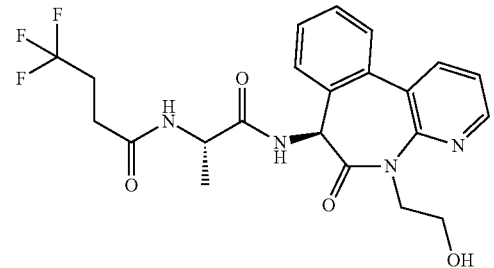

or a pharmaceutically acceptable salt of hydrate thereof.

Provided herein are combinations that include: (a) genetically engineered cells expressing a recombinant receptor; and (b) a compound of the structure:

Compound 1

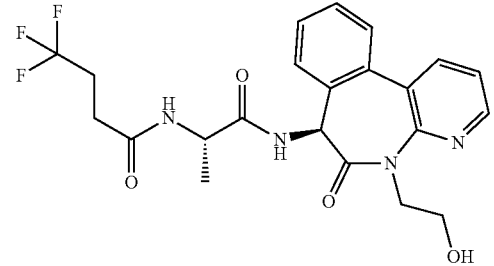

or a pharmaceutically acceptable salt of hydrate thereof.

In some embodiments of any one of the combinations provided herein, the recombinant receptor specifically binds to a target antigen associated with the disease or disorder. In some embodiments, the target antigen is selected from among, B cell maturation antigen (BCMA), carbonic anhydrase 9 (CAIX), Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag. In some embodiments, the target antigen is Muc1.

In some embodiments of any one of the combinations provided herein, the target antigen is BCMA. In some embodiments, the BCMA is surface BCMA. In some embodiments, the binding of the CAR to surface BCMA or a measure indicative of function or activity, following exposure to cells expressing surface BCMA, is not reduced or blocked or is not substantially reduced or blocked in the presence of a soluble or shed form of the BCMA, optionally at a concentration or amount of the soluble or shed form of the BCMA corresponding to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA CAR in the same assay. In some embodiments, the recombinant receptor does not bind soluble BCMA or binds to soluble BCMA with an affinity lower than the affinity of said recombinant receptor for binding to surface BCMA.

In some embodiments of any one of the combinations provided herein, the recombinant receptor is a transgenic T cell receptor (TCR) or a functional non-T cell receptor. In some embodiments, the recombinant receptor is a chimeric receptor, which optionally is a chimeric antigen receptor (CAR). In some embodiments, the chimeric antigen receptor (CAR) comprises an extracellular antigen-recognition domain that specifically binds to the antigen and an intracellular signaling domain comprising an ITAM. In some embodiments, the intracellular signaling domain comprises and intracellular domain of a CD3-zeta (CD3ζ) chain. In some embodiments, the chimeric antigen receptor (CAR) further comprises a costimulatory signaling region. In some embodiments, the costimulatory signaling region comprises a signaling domain derived from CD28 or 4-1BB, optionally human CD28 or human 4-1BB. In some embodiments, the costimulatory signaling region is a domain derived from 4-1BB, optionally human 4-1BB.

In some embodiments of any one of the combinations provided herein, the BCMA is human BCMA or the target antigen is a human antigen.

In some embodiments of any one of the combinations provided herein, the genetically engineered cells comprise T cells or NK cells. In some embodiments, the genetically engineered cells comprise T cells. In some embodiments, the T cells are CD4+ and/or CD8+. In some embodiments, the T cells are primary T cells obtained from a subject.

In some embodiments of any one of the combinations provided herein, the genetically engineered cells are formulated as a pharmaceutical composition for administration to a subject, optionally wherein the cells are formulated for administration in one or more unit doses for treating a disease or condition.

In some embodiments of any one of the combinations provided herein, the gamma secretase inhibitor is formulated as a pharmaceutical composition for administration to a subject, optionally wherein the gamma secretase inhibitor is formulated for administration in one or more unit doses.

Provided herein are kits that contain a combination and instructions for administering the components of the combination to a subject having a disease or disorder.

Provided herein are kits that contain: (a) a reagent for detecting expression of B cell maturation antigen (BCMA) on the surface of a cell; (b) an inhibitor of gamma secretase, optionally formulated for administration in one or more unit doses; and (c) instructions for administering the inhibitor to a subject based on the results of use of the reagent for detecting BCMA on the surface of plasma cells in a subject having a cancer.

In some embodiments of any one of the kits provided herein, the instructions specify administering the inhibitor to the subject if the plasma cells comprise low expression of surface BCMA and/or a level of expression of surface BCMA below a threshold level. In some embodiments, the threshold level of expression of surface BCMA is lower than the average or median expression or level of surface BCMA on plasma cells in a plurality of control subjects, optionally wherein the control subjects are a group of healthy or normal subjects. In some embodiments, the low expression of surface BCMA is present when less than or less than about 60%, less than or less than about 50%, less than or less than about 40%, less than or less than about 30%, less than or less than about 20% or less than or less than about 10% of the plasma cells, or cells with a plasma cell marker or phenotype, or the cancer cells in the subject express surface BCMA; or the threshold level of surface BCMA is less than or less than about 60%, less than or less than about 50%, less than or less than about 40%, less than or less than about 30%, less than or less than about 20% or less than or less than about 10% of the plasma cells, or cells with a plasma cell marker or phenotype or the cancer cells in the subject that express surface BCMA.

In some embodiments of any one of the kits provided herein, the kits further contain: genetically engineered cells expressing a recombinant receptor, optionally wherein the genetically engineered cells are formulated for administration of one or more unit doses to a subject having a disease or condition. In some embodiments, the recombinant receptor specifically binds to a target antigen associated with the disease or condition.

In some embodiments of any one of the kits provided herein, the instructions specify administering the gamma secretase inhibitor, or one or more unit doses thereof, to a subject having a disease or disorder prior to, concurrently with or after initiation of administration of a dose of the genetically engineered cells to the subject, optionally wherein the genetically engineered cells are formulated for administration of one or more unit doses to a subject having a disease or condition. In some embodiments, the instructions specify administering the gamma secretase inhibitor, or one or more unit doses thereof, to a subject having a disease or disorder prior to initiation of administration of a dose of the genetically engineered cells to the subject. In some embodiments, the instructions specify administering the inhibitor within, or within about, 1 hours, 2 hour, 6 hours, 12 hours, 24 hours, 48 hours, 72 hours, 96 hours or 1 week prior to the initiation of the administration of the cell therapy. In some embodiments, the instructions specify administering the gamma secretase inhibitor, or one or more unit doses thereof, to a subject having a disease or disorder after initiation of administration of a dose of the genetically engineered cells to the subject.

Provided herein are kits that contain: (a) a gamma secretase inhibitor, optionally wherein the gamma secretase inhibitor is formulated in one or more unit doses; and (b) instructions for administering the gamma secretase inhibitor to a subject after initiation of administration of a cell therapy to a subject, the cell therapy comprising a dose of genetically engineered cells expressing a recombinant receptor.

Provided herein are kits that contain: (a) a gamma secretase inhibitor, optionally wherein the gamma secretase inhibitor is formulated in one or more unit doses; and (b) instructions for administering the gamma secretase inhibitor to a subject after initiation of administration of a cell therapy to a subject, the cell therapy comprising a dose of genetically engineered cells expressing a recombinant receptor comprising a chimeric antigen receptor (CAR) comprising an antigen-binding domain that binds to surface B cell maturation antigen (BCMA), wherein binding of the CAR to surface BCMA or a measure indicative of function or activity, following exposure to cells expressing surface BCMA, is not reduced or blocked or is not substantially reduced or blocked in the presence of a soluble or shed form of the BCMA, optionally at a concentration or amount of the soluble or shed form of the BCMA corresponding to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA CAR in the same assay.

In some embodiments of any one of the kits provided herein, initiation of administration of the inhibitor is within, or within about, 1 hours, 2 hour, 6 hours, 12 hours, 24 hours, 48 hours, 72 hours, 96 hours, 1 week, 14 days, 21 days, 28 days or more after the initiation of the administration of the dose of genetically engineered cells.

In some embodiments of any one of the kits provided herein, the instructions specify the inhibitor is for administration at a time in which: the number of cells of the cell therapy detectable in the blood from the subject is decreased compared to in the subject at a preceding time point after initiation of the administration of the cells; the number of cells of the cell therapy detectable in the blood is less than or less than about 1.5-fold, 2-fold, 3-fold, 4-fold, 5-fold, 10-fold, 50-fold or 100-fold or less the peak or maximum number of the cells of the cell therapy detectable in the blood of the subject after initiation of administration of the administration of the cells; and/or at a time after a peak or maximum level of the cells of the cell therapy are detectable in the blood of the subject, the number of cells of or derived from the cells detectable in the blood from the subject is less than less than 10%, less than 5%, less than 1% or less than 0.1% of total peripheral blood mononuclear cells (PBMCs) in the blood of the subject.

In some embodiments of any one of the kits provided herein, the instructions specify the inhibitor is for administration up to 7 days, 14 days, 21 days, 28 days or more after initiation of the administration of the cells.

In some embodiments of any one of the kits provided herein, the recombinant receptor specifically binds to a target antigen associated with the disease or disorder. In some embodiments, the target antigen is selected from among, B cell maturation antigen (BCMA), carbonic anhydrase 9 (CAIX), Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag. In some embodiments, the target antigen is Muc1, optionally human Muc1. In some embodiments of any embodiment, the target antigen is a human antigen.

In some embodiments, the target antigen is BCMA, optionally human BCMA. In some embodiments, binding of the CAR to surface BCMA or a measure indicative of function or activity, following exposure to cells expressing surface BCMA, is not reduced or blocked or is not substantially reduced or blocked in the presence of a soluble or shed form of the BCMA, optionally at a concentration or amount of the soluble or shed form of the BCMA corresponding to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA CAR in the same assay. In some embodiments, the recombinant receptor does not bind soluble BCMA or binds to soluble BCMA with an affinity lower than the affinity of said recombinant receptor for binding to surface BCMA.

In some embodiments of any one of the kits provided herein, the recombinant receptor is a transgenic T cell receptor (TCR) or a functional non-T cell receptor. In some embodiments, the recombinant receptor is a chimeric receptor, which optionally is a chimeric antigen receptor (CAR). In some embodiments, the chimeric antigen receptor (CAR) comprises an extracellular antigen-recognition domain that specifically binds to the antigen and an intracellular signaling domain comprising an ITAM. In some embodiments, the intracellular signaling domain comprises and intracellular domain of a CD3-zeta (CD3) chain. In some embodiments, the chimeric antigen receptor (CAR) further comprises a costimulatory signaling region. In some embodiments, the costimulatory signaling region comprises a signaling domain derived from CD28 or 4-1BB, optionally human CD28 or human 4-1BB. In some embodiments, the costimulatory signaling region is a domain derived from 4-1BB, optionally human 4-1BB.

In some embodiments of any one of the kits provided herein, the genetically engineered cells comprise T cells or NK cells. In some embodiments, the genetically engineered cells comprise T cells. In some embodiments, the T cells are CD4+ and/or CD8+. In some embodiments, the T cells are primary T cells obtained from a subject.

In some embodiments of any one of the kits provided herein, the gamma secretase inhibitor inhibits or reduces or is capable of inhibiting or reducing cleavage of one or more targets selected from BCMA, Notch 1, Notch 2, Notch 3, Notch 4, Muc1, Ephrin B2, Betaglycan (TGFBR3), CD43, CD44, CSF1R, CXCR1, CXCL16, Delta1, E-cadherein, N-cadherin, HLA-A2, IFNaR2, IL1R1, IL1R2, IL6R or ameloid precursor protein (APP). In some embodiments, the one or more targets the cleavage of which is reduced or inhibited comprises Muc1. In some embodiments, the one or more targets the cleavage of which is reduced or inhibited comprises BCMA.

In some embodiments of any one of the kits provided herein, cleavage of one or more targets selected from BCMA, Notch 1, Notch 2, Notch 3, Notch 4, Muc1, Ephrin B2, Betaglycan (TGFBR3), CD43, CD44, CSF1R, CXCR1, CXCL16, Delta1, E-cadherein, N-cadherin, HLA-A2, IFNaR2, IL1R1, IL1R2, IL6R or ameloid precursor protein (APP) is inhibited or reduced or can be inhibited or reduced the gamma secretase inhibitor. In some embodiments, the one or more targets the cleavage of which is reduced or inhibited comprises Muc1. In some embodiments, the one or more targets the cleavage of which is reduced or inhibited comprises BCMA.

In some embodiments of any one of the kits provided herein, the gamma secretase inhibitor inhibits the target with a half-maximal inhibitory concentration ($IC_{50}$) of 0.01 nM to 1 µM, 0.01 nM to 100 nM, 0.01 nM to 10 nM, 0.01 nM to 5 nM, 0.01 nM to 1 nM, 0.01 nM to 0.5 nM, 0.01 nM to 0.25 nM, 0.01 nM to 0.1 nM, 0.01 nM to 0.05 nM, 0.05 nM to 1 µM, 0.05 nM to 100 nM, 0.05 nM to 10 nM, 0.05 nM to 5 nM, 0.05 nM to 1 nM, 0.05 nM to 0.5 nM, 0.05 nM to 0.25 nM, 0.05 nM to 0.1 nM, 0.1 nM to 1 µM, 0.1 nM to 100 nM, 0.1 nM to 10 nM, 0.1 nM to 5 nM, 0.1 nM to 1 nM, 0.1 nM to 0.5 nM, 0.1 nM to 0.25 nM, 0.25 nM to 1 µM, 0.25 nM to 100 nM, 0.25 nM to 10 nM, 0.25 nM to 5 nM, 0.25 nM to 1 nM, 0.25 nM to 0.5 nM, 0.5 nM to 1 µM, 0.5 nM to 100 nM, 0.5 nM to 10 nM, 0.5 nM to 5 nM, 0.5 nM to 1 nM, 1 nM to 1 µM, 1 nM to 100 nM, 1 nM to 10 nM, 1 nM to 5 nM, 5 nM to 1 µM, 5 nM to 100 nM, 5 nM to 10 nM, 10 nM to 1 µM, 10 nM to 100 nM or 100 nM to 1 µM.

In some embodiments of any one of the kits provided herein, the gamma secretase inhibitor inhibits the target with a half-maximal inhibitory concentration ($IC_{50}$) of less than or less than about 1 µM, 100 nM, 10 nM, 5 nM, 1 nM, 0.5 nM, 0.35 nM, 0.25 nM, 0.1 nM, 0.05 nM or 0.01 nM or less.

In some embodiments of any one of the kits provided herein, the gamma secretase inhibitor is a peptide inhibitor or non-peptide inhibitor. In some embodiments, the gamma secretase inhibitor is a peptide inhibitor and the peptide inhibitor is selected from among peptide aldehydes derivatives, difluoroketones derivatives, hydroxyethylene dipeptide isotere derivatives, alpha-helical peptide derivatives and dipeptide analogs. In some embodiments, the gamma secretase inhibitor is a non-peptide inhibitor and the non-peptide inhibitor is a benzodiazepines derivative or a sulfonamides derivative.

In some embodiments of any one of the kits provided herein, the gamma secretase inhibitor is a transition state inhibitor or non-transition state inhibitor.

In some embodiments of any one of the kits provided herein, the gamma secretase inhibitor is a nonsteroidal anti-inflammatory drug.

In some embodiments of any one of the kits provided herein, the gamma secretase inhibitor is selected from LY3039478, secretase inhibitor I (GSI I) Z-Leu-Leu-Norleucine; γ-secretase inhibitor II (GSI II); γ-secretase inhibitor III (GSI III), N-Benzyloxycarbonyl-Leu-leucinal, N-(2-Naphthoyl)-Val-phenylalaninal; γ-secretase inhibitor III (GSI IV); γ-secretase inhibitor III (GSI V), N-Benzyloxycarbonyl-Leu-phenylalaninal; γ-secretase inhibitor III (GSI VI), 1-(S)-endo-N-(1,3,3)-Trimethylbicyclo[2.2.1]hept-2-yl)-4-fluorophenyl Sulfonamide; γ-secretase inhibitor III (GSI VII), Menthyloxycarbonyl-LL-CHO; γ-secretase inhibitor III (GSI IX), (DAPT), N-[N-(3,5-Difluorophenacetyl-L-alanyl)]-S-phenylglycine t-Butyl Ester; γ-secretase inhibitor X (GSI X), {1 S-Benzyl-4R-[1-(1S-carbamoyl-2-phenethylcarbamoyl)-1S-3-methylbutylcarb-amoyl]-2R-hydroxy-5-phenylpentyl}carbamic Acid tert-butyl Ester; γ-secretase inhibitor XI (GSI XI), 7-Amino-4-chloro-3-methoxyisocoumarin; γ-secretase inhibitor XII (GSI XII), Z-Ile-Leu-CHO; γ-secretase inhibitor XIII (GSI XIII), Z-Tyr-Ile-Leu-CHO; γ-secretase inhibitor XIV (GSI XIV), Z-Cys(t-Bu)-Ile-Leu-CHO; γ-secretase inhibitor XVI (GSI XVI), N-[N-3,5-Difluorophenacetyl]-L-alanyl-S-phenylglycine Methyl Ester; γ-secretase inhibitor XVII (GSI XVII); γ-secretase inhibitor XIX (GSI XIX), benzo[e][1,4]diazepin-3-yl)-butyramide; γ-secretase inhibitor XX (GSI XX), (S,S)-2-[2-(3,5-Difluorophenyl)acetylamino]-N-(5-methyl-6-oxo-6,7-dihydro-5H-dibenzo[b,d]azepin-7-yl)propionamide; γ-secretase inhibitor XXI (GSI XXI), (S,S)-2-[2-(3,5-Difluorophenyl)-acetylamino]-N-(1-methyl-2-oxo-5-phenyl-2-,3-dihydro-1H-benzo[e][1,4]diazepin-3-yl)-propionamide; Gamma40 secretase inhibitor I, N-trans-3,5-Dimethoxycinnamoyl-Ile-leucinal; Gamma40 secretase inhibitor II, N-tert-Butyloxycarbonyl-Gly-Val-Valinal Isovaleryl-V V-Sta-A-Sta-OCH3; MK-0752; MRK-003 (Merck); semagacestat/LY450139; RO4929097; PF-03084, 014; BMS-708163; MPC-7869 (γ-secretase modifier), YO-01027 (Dibenzazepine), Compound E ([(2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide], LY411575, L-685,458, BMS-289948 (4-chloro-N-(2, 5-difluorophenyl)-N-((1R)-{4-fluoro-2-[3-(1H-imidazol-1-yl)propyl]phenyl}ethyl)benzenesulfonamide hydrochloride) and BMS-299897 (4-[2-((1R)-1-{[(4-chlorophenyl)sulfonyl]-2,5-difluoroanilino}ethyl)-5-fluorophenyl]butanoic acid).

In some embodiments of any one of the kits provided herein, the gamma secretase inhibitor is a compound of the structure:

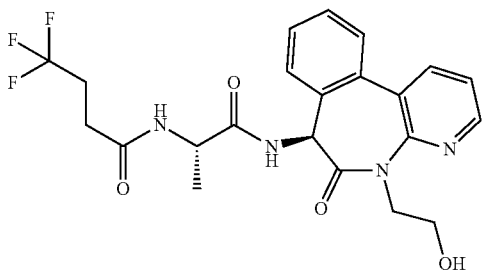

Compound 1 or a pharmaceutically acceptable salt of hydrate thereof.

In some embodiments of any one of the kits provided herein, the instructions specify administering a dose of genetically engineered cells to a subject having a disease or disorder. In some embodiments, the disease or disorder is a cancer. In some embodiments, the cancer is a B cell malignancy. In some embodiments, the cancer is multiple myeloma, plasmacytoma, a cancer of plasma cell origin and/or a cancer of B cell origin.

In some embodiments of any one of the kits provided herein, the dose comprises from or from about $1 \times 10^5$ to $5 \times 10^8$ total recombinant receptor-expressing cells, total T cells, or total peripheral blood mononuclear cells (PBMCs); the cell therapy comprises the administration of from or from about $1 \times 10^5$ to $1 \times 10^8$ total recombinant receptor-expressing cells, total T cells, or total PBMCs; from or from about $5 \times 10^5$ to $1 \times 10^7$ total recombinant receptor-expressing cells, total T cells, or total PBMCs; or from or from about $1 \times 10^6$ to $1 \times 10^7$ total recombinant receptor-expressing cells, total T cells, or total PBMCs, each inclusive; optionally wherein the instructions specify the administration of one or of a plurality of unit doses comprising the dose of cells and/or a volume corresponding to such one or plurality of unit doses comprising the dose of cells.

In some embodiments of any one of the kits provided herein, the dose comprises no more than $5 \times 10^8$ total recombinant receptor-expressing cells, total T cells, or total peripheral blood mononuclear cells (PBMCs); no more than $2.5 \times 10^8$ total recombinant receptor-expressing cells, total T cells, or total PBMCs; no more than $1 \times 10^8$ total recombinant receptor-expressing cells, total T cells, or total PBMCs; no more than $1 \times 10^7$ total recombinant receptor-expressing cells, total T cells, or total PBMCs; no more than $0.5 \times 10^7$ total recombinant receptor-expressing cells, total T cells, or total PBMCs; no more than $1 \times 10^6$ total recombinant receptor-expressing cells, total T cells, or total PBMCs; no more than $0.5 \times 10^6$ total recombinant receptor-expressing cells, total T cells, or total PBMCs; optionally wherein the instructions specify the administration of one or of a plurality of unit doses comprising the dose of cells and/or a volume corresponding to such one or plurality of unit doses comprising the dose of cells.

In some embodiments of any one of the kits provided herein, the instructions specify administering the inhibitor orally, subcutaneously or intravenously. In some embodiments, the instructions specify administering the inhibitor orally.

In some embodiments of any one of the kits provided herein, the instructions specify the inhibitor is to be administered at least six times daily, five times daily, four times daily, three times daily, twice daily, once daily, every other day, three times a week, at least once a week, or only one time. In some embodiments, the instructions specify the inhibitor is administered three times a week.

In some embodiments of any one of the kits provided herein, the instructions specify the administration of the inhibitor is to be carried out in a treatment cycle that is at least or at least about or 14 days, at least or at least about or 21 days or at least or at least about or 28 days.

In some embodiments of any one of the kits provided herein, the instructions specify the inhibitor is administered, or each administration of the inhibitor is independently administered, in an amount of 0.5 mg to 500 mg, 0.5 mg to 250 mg, 0.5 mg to 100 mg, 0.5 mg to 50 mg, 0.5 mg to 25 mg, 0.5 mg to 10 mg, 0.5 mg to 5.0 mg, 0.5 mg to 2.5 mg, 0.5 mg to 1.0 mg, 1.0 mg to 500 mg, 1.0 mg to 250 mg, 1.0 mg to 100 mg, 1.0 mg to 50 mg, 1.0 mg to 25 mg, 1.0 mg to 10 mg, 1.0 mg to 5.0 mg, 1.0 mg to 2.5 mg, 2.5 mg to 500 mg, 2.5 mg to 250 mg, 2.5 mg to 100 mg, 2.5 mg to 50 mg, 2.5 mg to 25 mg, 2.5 mg to 10 mg, 2.5 mg to 5.0 mg, 5.0 mg to 500 mg, 5.0 mg to 250 mg, 5.0 mg to 100 mg, 5.0 mg to 50 mg, 5.0 mg to 25 mg, 5.0 mg to 10 mg, 10 mg to 500 mg, 10 mg to 250 mg, 10 mg to 100 mg, 10 mg to 50 mg, 10 mg to 25 mg, 25 mg to 500 mg, 25 mg to 250 mg, 25 mg to 100 mg, 25 mg to 50 mg, 50 mg to 500 mg, 50 mg to 250 mg, 50 mg to 100 mg, 100 mg to 500 mg, 100 mg to 250 mg or 250 mg to 500 mg.

In some embodiments of any one of the kits provided herein, the instructions specify the inhibitor is administered, or each administration of the inhibitor is independently administered, in an amount that is at least or at least about or is or is about 0.5 mg, 1.0 mg, 2.5 mg, 5.0 mg, 10.0 mg, 25 mg, 50 mg, 100 mg, 250 mg or 500 mg.

BRIEF DESCRIPTION OF THE DRAWINGS

FIGS. 5A and 5B show the production of IFN-gamma, IL2, and TNF-alpha in the supernatant of anti-BCMA CAR-expressing T cells originally obtained from a healthy donor (FIG. 5A) and a donor with multiple myeloma (FIG. 5B) after a second round of stimulation with MM1S cells at day 4 a in the absence of a representative of gamma secretase inhibitor (LY3039478) (left bar) or in the presence of the inhibitor with a concentration of 0.001 µM (middle bar) or 0.001 µM (right bar).

FIG. 9A depicts tumor volume (mm$^3$) over days during the study. The dashed arrow below the graph indicates the time period during which LY3039478 was administered as described in Example 5.

FIG. 9B shows percent survival among animals treated over the course of 65 days following CAR T injection.

FIG. 10A depicts CD4+ CAR T+ cell counts per µL of blood over time. FIG. 10B depicts CD8+ CAR T+ cell counts per µL of blood over time GSI bar with arrows indicates the timing of LY3039478 (GSI) delivery if administered.

DETAILED DESCRIPTION

Figure 1:
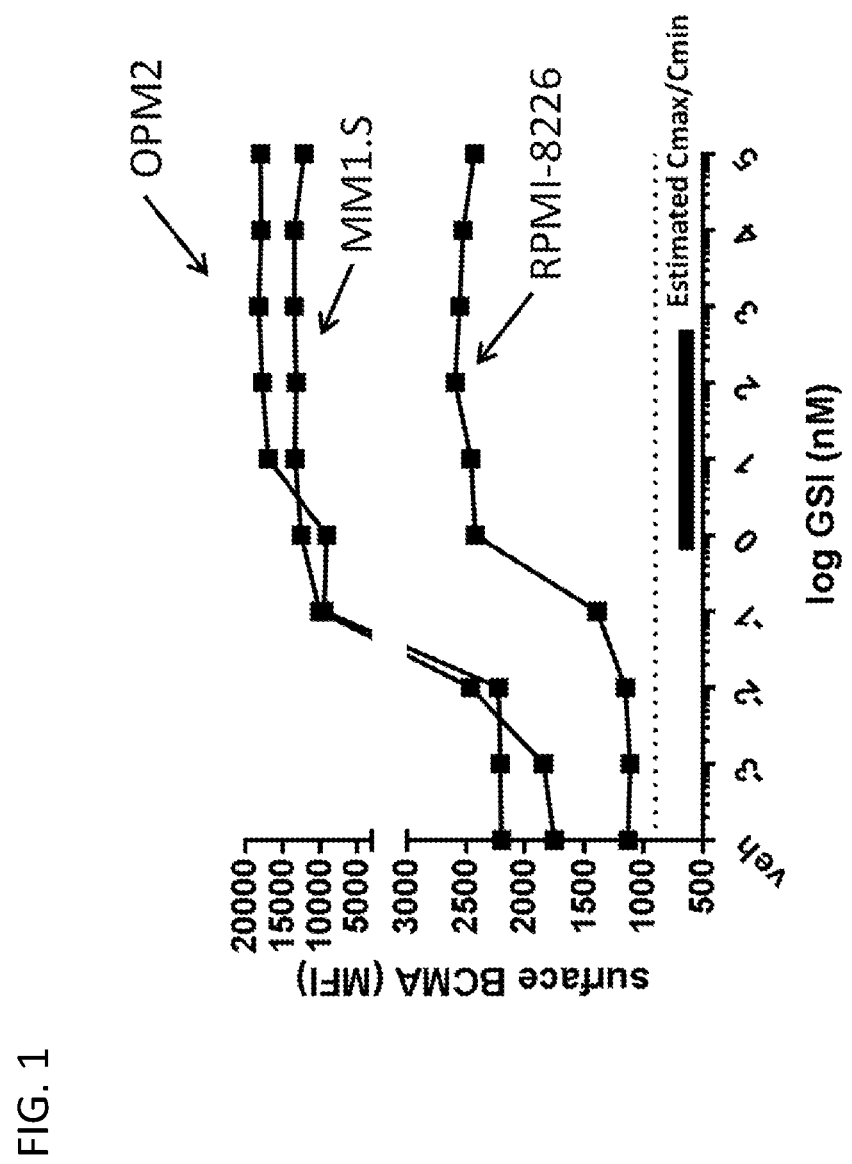
FIG. 1 shows expression level of surface B Cell Maturation Antigen (BCMA) on OPM2, MM1s or RPMI-8826 cells co-cultured with different concentrations of a representative gamma secretase inhibitor (LY3039478) after 24 hours of co-culture. The bar near the X-axis suggests the estimated $C_{max}$ and $C_{min}$ for the inhibitor.

Provided herein are combination therapies involving administration of an immunotherapy, such as a cell therapy, e.g a T cell therapy, and an inhibitor of gamma secretase. In some aspects, the provided methods involve administration of an immunotherapy or immunotherapeutic agent, such as a composition including cells for adoptive cell therapy, e.g., such as a T cell therapy (e.g. CAR-expressing T cells) and administration of a gamma secretase inhibitor to a subject having a disease or disorder. In some embodiments, the gamma secretase is administered prior to, concurrently with or subsequent to initiation of administration of the immunotherapy, e.g. cell therapy. In some embodiments, the gamma secretase inhibitor inhibits or reduces intramembrane cleavage of a target of a gamma secretase, e.g. BCMA, on a cell (such as a tumor/cancer cell). In some aspects, the target is the same as the target antigen of the cell therapy. In some embodiments, the cell therapy, such as CAR-expressing T cells, comprises an antigen-binding domain that binds to a B Cell Maturation Antigen (BCMA), such as surface BCMA. In some embodiments, the methods further comprise selecting a subject for treatment, wherein the subject has a low expression of surface BCMA on a cell, such as a tumor/cancer cell, e.g. cells of the cancer in the subject that express CD138, surface CD38 or a surface plasma cell marker or are derived from plasma cells. In some embodiments, the cell therapy comprises a recombinant receptor, such as chimeric antigen receptor (CAR), that binds to an antigen other than BCMA. In some embodiments, the methods are carried out in connection with adoptive cell therapy.

Cell therapies, such as T cell-based therapies, for example, adoptive T cell therapies (including those involving the administration of cells expressing chimeric receptors specific for a disease or disorder of interest, such as chimeric antigen receptors (CARs) and/or other recombinant antigen receptors, as well as other adoptive immune cell and adoptive T cell therapies) can be effective in the treatment of cancer and other diseases and disorders. The engineered expression of recombinant receptors, such as chimeric antigen receptors (CARs), on the surface of T cells enables the redirection of T-cell specificity. In clinical studies, CAR-T cells, for example anti-CD19 CAR-T cells, have produced durable, complete responses in both leukemia and lymphoma patients (Porter et al. (2015) Sci Transl Med., 7:303ra139; Kochenderfer (2015) J. Clin. Oncol., 33: 540-9; Lee et al. (2015) Lancet, 385:517-28; Maude et al. (2014) N Engl J Med, 371:1507-17).

In certain contexts, available approaches to adoptive cell therapy may not always be entirely satisfactory. In some contexts, optimal efficacy can depend on the ability of the administered cells to recognize and bind to a target, e.g., target antigen, to traffic, localize to and successfully enter appropriate sites within the subject, tumors, and environments thereof. In some contexts, optimal efficacy can depend on the ability of the administered cells to become activated, expand, to exert various effector functions, including cytotoxic killing and secretion of various factors such as cytokines, to persist, including long-term, to differentiate, transition or engage in reprogramming into certain phenotypic states (such as long-lived memory, less-differentiated, and effector states), to avoid or reduce immunosuppressive conditions in the local microenvironment of a disease, to provide effective and robust recall responses following clearance and re-exposure to target ligand or antigen, and avoid or reduce exhaustion, anergy, peripheral tolerance, terminal differentiation, and/or differentiation into a suppressive state.

In some embodiments, the exposure and persistence of engineered cells is reduced or declines after administration to the subject. Yet, observations indicate that, in some cases, increased exposure of the subject to administered cells expressing the recombinant receptors (e.g., increased number of cells or duration over time) may improve efficacy and therapeutic outcomes in adoptive cell therapy. Preliminary analyses conducted following the administration of different CD19-targeting CAR-expressing T cells to subjects with various CD19-expressing cancers in multiple clinical trials revealed a correlation between greater and/or longer degree of exposure to the CAR-expressing cells and treatment outcomes. Such outcomes included patient survival and remission, even in individuals with severe or significant tumor burden.

In some aspects, the provided methods and uses provide for or achieve improved or more durable responses or efficacy as compared to certain alternative methods, such as in particular groups of subjects treated. In some embodiments, the methods are advantageous by virtue of administering T cell therapy, such as a composition including cells for adoptive cell therapy, e.g., such as a T cell therapy (e.g. CAR-expressing T cells), and an inhibitor of gamma secretase.

The provided methods are based on observations that gamma secretase inhibitor improves one or more functional activities of recombinant receptor-expressing cells specific to BCMA following exposure to BCMA-expressing cells in the presence of a gamma secretase inhibitor. Such functional activities include, for example, antigen-dependent cytolytic activity and/or ability to produce one or more cytokines. In some aspects, the improved activity may be due to increased expression or stabilized expression of surface BCMA on cells (e.g., tumor/cancer cells, for example, multiple myeloma cells). In some aspects, increasing or stabilizing the expression of a target antigen, e.g. BCMA, on target cells improves the outcome for patients who may be or are low for expression of the target antigen, e.g. BCMA, so that sufficient antigen is available for targeting by the cell therapy, e.g. T cell therapy. In some embodiments, the provided embodiments reduce the variability in treatment outcomes among a group of subjects with variable surface expression of the target antigen, e.g. BCMA. In some embodiments of the provided methods, a patient is selected for administration of the provided combination therapy of a gamma secretase inhibitor and an immunotherapy, such as cell therapy (e.g. CAR-T cells) if cells of a cancer in the subject, such as cells that express CD138, surface CD38 or a surface plasma cell marker or are derived from plasma cells, have low expression of surface B cell maturation antigen (BCMA) and/or a level of surface BCMA about a threshold level. Hence, in some aspects, the gamma secretase inhibitor is administered in an amount to stabilize surface expression of BCMA, such as by reducing or inhibiting intramembrane cleavage of BCMA.

In some embodiments, the provided methods offer advantages in subjects that do not have, or that are not selected based on, high levels of serum or plasma or tumor levels of soluble or shed BCMA. In some embodiments, the patient is not selected for having high serum or plasma or tumor levels of soluble or shed BCMA. In some embodiments, the provided combination therapy involves administration of a cell therapy, e.g. CAR-expressing T cells, having an antigen-binding domain that binds to surface BCMA in which the antigen-binding domain binds to soluble BCMA with an affinity lower than the affinity of said antigen-binding domain binding to surface BCMA. In some contexts, the provided combination therapy involves administration of a cell therapy, such as recombinant receptor-expressing cells, e.g. CAR-expressing T cells, in which binding to surface BCMA by the recombinant receptor or CAR or a measure indicative of function or activity of the recombinant receptor-expressing cells (e.g. CAR-expressing cells), following exposure to cells expressing surface BCMA, is not reduced or blocked or is not substantially reduced or blocked in the presence of a soluble or shed form of the BCMA.

In some aspects, such results are achieved while enhancing or improving the activity, in some cases the intrinsic activity, of cells, e.g. T cells, of the cell therapy. In some aspects, this can be achieved in the presence of a gamma secretase inhibitor that exhibits activity for other targets beyond BCMA, such as activity for cleavage of a Notch. An example of such an inhibitor is LY3039478 or compound 1 herein, or stereoisomers, pharmaceutically acceptable salts or hydrates thereof. In some aspects, although notch signaling can regulate T cell differentiation and/or proliferation, observations herein demonstrate enhanced activities of T cells in the presence of an exemplary inhibitor known to target notch signaling, e.g. LY3039478. For example, as shown herein, in an exemplary serial stimulation assay assessing anti-BCMA CAR-T cell activities following repeated stimulation with BCMA-expressing cells, increased CAR+ T cell expansion and/or survival was observed in the presence of the exemplary gamma secretase inhibitor. Such results indicate that the provided combination therapy improves T cell function, including functions related to the expansion, proliferation and persistence of T cells.

The provided findings indicate that combination therapy of the gamma secretase inhibitor in methods involving cell therapy, such as involving administration of adoptive T cell therapy, achieves improved function of the T cell therapy. In some embodiments, combination of the cell therapy (e.g., administration of engineered T cells) with the gamma secretase inhibitor improves or enhances one or more functions and/or effects of the T cell therapy, including after encounter with antigen, such as persistence, expansion, cytotoxicity, and/or therapeutic outcomes, e.g., ability to kill or reduce the burden of tumor or other disease or target cell. In some aspects, the provided methods increase overall response and/or survival by or more than 1.5-fold, 2.0-fold, 3.0-fold, 4.0-fold, 5.0-fold, 10-fold or more compared to an alternative treatment, such as compared to a monotherapy involving administration of the T cell therapy (e.g. CAR-T cell) or a gamma secretase inhibitor, or a pharmaceutically acceptable salt of hydrate thereof.

In some aspects, the provided methods can enhance, increase or potentiate T cell therapy, such as to overcome lack of persistence and/or exhaustion of T cells. In some embodiments, a subject having received administration of a T cell therapy, e.g. CAR-T cell, is monitored for the presence, absence or level of T cells of the therapy in the subject, such as in a biological sample of the subject, e.g. in the blood of the subject. In some embodiments, a gamma secretase inhibitor, or a pharmaceutically acceptable salt of hydrate thereof, is administered to a subject having received the T cell therapy (e.g. CAR-T cells) but in which such cells have weakly expanded and/or are at or below a threshold level in a sample of the subject, e.g. blood sample, at a time when strong or robust expansion of the CAR-T cells in the subject is typically observed in a plurality of subjects administered a T cell therapy (e.g. CAR-T), in some cases, this same T cell therapy (e.g. same CAR-T cells). In some of any such embodiments, the level of engineered, e.g., CAR+, cells in the sample is determined as the number of the cells, e.g., CAR+ cells, per microliter of the sample; in some embodiments, the peak level is the highest such measurement following, optionally over a specified period of time following, administration of the cells or cell therapy to the subject. In some aspects, a gamma secretase inhibitor is administered to a subject having previously received a cell therapy, if, at or about days 1-15 days after initiation of administration of the T cell therapy to the subject, less than 10 cells per μL, such as less than 5 cells per μL or less than 1 cells per μL of cells of the T cell therapy, e.g. CAR-T cells, or a CD8+ or CD3+ subset thereof, are detectable in the blood. In some embodiments, a gamma secretase inhibitor is administered to a subject having previously received a cell therapy, if, at or about day 12-15 cells after initiation of administration of the T cell therapy to the subject, e.g. CAR-T cells, less than 10 cells per μL, such as less than 5 cell pers μL or less than 1 cell per μL of such cells, or a CD8+ or CD3+ subset thereof, are detectable in the blood.

In certain aspects, the provided methods can enhance, increase or potentiate T cell therapy in subjects in which a peak response (e.g. presence of T cells and/or reduction in tumor burden) to the T cell therapy has been observed, but in which the response, e.g. presence of T cells and/or reduction in tumor burden, has become reduced or is no longer detectable. In some aspects, a gamma secretase inhibitor is administered to a subject within a week, such as within 1, 2 or 3 days after: (i) peak or maximum level of the cells of the T cell therapy are detectable in the blood of the subject; (ii) the number of cells of the T cell therapy detectable in the blood, after having been detectable in the blood, is not detectable or is reduced, optionally reduced compared to a preceding time point after administration of the T cell therapy; (iii) the number of cells of the T cell therapy detectable in the blood is decreased by or more than 1.5-fold, 2.0-fold, 3.0-fold, 4.0-fold, 5.0-fold, 10-fold or more compared to the peak or maximum number cells of the T cell therapy detectable in the blood of the subject after initiation of administration of the T cell therapy; (iv) at a time after a peak or maximum level of the cells of the T cell therapy are detectable in the blood of the subject, the number of cells of or derived from the T cells detectable in the blood from the subject is less than 10%, less than 5%, less than 1% or less than 0.1% of total peripheral blood mononuclear cells (PBMCs) in the blood of the subject; (v) the subject exhibits disease progression and/or has relapsed following remission after treatment with the T cell therapy; and/or (iv) the subject exhibits increased tumor burden as compared to tumor burden at a time prior to or after administration of the T cells and prior to initiation of administration of the gamma secretase inhibitor, or a pharmaceutically acceptable salt of hydrate thereof.

In some embodiments, a gamma secretase inhibitor is administered to a subject having received a cell therapy, e.g. CAR-T cells, but who has relapsed following treatment with the T cell therapy, such as at a time in which the response, e.g. presence of T cells and/or reduction in tumor burden, has become reduced or is no longer detectable. In some aspects, relapse may occur due to BCMA antigen loss, which, in some cases, can be due to BCMA antigen downregulation/antigen escape. In some cases, it may be due to cleavage or shedding of BCMA antigen from the cells surface. In some aspects, antigen loss may lead to a reduction in cells presenting a target antigen (e.g., BCMA), thereby diminishing or reducing the activity and/or function of the CAR T cells and/or decreasing the number of CAR T cells, for example, in the blood. In some embodiments, administration of gamma secretase inhibitor can be administered at a time in which the subject has relapsed or is suspected or likely to relapse to cell therapy to reduce or prevent cleavage or shedding of the target antigen (e.g., BCMA) from the cell surface. In such embodiments, administering gamma secretase inhibitor can reinvigorate or boost CAR T cells following relapse by preventing or reducing cleavage and/or shedding of the target antigen (e.g., BCMA).

In some embodiments, the provided methods involving combination therapy with a cell therapy and a gamma secretase inhibitor result in genetically engineered cells with increased persistence and/or better potency in a subject to which it is administered compared to administration of the cell therapy in the absence of the gamma secretase inhibitor. In some embodiments, the persistence is increased at least or about at least 1.5-fold, 2-fold, 3-fold, 4-fold, 5-fold, 6-fold, 7-fold, 8-fold, 9-fold, 10-fold, 20-fold, 30-fold, 50-fold, 60-fold, 70-fold, 80-fold, 90-fold, 100-fold or more. In some embodiments, the degree or extent of persistence of administered cells can be detected or quantified after administration to a subject. For example, in some aspects, quantitative PCR (qPCR) is used to assess the quantity of cells expressing the recombinant receptor (e.g., CAR-expressing cells) in the blood or serum or organ or tissue (e.g., disease site) of the subject. In some aspects, persistence is quantified as copies of DNA or plasmid encoding the receptor, e.g., CAR, per microgram of DNA, or as the number of receptor-expressing, e.g., CAR-expressing, cells per microliter of the sample, e.g., of blood or serum, or per total number of peripheral blood mononuclear cells (PBMCs) or white blood cells or T cells per microliter of the sample. In some embodiments, flow cytometric assays detecting cells expressing the receptor generally using antibodies specific for the receptors also can be performed. Cell-based assays may also be used to detect the number or percentage of functional cells, such as cells capable of binding to and/or neutralizing and/or inducing responses, e.g., cytotoxic responses, against cells of the disease or condition or expressing the antigen recognized by the receptor. In any of such embodiments, the extent or level of expression of another marker associated with the recombinant receptor (e.g. CAR-expressing cells) can be used to distinguish the administered cells from endogenous cells in a subject.

In aspects of the methods provided herein, combining cell therapy with a gamma secretase inhibitor that increases potency and/or promotes sustained CAR T cell activity allows administration of a lower dose of CAR T cells to achieve the same therapeutic effect as that seen with a higher dose of CAR T cells without a gamma secretase inhibitor. In some embodiments, the dose of CAR T cells administered when combined with gamma secretase inhibitor can be reduced by 10%, 20%, 30%, 40%, 50%, 60%, 70%, or more of a dose of CART cells administered without gamma secretase inhibitor.

In some embodiments, the methods can be used for treating a disease or condition, such as a cancer, including a B cell malignancy or hematological malignancy. In some aspects, the cancer is multiple myeloma, plasmacytoma, a cancer of plasma cell origin and/or a cancer of B cell origin. In some aspects, such diseases, conditions or malignancies include those in which responses, e.g. complete response (CR), to treatment with the cell therapy alone, such as a composition including cells for adoptive cell therapy, e.g., such as a T cell therapy (e.g. CAR-expressing T cells), is relatively low compared to treatment with other T cell therapies or treatment of other diseases or malignancies (e.g. a CR in less than or less than about 60%, less than about 50% or less than about 45% of the subjects so treated).

In some embodiments, the provided methods reduce or ameliorate a symptom or outcome or burden of the disease or condition to a degree that is greater than the combination of (i) the degree of reduction or amelioration effected by the administration of the gamma secretase inhibitor alone, optionally on average in a population of subjects having the disease or condition, and (ii) the degree of reduction or amelioration by the administration of the T cell therapy alone, optionally on average in a population of subjects having the disease or condition. In some embodiments, the method reduces or ameliorates such symptoms, outcomes or burdens of the disease, e.g. compared to on average in a population of subjects having the disease or condition, by greater than or greater than about 1.5-fold, 2.0-fold, 3.0-fold, 4.0-fold, 5.0-fold, 6.0-fold, 7.0-fold, 8.0-fold, 9.0-fold, 10.0 fold, 20.0-fold, 30.0-fold, 40.0-fold, 50.0-fold or more.

Also provided are methods for engineering, preparing, and producing the cells (e.g. CAR-expressing T cells), compositions containing the cells and/or gamma secretase inhibitor, and kits and devices containing and for using, producing and administering the cells and/or gamma secretase inhibitor, such as in accord with the provided combination therapy methods.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Combination Therapy

Provided herein are methods for combination therapy for treating a disease or disorder, e.g. a cancer or proliferative disease, that include administering to a subject a combination therapy of 1) a gamma secretase inhibitor and 2) an immunotherapy, e.g. a cell therapy, e.g. T cell therapy, e.g., CAR-expressing cell (e.g., T cell). In some embodiments, the cell therapy is an adoptive immune cell therapy comprising T cells that specifically recognize and/or target an antigen associated with a disease or disorder, e.g. a cancer or proliferative disease. Also provided are combinations and articles of manufacture, such as kits, that contain a composition comprising the immunotherapy, e.g. T cell therapy, and/or a composition comprising the gamma secretase inhibitor, and uses of such compositions and combinations to treat or prevent diseases, conditions, and disorders, including cancers.

In some embodiments, such methods can include administration of the gamma secretase inhibitor prior to, simultaneously with, during, during the course of (including once and/or periodically during the course of), and/or subsequently to, the administration (e.g., initiation of administration) of the immunotherapy, e.g. cell therapy (e.g. CAR-expressing T cells). In some embodiments, the administrations can involve sequential or intermittent administrations of the gamma secretase inhibitor and cell therapy.

In some embodiments, the cell therapy is adoptive cell therapy. In some embodiments, the cell therapy is or comprises a tumor infiltrating lymphocytic (TIL) therapy, a transgenic TCR therapy or a recombinant-receptor expressing cell therapy (optionally T cell therapy), which optionally is a chimeric antigen receptor (CAR)-expressing cell therapy. In some embodiments, the therapy is a B cell targeted therapy. In some embodiments, the therapy targets B cell maturation antigen (BCMA). In some embodiments, the therapy targets CD19. In some embodiments, the therapy targets cell surface associated Mucin 1 (MUC1). In some embodiments, the cells and dosage regimens for administering the cells can include any as described in the following subsection A under "Administration of Cells." In some embodiments, the dosage regimens for administering the gamma secretase inhibitor can include any as described in the following subsection B under "Administration of gamma secretase inhibitor."

In some embodiments, the immunotherapy, e.g. cell therapy (e.g. CAR-expressing T cells), and gamma secretase inhibitor are provided as pharmaceutical compositions for administration to the subject. In some embodiments, the pharmaceutical compositions contain therapeutically effective amounts of one or both of the agents for combination therapy, e.g., T cells for adoptive cell therapy and a gamma secretase inhibitor as described. In some embodiments, the agents are formulated for administration in separate pharmaceutical compositions. In some embodiments, any of the pharmaceutical compositions provided herein can be formulated in dosage forms appropriate for each route of administration.

In some embodiments, the combination therapy, which includes administering an immunotherapy, e.g. cell therapy, including engineered cells, such as CAR-T cell therapy, and the gamma secretase inhibitor is administered to a subject or patient having a disease or condition to be treated (e.g. cancer) or at risk for having the disease or condition (e.g. cancer). In some aspects, the methods treat, e.g., ameliorate one or more symptom of, the disease or condition, such as by lessening tumor burden in a cancer expressing an antigen recognized by the immunotherapy or immunotherapeutic agent, e.g. recognized by an engineered T cell.

In some embodiments, the disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by bacterial, viral or other pathogens. Exemplary antigens, which include antigens associated with various diseases and conditions that can be treated, include any of antigens described herein. In particular embodiments, the recombinant receptor expressed on engineered cells of a combination therapy, including a chimeric antigen receptor or transgenic TCR, specifically binds to an antigen associated with the disease or condition.

In some embodiments, the disease or condition is a cancer or proliferative disease that expresses BCMA. In some embodiments, the provided methods employ a recombinant receptor-expressing cell (e.g. CAR-T cell) that targets BCMA. In particular embodiments, the disease or condition is a multiple myeloma. In some cases, the multiple myeloma is a relapsed or refractory multiple myeloma.

Among the diseases to be treated is any disease or disorder associated with BCMA or any disease or disorder in which BCMA is specifically expressed and/or in which BCMA has been targeted for treatment (also referred to herein interchangeably as a "BCMA-associated disease or disorder"). Cancers associated with BCMA expression include hematologic malignancies such as multiple myeloma, Waldenstrom macroglobulinemia, as well as both Hodgkin's and non-Hodgkin's lymphomas. See Coquery et al., *Crit Rev Immunol.*, 2012, 32(4):287-305 for a review of BCMA. Since BCMA has been implicated in mediating tumor cell survival, it is a potential target for cancer therapy. Chimeric antigen receptors containing anti-BCMA antibodies, including mouse anti-human BCMA antibodies and human anti-human antibodies, and cells expressing such chimeric receptors have been previously described. See Carpenter et al., *Clin Cancer Res.*, 2013, 19(8):2048-2060, WO 2016/090320, WO2016090327, WO2010104949A2 and WO2017173256. Exemplary CARS containing anti-BCMA antibodies are described herein.

In some embodiments, prior to the initiation of administration of the engineered cells, such as anti-BCMA CAR, the subject has received one or more prior therapies. In some embodiments, the subject has received at least 1, 2, 3, 4, 5, 6, 7, 8, 9, 10, 11, 12, 13, 14, 15, 16, 17, 18, 19 or 20 or more prior therapies. In some embodiments, the subject has received at least 3, 4, 5, 6, 7, 8, 9, 10 or more prior therapies. In some aspects, the subject has relapsed following, or has been treatment refractory to, one or more of, for example, each, individually, of the one or more prior therapies. In some aspects, the prior therapies include treatment with autologous stem cell transplant (ASCT); an immunomodulatory agent, e.g. an IMiD; a proteasome inhibitor; and an anti-CD38 antibody; unless the subject was not a candidate for or was contraindicated for one or more of the therapies. In some embodiments, the immunomodulatory agent, e.g. an IMiD, is selected from among thalidomide, lenalidomide or pomalidomide. In some embodiments, the proteasome inhibitor is selected from among bortezomib, carfilzomib or ixazomib. In some embodiments, the anti-CD38 antibody is or comprises daratumumab. In some embodiments, the subject must have undergone at least 2 consecutive cycles of treatment for each regimen unless progressive disease was the best response to the regimen. In some aspects, a subject for treatment with the method herein has a myeloma that has relapsed or is treatment refractory with greater than 10% CD138+ malignant plasma cells immunohistochemistry (IHC) on bone marrow core biopsy, either following ASCT or, if the subject has not undergone ASCT, the subject is transplant ineligible, e.g. due to age comorbidity, patient choice, state of disease and/or discretion of physician, and has disease that has persisted after more than four cycles of induction therapy and/or that is refractory to or is not tolerant to therapy with a proteasome inhibitor and immunomodulatory drug, e.g. IMiD.

In some embodiments, the disease or condition is a tumor, such as a solid tumor, lymphoma, leukemia, blood tumor, metastatic tumor, or other cancer or tumor type.

In some embodiments, the antigen associated with the disease or disorder is selected from the group consisting of B cell maturation antigen (BCMA), ROR1, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, erbB dimers, EGFR vIII, FBP, FCRL5, FCRH5, fetal acethycholine e receptor, GD2, GD3, HMW-MAA, IL-22R-alpha, IL-13R-alpha2, kdr, kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, EGP2, EGP40, TAG72, B7-H6, IL-13 receptor a2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, and an antigen associated with a universal tag, a cancer-testes antigen, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, and a pathogen-specific antigen. In some embodiments, the antigen is associated with or is a universal tag. In some embodiments, the antigen associated with the disease or disorder is selected from the group consisting of Notch 1, Notch 2, Notch 3, Notch 4, cell surface associated Mucin 1 (MUC1), Ephrin B2, Betaglycan (TGFBR3), CD43, CD44, CSF1R, CX3CR1, CXCL16, Delta1, E-cadherin, N-cadherin, HLA-A2, IFNaR2, IL1R1, IL1R2, IL6R, and amyloid precursor protein (APP).

In some embodiments, the disease or disorder is a B cell-related disorder. In some embodiments, the disease or disorder is one or more diseases or conditions from among glioblastoma, lymphomatoid granulomatosis, post-transplant lymphoproliferative disorder, an immunoregulatory disorder, heavy-chain disease, primary or immunocyte-associated amyloidosis, or monoclonal gammopathy of undetermined significance.

In some embodiments, the disease or disorder is an autoimmune disease or disorder. Such autoimmune diseases or disorder include, but are not limited to, systemic lupus erythematosus (SLE), lupus nephritis, inflammatory bowel disease, rheumatoid arthritis (e.g., juvenile rheumatoid arthritis), ANCA associated vasculitis, idiopathic thrombocytopenia purpura (ITP), thrombotic thrombocytopenia purpura (TTP), autoimmune thrombocytopenia, Chagas' disease, Grave's disease, Wegener's granulomatosis, polyarteritis nodosa, Sjogren's syndrome, pemphigus vulgaris, scleroderma, multiple sclerosis, psoriasis, IgA nephropathy, IgM polyneuropathies, vasculitis, diabetes mellitus, Reynaud's syndrome, anti-phospholipid syndrome, Goodpasture's disease, Kawasaki disease, autoimmune hemolytic anemia, myasthenia gravis, or progressive glomerulonephritis.

In some embodiments, the disease or disorder is a B cell malignancy. In some embodiments, the cancer (e.g., a BCMA-expressing cancer) is a lymphoma, a leukemia, or a plasma cell malignancy. Lymphomas contemplated herein include, but are not limited to, Burkitt lymphoma (e.g., endemic Burkitt's lymphoma or sporadic Burkitt's lymphoma), non-Hodgkin's lymphoma (NHL), Hodgkin's lymphoma, Waldenstrom macroglobulinemia, follicular lymphoma, small non-cleaved cell lymphoma, mucosa-associated lymphatic tissue lymphoma (MALT), marginal zone lymphoma, splenic lymphoma, nodal monocytoid B cell lymphoma, immunoblastic lymphoma, large cell lymphoma, diffuse mixed cell lymphoma, pulmonary B cell angiocentric lymphoma, small lymphocytic lymphoma, primary mediastinal B cell lymphoma, lymphoplasmacytic lymphoma (LPL), or mantle cell lymphoma (MCL). Leukemias contemplated herein, include, but are not limited to, chronic lymphocytic leukemia (CLL), plasma cell leukemia or acute lymphocytic leukemia (ALL). Also contemplated herein are plasma cell malignancies including, but not limited to, multiple myeloma (e.g., non-secretory multiple myeloma, smoldering multiple myeloma) or plasmacytoma. In some embodiments the disease or condition is multiple myeloma, such as relapsed and/or refractory multiple myeloma. Among the diseases, disorders or conditions that can be treated include, but are not limited to, neuroblastoma, renal cell carcinoma, colon cancer, colorectal cancer, breast cancer, epithelial squamous cell cancer, melanoma, myeloma (e.g., multiple myeloma), stomach cancer, brain cancer, lung cancer, pancreatic cancer, cervical cancer, ovarian cancer, liver cancer, bladder cancer, prostate cancer, testicular cancer, thyroid cancer, uterine cancer, adrenal cancer and head and neck cancer.

In some embodiments, the cancer or proliferative disease is a B cell malignancy or hematological malignancy. In some embodiments the cancer or proliferative disease is acute lymphoblastic leukemia (ALL), non-Hodgkin's lymphoma (NHL), or chronic lymphocytic leukemia (CLL). In some embodiments, the cancer is CLL. In some embodiments, the methods can be used to treat a myeloma, a lymphoma or a leukemia. In some embodiments, the methods can be used to treat a non-Hodgkin lymphoma (NHL), an acute lymphoblastic leukemia (ALL), a chronic lymphocytic leukemia (CLL), a diffuse large B-cell lymphoma (DLBCL), acute myeloid leukemia (AML), or a myeloma, e.g., a multiple myeloma (MM). In some embodiments, the methods can be used to treat a MM or a DBCBL.

In some embodiments, the methods can be used to treat a non-hematologic cancer, such as a solid tumor. In some embodiments, the methods can be used to treat bladder, lung, brain, melanoma (e.g. small-cell lung, melanoma), breast, cervical, ovarian, colorectal, pancreatic, endometrial, esophageal, kidney, liver, prostate, skin, thyroid, or uterine cancers. In some embodiments, the cancer or proliferative disease is pancreatic cancer, bladder cancer, colorectal cancer, breast cancer, prostate cancer, renal cancer, hepatocellular cancer, lung cancer, ovarian cancer, cervical cancer, pancreatic cancer, rectal cancer, thyroid cancer, uterine cancer, gastric cancer, esophageal cancer, head and neck cancer, melanoma, neuroendocrine cancers, CNS cancers, brain tumors, bone cancer, or soft tissue sarcoma.

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Graves disease, Crohn's disease, multiple sclerosis, asthma, and/or a disease or condition associated with transplant.

For the prevention or treatment of disease, the appropriate dosage of gamma secretase inhibitor and/or immunotherapy, such as a cell therapy (e.g. CAR-expressing T cells), may depend on the type of disease to be treated, cells and/or recombinant receptors expressed on the cells, the severity and course of the disease, route of administration, whether the gamma secretase inhibitor and/or the T cell therapy are administered for preventive or therapeutic purposes, previous therapy, frequency of administration, the subject's clinical history and response to the cells, and the discretion of the attending physician. The compositions and cells are in some embodiments suitably administered to the subject at one time or over a series of treatments. Exemplary dosage regimens and schedules for the provided combination therapy are described.

In some embodiments, the immunotherapy, such as cell therapy (e.g. CAR-T cell therapy) and the gamma secretase inhibitor are administered as part of a further combination treatment, which can be administered simultaneously with or sequentially to, in any order, another therapeutic intervention. In some contexts, the immunotherapy, such as cell therapy, e.g. engineered T cells, such as CAR-expressing T cells, are co-administered with another therapy sufficiently close in time such that the cell therapy enhances the effect of one or more additional therapeutic agents, or vice versa. In some embodiments, the cells are administered prior to the one or more additional therapeutic agents. In some embodiments, the cell therapy, e.g. engineered T cells, such as CAR-expressing T cells, are administered after the one or more additional therapeutic agents. In some embodiments, the combination therapy methods further include a lymphodepleting therapy, such as administration of a chemotherapeutic agent. In some embodiments, the combination therapy further comprises administering another therapeutic agent, such as an anti-cancer agent, a checkpoint inhibitor, or another immune modulating agent. In some embodiments, the combination therapy further comprises administering a steroid, such as dexamethasone. Uses include uses of the combination therapies in such methods and treatments, and uses of such compositions in the preparation of a medicament in order to carry out such combination therapy methods. In some embodiments, the methods and uses thereby treat the disease or condition or disorder, such as a cancer or proliferative disease, in the subject.

Prior to, during or following administration of the immunotherapy (e.g. T cell therapy, such as CAR-T cell therapy) and/or a gamma secretase inhibitor, the biological activity of the T cell therapy, e.g. the biological activity of the engineered cell populations, in some embodiments is measured, e.g., by any of a number of known methods. Parameters to assess include the ability of the engineered cells to destroy target cells, persistence and other measures of T cell activity, such as measured using any suitable method known in the art, such as assays described further below in Section III. In some embodiments, the biological activity of the cells, e.g., T cells administered for the T cell based therapy, is measured by assaying cytotoxic cell killing, expression and/or secretion of one or more cytokines, proliferation or expansion, such as upon restimulation with antigen. In some aspects the biological activity is measured by assessing the disease burden and/or clinical outcome, such as reduction in tumor burden or load. In some embodiments, administration of one or both agents of the combination therapy and/or any repeated administration of the therapy, can be determined based on the results of the assays before, during, during the course of or after administration of one or both agents of the combination therapy.

In some embodiments, the combined effect of the gamma secretase inhibitor in combination with the cell therapy can be synergistic compared to treatments involving only the gamma secretase inhibitor or monotherapy with the cell therapy. For example, in some embodiments, the methods provided herein result in an increase or an improvement in a desired therapeutic effect, such as an increased or an improvement in the reduction or inhibition of one or more symptoms associated with cancer.

In some embodiments, the gamma secretase inhibitor increases the expansion or proliferation of the engineered T cells, such as CAR T-Cells. In some embodiments, the increase in expansion or proliferation is observed in vivo upon administration to a subject. In some embodiments, the increase in the number of engineered T cells, e.g. CAR-T cells, is increased by greater than or greater than about 1.2-fold, 1.5-fold, 2.0-fold, 3.0-fold, 4.0-fold, 5.0-fold, 6.0-fold, 7.0-fold, 8.0-fold, 9.0-fold, 10.0 fold or more. In some embodiments, the gamma secretase inhibitor prolongs and/or sustains the activity and/or function of engineered T cells, such as CAR T-Cells.

A. Administration of an Immunotherapy

In some embodiments, an immunotherapy that binds to or targets an antigen on an immune cell and/or that is involved in a disease or disorder is administered in accord with the provided combination therapy methods. In particular embodiments, the immunotherapy binds to and/or recognizes an antigen that is expressed on or in a cell or tissue. In certain embodiments, the antigen is expressed on or in a cell or tissue. In particular embodiments, the antigen is expressed on the surface of a cell. In some embodiments, the cell is a B cell, a T cell and/or a tumor or cancer cell. In particular embodiments, the antigen is expressed in or on a circulating cell. In some embodiments, the antigen is expressed on the surface of a circulating cell.

In particular embodiments, the immunotherapy binds to and/or recognizes at least one antigen associated with a disease. Among the diseases, conditions, and disorders that may be treated in human subjects with the immunotherapy are tumors, including solid tumors, hematologic malignancies, and melanomas, and including localized and metastatic tumors, infectious diseases, such as infection with a virus or other pathogen, e.g., HIV, HCV, HBV, CMV, HPV, and parasitic disease, and autoimmune and inflammatory diseases. In some embodiments, the disease or condition is a tumor, cancer, malignancy, neoplasm, or other proliferative disease or disorder. Such diseases include but are not limited to leukemia, lymphoma, e.g., chronic lymphocytic leukemia (CLL), ALL, non-Hodgkin's lymphoma, acute myeloid leukemia, multiple myeloma, refractory follicular lymphoma, mantle cell lymphoma, indolent B cell lymphoma, B cell malignancies, cancers of the colon, lung, liver, breast, prostate, ovarian, skin, melanoma, bone, and brain cancer, ovarian cancer, epithelial cancers, renal cell carcinoma, pancreatic adenocarcinoma, Hodgkin lymphoma, cervical carcinoma, colorectal cancer, glioblastoma, neuroblastoma, Ewing sarcoma, medulloblastoma, osteosarcoma, synovial sarcoma, and/or mesothelioma.

In some embodiments, the immunotherapy binds to at least one antigen that is a target for cleavage by a gamma secretase. In some embodiments, the antigen is BCMA or is mucin 1 (Muc1).

1. Therapeutic Agents, e.g. Antibodies

In certain embodiments, the immunotherapy is a therapeutic agent, such as an antibody or antigen-binding fragment thereof. In some aspects, the antibody or antigen-binding fragment is a bispecific antibody.

In some aspects, the immunotherapy is a therapeutic agent that is or contains an immune system activator or stimulator. In certain embodiments, the immune system stimulator is an agent or therapy that activates at least one immune cell. In some embodiments, the immune cell is a T cell. In certain embodiments, the immune cell activator is IL-2, e.g., Proleukin; rhu-IFN-alpha-2a and/or rhu-IFN-alpha-2b, e.g., Pegasys, Roferon-A, Intron-A, and PEG intron; Anti-CD3 monoclonal antibody, e.g., Muromonab-CD3 and/or Orthoclone OKT 3; TGN-1412; and/or Blinatumomab, e.g., anti-CD3×CD3 BiTE.

In some embodiments, the immunotherapy is or contains a T cell-engaging therapy that is or comprises a binding molecule capable of binding to a surface molecule expressed on a T cell. In some embodiments, the surface molecule is an activating component of a T cell, such as a component of the T cell receptor complex. In some embodiments, the surface molecule is CD3 or is CD2. In some embodiments, the T cell-engaging therapy is or comprises an antibody or antigen-binding fragment. In some embodiments, the T cell-engaging therapy is a bispecific antibody containing at least one antigen-binding domain binding to an activating component of the T cell (e.g. a T cell surface molecule, e.g. CD3 or CD2) and at least one antigen-binding domain binding to a surface antigen on a target cell, such as a surface antigen on a tumor or cancer cell, for example any of the listed antigens as described herein, e.g. BCMA or Muc1. In some embodiments, the simultaneous or near simultaneous binding of such an antibody to both of its targets can result in a temporary interaction between the target cell and T cell, thereby resulting in activation, e.g. cytotoxic activity, of the T cell and subsequent lysis of the target cell.

Among such exemplary bispecific antibody T cell-engagers are bispecific T cell engager (BiTE) molecules, which contain tandem scFv molecules fused by a flexible linker (see e.g. Nagorsen and Bauerle, Exp Cell Res 317, 1255-1260 (2011); tandem scFv molecules fused to each other via, e.g. a flexible linker, and that further contain an Fc domain composed of a first and a second subunit capable of stable association (WO2013026837); diabodies and derivatives thereof, including tandem diabodies (Holliger et al, Prot Eng 9, 299-305 (1996); Kipriyanov et al, J Mol Biol 293, 41-66 (1999)); dual affinity retargeting (DART) molecules that can include the diabody format with a C-terminal disulfide bridge; or triomabs that include whole hybrid mouse/rat IgG molecules (Seimetz et al, Cancer Treat Rev 36, 458-467 (2010). In some embodiments, the T-cell engaging therapy is blinatumomab or AMG 330. Any of such T cell-engagers can be used in the provided methods, compositions or combinations.

In some embodiments, the therapeutic agent is a BCMA-specific binding capable of binding to BCMA and at least one additional antigen. In some embodiments, the at least one additional antigen CD19, CD20, CD22, CD33, CD38, CS1, ROR1, GPC3, CD123, IL-13R, CD138, c-Met, EGFRvIII, GD-2, NY-ESO-1, MAGE A3, or glycolipid F77. Examples of such bispecific antibodies are described in WO2017/025038.

The therapeutic agent, such as immunotherapy, can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, the therapeutic agent, such as immunotherapy, is administered by parenteral, intrapulmonary, and intranasal and, if desired for local treatment, intralesional administration. Parenteral infusions include intramuscular, intravenous, intraarterial, intraperitoneal, intrathoracic, intracranial, or subcutaneous administration.

In certain embodiments, one or more doses of a T cell engaging therapy and/or an immune system stimulator are administered. In particular embodiments, between 0.001 µg-5,000 µg of the T cell engaging therapy and/or an immune system stimulator are administered. In particular embodiments, between 0.001 µg to 1,000 µg, 0.001 µg to 1 µg, 0.01 µg to 1 µg, 0.1 µg to 10 µg, 0.01 µg to 1 µg, 0.1 µg to 5 g, 0.1 g to 50 g, 1 µg to 100 µg, 10 µg to 100 µg, 50 µg to 500 µg, 100 µg to 1,000 µg, 1,000 µg to 2,000 µg, or 2,000 µg to 5,000 µg of the T cell engaging therapy is administered. In some embodiments, the dose of the T cell engaging therapy is or includes between 0.01 µg/kg and 100 mg/kg, between 0.1 µg/kg and 10 µg/kg, between 10 µg/kg and 50 µg/kg, between 50 µg/kg and 100 µg/kg, between 0.1 mg/kg and 1 mg/kg, between 1 mg/kg and 10 mg/kg, between 10 mg/kg and 100 mg/kg, between 100 mg/kg and 500 mg/kg, between 200 mg/kg and 300 mg/kg, between 100 mg/kg and 250 mg/kg, between 200 mg/kg and 400 mg/kg, between 250 mg/kg and 500 mg/kg, between 250 mg/kg and 750 mg/kg, between 50 mg/kg and 750 mg/kg, between 1 mg/kg and 10 mg/kg, or between 100 mg/kg and 1,000 mg/kg (amount of the lymphodepleting agent over body weight). In some embodiments, the dose of the T cell engaging therapy is or is about 0.1 µg/kg, 0.5 µg/kg, 1 µg/kg, 5 µg/kg, 10 µg/kg, 20 µg/kg, 30 µg/kg, 40 µg/kg, 50 µg/kg, 60 µg/kg, 70 µg/kg, 80 µg/kg, 90 µg/kg, 0.1 mg/kg, 0.5 mg/kg, 1 mg/kg, 2.5 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 200 mg/kg, 300 mg/kg, 400 mg/kg, 500 mg/kg, 600 mg/kg, 700 mg/kg, 800 mg/kg, 900 mg/kg, or 1,000 mg/kg. In particular embodiments, the T cell engaging therapy is administered orally, intravenously, intraperitoneally, transdermally, intrathecally, intramuscularly, intranasally, transmucosally, subcutaneously, or rectally.

In some embodiments, the dose of CAR T cells administered can be reduced by 10%, 20%, 30%, 40%, 50%, 60%, 70%, or more of a dose of CAR T cells when administered in combination with a gamma secretase inhibitor. In some embodiments, the dose of CAR T cells administered when combined with gamma secretase inhibitor can be reduced by 10%, 20%, 30%, 40%, 50%, 60%, 70%, or more of a dose of CAR T cells administered without gamma secretase inhibitor.

2. Cell Therapy

In some embodiments of the methods, compositions, combinations, kits and uses provided herein, the combination therapy includes administering to a subject an immune cell therapy, such as a T cell therapy (e.g. CAR-expressing T cells). Administration of such therapies can be initiated prior to, subsequent to, simultaneously with administration of the gamma secretase inhibitor as described. Exemplary cell therapies and engineered cells for use in the provided methods, compositions, combinations, kits and uses provided herein are described in Section II.

In some embodiments, the cell-based therapy is or comprises administration of cells, such as immune cells, for example T cell or NK cells, that target a molecule expressed on the surface of a lesion, such as a tumor or a cancer. In some embodiments, the immune cells express a T cell receptor (TCR) or other antigen-binding receptor. In some embodiments, the immune cells express a recombinant receptor, such as a transgenic TCR or a chimeric antigen receptor (CAR). In some embodiments, the cells are autologous to the subject. In some embodiments, the cells are allogeneic to the subject.

In some aspects, the cell therapy is or comprises a tumor infiltrating lymphocytic (TIL) therapy, a transgenic TCR therapy or a T cell therapy comprising genetically engineered cells, such as a recombinant-receptor expressing cell therapy. In some embodiments, the recombinant receptor specifically binds to a ligand, such as one associated with a disease or condition, e.g. associated with or expressed on a cell of a tumor or cancer. In some embodiments, the cell therapy includes administering T cells engineered to express a chimeric antigen receptor (CAR).

In some embodiments, the provided cells express and/or are engineered to express receptors, such as recombinant receptors, including those containing ligand-binding domains or binding fragments thereof, and T cell receptors (TCRs) and components thereof, and/or functional non-TCR antigen receptors, such as chimeric antigen receptors (CARs). In some embodiments, the recombinant receptor contains an extracellular ligand-binding domain that specifically binds to an antigen. In some embodiments, the recombinant receptor is a CAR that contains an extracellular antigen-recognition domain that specifically binds to an antigen. In some embodiments, the ligand, such as an antigen, is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Among the engineered cells, including engineered cells containing recombinant receptors, are described further herein. Exemplary recombinant receptors, including CARs and recombinant TCRs, as well as methods for engineering and introducing the receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) *PLoS ONE* 8(4): e61338; Turtle et al., *Curr. Opin. Immunol.,* 2012 October; 24(5): 633-39; Wu et al., *Cancer,* 2012 March 18(2): 160-75. In some aspects, the genetically engineered antigen receptors include a CAR as described in U.S. Pat. No. 7,446,190, and those described in International Patent Application Publication No.: WO/2014055668 A1.

In some embodiments, the combination therapy includes administration to a subject cells, e.g. T cells, expressing a recombinant receptor that specifically recognize and/or target an antigen associated with the cancer and/or present on a universal tag. In some embodiments, the antigen recognized or targeted by the T cells is B cell maturation antigen (BCMA), ROR1, carbonic anhydrase 9 (CAIX), Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, optionally a human antigen of any of the foregoing; a pathogen-specific antigen. In some embodiments, the antigen recognized and/or targeted by T cells is selected from the group consisting of Notch 1, Notch 2, Notch 3, Notch 4, cell surface associated Mucin 1 (MUC1), Ephrin B2, Betaglycan (TGFBR3), CD43, CD44, CSF1R, CX3CR1, CXCL16, Delta1, E-cadherin, N-cadherin, HLA-A2, IFNaR2, IL1R1, IL1R2, IL6R, and amyloid precursor protein (APP).

In some embodiments the antigen recognized and/targeted by T cells is B Cell Maturation Antigen (BCMA). Exemplary antigen-binding domains, and CARs containing such antigen-binding domains, that target or specifically bind BCMA are known, see e.g. WO 2016/090320, WO2016090327, WO2010104949A2 and WO2017173256. In some embodiments, the antigen binding domain is an scFv that contains a VH and a VL derived from an antibody or an antibody fragment specific to BCMA. In some embodiments, the antibody or antibody fragment that binds BCMA is or contains a VH and a VL from an antibody or antibody fragment set forth in International Patent Applications, Publication Number WO 2016/090327 and WO 2016/090320.

Methods for administration of engineered cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) *Nat Rev Clin Oncol.* 8(10):577-85). See, e.g., Themeli et al., (2013) *Nat Biotechnol.* 31(10): 928-933; Tsukahara et al., (2013) *Biochem Biophys Res Commun* 438(1): 84-9; Davila et al., (2013) *PLoS ONE* 8(4): e61338.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

The cells can be administered by any suitable means. The cells are administered in a dosing regimen to achieve a therapeutic effect, such as a reduction in tumor burden. Dosing and administration may depend in part on the schedule of administration of the gamma secretase inhibitor, which can be administered prior to, subsequent to and/or simultaneously with initiation of administration of the T cell therapy. Various dosing schedules of the T cell therapy include but are not limited to single or multiple administrations over various time-points, bolus administration, and pulse infusion.

a. Compositions and Formulations

In some embodiments, the dose of cells of the cell therapy, such a T cell therapy comprising cells engineered with a recombinant antigen receptor, e.g. CAR or TCR, is provided as a composition or formulation, such as a pharmaceutical composition or formulation. Such compositions can be used in accord with the provided methods, such as in the prevention or treatment of diseases, conditions, and disorders.

In some embodiments, the cell therapy, such as engineered T cells (e.g. CAR T cells), are formulated with a pharmaceutically acceptable carrier. In some aspects, the choice of carrier is determined in part by the particular cell or agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being prevented or treated with the cells or agents, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

The pharmaceutical composition in some embodiments contains cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The cells may be administered using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

In some cases, the cell therapy is administered as a single pharmaceutical composition comprising the cells. In some embodiments, a given dose is administered by a single bolus administration of the cells or agent. In some embodiments, it is administered by multiple bolus administrations of the cells or agent, for example, over a period of no more than 3 days, or by continuous infusion administration of the cells or agent.

b. Dosage Schedule and Administration

In some embodiments, a dose of cells is administered to subjects in accord with the provided combination therapy methods. In some embodiments, the size or timing of the doses is determined as a function of the particular disease or condition in the subject. It is within the level of a skilled artisan to empirically determine the size or timing of the doses for a particular disease in view of the provided description.

In certain embodiments, the cells, or individual populations of sub-types of cells, are administered to the subject at a range of about 0.1 million to about 100 billion cells and/or that amount of cells per kilogram of body weight of the subject, such as, e.g., 0.1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight of the subject. Dosages may vary depending on attributes particular to the disease or disorder and/or patient and/or other treatments. In some embodiments, such values refer to numbers of recombinant receptor-expressing cells; in other embodiments, they refer to number of T cells or PBMCs or total cells administered.

In some embodiments, for example, where the subject is a human, the cells are administered at a dose of total recombinant receptor (e.g., CAR)-expressing cells, T cells, or peripheral blood mononuclear cells (PBMCs) that is in the range of about $1 \times 10^6$ to about $1.2 \times 10^9$ such cells, such as at or about $1 \times 10^7$, at or about $5 \times 10^7$, at or about $1 \times 10^8$, at or about $2 \times 10^8$, at or about $2.5 \times 10^8$, at or about $3 \times 10^8$, at or about $3.5 \times 10^8$, at or about $4 \times 10^8$, at or about $4.5 \times 10^8$ at or about $5 \times 10^8$ total such cells, at or about $6 \times 10^8$, at or about $7 \times 10^8$, at or about $8 \times 10^8$, at or about $9 \times 10^8$ or at or about $1 \times 10^9$ of such cells, or the range between any two of the foregoing values. In some embodiments, for example, where the subject is a human, the dose includes fewer than about or about $5 \times 10^8$ total recombinant receptor (e.g., CAR)-expressing cells, T cells, or peripheral blood mononuclear cells (PBMCs). In some embodiments, for example, where the subject is a human, the dose includes fewer than about or about $3.0 \times 10^8$ total recombinant receptor (e.g., CAR)-expressing cells, T cells, or peripheral blood mononuclear cells (PBMCs). In some embodiments, for example, where the subject is a human, the dose includes fewer than about or about $1.5 \times 10^8$ total recombinant receptor (e.g., CAR)-expressing cells, T cells, or peripheral blood mononuclear cells (PBMCs). In some embodiments, for example, where the subject is a human, the dose includes fewer than about $1 \times 10^8$ total recombinant receptor (e.g., CAR)-expressing cells, T cells, or peripheral blood mononuclear cells (PBMCs). In some embodiments, for example, where the subject is a human, the dose includes fewer than about $5 \times 10^7$ total recombinant receptor (e.g., CAR)-expressing cells, T cells, or peripheral blood mononuclear cells (PBMCs).

In some embodiments, the dose of total cells administered comprises from or from about $1 \times 10^5$ to $8 \times 10^8$ total CAR-expressing T cells, $1 \times 10^5$ to $5 \times 10^8$ total CAR-expressing T cells, $1 \times 10^5$ to $2.5 \times 10^8$ total CAR-expressing T cells, $1 \times 10^5$ to $1 \times 10^8$ total CAR-expressing T cells, $1 \times 10^5$ to $5 \times 10^7$ total CAR-expressing T cells, $1 \times 10^5$ to $2.5 \times 10^7$ total CAR-expressing T cells, $1 \times 10^5$ to $1 \times 10^7$ total CAR-expressing T cells, $1 \times 10^5$ to $5 \times 10^6$ total CAR-expressing T cells, $1 \times 10^5$ to $2.5 \times 10^6$ total CAR-expressing T cells, $1 \times 10^5$ to $1 \times 10^6$ total CAR-expressing T cells, $1 \times 10^6$ to $8 \times 10^8$ total CAR-expressing T cells, $1 \times 10^6$ to $5 \times 10^8$ total CAR-expressing T cells, $1 \times 10^6$ to $2.5 \times 10^8$ total CAR-expressing T cells, $1 \times 10^6$ to $1 \times 10^8$ total CAR-expressing T cells, $1 \times 10^6$ to $5 \times 10^7$ total CAR-expressing T cells, $1 \times 10^6$ to $2.5 \times 10^7$ total CAR-expressing T cells, $1 \times 10^6$ to $1 \times 10^7$ total CAR-expressing T cells, $1 \times 10^6$ to $5 \times 10^6$ total CAR-expressing T cells, $1 \times 10^6$ to $2.5 \times 10^6$ total CAR-expressing T cells, $2.5 \times 10^6$ to $8 \times 10^8$ total CAR-expressing T cells, $2.5 \times 10^6$ to $5 \times 10^8$ total CAR-expressing T cells, $2.5 \times 10^6$ to $2.5 \times 10^8$ total CAR-expressing T cells, $2.5 \times 10^6$ to $1 \times 10^8$ total CAR-expressing T cells, $2.5 \times 10^6$ to $5 \times 10^7$ total CAR-expressing T cells, $2.5 \times 10^6$ to $2.5 \times 10^7$ total CAR-expressing T cells, $2.5 \times 10^6$ to $1 \times 10^7$ total CAR-expressing T cells, $2.5 \times 10^6$ to $5 \times 10^6$ total CAR-expressing T cells, $5 \times 10^6$ to $8 \times 10^8$ total CAR-expressing T cells, $5 \times 10^6$ to $5 \times 10^8$ total CAR-expressing T cells, $5 \times 10^6$ to $2.5 \times 10^8$ total CAR-expressing T cells, $5 \times 10^6$ to $1 \times 10^8$ total CAR-expressing T cells, $5 \times 10^6$ to $5 \times 10^7$ total CAR-expressing T cells, $5 \times 10^6$ to $2.5 \times 10^7$ total CAR-expressing T cells, $5 \times 10^6$ to $1 \times 10^7$ total CAR-expressing T cells, $1 \times 10^7$ to $8 \times 10^8$ total CAR-expressing T cells, $1 \times 10^7$ to $5 \times 10^8$ total CAR-expressing T cells, $1 \times 10^7$ to $2.5 \times 10^8$ total CAR-expressing T cells, $1 \times 10^7$ to $1 \times 10^8$ total CAR-expressing T cells, $1 \times 10^7$ to $5 \times 10^7$ total CAR-expressing T cells, $1 \times 10^7$ to $2.5 \times 10^7$ total CAR-expressing T cells, $2.5 \times 10^7$ to $8 \times 10^8$ total CAR-expressing T cells, $2.5 \times 10^7$ to $5 \times 10^8$ total CAR-expressing T cells, $2.5 \times 10^7$ to $2.5 \times 10^8$ total CAR-expressing T cells, $2.5 \times 10^7$ to $1 \times 10^8$ total CAR-expressing T cells, $2.5 \times 10^7$ to $5 \times 10^7$ total CAR-expressing T cells, $5 \times 10^7$ to $8 \times 10^8$ total CAR-expressing T cells, $5 \times 10^7$ to $5 \times 10^8$ total CAR-expressing T cells, $5 \times 10^7$ to $2.5 \times 10^8$ total CAR-expressing T cells, $5 \times 10^7$ to $1 \times 10^8$ total CAR-expressing T cells, $1 \times 10^8$ to $8 \times 10^8$ total CAR-expressing T cells, $1 \times 10^8$ to $5 \times 10^8$ total CAR-expressing T cells, $1 \times 10^8$ to $2.5 \times 10^8$ total CAR-expressing T cells, $2.5 \times 10^8$ to $8 \times 10^8$ total CAR-expressing T cells, $2.5 \times 10^8$ to $5 \times 10^8$ total CAR-expressing T cells, or $5 \times 10^8$ total CAR-expressing T cells to $8 \times 10^8$ total CAR-expressing T cells, each inclusive.

In some embodiments, the dose of genetically engineered cells comprises from or from about $50 \times 10^6$ to $800 \times 10^6$ total CAR-expressing T cells, from or from about $50 \times 10^6$ to $450 \times 10^6$ total CAR-expressing T cells, from or from about $50 \times 10^6$ to $300 \times 10^6$ total CAR-expressing T cells, from or from about $50 \times 10^6$ to $150 \times 10^6$ total CAR-expressing T cells, from or from about $150 \times 10^6$ to $800 \times 10^6$ total CAR-expressing T cells, from or from about $150 \times 10^6$ to $450 \times 10^6$ total CAR-expressing T cells, from or from about $150 \times 10^6$ to $300 \times 10^6$ total CAR-expressing T cells, $300 \times 10^6$ to $800 \times 10^6$ total CAR-expressing T cells, from or from about $300 \times 10^6$ to $450 \times 10^6$ total CAR-expressing T cells, or $450 \times 10^6$ to $800 \times 10^6$ total CAR-expressing T cells. In some embodiments, the dose of genetically engineered cells is or is about $50 \times 10^6$ CAR-expressing T cells, is or is about $150 \times 10^6$ CAR-expressing T cells, cells, is or is about $450 \times 10^6$ CAR-expressing T cells, or is or is about $800 \times 10^6$ CAR-expressing T cells.

In some of any of the embodiments, the number is with reference to the total number of CD3+, total number of CD8+ or total number of CD4+ and CD8+ T cells, in some recombinant receptor-expressing (e.g. CAR+) cells of such cells.

In some embodiments, the cell therapy comprises administration of a dose comprising a number of cells from or from about $1 \times 10^5$ to $1 \times 10^8$ total recombinant receptor-expressing cells, total T cells, or total peripheral blood mononuclear cells (PBMCs); from or from about $5 \times 10^5$ to $1 \times 10^7$ total recombinant receptor-expressing cells, total T cells, or total PBMCs or from or from about $1 \times 10^6$ to $1 \times 10^7$ total recombinant receptor-expressing cells, total T cells, or total PBMCs), each inclusive. In some embodiments, the cell therapy comprises administration of a dose of cells comprising a number of cells at least or about at least $1 \times 10^5$ total recombinant receptor-expressing cells, total T cells, or total PBMCs, such at least or at least $1 \times 10^6$, at least or about at least $1 \times 10^7$, at least or about at least $1 \times 10^8$ of such cells. In some embodiments, the number is with reference to the total number of CD3+ or CD8+, in some cases also recombinant receptor-expressing (e.g. CAR+) cells. In some embodiments, the cell therapy comprises administration of a dose comprising a number of cells from or from about $1 \times 10^5$ to $1 \times 10^8$ CD3+ or CD8+ total T cells or CD3+ or CD8+ recombinant receptor-expressing cells, from or from about $5 \times 10^5$ to $1 \times 10^7$ CD3+ or CD8+ total T cells or CD3+ or CD8+ recombinant receptor-expressing cells, or from or from about $1 \times 10^6$ to $1 \times 10^7$ CD3+ or CD8+ total T cells or CD3+ or CD8+ recombinant receptor-expressing cells, each inclusive. In some embodiments, the cell therapy comprises administration of a dose comprising a number of cells from or from about $1 \times 10^5$ to $1 \times 10^8$ total CD3+/CAR+ or CD8+/CAR+ cells, from or from about $5 \times 10^5$ to $1 \times 10^7$ total CD3+/CAR+ or CD8+/CAR+ cells, or from or from about $1 \times 10^6$ to $1 \times 10^7$ total CD3+/CAR+ or CD8+/CAR+ cells, each inclusive.

In some embodiments, the T cells of the dose include CD4+ T cells, CD8+ T cells or CD4+ and CD8+ T cells.

In some embodiments, for example, where the subject is human, the CD8+ T cells of the dose, including in a dose including CD4+ and CD8+ T cells, includes between about $1 \times 10^6$ and $5 \times 10^8$ total recombinant receptor (e.g., CAR)-expressing CD8+ cells, e.g., in the range of about $5 \times 10^6$ to $1 \times 10^8$ such cells, such cells $1 \times 10^7$, $2.5 \times 10^7$, $5 \times 10^7$, $7.5 \times 10^7$, $1 \times 10^8$, or $5 \times 10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1 \times 10^7$ to $0.75 \times 10^8$ total recombinant receptor-expressing CD8+ T cells, $1 \times 10^7$ to $2.5 \times 10^7$ total recombinant receptor-expressing CD8+ T cells, from or from about $1 \times 10^7$ to $0.75 \times 10^8$ total recombinant receptor-expressing CD8+ T cells, each inclusive. In some embodiments, the dose of cells comprises the administration of or about $1 \times 10^7$, $2.5 \times 10^7$, $5 \times 10^7$ $7.5 \times 10^7$, $1 \times 10^8$, or $5 \times 10^8$ total recombinant receptor-expressing CD8+ T cells.

In some embodiments, the cell therapy comprises administration of a dose comprising a number of cells that is at least or at least about or is or is about $0.1 \times 10^6$ cells/kg body weight of the subject, $0.2 \times 10^6$ cells/kg, $0.3 \times 10^6$ cells/kg, $0.4 \times 10^6$ cells/kg, $0.5 \times 10^6$ cells/kg, $1 \times 10^6$ cell/kg, $2.0 \times 10^6$ cells/kg, $3 \times 10^6$ cells/kg or $5 \times 10^6$ cells/kg.

In some embodiments, the cell therapy comprises administration of a dose comprising a number of cells between or between about $0.1 \times 10^6$ cells/kg body weight of the subject and $1.0 \times 10^7$ cells/kg, between or between about $0.5 \times 10^6$ cells/kg and $5 \times 10^6$ cells/kg, between or between about $0.5 \times 10^6$ cells/kg and $3 \times 10^6$ cells/kg, between or between about $0.5 \times 10^6$ cells/kg and $2 \times 10^6$ cells/kg, between or between about $0.5 \times 10^6$ cells/kg and $1 \times 10^6$ cell/kg, between or between about $1.0 \times 10^6$ cells/kg body weight of the subject and $5 \times 10^6$ cells/kg, between or between about $1.0 \times 10^6$ cells/kg and $3 \times 10^6$ cells/kg, between or between about $1.0 \times 10^6$ cells/kg and $2 \times 10^6$ cells/kg, between or between about $2.0 \times 10^6$ cells/kg body weight of the subject and $5 \times 10^6$ cells/kg, between or between about $2.0 \times 10^6$ cells/kg and $3 \times 10^6$ cells/kg, or between or between about $3.0 \times 10^6$ cells/kg body weight of the subject and $5 \times 10^6$ cells/kg, each inclusive.

In some embodiments, the dose of cells comprises between at or about $2 \times 10^5$ of the cells/kg and at or about $2 \times 10^6$ of the cells/kg, such as between at or about $4 \times 10^5$ of the cells/kg and at or about $1 \times 10^6$ of the cells/kg or between at or about $6 \times 10^5$ of the cells/kg and at or about $8 \times 10^5$ of the cells/kg. In some embodiments, the dose of cells comprises no more than $2 \times 10^5$ of the cells (e.g. antigen-expressing, such as CAR-expressing cells) per kilogram body weight of the subject (cells/kg), such as no more than at or about $3 \times 10^5$ cells/kg, no more than at or about $4 \times 10^5$ cells/kg, no more than at or about $5 \times 10^5$ cells/kg, no more than at or about $6 \times 10^5$ cells/kg, no more than at or about $7 \times 10^5$ cells/kg, no more than at or about $8 \times 10^5$ cells/kg, nor more than at or about $9 \times 10^5$ cells/kg, no more than at or about $1 \times 10^6$ cells/kg, or no more than at or about $2 \times 10^6$ cells/kg. In some embodiments, the dose of cells comprises at least or at least about or at or about $2 \times 10^5$ of the cells (e.g. antigen-expressing, such as CAR-expressing cells) per kilogram body weight of the subject (cells/kg), such as at least or at least about or at or about $3 \times 10^5$ cells/kg, at least or at least about or at or about $4 \times 10^5$ cells/kg, at least or at least about or at or about $5 \times 10^5$ cells/kg, at least or at least about or at or about $6 \times 10^5$ cells/kg, at least or at least about or at or about $7 \times 10^5$ cells/kg, at least or at least about or at or about $8 \times 10^5$ cells/kg, at least or at least about or at or about $9 \times 10^5$ cells/kg, at least or at least about or at or about $1 \times 10^6$ cells/kg, or at least or at least about or at or about $2 \times 10^6$ cells/kg.

In some embodiments, the dose of cells, e.g., recombinant receptor-expressing T cells, is administered to the subject as a single dose or is administered only one time within a period of two weeks, one month, three months, six months, 1 year or more.

In some aspects, the pharmaceutical compositions and formulations are provided as unit dose form compositions including the number of cells for administration in a given dose or fraction thereof.

In some embodiments, cells of the dose may be administered by administration of a plurality of compositions or solutions, such as a first and a second, optionally more, each containing some cells of the dose. In some aspects, the plurality of compositions, each containing a different population and/or sub-types of cells, are administered separately or independently, optionally within a certain period of time. For example, the populations or sub-types of cells can include CD8+ and CD4+ T cells, respectively, and/or CD8+- and CD4+-enriched populations, respectively, e.g., CD4+ and/or CD8+ T cells each individually including cells genetically engineered to express the recombinant receptor. In some embodiments, the administration of the dose comprises administration of a first composition comprising a dose of CD8+ T cells or a dose of CD4+ T cells and administration of a second composition comprising the other of the dose of CD4+ T cells and the CD8+ T cells.

In some embodiments, the administration of the composition or dose, e.g., administration of the plurality of cell compositions, involves administration of the cell compositions separately. In some aspects, the separate administrations are carried out simultaneously, or sequentially, in any order. In some embodiments, the dose comprises a first composition and a second composition, and the first composition and second composition are administered 0 to 12 hours apart, 0 to 6 hours apart or 0 to 2 hours apart. In some embodiments, the initiation of administration of the first composition and the initiation of administration of the second composition are carried out no more than 2 hours, no more than 1 hour, or no more than 30 minutes apart, no more than 15 minutes, no more than 10 minutes or no more than 5 minutes apart. In some embodiments, the initiation and/or completion of administration of the first composition and the completion and/or initiation of administration of the second composition are carried out no more than 2 hours, no more than 1 hour, or no more than 30 minutes apart, no more than 15 minutes, no more than 10 minutes or no more than 5 minutes apart.

In some composition, the first composition, e.g., first composition of the dose, comprises CD4+ T cells. In some composition, the first composition, e.g., first composition of the dose, comprises CD8+ T cells. In some embodiments, the first composition is administered prior to the second composition.

In some embodiments, the dose or composition of cells includes a defined or target ratio of CD4+ cells expressing a recombinant receptor to CD8+ cells expressing a recombinant receptor and/or of CD4+ cells to CD8+ cells, which ratio optionally is approximately 1:1 or is between approximately 1:3 and approximately 3:1, such as approximately 1:1. In some aspects, the administration of a composition or dose with the target or desired ratio of different cell populations (such as CD4+:CD8+ ratio or CAR+CD4+:CAR+CD8+ ratio, e.g., 1:1) involves the administration of a cell composition containing one of the populations and then administration of a separate cell composition comprising the other of the populations, where the administration is at or approximately at the target or desired ratio. In some aspects, administration of a dose or composition of cells at a defined ratio leads to improved expansion, persistence and/or anti-tumor activity of the T cell therapy.

In the context of adoptive cell therapy, administration of a given "dose" of cells encompasses administration of the given amount or number of cells as a single composition and/or single uninterrupted administration, e.g., as a single injection or continuous infusion, and also encompasses administration of the given amount or number of cells as a split dose, provided in multiple individual compositions or infusions, over a specified period of time, which is no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells of the dose are administered in a single pharmaceutical composition. In some embodiments, the cells of the dose are administered in a plurality of compositions, collectively containing the cells of the dose.

The term "split dose" refers to a dose that is split so that it is administered over more than one day. This type of dosing is encompassed by the present methods and is considered to be a single dose. In some embodiments, the cells of a split dose are administered in a plurality of compositions, collectively comprising the cells of the dose, over a period of no more than three days.

Thus, the dose of cells may be administered as a split dose. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, the subject receives multiple doses, e.g., two or more doses or multiple consecutive doses, of the cells. In some embodiments, two doses are administered to a subject. In some embodiments, the subject receives the consecutive dose, e.g., second dose, is administered approximately 4, 5, 6, 7, 8, 9, 10, 11, 12, 13, 14, 15, 16, 17, 18, 19, 20 or 21 days after the first dose. In some embodiments, multiple consecutive doses are administered following the first dose, such that an additional dose or doses are administered following administration of the consecutive dose. In some aspects, the number of cells administered to the subject in the additional dose is the same as or similar to the first dose and/or consecutive dose. In some embodiments, the additional dose or doses are larger than prior doses.

In some aspects, the size of the first and/or consecutive dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the time between the administration of the first dose and the administration of the consecutive dose is about 9 to about 35 days, about 14 to about 28 days, or 15 to 27 days. In some embodiments, the administration of the consecutive dose is at a time point more than about 14 days after and less than about 28 days after the administration of the first dose. In some aspects, the time between the first and consecutive dose is about 21 days. In some embodiments, an additional dose or doses, e.g. consecutive doses, are administered following administration of the consecutive dose. In some aspects, the additional consecutive dose or doses are administered at least about 14 and less than about 28 days following administration of a prior dose. In some embodiments, the additional dose is administered less than about 14 days following the prior dose, for example, 4, 5, 6, 7, 8, 9, 10, 11, 12, or 13 days after the prior dose. In some embodiments, no dose is administered less than about 14 days following the prior dose and/or no dose is administered more than about 28 days after the prior dose.

In some embodiments, the dose of cells, e.g., recombinant receptor-expressing cells, comprises two doses (e.g., a double dose), comprising a first dose of the T cells and a consecutive dose of the T cells, wherein one or both of the first dose and the second dose comprises administration of the split dose of T cells.

In some embodiments, the dose of cells is generally large enough to be effective in reducing disease burden.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as CD8+ and CD4+ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells administered at the desired dose, the individual populations or sub-types are present at or near a desired output ratio (such as CD4+ to CD8+ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of CD4+ to CD8+ cells, and/or is based on a desired fixed or minimum dose of CD4+ and/or CD8+ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios. For example, in some embodiments, the desired ratio (e.g., ratio of CD4+ to CD8+ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

The cells can be administered by any suitable means. The cells are administered in a dosing regimen to achieve a therapeutic effect, such as a reduction in tumor burden. Dosing and administration may depend in part on the schedule of administration of the immunomodulatory compound, which can be administered prior to, subsequent to and/or simultaneously with initiation of administration of the T cell therapy. Various dosing schedules of the T cell therapy include but are not limited to single or multiple administrations over various time-points, bolus administration, and pulse infusion. In certain embodiments, the engineered T cells express a recombinant receptor. In certain embodiments, the engineered T cells express a CAR.

In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some embodiments, administration of the gamma secretase inhibitor in combination with the cells is able to increase, such as substantially or significantly increase, the expansion or proliferation of the cells, and thus a lower dose of cells can be administered to the subject. In some cases, the provided methods allow a lower dose of such cells to be administered, to achieve the same or better efficacy of treatment as the dose in a method in which the cell therapy is administered without administering the gamma secretase inhibitor, such as at least 1.5-fold, 2-fold, 3-fold, 4-fold, 5-fold or 10-fold less than the dose in a method in which the cell therapy is administered without administering the gamma secretase inhibitor.

In some embodiments, for example, the dose contains between or between about $5.0 \times 10^6$ and $2.25 \times 10^7$, $5.0 \times 10^6$ and $2.0 \times 10^7$, $5.0 \times 10^6$ and $1.5 \times 10^7$, $5.0 \times 10^6$ and $1.0 \times 10^7$, $5.0 \times 10^6$ and $7.5 \times 10^6$, $7.5 \times 10^6$ and $2.25 \times 10^7$, $7.5 \times 10^6$ and $2.0 \times 10^7$, $7.5 \times 10^6$ and $1.5 \times 10^7$, $7.5 \times 10^6$ and $1.0 \times 10^7$, $1.0 \times 10^7$ and $2.25 \times 10^7$, $1.0 \times 10^7$ and $2.0 \times 10^7$, $1.0 \times 10^7$ and $1.5 \times 10^7$, $1.5 \times 10^7$ and $2.25 \times 10^7$, $1.5 \times 10^7$ and $2.0 \times 10^7$, $2.0 \times 10^7$ and $2.25 \times 10^7$. In some embodiments, the dose of cells contains a number of cells, that is between at least or at least about $5 \times 10^6$, $6 \times 10^6$, $7 \times 10^6$, $8 \times 10^6$, $9 \times 10^6$, $10 \times 10^6$ and about $15 \times 10^6$ recombinant-receptor expressing cells, such as recombinant-receptor expressing cells that are CD8+. In some embodiments, such dose, such as such target number of cells refers to the total recombinant-receptor expressing cells in the administered composition.

In some embodiments, for example, the lower dose contains less than about $5 \times 10^6$ cells, recombinant receptor (e.g. CAR)-expressing cells, T cells, and/or PBMCs per kilogram body weight of the subject, such as less than about $4.5 \times 10^6$, $4 \times 10^6$, $3.5 \times 10^6$, $3 \times 10^6$, $2.5 \times 10^6$, $2 \times 10^6$, $1.5 \times 10^6$, $1 \times 10^6$, $5 \times 10^5$, $2.5 \times 10^5$, or $1 \times 10^5$ such cells per kilogram body weight of the subject. In some embodiments, the lower dose contains less than about $1 \times 10^5$, $2 \times 10^5$, $5 \times 10^5$, or $1 \times 10^6$ of such cells per kilogram body weight of the subject, or a value within the range between any two of the foregoing values. In some embodiments, such values refer to numbers of recombinant receptor-expressing cells; in other embodiments, they refer to the number of T cells or PBMCs or total cells administered.

In some embodiments, one or more subsequent dose of cells can be administered to the subject. In some embodiments, the subsequent dose of cells is administered greater than or greater than about 7 days, 14 days, 21 days, 28 days or 35 days after initiation of administration of the first dose of cells. The subsequent dose of cells can be more than, approximately the same as, or less than the first dose. In some embodiments, administration of the T cell therapy, such as administration of the first and/or second dose of cells, can be repeated.

In some embodiments, initiation of administration of the cell therapy, e.g. the dose of cells or a first dose of a split dose of cells, is administered before (prior to), concurrently with or after (subsequently or subsequent to) the administration of the gamma secretase inhibitor, or a pharmaceutically acceptable salt of hydrate thereof.

In some embodiments, the dose of cells, or the subsequent dose of cells, is administered concurrently with initiating administration of the gamma secretase inhibitor in accord with the combination therapy methods. In some embodiments, the dose of cells, or the subsequent dose of cells, is administered on the same day as initiating administration of the gamma secretase inhibitor in accord with the combination therapy methods. In some embodiments, the dose of cells, or the subsequent dose of cells, is administered within 1 day, within 2 days, within 3 days, within 4 days, within 5 days, within 6 days, or within 7 days of initiating administration of the gamma secretase inhibitor in accord with the combination therapy methods.

In some embodiments, the dose of cells, or the subsequent dose of cells, is administered prior to starting or initiating administration of the gamma secretase inhibitor in accord with the provided combination therapy. In some embodiments, the dose of cells is administered at least or at least about 1 hour, at least or at least about 2 hours, at least or at least about 3 hours, at least or at least about 6 hours, at least or at least about 12 hours, at least or at least about 1 day, at least or at least about 2 days, at least or at least about 3 days, at least or about at least 4 days, at least or at least about 5 days, at least or about at least 6 days, at least or at least about 7 days, at least or about at least 12 days, at least or at least about 14 days, at least or about at least 15 days, at least or at least about 21 days, at least or at least about 28 days, at least or about at least 30 days, at least or at least about 35 days, at least or at least about 42 days, at least or about at least 60 days or at least or about at least 90 days prior to administering the gamma secretase inhibitor in accord with the provided combination therapy.

In some embodiments, the administration of the gamma secretase inhibitor in accord with the provided combination therapy is at a time in which the prior administration of the immunotherapy (e.g., T cell therapy, such as CAR-T cell therapy) is associated with, or is likely to be associated with, a decreased functionality of the T cells compared to the functionality of the T cells at a time just prior to initiation of the immunotherapy (e.g., T cell therapy, such as CAR-T cell therapy) or at a preceding time point after initiation of the T cell therapy. In some embodiments, the method involves, subsequent to administering the dose of cells of the T cell therapy, e.g., adoptive T cell therapy, but prior to administering the gamma secretase inhibitor, assessing a sample from the subject for one or more functions of T cells, such as expansion or persistence of the cells, e.g. as determined by level or amount in the blood, or other phenotypes or desired outcomes as described herein, e.g., such as those described in Section III. Various parameters for determining or assessing the regimen of the combination therapy are described in Section III.

B. Administration of Gamma Secretase Inhibitor

In some embodiments of the methods, compositions, combinations, kits and uses provided herein, the combination therapy can be administered in one or more compositions, e.g., a pharmaceutical composition containing an inhibitor of gamma secretase, and/or the cell therapy, e.g., T cell therapy.

In some embodiments, the gamma secretase inhibitor inhibits or reduces the intramembrane cleavage of one or more receptors on a cell, for example, a tumor/cancer cell. In some embodiments, the $IC_{50}$ of the inhibition of the intramembrane cleavage of the cell surface receptor on the cancer/tumor cell is less than about 100 µM, 50 µM, 25 µM, 10 µM, 1 µM, 0.75 µM, 0.5 µM, 0.25 µM, 0.1 µM, 75 nM, 50 nM, 25 nM, or 10 nM. In some embodiments, the gamma secretase inhibitor inhibits intramembrane cleavage of the cell surface receptor on the cancer/tumor cell with a half-maximal inhibitory concentration ($IC_{50}$) of 0.01 nM to 10 nM, 0.01 nM to 5 nM, 0.01 nM to 1 nM, 0.01 nM, to 0.5 nM, 0.01 nM to 0.35 nM, 0.01 nM to 0.25 nM, 0.01 nM to 1.0 nM, 0.01 nM to 0.05 nM, 0.05 nM to 10 nM, 0.05 nM to 5 nM, 0.05 nM to 1 nM, 0.05 nM, to 0.5 nM, 0.05 nM to 0.35 nM, 0.05 nM to 0.25 nM, 0.05 nM to 1.0 nM, 1.0 nM to 10 nM, 1.0 nM nM to 5 nM, 1.0 nM nM to 1 nM, 1.0 nM nM, to 0.5 nM, 1.0 nM nM to 0.35 nM, 1.0 nM nM to 0.25 nM, 0.25 nM to 10 nM, 0.25 nM to 5 nM, 0.25 nM to 1 nM, 0.25 nM, to 0.5 nM, 0.25 nM to 0.35 nM, 0.35 nM to 10 nM, 0.35 nM to 5 nM, 0.35 nM to 1 nM, 0.35 nM, to 0.5 nM, 0.5 nM to 10 nM, 0.5 nM to 5 nM, 0.5 nM to 1 nM, 1 nM to 10 nM, 1 nM to 5 nM or 5 nM to 10 nM. In some embodiments, the $IC_{50}$ of the inhibition of the intramembrane cleavage of the cell surface receptor on the cancer/tumor cell is about 10 nM-25 nM, 25 nM-50 nM, 50 nM-75 nM, 75 nM-0.1 µM, 0.1 µM-0.25 µM, 0.25 µM-0.5 µM, 0.5 µM-0.75 µM, 0.75 µM-1 µM, 1 µM-10 µM, 10 µM-25 µM, 25 µM-50 µM, 50 µM-75 µM, or 75 µM-100 µM. In some embodiments, the receptor(s) is/are selected from the group consisting of B cell maturation antigen (BCMA), Notch 1, Notch 2, Notch 3, Notch 4, cell surface associated Mucin 1 (MUC1), Ephrin B2, Betaglycan (TGFBR3), CD43, CD44, CSF1R, CX3CR1, CXCL16, Delta1, E-cadherin, N-cadherin, HLA-A2, IFNaR2, IL1R1, IL1R2, IL6R, and amyloid precursor protein (APP). In some embodiments, the receptor is cell surface associated Mucin 1 (MUC1).

In some embodiments, the an inhibitor of gamma secretase inhibits or reduces the intramembrane cleavage of one or more receptors described above on a cell, for example, a tumor/cancer cell, and wherein the administration of the gamma secretase increases the level of the receptor expression on the cell. In some embodiments, the receptor is surface B cell maturation antigen (BCMA). In some embodiments, the gamma secretase inhibitor prohibits intramembrane cleavage of surface B cell maturation antigen (BCMA), and wherein the $IC_{50}$ of the inhibition of the cleavage of surface BCMA is less than about 100 µM, 50 M, 25 µM, 10 µM, 1 µM, 0.75 µM, 0.5 M, 0.25 µM, 0.1 µM, 75 nM, 50 nM, 25 nM, or 10 nM. In some embodiments, the $IC_{50}$ of the inhibition of the intramembrane cleavage of the cell surface receptor on the cancer/tumor cell is about 10 nM-25 nM, 25 nM-50 nM, 50 nM-75 nM, 75 nM-0.1 µM, 0.1 µM-0.25 µM, 0.25 µM-0.5 µM, 0.5 µM-0.75 µM, 0.75

μM-1 μM, 1 μM-10 μM, 10 μM-25 μM, 25 μM-50 μM, 50 μM-75 μM, or 75 μM-100 μM. In some embodiments, the IC$_{50}$ of the inhibition of the cleavage of surface BCMA is less than 0.5 nM. In some embodiments, the IC$_{50}$ of the inhibition of the cleavage of surface BCMA is about 0.01 nM to about 0.5 nM, or 0.01 nM to about 0.5 nM, or about 0.01 nM to about 0.35 nM.

In some embodiments, the inhibitor of gamma secretase has a low brain penetration. In some embodiments, only 0.1%, 0.25%, 0.5%, 0.75%, 1%, 2.5%, 5%, 7.5%, 10%, 20%, 30%, 40%, 50%, 60%, 70%, 80% or 90% of the gamma secretase inhibitor can penetrate the brain after administration.

In some embodiments, the inhibitor of gamma secretase selectively inhibits or reduces intramembrane cleavage of part of the substrates of gamma secretase. In some embodiments, the gamma secretase inhibitor selectively inhibits or reduces the intramembrane cleavage of surface B cell maturation antigen (BCMA).

In some embodiments, the gamma secretase inhibitor is a peptide inhibitor or non-peptide inhibitor. In some embodiments, the gamma secretase inhibitor is a peptide inhibitor from among peptide aldehydes derivatives, difluoroketones derivatives, hydroxyethylene dipeptide isotere derivatives, alpha-helical peptide derivatives and dipeptide analogs. In some embodiments, the gamma secretase inhibitor is a non-peptide inhibitor selected from benzodiazepines derivatives and sulfonamides derivatives. In some embodiments, the gamma secretase is a transition state inhibitor, for example, LY-411575-I or LY685,458. In some embodiments, the gamma secretase inhibitor is a non-transition state inhibitor such as DAPT, RO4929097. In some embodiments, the gamma secretase inhibitor is a gamma secretase modulator. In some embodiments, gamma secretase modulator is a nonsteroidal anti-inflammatory drugs-type modulator.

In some embodiments, the gamma secretase inhibitor is LY3039478, secretase inhibitor I (GSI I) Z-Leu-Leu-Norleucine; γ-secretase inhibitor II (GSI II); γ-secretase inhibitor III (GSI III), N-Benzyloxycarbonyl-Leu-leucinal, N-(2-Naphthoyl)-Val-phenylalaninal; γ-secretase inhibitor III (GSI IV); γ-secretase inhibitor III (GSI V), N-Benzyloxycarbonyl-Leu-phenylalaninal; γ-secretase inhibitor III (GSI VI), 1-(S)-endo-N-(1,3,3)-Trimethylbicyclo[2.2.1]hept-2-yl)-4-fluorophenyl Sulfonamide; γ-secretase inhibitor III (GSI VII), Menthyloxycarbonyl-LL-CHO; γ-secretase inhibitor III (GSI IX), (DAPT), N-[N-(3,5-Difluorophenacetyl-L-alanyl)]-S-phenylglycine t-Butyl Ester; γ-secretase inhibitor X (GSI X), {1 S-Benzyl-4R-[1-(1S-carbamoyl-2-phenethylcarbamoyl)-1S-3-methylbutylcarb-amoyl]-2R-hydroxy-5-phenylpentyl}carbamic Acid tert-butyl Ester; γ-secretase inhibitor XI (GSI XI), 7-Amino-4-chloro-3-methoxyisocoumarin; γ-secretase inhibitor XII (GSI XII), Z-Ile-Leu-CHO; Y-secretase inhibitor XIII (GSI XIII), Z-Tyr-Ile-Leu-CHO; γ-secretase inhibitor XIV (GSI XIV), Z-Cys(t-Bu)-Ile-Leu-CHO; γ-secretase inhibitor XVI (GSI XVI), N-[N-3,5-Difluorophenacetyl]-L-alanyl-S-phenylglycine Methyl Ester; γ-secretase inhibitor XVII (GSI XVII); γ-secretase inhibitor XIX (GSI XIX), benzo[e][1,4]diazepin-3-yl)-butyramide; Y-secretase inhibitor XX (GSI XX), (S,S)-2-[2-(3,5-Difluorophenyl)acetylamino]-N-(5-methyl-6-oxo-6,7-dihydro-5H-dibenzo[b,d]azepin-7-yl)propionamide; γ-secretase inhibitor XXI (GSI XXI), (S,S)-2-[2-(3,5-Difluorophenyl)-acetylamino]-N-(1-methyl-2-oxo-5-phenyl-2-,3-dihydro-1H-benzo[e][1,4]diazepin-3-yl)-propionamide; Gamma40 secretase inhibitor I, N-trans-3,5-Dimethoxycinnamoyl-Ile-leucinal; Gamma40 secretase inhibitor II, N-tert-Butyloxycarbonyl-Gly-Val-Valinal Isovaleryl-V V-Sta-A-Sta-OCH3; MK-0752 (Merck); MRK-003 (Merck); semagacestat/LY450139 (Eli Lilly); RO4929097; PF-03084,014; BMS-708163; MPC-7869 (γ-secretase modifier), YO-01027 (Dibenzazepine), Compound E ([(2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide], available from Alexis Biochemicals), LY411575 (Eli Lilly and Co.), L-685,458 (Sigma-Aldrich), BMS-289948 (4-chloro-N-(2,5-difluorophenyl)-N-((1R)-{4-fluoro-2-[3-(1H-imidazol-1-yl)propyl]phenyl}ethyl)benzenesulfonamide hydrochloride) and BMS-299897 (4-[2-((1R)-1-{[(4-chlorophenyl) sulfonyl]-2,5-difluoroanilino}ethyl)-5-fluorophenyljbutanoic acid) (Bristol Myers Squibb).

In some embodiments, the gamma secretase inhibitor is LY3039478 or is a stereoisomer thereof or is a pharmaceutically acceptable salt or hydrate of the foregoing.

In some embodiments, the gamma secretase inhibitor is a compound of the structure:

Compound 1

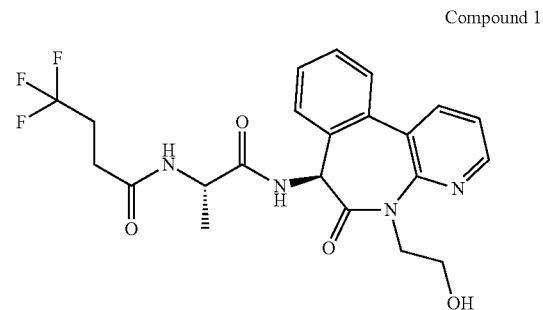 [SMILES: C[C@H](NC(=O)CCC(F)(F)F)C(=O)N[C@@H]1C(=O)N(CCO)c2ncccc2-c2ccccc21]

or a stereoisomer thereof or a pharmaceutically acceptable salt or hydrate of the foregoing.

In some embodiments, Compound 1 is a single stereoisomer as depicted. In some cases, there are two chiral centers giving rise to four stereoisomers. Thus, in some embodiments, reference to Compound 1 also includes racemic mixtures including Compound 1. Specific stereoisomers can be prepared by stereospecific synthesis using enantiomerically pure or enriched starting materials. The specific stereoisomers of either starting materials, intermediates, or racemic mixtures including Compound 1 can be resolved by techniques well known in the art, such as those found in Stereochemistry of Organic Compounds, E. I. Eliel and S. H. Wilen (Wiley 1994) and Enantiomers, Racemates, and Resolutions, J., Jacques, A. Collet, and S. H. Wilen (Wiley 1991), including chromatography on chiral stationary phases, enzymatic resolutions, or fractional crystallization or chromatography of diastereomers formed for that purpose, such as diastereomeric salts.

In some embodiments, the gamma secretase inhibitor is a compound of the structure:

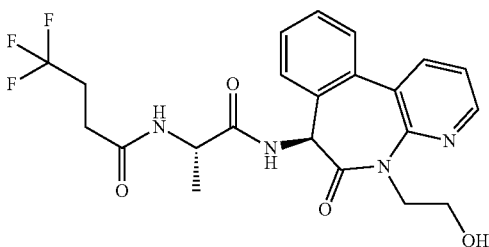 [SMILES: C[C@H](NC(=O)CCC(F)(F)F)C(=O)N[C@@H]1C(=O)N(CCO)c2ncccc2-c2ccccc21]

or a pharmaceutically acceptable salt or hydrate thereof.
In some embodiments, the gamma secretase inhibitor is a compound of the structure:

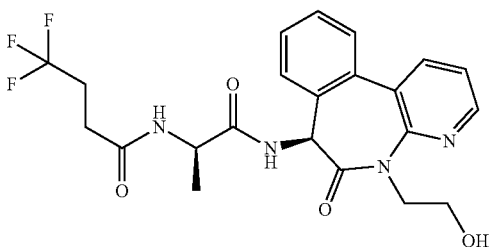 [SMILES: C[C@@H](NC(=O)CCC(F)(F)F)C(=O)N[C@@H]1C(=O)N(CCO)c2ncccc2-c2ccccc21]

or a pharmaceutically acceptable salt or hydrate thereof.
In some embodiments, the gamma secretase inhibitor is a compound of the structure:

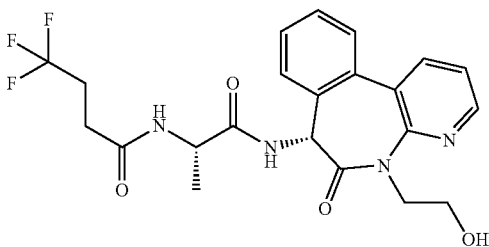 [SMILES: C[C@H](NC(=O)CCC(F)(F)F)C(=O)N[C@H]1C(=O)N(CCO)c2ncccc2-c2ccccc21]

or a pharmaceutically acceptable salt or hydrate thereof.
In some embodiments, the gamma secretase inhibitor is a compound of the structure:

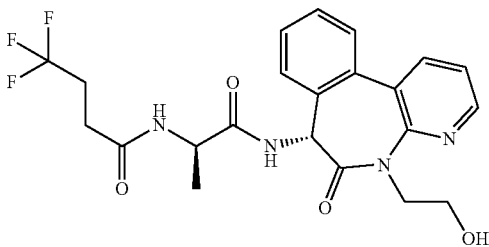 [SMILES: C[C@@H](NC(=O)CCC(F)(F)F)C(=O)N[C@H]1C(=O)N(CCO)c2ncccc2-c2ccccc21]

or a pharmaceutically acceptable salt or hydrate thereof.
In some embodiments, the compound is Compound 1. In some embodiments, Compound 1 is named: 4,4,4-trifluoro-N-[(1S)-2-[[(7S)-5-(2-hydroxyethyl)-6-oxo-7H-pyrido[2,3-d][3]benzazepin-7-yl]amino]-1-methyl-2-oxo-ethyl]butanamide; and may also be named: N-[(1S)-2-[[(7S)-6,7-dihydro-5-(2-hydroxyethyl)-6-oxo-5H-pyrido[3,2-a][3]benzazepin-7-yl]amino]-1-methyl-2-oxoethyl]-4,4,4-trifluorobutanamide; and other names may be used to unambiguously identify Compound 1. In some embodiments, Compound 1 is known as LY3039478. See also published PCT App. No. WO2013/016081 for the synthesis and preparion of Compound 1.

1. Compositions and Formulations

In some embodiments of the combination therapy methods, compositions, combinations, kits and uses provided herein, the combination therapy can be administered in one or more compositions, e.g., a pharmaceutical composition containing a gamma secretase inhibitor, or a pharmaceutically acceptable salt of hydrate thereof.

In some embodiments, the composition, e.g., a pharmaceutical composition containing the gamma secretase inhibitor, or a pharmaceutically acceptable salt of hydrate thereof, can include carriers such as a diluent, adjuvant, excipient, or vehicle with which gamma secretase inhibitor, or a pharmaceutically acceptable salt of hydrate thereof, and/or the cells are administered. Examples of suitable pharmaceutical carriers are described in "Remington's Pharmaceutical Sciences" by E. W. Martin. Such compositions will contain a therapeutically effective amount of the gamma secretase inhibitor, or a pharmaceutically acceptable salt of hydrate thereof, generally in purified form, together with a suitable amount of carrier so as to provide the form for proper administration to the patient. Such pharmaceutical carriers can be sterile liquids, such as water and oils, including those of petroleum, animal, vegetable or synthetic origin, such as peanut oil, soybean oil, mineral oil, and sesame oil. Saline solutions and aqueous dextrose and glycerol solutions also can be employed as liquid carriers, particularly for injectable solutions. The pharmaceutical compositions can contain any one or more of a diluents(s), adjuvant(s), antiadherent(s), binder(s), coating(s), filler(s), flavor(s), color(s), lubricant(s), glidant(s), preservative(s), detergent(s), sorbent(s), emulsifying agent(s), pharmaceutical excipient(s), pH buffering agent(s), or sweetener(s) and a combination thereof. In some embodiments, the pharmaceutical composition can be liquid, solid, a lyophilized powder, in gel form, and/or combination thereof. In some aspects, the choice of carrier is determined in part by the particular inhibitor and/or by the method of administration.

Pharmaceutically acceptable carriers are generally non-toxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG), stabilizers and/or preservatives. The compositions containing gamma secretase inhibitor or a pharmaceutically acceptable salt of hydrate thereof can also be lyophilized.

In some embodiments, the pharmaceutical compositions can be formulated for administration by any route known to those of skill in the art including intramuscular, intravenous, intradermal, intralesional, intraperitoneal injection, subcutaneous, intratumoral, epidural, nasal, oral, vaginal, rectal, topical, local, otic, inhalational, buccal (e.g., sublingual), and transdermal administration or any route. In some embodiments, other modes of administration also are contemplated. In some embodiments, the administration is by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, administration is by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration. In some embodiments, it is administered by multiple bolus administrations, for example, over a period of no more than 3 days, or by continuous infusion administration.

In some embodiments, the administration can be local, topical or systemic depending upon the locus of treatment. In some embodiments local administration to an area in need of treatment can be achieved by, for example, but not limited to, local infusion during surgery, topical application, e.g., in conjunction with a wound dressing after surgery, by injection, by means of a catheter, by means of a suppository, or by means of an implant. In some embodiments, compositions also can be administered with other biologically active agents, either sequentially, intermittently or in the same composition. In some embodiments, administration also can include controlled release systems including controlled release formulations and device controlled release, such as by means of a pump. In some embodiments, the administration is oral.

In some embodiments, pharmaceutically and therapeutically active compounds and derivatives thereof are typically formulated and administered in unit dosage forms or multiple dosage forms. Each unit dose contains a predetermined quantity of therapeutically active compound sufficient to produce the desired therapeutic effect, in association with the required pharmaceutical carrier, vehicle or diluent. In some embodiments, unit dosage forms, include, but are not limited to, tablets, capsules, pills, powders, granules, sterile parenteral solutions or suspensions, and oral solutions or suspensions, and oil water emulsions containing suitable quantities of the compounds or pharmaceutically acceptable derivatives thereof. Unit dose forms can be contained ampoules and syringes or individually packaged tablets or capsules. Unit dose forms can be administered in fractions or multiples thereof. In some embodiments, a multiple dose form is a plurality of identical unit dosage forms packaged in a single container to be administered in segregated unit dose form. Examples of multiple dose forms include vials, bottles of tablets or capsules or bottles of pints or gallons.

2. Dosage Schedule of Gamma Secretase Inhibitor

In some embodiments, the provided combination therapy method involves administering to the subject a therapeutically effective amount of a gamma secretase inhibitor, or a pharmaceutically acceptable salt of hydrate thereof, and the cell therapy, such as a T cell therapy (e.g. CAR-expressing T cells).

In some embodiments, the administration of the gamma secretase inhibitor, or a pharmaceutically acceptable salt of hydrate thereof, is initiated prior to, subsequently to, during, during the course of, simultaneously, near simultaneously, sequentially and/or intermittently with the administration of the cell therapy, such as a T cell therapy (e.g. CAR-expressing T cells). In some embodiments, the method involves initiating the administration of gamma secretase inhibitor, or a pharmaceutically acceptable salt of hydrate thereof, prior to administration of the T cell therapy. In other embodiments, the method involves initiating the administration of the gamma secretase inhibitor, or a pharmaceutically acceptable salt of hydrate thereof, after administration of a cell therapy (e.g., a CAR-expressing T cell therapy). In some embodiments, the dosage schedule comprises initiating the administration of gamma secretase inhibitor, or a pharmaceutically acceptable salt of hydrate thereof, concurrently or simultaneously with the administration of a cell therapy (e.g., a CAR-expressing T cell therapy).

In some embodiments, the gamma secretase inhibitor, or a pharmaceutically acceptable salt of hydrate thereof is administered in a cycle. In some embodiments, the cycle comprises an administration period in which the gamma secretase inhibitor is administered followed by a rest period during which the gamma secretase inhibitor is not administered. In some embodiments, the total number of days of the cycle, e.g. from the beginning of initiating administration of the gamma secretase inhibitor, is greater than or greater than about or is about 1 day, 3, days, 7 days, 14 days, 21 days, 28 days, 30 days, 40 days, 50 days, 60 days or more.

In some embodiments, the initiation of the administration of the gamma secretase inhibitor is carried out in at least one cycle and initiation of administration of the cell therapy (e.g., CAR-expressing T cells) are carried out on the same day, optionally concurrently. In some embodiments, the initiation of the administration of the gamma secretase inhibitor in at least one cycle is prior to initiation of administration of the cell therapy. In some embodiments, the initiation of the administration of the gamma secretase inhibitor in at least one cycle is concurrent with or on the same day as initiation of administration of the cell therapy. In some embodiments, the gamma secretase inhibitor is administered from or from about 0 to 30 days, such as 0 to 15 days, 0 to 6 days, 0 to 96 hours, 0 to 24 hours, 0 to 12 hours, 0 to 6 hours, or 0 to 2 hours, 2 hours to 15 days, 2 hours to 6 days, 2 hours to 96 hours, 2 hours to 24 hours, 2 hours to 12 hours, 2 hours to 6 hours, 6 hours to 30 days, 6 hours to 15 days, 6 hours to 6 days, 6 hours to 96 hours, 6 hours to 24 hours, 6 hours to 12 hours, 12 hours to 30 days, 12 hours to 15 days, 12 hours to 6 days, 12 hours to 96 hours, 12 hours to 24 hours, 24 hours to 30 days, 24 hours to 15 days, 24 hours to 6 days, 24 hours to 96 hours, 96 hours to 30 days, 96 hours to 15 days, 96 hours to 6 days, 6 days to 30 days, 6 days to 15 days, or 15 days to 30 days prior to initiation of the cell therapy (e.g., CAR-expressing T cell therapy). In some aspects, the gamma secretase inhibitor is administered no more than about 96 hours, 72 hours, 48 hours, 24 hours, 12 hours, 6 hours, 2 hours or 1 hour prior to initiation of the T cell therapy.

In some of any such embodiments in which the gamma secretase inhibitor, or a pharmaceutically acceptable salt of hydrate thereof, is given prior to the cell therapy (e.g. T cell therapy, such as CAR-T cell therapy), the administration of the gamma secretase inhibitor, continues at regular intervals until the initiation of the cell therapy and/or for a time after the initiation of the cell therapy.

In some embodiments, the gamma secretase inhibitor is administered, or is further administered, after administration of the cell therapy (e.g. T cell therapy, such as CAR-T cell therapy). In some embodiments, the gamma secretase inhibitor is administered within or within about 1 hours, 2 hours, 6 hours, 12 hours, 24 hours, 48 hours, 96 hours, 4 days, 5 days, 6 days or 7 days, 14 days, 15 days, 21 days, 24 days, 28 days, 30 days, 36 days, 42 days, 60 days, 72 days or 90 days after initiation of administration of the cell therapy (e.g. T cell therapy).

In some embodiments, the provided methods involve continued administration, such as at regular intervals, of the gamma secretase inhibitor after initiation of administration of the cell therapy. For example, the gamma secretase inhibitor is administered at regular intervals of daily, every other day, every third day, three times a week, or once a week for a period of time.

In some embodiments, the gamma secretase inhibitor is administered, such as at regular intervals as described, for up to or up to about 1 day, up to or up to about 2 days, up to or up to about 3 days, up to or up to about 4 days, up to or up to about 5 days, up to or up to about 6 days, up to or up to about 7 days, up to or up to about 12 days, up to or up to about 14 days, up to or up to about 21 days, up to or up to about 24 days, up to or up to about 28 days, up to or up to about 30 days, up to or up to about 35 days, up to or up to about 42 days, up to or up to about 60 days or up to or up to about 90 days, up to or up to about 120 days, up to or up to about 180 days, up to or up to about 240 days, up to or up about 360 days, or up to or up to about 720 days or more after the initiation of administration of the cell therapy (e.g. T cell therapy, such as CAR-T cell therapy).

In some of any such above embodiments, the gamma secretase inhibitor is administered prior to and after initiation of administration of the cell therapy (e.g. T cell therapy, such as CAR-T cell therapy).

In some embodiments, the initiation of the administration of the gamma secretase inhibitor is carried out at or after, optionally immediately after or within 1 to 3 days after: (i) peak or maximum level of the cells of the T cell therapy are detectable in the blood of the subject; (ii) the number of cells of the T cell therapy detectable in the blood, after having been detectable in the blood, is not detectable or is reduced, optionally reduced compared to a preceding time point after administration of the T cell therapy; (iii) the number of cells of the T cell therapy detectable in the blood is decreased by or more than 1.2-fold, 1.5-fold, 2.0-fold, 3.0-fold, 4.0-fold, 5.0-fold, 10-fold or more the peak or maximum number cells of the T cell therapy detectable in the blood of the subject after initiation of administration of the T cell therapy; (iv) at a time after a peak or maximum level of the cells of the T cell therapy are detectable in the blood of the subject, the number of cells of or derived from the T cells detectable in the blood from the subject is less than 10%, less than 5%, less than 1% or less than 0.1% of total peripheral blood mononuclear cells (PBMCs) in the blood of the subject; (v) the subject exhibits disease progression and/or has relapsed following remission after treatment with the T cell therapy; and/or (iv) the subject exhibits increased tumor burden as compared to tumor burden at a time prior to or after administration of the T cells and prior to initiation of administration of the gamma secretase inhibitor.

In some aspects, initiation of administration of the gamma secretase inhibitior is at a time after the subject has relapsed or is suspected to or likely to relapse following administration of the cell therapy (e.g. T cell therapy, such as CAR T-cell therapy). In some cases, the cell therapy is an anti-BCMA CAR-T cell therapy and the gamma secretase inhibitor is administered at a time after the subject has relapsed or is suspected to or likely to relapse following administration of the anti-BCMA CAR-T cell therapy.

In some embodiments, the initiation of the administration of the gamma secretase inhibitor in at least one cycle is after initiation of administration of the cell therapy. In some embodiments, the initiation of the administration of the gamma secretase inhibitor is at least or about at least 1 day, at least or about at least 2 days, at least or about at least 3 days, at least or about at least 4 days, at least or about at least 5 days, at least or about at least 6 days, at least or about at least 7 days, at least or about at least 8 days, at least or about at least 9 days, at least or about at least 10 days, at least or at least about 12 days, at least or about at least 14 days, at least or at least about 15 days, at least or about at least 21 days, at least or at least about 24 days, at least or about at least 28 days, at least or about at least 30 days, at least or about at least 35 days or at least or about at least 42 days, at least or about at least 60 days, or at least or about at least 90 days after initiation of the administration of the cell therapy. In some embodiments, the initiation of the administration of the gamma secretase inhibitor is carried out at least 2 days after, at least 1 week after, at least 2 weeks after, at least 3 weeks after, or at least 4 weeks after, the initiation of the administration of the cell therapy. In some embodiments, the initiation of the administration of the gamma secretase inhibitor is carried out 2 to 28 days or 7 to 21 days after initiation of administration of the cell therapy. In some embodiments, the initiation of the administration of the gamma secretase inhibitor is carried out at a time that is greater than or greater than about 14 days, 15 days, 16 days, 17 days, 18 days, 19, days, 20 days, 21 days, 24 days, or 28 days after initiation of the administration of the cell therapy.

In some embodiments, the gamma secretase inhibitor is administered several times a day, twice a day, daily, every other day, three times a week, twice a week, or once a week after initiation of the cell therapy. In some embodiments, the gamma secretase inhibitor is administered daily. In some embodiments the gamma secretase inhibitor is administered twice a day. In some embodiments, the gamma secretase inhibitor is administered three times a day. In other embodiments, the gamma secretase inhibitor is administered every other day.

In some embodiments, the gamma secretase inhibitor is administered daily. In some embodiments, the gamma secretase inhibitor is administered during the administration period for a plurality of consecutive days, such as for up to about 7, 8, 9, 10, 11, 12, 13, 14, 15, 16, 17, 18, 19, 20, 21, 22, 23, 24, 25, 26, 27, 28, 29, 30, or more than 30 consecutive days. In some embodiments, the gamma secretase inhibitor, is administered for greater than or greater than about 7 consecutive days, greater than or greater than about 14 consecutive days, greater than or greater than about 21 consecutive days, greater than or greater than about 21 consecutive days, or greater than or greater than about 28 consecutive days. In some embodiments, the gamma secretase inhibitor, is administered during the administration period for up to 21 consecutive . . . days. In some embodiments, the gamma secretase inhibitor, is administered during the administration period for up to 21 consecutive days, wherein the cycle comprises greater than 30 days beginning upon initiation of the administration of the gamma secretase inhibitor.

In some embodiments, the gamma secretase inhibitor is administered during the administration period for no more than about 7, 8, 9, 10, 11, 12, 13, 14, 15, 16, 17, 18, 19, 20, 21, 22, 23, 24, 25, 26, 27, 28, 29, 30, or no more than 30 consecutive days. In certain embodiments, the gamma secretase inhibitor is administered once daily for 14 days over a 21 day treatment cycle. In certain embodiments, the gamma secretase inhibitor is administered once daily for 21 days over a 28 day treatment cycle. In some embodiments, the gamma secretase inhibitor is administered during the administration period for no more than 14 consecutive days.

In some embodiments, the gamma secretase inhibitor is administered in a cycle, wherein the cycle comprises the administration of the gamma secretase inhibitor for a plurality of consecutive days followed by a rest period during which the gamma secretase inhibitor is not administered. In some embodiments, the rest period is greater than about 1 day, greater than about 3 consecutive days, greater than about 5 consecutive days, greater than about 7 consecutive days, greater than about 8 consecutive days, greater than about 9 consecutive days, greater than about 10 consecutive days, greater than about 11 consecutive days, greater than about 12 consecutive days, greater than about 13 consecutive days, greater than about 14 consecutive days, greater than about 15 consecutive days, greater than about 16 consecutive days, greater than about 17 consecutive days, greater than about 18 consecutive days, greater than about 19 consecutive days, greater than about 20 consecutive days, or greater than about 21 or more consecutive days. In some embodiments, the rest period is greater than 7 consecutive days, greater than 14 consecutive days, greater than 21 days, or greater than 28 days. In some embodiments, the rest period is greater than about 14 consecutive days. In some embodiments, the cycle of administration of the gamma secretase inhibitor does not contain a rest period.

In some embodiments, the gamma secretase inhibitor is administered in a cycle, wherein the cycle is repeated at least one time. In some embodiments, the gamma secretase inhibitor is administered for at least 2 cycles, at least 3 cycles, at least 4 cycles, at least 5 cycles, at least 6 cycles, at least 7 cycles, at least 8 cycles, at least 9 cycles, at least 10 cycles, at least 11 cycles, or at least 12 cycles. In some embodiments, the gamma secretase inhibitor is administered for 1, 2, 3, 4, 5, 6, 7, 8, 9, 10, 11, 12, 13, 14, 15, 16, 17, 18, 19, 20, 21, 22, 23, or 24 cycles.

In some embodiments, the gamma secretase inhibitor is administered at least six times daily, five times daily, four times daily, three times daily, twice daily, once daily, every other day, every three days, three times a week, twice weekly, once weekly or only one time prior to or subsequently to initiation of administration of the cell therapy. In some embodiments, the gamma secretase inhibitor is administered three times a week. In some embodiments, the administration of the inhibitor is carried out in a treatment cycle that is at least or at least about or 14 days, at least or at least about or 21 days or at least or at least about or 28 days. In some embodiments, the gamma secretase inhibitor is administered in multiple doses in regular intervals prior to, during, during the course of, and/or after the period of administration of the cell therapy. In some embodiments, the gamma secretase inhibitor is administered in one or more doses in regular intervals prior to the administration of the cell therapy. In some embodiments, the gamma secretase inhibitor is administered in one or more doses in regular intervals after the administration of the cell therapy. In some embodiments, one or more of the doses of the gamma secretase inhibitor, can occur simultaneously with the administration of a dose of the cell therapy.

In some embodiments, the dose, frequency, duration, timing and/or order of administration of the gamma secretase inhibitor, is determined, based on particular thresholds or criteria of results of the screening step and/or assessment of treatment outcomes described herein, e.g., those described in Section III herein.

In some embodiments, the method involves administering the cell therapy to a subject that has been previously administered a therapeutically effective amount of the gamma secretase inhibitor. In some embodiments, the gamma secretase inhibitor is administered to a subject before administering a dose of cells expressing a recombinant receptor to the subject. In some embodiments, the treatment with the gamma secretase inhibitor occurs at the same time as the administration of the dose of cells. In some embodiments, the gamma secretase inhibitor is administered after the administration of the dose of cells.

In some embodiments, administration of the gamma secretase inhibitor is carried out for an administration period of 2 to 28 days, such as 7, 8, 9, 10, 11, 12, 13, 14, 15, 16, 17, 18, 19, 20, 21, or more than 21 days. In some embodiments, the gamma secretase inhibitor is administered daily for 7, 8, 9, 10, 11, 12, 13, 14, 15, 16, 17, 18, 19, 20, 21, or more than 21 days. In some embodiments, the gamma secretase inhibitor is administered twice a day for 7, 8, 9, 10, 11, 12, 13, 14, 15, 16, 17, 18, 19, 20, 21, or more than 21 days. In some embodiments, the gamma secretase inhibitor is administered three times a day for 7, 8, 9, 10, 11, 12, 13, 14, 15, 16, 17, 18, 19, 20, 21, or more than 21 days. In some embodiments, the gamma secretase inhibitor is administered every other day for 7, 8, 9, 10, 11, 12, 13, 14, 15, 16, 17, 18, 19, 20, 21, or more than 21 days. In some embodiments, the gamma secretase inhibitor is administered three times a week for 7, 8, 9, 10, 11, 12, 13, 14, 15, 16, 17, 18, 19, 20, 21, or more than 21 days.

In some embodiments, the gamma secretase inhibitor is administered on days 2, 4, 7, 9, 11, 14, 16, and 18 after initiation of administration of the cell therapy (e.g. T cell therapy).

In some embodiments of the methods provided herein, the gamma secretase inhibitor, and the cell therapy are administered simultaneously or near simultaneously.

In some embodiments, gamma secretase inhibitor is administered at a total daily dosage amount of at most or at most about 50 mg/day, 100 mg/day, 150 mg/day, 175 mg/day, 200 mg/day, 250 mg/day, 300 mg/day, 350 mg/day, 400 mg/day, 450 mg/day, 500 mg/day, 600 mg/day, 700 mg/day, 800 mg/day or less. In some embodiments, the gamma secretase inhibitor is administered, or each administration of the inhibitor is independently administered, in an amount of 0.5 mg to 500 mg, 0.5 mg to 250 mg, 0.5 mg to 100 mg, 0.5 mg to 50 mg, 0.5 mg to 25 mg, 0.5 mg to 10 mg, 0.5 mg to 5.0 mg, 0.5 mg to 2.5 mg, 0.5 mg to 1.0 mg, 1.0 mg to 500 mg, 1.0 mg to 250 mg, 1.0 mg to 100 mg, 1.0 mg to 50 mg, 1.0 mg to 25 mg, 1.0 mg to 10 mg, 1.0 mg to 5.0 mg, 1.0 mg to 2.5 mg, 2.5 mg to 500 mg, 2.5 mg to 250 mg, 2.5 mg to 100 mg, 2.5 mg to 50 mg, 2.5 mg to 25 mg, 2.5 mg to 10 mg, 2.5 mg to 5.0 mg, 5.0 mg to 500 mg, 5.0 mg to 250 mg, 5.0 mg to 100 mg, 5.0 mg to 50 mg, 5.0 mg to 25 mg, 5.0 mg to 10 mg, 10 mg to 500 mg, 10 mg to 250 mg, 10 mg to 100 mg, 10 mg to 50 mg, 10 mg to 25 mg, 25 mg to 500 mg, 25 mg to 250 mg, 25 mg to 100 mg, 25 mg to 50 mg, 50 mg to 500 mg, 50 mg to 250 mg, 50 mg to 100 mg, 100 mg to 500 mg, 100 mg to 250 mg or 250 mg to 500 mg. In some embodiments, the inhibitor is administered, or each administration of the inhibitor is independently administered, in an amount that is at least or at least about or is or is about 0.5 mg, 1.0 mg, 2.5 mg, 5.0 mg, 10.0 mg, 25 mg, 50 mg, 100 mg, 250 mg or 500 mg. In some embodiments, the amount is a once daily amount of the gamma secretase inhibitor. Such dosage amounts can be administered at regular intervals as described, such as every other day, every third day, three times a week or once a week for an administration period. In some embodiments, the administration period is 2 to 28 days, such as 7, 8, 9, 10, 11, 12, 13, 14, 15, 16, 17, 18, 19, 20, 21, or more than 21 days.

In some embodiments, the gamma secretase inhibitor is administered at a dosage of from about 1 mg to about 20 mg, e.g., from about 1 mg to about 10 mg, from about 2.5 mg to about 7.5 mg, from about 5 mg to about 15 mg, such as about 5 mg, 10 mg, 15 mg or 20 mg. In some embodiments, the gamma secretase inhibitor is administered at a dose of from at or about 10 µg/kg to at or about 5 mg/kg, such as at or about 50 µg/kg to at or about 2 mg/kg, at or about 50 µg/kg to at or about 1 mg/kg, at or about 50 µg/kg to at or about 500 µg/kg, at or about 50 µg/kg to at or about 250 µg/kg, at or about 100 µg/kg to at or about 200 µg/kg, at or about 50 to at or bout 100 µg/kg, at or about 100 µg/kg to about 2 mg/kg, at or about 100 µg/kg to at or about 1 mg/kg, at or about 100 µg/kg to at or about 500 µg/kg, at or about 100 µg/kg to at or about 250 µg/kg, at or about 100 µg/kg to at or about 200 µg/kg, at or about 100 µg/kg, at or about 200 µg/kg to about 2 mg/kg, at or about 200 µg/kg to at or about 1 mg/kg, at or about 200 µg/kg to at or about at or about 500 µg/kg, at or about 200 µg/kg to at or about 250 µg/kg or at or about 250 µg/kg to at or about 2 mg/kg, at or about 250 µg/kg to at or about 1 mg/kg, at or about 250 µg/kg to at or about at or about 500 µg/kg, In some embodiments, the gamma secretase inhibitor is administered at a dose of from at or about 400 µg/kg to at or about 600 µg/kg, such as at or about 500 µg/kg. In some embodiments, the amount is a once daily amount of the gamma secretase inhibitor. Such dosage amounts can be administered at regular intervals as described, such as every other day, every third day, three times a week or once a week for an administration period. In some embodiments, the administration period is 2 to 28 days, such as 7, 8, 9, 10, 11, 12, 13, 14, 15, 16, 17, 18, 19, 20, 21, or more than 21 days.

In some embodiments, the gamma secretase inhibitor is administered at a total daily dosage amount of at least or at least about 0.1 mg per day, 0.5 mg per day, 1.0 mg per day, 2.5 mg per day, 5 mg per day, 10 mg per day, 25 mg per day, 50 mg per day or 100 mg per day. In some embodiments, the dose of the inhibitor is about 25 mg per day. In particular embodiments, the dose of the inhibitor is or is about 10 mg per day. Such dosage amounts can be administered at regular intervals as described, such as every other day, every third day, three times a week or once a week for an administration period. In some embodiments, the administration period is 2 to 28 days, such as 7, 8, 9, 10, 11, 12, 13, 14, 15, 16, 17, 18, 19, 20, 21, or more than 21 days.

In some embodiments, the gamma secretase inhibitor is administered in an amount greater than or greater than about 1 mg, 2.5 mg, 5 mg, 7.5 mg, 10 mg, 15 mg and less than 25 mg. In some embodiments, the gamma secretase inhibitor is administered in an amount greater than or greater than about 1 mg per day, 2.5 mg per day, 5 mg per day, 7.5 mg per day, 10 mg per day, 15 mg per day and less than 25 mg per day. Such dosage amounts can be administered at regular intervals as described, such as every other day, every third day, three times a week or once a week for an administration period. In some embodiments, the administration period is 2 to 28 days, such as 7, 8, 9, 10, 11, 12, 13, 14, 15, 16, 17, 18, 19, 20, 21, or more than 21 days.

In some embodiments, the gamma secretase inhibitor is administered on days 2, 4, 7, 9, 11, 14, 16, and 18 after initiation of administration of the cell therapy (e.g. T cell therapy).

In some embodiments, dosages, such as daily dosages, are administered in one or more divided doses, such as 2, 3, or 4 doses, or in a single formulation. The gamma secretase inhibitor can be administered alone, in the presence of a pharmaceutically acceptable carrier, or in the presence of other therapeutic agents.

One skilled in the art will recognize that higher or lower dosages of the gamma secretase inhibitor could be used, for example depending on the particular agent and the route of administration. In some embodiments, the gamma secretase inhibitor may be administered alone or in the form of a pharmaceutical composition wherein the compound is in admixture or mixture with one or more pharmaceutically acceptable carriers, excipients, or diluents. In some embodiments, the gamma secretase inhibitor may be administered either systemically or locally to the organ or tissue to be treated. Exemplary routes of administration include, but are not limited to, topical, injection (such as subcutaneous, intramuscular, intradermal, intraperitoneal, intratumoral, and intravenous), oral, sublingual, rectal, transdermal, intranasal, vaginal and inhalation routes. In some embodiments, the route of administration is oral, parenteral, rectal, nasal, topical, or ocular routes, or by inhalation. In some embodiments, the gamma secretase inhibitor is administered orally. In some embodiments, the gamma secretase inhibitor is administered orally in solid dosage forms, such as capsules, tablets and powders, or in liquid dosage forms, such as elixirs, syrups and suspensions.

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. If symptoms have been alleviated to an appropriate level, treatment may cease. Patients may, however, require intermittent treatment on a long-term basis upon any recurrence of symptoms. Patients may also require chronic treatment on a long-term basis.

3. Additional Therapy

In some aspects, the provided methods can further include administering one or more lymphodepleting therapies, such as prior to or simultaneous with initiation of administration of the cell therapy (e.g., T cell therapy). In some embodiments, the lymphodepleting therapy comprises administration of a phosphamide, such as cyclophosphamide. In some embodiments, the lymphodepleting therapy can include administration of fludarabine.

In some aspects, preconditioning subjects with immunodepleting (e.g., lymphodepleting) therapies can improve the effects of adoptive cell therapy (ACT). Preconditioning with lymphodepleting agents, including combinations of cyclosporine and fludarabine, have been effective in improving the efficacy of transferred tumor infiltrating lymphocyte (TIL) cells in cell therapy, including to improve response and/or persistence of the transferred cells. See, e.g., Dudley et al., *Science,* 298, 850-54 (2002); Rosenberg et al., *Clin Cancer Res,* 17 (13): 4550-4557 (2011). Likewise, in the context of CAR+ T cells, several studies have incorporated lymphodepleting agents, most commonly cyclophosphamide, fludarabine, bendamustine, or combinations thereof, sometimes accompanied by low-dose irradiation. See Han et al. *Journal of Hematology & Oncology,* 6:47 (2013); Kochenderfer et al., *Blood,* 119:2709-2720 (2012); Kalos et al., *Sci Transl Med,* 3 (95): 95ra73 (2011); Clinical Trial Study Record Nos.: NCT02315612; NCT01822652.

Such preconditioning can be carried out with the goal of reducing the risk of one or more of various outcomes that could dampen efficacy of the therapy. These include the phenomenon known as "cytokine sink," by which T cells, B cells, NK cells compete with TILs for homeostatic and activating cytokines, such as IL-2, IL-7, and/or IL-15; suppression of TILs by regulatory T cells, NK cells, or other cells of the immune system; impact of negative regulators in the tumor microenvironment. Muranski et al., *Nat Clin Pract Oncol.* December; 3 (12): 668-681 (2006).

Thus in some embodiments, the provided method further involves administering a lymphodepleting therapy to the subject. In some embodiments, the method involves administering the lymphodepleting therapy to the subject prior to the administration of the dose of cells. In some embodiments, the lymphodepleting therapy contains a chemotherapeutic agent such as fludarabine and/or cyclophosphamide. In some embodiments, the administration of the cells and/or the lymphodepleting therapy is carried out via outpatient delivery.

In some embodiments, the methods include administering a preconditioning agent, such as a lymphodepleting or chemotherapeutic agent, such as cyclophosphamide, fludarabine, or combinations thereof, to a subject prior to the administration of the dose of cells. For example, the subject may be administered a preconditioning agent at least 2 days prior, such as at least 3, 4, 5, 6, or 7 days prior, to the first or subsequent dose. In some embodiments, the subject is administered a preconditioning agent no more than 7 days prior, such as no more than 6, 5, 4, 3, or 2 days prior, to the administration of the dose of cells.

In some embodiments, the subject is preconditioned with cyclophosphamide at a dose between or between about 20 mg/kg and 100 mg/kg of body surface area of the subject, such as between or between about 40 mg/kg and 80 mg/kg. In some aspects, the subject is preconditioned with or with about 60 mg/kg of cyclophosphamide. In some embodiments, the fludarabine can be administered in a single dose or can be administered in a plurality of doses, such as given daily, every other day or every three days. In some embodiments, the cyclophosphamide is administered once daily for one or two days. In some embodiments, where the lymphodepleting agent comprises cyclophosphamide, the subject is administered cyclophosphamide at a dose between or between about 100 mg/m$^2$ and 500 mg/m$^2$ body surface area of the subject, such as between or between about 200 mg/m$^2$ and 400 mg/m$^2$, or 250 mg/m$^2$ and 350 mg/m$^2$, inclusive. In some instances, the subject is administered about 300 mg/m$^2$ of cyclophosphamide. In some embodiments, the cyclophosphamide can be administered in a single dose or can be administered in a plurality of doses, such as given daily, every other day or every three days. In some embodiments, cyclophosphamide is administered daily, such as for 1-5 days, for example, for 2 to 4 days. In some instances, the subject is administered about 300 mg/m$^2$ body surface area of the subject, of cyclophosphamide, daily for 3 days, prior to initiation of the cell therapy. In some embodiments, where the lymphodepleting agent comprises fludarabine, the subject is administered fludarabine at a dose between or between about 1 mg/m$^2$ and 100 mg/m$^2$ of body surface area of the subject, such as between or between about 10 mg/m$^2$ and 75 mg/m$^2$, 15 mg/m$^2$ and 50 mg/m$^2$, 20 mg/m$^2$ and 30 mg/m$^2$, 20 mg/m$^2$ and 40 mg/m$^2$, 24 mg/m$^2$ and 35 mg/m$^2$, or 24 mg/m$^2$ and 26 mg/m$^2$, each inclusive. In some instances, the subject is administered about 30 mg/m$^2$ of fludarabine. In some instances, the subject is administered 25 mg/m$^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days or for 3-4 days. In some instances, the subject is administered about 30 mg/m$^2$ body surface area of the subject, of fludarabine, daily for 3 days, prior to initiation of the cell therapy.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 g/m$^2$) of cyclophosphamide and 3 to 5 doses of 25 mg/m$^2$ fludarabine prior to the dose of cells. In some aspects, the subject is administered fludarabine at or about 30 mg/m$^2$ body surface area of the subject, daily, and cyclophosphamide at or about 300 mg/m$^2$ body surface area of the subject, daily, for 3 days.

In one exemplary dosage regime, prior to receiving the first dose, subjects receive a gamma secretase inhibitor 1 day before the administration of cells and a lymphodepleting preconditioning chemotherapy of cyclophosphamide and fludarabine (CY/FLU), which is administered at least two days before the first dose of CAR-expressing cells and generally no more than 7 days before administration of cells. In another exemplary dosage regime, subjects receive the gamma secretase inhibitor concurrently with the administration of cells, such as on the same day. In yet another exemplary dosage regime, subjects receive the gamma secretase inhibitor several days after the administration of cells, such as 7, 8, 9, 10, 11, 12, 13, 14, or more than 14 days after. In some cases, for example, cyclophosphamide is given from 24 to 27 days after the administration of the gamma secretase inhibitor. After preconditioning treatment, subjects are administered the dose of CAR-expressing T cells as described above.

In some embodiments, the administration of the preconditioning agent prior to infusion of the dose of cells improves an outcome of the treatment. For example, in some aspects, preconditioning improves the efficacy of treatment with the dose or increases the persistence of the recombinant receptor-expressing cells (e.g., CAR-expressing cells, such as CAR-expressing T cells) in the subject. In some embodiments, preconditioning treatment increases disease-free survival, such as the percent of subjects that are alive and exhibit no minimal residual or molecularly detectable disease after a given period of time following the dose of cells. In some embodiments, the time to median disease-free survival is increased.

Once the cells are administered to the subject (e.g., human), the biological activity of the engineered cell populations in some aspects is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., *J. Immunotherapy,* 32 (7): 689-702 (2009), and Herman et al. *J. Immunological Methods,* 285 (1): 25-40 (2004). In certain embodiments, the biological activity of the cells also can be measured by assaying expression and/or secretion of certain cytokines, such as CD 107a, IFNγ, IL-2, and TNF. In some aspects the biological activity is measured by assessing clinical outcome, such as reduction in tumor burden or load. In some aspects, toxic outcomes, persistence and/or expansion of the cells, and/or presence or absence of a host immune response, are assessed.

In some embodiments, the administration of the preconditioning agent prior to infusion of the dose of cells improves an outcome of the treatment such as by improving the efficacy of treatment with the dose or increases the persistence of the recombinant receptor-expressing cells (e.g., CAR-expressing cells, such as CAR-expressing T cells) in the subject. Therefore, in some embodiments, the dose of preconditioning agent given in the method which is a combination therapy with the gamma secretase inhibitor and cell therapy is higher than the dose given in the method without the gamma secretase inhibitor.

II. Cell Therapy and Engineering Cells

In some embodiments, the cell therapy (e.g., T cell therapy) for use in accord with the provided combination therapy methods includes administering engineered cells expressing recombinant receptors designed to recognize and/or specifically bind to molecules associated with the disease or condition and result in a response, such as an immune response against such molecules upon binding to such molecules. The receptors may include chimeric receptors, e.g., chimeric antigen receptors (CARs), and other transgenic antigen receptors including transgenic T cell receptors (TCRs).

In some embodiments, the cells contain or are engineered to contain an engineered receptor, e.g., an engineered antigen receptor, such as a chimeric antigen receptor (CAR), or a T cell receptor (TCR). Also provided are populations of such cells, compositions containing such cells and/or enriched for such cells, such as in which cells of a certain type such as T cells or CD8+ or CD4+ cells are enriched or selected. Among the compositions are pharmaceutical compositions and formulations for administration, such as for adoptive cell therapy. Also provided are therapeutic methods for administering the cells and compositions to subjects, e.g., patients.

Thus, in some embodiments, the cells include one or more nucleic acids introduced via genetic engineering, and thereby express recombinant or genetically engineered products of such nucleic acids. In some embodiments, gene transfer is accomplished by first stimulating the cells, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

A. Recombinant Receptors

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors.

In some embodiments of the provided methods and uses, recombinant receptors, including chimeric receptors, such as a chimeric antigen receptors, contain one or more domains that combine a ligand-binding domain (e.g. antibody or antibody fragment) that provides specificity for a desired antigen (e.g., tumor antigen) with intracellular signaling domains. In some embodiments, the intracellular signaling domain is an activating intracellular domain portion, such as a T cell activating domain, providing a primary activation signal. In some embodiments, the intracellular signaling domain contains or additionally contains a costimulatory signaling domain to facilitate effector functions. In some embodiments, chimeric receptors when genetically engineered into immune cells can modulate T cell activity, and, in some cases, can modulate T cell differentiation or homeostasis, thereby resulting in genetically engineered cells with improved longevity, survival and/or persistence in vivo, such as for use in adoptive cell therapy methods.

1. Chimeric Antigen Receptors (CARs)

In some embodiments, engineered cells, such as T cells, are provided that express a CAR with specificity for a particular antigen (or marker or ligand or receptor), such as an antigen expressed on the surface of a particular cell type.

In particular embodiments, the recombinant receptor, such as a chimeric receptor, contains an intracellular signaling region, which includes a cytoplasmic signaling domain (also interchangeably called an intracellular signaling domain), such as a cytoplasmic (intracellular) region capable of inducing a primary activation signal in a T cell, for example, a cytoplasmic signaling domain of a T cell receptor (TCR) component (e.g. a cytoplasmic signaling domain of a zeta chain of a CD3-zeta (CD3ζ) chain or a functional variant or signaling portion thereof) and/or that comprises an immunoreceptor tyrosine-based activation motif (ITAM).

In some embodiments, the chimeric receptor further contains an extracellular ligand-binding domain that specifically binds to a ligand (e.g. antigen) antigen. In some embodiments, the chimeric receptor is a CAR that contains an extracellular antigen-recognition domain that specifically binds to an antigen. In some embodiments, the ligand, such as an antigen, is a protein expressed on the surface of cells. The chimeric receptors, such as CARs, generally include an extracellular antigen binding domain, such as a portion of an antibody molecule, generally a variable heavy ($V_H$) chain region and/or variable light ($V_L$) chain region of the antibody, e.g., an scFv antibody fragment. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061, WO2016/0046724, WO2016/014789, WO2016/090320, WO2016/094304, WO2017/025038, WO2017/173256, U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, 8,479,118, and 9,765,342, and European patent application number EP2537416, and/or those described by Sadelain et al., *Cancer Discov.*, 3 (4): 388-398 (2013); Davila et al., *PLoS ONE* 8 (4): e61338 (2013); Turtle et al., *Curr. Opin. Immunol.*, 24 (5): 633-39 (2012); Wu et al., *Cancer*, 18 (2): 160-75 (2012). In some aspects, the antigen receptors include a CAR as described in U.S. Pat. No. 7,446,190, and those described in International Patent Application Publication No. WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., *Nature Reviews Clinical Oncology*, 10, 267-276 (2013); Wang et al., *J. Immunother.* 35 (9): 689-701 (2012); and Brentjens et al.,

*Sci Transl Med.* 5 (177) (2013). See also WO2014031687, U.S. Pat. Nos. 8,339,645, 7,446,179, US 2013/0149337, U.S. Pat. Nos. 7,446,190, 8,389,282, WO 2016/090320, WO2016090327, WO2010104949A2 and WO2017173256.

In some embodiments, the CAR is constructed with a specificity for a particular antigen (or marker or ligand or receptor), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In some embodiments, the antibody or antigen-binding portion thereof is expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR. In some embodiments, the extracellular antigen binding domain specific for an MHC-peptide complex of a TCR-like CAR is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

In some embodiments, the recombinant receptor, such as a chimeric receptor (e.g. CAR), includes a ligand-binding domain that binds, such as specifically binds, to an antigen (or a ligand or receptor). Among the antigens targeted by the chimeric receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas.

In some embodiments, the antigen targeted by the receptor is a polypeptide. In some embodiments, it is a carbohydrate or other molecule. In some embodiments, the antigen is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the CAR contains an antibody or an antigen-binding fragment (e.g. scFv) that specifically recognizes an antigen, such as an intact antigen, expressed on the surface of a cell.

In some embodiments, the antigen (or a ligand or receptor) is a tumor antigen or cancer marker. In certain embodiments, the antigen is or includes αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPCR5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes BCMA, CD20, CD19, CD22, ROR1, CD45, CD21, CD5, CD33, Igkappa, Iglambda, CD79a, CD79b or CD30.

In some embodiments, the antigen (or a ligand) is or includes orphan tyrosine kinase receptor ROR1, B cell maturation antigen (BCMA), carbonic anhydrase 9 (CAIX), Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30.

Antigens targeted by the receptors in some embodiments include orphan tyrosine kinase receptor ROR1, Her2, L1-CAM, CD19, CD20, CD22, mesothelin, CEA, and hepatitis B surface antigen, anti-folate receptor, CD23, CD24, CD30, CD33, CD38, CD44, EGFR, EGP-2, EGP-4, EPHa2, ErbB2, 3, or 4, FBP, fetal acetylcholine e receptor, GD2, GD3, HMW-MAA, IL-22R-alpha, IL-13R-alpha2, kdr, kappa light chain, Lewis Y, L1-cell adhesion molecule, MAGE-A1, mesothelin, MUC1, MUC16, PSCA, NKG2D Ligands, NY-ESO-1, MART-1, gp100, oncofetal antigen, ROR1, TAG72, VEGF-R2, carcinoembryonic antigen (CEA), prostate specific antigen, PSMA, Her2/neu, estrogen receptor, progesterone receptor, ephrinB2, CD123, c-Met, GD-2, and MAGE A3, CE7, Wilms Tumor 1 (WT-1), a cyclin, such as cyclin A1 (CCNA1), and/or biotinylated molecules, and/or molecules expressed by HIV, HCV, HBV or other pathogens.

In some embodiments, the CAR binds a pathogen-specific or pathogen-expressed antigen. In some embodiments, the CAR is specific for viral antigens (such as HIV, HCV, HBV, etc.), bacterial antigens, and/or parasitic antigens.

In some embodiments, the CAR contains a TCR-like antibody, such as an antibody or an antigen-binding fragment (e.g. scFv) that specifically recognizes an intracellular antigen, such as a tumor-associated antigen, presented on the cell surface as a MHC-peptide complex. In some embodiments, an antibody or antigen-binding portion thereof that recognizes an MHC-peptide complex can be expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR.

Reference to "Major histocompatibility complex" (MHC) refers to a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MHC class I molecules are heterodimers having a membrane spanning a chain, in some cases with three a domains, and a non-covalently associated β2 microglobulin. Generally, MHC class II molecules are composed of two transmembrane glycoproteins, α and β, both of which typically span the membrane. An MHC molecule can include an effective portion of an MHC that contains an antigen binding site or sites for binding a peptide and the sequences necessary for recognition by the appropriate antigen receptor. In some embodiments, MHC class I molecules deliver peptides originating in the cytosol to the cell surface, where a MHC-peptide complex is recognized by T cells, such as generally $CD8^+$ T cells, but in some cases CD4+ T cells. In some embodiments, MHC class II molecules deliver peptides originating in the vesicular system to the cell surface, where they are typically recognized by $CD4^+$ T cells. Generally, MHC molecules are encoded by a group of linked loci, which are collectively termed H-2 in the mouse and human leukocyte antigen (HLA) in humans. Hence, typically human MHC can also be referred to as human leukocyte antigen (HLA).

The term "MHC-peptide complex" or "peptide-MHC complex" or variations thereof, refers to a complex or association of a peptide antigen and an MHC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

In some embodiments, a peptide, such as a peptide antigen or epitope, of a polypeptide can associate with an MHC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the MHC Class II complex. In some embodiments, a peptide has a length of from or from about 8 to 13 amino acids for recognition in the MHC Class I complex. In some embodiments, upon recognition of the peptide in the context of an MHC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, a TCR-like antibody or antigen-binding portion, are known or can be produced by methods known in the art (see e.g. US Published Application Nos. US 2002/0150914; US 2003/0223994; US 2004/0191260; US 2006/0034850; US 2007/00992530; US20090226474; US20090304679; and International PCT Publication No. WO 03/068201).

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFv or other antibody forms can be generated, for example, in which members of the library are mutated at one or more residues of a CDR or CDRs. See e.g. US published application No. US20020150914, US2014/0294841; and Cohen C J. et al. (2003) *J Mol. Recogn.* 16:324-332.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

In certain embodiments, multispecific binding molecules, e.g., multispecific chimeric receptors, such as multispecific CARs, can contain any of the multispecific antibodies, including, e.g. bispecific antibodies, multispecific single-chain antibodies, e.g., diabodies, triabodies, and tetrabodies, tandem di-scFvs, and tandem tri-scFvs.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" or "antigen-binding fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; variable heavy chain ($V_H$) regions, single-chain antibody molecules such as scFvs and single-domain $V_H$ single antibodies; and multispecific antibodies formed from antibody fragments. In some embodiments, the antigen-binding domain in the provided CARs is or comprises an antibody fragment comprising a variable heavy chain ($V_H$) and a variable light chain ($V_L$) region. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ Or $V_L$ domain from an antibody that binds the antigen to screen a library of complementary $V_L$ or $V_H$ domains, respectively. Sec, e.g., Portolano et al., J. Immunol. 150: 880-887 (1993); Clarkson et al., Nature 352:624-628 (1991).

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273, 927-948 ("Chothia" numbering scheme); MacCallum et al., J. Mol. Biol. 262: 732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January;27 (1): 55-77 ("IMGT" numbering scheme); Honegger A and Plückthun A, "Yet another numbering scheme for immunoglobulin variable domains: an automatic modeling and analysis tool," J Mol Biol, 2001 Jun. 8;309 (3): 657-70, ("Aho" numbering scheme); and Martin et al., "Modeling antibody hypervariable loops: a combined algorithm," PNAS, 1989, 86 (23): 9268-9272, ("AbM" numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The AbM scheme is a compromise between Kabat and Chothia definitions based on that used by Oxford Molecular's AbM antibody modeling software.

Table 1, below, lists exemplary position boundaries of CDR-L1, CDR-L2, CDR-L3 and CDR-H1, CDR-H2, CDR-H3 as identified by Kabat, Chothia, AbM, and Contact schemes, respectively. For CDR-H1, residue numbering is listed using both the Kabat and Chothia numbering schemes. FRs are located between CDRs, for example, with FR-L1 located before CDR-L1, FR-L2 located between CDR-L1 and CDR-L2, FR-L3 located between CDR-L2 and CDR-L3 and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1

Boundaries of CDRs according to various numbering schemes.

| CDR | Kabat | Chothia | AbM | Contact |
|---|---|---|---|---|
| CDR-L1 | L24--L34 | L24--L34 | L24--L34 | L30--L36 |
| CDR-L2 | L50--L56 | L50--L56 | L50--L56 | L46--L55 |
| CDR-L3 | L89--L97 | L89--L97 | L89--L97 | L89--L96 |
| CDR-H1 (Kabat Numbering[1]) | H31--H35B | H26--H32 . . . 34 | H26--H35B | H30--H35B |
| CDR-H1 (Chothia Numbering[2]) | H31--H35 | H26--H32 | H26--H35 | H30--H35 |
| CDR-H2 | H50--H65 | H52--H56 | H50--H58 | H47--H58 |
| CDR-H3 | H95--H102 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

Thus, unless otherwise specified, a "CDR" or "complementary determining region," or individual specified CDRs (e.g., CDR-H1, CDR-H2, CDR-H3), of a given antibody or region thereof, such as a variable region thereof, should be understood to encompass a (or the specific) complementary determining region as defined by any of the aforementioned schemes, or other known schemes. For example, where it is stated that a particular CDR (e.g., a CDR-H3) contains the amino acid sequence of a corresponding CDR in a given $V_H$ or $V_L$ region amino acid sequence, it is understood that such a CDR has a sequence of the corresponding CDR (e.g., CDR-H3) within the variable region, as defined by any of the aforementioned schemes, or other known schemes. In some embodiments, specific CDR sequences are specified. Exemplary CDR sequences of provided antibodies are described using various numbering schemes, although it is understood that a provided antibody can include CDRs as described according to any of the other aforementioned numbering schemes or other numbering schemes known to a skilled artisan.

Likewise, unless otherwise specified, a FR or individual specified FR(s) (e.g., FR-H1, FR-H2, FR-H3, FR-H4), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, AbM or Contact method, or other known schemes. In other cases, the particular amino acid sequence of a CDR or FR is given.

Single-domain antibodies (sdAbs) are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known in the art.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Thus, in some embodiments, the chimeric antigen receptor, including TCR-like CARs, includes an extracellular portion containing an antibody or antibody fragment. In some embodiments, the antibody or fragment includes an scFv. In some embodiments, the antibody or antigen-binding fragment thereof is a single-chain antibody fragment, such as a single chain variable fragment (scFv) or a diabody or a single domain antibody (sdAb). In some embodiments, the antibody or antigen-binding fragment is a single domain antibody comprising only the $V_H$ region. In some embodiments, the antibody or antigen binding fragment is an scFv comprising a heavy chain variable ($V_H$) region and a light chain variable ($V_L$) region.

In some embodiments, the antibody is an antigen-binding fragment, such as a scFv, that includes one or more linkers joining two antibody domains or regions, such as a heavy chain variable ($V_H$) region and a light chain variable ($V_L$) region. The linker typically is a peptide linker, e.g., a flexible and/or soluble peptide linker. Among the linkers are those rich in glycine and serine and/or in some cases threonine. In some embodiments, the linkers further include charged residues such as lysine and/or glutamate, which can improve solubility. In some embodiments, the linkers further include one or more proline. In some aspects, the linkers rich in glycine and serine (and/or threonine) include at least 80%, 85%, 90%, 91%, 92%, 93%, 94%, 95%, 96%, 97%, 98%, or 99% such amino acid(s). In some embodiments, they include at least at or about 50%, 55%, 60%, 70%, or 75%, glycine, serine, and/or threonine. In some embodiments, the linker is comprised substantially entirely of glycine, serine, and/or threonine. The linkers generally are between about 5 and about 50 amino acids in length, typically between at or about 10 and at or about 30, e.g., 10, 11, 12, 13, 14, 15, 16, 17, 18, 19, 20, 21, 22, 23, 24, 25, 26, 27, 28, 29, or 30, and in some examples between 10 and 25 amino acids in length. Exemplary linkers include linkers having various numbers of repeats of the sequence GGGGS (4GS; SEQ ID NO:26) or GGGS (3GS; SEQ ID NO:27), such as between 2, 3, 4, and 5 repeats of such a sequence. Exemplary linkers include those having or consisting of an sequence set forth in SEQ ID NO:28 (GGGGSGGGGSGGGGS), SEQ ID NO:29 (GSTSGSGKPGSGEGSTKG), SEQ ID NO: 30 (SRGGGGSGGGGSGGGGSLEMA), or SEQ ID NO: 38 (ASGGGGSGGRASGGGGS).

In some embodiments, the CAR is an anti-BCMA CAR that is specific for BCMA, e.g. human BCMA. Chimeric antigen receptors containing anti-BCMA antibodies, including mouse anti-human BCMA antibodies and human anti-human BCMA antibodies, and cells expressing such chimeric receptors have been previously described. See Carpenter et al., Clin Cancer Res., 2013, 19 (8): 2048-2060, U.S. Pat. No. 9,765,342, WO 2016/090320, WO2016090327, WO2010104949A2, WO2016/0046724, WO2016/014789, WO2016/090320, WO2016/094304, WO2017/025038, and WO2017173256. In some embodiments, the anti-BCMA CAR contains an antigen-binding domain, such as an scFv, containing a variable heavy (VH) and/or a variable light (VL) region derived from an antibody described in WO 2016/090320 or WO2016090327. In some embodiments, the anti-BCMA CAR contains an antigen-binding domain, such as an scFv, containing a variable heavy ($V_H$) and/or a variable light ($V_L$) region derived from an antibody described in WO 2016/090320 or WO2016090327. In some embodiments, the antigen-binding domain is an antibody fragment containing a variable heavy chain ($V_H$) and a variable light chain ($V_L$) region. In some aspects, the $V_H$ region is or includes an amino acid sequence having at least 90%, 91%, 92%, 93%, 94%, 95%, 96%, 97%, 98% or 99% sequence identity to the $V_H$ region amino acid sequence set forth in any of SEQ ID NOs: 18, 20, 22, 24, 32, 34, 36, 41, 43, 45, 47, 49, 51, 53, 55, 57, 59, 61, 63, 65, 67, 69, 71, 73, 75, 145, 147, 149 and 151; and/or the $V_L$ region is or includes an amino acid sequence having at least 90%, 91%, 92%, 93%, 94%, 95%, 96%, 97%, 98%, or 99% sequence identity to the $V_L$ region amino acid sequence set forth in any of SEQ ID NOs: 19, 21, 23, 25, 33, 35, 37, 42, 44, 46, 48, 50, 52, 54, 56, 58, 60, 62, 64, 66, 68, 70, 72, 74, 76, 146, 148, 150 and 152.

In some embodiments, the antigen-binding domain, such as an scFv, contains a $V_H$ set forth in SEQ ID NO: 18 and a $V_L$ set forth in SEQ ID NO:19. In some embodiments, the antigen-binding domain, such as an scFv, contains a $V_H$ set forth in SEQ ID NO: 20 and a $V_L$ set forth in SEQ ID NO:21. In some embodiments, the antigen-binding domain, such as an scFv, contains a $V_H$ set forth in SEQ ID NO: 22 and a $V_L$ set forth in SEQ ID NO:23. In some embodiments, the antigen-binding domain, such as an scFv, contains a $V_H$ set forth in SEQ ID NO: 24 and a $V_L$ set forth in SEQ ID NO:25. In some embodiment the antigen-binding domain, such as an scFv, contains a $V_H$ set forth in SEQ ID NO: 32 and a $V_L$ set forth in SEQ ID NO:33. In some embodiments, the antigen-binding domain, such as an scFv, contains a $V_H$ set forth in SEQ ID NO:34 and a $V_L$ set forth in SEQ ID NO:35. In some embodiments, the antigen-binding domain, such as an scFv, contains a $V_H$ set forth in SEQ ID NO: 36 and a $V_L$ set forth in SEQ ID NO:37. In some embodiments, the antigen-binding domain, such as an scFv, contains a $V_H$ set forth in SEQ ID NO: 41 and a $V_L$ set forth in SEQ ID NO: 42. In some embodiments, the antigen-binding domain, such as an scFv, contains a $V_H$ set forth in SEQ ID NO: 43 and a $V_L$ set forth in SEQ ID NO: 44. In some embodiments, the antigen-binding domain, such as an scFv, contains a $V_H$ set forth in SEQ ID NO: 45 and a $V_L$ set forth in SEQ ID NO: 46. In some embodiments, the antigen-binding domain, such as an scFv, contains a $V_H$ set forth in SEQ ID NO: 47 and a $V_L$ set forth in SEQ ID NO: 48. In some embodiments, the antigen-binding domain, such as an scFv, contains a $V_H$ set forth in SEQ ID NO: 49 and a $V_L$ set forth in SEQ ID NO: 50. In some embodiments, the antigen-binding domain, such as an scFv, contains a $V_H$ set forth in SEQ ID NO: 51 and a $V_L$ set forth in SEQ ID NO: 52. In some embodiments, the antigen-binding domain, such as an scFv, contains a $V_H$ set forth in SEQ ID NO: 53 and a $V_L$ set forth in SEQ ID NO: 54. In some embodiments, the antigen-binding domain, such as an scFv, contains a $V_H$ set forth in SEQ ID NO: 55 and a $V_L$ set forth in SEQ ID NO: 56. In some embodiments, the antigen-binding domain, such as an scFv, contains a $V_H$ set forth in SEQ ID NO: 57 and a $V_L$ set forth in SEQ ID NO: 58. In some embodiments, the antigen-binding domain, such as an scFv, contains a Vu set forth in SEQ ID NO: 59 and a $V_L$ set forth in SEQ ID NO: 60. In some embodiments, the antigen-binding domain, such as an scFv, contains a $V_H$ set forth in SEQ ID NO: 61 and a $V_L$ set forth in SEQ ID NO: 62. In some embodiments, the antigen-binding domain, such as an scFv, contains a $V_H$ set forth in SEQ ID NO: 63 and a $V_L$ set forth in SEQ ID NO: 64. In some embodiments, the antigen-binding domain, such as an scFv, contains a $V_H$ set forth in SEQ ID NO: 65 and a $V_L$ set forth in SEQ ID NO: 66. In some embodiments, the antigen-binding domain, such as an scFv, contains a $V_H$ set forth in SEQ ID NO: 67 and a $V_L$ set forth in SEQ ID NO: 68. In some embodiments, the antigen-binding domain, such as an scFv, contains a $V_H$ set forth in SEQ ID NO: 69 and a $V_L$ set forth in SEQ ID NO: 70. In some embodiments, the antigen-binding domain, such as an scFv, contains a $V_H$ set forth in SEQ ID NO: 71 and a $V_L$ set forth in SEQ ID NO: 72. In some embodiments, the antigen-binding domain, such as an scFv, contains a $V_H$ set forth in SEQ ID NO: 73 and a $V_L$ set forth in SEQ ID NO: 74. In some embodiments, the antigen-binding domain, such as an scFv, contains a $V_H$ set forth in SEQ ID NO: 75 and a $V_L$ set forth in SEQ ID NO: 76. In some embodiments, the antigen-binding domain, such as an scFv, contains a $V_H$ set forth in SEQ ID NO: 145 and a $V_L$ set forth in SEQ ID NO: 146. In some embodiments, the antigen-binding domain, such as an scFv, contains a $V_H$ set forth in SEQ ID NO: 147 and a $V_L$ set forth in SEQ ID NO: 148. In some embodiments, the antigen-binding domain, such as an scFv, contains a $V_H$ set forth in SEQ ID NO: 149 and a $V_L$ set forth in SEQ ID NO: 150. In some embodiments, the antigen-binding domain, such as an scFv, contains a $V_H$ set forth in SEQ ID NO: 151 and a $V_L$ set forth in SEQ ID NO: 152. In some embodiments, the $V_H$ or $V_L$ has a sequence of amino acids that exhibits at least 85%, 86%, 87%, 88%, 89%, 90%, 91%, 92%, 93%, 94%, 95%, 96%, 97%, 98%, 99% or more sequence identity to any of the foregoing $V_H$ or $V_L$ sequences, and retains binding to BCMA. In some embodiments, the $V_H$ region is amino-terminal to the $V_L$ region. In some embodiments, the $V_H$ region is carboxy-terminal to the $V_L$ region. In some embodiments, the variable heavy and variable light chains are connected by a linker. In some embodiments, the linker is set forth in SEQ ID NO: 28, 29, 30, or 38.

Among a provided anti-BCMA CAR is a CAR in which the antibody or antigen-binding fragment contains a $V_H$ region comprising the sequence set forth in SEQ ID NO: 24 or an amino acid sequence having at least at or about 90%, at or about 91%, at or about 92%, at or about 93%, at or about 94%, at or about 95%, at or about 96%, at or about 97%, at or about 98%, at or about 99% identity to SEQ ID NO:24; and contains a $V_L$ region comprising the sequence set forth in SEQ ID NO:25 or an amino acid sequence having at least at or about 90%, at or about 91%, at or about 92%, at or about 93%, at or about 94%, at or about 95%, at or about 96%, at or about 97%, at or about 98%, or at or about 99% identity to SEQ ID NO:25. In some embodiments, the antibody or antigen-binding fragment of the provided CAR contains a $V_H$ region that has a CDRH1, a CDRH2 and a CDRH3 comprising the amino acid sequence of SEQ ID NOS: 173, 174 and 175, respectively and a $V_L$ region that has a CDRL1, a CDRL2 and a CDRL3 comprising the amino acid sequence of SEQ ID NOS: 183, 184 and 185, respectively. In some embodiments, the antibody or antigen-binding fragment of the provided CAR contains a $V_H$ region that has a CDRH1, a CDRH2 and a CDRH3 comprising the amino acid sequence of SEQ ID NOS: 176, 177 and 175, respectively and a $V_L$ region that has a CDRL1, a CDRL2 and a CDRL3 comprising the amino acid sequence of SEQ ID NOS: 183, 184 and 185, respectively. In some embodiments, the antibody or antigen-binding fragment of the provided CAR contains a $V_H$ region that has a CDRH1, a CDRH2 and a CDRH3 comprising the amino acid sequence of SEQ ID NOS: 178, 179 and 175, respectively and a $V_L$ region that has a CDRL1, a CDRL2 and a CDRL3 comprising the amino acid sequence of SEQ ID NOS: 183, 184 and 185, respectively. In some embodiments, the antibody or antigen-binding fragment of the provided CAR contains a $V_H$ region that has a CDRH1, a CDRH2 and a CDRH3 comprising the amino acid sequence of SEQ ID NOS: 180, 181 and 182, respectively and a $V_L$ region that has a CDRL1, a CDRL2 and a CDRL3 comprising the amino acid sequence of SEQ ID NOS: 186, 187 and 185, respectively. In some embodiments, the $V_H$ region comprises the sequence set forth in SEQ ID NO:24 and the $V_L$ region comprises the sequence set forth in SEQ ID NO:25. In some embodiments, the antibody or antigen-binding fragment is a single-chain antibody fragment, such as an scFv. In some embodiments, the scFv comprises the sequence of amino acids set forth in SEQ ID NO: 188 or a sequence of amino acids at least at or about 90%, at or about 91%, at or about 92%, at or about 93%, at or about 94%, at or about 95%, at or about 96%, at or about 97%, at or about 98%, or at or about 99% identity to SEQ ID NO: 188. In some embodiments, the anti-BCMA CAR has the sequence of amino acids set forth in SEQ NO: 124 or a sequence of amino acids at least at or about 90%, at or about 91%, at or about 92%, at or about 93%, at or about 94%, at or about 95%, at or about 96%, at or about 97%, at or about 98%, or at or about 99% identity to SEQ ID NO:124. In some embodiments, the anti-BCMA CAR has the sequence of amino acids set forth in SEQ NO: 125 or a sequence of amino acids at least at or about 90%, at or about 91%, at or about 92%, at or about 93%, at or about 94%, at or about 95%, at or about 96%, at or about 97%, at or about 98%, or at or about 99% identity to SEQ ID NO: 125.

In some embodiments, the antigen-binding domain comprises an sdAb. In some embodiments, the antigen-binding domain contains the sequence set forth by SEQ ID NO:77. In some embodiments, the antigen-binding domain comprises a sequence at least or about 50, 60, 70, 80, 85, 90, 95, 96, 97, 98, 99, or 100% identical to the sequence set forth by SEQ ID NO:77.

In some embodiments, among such antibodies or antigen-binding domains in the provided CARs are antibodies capable of binding BCMA protein, such as human BCMA protein, with at least a certain affinity, as measured by any of a number of known methods. In some embodiments, the affinity is represented by an equilibrium dissociation constant ($K_D$); in some embodiments, the affinity is represented by EC50.

In some embodiments, among such antibodies or antigen-binding domains in the provided CARs, are antibodies or antigen-binding domains or CARs in which binding to soluble or shed BCMA protein is less than or at or about 10% of the binding of the antibody to membrane-bound BCMA protein.

A variety of assays are known for assessing binding affinity and/or determining whether a binding molecule (e.g., an antibody or fragment thereof) specifically binds to a particular ligand (e.g., an antigen, such as a BCMA protein). It is within the level of a skilled artisan to determine the binding affinity of a binding molecule, e.g., an antibody, for an antigen, e.g., BCMA. For example, in some embodiments, a BIAcore® instrument can be used to determine the binding kinetics and constants of a complex between two proteins (e.g., an antibody or fragment thereof, and an antigen, such as a BCMA cell surface protein, soluble BCMA protein), using surface plasmon resonance (SPR) analysis (see, e.g., Scatchard et al., Ann. N.Y. Acad. Sci. 51:660, 1949; Wilson, Science 295:2103, 2002; Wolff et al., Cancer Res. 53:2560, 1993; and U.S. Pat. Nos. 5,283,173, 5,468,614, or the equivalent).

SPR measures changes in the concentration of molecules at a sensor surface as molecules bind to or dissociate from the surface. The change in the SPR signal is directly proportional to the change in mass concentration close to the surface, thereby allowing measurement of binding kinetics between two molecules. The dissociation constant for the complex can be determined by monitoring changes in the refractive index with respect to time as buffer is passed over the chip. Other suitable assays for measuring the binding of one protein to another include, for example, immunoassays such as enzyme linked immunosorbent assays (ELISA) and radioimmunoassays (RIA), or determination of binding by monitoring the change in the spectroscopic or optical properties of the proteins through fluorescence, UV absorption, circular dichroism, or nuclear magnetic resonance (NMR). Other exemplary assays include, but are not limited to, Western blot, ELISA, analytical ultracentrifugation, spectroscopy, flow cytometry, sequencing and other methods for detection of expressed polynucleotides or binding of proteins.

In some embodiments, the binding molecule, e.g., antibody or fragment thereof or antigen-binding domain of a CAR, binds, such as specifically binds, to an antigen, e.g., a cell surface BCMA protein or soluble BCMA protein or an epitope therein, with an affinity or $K_A$ (i.e., an equilibrium association constant of a particular binding interaction with units of 1/M; equal to the ratio of the on-rate [$k_{on}$ or $k_a$] to the off-rate [$k_{off}$ or $k_d$] for this association reaction, assuming bimolecular interaction) equal to or greater than $10^5$ $M^{-1}$. In some embodiments, the antibody or fragment thereof or antigen-binding domain of a CAR exhibits a binding affinity for the peptide epitope with a $K_D$ (i.e., an equilibrium dissociation constant of a particular binding interaction with units of M; equal to the ratio of the off-rate [$k_{off}$ or $k_d$] to the on-rate [$k_{on}$ or $k_a$] for this association reaction, assuming bimolecular interaction) of equal to or less than $10^{-5}$ M. For example, the equilibrium dissociation constant $K_D$ ranges from $10^{-5}$ M to $10^{-13}$ M, such as $10^{-7}$ M to $10^{-11}$ M, $10^{-8}$ M to $10^{-10}$ M, or 10-9 M to 10-10 M. The on-rate (association rate constant; $k_{on}$ or $k_a$; units of 1/Ms) and the off-rate (dissociation rate constant; $k_{off}$ or $k_d$; units of 1/s) can be determined using any of the assay methods known in the art, for example, surface plasmon resonance (SPR).

In some embodiments, the binding affinity (EC50) and/or the dissociation constant of the antibody (e.g. antigen-binding fragment) or antigen-binding domain of a CAR to a BCMA protein, such as human BCMA protein, is from or from about 0.01 nM to about 500 nM, from or from about 0.01 nM to about 400 nM, from or from about 0.01 nM to about 100 nM, from or from about 0.01 nM to about 50 nM, from or from about 0.01 nM to about 10 nM, from or from about 0.01 nM to about 1 nM, from or from about 0.01 nM to about 0.1 nM, is from or from about 0.1 nM to about 500 nM, from or from about 0.1 nM to about 400 nM, from or from about 0.1 nM to about 100 nM, from or from about 0.1 nM to about 50 nM, from or from about 0.1 nM to about 10 nM, from or from about 0.1 nM to about 1 nM, from or from about 0.5 nM to about 200 nM, from or from about 1 nM to about 500 nM, from or from about 1 nM to about 100 nM, from or from about 1 nM to about 50 nM, from or from about 1 nM to about 10 nM, from or from about 2 nM to about 50 nM, from or from about 10 nM to about 500 nM, from or from about 10 nM to about 100 nM, from or from about 10 nM to about 50 nM, from or from about 50 nM to about 500 nM, from or from about 50 nM to about 100 nM or from or from about 100 nM to about 500 nM. In certain embodiments, the binding affinity (EC50) and/or the equilibrium dissociation constant, $K_D$, of the antibody to a BCMA protein, such as human BCMA protein, is at or less than or about 400 nM, 300 nM, 200 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less. In some embodiments, the antibodies bind to a BCMA protein, such as human BCMA protein, with a sub-nanomolar binding affinity, for example, with a binding affinity less than about 1 nM, such as less than about 0.9 nM, about 0.8 nM, about 0.7 nM, about 0.6 nM, about 0.5 nM, about 0.4 nM, about 0.3 nM, about 0.2 nM or about 0.1 nM or less.

In some embodiments, the binding affinity may be classified as high affinity or as low affinity. In some cases, the binding molecule (e.g. antibody or fragment thereof) or antigen-binding domain of a CAR that exhibits low to moderate affinity binding exhibits a $K_A$ of up to $10^7$ M$^{-1}$, up to $10^6$ M$^{-1}$, up to $10^5$ M$^{-1}$. In some cases, a binding molecule (e.g. antibody or fragment thereof) that exhibits high affinity binding to a particular epitope interacts with such epitope with a $K_A$ of at least $10^7$ M$^{-1}$, at least $10^8$ M$^{-1}$, at least $10^9$ M$^{-1}$, at least $10^{10}$ M$^{-1}$, at least $10^{11}$ M$^{-1}$, at least $10^{12}$ M$^{-1}$, or at least $10^{13}$ M$^{-1}$. In some embodiments, the binding affinity (EC50) and/or the equilibrium dissociation constant, $K_D$, of the binding molecule, e.g., anti-BCMA antibody or fragment thereof or antigen-binding domain of a CAR, to a BCMA protein, is from or from about 0.01 nM to about 1 μM, 0.1 nM to 1 μM, 1 nM to 1 μM, 1 nM to 500 nM, 1 nM to 100 nM, 1 nM to 50 nM, 1 nM to 10 nM, 10 nM to 500 nM, 10 nM to 100 nM, 10 nM to 50 nM, 50 nM to 500 nM, 50 nM to 100 nM or 100 nM to 500 nM. In certain embodiments, the binding affinity (EC50) and/or the dissociation constant of the equilibrium dissociation constant, $K_D$, of the binding molecule, e.g., anti-BCMA antibody or fragment thereof or antigen-binding domain of a CAR, to a BCMA protein, is at or about or less than at or about 1 μM, 500 nM, 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM or less. The degree of affinity of a particular antibody can be compared with the affinity of a known antibody, such as a reference antibody (e.g., anti-BCMA reference antibody).

In some embodiments, the binding affinity of the anti-BCMA antibody or antigen-binding domain of a CAR, for different form or topological type of antigens, e.g., soluble or shed BCMA protein compared to the binding affinity to a membrane-bound BCMA, to determine the preferential binding or relative affinity for a particular form or topological type. For example, in some aspects, an anti-BCMA antibodies or antigen-binding domain of a CAR can exhibit preferential binding to membrane-bound BCMA as compared to soluble or shed BCMA and/or exhibit greater binding affinity for, membrane-bound BCMA compared to soluble or shed BCMA. In some embodiments, the equilibrium dissociation constant, $K_D$, for different form or topological type of BCMA proteins, can be compared to determine preferential binding or relative binding affinity. In some embodiments, the preferential binding or relative affinity to a membrane-bound BCMA compared to soluble or shed BCMA can be high. For example, in some cases, the ratio of Kp for soluble or shed BCMA and the $K_D$ for membrane-bound BCMA is more than 10, 15, 20, 25, 30, 40, 50, 60, 70, 80, 90, 100, 200, 500, 1000, 2000 or more and the antibody or antigen-binding domain preferentially binds or has higher binding affinity for membrane-bound BCMA. In some cases, the ratio of $K_A$ for membrane-bound BCMA and the $K_A$ for soluble or shed BCMA is more than 10, 15, 20, 25, 30, 40, 50, 60, 70, 80, 90, 100, 200, 500, 1000, 2000 or more and the antibody or antigen-binding domain preferentially binds or has higher binding affinity for membrane-bound BCMA. In some cases, the antibody or antigen-binding domain of CAR binds soluble or shed BCMA and membrane-bound BCMA to a similar degree, e.g., the ratio of $K_D$ for soluble BCMA and KD for membrane-bound BCMA is or is about 1. In some cases, the antibody or antigen-binding domain of CAR binds soluble or shed BCMA and membrane-bound BCMA to a similar degree, e.g., the ratio of $K_A$ for soluble BCMA and $K_A$ for membrane-bound BCMA is or is about 1. The degree of preferential binding or relative affinity for membrane-bound BCMA or soluble or shed BCMA can be compared with that of a known antibody, such as a reference antibody (e.g., reference anti-BCMA CAR). In some embodiments, the reference antibody (e.g., reference anti-BCMA CAR) binds to membrane-bound and soluble or shed BCMA protein.

In some aspects, the chimeric antigen receptor includes an extracellular portion containing the antibody or fragment and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

In some embodiments, the antibody portion of the recombinant receptor, e.g., CAR, further includes a spacer, which may be or include at least a portion of an immunoglobulin constant region or variant or modified version thereof, such as a hinge region, e.g., an IgG4 hinge region, an IgG1 hinge region, a CHI/CL, and/or Fc region. In some embodiments, the recombinant receptor further comprises a spacer and/or a hinge region. In some embodiments, the constant region or portion is of a human IgG, such as IgG4 or IgG1. In some aspects, the portion of the constant region serves as a spacer region between the antigen-recognition component, e.g., scFv, and transmembrane domain.

The spacer can be of a length that provides for increased responsiveness of the cell following antigen binding, as compared to in the absence of the spacer. Exemplary spacers, e.g., hinge regions, include those described in international patent application publication number WO2014031687. In some examples, the spacer is or is about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. In some embodiments, the spacer is a spacer having at least a particular length, such as having a length that is at least 100 amino acids, such as at least 110, 125, 130, 135, 140, 145, 150, 160, 170, 180, 190, 200, 210, 220, 230, 240, or 250 amino acids in length. Exemplary spacers include IgG4 hinge alone, IgG4 hinge linked to $C_H2$ and $C_H3$ domains, or IgG4 hinge linked to the $C_H3$ domain. Exemplary spacers include IgG4 hinge alone, IgG4 hinge linked to $C_H2$ and $C_H3$ domains, or IgG4 hinge linked to the $C_H3$ domain. Exemplary spacers include IgG4 hinge alone, IgG4 hinge linked to $C_H2$ and $C_H3$ domains, or IgG4 hinge linked to the $C_H3$ domain. Exemplary spacers include, but are not limited to, those described in Hudecek et al., *Clin. Cancer Res.*, 19:3153 (2013), Hudecek et al. (2015) *Cancer Immunol Res.* 3 (2): 125-135, international patent application publication number WO2014031687, U.S. Pat. No. 8,822,647 or published app. No. US2014/0271635. In some embodiments, the spacer includes a sequence of an immunoglobulin hinge region, a $C_H2$ and $C_H3$ region. In some embodiments, one of more of the hinge, $C_H2$ and $C_H3$ is derived all or in part from IgG4 or IgG2. In some cases, the hinge, $C_H2$ and $C_H3$ is derived from IgG4. In some aspects, one or more of the hinge, $C_H2$ and $C_H3$ is chimeric and contains sequence derived from IgG4 and IgG2. In some examples, the spacer contains an IgG4/2 chimeric hinge, an IgG2/4 $C_H2$, and an IgG4 $C_H3$ region.

In some embodiments, the spacer can be derived all or in part from IgG4 and/or IgG2 and can contain mutations, such as one or more single amino acid mutations in one or more domains. In some examples, the amino acid modification is a substitution of a proline (P) for a serine(S) in the hinge region of an IgG4. In some embodiments, the amino acid modification is a substitution of a glutamine (Q) for an asparagine (N) to reduce glycosylation heterogeneity, such as an N177Q mutation at position 177, in the $C_H2$ region, of the full-length IgG4 Fc sequence or an N176Q at position 176, in the $C_H2$ region, of the full-length IgG4 Fc sequence.

In some embodiments, the spacer has the sequence ESKYGPPCPPCP (set forth in SEQ ID NO: 1), and is encoded by the sequence set forth in SEQ ID NO: 2. In some embodiments, the spacer has the sequence set forth in SEQ ID NO: 3. In some embodiments, the spacer has the sequence set forth in SEQ ID NO: 4. In some embodiments, the encoded spacer is or contains the sequence set forth in SEQ ID NO: 31. In some embodiments, the constant region or portion is of IgD. In some embodiments, the spacer has the sequence set forth in SEQ ID NO: 5. In some embodiments, the spacer has the sequence set forth in SEQ ID NO: 89.

Other exemplary spacer regions include hinge regions derived from CD8a, CD28, CTLA4, PD-1, or FcγRIIIa. In some embodiments, the spacer contains a truncated extracellular domain or hinge region of a CD8a, CD28, CTLA4, PD-1, or FcγRIIIa. In some embodiments, the spacer is a truncated CD28 hinge region. In some embodiments, a short oligo- or polypeptide linker, for example, a linker of between 2 and 10 amino acids in length, such as one containing alanines or alanine and arginine, e.g., alanine triplet (AAA) or RAAA (SEQ ID NO: 144), is present and forms a linkage between the scFv and the spacer region of the CAR. In some embodiments, the spacer has the sequence set forth in SEQ ID NO: 78. In some embodiments, the spacer has the sequence set forth in SEQ ID NO: 80. In some embodiments, the spacer has the sequence set forth in any of SEQ ID NOs: 81-83, In some embodiments, the spacer has the sequence set forth in SEQ ID NO: 84. In some embodiments, the spacer has the sequence set forth in SEQ ID NO: 86. In some embodiments, the spacer has the sequence set forth in SEQ ID NO: 88.

In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4, 5, 31, 78, 80, 81, 82, 83, 84, 86, 88, or 89.

In some embodiments, the spacer has the sequence set forth in SEQ ID NOS: 157-165. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 157-165.

This antigen recognition domain generally is linked to one or more intracellular signaling components, such as signaling components that mimic stimulation and/or activation through an antigen receptor complex, such as a TCR complex, in the case of a CAR, and/or signal via another cell surface receptor. Thus, in some embodiments, the antigen-binding component (e.g., antibody) is linked to one or more transmembrane and intracellular signaling domains. In some embodiments, the chimeric antigen receptor includes a transmembrane domain linking the extracellular domain and the intracellular signaling domain. In some embodiments, the transmembrane domain is fused to the extracellular domain, such as linked or fused between the extracellular domain (e.g. scFv) and intracellular signaling domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD8a, CD9, CD16, CD22, CD33, CD37, CD64, CD80, CD86, CD134, CD137 (4-1BB), CD154, CTLA-4 or PD-1. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s). In some aspects, the transmembrane domain contains a transmembrane portion of CD28. Exemplary sequences of transmembrane domains are or comprise the sequences set forth in SEQ ID NOs: 8, 79, 85, 87, 142, or 143.

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR CD3 chain that mediates T-cell stimulation and/or activation and cytotoxicity, e.g., CD3 zeta chain, CD3 gamma, CD3 delta, CD3 epsilon, FcR gamma, FcR beta, CDS, CD22, CD79a, CD79b and CD66d. In some examples of ITAM containing primary cytoplasmic signaling sequences include those derived from CD3 zeta chain, FcR gamma, CD3 gamma, CD3 delta and CD3 epsilon. In some embodiments, cytoplasmic signaling molecule(s) in the CAR contain(s) a cytoplasmic signaling domain, portion thereof, or sequence derived from CD3 zeta.

In some embodiments, the receptor includes an intracellular component of a TCR complex, such as a TCR CD3 chain that mediates T-cell stimulation and/or activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25 or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor stimulates and/or activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell stimulation and/or activation is in some aspects described as being mediated by two classes of cytoplasmic signaling sequences: those that initiate antigen-dependent primary stimulation and/or activation through the TCR (primary cytoplasmic signaling regions, domains or sequences), and those that act in an antigen-independent manner to provide a secondary or co-stimulatory signal (secondary cytoplasmic signaling regions, domains or sequences). In some aspects, the CAR includes one or both of such signaling components.

In some embodiments, the CAR includes a signaling region and/or transmembrane portion of a costimulatory receptor, such as CD28, 4-1BB, OX40 (CD134), CD27, DAP10, DAP12, ICOS and/or other costimulatory receptors. In some aspects, the same CAR includes both the primary cytoplasmic signaling region and costimulatory signaling components. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

In some embodiments, one or more different recombinant receptors can contain one or more different intracellular signaling region(s) or domain(s). In some embodiments, the primary cytoplasmic signaling region is included within one CAR, whereas the costimulatory component is provided by another receptor, e.g., another CAR recognizing another antigen. In some embodiments, the CARs include activating or stimulatory CARs, and costimulatory CARs, both expressed on the same cell (see WO2014/055668).

In some aspects, the cells include one or more stimulatory or activating CAR and/or a costimulatory CAR. In some embodiments, the cells further include inhibitory CARs (iCARs, see Fedorov et al., *Sci. Transl. Medicine,* 5 (215) (2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In some embodiments, the two receptors induce, respectively, an activating and an inhibitory signal to the cell, such that ligation of one of the receptor to its antigen activates the cell or induces a response, but ligation of the second inhibitory receptor to its antigen induces a signal that suppresses or dampens that response. Examples are combinations of activating CARs and inhibitory CARs (iCARs). Such a strategy may be used, for example, to reduce the likelihood of off-target effects in the context in which the activating CAR binds an antigen expressed in a disease or condition but which is also expressed on normal cells, and the inhibitory receptor binds to a separate antigen which is expressed on the normal cells but not cells of the disease or condition.

In some aspects, the chimeric receptor is or includes an inhibitory CAR (e.g. iCAR) and includes intracellular components that dampen or suppress an immune response, such as an ITAM- and/or co stimulatory-promoted response in the cell. Exemplary of such intracellular signaling components are those found on immune checkpoint molecules, including PD-1, CTLA4, LAG3, BTLA, OX2R, TIM-3, TIGIT, LAIR-1, PGE2 receptors, EP2/4 Adenosine receptors including A2AR. In some aspects, the engineered cell includes an inhibitory CAR including a signaling domain of or derived from such an inhibitory molecule, such that it serves to dampen the response of the cell, for example, that induced by an activating and/or costimulatory CAR In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and primary cytoplasmic signaling region, in the cytoplasmic portion. Exemplary CARs include intracellular components, such as intracellular signaling region(s) or domain(s), of CD3-zeta, CD28, CD137 (4-1BB), OX40 (CD134), CD27, DAP10, DAP12, NKG2D and/or ICOS. In some embodiments, the chimeric antigen receptor contains an intracellular signaling region or domain of a T cell costimulatory molecule, e.g., from CD28, CD137 (4-1BB), OX40 (CD134), CD27, DAP10, DAP12, NKG2D and/or ICOS, in some cases, between the transmembrane domain and intracellular signaling region or domain. In some aspects, the T cell costimulatory molecule is one or more of CD28, CD137 (4-1BB), OX40 (CD134), CD27, DAP10, DAP12, NKG2D and/or ICOS.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain linking the extracellular domain and the intracellular signaling domain. In some aspects, the transmembrane domain contains a transmembrane portion of CD28. In some embodiments, the chimeric antigen receptor contains an intracellular domain of a T cell costimulatory molecule. The extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

In some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the recombinant receptor, e.g., the CAR, is or includes a transmembrane domain of human CD28 (e.g. Accession No. P10747.1), or CD8a (Accession No. P01732.1), or variant thereof, such as a transmembrane domain that comprises the sequence of amino acids set forth in SEQ ID NO: 8, 79, 142, or 143 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 8, 79, 142, or 143; in some embodiments, the transmembrane-domain containing portion of the recombinant receptor comprises the sequence of amino acids set forth in SEQ ID NO: 9 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the intracellular signaling component(s) of the recombinant receptor, e.g. the CAR, contains an intracellular costimulatory signaling domain of human CD28 or a functional variant or portion thereof, such as a domain with an LL to GG substitution at positions 186-187 of a native CD28 protein. For example, the intracellular signaling domain can comprise the sequence of amino acids set forth in SEQ ID NO: 10 or 11 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular domain comprises an intracellular costimulatory signaling domain of 4-1BB (e.g. Accession No. Q07011.1) or functional variant or portion thereof, such as the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling domain of the recombinant receptor, e.g. the CAR, comprises a human CD3 zeta stimulatory signaling domain or functional variant thereof, such as a 112 AA cytoplasmic domain of isoform 3 of human CD3ζ (Accession No. P20963.2) or a CD3 zeta signaling domain as described in U.S. Pat. No. 7,446,190 or U.S. Pat. No. 8,911,993. For example, in some embodiments, the intracellular signaling domain comprises the sequence of amino acids as set forth in SEQ ID NO: 13, 14 or 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO: 1 or SEQ ID NO: 89. In other embodiments, the spacer is or contains an Ig hinge, e.g., an IgG4-derived hinge, optionally linked to a $C_H2$ and/or $C_H3$ domains. In some embodiments, the spacer is an Ig hinge, e.g., an IgG4 hinge, linked to $C_H2$ and $C_H3$ domains, such as set forth in SEQ ID NO: 4. In some embodiments, the spacer is an Ig hinge, e.g., an IgG4 hinge, linked to a $C_H3$ domain only, such as set forth in SEQ ID NO: 3. In some embodiments, the spacer is or comprises a glycine-serine rich sequence or other flexible linker such as known flexible linkers. In some embodiments, the spacer is a CD8a hinge, such as set forth in any of SEQ ID NOs: 81-83, an FcγRIIIa hinge, such as set forth in SEQ ID NO: 88, a CTLA4 hinge, such as set forth in SEQ ID NO: 84, or a PD-1 hinge, such as set forth in SEQ ID NO: 86.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, the antigen receptor further includes a marker and/or cells expressing the CAR or other antigen receptor further includes a surrogate marker, such as a cell surface marker, which may be used to confirm transduction or engineering of the cell to express the receptor. In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred. In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand. In some aspects, the marker includes all or part (e.g., truncated form) of CD34, a NGFR, or epidermal growth factor receptor, such as truncated version of such a cell surface receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence.

An exemplary polypeptide for a truncated EGFR (e.g. tEGFR) comprises the sequence of amino acids set forth in SEQ ID NO: 7 or 166 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 166. An exemplary T2A linker sequence comprises the sequence of amino acids set forth in SEQ ID NO: 6 or 167 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 167

In some embodiments, nucleic acid molecules encoding such CAR constructs further includes a sequence encoding a T2A ribosomal skip element and/or a tEGFR sequence, e.g., downstream of the sequence encoding the CAR. In some embodiments, the sequence encodes a T2A ribosomal skip element set forth in SEQ ID NO: 6 or 167, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 167. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802,374). In some embodiments, the sequence encodes an tEGFR sequence set forth in SEQ ID NO: 7 or 166, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7.

In some embodiments, the encoded CAR can sequence can further include a signal sequence or signal peptide that directs or delivers the CAR to the surface of the cell in which the CAR is expressed. In some embodiments, the signal peptide is derived from a transmembrane protein. In some examples the signal peptide is derived from CD8a, CD33, or an IgG. Exemplary signal peptides include the sequences set forth in SEQ ID NOs: 39, 40 and 153.

In some embodiments, the CAR includes an anti-BCMA antibody or fragment, such as any of the anti-human BCMA antibodies, including sdAbs and scFvs, described herein, a spacer such as any of the Ig-hinge containing spacers or other spacers described herein, a CD28 transmembrane domain, a CD28 intracellular signaling domain, and a CD3 zeta signaling domain. In some embodiments, the CAR includes an anti-BCMA antibody or fragment, such as any of the anti-human BCMA antibodies, including sdAbs and scFvs described herein, a spacer such as any of the Ig-hinge containing spacers or other spacers described herein, a CD28 transmembrane domain, a 4-1BB intracellular signaling domain, and a CD3 zeta signaling domain. In some embodiments, such CAR constructs further includes a T2A ribosomal skip element and/or a tEGFR sequence, e.g., downstream of the CAR.

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition. In some embodiments, the CAR specifically binds to BCMA, such as human BCMA, and includes an anti-human BCMA antibody or fragment as described. Non-limiting exemplary CAR sequences, including anti-BCMA CAR sequences, are set forth in SEQ ID NOs: 90-141. In some embodiments, an anti-BCMA CAR includes the amino acid sequence set forth in any of SEQ ID NOS: 90-141 or an amino acid sequence that exhibits at least at or about 90%, at or about 91%, at or about 92%, at or about 93%, at or about 94%, at or about 95%, at or about 96%, at or about 97%, at or about 96%, at or about 97%, at or about 98%, at or about 99% sequence identity to any one of SEQ ID NOS: 90-141, and wherein the CAR specifically binds BCMA, e.g. human BCMA.

2. Chimeric Auto-Antibody Receptor (CAAR)

In some embodiments, the recombinant receptor is a chimeric autoantibody receptor (CAAR). In some embodiments, the CAAR binds, e.g., specifically binds, or recognizes, an autoantibody. In some embodiments, a cell expressing the CAAR, such as a T cell engineered to express a CAAR, can be used to bind to and kill autoantibody-expressing cells, but not normal antibody expressing cells. In some embodiments, CAAR-expressing cells can be used to treat an autoimmune disease associated with expression of self-antigens, such as autoimmune diseases. In some embodiments, CAAR-expressing cells can target B cells that ultimately produce the autoantibodies and display the autoantibodies on their cell surfaces, mark these B cells as disease-specific targets for therapeutic intervention. In some embodiments, CAAR-expressing cells can be used to efficiently targeting and killing the pathogenic B cells in autoimmune diseases by targeting the disease-causing B cells using an antigen-specific chimeric autoantibody receptor. In some embodiments, the recombinant receptor is a CAAR, such as any described in U.S. Patent Application Pub. No. US 2017/0051035.

In some embodiments, the CAAR comprises an autoantibody binding domain, a transmembrane domain, and one or more intracellular signaling region or domain (also interchangeably called a cytoplasmic signaling domain or region). In some embodiments, the intracellular signaling region comprises an intracellular signaling domain. In some embodiments, the intracellular signaling domain is or comprises a primary signaling region, a signaling domain that is capable of stimulating and/or inducing a primary activation signal in a T cell, a signaling domain of a T cell receptor (TCR) component (e.g. an intracellular signaling domain or region of a zeta chain of a CD3-zeta (CD3ζ) chain or a functional variant or signaling portion thereof), and/or a signaling domain comprising an immunoreceptor tyrosine-based activation motif (ITAM).

In some embodiments, the autoantibody binding domain comprises an autoantigen or a fragment thereof. The choice of autoantigen can depend upon the type of autoantibody being targeted. For example, the autoantigen may be chosen because it recognizes an autoantibody on a target cell, such as a B cell, associated with a particular disease state, e.g. an autoimmune disease, such as an autoantibody-mediated autoimmune disease. In some embodiments, the autoimmune disease includes pemphigus vulgaris (PV). Exemplary autoantigens include desmoglein 1 (Dsg1) and Dsg3.

3. TCRs

In some embodiments, engineered cells, such as T cells, are provided that express a T cell receptor (TCR) or antigen-binding portion thereof that recognizes an peptide epitope or T cell epitope of a target polypeptide, such as an antigen of a tumor, viral or autoimmune protein. In some aspects, the TCR is or includes a recombinant TCR.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., *Immunobiology: The Immune System in Health and Disease,* 3rd Ed., *Current Biology Publications*, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or Cβ, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the recombinant receptors include recombinant TCRs and/or TCRs cloned from naturally occurring T cells. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15:169-180 and Cohen et al. (2005) J Immunol. 175:5799-5808. In some embodiments, phage display is used to isolate TCRs against a target antigen (see, e.g., Varela-Rohena et al. (2008) Nat Med. 14:1390-1395 and Li (2005) Nat Biotechnol. 23:349-354.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4$^+$ or CD8$^+$ cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al., (2003) *Nat Immunol,* 4, 55-62; Holler et al., (2000) *Proc Natl Acad Sci USA,* 97, 5387-92), phage display (Li et al., (2005) *Nat Biotechnol,* 23, 349-54), or T cell display (Chervin et al., (2008) *J Immunol Methods,* 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified. In some embodiments, peptides suitable for use in generating TCRs or antigen-binding portions can be determined based on the presence of an HLA-restricted motif in a target polypeptide of interest, such as a target polypeptide described herein. In some embodiments, peptides are identified using available computer prediction models. In some embodiments, for predicting MHC class I binding sites, such models include, but are not limited to, ProPred1 (Singh and Raghava (2001) *Bioinformatics* 17 (12): 1236-1237, and SYFPEITHI (see Schuler et al., (2007) *Immunoinformatics Methods in Molecular Biology,* 409 (1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models. For predicting MHC class I binding sites, such models include, but are not limited to, ProPred1 (described in more detail in Singh and Raghava, ProPred: prediction of HLA-DR binding sites. *BIOINFORMATICS* 17 (12): 1236-1237 2001), and SYFPEITHI (see Schuler et al., SYFPEITHI, Database for Searching and T-Cell Epitope Prediction. in *Immunoinformatics Methods in Molecular Biology,* vol 409 (1): 75-93 2007)

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO2011/044186.

In some embodiments, the TCR contains a sequence corresponding to the transmembrane sequence. In some embodiments, the TCR docs contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known, See e.g., Soo Hoo, W. F. et al., *PNAS (USA)* 89, 4759 (1992); Wülfing, C. and Plückthun, A., *J. Mol. Biol.* 242, 655 (1994); Kurucz, I. et al., *PNAS (USA)* 90 3830 (1993); International published PCT Nos. WO 96/13593, WO 96/18105, WO99/60120, WO99/18129, WO 03/020763, WO2011/044186; and Schlueter, C. J. et al., *J. Mol. Biol.* 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contains a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from 10 to 45 amino acids or from about 10 to 45 amino acids, such as 10 to 30 amino acids or 26 to 41 amino acids residues, for example 29, 30, 31 or 32 amino acids. In some embodiments, the linker has the formula -PGGG-(SGGGG)5-P- wherein P is proline, G is glycine and S is serine (SEQ ID NO: 16). In some embodiments, the linker has the sequence GSADDAKK-DAAKKDGKS (SEQ ID NO: 17)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about 10-5 and 10-12 M and all individual values and ranges therein. In some embodiments, the target antigen is an MHC-peptide complex or ligand.

In some embodiments, nucleic acid or nucleic acids encoding a TCR, such as α and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-C1, pMAM and pMAM-neo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

4. Multi-Targeting

In some embodiments, the cells and methods include multi-targeting strategies, such as expression of two or more genetically engineered receptors on the cell, each recognizing the same or a different antigen and typically each including a different intracellular signaling component. Such multi-targeting strategies are described, for example, in PCT Pub. No. WO 2014055668 A1 (describing combinations of activating and costimulatory CARs, e.g., targeting two different antigens present individually on off-target, e.g., normal cells, but present together only on cells of the disease or condition to be treated) and Fedorov et al., *Sci. Transl. Medicine,* 5 (215) (2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating signal to the cell, generally upon specific binding to the antigen recognized by the first receptor, e.g., a first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains of costimulatory receptors such as CD28, CD137 (4-1BB), OX40, and/or ICOS. In some embodiments, the first and second receptors include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the cells expressing the recombinant receptor further include inhibitory CARs (iCARs, see Fedorov et al., Sci. Transl. Medicine, 5 (215) (2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some aspects, the chimeric receptor is or includes an inhibitory CAR (e.g. iCAR) and includes intracellular components that dampen or suppress an immune response, such as an ITAM- and/or co stimulatory-promoted response in the cell. Examples of such intracellular signaling components are those found on immune checkpoint molecules, including PD-1, CTLA4, LAG3, BTLA, OX2R, TIM-3, TIGIT, LAIR-1, PGE2 receptors, EP2/4 Adenosine receptors including A2AR. In some aspects, the engineered cell includes an inhibitory CAR including a signaling domain of or derived from such an inhibitory molecule, such that it serves to dampen the response of the cell, for example, that induced by an activating and/or costimulatory CAR.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

B. Cells and Preparation of Cells for Genetic Engineering

Among the cells expressing the receptors and administered by the provided methods are engineered cells. The genetic engineering generally involves introduction of a nucleic acid encoding the recombinant or engineered component into a composition containing the cells, such as by retroviral transduction, transfection, or transformation.

In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). The cells typically are primary cells, such as those isolated directly from a subject and/or isolated from a subject and frozen. In some embodiments, the cells include one or more subsets of T cells or other cell types, such as whole T cell populations, $CD4^+$ cells, $CD8^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of $CD4^+$ and/or of $CD8^+$ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as THI cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contain cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., $CD28^+$, $CD62L^+$, $CCR7^+$, $CD27^+$, $CD127^+$, $CD4^+$, $CD8^+$, $CD45RA^+$, and/or $CD45RO^+$ T cells, are isolated by positive or negative selection techniques.

For example, $CD3^+$, $CD28^+$ T cells can be positively selected using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed ($marker^+$) at a relatively higher level (markerhigh) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ populations can be further sorted into sub-populations by positive or negative selection for markers expressed or expressed to a relatively higher degree on one or more naive, memory, and/or effector T cell subpopulations.

In some embodiments, $CD8^+$ cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such subpopulations. See Terakura et al., *Blood.* 1:72-82 (2012); Wang et al., *J Immunother.* 35 (9): 689-701 (2012). In some embodiments, combining $T_{CM}$-enriched $CD8^+$ T cells and $CD4^+$ T cells further enhances efficacy.

In embodiments, memory T cells are present in both $CD62L^+$ and CD62L-subsets of $CD8^+$ peripheral blood lymphocytes. PBMC can be enriched for or depleted of $CD62L-CD8^+$ and/or $CD62L^+CD8^+$ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a $CD8^+$ population enriched for $T_{CM}$ cells is carried out by depletion of cells expressing CD4, CD14, CD45RA, and positive selection or enrichment for cells expressing CD62L. In one aspect, enrichment for central memory T ($T_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the $CD8^+$ cell population or subpopulation, also is used to generate the $CD4^+$ cell population or subpopulation, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of $CD4^+$ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4" T helper cells are sorted into naïve, central memory, and effector cells by identifying cell populations that have cell surface antigens. $CD4^+$ lymphocytes can be obtained by standard methods. In some embodiments, naive $CD4^+$ T lymphocytes are CD45RO-, $CD45RA^+$, $CD62L^+$, $CD4^+$ T cells. In some embodiments, central memory $CD4^+$ cells are $CD62L^+$ and $CD45RO^+$. In some embodiments, effector $CD4^+$ cells are CD62L- and CD45RO-.

In one example, to enrich for $CD4^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In vitro and In vivo, p 17-25 Edited by: S. A. Brooks and U. Schumacher © Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in PCT Pub. Number WO2009/072003, or US20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al., *J Immunother.* 35 (9): 651-660 (2012), Terakura et al., *Blood.* 1:72-82 (2012), and Wang et al., *J Immunother.* 35 (9): 689-701 (2012).

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al., *Lab Chip* 10, 1567-1573 (2010); and Godin et al., *J Biophoton.* 1 (5): 355-376 (2008). In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/mL.

In some aspects, incubation is carried out in accordance with techniques such as those described in U.S. Pat. No. 6,040,177 to Riddell et al., Klebanoff et al., *J Immunother.* 35 (9): 651-660 (2012), Terakura et al., *Blood.* 1:72-82 (2012), and/or Wang et al., *J Immunother.* 35 (9): 689-701 (2012).

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4$^+$ and/or CD8$^+$ T cells, are obtained by stimulating naive or antigen specific T lymphocytes with antigen. For example, antigen-specific T cell lines or clones can be generated to cytomegalovirus antigens by isolating T cells from infected subjects and stimulating the cells in vitro with the same antigen.

C. Nucleic Acids, Vectors and Methods for Genetic Engineering

In some embodiments, the cells, e.g., T cells, are genetically engineered to express a recombinant receptor. In some embodiments, the engineering is carried out by introducing nucleic acid molecules that encode the recombinant receptor. Also provided are nucleic acid molecules encoding a recombinant receptor, and vectors or constructs containing such nucleic acids and/or nucleic acid molecules.

In some cases, the nucleic acid sequence encoding the recombinant receptor, e.g., chimeric antigen receptor (CAR), contains a signal sequence that encodes a signal peptide. In some aspects, the signal sequence may encode a signal peptide derived from a native polypeptide. In other aspects, the signal sequence may encode a heterologous or non-native signal peptide. In some embodiments, the signal peptide is derived from a transmembrane protein. In some examples the signal peptide is derived from CD8a, CD33, or an IgG. Non-limiting exemplary examples of signal peptides include, for example, the CD33 signal peptide set forth in SEQ ID NO:153, CD8a signal peptide set forth in SEQ ID NO:39, or the signal peptide set forth in SEQ ID NO:40 or modified variant thereof.

In some embodiments, the nucleic acid molecule encoding the recombinant receptor contains at least one promoter that is operatively linked to control expression of the recombinant receptor. In some examples, the nucleic acid molecule contains two, three, or more promoters operatively linked to control expression of the recombinant receptor. In some embodiments, nucleic acid molecule can contain regulatory sequences, such as transcription and translation initiation and termination codons, which are specific to the type of host (e.g., bacterium, fungus, plant, or animal) into which the nucleic acid molecule is to be introduced, as appropriate and taking into consideration whether the nucleic acid molecule is DNA- or RNA-based. In some embodiments, the nucleic acid molecule can contain regulatory/control elements, such as a promoter, an enhancer, an intron, a polyadenylation signal, a Kozak consensus sequence, and splice acceptor or donor. In some embodiments, the nucleic acid molecule can contain a nonnative promoter operably linked to the nucleotide sequence encoding the recombinant receptor and/or one or more additional polypeptide(s). In some embodiments, the promoter is selected from among an RNA pol I, pol II or pol III promoter. In some embodiments, the promoter is recognized by RNA polymerase II (e.g., a CMV, SV40 early region or adenovirus major late promoter). In another embodiment, the promoter is recognized by RNA polymerase III (e.g., a U6 or H1 promoter). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, the promoter is or comprises a constitutive promoter. Exemplary constitutive promoters include, e.g., simian virus 40 early promoter (SV40), cytomegalovirus immediate-early promoter (CMV), human Ubiquitin C promoter (UBC), human elongation factor 1α promoter (EF1α), mouse phosphoglycerate kinase 1 promoter (PGK), and chicken β-Actin promoter coupled with CMV early enhancer (CAGG). In some embodiments, the constitutive promoter is a synthetic or modified promoter. In some embodiments, the promoter is or comprises an MND promoter, a synthetic promoter that contains the U3 region of a modified MoMuLV LTR with myeloproliferative sarcoma virus enhancer (see Challita et al. (1995) J. Virol. 69 (2): 748-755). In some embodiments, the promoter is a tissue-specific promoter. In another embodiment, the promoter is a viral promoter. In another embodiment, the promoter is a non-viral promoter.

In another embodiment, the promoter is a regulated promoter (e.g., inducible promoter). In some embodiments, the promoter is an inducible promoter or a repressible promoter. In some embodiments, the promoter comprises a Lac operator sequence, a tetracycline operator sequence, a galactose operator sequence or a doxycycline operator sequence, or is an analog thereof or is capable of being bound by or recognized by a Lac repressor or a tetracycline repressor, or an analog thereof. In some embodiments, the nucleic acid molecule does not include a regulatory element, e.g. promoter.

In some embodiments, the nucleic acid molecule encoding the recombinant receptor, e.g., CAR or other antigen receptor, further includes nucleic acid sequences encoding a marker and/or cells expressing the CAR or other antigen receptor further includes a marker, e.g., a surrogate marker, such as a cell surface marker, which may be used to confirm transduction or engineering of the cell to express the receptor, such as a truncated version of a cell surface receptor, such as truncated EGFR (EGFR). In some embodiments, the one or more marker(s) is a transduction marker, surrogate marker and/or a selection marker.

In some embodiments, the marker is a transduction marker or a surrogate marker. A transduction marker or a surrogate marker can be used to detect cells that have been introduced with the nucleic acid molecule, e.g., a nucleic acid molecule encoding a recombinant receptor. In some embodiments, the transduction marker can indicate or confirm modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same nucleic acid molecule that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence, such as a T2A (e.g., SEQ ID NO: 6 or 167), a P2A (e.g., SEQ ID NO: 168 or 169), an E2A (e.g., SEQ ID NO: 170) or an F2A (e.g., SEQ ID NO: 172). Extrinsic marker genes may in some cases be utilized in connection with engineered cell to permit detection or selection of cells and, in some cases, also to promote cell suicide.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing. Exemplary truncated cell surface polypeptides including truncated forms of growth factors or other receptors such as a truncated human epidermal growth factor receptor 2 (tHER2), a truncated epidermal growth factor receptor (tEGFR, exemplary tEGFR sequence set forth in SEQ ID NO:7 or 166) or a prostate-specific membrane antigen (PSMA) or modified form thereof. tEGFR may contain an epitope recognized by the antibody cetuximab (Erbitux®) or other therapeutic anti-EGFR antibody or binding molecule, which can be used to identify or select cells that have been engineered with the tEGFR construct and an encoded exogenous protein, and/or to eliminate or separate cells expressing the encoded exogenous protein. See U.S. Pat. No. 8,802,374 and Liu et al., Nature Biotech. 2016 April; 34 (4): 430-434). In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR). In some embodiments, the marker is or comprises a fluorescent protein, such as green fluorescent protein (GFP), enhanced green fluorescent protein (EGFP), such as super-fold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In some aspects, the marker, e.g. surrogate marker, includes all or part (e.g., truncated form) of CD34, a NGFR, or epidermal growth factor receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in PCT Pub. No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 7 or 166, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 166. An exemplary T2A linker sequence comprises the sequence of amino acids set forth in SEQ ID NO: 6 or 167 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 167.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some embodiments, a single promoter may direct expression of an RNA that contains, in a single open reading frame (ORF), two or three genes separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known in the art. Examples of 2A sequences that can be used in the methods and nucleic acids disclosed herein, without limitation, 2A sequences from the foot-and-mouth disease virus (F2A), equine rhinitis A virus (E2A), Thosea asigna virus (T2A, e.g., SEQ ID NO: 6), and porcine teschovirus-1 (P2A) as described in U.S. Patent Publication No. 20070116690.

Introduction of the nucleic acid molecules encoding the recombinant receptor in the cell may be carried out using any of a number of known vectors. Such vectors include viral and non-viral systems, including lentiviral and gammaretroviral systems, as well as transposon-based systems such as PiggyBac or Sleeping Beauty-based gene transfer systems. Exemplary methods include those for transfer of nucleic acids encoding the receptors, including via viral, e.g., retroviral or lentiviral, transduction, transposons, and electroporation.

In some embodiments, gene transfer is accomplished by first stimulating the cell, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

In some embodiments, prior to or during gene transfer, the cells are incubated or cultured in the presence of an gamma secretase inhibitor, including any as described herein. In some embodiments, the gamma secretase inhibitor is added during the cell manufacturing process, for example, during the process of engineering CAR-T cells. In some aspects, the presence of the gamma secretase inhibitor can improve the quality of the population of cells produced. In some aspects, the gamma secretase inhibitor may increase the proliferation or expansion of cells or may alter one or more signaling pathways thereby resulting in cells with a less-differentiated or less activated surface phenotype, despite exhibiting substantial expansion and/or effector function.

In some contexts, overexpression of a stimulatory factor (for example, a lymphokine or a cytokine) may be toxic to a subject. Thus, in some contexts, the engineered cells include gene segments that cause the cells to be susceptible to negative selection in vivo, such as upon administration in adoptive immunotherapy. For example in some aspects, the cells are engineered so that they can be eliminated as a result of a change in the in vivo condition of the patient to which they are administered. The negative selectable phenotype may result from the insertion of a gene that confers sensitivity to an administered agent, for example, a compound. Negative selectable genes include the Herpes simplex virus type I thymidine kinase (HSV-I TK) gene (Wigler et al., Cell II: 223, 1977) which confers ganciclovir sensitivity; the cellular hypoxanthine phosphribosyltransferase (HPRT) gene, the cellular adenine phosphoribosyltransferase (APRT) gene, bacterial cytosine deaminase, (Mullen et al., Proc. Natl. Acad. Sci. USA. 89:33 (1992)).

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28 (10): 1137-46; Alonso-Camino et al. (2013) Mol Ther Nucl Acids 2, e93; Park et al., Trends Biotechnol. 2011 Nov. 29 (11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207, 453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) *J. Immunother.* 35 (9): 689-701; Cooper et al. (2003) *Blood.* 101: 1637-1644; Verhocyen et al. (2009) *Methods Mol Biol.* 506:97-114; and Cavalieri et al. (2003) Blood. 102 (2): 497-505.

In some embodiments, recombinant nucleic acids are transferred into T cells via electroporation (see, e.g., Chicaybam et al, (2013) *PLoS ONE* 8 (3): e60298 and Van Tedeloo et al. (2000) Gene Therapy 7 (16): 1431-1437). In some embodiments, recombinant nucleic acids are transferred into T cells via transposition (see, e.g., Manuri et al. (2010) *Hum Gene Ther* 21 (4): 427-437; Sharma et al. (2013) *Molec Ther Nucl Acids* 2, e74; and Huang et al. (2009) *Methods Mol Biol* 506:115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346:776-777 (1990)); and strontium phosphate DNA co-precipitation (Brash et al., Mol. Cell Biol., 7:2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the CD3/CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65:333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

In some aspects, the cells further are engineered to promote expression of cytokines or other factors. Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

III. Exemplary Treatment Outcomes and Methods for Assessing Same

In some embodiments of the methods, compositions, combinations, kits and uses provided herein, the provided combination therapy results in one or more treatment outcomes, such as a feature associated with any one or more of the parameters associated with the therapy or treatment, as described herein. In some embodiments, the method includes assessment of the exposure, persistence and proliferation of the T cells, e.g., T cells administered for the T cell based therapy. In some embodiments, the exposure, or prolonged expansion and/or persistence of the cells, and/or changes in cell phenotypes or functional activity of the cells, e.g., cells administered for immunotherapy, e.g. T cell therapy, in the methods provided herein, can be measured by assessing the characteristics of the T cells in vitro or ex vivo. In some embodiments, such assays can be used to determine or confirm the function of the T cells, e.g. T cell therapy, before or after administering the combination therapy provided herein.

In some embodiments, the combination therapy can further include one or more screening steps to identify subjects for treatment with the combination therapy and/or continuing the combination therapy, and/or a step for assessment of treatment outcomes and/or monitoring treatment outcomes. In some embodiments, subjects suitable for treatment have low surface expression of BCMA. In some embodiments, low surface expression of BCMA is determined by comparing BCMA expression in a subject against average surface BCMA expression in a healthy population of subjects. In some embodiments, low BCMA expression is a BCMA expression level that is less than the population average. In some embodiments, low BCMA expression is a BCMA expression level that is, is about, is at least 1.1, 1.2, 1.3, 1.4, 1.5, 1.6, 1.7, 1.8, 1.9, 2, 3, 4, 5, 10, 15, 20, 30, 40, 50, 100, 150, 200, 250-fold or more less than, or 10%, 20%, 30%, 40%, 50%, 60%, 70%, 80%, 90%, or more below, the average BCMA expression level in a healthy population of subjects. In some embodiments, low surface expression of BCMA is determined by comparing BCMA expression in a subject against median surface BCMA expression in a healthy population of subjects. In some embodiments, low BCMA expression is a BCMA expression level that is less than the population median. In some embodiments, low BCMA expression is a BCMA expression level that is, is about, is at least 1.1, 1.2, 1.3, 1.4, 1.5, 1.6, 1.7, 1.8, 1.9, 2, 3, 4, 5, 10, 15, 20, 30, 40, 50, 100, 150, 200, 250-fold or more less than, or 10%, 20%, 30%, 40%, 50%, 60%, 70%, 80%, 90%, or more below, the median BCMA expression level in a healthy population of subjects. In some embodiments, low surface expression of BCMA is determined by comparing BCMA expression in a subject against average surface BCMA expression in a patient population (e.g., multiple myeloma patient population). In some embodiments, low BCMA expression is a BCMA expression level that is less than the patient population average. In some embodiments, low BCMA expression is a BCMA expression level that is, is about, is at least 1.1, 1.2, 1.3, 1.4, 1.5, 1.6, 1.7, 1.8, 1.9, 2, 3, 4, 5, 10, 15, 20, 30, 40, 50, 100, 150, 200, 250-fold or more less than, or 10%, 20%, 30%, 40%, 50%, 60%, 70%, 80%, 90%, or more below, the average BCMA expression level in a patient population (e.g., multiple myeloma patient population). In some embodiments, low surface expression of BCMA is determined by comparing BCMA expression in a subject against median surface BCMA expression in a patient population (e.g., multiple myeloma patient population). In some embodiments, low BCMA expression is a BCMA expression level that is less than the patient population median. In some embodiments, low BCMA expression is a BCMA expression level that is, is about, is at least 1.1, 1.2, 1.3, 1.4, 1.5, 1.6, 1.7, 1.8, 1.9, 2, 3, 4, 5, 10, 15, 20, 30, 40, 50, 100, 150, 200, 250-fold or more less than, or 10%, 20%, 30%, 40%, 50%, 60%, 70%, 80%, 90%, or more below, the median BCMA expression level in a patient population (e.g., multiple myeloma patient population). In some embodiments, determination of low BCMA expression in a subject can be determined by comparing BCMA expression in the subject at two or more different time point (e.g., before diagnosis and after diagnosis, at diagnosis and at a time point following diagnosis, before treatment and after treatment, etc.). In some embodiments according to this method, low BCMA expression would be considered about or at least 10%, 20%, 30%, 40%, 50%, 60%, 70%, 80%, 90%, or more decrease in BCMA expression compared to the earlier time point.

In some embodiments, low BCMA expression is considered BCMA expression below a threshold level. In some embodiments, the threshold level is, is about, is at least, 10%, 20%, 30%, 40%, 50%, 60%, 70%, 80%, 90% or more below the average or median BCMA expression level ascertained from a population of healthy subjects. In some embodiments, the threshold level is, is about, is at least, 10%, 20%, 30%, 40%, 50%, 60%, 70%, 80%, 90% or more below the average or median BCMA expression level ascertained from a population of patients (e.g., multiple myeloma patients). In some embodiments, the threshold level is, is about, is at least, 10%, 20%, 30%, 40%, 50%, 60%, 70%, 80%, 90% or more below a BCMA expression level obtained from the subject.

In some embodiments, the step for assessment of treatment outcomes can include steps to evaluate and/or to monitor treatment and/or to identify subjects for administration of further or remaining steps of the therapy and/or for repeat therapy. In some embodiments, the screening step and/or assessment of treatment outcomes can be used to determine the dose, frequency, duration, timing and/or order of the combination therapy provided herein.

In some embodiments, any of the screening steps and/or assessment of treatment of outcomes described herein can be used prior to, during, during the course of, or subsequent to administration of one or more steps of the provided combination therapy, e.g., administration of the T cell therapy (e.g. CAR-expressing T cells), and/or an gamma secretase inhibitor. In some embodiments, assessment is made prior to, during, during the course of, or after performing any of the methods provided herein. In some embodiments, the assessment is made prior to performing the methods provided herein. In some embodiments, assessment is made after performing one or more steps of the methods provided herein. In some embodiments, the assessment is performed prior to administration of administration of one or more steps of the provided combination therapy, for example, to screen and identify patients suitable and/or susceptible to receive the combination therapy. In some embodiments, the assessment is performed during, during the course of, or subsequent to administration of one or more steps of the provided combination therapy, for example, to assess the intermediate or final treatment outcome, e.g., to determine the efficacy of the treatment and/or to determine whether to continue or repeat the treatments and/or to determine whether to administer the remaining steps of the combination therapy.

In some embodiments, treatment of outcomes includes improved immune function, e.g., immune function of the T cells administered for cell based therapy and/or of the endogenous T cells in the body. In some embodiments, exemplary treatment outcomes include, but are not limited to, enhanced T cell proliferation, enhanced T cell functional activity, changes in immune cell phenotypic marker expression, such as such features being associated with the engineered T cells, e.g. CAR-T cells, administered to the subject.

In some embodiments, exemplary treatment outcomes include decreased disease burden, e.g., tumor burden, improved clinical outcomes and/or enhanced efficacy of therapy.

In some embodiments, the screening step and/or assessment of treatment of outcomes includes assessing the survival and/or function of the T cells administered for cell based therapy. In some embodiments, the screening step and/or assessment of treatment of outcomes includes assessing the levels of cytokines or growth factors. In some embodiments, the screening step and/or assessment of treatment of outcomes includes assessing disease burden and/or improvements, e.g., assessing tumor burden and/or clinical outcomes. In some embodiments, either of the screening step and/or assessment of treatment of outcomes can include any of the assessment methods and/or assays described herein and/or known in the art, and can be performed one or more times, e.g., prior to, during, during the course of, or subsequently to administration of one or more steps of the combination therapy. Exemplary sets of parameters associated with a treatment outcome, which can be assessed in some embodiments of the methods provided herein, include peripheral blood immune cell population profile and/or tumor burden.

In some embodiments, the methods affect efficacy of the cell therapy in the subject. In some embodiments, the persistence, expansion, and/or presence of recombinant receptor-expressing, e.g., CAR-expressing, cells in the subject following administration of the dose of cells in the method with the gamma secretase inhibitor is greater as compared to that achieved via a method without the administration of the gamma secretase inhibitor. In some embodiments of the immunotherapy methods provided herein, such as a T cell therapy (e.g. CAR-expressing T cells), assessment of the parameter includes assessing the expansion and/or persistence in the subject of the administered T cells for the immunotherapy, e.g., T cell therapy, as compared to a method in which the immunotherapy is administered to the subject in the absence of the gamma secretase inhibitor. In some embodiments, the methods result in the administered T cells exhibiting increased or prolonged expansion and/or persistence in the subject as compared to a method in which the T cell therapy is administered to the subject in the absence of the gamma secretase inhibitor.

In some embodiments, the administration of the gamma secretase inhibitor decreases disease burden, e.g., tumor burden, in the subject as compared to a method in which the dose of cells expressing the recombinant receptor is administered to the subject in the absence of the gamma secretase inhibitor. In some embodiments, the administration of the gamma secretase inhibitor decreases blast marrow in the subject as compared to a method in which the dose of cells expressing the recombinant receptor is administered to the subject in the absence of the gamma secretase inhibitor. In some embodiments, the administration of the gamma secretase inhibitor results in improved clinical outcomes, e.g., objective response rate (ORR), progression-free survival (PFS) and overall survival (OS), compared to a method in which the dose of cells expressing the recombinant receptor is administered to the subject in the absence of the gamma secretase inhibitor.

In some embodiments, the subject can be screened prior to the administration of one or more steps of the combination therapy. For example, the subject can be screened for characteristics of the disease and/or disease burden, e.g., tumor burden, prior to administration of the combination therapy, to determine suitability, responsiveness and/or susceptibility to administering the combination therapy. In some embodiments, the screening step and/or assessment of treatment outcomes can be used to determine the dose, frequency, duration, timing and/or order of the combination therapy provided herein.

In some embodiments, the subject can be screened after administration of one of the steps of the combination therapy, to determine and identify subjects to receive the remaining steps of the combination therapy and/or to monitor efficacy of the therapy. In some embodiments, the number, level or amount of administered T cells and/or proliferation and/or activity of the administered T cells is assessed prior to administration and/or after administration of the gamma secretase inhibitor.

In some embodiments, the gamma secretase inhibitor is administered until the concentration or number of engineered cells in the blood of the subject is (i) at least at or about 10 engineered cells per microliter, (ii) at least 20%, 30%, 40% or 50% of the total number of peripheral blood mononuclear cells (PBMCs), (iii) at least or at least about $1 \times 10^5$ engineered cells; or (iv) at least 5,000 copies of recombinant receptor-encoding DNA per micrograms DNA; and/or at day 90 following the initiation of the administration in (a), CAR-expressing cells are detectable in the blood or serum of the subject; and/or at day 90 following the initiation of the administration in (a), the blood of the subject contains at least 20% CAR-expressing cells, at least 10 CAR-expressing cells per microliter or at least $1 \times 10^4$ CAR-expressing cells.

In some embodiments, the gamma secretase inhibitor is administered until there is a clinical benefit to the treatment, such as at least or greater than a 50% decrease in the total tumor volume, a complete response (CR) in which detectable tumor has disappeared, progression free survival or disease free survival for greater than 6 months or greater than 1 year or more.

In some embodiments, a change and/or an alteration, e.g., an increase, an elevation, a decrease or a reduction, in levels, values or measurements of a parameter or outcome compared to the levels, values or measurements of the same parameter or outcome in a different time point of assessment, a different condition, a reference point and/or a different subject is determined or assessed. For example, in some embodiments, a fold change, e.g., an increase or decrease, in particular parameters, e.g., number of engineered T cells in a sample, compared to the same parameter in a different condition, e.g., before or after administration of the gamma secretase inhibitor can be determined. In some embodiments, the levels, values or measurements of two or more parameters are determined, and relative levels are compared. In some embodiments, the determined levels, values or measurements of parameters are compared to the levels, values or measurements from a control sample or an untreated sample. In some embodiments, the determined levels, values or measurements of parameters are compared to the levels from a sample from the same subject but at a different time point. The values obtained in the quantification of individual parameter can be combined for the purpose of disease assessment, e.g., by forming an arithmetical or logical operation on the levels, values or measurements of parameters by using multi-parametric analysis. In some embodiments, a ratio of two or more specific parameters can be calculated.

A. T Cell Exposure, Persistence and Proliferation

In some embodiments, the parameter associated with therapy or a treatment outcome, which include parameters that can be assessed for the screening steps and/or assessment of treatment of outcomes and/or monitoring treatment outcomes, is or includes assessment of the exposure, persistence and proliferation of the T cells, e.g., T cells administered for the T cell based therapy. In some embodiments, the increased exposure, or prolonged expansion and/or persistence of the cells, and/or changes in cell phenotypes or functional activity of the cells, e.g., cells administered for immunotherapy, e.g. T cell therapy, in the methods provided herein, can be measured by assessing the characteristics of the T cells in vitro or ex vivo. In some embodiments, such assays can be used to determine or confirm the function of the T cells used for the immunotherapy, e.g. T cell therapy, before or after administering one or more steps of the combination therapy provided herein.

In some embodiments, the administration of the gamma secretase inhibitor are designed to promote exposure of the subject to the cells, e.g., T cells administered for T cell based therapy, such as by promoting their expansion and/or persistence over time. In some embodiments, the T cell therapy exhibits increased or prolonged expansion and/or persistence in the subject as compared to a method in which the T cell therapy is administered to the subject in the absence of the gamma secretase inhibitor.

In some embodiments, the provided methods increase exposure of the subject to the administered cells (e.g., increased number of cells or duration over time) and/or improve efficacy and therapeutic outcomes of the immunotherapy, e.g. T cell therapy. In some aspects, the methods are advantageous in that a greater and/or longer degree of exposure to the cells expressing the recombinant receptors, e.g., CAR-expressing cells, improves treatment outcomes as compared with other methods. Such outcomes may include patient survival and remission, even in individuals with severe tumor burden.

In some embodiments, the administration of the gamma secretase inhibitor can increase the maximum, total, and/or duration of exposure to the cells, e.g. T cells administered for the T cell based therapy, in the subject as compared to administration of the T cells alone in the absence of the gamma secretase inhibitor. In some aspects, administration of the gamma secretase inhibitor, in the context of high disease burden (and thus higher amounts of antigen) and/or a more aggressive or resistant cancer enhances efficacy as compared with administration of the T cells alone in the absence of the gamma secretase inhibitor in the same context, which may result in immunosuppression, anergy and/or exhaustion which may prevent expansion and/or persistence of the cells.

In some embodiments, the presence and/or amount of cells expressing the recombinant receptor (e.g., CAR-expressing cells administered for T cell based therapy) in the subject following the administration of the T cells and before, during and/or after the administration of the gamma secretase inhibitor is detected. In some aspects, quantitative PCR (qPCR) is used to assess the quantity of cells expressing the recombinant receptor (e.g., CAR-expressing cells administered for T cell based therapy) in the blood or serum or organ or tissue sample (e.g., disease site, e.g., tumor sample) of the subject. In some aspects, persistence is quantified as copies of DNA or plasmid encoding the receptor, e.g., CAR, per microgram of DNA, or as the number of receptor-expressing, e.g., CAR-expressing, cells per microliter of the sample, e.g., of blood or serum, or per total number of peripheral blood mononuclear cells (PBMCs) or white blood cells or T cells per microliter of the sample.

In some embodiments, the cells are detected in the subject at or at least at 4, 14, 15, 27, or 28 days following the administration of the T cells, e.g., CAR-expressing T cells. In some aspects, the cells are detected at or at least at 2, 4, or 6 weeks following, or 3, 6, 12, 18, 24, 30 or 36 months, or 1, 2, 3, 4, 5, or more years, following the administration of the T cells, e.g., CAR-expressing T cells and/or the gamma secretase inhibitor.

In some embodiments, the persistence of receptor-expressing cells (e.g. CAR-expressing cells) in the subject by the methods, following the administration of the T cells, e.g., CAR-expressing T cells and/or the gamma secretase inhibitor, is greater as compared to that which would be achieved by alternative methods such as those involving the administration of the immunotherapy alone, e.g., administration the T cells, e.g., CAR-expressing T cells, in the absence of the gamma secretase inhibitor.

The exposure, e.g., number of cells, e.g. T cells administered for T cell therapy, indicative of expansion and/or persistence, may be stated in terms of maximum numbers of the cells to which the subject is exposed, duration of detectable cells or cells above a certain number or percentage, area under the curve for number of cells over time, and/or combinations thereof and indicators thereof. Such outcomes may be assessed using known methods, such as qPCR to detect copy number of nucleic acid encoding the recombinant receptor compared to total amount of nucleic acid or DNA in the particular sample, e.g., blood, serum, plasma or tissue, such as a tumor sample, and/or flow cytometric assays detecting cells expressing the receptor generally using antibodies specific for the receptors. Cell-based assays may also be used to detect the number or percentage of functional cells, such as cells capable of binding to and/or neutralizing and/or inducing responses, e.g., cytotoxic responses, against cells of the disease or condition or expressing the antigen recognized by the receptor.

In some aspects, increased exposure of the subject to the cells includes increased expansion of the cells. In some embodiments, the receptor expressing cells, e.g. CAR-expressing cells, expand in the subject following administration of the T cells, e.g., CAR-expressing T cells, and/or following administration of gamma secretase inhibitor. In some aspects, the methods result in greater expansion of the cells compared with other methods, such as those involving the administration of the T cells, e.g., CAR-expressing T cells, in the absence of administering the gamma secretase inhibitor.

In some aspects, the method results in high in vivo proliferation of the administered cells, for example, as measured by flow cytometry. In some aspects, high peak proportions of the cells are detected. For example, in some embodiments, at a peak or maximum level following the administration of the T cells, e.g., CAR-expressing T cells and/or the gamma secretase inhibitor, in the blood or disease-site of the subject or white blood cell fraction thereof, e.g., PBMC fraction or T cell fraction, at least about 10%, at least about 20%, at least about 30%, at least about 40%, at least about 50%, at least about 60%, at least about 70%, at least about 80%, or at least about 90% of the cells express the recombinant receptor, e.g., the CAR.

In some embodiments, the method results in a maximum concentration, in the blood or serum or other bodily fluid or organ or tissue of the subject, of at least 100, 500, 1000, 1500, 2000, 5000, 10,000 or 15,000 copies of or nucleic acid encoding the receptor, e.g., the CAR, per microgram of DNA, or at least 0.1, 0.2, 0.3, 0.4, 0.5, 0.6, 0.7, 0.8, or 0.9 receptor-expressing, e.g., CAR-expressing cells per total number of peripheral blood mononuclear cells (PBMCs), total number of mononuclear cells, total number of T cells, or total number of microliters. In some embodiments, the cells expressing the receptor are detected as at least 10, 20, 30, 40, 50, or 60% of total PBMCs in the blood of the subject, and/or at such a level for at least 1, 2, 3, 4, 5, 6, 7, 8, 9, 10, 11, 12, 24, 36, 48, or 52 weeks following the T cells, e.g., CAR-expressing T cells and/or the gamma secretase inhibitor, or for 1, 2, 3, 4, or 5, or more years following such administration.

In some aspects, the method results in at least a 2-fold, at least a 4-fold, at least a 10-fold, or at least a 20-fold increase in copies of nucleic acid encoding the recombinant receptor, e.g., CAR, per microgram of DNA, e.g., in the serum, plasma, blood or tissue, e.g., tumor sample, of the subject.

In some embodiments, cells expressing the receptor are detectable in the serum, plasma, blood or tissue, e.g., tumor sample, of the subject, e.g., by a specified method, such as qPCR or flow cytometry-based detection methods, at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 or more days following administration of the T cells, e.g., CAR-expressing T cells, or after administration of the gamma secretase inhibitor, for at least at or about 2, 3, 4, 5, 6, 7, 8, 9, 10, 11, 12, 13, 14, 15, 16, 17, 18, 19, 20, 21, 22, 23, or 24 or more weeks following the administration of the T cells, e.g., CAR-expressing T cells, and/or the gamma secretase inhibitor.

In some aspects, at least about $1\times10^2$, at least about $1\times10^3$, at least about $1\times10^4$, at least about $1\times10^5$, or at least about $1\times10^6$ or at least about $5\times10^6$ or at least about $1\times10^7$ or at least about $5\times10^7$ or at least about $1\times10^8$ recombinant receptor-expressing, e.g., CAR-expressing cells, and/or at least 10, 25, 50, 100, 200, 300, 400, or 500, or 1000 receptor-expressing cells per microliter, e.g., at least 10 per microliter, are detectable or are present in the subject or fluid, plasma, serum, tissue, or compartment thereof, such as in the blood, e.g., peripheral blood, or disease site, e.g., tumor, thereof. In some embodiments, such a number or concentration of cells is detectable in the subject for at least about 20 days, at least about 40 days, or at least about 60 days, or at least about 3, 4, 5, 6, 7, 8, 9, 10, 11, or 12 months, or at least 2 or 3 years, following administration of the T cells, e.g., CAR-expressing T cells, and/or following the administration of the gamma secretase inhibitor. Such cell numbers may be as detected by flow cytometry-based or quantitative PCR-based methods and extrapolation to total cell numbers using known methods. See, e.g., Brentjens et al., *Sci Transl Med.* 2013 5 (177), Park et al, Molecular Therapy 15 (4): 825-833 (2007), Savoldo et al., *JCI* 121 (5): 1822-1826 (2011), Davila et al., (2013) *PLoS ONE* 8 (4): e61338, Davila et al., *Oncoimmunology* 1 (9): 1577-1583 (2012), Lamers, *Blood* 2011 117:72-82, Jensen et al., *Biol Blood Marrow Transplant* 2010 September; 16 (9): 1245-1256, Brentjens et al., *Blood* 2011 118 (18): 4817-4828.

In some aspects, the copy number of nucleic acid encoding the recombinant receptor, e.g., vector copy number, per 100 cells, for example in the peripheral blood or bone marrow or other compartment, as measured by immunohistochemistry, PCR, and/or flow cytometry, is at least 0.01, at least 0.1, at least 1, or at least 10, at about 1 week, about 2 weeks, about 3 weeks, about 4 weeks, about 5 weeks, or at least about 6 weeks, or at least about 2, 3, 4, 5, 6, 7, 8. 9, 10, 11, or 12 months or at least 2 or 3 years following administration of the cells, e.g., CAR-expressing T cells, and/or the gamma secretase inhibitor. In some embodiments, the copy number of the vector expressing the receptor, e.g. CAR, per microgram of genomic DNA is at least 100, at least 1000, at least 5000, or at least 10,000, or at least 15,000 or at least 20,000 at a time about 1 week, about 2 weeks, about 3 weeks, or at least about 4 weeks following administration of the T cells, e.g., CAR-expressing T cells, or gamma secretase inhibitor, or at least 2, 3, 4, 5, 6, 7, 8, 9, 10, 11, or 12 months or at least 2 or 3 years following such administration.

In some aspects, the receptor, e.g. CAR, expressed by the cells, is detectable by quantitative PCR (qPCR) or by flow cytometry in the subject, plasma, serum, blood, tissue and/or disease site thereof, e.g., tumor site, at a time that is at least about 3 months, at least about 6 months, at least about 12 months, at least about 1 year, at least about 2 years, at least about 3 years, or more than 3 years, following the administration of the cells, e.g., following the initiation of the administration of the T cells, e.g., CAR-expressing T cells, and/or the gamma secretase inhibitor.

In some embodiments, the area under the curve (AUC) for concentration of receptor- (e.g., CAR-) expressing cells in a fluid, plasma, serum, blood, tissue, organ and/or disease site, e.g. tumor site, of the subject over time following the administration of the T cells, e.g., CAR-expressing T cells and/or gamma secretase inhibitor, is greater as compared to that achieved via an alternative dosing regimen where the subject is administered the T cells, e.g., CAR-expressing T cells, in the absence of administering the gamma secretase inhibitor.

In some aspects, the method results in high in vivo proliferation of the administered cells, for example, as measured by flow cytometry. In some aspects, high peak proportions of the cells are detected. For example, in some embodiments, at a peak or maximum level following the T cells, e.g., CAR-expressing T cells and/or gamma secretase inhibitor, in the blood, plasma, serum, tissue or disease site of the subject or white blood cell fraction thereof, e.g., PBMC fraction or T cell fraction, at least about 10%, at least about 20%, at least about 30%, at least about 40%, at least about 50%, at least about 60%, at least about 70%, at least about 80%, or at least about 90% of the cells express the recombinant receptor, e.g., the CAR.

In some aspects, the increased or prolonged expansion and/or persistence of the dose of cells in the subject administered with the gamma secretase inhibitor is associated with a benefit in tumor related outcomes in the subject. In some embodiments, the tumor related outcome includes a decrease in tumor burden or a decrease in blast marrow in the subject. In some embodiments, the tumor burden is decreased by or by at least at or about 10, 20, 30, 40, 50, 60, 70, 80, 90, or 100 percent after administration of the method. In some embodiments, disease burden, tumor size, tumor volume, tumor mass, and/or tumor load or bulk is reduced following the dose of cells by at least at or about 50%, 60%, 70%, 80%, 90% or more compared a subject that has been treated with a method that does not involve the administration of an gamma secretase inhibitor.

B. T Cell Functional Activity

In some embodiments, parameters associated with therapy or a treatment outcome, which include parameters that can be assessed for the screening steps and/or assessment of treatment of outcomes and/or monitoring treatment outcomes, includes one or more of activity, phenotype, proliferation or function of T cells. In some embodiments, any of the known assays in the art for assessing the activity, phenotypes, proliferation and/or function of the T cells, e.g., T cells administered for T cell therapy, can be used. Prior to and/or subsequent to administration of the cells and/or gamma secretase inhibitor, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., *J. Immunotherapy*, 32 (7): 689-702 (2009), and Herman et al., *J. Immunological Methods*, 285 (1): 25-40 (2004). In certain embodiments, the biological activity of the cells is measured by assaying expression and/or secretion of one or more cytokines, such as CD107a, IFNγ, IL-2, GM-CSF and TNFα, and/or by assessing cytolytic activity.

In some embodiments, assays for the activity, phenotypes, proliferation and/or function of the T cells, e.g., T cells administered for T cell therapy include, but are not limited to, ELISPOT, ELISA, cellular proliferation, cytotoxic lymphocyte (CTL) assay, binding to the T cell epitope, antigen or ligand, or intracellular cytokine staining, proliferation assays, lymphokine secretion assays, direct cytotoxicity assays, and limiting dilution assays. In some embodiments, proliferative responses of the T cells can be measured, e.g. by incorporation of 3H-thymidine, BrdU (5-Bromo-2'-Deoxyuridine) or 2'-deoxy-5-ethynyluridine (EdU) into their DNA or dye dilution assays, using dyes such as carboxyfluorescein diacetate succingamma secretase inhibitoryl ester (CFSE), CellTrace Violet, or membrane dye PKH26.

In some embodiments, assessing the activity, phenotypes, proliferation and/or function of the T cells, e.g., T cells administered for T cell therapy, include measuring cytokine production from T cells, and/or measuring cytokine production in a biological sample from the subject, e.g., plasma, serum, blood, and/or tissue samples, e.g., tumor samples. In some cases, such measured cytokines can include, without limitation, interleukin-2 (IL-2), interferon-gamma (IFNγ), interleukin-4 (IL-4), TNF-alpha (TNFα), interleukin-6 (IL-6), interleukin-10 (IL-10), interleukin-12 (IL-12), granulocyte-macrophage colony-stimulating factor (GM-CSF), CD107a, and/or TGF-beta (TGFβ). Assays to measure cytokines are well known in the art, and include but are not limited to, ELISA, intracellular cytokine staining, cytometric bead array, RT-PCR, ELISPOT, flow cytometry and bio-assays in which cells responsive to the relevant cytokine are tested for responsiveness (e.g. proliferation) in the presence of a test sample.

In some embodiments, assessing the activity, phenotypes, proliferation and/or function of the T cells, e.g., T cells administered for T cell therapy, include assessing cell phenotypes, e.g., expression of particular cell surface markers. In some embodiments, the T cells, e.g., T cells administered for T cell therapy, are assessed for expression of T cell activation markers, T cell exhaustion markers, and/or T cell differentiation markers. In some embodiments, the cell phenotype is assessed before administration. In some embodiments, the cell phenotype is assessed after administration. T cell activation markers, T cell exhaustion markers, and/or T cell differentiation markers for assessment include any markers known in the art for particular subsets of T cells, e.g., CD25, CD38, human leukocyte antigen-DR (HLA-DR), CD69, CD44, CD137, KLRG1, CD62L$^{Low}$, CCR7$^{low}$, CD71, CD2, CD54, CD58, CD244, CD160, programmed cell death protein 1 (PD-1), lymphocyte activation gene 3 protein (LAG-3), T-cell immunoglobulin domain and mucin domain protein 3 (TIM-3), cytotoxic T lymphocyte antigen-4 (CTLA-4), band T lymphocyte attenuator (BTLA) and/or T-cell immunoglobulin and immunoreceptor tyrosine-based inhibitory motif domain (TIGIT) (see, e.g., Liu et al., Cell Death and Disease (2015) 6, e1792). In some embodiments, the assessed cell surface marker is CD25, PD-1 and/or TIM-3. In some embodiments, the assessed cell surface marker is CD25.

In some aspects, detecting the expression levels includes performing an in vitro assay. In some embodiments, the in vitro assay is an immunoassay, an aptamer-based assay, a histological or cytological assay, or an mRNA expression level assay. In some embodiments, the parameter or parameters for one or more of each of the one or more factors, effectors, enzymes and/or surface markers are detected by an enzyme linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay or avidity assay. In some embodiments, detection of cytokines and/or surface markers is determined using a binding reagent that specifically binds to at least one biomarker. In some cases, the binding reagent is an antibody or antigen-binding fragment thereof, an aptamer or a nucleic acid probe.

In some embodiments, the administration of the gamma secretase inhibitor increases the level of circulating CAR T cells.

C. Disease Burden

In some embodiments, parameters associated with therapy or a treatment outcome, which include parameters that can be assessed for the screening steps and/or assessment of treatment of outcomes and/or monitoring treatment outcomes, includes tumor or disease burden. The administration of the immunotherapy, such as a T cell therapy (e.g. CAR-expressing T cells) and/or the gamma secretase inhibitor, can reduce or prevent the expansion or burden of the disease or condition in the subject. For example, where the disease or condition is a tumor, the methods generally reduce tumor size, bulk, metastasis, percentage of blasts in the bone marrow or molecularly detectable cancer and/or improve prognosis or survival or other symptom associated with tumor burden.

In some embodiments, the provided methods result in a decreased tumor burden in treated subjects compared to alternative methods in which the immunotherapy, such as a T cell therapy (e.g. CAR-expressing T cells) is given without administration of the gamma secretase inhibitor. It is not necessary that the tumor burden actually be reduced in all subjects receiving the combination therapy, but that tumor burden is reduced on average in subjects treated, such as based on clinical data, in which a majority of subjects treated with such a combination therapy exhibit a reduced tumor burden, such as at least 50%, 60%, 70%, 80%, 90%, 95% or more of subjects treated with the combination therapy, exhibit a reduced tumor burden.

Disease burden can encompass a total number of cells of the disease in the subject or in an organ, tissue, or bodily fluid of the subject, such as the organ or tissue of the tumor or another location, e.g., which would indicate metastasis. For example, tumor cells may be detected and/or quantified in the blood, lymph or bone marrow in the context of certain hematological malignancies. Disease burden can include, in some embodiments, the mass of a tumor, the number or extent of metastases and/or the percentage of blast cells present in the bone marrow.

In some embodiments, the subject has a myeloma, a lymphoma or a leukemia. In some embodiments, the subject has a non-Hodgkin lymphoma (NHL), an acute lymphoblastic leukemia (ALL), a chronic lymphocytic leukemia (CLL), a diffuse large B-cell lymphoma (DLBCL) or a myeloma, e.g., a multiple myeloma (MM). In some embodiments, the subject has a MM or a DBCBL.

In some embodiments, the subject has a solid tumor.

In some embodiments, the subject has a MM. In some cases, the MM is a relapsed and/or refractory MM. In the case of MM, exemplary parameters to assess the extent of disease burden include such parameters as number of clonal plasma cells (e.g., >10% on bone marrow biopsy or in any quantity in a biopsy from other tissues; plasmacytoma), presence of monoclonal protein (paraprotein) in either serum or urine, evidence of end-organ damage felt related to the plasma cell disorder (e.g., hypercalcemia (corrected calcium >2.75 mmol/l); renal insufficiency attributable to myeloma; anemia (hemoglobin <10 g/dl); and/or bone lesions (lytic lesions or osteoporosis with compression fractures)).

In the case of DLBCL, exemplary parameters to assess the extent of disease burden include such parameters as cellular morphology (e.g., centroblastic, immunoblastic, and anaplastic cells), gene expression, miRNA expression and protein expression (e.g., expression of BCL2, BCL6, MUM1, LMO2, MYC, and p21).

In the case of leukemia, the extent of disease burden can be determined by assessment of residual leukemia in blood or bone marrow. In some embodiments, a subject exhibits morphologic disease if there are greater than or equal to 5% blasts in the bone marrow, for example, as detected by light microscopy. In some embodiments, a subject exhibits complete or clinical remission if there are less than 5% blasts in the bone marrow.

In some embodiments, for leukemia, a subject may exhibit complete remission, but a small proportion of morphologically undetectable (by light microscopy techniques) residual leukemic cells are present. A subject is said to exhibit minimum residual disease (MRD) if the subject exhibits less than 5% blasts in the bone marrow and exhibits molecularly detectable cancer. In some embodiments, molecularly detectable cancer can be assessed using any of a variety of molecular techniques that permit sensitive detection of a small number of cells. In some aspects, such techniques include PCR assays, which can determine unique Ig/T-cell receptor gene rearrangements or fusion transcripts produced by chromosome translocations. In some embodiments, flow cytometry can be used to identify cancer cells based on leukemia-specific immunophenotypes. In some embodiments, molecular detection of cancer can detect as few as 1 leukemia cell in 100,000 normal cells. In some embodiments, a subject exhibits MRD that is molecularly detectable if at least or greater than 1 leukemia cell in 100,000 cells is detected, such as by PCR or flow cytometry. In some embodiments, the disease burden of a subject is molecularly undetectable or MRD, such that, in some cases, no leukemia cells are able to be detected in the subject using PCR or flow cytometry techniques.

In some embodiments, the methods and/or administration of an immunotherapy, such as a T cell therapy (e.g. CAR-expressing T cells) and/or gamma secretase inhibitor decrease(s) disease burden as compared with disease burden at a time immediately prior to the administration of the immunotherapy, e.g., T cell therapy and/or gamma secretase inhibitor.

In some aspects, administration of the immunotherapy, e.g. T cell therapy and/or gamma secretase inhibitor, may prevent an increase in disease burden, and this may be evidenced by no change in disease burden.

In some embodiments, the method reduces the burden of the disease or condition, e.g., number of tumor cells, size of tumor, duration of patient survival or event-free survival, to a greater degree and/or for a greater period of time as compared to the reduction that would be observed with a comparable method using an alternative therapy, such as one in which the subject receives immunotherapy, e.g. T cell therapy alone, in the absence of administration of the gamma secretase inhibitor In some embodiments, disease burden is reduced to a greater extent or for a greater duration following the combination therapy of administration of the immunotherapy, e.g., T cell therapy, and the gamma secretase inhibitor, compared to the reduction that would be effected by administering each of the agent alone, e.g., administering the gamma secretase inhibitor to a subject having not received the immunotherapy, e.g. T cell therapy; or administering the immunotherapy, e.g. T cell therapy, to a subject having not received the gamma secretase inhibitor.

In some embodiments, the burden of a disease or condition in the subject is detected, assessed, or measured. Disease burden may be detected in some aspects by detecting the total number of disease or disease-associated cells, e.g., tumor cells, in the subject, or in an organ, tissue, or bodily fluid of the subject, such as blood or serum. In some embodiments, disease burden, e.g. tumor burden, is assessed by measuring the mass of a solid tumor and/or the number or extent of metastases. In some aspects, survival of the subject, survival within a certain time period, extent of survival, presence or duration of event-free or symptom-free survival, or relapse-free survival, is assessed. In some embodiments, any symptom of the disease or condition is assessed. In some embodiments, the measure of disease or condition burden is specified. In some embodiments, exemplary parameters for determination include particular clinical outcomes indicative of amelioration or improvement in the disease or condition, e.g., tumor. Such parameters include: duration of disease control, including complete response (CR), partial response (PR) or stable disease (SD) (see, e.g., Response Evaluation Criteria In Solid Tumors (RECIST) guidelines), objective response rate (ORR), progression-free survival (PFS) and overall survival (OS). Specific thresholds for the parameters can be set to determine the efficacy of the method of combination therapy provided herein.

In some aspects, disease burden is measured or detected prior to administration of the immunotherapy, e.g. T cell therapy, following the administration of the immunotherapy, e.g. T cell therapy but prior to administration of the gamma secretase inhibitor, following administration of the gamma secretase inhibitor but prior to the administration of the immunotherapy, e.g., T cell therapy, and/or following the administration of both the immunotherapy, e.g. T cell therapy and the gamma secretase inhibitor. In the context of multiple administration of one or more steps of the combination therapy, disease burden in some embodiments may be measured prior to or following administration of any of the steps, doses and/or cycles of administration, or at a time between administration of any of the steps, doses and/or cycles of administration.

In some embodiments, the burden is decreased by or by at least at or about 10, 20, 30, 40, 50, 60, 70, 80, 90, or 100 percent by the provided methods compared to immediately prior to the administration of the gamma secretase inhibitor and the immunotherapy, e.g. T cell therapy. In some embodiments, disease burden, tumor size, tumor volume, tumor mass, and/or tumor load or bulk is reduced following administration of the immunotherapy, e.g. T cell therapy and the gamma secretase inhibitor, by at least at or about 10, 20, 30, 40, 50, 60, 70, 80, 90% or more compared to that immediately prior to the administration of the immunotherapy, e.g. T cell therapy and/or the gamma secretase inhibitor.

In some embodiments, reduction of disease burden by the method comprises an induction in morphologic complete remission, for example, as assessed at 1 month, 2 months, 3 months, or more than 3 months, after administration of, e.g., initiation of, the combination therapy.

In some aspects, an assay for minimal residual disease, for example, as measured by multiparametric flow cytometry, is negative, or the level of minimal residual disease is less than about 0.3%, less than about 0.2%, less than about 0.1%, or less than about 0.05%.

In some embodiments, the event-free survival rate or overall survival rate of the subject is improved by the methods, as compared with other methods. For example, in some embodiments, event-free survival rate or probability for subjects treated by the methods at 6 months following the method of combination therapy provided herein, is greater than about 40%, greater than about 50%, greater than about 60%, greater than about 70%, greater than about 80%, greater than about 90%, or greater than about 95%. In some aspects, overall survival rate is greater than about 40%, greater than about 50%, greater than about 60%, greater than about 70%, greater than about 80%, greater than about 90%, or greater than about 95%. In some embodiments, the subject treated with the methods exhibits event-free survival, relapse-free survival, or survival to at least 6 months, or at least 1, 2, 3, 4, 5, 6, 7, 8, 9, or 10 years. In some embodiments, the time to progression is improved, such as a time to progression of greater than at or about 6 months, or at least 1, 2, 3, 4, 5, 6, 7, 8, 9, or 10 years.

In some embodiments, following treatment by the method, the probability of relapse is reduced as compared to other methods. For example, in some embodiments, the probability of relapse at 6 months following the method of combination therapy, is less than about 80%, less than about 70%, less than about 60%, less than about 50%, less than about 40%, less than about 30%, less than about 20%, or less than about 10%.

IV. Articles of Manufacture and Kits

Also provided are articles of manufacture containing a gamma secretase inhibitor, and components for the immunotherapy, e.g., antibody or antigen binding fragment thereof or T cell therapy, e.g. engineered cells, and/or compositions thereof. The articles of manufacture may include a container and a label or package insert on or associated with the container. Suitable containers include, for example, bottles, vials, syringes, IV solution bags, etc. The containers may be formed from a variety of materials such as glass or plastic. The container in some embodiments holds a composition which is by itself or combined with another composition effective for treating, preventing and/or diagnosing the condition. In some embodiments, the container has a sterile access port. Exemplary containers include an intravenous solution bags, vials, including those with stoppers pierceable by a needle for injection, or bottles or vials for orally administered agents. The label or package insert may indicate that the composition is used for treating a disease or condition.

The article of manufacture may include (a) a first container with a composition contained therein, wherein the composition includes the antibody or engineered cells used for the immunotherapy, e.g. T cell therapy; and (b) a second container with a composition contained therein, wherein the composition includes the second agent, such as a gamma secretase inhibitor. The article of manufacture may further include a package insert indicating that the compositions can be used to treat a particular condition. Alternatively, or additionally, the article of manufacture may further include another or the same container comprising a pharmaceutically-acceptable buffer. It may further include other materials such as other buffers, diluents, filters, needles, and/or syringes.

V. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, a "subject" is a mammal, such as a human or other animal, and typically is human. In some embodiments, the subject, e.g., patient, to whom the immunomodulatory polypeptides, engineered cells, or compositions, such as containing a compound, e.g. gamma secretase inhibitor, are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent. In particular embodiments, the subject is a human.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or engineered cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the immunomodulatory polypeptides or engineered cells administered. In some embodiments, the provided methods involve administering the immunomodulatory polypeptides, engineered cells, or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48:1073).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors." Among the vectors are viral vectors, such as retroviral, e.g., gammaretroviral and lentiviral vectors.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

As used herein, a composition refers to any mixture of two or more products, substances, or compounds, including cells. It may be a solution, a suspension, liquid, powder, a paste, aqueous, non-aqueous or any combination thereof.

VI. EXEMPLARY EMBODIMENTS

Among the provided embodiments are:
1. A method of treatment, the method comprising:
(a) administering a cell therapy to a subject having a disease or disorder, said cell therapy comprising a dose of genetically engineered cells expressing a recombinant receptor; and
(b) administering to the subject LY3039478 or a compound of the structure:

Compound 1

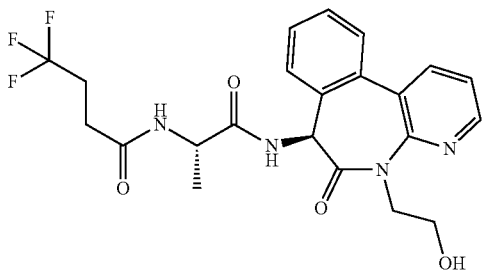

or a stereoisomer or a pharmaceutically acceptable salt or hydrate of any of the foregoing.
2. A method of treatment, the method comprising administering a cell therapy to a subject having a disease or disorder, said cell therapy comprising a dose of genetically engineered cells expressing a recombinant receptor, wherein, at the time of initiation of the administration of the cell therapy, the subject has been previously administered, and/or is undergoing treatment with, LY3039478 or a compound of the structure:

Compound 1

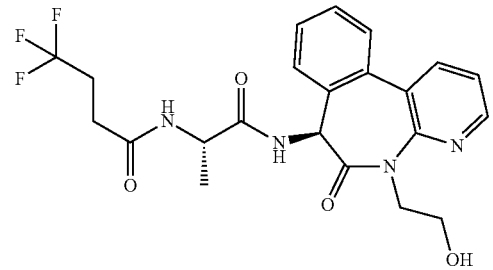

or a stereoisomer or a pharmaceutically acceptable salt or hydrate of any of the foregoing.
3. A method of treatment, the method comprising administering to a subject having a disease or disorder LY3039478 or a compound of the structure:

Compound 1

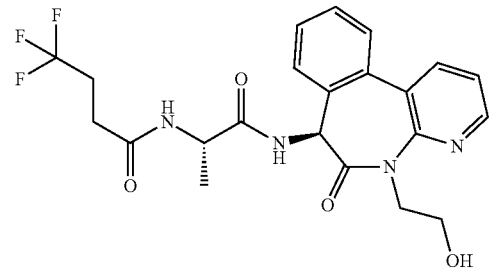

or a stereoisomer or a pharmaceutically acceptable salt or hydrate of any of the foregoing,
wherein, at the time of initiation of the administration, the subject has been previously administered, and/or is undergoing treatment with, a cell therapy, said cell therapy comprising a dose of genetically engineered cells expressing a recombinant receptor.
4. The method of any of embodiments 1-3, wherein the recombinant receptor specifically binds to a target antigen associated with the disease or disorder.
5. The method of embodiment 4, wherein the target antigen is selected from among, B cell maturation antigen (BCMA), carbonic anhydrase 9 (CAIX), Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor. (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag.

6. The method of embodiment 4 or embodiment 5, wherein the target antigen is Muc1.

7. The method of embodiment 4 or embodiment 5, wherein the target antigen is BCMA.

8. The method of embodiment 7, wherein the BCMA is surface BCMA.

9. The method of embodiment 8, wherein binding of the recombinant receptor to surface BCMA or a measure indicative of function or activity of recombinant receptor-expressing cells, following exposure to cells expressing surface BCMA, is not reduced or blocked or is not substantially reduced or blocked in the presence of a soluble or shed form of the BCMA.

10. The method of embodiment 9, wherein the concentration or amount of the soluble or shed form of the BCMA corresponds to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA recombinant receptor, optionally a reference anti-BCMA CAR, in the same assay.

11. A method of treatment, the method comprising:
(a) administering a cell therapy to a subject having a disease or disorder, said cell therapy comprising a dose of genetically engineered cells expressing a chimeric antigen receptor (CAR) comprises an antigen-binding domain that specifically binds to surface B cell maturation antigen (BCMA); and
(b) administering to the subject an inhibitor of gamma secretase,
wherein binding of the CAR to surface BCMA or a measure indicative of function or activity of the CAR-expressing cells, following exposure to cells expressing surface BCMA, is not reduced or blocked or is not substantially reduced or blocked in the presence of a soluble or shed form of the BCMA,
optionally at a concentration or amount of the soluble or shed form of the BCMA corresponding to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA CAR in the same assay.

12. A method of treatment, the method comprising administering a cell therapy to a subject having a disease or disorder, said cell therapy comprising a dose of genetically engineered cells expressing a chimeric antigen receptor that specifically binds to surface B cell maturation antigen (BCMA), wherein:
binding of the CAR to surface BCMA or a measure indicative of function or activity of the CAR-expressing cells, following exposure to cells expressing surface BCMA, is not reduced or blocked or is not substantially reduced or blocked in the presence of a soluble or shed form of the BCMA, optionally at a concentration or amount of the soluble or shed form of the BCMA corresponding to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA CAR in the same assay; and
at the time of initiation of the administration of the cell therapy, the subject has been previously administered, and/or is undergoing treatment with, an inhibitor of gamma secretase.

13. A method of treatment, the method comprising administering an inhibitor of gamma secretase to a subject having a disease or disorder, wherein, at the time of initiation of the administration of the inhibitor, the subject has been previously administered, and/or is undergoing treatment with, a cell therapy, said cell therapy comprising a dose of genetically engineered cells expressing a chimeric antigen receptor that specifically binds surface B cell maturation antigen (BCMA),
wherein binding of the CAR to surface BCMA or a measure indicative of function or activity of the CAR-expressing cells, following exposure to cells expressing surface BCMA, is not reduced or blocked or is not substantially reduced or blocked in the presence of a soluble or shed form of the BCMA,
optionally at a concentration or amount of the soluble or shed form of the BCMA corresponding to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA CAR in the same assay.

14. The method of any of embodiments 1-13, wherein the method comprises selecting a subject having a cancer in which cells of the cancer in the subject (i) express CD138, surface CD38 or a surface plasma cell marker or are derived from plasma cells and (ii) comprise low expression of surface B cell maturation antigen (BCMA) and/or a level of expression of surface BCMA below a threshold level;

15. The method of embodiment 14, wherein the cell therapy and/or the gamma secretase inhibitor is administered to the selected subject.

16. The method of embodiment 14 or embodiment 15, wherein the threshold level of expression of surface BCMA is lower than the average or median expression or level of surface BCMA on plasma cells in a plurality of control subjects, optionally wherein the control subjects are a group of healthy or normal subjects.

17. The method of any of embodiments 14-16, wherein;
the low expression of surface BCMA is present when less than or less than about 60%, less than or less than about 50%, less than or less than about 40%, less than or less than about 30%, less than or less than about 20% or less than or less than about 10% of the plasma cells, or cells with a plasma marker or phenotype or the cancer cells, in the subject express surface BCMA; or the threshold level of surface BCMA is less than or less than about 60%, less than or less than about 50%, less than or less than about 40%, less than or less than about 30%, less than or less than about 20% or less than or less than about 10% of the plasma cells, or cells with a plasma marker or phenotype or the cancer cells, in the subject that express surface BCMA.

18. The method of any of embodiments 14-17, wherein expression of surface BCMA is determined by flow cytometry and/or an immunoassay.

19. The method of any of embodiments 14-18, wherein binding of the recombinant receptor to surface BCMA or a measure indicative of function or activity of the recombinant receptor-expressing cells, following exposure to cells expressing surface BCMA, is not reduced or blocked or is not substantially reduced or blocked in the presence of a soluble or shed form of the BCMA.

20 The method of embodiment 19, wherein the concentration or amount of the soluble or shed form of the BCMA corresponding to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA recombinant receptor, optionally a reference anti-BCMA CAR, in the same assay.

21. The method of any one of embodiments 1-20, wherein the gamma secretase inhibitor inhibits intramembrane cleavage of BCMA.

22. The method of embodiment 21, wherein the gamma secretase inhibitor inhibits intramembrane cleavage of BCMA with a half-maximal inhibitory concentration ($IC_{50}$) of 0.01 nM to 10 nM, 0.01 nM to 5 nM, 0.01 nM to 1 nM, 0.01 nM to 0.5 nM, 0.01 nM to 0.35 nM, 0.01 nM to 0.25 nM, 0.01 nM to 0.1 nM, 0.01 nM to 0.05 nM, 0.05 nM to 10 nM, 0.05 nM to 5 nM, 0.05 nM to 1 nM, 0.05 nM to 0.5 nM, 0.05 nM to 0.35 nM, 0.05 nM to 0.25 nM, 0.05 nM to 0.1 nM, 0.1 nM to 10 nM, 0.1 nM to 5 nM, 0.1 nM to 1 nM, 0.1 nM, to 0.5 nM, 0.1 nM to 0.35 nM, 0.1 nM to 0.25 nM, 0.25 nM to 10 nM, 0.25 nM to 5 nM, 0.25 nM to 1 nM, 0.25 nM to 0.5 nM, 0.25 nM to 0.35 nM, 0.35 nM to 10 nM, 0.35 nM to 5 nM, 0.35 nM to 1 nM, 0.35 nM to 0.5 nM, 0.5 nM to 10 nM, 0.5 nM to 5 nM, 0.5 nM to 1 nM, 1 nM to 10 nM, 1 nM to 5 nM or 5 nM to 10 nM.

23. The method of embodiment 21 or embodiment 22, wherein the gamma secretase inhibitor inhibits intramembrane cleavage of BCMA with a half-maximal inhibitory concentration ($IC_{50}$) of less than or less than about 10 nM, 5 nM, 1 nM, 0.5 nM, 0.35 nM, 0.25 nM, 0.1 nM, 0.05 nM or 0.01 nM or less.

24. A method of treatment, the method comprising:
(a) administering a cell therapy to a subject having a disease or disorder, said cell therapy comprising a dose of genetically engineered cells expressing a recombinant receptor, wherein the recombinant receptor does not specifically bind to surface B cell maturation antigen (BCMA); and
(b) administering an inhibitor of gamma secretase.

25. A method of treatment, the method comprising administering a cell therapy to a subject having a disease or disorder, said cell therapy comprising a dose of genetically engineered cells expressing a recombinant receptor, wherein the recombinant receptor does not specifically bind to surface B cell maturation antigen (BCMA), wherein, at the time of initiation of the administration of the cell therapy, the subject has been previously administered, and/or is undergoing treatment with, an inhibitor of gamma secretase.

26. A method of treatment, the method comprising administering an inhibitor of gamma secretase to a subject having a disease or disorder, wherein, at the time of initiation of the administration of the inhibitor, the subject has been previously administered, and/or is undergoing treatment with, a cell therapy, said cell therapy comprising a dose of genetically engineered cells expressing a recombinant receptor, wherein the recombinant receptor does not specifically bind to surface B cell maturation antigen (BCMA).

27. The method of any of embodiments 24-26, wherein the recombinant receptor specifically binds to a target antigen associated with the disease or disorder.

28. The method of embodiment 27, wherein the target antigen is selected from among, carbonic anhydrase 9 (CAIX), Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag.

29. A method of modulating activity of a cell therapy, the method comprising
(a) administering a cell therapy to a subject having a disease or disorder, said cell therapy comprising a dose of genetically engineered cells expressing a recombinant receptor; and
(b) subsequent to the administration in (a) administering to the subject an inhibitor of gamma secretase.

30. A method of modulating activity of a cell therapy, the method comprising administering an inhibitor of gamma secretase to a subject having a disease or disorder, wherein, at the time of initiation of the administration of the inhibitor, the subject has been previously administered, and/or is undergoing treatment with, a cell therapy, said cell therapy comprising a dose of genetically engineered cells expressing recombinant receptor.

31. The method of embodiment 29 or embodiment 30, wherein the recombinant receptor specifically binds to a target antigen associated with the disease or disorder.

32. The method of embodiment 31, wherein the target antigen is selected from among, B cell maturation antigen (BCMA), carbonic anhydrase 9 (CAIX), Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag.

33. The method of embodiment 27, 28, 31 or 32, wherein the target antigen is Muc1.

34. The method of embodiment 31 or embodiment 32, wherein the target antigen is BCMA.

35. The method of embodiment 34, wherein the BCMA is surface BCMA.

36. The method of any of embodiments 14-35, wherein the gamma secretase inhibitor inhibits or reduces or is capable of inhibiting or reducing cleavage of one or more targets selected from BCMA, Notch 1, Notch 2, Notch 3, Notch 4, Muc1, Ephrin B2, Betaglycan (TGFBR3), CD43, CD44, CSF1R, CXCR1, CXCL16, Delta1, E-cadherein, N-cadherin, HLA-A2, IFNaR2, IL1R1, IL1R2, IL6R or ameloid precursor protein (APP).

37. The method of embodiment 36, wherein the one or more target of the gamma secretase inhibitor comprises Muc1.

38. The method of embodiment 36, wherein the one or more target of the gamma secretase inhibitor comprises BCMA.

39. The method of any of embodiments 36-38, wherein the gamma secretase inhibitor inhibits the target with a half-maximal inhibitory concentration ($IC_{50}$) of 0.01 nM to 1 µM, 0.01 nM to 100 nM, 0.01 nM to 10 nM, 0.01 nM to 5 nM, 0.01 nM to 1 nM, 0.01 nM to 0.5 nM, 0.01 nM to 0.25 nM, 0.01 nM to 0.1 nM, 0.01 nM to 0.05 nM, 0.05 nM to 1 µM, 0.05 nM to 100 nM, 0.05 nM to 10 nM, 0.05 nM to 5 nM, 0.05 nM to 1 nM, 0.05 nM to 0.5 nM, 0.05 nM to 0.25 nM, 0.05 nM to 0.1 nM, 0.1 nM to 1 µM, 0.1 nM to 100 nM, 0.1 nM to 10 nM, 0.1 nM to 5 nM, 0.1 nM to 1 nM, 0.1 nM to 0.5 nM, 0.1 nM to 0.25 nM, 0.25 nM to 1 µM, 0.25 nM to 100 nM, 0.25 nM to 10 nM, 0.25 nM to 5 nM, 0.25 nM to 1 nM, 0.25 nM to 0.5 nM, 0.5 nM to 1 µM, 0.5 nM to 100 nM, 0.5 nM to 10 nM, 0.5 nM to 5 nM, 0.5 nM to 1 nM, 1 nM to 1 µM, 1 nM to 100 nM, 1 nM to 10 nM, 1 nM to 5 nM, 5 nM to 1 µM, 5 nM to 100 nM, 5 nM to 10 nM, 10 nM to 1 µM, 10 nM to 100 nM or 100 nM to 1 µM.

40. The method of any of embodiments 36-39, wherein the gamma secretase inhibitor inhibits the target with a half-maximal inhibitory concentration ($IC_{50}$) of less than or less than about 1 µM, 100 nM, 10 nM, 5 nM, 1 nM, 0.5 nM, 0.35 nM, 0.25 nM, 0.1 nM, 0.05 nM or 0.01 nM or less.

41. The method of any of embodiments 11-40, wherein the gamma secretase inhibitor is a peptide inhibitor or non-peptide inhibitor.

42. The method of embodiment 41, wherein the gamma secretase inhibitor is a peptide inhibitor and the peptide inhibitor is selected from among peptide aldehydes derivatives, difluoroketones derivatives, hydroxyethylene dipeptide isotere derivatives, alpha-helical peptide derivatives and dipeptide analogs.

43. The method of embodiment 41, wherein the gamma secretase inhibitor is a non-peptide inhibitor and the non-peptide inhibitor is a benzodiazepines derivative or a sulfonamides derivative.

44. The method of any of embodiments 41-43, wherein the gamma secretase inhibitor is a transition state inhibitor or non-transition state inhibitor.

45. The method of any of embodiments 41-44, wherein the gamma secretase inhibitor is a nonsteroidal anti-inflammatory drug.

46. The method of any of embodiments 41-45, wherein the gamma secretase inhibitor is selected from LY3039478, secretase inhibitor I (GSI I) Z-Leu-Leu-Norleucine; γ-secretase inhibitor II (GSI II); γ-secretase inhibitor III (GSI III), N-Benzyloxycarbonyl-Leu-leucinal, N-(2-Naphthoyl)-Val-phenylalaninal; γ-secretase inhibitor III (GSI IV); γ-secretase inhibitor III (GSI V), N-Benzyloxycarbonyl-Leu-phenylalaninal; γ-secretase inhibitor III (GSI VI), 1-(S)-endo-N-(1,3,3)-Trimethylbicyclo[2.2.1]hept-2-yl)-4-fluorophenyl Sulfonamide; γ-secretase inhibitor III (GSI VII), Menthyloxycarbonyl-LL-CHO; γ-secretase inhibitor III (GSI IX), (DAPT), N-[N-(3,5-Difluorophenacetyl-L-alanyl)]-S-phenylglycine t-Butyl Ester; γ-secretase inhibitor X (GSI X), {1 S-Benzyl-4R-[1-(1S-carbamoyl-2-phenethyl-carbamoyl)-1S-3-methylbutylcarb-amoyl]-2R-hydroxy-5-phenylpentyl}carbamic Acid tert-butyl Ester; γ-secretase inhibitor XI (GSI XI), 7-Amino-4-chloro-3-methoxyisocoumarin; γ-secretase inhibitor XII (GSI XII), Z-Ile-Leu-CHO; γ-secretase inhibitor XIII (GSI XIII), Z-Tyr-Ile-Leu-CHO; γ-secretase inhibitor XIV (GSI XIV), Z-Cys(t-Bu)-Ile-Leu-CHO; γ-secretase inhibitor XVI (GSI XVI), N-[N-3,5-Difluorophenacetyl]-L-alanyl-S-phenylglycine Methyl Ester; γ-secretase inhibitor XVII (GSI XVII); γ-secretase inhibitor XIX (GSI XIX), benzo[e][1,4]diazepin-3-yl)-butyramide; γ-secretase inhibitor XX (GSI XX), (S,S)-2-[2-(3,5-Difluorophenyl)acetylamino]-N-(5-methyl-6-oxo-6,7-dihydro-5H-dibenzo[b,d]azepin-7-yl)propionamide; γ-secretase inhibitor XXI (GSI XXI), (S,S)-2-[2-(3,5-Difluorophenyl)-acetylamino]-N-(1-methyl-2-oxo-5-phenyl-2-,3-dihydro-1H-benzo[e][1,4]diazepin-3-yl)-propionamide; Gamma40 secretase inhibitor I, N-trans-3,5-Dimethoxycinnamoyl-Ile-leucinal; Gamma40 secretase inhibitor II, N-tert-Butyloxycarbonyl-Gly-Val-Valinal Isovaleryl-V V-Sta-A-Sta-OCH3; MK-0752; MRK-003 (Merck); semagacestat/LY450139; RO4929097; PF-03084,014; BMS-708163; MPC-7869 (γ-secretase modifier), YO-01027 (Dibenzazepine), Compound E ([(2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide], LY411575, L-685,458, BMS-289948 (4-chloro-N-(2,5-difluorophenyl)-N-((1R)-{4-fluoro-2-[3-(1H-imidazol-1-yl)propyl]phenyl}ethyl) benzenesulfonamide hydrochloride) and BMS-299897 (4-[2-((1R)-1-{[(4-chlorophenyl) sulfonyl]-2,5-difluoroanilino}ethyl)-5-fluorophenyl]butanoic acid).

47. The method of any of embodiments 11-46, wherein the gamma secretase inhibitor is LY3039478 or a compound of the structure:

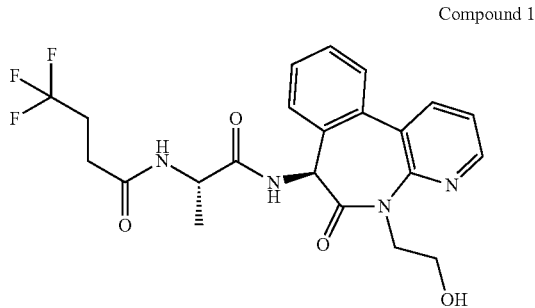 [SMILES: C[C@H](NC(=O)CCC(F)(F)F)C(=O)N[C@@H]1C(=O)N(CCO)c2ncccc2-c2ccccc21]

Compound 1 or a stereoisomer or a pharmaceutically acceptable salt or hydrate of any of the foregoing.

48. The method of any of embodiments 1-47, wherein the subject comprises plasma cells, or cancer cells or myeloma cells or cells expressing plasma cell markers, expressing surface BCMA.

49. The method of any of embodiments 21-48, wherein:
the subject has a cancer in which cells of the cancer in the subject (i) express CD138, surface CD38 or a surface plasma cell marker or are derived from plasma cells and (ii) comprise low expression of surface B cell maturation antigen (BCMA) and/or a level of expression of surface BCMA below a threshold level; and/or
the method further comprises selecting a subject that has a cancer in which cells of the cancer in the subject (i) express CD138, surface CD38 or a surface plasma cell marker or are derived from plasma cells and (ii) comprise low expression of surface B cell maturation antigen (BCMA) and/or a level of expression of surface BCMA below a threshold level.

50. The method of any of embodiments 4-8, 27-29 and 31-49, wherein the target of the gamma secretase inhibitor is the target antigen and the gamma secretase inhibitor inhibits cleavage of the target antigen.

51. The method of any of embodiments 7-23 and 34-50, wherein administration of the inhibitor:
decreases BCMA cleavage or shedding from cells, optionally plasma cells, by greater than or greater than about 5%, 10%, 20%, 30%, 40%, 50%, 60%, 70%, 80%, 90% or more compared to the level of BCMA cleavage or shedding from cells in the subject prior to administration of the inhibitor;
decreases the level or amount of BCMA detected in the serum of a subject by greater than or greater than about 5%, 10%, 20%, 30%, 40%, 50%, 60%, 70%, 80%, 90% or more compared to the level or amount of BCMA in the serum of the subject prior to administration of the inhibitor; and/or
increases expression of surface BCMA on cells, optionally plasma cells by greater than or greater than about 5%, 10%, 20%, 30%, 40%, 50%, 60%, 70%, 80%, 90% or more compared to the level of surface BCMA on the cells in the subject prior to administration of the inhibitor.

52. The method of any of embodiments 1-51, wherein administration of the inhibitor:
decreases cleavage or shedding of the target or the target antigen, optionally BCMA or Muc1, from cells, optionally plasma cells, by greater than or greater than about 5%, 10%, 20%, 30%, 40%, 50%, 60%, 70%, 80%, 90% or more compared to the level of cleavage or shedding of the target or target antigen from cells in the subject prior to administration of the inhibitor;
decreases the level or amount of the target or target antigen, optionally BCMA or Muc1, detected in the serum of a subject by greater than or greater than about 5%, 10%, 20%, 30%, 40%, 50%, 60%, 70%, 80%, 90% or more compared to the level or amount of the target or target antigen in the serum of the subject prior to administration of the inhibitor; and/or increases expression of surface target or target antigen, optionally BCMA or Muc1, on cells, optionally plasma cells, by greater than or greater than about 5%, 10%, 20%, 30%, 40%, 50%, 60%, 70%, 80%, 90% or more compared to the level of surface target or target antigen on the cells in the subject prior to administration of the inhibitor.

53. The method of any of embodiments 1-52, wherein the disease or disorder is a cancer.

54. The method of embodiment 53, wherein the cancer is a B cell malignancy.

55. The method of embodiment 53 or embodiment 54, wherein the cancer is multiple myeloma, plasmacytoma, a cancer of plasma cell origin and/or a cancer of B cell origin.

56. The method of any one of embodiments 1-55, wherein the inhibitor is administered orally, subcutaneously or intravenously.

57. The method of any of embodiments 1-56, wherein the inhibitor is administered orally.

58. The method of any one of embodiments 1-57, wherein the inhibitor is administered at least or is administered six times daily, five times daily, four times daily, three times daily, twice daily, once daily, every other day, three times a week, at least once a week, or only one time.

59. The method of any of embodiments 1-58, wherein the inhibitor is administered three times a week.

60. The method of embodiment 58 or embodiment 59, wherein the administration of the inhibitor is carried out in a treatment cycle that is at least or at least about or 14 days, at least or at least about or 21 days or at least or at least about or 28 days.

61. The method of any of embodiments 1-60, wherein the inhibitor is administered, or each administration of the inhibitor is independently administered, in an amount of 0.5 mg to 500 mg, 0.5 mg to 250 mg, 0.5 mg to 100 mg, 0.5 mg to 50 mg, 0.5 mg to 25 mg, 0.5 mg to 10 mg, 0.5 mg to 5.0 mg, 0.5 mg to 2.5 mg, 0.5 mg to 1.0 mg, 1.0 mg to 500 mg, 1.0 mg to 250 mg, 1.0 mg to 100 mg, 1.0 mg to 50 mg, 1.0 mg to 25 mg, 1.0 mg to 10 mg, 1.0 mg to 5.0 mg, 1.0 mg to 2.5 mg, 2.5 mg to 500 mg, 2.5 mg to 250 mg, 2.5 mg to 100 mg, 2.5 mg to 50 mg, 2.5 mg to 25 mg, 2.5 mg to 10 mg, 2.5 mg to 5.0 mg, 5.0 mg to 500 mg, 5.0 mg to 250 mg, 5.0 mg to 100 mg, 5.0 mg to 50 mg, 5.0 mg to 25 mg, 5.0 mg to 10 mg, 10 mg to 500 mg, 10 mg to 250 mg, 10 mg to 100 mg, 10 mg to 50 mg, 10 mg to 25 mg, 25 mg to 500 mg, 25 mg to 250 mg, 25 mg to 100 mg, 25 mg to 50 mg, 50 mg to 500 mg, 50 mg to 250 mg, 50 mg to 100 mg, 100 mg to 500 mg, 100 mg to 250 mg or 250 mg to 500 mg.

62. The method of any of embodiments 1-61, wherein the inhibitor is administered, or each administration of the inhibitor is independently administered, in an amount that is at least or at least about or is or is about 0.5 mg, 1.0 mg, 2.5 mg, 5.0 mg, 10.0 mg, 25 mg, 50 mg, 100 mg, 250 mg or 500 mg.

63. The method of any one of embodiments of 14-62, wherein the recombinant receptor is a transgenic T cell receptor (TCR) or a functional non-T cell receptor.

64. The method of any one of embodiments of 14-63, wherein the recombinant receptor is a chimeric receptor, which optionally is a chimeric antigen receptor (CAR).

65. The method of any of embodiments 1-13 and 64, wherein the chimeric antigen receptor (CAR) comprises an extracellular antigen-recognition domain that specifically binds to the antigen and an intracellular signaling domain comprising an ITAM.

66. The method of embodiment 65, wherein the intracellular signaling domain comprises and intracellular domain of a CD3-zeta (CD3ζ) chain.

67. The method of embodiment 65 or embodiment 66, wherein the chimeric antigen receptor (CAR) further comprises a costimulatory signaling region. 68. The method of embodiment 67, wherein the costimulatory signaling region comprises a signaling domain derived from CD28 or 4-1BB, optionally human CD28 or human 4-1BB.

69. The method of embodiment 67 or embodiment 68, wherein the costimulatory signaling region is a domain derived from 4-1BB, optionally human 4-1BB.

70. The method of any one of embodiments 1-69, wherein the subject is a human.

71. The method of any of embodiments 1-70, wherein the BCMA is human BCMA or the target antigen is a human antigen.

72. The method of any of embodiments 1-72, wherein the genetically engineered cells comprise T cells or NK cells.

73. The method of embodiment 72, wherein the cell therapy is a T cell therapy and the dose of genetically engineered cells comprises T cells.

74. The method of embodiment 72 or embodiment 73, wherein the T cells are CD4$^+$ and/or CD8+.

75. The method of any of the embodiments 72-74, wherein the T cells are primary T cells obtained from a subject.

76. The method of any of embodiments 1-75, wherein the cell therapy comprises cells that are autologous to the subject.

77. The method of any of embodiments 1-76, wherein the cell therapy comprises cells that are allogeneic to the subject.

78. The method of any of embodiments 1-77, wherein the cell therapy comprises the administration of from or from about $1\times10^5$ to $5\times10^8$ total recombinant receptor-expressing cells, total T cells, or total peripheral blood mononuclear cells (PBMCs), the cell therapy comprises the administration of from or from about $1\times10^5$ to $1\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive.

79. The method of any of embodiments 1-78, wherein the cell therapy comprises the administration of no more than $5\times10^8$ total recombinant receptor-expressing cells, total T cells, or total peripheral blood mononuclear cells (PBMCs), no more than $2.5\times10^8$ total recombinant receptor-expressing cells, total T cells, or total peripheral blood mononuclear cells (PBMCs), no more than $1\times10^8$ total recombinant receptor-expressing cells, total T cells, or total peripheral blood mononuclear cells (PBMCs), no more than $1\times10^7$ total recombinant receptor-expressing cells, total T cells, or total peripheral blood mononuclear cells (PBMCs), no more than $0.5\times10^7$ total recombinant receptor-expressing cells, total T cells, or total peripheral blood mononuclear cells (PBMCs), no more than $1\times10^6$ total recombinant receptor-expressing cells, total T cells, or total peripheral blood mononuclear cells (PBMCs), no more than $0.5\times10^6$ total recombinant receptor-expressing cells, total T cells, or total peripheral blood mononuclear cells (PBMCs).

80. The method of any one of embodiments 1, 4, 5, 14, and 38, wherein the initiation of administration of the inhibitor is prior to, concurrently with or subsequently to initiation of administration of the cell therapy.

81. The method of embodiment 80, wherein the inhibitor is administered prior to initiation of administration of the cell therapy.

82. The method of 1, 2, 4, 5, 14, 15, 38, 39 and 81, wherein initiation of administration of the inhibitor is within, or within about, 1 hours, 2 hour, 6 hours, 12 hours, 24 hours, 48 hours, 72 hours, 96 hours or 1 week prior to the initiation of the administration of the cell therapy.

83. The method of embodiment 80, wherein the inhibitor is administered subsequently to initiation of administration of the cell therapy.

84. The method of 1, 3, 4, 5, 14, 16, 19, 20, 38, 40 and 83, wherein initiation of administration of the inhibitor is within, or within about, 1 hours, 2 hour, 6 hours, 12 hours, 24 hours, 48 hours, 72 hours, 96 hours, 1 week, 14 days, 21 days, 28 days or more after the initiation of the administration of the cell therapy.

85. The method of any of embodiments 1, 3, 4, 5, 14, 16, 19, 20, 38, 40, 83 and 84, wherein the inhibitor is administered at a time in which:
the number of cells of the cell therapy detectable in the blood from the subject is decreased compared to in the subject at a preceding time point after initiation of the administration of the cells;
the number of cells of the cell therapy detectable in the blood is less than or less than about 1.5-fold, 2-fold, 3-fold, 4-fold, 5-fold, 10-fold, 50-fold or 100-fold or less the peak or maximum number of the cells of the cell therapy detectable in the blood of the subject after initiation of administration of the administration of the cells; and/or
at a time after a peak or maximum level of the cells of the cell therapy are detectable in the blood of the subject, the number of cells of or derived from the cells detectable in the blood from the subject is less than less than 10%, less than 5%, less than 1% or less than 0.1% of total peripheral blood mononuclear cells (PBMCs) in the blood of the subject.

86. The method of any of embodiments 1, 3, 4, 5, 14, 16, 19, 20, 38, 40, 83-854, wherein the inhibitor is administered up to 7 days, 14 days, 21 days, 28 days or more after initiation of the administration of the cells.

87. The method of any of embodiments 1-86, wherein the method further comprises administering a lymphodepleting chemotherapy prior to administration of the cell therapy and/or wherein the subject has received a lymphodepleting chemotherapy prior to administration of the cells.

88. The method of embodiment 87, wherein the lymphodepleting chemotherapy comprises administering fludarabine and/or cyclophosphamide to the subject.

89. The method of any of embodiments 1-88, wherein the method further comprises administering a steroid, optionally wherein the steroid is administered prior to, concurrently with and/or subsequently to initiation of administration of the inhibitor, optionally wherein the steroid is administered during the cycle of treatment with the inhibitor.

90. The method of embodiment 89, wherein the steroid is or comprises dexamethasone.

91. The method of any one of embodiments 1-90, wherein the cell therapy exhibits increased or prolonged expansion and/or persistence in the subject as compared to a method in which the cell therapy is administered to the subject in the absence of the gamma secretase inhibitor.

92. The method of any one of embodiments 1-91, wherein the method thereby prevents, reduces or ameliorates one or more symptoms or outcomes of the disease or disorder.

93. A method of treatment, the method comprising:
(a) administering, to a subject having a disease or disorder, a therapeutic agent or therapy that targets or is specific for B cell maturation antigen (BCMA); and
(b) administering a gamma secretase inhibitor to the subject.

94. The method of embodiment 93, wherein the therapeutic agent or therapy is or comprises an antibody or antigen-binding fragment thereof, optionally a bispecific antibody.

95. The method of embodiment 93 or embodiment 94, wherein the therapeutic agent or therapy is a bispecific antibody that further targets or specifically binds to a T cell antigen, optionally CD2 or CD3.

96. The method of embodiment 93 or embodiment 94, wherein the therapeutic agent or therapy is a bispecific antibody that further targets a second antigen, optionally wherein the second antigen is selected from CD19, CD20, CD22, CD33, CD38, CS1, ROR1, GPC3, CD123, IL-13R, CD138, c-Met, EGFRVIII, GD-2, NY-ESO-1, MAGE A3, and glycolipid F77.

97. The method of any of embodiments 93-96, wherein the gamma secretase inhibitor is selected from LY3039478, secretase inhibitor I (GSI I) Z-Leu-Leu-Norleucine; γ-secretase inhibitor II (GSI II); γ-secretase inhibitor III (GSI III), N-Benzyloxycarbonyl-Leu-leucinal, N-(2-Naphthoyl)-Val-phenylalaninal; γ-secretase inhibitor III (GSI IV); γ-secretase inhibitor III (GSI V), N-Benzyloxycarbonyl-Leu-phenylalaninal; γ-secretase inhibitor III (GSI VI), 1-(S)-endo-N-(1,3,3)-Trimethylbicyclo[2.2.1]hept-2-yl)-4-fluorophenyl Sulfonamide; γ-secretase inhibitor III (GSI VII), Menthyloxycarbonyl-LL-CHO; γ-secretase inhibitor III (GSI IX), (DAPT), N-[N-(3,5-Difluorophenacetyl-L-alanyl)]-S-phenylglycine t-Butyl Ester; γ-secretase inhibitor X (GSI X), {1 S-Benzyl-4R-[1-(1S-carbamoyl-2-phenethyl-carbamoyl)-1S-3-methylbutylcarb-amoyl]-2R-hydroxy-5-phenylpentyl}carbamic Acid tert-butyl Ester; γ-secretase inhibitor XI (GSI XI), 7-Amino-4-chloro-3-methoxyisocoumarin; γ-secretase inhibitor XII (GSI XII), Z-Ile-Leu-CHO; γ-secretase inhibitor XIII (GSI XIII), Z-Tyr-Ile-Leu-CHO; γ-secretase inhibitor XIV (GSI XIV), Z-Cys(t-Bu)-Ile-Leu-CHO; γ-secretase inhibitor XVI (GSI XVI), N-[N-3,5-Difluorophenacetyl]-L-alanyl-S-phenylglycine Methyl Ester; γ-secretase inhibitor XVII (GSI XVII); γ-secretase inhibitor XIX (GSI XIX), benzo[e][1,4]diazepin-3-yl)-butyramide; γ-secretase inhibitor XX (GSI XX), (S,S)-2-[2-(3,5-Difluorophenyl)acetylamino]-N-(5-methyl-6-oxo-6,7-dihydro-5H-dibenzo[b,d]azepin-7-yl)propionamide; γ-secretase inhibitor XXI (GSI XXI), (S,S)-2-[2-(3,5-Difluorophenyl)-acetylamino]-N-(1-methyl-2-oxo-5-phenyl-2-,3-dihydro-1H-benzo[e][1,4]diazepin-3-yl)-propionamide; Gamma40 secretase inhibitor I, N-trans-3,5-Dimethoxycinnamoyl-Ile-leucinal; Gamma40 secretase inhibitor II, N-tert-Butyloxycarbonyl-Gly-Val-Valinal Isovaleryl-V V-Sta-A-Sta-OCH3; MK-0752; MRK-003 (Merck); semagacestat/LY450139; RO4929097; PF-03084,014; BMS-708163; MPC-7869 (γ-secretase modifier), YO-01027 (Dibenzazepine), Compound E ([(2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide], LY411575, L-685,458, BMS-289948 (4-chloro-N-(2,5-difluorophenyl)-N-((1R)-{4-fluoro-2-[3-(1H-imidazol-1-yl)propyl]phenyl}ethyl) benzenesulfonamide hydrochloride) and BMS-299897 (4-[2-((1R)-1-{[(4-chlorophenyl) sulfonyl]-2,5-difluoroanilino}ethyl)-5-fluorophenyl}butanoic acid).

98. The method of any of embodiments 93-97, wherein the gamma secretase inhibitor is LY3039478 or a compound of the structure:

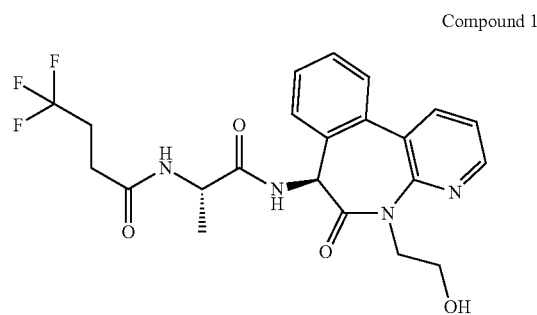

Compound 1 or a stereoisomer or a pharmaceutically acceptable salt or hydrate of any of the foregoing.

99. A combination, comprising:
(a) genetically engineered cells expressing a chimeric antigen receptor (CAR) comprising an antigen binding domain that specifically binds to surface B cell maturation antigen (BCMA); and
(b) an inhibitor of gamma secretase,
wherein binding of the CAR to surface BCMA or a measure indicative of function or activity of the CAR-expressing cells, following exposure to cells expressing surface BCMA, is not reduced or blocked or is not substantially reduced or blocked in the presence of a soluble or shed form of the BCMA,
optionally at a concentration or amount of the soluble or shed form of the BCMA corresponding to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA CAR in the same assay.

100. The combination of embodiment 99, wherein the gamma secretase inhibitor inhibits or reduces or is capable of inhibiting or reducing intramembrane cleavage of BCMA.

101. The combination of embodiment 100, wherein the gamma secretase inhibitor inhibits intramembrane cleavage of BCMA with a half-maximal inhibitory concentration (IC$_{50}$) of 0.01 nM to 10 nM, 0.01 nM to 5 nM, 0.01 nM to 1 nM, 0.01 nM to 0.5 nM, 0.01 nM to 0.35 nM, 0.01 nM to 0.25 nM, 0.01 nM to 0.1 nM, 0.01 nM to 0.05 nM, 0.05 nM to 10 nM, 0.05 nM to 5 nM, 0.05 nM to 1 nM, 0.05 nM to 0.5 nM, 0.05 nM to 0.35 nM, 0.05 nM to 0.25 nM, 0.05 nM to 0.1 nM, 0.1 nM to 10 nM, 0.1 nM to 5 nM, 0.1 nM to 1 nM, 0.1 nM, to 0.5 nM, 0.1 nM to 0.35 nM, 0.1 nM to 0.25 nM, 0.25 nM to 10 nM, 0.25 nM to 5 nM, 0.25 nM to 1 nM, 0.25 nM to 0.5 nM, 0.25 nM to 0.35 nM, 0.35 nM to 10 nM, 0.35 nM to 5 nM, 0.35 nM to 1 nM, 0.35 nM to 0.5 nM, 0.5 nM to 10 nM, 0.5 nM to 5 nM, 0.5 nM to 1 nM, 1 nM to 10 nM, 1 nM to 5 nM or 5 nM to 10 nM.

102. The combination of embodiment 100 or embodiment 101, wherein the gamma secretase inhibitor inhibits intramembrane cleavage of BCMA with a half-maximal inhibitory concentration ($IC_{50}$) of less than or less than about 10 nM, 5 nM, 1 nM, 0.5 nM, 0.35 nM, 0.25 nM, 0.1 nM, 0.05 nM or 0.01 nM or less.

103. A combination, comprising:
   (a) genetically engineered cells expressing a recombinant receptor, wherein the recombinant receptor does not specifically binds to surface B cell maturation antigen (BCMA); and
   (b) an inhibitor of gamma secretase.

104. The method of embodiment 103, wherein the recombinant receptor specifically binds to a target antigen associated with the disease or disorder.

105. The combination of embodiment 104, wherein the target antigen is selected from among, carbonic anhydrase 9 (CAIX), Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag.

106. The combination of embodiment 104 or embodiment 105, wherein the target antigen is Muc1.

107. The combination of any of embodiments 99-106, wherein the gamma secretase inhibitor inhibits or reduces or is capable of inhibiting or reducing cleavage of one or more targets selected from BCMA, Notch 1, Notch 2, Notch 3, Notch 4, Muc1, Ephrin B2, Betaglycan (TGFBR3), CD43, CD44, CSF1R, CXCR1, CXCL16, Delta1, E-cadherin, N-cadherin, HLA-A2, IFNaR2, IL1R1, IL1R2, IL6R or ameloid precursor protein (APP).

108. The combination of embodiment 107, wherein the one or more target of the gamma secretase inhibitor comprises Muc1.

109. The combination of embodiment 107, wherein the one or more target of the gamma secretase inhibitor comprises BCMA.

110. The combination of any of embodiments 103-109, wherein the gamma secretase inhibitor inhibits the target with a half-maximal inhibitory concentration ($IC_{50}$) of 0.01 nM to 1 µM, 0.01 nM to 100 nM, 0.01 nM to 10 nM, 0.01 nM to 5 nM, 0.01 nM to 1 nM, 0.01 nM to 0.5 nM, 0.01 nM to 0.25 nM, 0.01 nM to 0.1 nM, 0.01 nM to 0.05 nM, 0.05 nM to 1 µM, 0.05 nM to 100 nM, 0.05 nM to 10 nM, 0.05 nM to 5 nM, 0.05 nM to 1 nM, 0.05 nM to 0.5 nM, 0.05 nM to 0.25 nM, 0.05 nM to 0.1 nM, 0.1 nM to 1 µM, 0.1 nM to 100 nM, 0.1 nM to 10 nM, 0.1 nM to 5 nM, 0.1 nM to 1 nM, 0.1 nM to 0.5 nM, 0.1 nM to 0.25 nM, 0.25 nM to 1µ, 0.25 nM to 100 nM, 0.25 nM to 10 nM, 0.25 nM to 5 nM, 0.25 nM to 1 nM, 0.25 nM to 0.5 nM, 0.5 nM to 1 µM, 0.5 nM to 100 nM, 0.5 nM to 10 nM, 0.5 nM to 5 nM, 0.5 nM to 1 nM, 1 nM to 1 µM, 1 nM to 100 nM, 1 nM to 10 nM, 1 nM to 5 nM, 5 nM to 1 µM, 5 nM to 100 nM, 5 nM to 10 nM, 10 nM to 1 µM, 10 nM to 100 nM or 100 nM to 1 µM.

111. The combination of any of embodiments 103-110, wherein the gamma secretase inhibitor inhibits the target with a half-maximal inhibitory concentration ($IC_{50}$) of less than or less than about 1 µM, 100 nM, 10 nM, 5 nM, 1 nM, 0.5 nM, 0.35 nM, 0.25 nM, 0.1 nM, 0.05 nM or 0.01 nM or less.

112. The combination of any of embodiments 99-111, wherein the gamma secretase inhibitor is a peptide inhibitor or non-peptide inhibitor.

113. The combination of embodiment 112, wherein the gamma secretase inhibitor is a peptide inhibitor and the peptide inhibitor is selected from among peptide aldehydes derivatives, difluoroketones derivatives, hydroxyethylene dipeptide isotere derivatives, alpha-helical peptide derivatives and dipeptide analogs.

114. The combination of embodiment 113, wherein the gamma secretase inhibitor is a non-peptide inhibitor and the non-peptide inhibitor is a benzodiazepines derivative or a sulfonamides derivative.

115. The combination of any of embodiments 99-114, wherein the gamma secretase inhibitor is a transition state inhibitor or non-transition state inhibitor.

116. The combination of any of embodiments 99-115, wherein the gamma secretase inhibitor is a nonsteroidal anti-inflammatory drug.

117. The combination of any of embodiments 99-116, wherein the gamma secretase inhibitor is selected from LY3039478, secretase inhibitor I (GSI I) Z-Leu-Leu-Norleucine; γ-secretase inhibitor II (GSI II); γ-secretase inhibitor III (GSI III), N-Benzyloxycarbonyl-Leu-leucinal, N-(2-Naphthoyl)-Val-phenylalaninal; γ-secretase inhibitor III (GSI IV); γ-secretase inhibitor III (GSI V), N-Benzyloxy-carbonyl-Leu-phenylalaninal; Y-secretase inhibitor III (GSI VI), 1-(S)-endo-N-(1,3,3)-Trimethylbicyclo[2.2.1]hept-2-yl)-4-fluorophenyl Sulfonamide; γ-secretase inhibitor III (GSI VII), Menthyloxycarbonyl-LL-CHO; γ-secretase inhibitor III (GSI IX), (DAPT), N-[N-(3,5-Difluorophenacetyl-L-alanyl)]-S-phenylglycine t-Butyl Ester; γ-secretase inhibitor X (GSI X), {1 S-Benzyl-4R-[1-(1S-carbamoyl-2-phenethylcarbamoyl)-1S-3-methylbutylcarb-amoyl]-2R-hydroxy-5-phenylpentyl}carbamic Acid tert-butyl Ester; γ-secretase inhibitor XI (GSI XI), 7-Amino-4-chloro-3-methoxyisocoumarin; γ-secretase inhibitor XII (GSI XII), Z-Ile-Leu-CHO; γ-secretase inhibitor XIII (GSI XIII), Z-Tyr-Ile-Leu-CHO; γ-secretase inhibitor XIV (GSI XIV), Z-Cys(t-Bu)-Ile-Leu-CHO; γ-secretase inhibitor XVI (GSI XVI), N-[N-3,5-Difluorophenacetyl]-L-alanyl-S-phenylglycine Methyl Ester; γ-secretase inhibitor XVII (GSI XVII); γ-secretase inhibitor XIX (GSI XIX), benzo[e][1,4]diazepin-3-yl)-butyramide; γ-secretase inhibitor XX (GSI XX), (S,S)-2-[2-(3,5-Difluorophenyl)acetylamino]-N-(5-methyl-6-oxo-6,7-dihydro-5H-dibenzo[b,d]azepin-7-yl)propionamide; γ-secretase inhibitor XXI (GSI XXI), (S,S)-2-[2-(3, 5-Difluorophenyl)-acetylamino]-N-(1-methyl-2-oxo-5-phenyl-2-,3-dihydro-1H-benzo[e][1,4]diazepin-3-yl)- propionamide; Gamma40 secretase inhibitor I, N-trans-3,5-Dimethoxycinnamoyl-Ile-leucinal; Gamma40 secretase inhibitor II, N-tert-Butyloxycarbonyl-Gly-Val-Valinal Isovaleryl-V V-Sta-A-Sta-OCH3; MK-0752; MRK-003 (Merck); semagacestat/LY450139; RO4929097; PF-03084, 014; BMS-708163; MPC-7869 (γ-secretase modifier), YO-01027 (Dibenzazepine), Compound E ([(2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide], LY411575, L-685,458, BMS-289948 (4-chloro-N-(2, 5-difluorophenyl)-N-((1R)-{4-fluoro-2-[3-(1H-imidazol-1-yl)propyl]phenyl}ethyl)benzenesulfonamide hydrochloride) and BMS-299897 (4-[2-((1R)-1-{[(4-chlorophenyl) sulfonyl]-2,5-difluoroanilino}ethyl)-5-fluorophenyl]butanoic acid).

118. The combination of any of embodiments 99-117, wherein the gamma secretase inhibitor is LY3039478 or a compound of the structure:

Compound 1

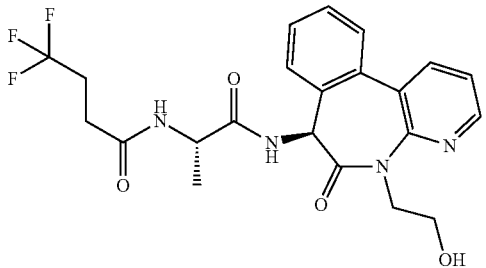

or a stereoisomer or a pharmaceutically acceptable salt or hydrate of any of the foregoing.

119. A combination, comprising:
(a) genetically engineered cells expressing a recombinant receptor; and
(b) LY3039478 or a compound of the structure:

Compound 1

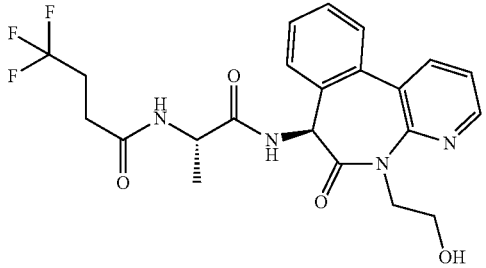

or a stereoisomer or a pharmaceutically acceptable salt or hydrate of any of the foregoing.

120. The combination of embodiment 119, wherein the recombinant receptor specifically binds to a target antigen associated with the disease or disorder.

121. The combination of embodiment 120, wherein the target antigen is selected from among, B cell maturation antigen (BCMA), carbonic anhydrase 9 (CAIX), Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag.

122. The combination of embodiment 120 or embodiment 121, wherein the target antigen is Muc1.

123. The combination of embodiment 120 or embodiment 121, wherein the target antigen is BCMA.

124. The combination of embodiment 123, wherein the BCMA is surface BCMA.

125. The combination of embodiment 124, wherein binding of the recombinant receptor, optionally the CAR, to surface BCMA or a measure indicative of function or activity of the recombinant receptor-expressing cells, optionally CAR-expressing cells, following exposure to cells expressing surface BCMA, is not reduced or blocked or is not substantially reduced or blocked in the presence of a soluble or shed form of the BCMA, optionally at a concentration or amount of the soluble or shed form of the BCMA corresponding to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA recombinant receptor, optionally, anti-BCMA CAR, in the same assay.

126. The combination of any of embodiments 103-125, wherein the recombinant receptor is a transgenic T cell receptor (TCR) or a functional non-T cell receptor.

127. The combination of any of embodiments 103-126, wherein the recombinant receptor is a chimeric receptor, which optionally is a chimeric antigen receptor (CAR).

128. The combination of any of embodiments 99-102 and 127, wherein the chimeric antigen receptor (CAR) comprises an extracellular antigen-recognition domain that specifically binds to the antigen and an intracellular signaling domain comprising an ITAM.

129. The combination of embodiment 128, wherein the intracellular signaling domain comprises and intracellular domain of a CD3-zeta (CD3ζ) chain.

130. The combination of embodiment 128 or embodiment 129, wherein the chimeric antigen receptor (CAR) further comprises a costimulatory signaling region.

131. The combination of embodiment 130, wherein the costimulatory signaling region comprises a signaling domain derived from CD28 or 4-1BB, optionally human CD28 or human 4-1BB.

132. The combination of embodiment 130 or embodiment 131, wherein the costimulatory signaling region is a domain derived from 4-1BB, optionally human 4-1BB.

133. The combination of any of embodiments 99-132, wherein the BCMA is human BCMA or the target antigen is a human antigen.

134. The combination of any of embodiments 99-134, wherein the genetically engineered cells comprise T cells or NK cells.

135. The combination of embodiment 134, wherein the genetically engineered cells comprises T cells.

136. The combination of embodiment 134 or embodiment 135, wherein the T cells are CD4$^+$ and/or CD8+.

137. The combination of any of embodiments 134-136, wherein the T cells are primary T cells obtained from a subject.

138. The combination of any of embodiments 99-137, wherein the genetically engineered cells are formulated as a pharmaceutical composition for administration to a subject, optionally wherein the cells are formulated for administration in one or more unit doses for treating a disease or condition.

139. The combination of any of embodiments 99-138, wherein the gamma secretase inhibitor is formulated as a pharmaceutical composition for administration to a subject, optionally wherein the gamma secretase inhibitor is formulated for administration in one or more unit doses.

140. A kit comprising the combination of any of embodiments 99-139 and instructions for administering the genetically engineered cells and/or the gamma secretase inhibitor to a subject having a disease or disorder.

141. The kit of embodiment 140, further comprising a reagent for detecting expression of B cell maturation antigen (BCMA) on the surface of a cell, and instructions for administering the inhibitor to a subject based on the results of use of the reagent for detecting BCMA on the surface of cells of a cancer in the subject, optionally wherein the cells of the cancer express CD138, surface CD38 or a surface plasma cell marker or are derived from plasma cells.

142. The kit of embodiment 141, wherein the instructions specify administering the inhibitor to the subject if the cells comprise low expression of surface BCMA and/or a level of expression of surface BCMA below a threshold level.

143. The kit of embodiment 142, wherein the threshold level of expression of surface BCMA is lower than the average or median expression or level of surface BCMA on plasma cells in a plurality of control subjects, optionally wherein the control subjects are a group of healthy or normal subjects.

144. The kit of embodiment 142 or embodiment 143, wherein;
the low expression of surface BCMA is present when less than or less than about 60%, less than or less than about 50%, less than or less than about 40%, less than or less than about 30%, less than or less than about 20% or less than or less than about 10% of the plasma cells, or cells with a plasma marker or phenotype or the cancer cells, in the subject express surface BCMA; or
the threshold level of surface BCMA is less than or less than about 60%, less than or less than about 50%, less than or less than about 40%, less than or less than about 30%, less than or less than about 20% or less than or less than about 10% of the plasma cells, or cells with a plasma marker or phenotype or the cancer cells, in the subject that express surface BCMA.

145. The kit of any of embodiments 141-144, further comprising genetically engineered cells expressing a recombinant receptor, optionally wherein the genetically engineered cells are formulated for administration of one or more unit doses to a subject having a disease or condition.

146. The kit of embodiment 145, wherein the recombinant receptor specifically binds to a target antigen associated with the disease or condition.

147. The kit of any of embodiments 140, 145 and 146, wherein the instructions specify administering the gamma secretase inhibitor, or one or more unit doses thereof, to a subject having a disease or disorder prior to, concurrently with or after initiation of administration of a dose of the genetically engineered cells to the subject.

148. The kit of embodiment 147, wherein the instructions specify administering the gamma secretase inhibitor, or one or more unit doses thereof, to a subject having a disease or disorder prior to initiation of administration of a dose of the genetically engineered cells to the subject.

149. The kit of embodiment 148, wherein the instructions specify administering the inhibitor within, or within about, 1 hours, 2 hour, 6 hours, 12 hours, 24 hours, 48 hours, 72 hours, 96 hours or 1 week prior to the initiation of the administration of the cell therapy.

150. The kit of embodiment 147, wherein the instructions specify administering the gamma secretase inhibitor, or one or more unit doses thereof, to a subject having a disease or disorder after initiation of administration of a dose of the genetically engineered cells to the subject.

151. A kit, comprising:
(a) a gamma secretase inhibitor, optionally wherein the gamma secretase inhibitor is formulated in one or more unit doses; and
(b) instructions for administering the gamma secretase inhibitor to a subject after initiation of administration of a cell therapy to a subject, the cell therapy comprising a dose of genetically engineered cells expressing a recombinant receptor.

152. The kit of embodiment 150 or embodiment 151, wherein initiation of administration of the inhibitor is within, or within about, 1 hours, 2 hour, 6 hours, 12 hours, 24 hours, 48 hours, 72 hours, 96 hours, 1 week, 14 days, 21 days, 28 days or more after the initiation of the administration of the dose of genetically engineered cells.

153. The kit of any of embodiments 150-152, wherein the instructions specify the inhibitor is for administration at a time in which:
the number of cells of the cell therapy detectable in the blood from the subject is decreased compared to in the subject at a preceding time point after initiation of the administration of the cells;
the number of cells of the cell therapy detectable in the blood is less than or less than about 1.5-fold, 2-fold, 3-fold, 4-fold, 5-fold, 10-fold, 50-fold or 100-fold or less the peak or maximum number of the cells of the cell therapy detectable in the blood of the subject after initiation of administration of the administration of the cells; and/or
at a time after a peak or maximum level of the cells of the cell therapy are detectable in the blood of the subject, the number of cells of or derived from the cells detectable in the blood from the subject is less than less than 10%, less than 5%, less than 1% or less than. 0.1% of total peripheral blood mononuclear cells (PBMCs) in the blood of the subject.

154. The kit of any of embodiments 150-153, wherein the instructions specify the inhibitor is for administration up to 7 days, 14 days, 21 days, 28 days or more after initiation of the administration of the cells.

155. The kit of any of embodiments 150-154, wherein the recombinant receptor specifically binds to a target antigen associated with the disease or disorder.

156. The kit of embodiment 146 or embodiment 155, wherein the target antigen is selected from among, B cell maturation antigen (BCMA), carbonic anhydrase 9 (CAIX), Her2/neu (receptor tyrosine kinase erbB2), L1-CAM, CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, HMW-MAA, IL-22R-alpha, IL-13R-alpha2, kinase insert domain receptor (kdr), kappa light chain, Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, HLA-AI MAGE A1, HLA-A2 NY-ESO-1, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag.

157. The kit of embodiment 156, wherein the target antigen is Muc1, optionally human Muc1.

158. The kit of embodiment 156, wherein the target antigen is BCMA, optionally human BCMA.

159. The kit of embodiment 158, wherein binding of the recombinant receptor, optionally the CAR, to surface BCMA or a measure indicative of function or activity of the recombinant receptor-expressing cells, optionally CAR-expressing cells, following exposure to cells expressing surface BCMA, is not reduced or blocked or is not substantially reduced or blocked in the presence of a soluble or shed form of the BCMA, optionally at a concentration or amount of the soluble or shed form of the BCMA corresponding to a concentration or amount present in serum or blood or plasma of the subject or of a multiple myeloma patient, or on average in a patient population for the disease or disorder, or at a concentration or amount of the soluble or shed BCMA at which the binding or measure is reduced or blocked, or is substantially reduced or blocked, for cells expressing a reference anti-BCMA recombinant receptor, optionally, anti-BCMA CAR, in the same assay.

160. The kit of any of embodiments 146-159, wherein the recombinant receptor is a transgenic T cell receptor (TCR) or a functional non-T cell receptor.

161. The kit of any of embodiments 146-160, wherein the recombinant receptor is a chimeric receptor, which optionally is a chimeric antigen receptor (CAR).

162. The kit of embodiment 161, wherein the chimeric antigen receptor (CAR) comprises an extracellular antigen-recognition domain that specifically binds to the antigen and an intracellular signaling domain comprising an ITAM.

163. The kit of embodiment 162, wherein the intracellular signaling domain comprises and intracellular domain of a CD3-zeta (CD3ζ) chain.

164. The kit of any of embodiments 161-163, wherein the chimeric antigen receptor (CAR) further comprises a costimulatory signaling region.

165. The kit of embodiment 164, wherein the costimulatory signaling region comprises a signaling domain derived from CD28 or 4-1BB, optionally human CD28 or human 4-1BB.

166. The kit of embodiment 164 or embodiment 165, wherein the costimulatory signaling region is a domain derived from 4-1BB, optionally human 4-1BB.

167. The kit of any of embodiments 146-166, wherein the genetically engineered cells comprise T cells or NK cells.

168. The kit of embodiment 167, wherein the genetically engineered cells comprises T cells.

169. The kit of embodiment 167 or embodiment 168, wherein the T cells are CD4+ and/or CD8+.

170. The kit of any of embodiments 167-169, wherein the T cells are primary T cells obtained from a subject.

171. The kit of any of embodiments 141-170, wherein the gamma secretase inhibitor inhibits cleavage of one or more targets selected from BCMA, Notch 1, Notch 2, Notch 3, Notch 4, Muc1, Ephrin B2, Betaglycan (TGFBR3), CD43, CD44, CSF1R, CXCR1, CXCL16, Delta1, E-cadherin, N-cadherin, HLA-A2, IFNaR2, IL1R1, IL1R2, IL6R or ameloid precursor protein (APP).

172. The kit of embodiment 171, wherein the one or more target of the gamma secretase inhibitor comprises Muc1.

173. The kit of embodiment 171, wherein the one or more target of the gamma secretase inhibitor comprises BCMA.

174. The kit of any of embodiments 141-173, wherein the gamma secretase inhibitor inhibits the target with a half-maximal inhibitory concentration ($IC_{50}$) of 0.01 nM to 1 µM, 0.01 nM to 100 nM, 0.01 nM to 10 nM, 0.01 nM to 5 nM, 0.01 nM to 1 nM, 0.01 nM to 0.5 nM, 0.01 nM to 0.25 nM, 0.01 nM to 0.1 nM, 0.01 nM to 0.05 nM, 0.05 nM to 1 µM, 0.05 nM to 100 nM, 0.05 nM to 10 nM, 0.05 nM to 5 nM, 0.05 nM to 1 nM, 0.05 nM to 0.5 nM, 0.05 nM to 0.25 nM, 0.05 nM to 0.1 nM, 0.1 nM to 1 µM, 0.1 nM to 100 nM, 0.1 nM to 10 nM, 0.1 nM to 5 nM, 0.1 nM to 1 nM, 0.1 nM to 0.5 nM, 0.1 nM to 0.25 nM, 0.25 nM to 1 µM, 0.25 nM to 100 nM, 0.25 nM to 10 nM, 0.25 nM to 5 nM, 0.25 nM to 1 nM, 0.25 nM to 0.5 nM, 0.5 nM to 1 µM, 0.5 nM to 100 nM, 0.5 nM to 10 nM, 0.5 nM to 5 nM, 0.5 nM to 1 nM, 1 nM to 1 M, 1 nM to 100 nM, 1 nM to 10 nM, 1 nM to 5 nM, 5 nM to 1 µM, 5 nM to 100 nM, 5 nM to 10 nM, 10 nM to 1 µM, 10 nM to 100 nM or 100 nM to 1 µM.

175. The kit of any of embodiments 141-174, wherein the gamma secretase inhibitor inhibits the target with a half-maximal inhibitory concentration ($IC_{50}$) of less than or less than about 1 µM, 100 nM, 10 nM, 5 nM, 1 nM, 0.5 nM, 0.35 nM, 0.25 nM, 0.1 nM, 0.05 nM or 0.01 nM or less.

176. The kit of any of embodiments 141-175, wherein the gamma secretase inhibitor is a peptide inhibitor or non-peptide inhibitor.

177. The kit of embodiment 176, wherein the gamma secretase inhibitor is a peptide inhibitor and the peptide inhibitor is selected from among peptide aldehydes derivatives, difluoroketones derivatives, hydroxyethylene dipeptide isotere derivatives, alpha-helical peptide derivatives and dipeptide analogs.

178. The kit of embodiment 177, wherein the gamma secretase inhibitor is a non-peptide inhibitor and the non-peptide inhibitor is a benzodiazepines derivative or a sulfonamides derivative.

179. The kit of any of embodiments 141-178, wherein the gamma secretase inhibitor is a transition state inhibitor or non-transition state inhibitor.

180. The kit of any of embodiments 141-179, wherein the gamma secretase inhibitor is a nonsteroidal anti-inflammatory drug.

181. The kit of any of embodiments 141-180, wherein the gamma secretase inhibitor is selected from LY3039478, secretase inhibitor I (GSI I) Z-Leu-Leu-Norleucine; γ-secretase inhibitor II (GSI II); γ-secretase inhibitor III (GSI III), N-Benzyloxycarbonyl-Leu-leucinal, N-(2-Naphthoyl)-Val-phenylalaninal; γ-secretase inhibitor III (GSI IV); γ-secretase inhibitor III (GSI V), N-Benzyloxycarbonyl-Leu-phenylalaninal; γ-secretase inhibitor III (GSI VI), 1-(S)-endo-N-(1,3,3)-Trimethylbicyclo[2.2.1]hept-2-yl)-4-fluorophenyl Sulfonamide; γ-secretase inhibitor III (GSI VII), Menthyloxycarbonyl-LL-CHO; γ-secretase inhibitor III (GSI IX), (DAPT), N-[N-(3,5-Difluorophenacetyl-L-alanyl)]-S-phenylglycine t-Butyl Ester; γ-secretase inhibitor X (GSI X), {1 S-Benzyl-4R-[1-(1S-carbamoyl-2-phenethylcarbamoyl)-1S-3-methylbutylcarb-amoyl]-2R-hydroxy-5-phenylpentyl}carbamic Acid tert-butyl Ester; γ-secretase inhibitor XI (GSI XI), 7-Amino-4-chloro-3-methoxyisocoumarin; γ-secretase inhibitor XII (GSI XII), Z-Ile-Leu-CHO; γ-secretase inhibitor XIII (GSI XIII), Z-Tyr-Ile-Leu-CHO; γ-secretase inhibitor XIV (GSI XIV), Z-Cys(t-Bu)-Ile-Leu-CHO; γ-secretase inhibitor XVI (GSI XVI), N-[N-3,5-Difluorophenacetyl]-L-alanyl-S-phenylglycine Methyl Ester; γ-secretase inhibitor XVII (GSI XVII); γ-secretase inhibitor XIX (GSI XIX), benzo[e][1,4]diazepin-3-yl)-butyramide; γ-secretase inhibitor XX (GSI XX), (S,S)-2-[2-(3,5-Difluorophenyl)acetylamino]-N-(5-methyl-6-oxo-6,7-dihydro-5H-dibenzo[b,d]azepin-7-yl)propionamide; γ-secretase inhibitor XXI (GSI XXI), (S,S)-2-[2-(3,5-Difluorophenyl)-acetylamino]-N-(1-methyl-2-oxo-5-phenyl-2-,3-dihydro-1H-benzo[e][1,4]diazepin-3-yl)-propionamide; Gamma40 secretase inhibitor I, N-trans-3,5-Dimethoxycinnamoyl-Ile-leucinal; Gamma40 secretase inhibitor II, N-tert-Butyloxycarbonyl-Gly-Val-Valinal Isovaleryl-V V-Sta-A-Sta-OCH3; MK-0752; MRK-003 (Merck); semagacestat/LY450139; RO4929097; PF-03084,014; BMS-708163; MPC-7869 (γ-secretase modifier), YO-01027 (Dibenzazepine), Compound E ([(2S)-2-{[(3,5-Difluorophenyl)acetyl]amino}-N-[(3S)-1-methyl-2-oxo-5-phenyl-2,3-dihydro-1H-1,4-benzodiazepin-3-yl]propanamide], LY411575, L-685,458, BMS-289948 (4-chloro-N-(2,5-difluorophenyl)-N-((1R)-{4-fluoro-2-[3-(1H-imidazol-1-yl)propyl]phenyl}ethyl)benzenesulfonamide hydrochloride) and BMS-299897 (4-[2-((1R)-1-{[(4-chlorophenyl) sulfonyl]-2,5-difluoroanilino}ethyl)-5-fluorophenyl]butanoic acid).

182. The kit of any of embodiments 141-181, wherein the gamma secretase inhibitor is LY3039478 or a compound of the structure:

Compound 1

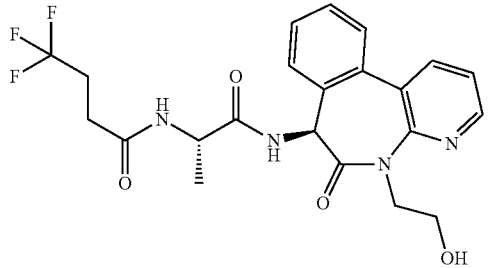

or a stereoisomer or a pharmaceutically acceptable salt or hydrate of any of the foregoing.

183. The kit of any of embodiments 99-182, wherein the instructions specify administering a dose of genetically engineered cells to a subject having a disease or disorder.

184. The kit of embodiment 183, wherein the disease or disorder is a cancer.

185. The kit of embodiment 184, wherein the cancer is a B cell malignancy.

186. The kit of embodiment 184 or embodiment 185, wherein the cancer is multiple myeloma.

187. The kit of any of embodiments 183-186, wherein the dose comprises from or from about $1 \times 10^5$ to $5 \times 10^8$ total recombinant receptor-expressing cells, total T cells, or total peripheral blood mononuclear cells (PBMCs), the cell therapy comprises the administration of from or from about $1 \times 10^5$ to $1 \times 10^8$ total recombinant receptor-expressing cells, total T cells, or total peripheral blood mononuclear cells (PBMCs), from or from about $5 \times 10^5$ to $1 \times 10^7$ total recombinant receptor-expressing cells, total T cells, or total peripheral blood mononuclear cells (PBMCs) or from or from about $1 \times 10^6$ to $1 \times 10^7$ total recombinant receptor-expressing cells, total T cells, or total peripheral blood mononuclear cells (PBMCs), each inclusive, optionally wherein the instructions specify the administration of one or of a plurality of unit doses comprising the dose of cells and/or a volume corresponding to such one or plurality of unit doses comprising the dose of cells.

188. The kit of any of embodiments 183-186, wherein the dose comprises no more than $5 \times 10^8$ total recombinant receptor-expressing cells, total T cells, or total peripheral blood mononuclear cells (PBMCs), no more than $2.5 \times 10^8$ total recombinant receptor-expressing cells, total T cells, or total peripheral blood mononuclear cells (PBMCs), no more than $1 \times 10^8$ total recombinant receptor-expressing cells, total T cells, or total peripheral blood mononuclear cells (PBMCs), no more than $1 \times 10^7$ total recombinant receptor-expressing cells, total T cells, or total peripheral blood mononuclear cells (PBMCs), no more than $0.5 \times 10^7$ total recombinant receptor-expressing cells, total T cells, or total peripheral blood mononuclear cells (PBMCs), no more than $1 \times 10^6$ total recombinant receptor-expressing cells, total T cells, or total peripheral blood mononuclear cells (PBMCs), no more than $0.5 \times 10^6$ total recombinant receptor-expressing cells, total T cells, or total peripheral blood mononuclear cells (PBMCs), optionally wherein the instructions specify the administration of one or of a plurality of unit doses comprising the dose of cells and/or a volume corresponding to such one or plurality of unit doses comprising the dose of cells.

189. The kit of any of embodiments 99-188, wherein the instructions specify administering the inhibitor orally, subcutaneously or intravenously.

190. The kit of embodiment 189, wherein the instructions specify administering the inhibitor orally.

191. The kit of any one of embodiments 99-190, wherein the instructions specify the inhibitor is to be administered at least six times daily, five times daily, four times daily, three times daily, twice daily, once daily, every other day, three times a week, at least once a week, or only one time.

192. The kit of any of embodiments 99-191, wherein the instructions specify the inhibitor is administered three times a week.

193. The kit of embodiment 191 or embodiment 192, wherein the instructions specify the administration of the inhibitor is to be carried out in a treatment cycle that is at least or at least about or 14 days, at least or at least about or 21 days or at least or at least about or 28 days.

194. The kit of any of embodiments 99-193, wherein the instructions specify the inhibitor is administered, or each administration of the inhibitor is independently administered, in an amount of 0.5 mg to 500 mg, 0.5 mg to 250 mg, 0.5 mg to 100 mg, 0.5 mg to 50 mg, 0.5 mg to 25 mg, 0.5 mg to 10 mg, 0.5 mg to 5.0 mg, 0.5 mg to 2.5 mg, 0.5 mg to 1.0 mg, 1.0 mg to 500 mg, 1.0 mg to 250 mg, 1.0 mg to 100 mg, 1.0 mg to 50 mg, 1.0 mg to 25 mg, 1.0 mg to 10 mg, 1.0 mg to 5.0 mg, 1.0 mg to 2.5 mg, 2.5 mg to 500 mg, 2.5 mg to 250 mg, 2.5 mg to 100 mg, 2.5 mg to 50 mg, 2.5 mg to 25 mg, 2.5 mg to 10 mg, 2.5 mg to 5.0 mg, 5.0 mg to 500 mg, 5.0 mg to 250 mg, 5.0 mg to 100 mg, 5.0 mg to 50 mg, 5.0 mg to 25 mg, 5.0 mg to 10 mg, 10 mg to 500 mg, 10 mg to 250 mg, 10 mg to 100 mg, 10 mg to 50 mg, 10 mg to 25 mg, 25 mg to 500 mg, 25 mg to 250 mg, 25 mg to 100 mg, 25 mg to 50 mg, 50 mg to 500 mg, 50 mg to 250 mg, 50 mg to 100 mg, 100 mg to 500 mg, 100 mg to 250 mg or 250 mg to 500 mg.

195. The kit of any of embodiments 99-194, wherein the instructions specify the inhibitor is administered, or each administration of the inhibitor is independently administered, in an amount that is at least or at least about or is or is about 0.5 mg, 1.0 mg, 2.5 mg, 5.0 mg, 10.0 mg, 25 mg, 50 mg, 100 mg, 250 mg or 500 mg.

196. An article of manufacture comprising the combination or kit of any of embodiments 99-195.

VII. EXAMPLES

The following examples are included for illustrative purposes only and are not intended to limit the scope of the invention.

Example 1: Assessment of Surface Expression of BCMA on Multiple Myeloma (MM) Cell Lines in the Presence of a Gamma Secretase Inhibitor Effects of the exemplary gamma secretase inhibitor (GSI), LY3039478, on surface levels of B cell maturation antigen (BCMA) on multiple myeloma (MM) cell lines were assessed. Different concentrations of LY3039478, including concentrations within the estimated Cmax/Cmin for the inhibitor, were incubated with RPMI 8226 cells (BCMA$^{low}$ human multiple myeloma cell line), MM1.S cells (BCMA$^{med}$ human multiple myeloma cell line) and OPM2 cells (BCMA med human multiple myeloma cell line) for 24 hours at 37° C. The cell lines also were incubated in the absence of the inhibitor (vehicle control). Surface expression of BCMA on each cell line was assessed by flow cytometry using an-anti-BCMA antibody. As shown in FIG. 1, LY3039478 achieved potent inhibition of BCMA cleavage from the surface of the assessed cell lines, with an IC$_{50}$ of 0.01 nM to 0.35 nM.

Example 2: Assessment of Anti-BCMA CAR-T Cell Function in the Presence of a Gamma Secretase Inhibitor Certain functional activities of anti-BCMA CAR-T cells against BCMA-expressing target cells were assessed in the presence or absence of the exemplary GSI LY3039478.

In this study, to generate anti-BCMA CAR-expressing T cells, CD4+ and CD8+ T cells were isolated by immunoaffinity-based enrichment from leukapheresis samples from two healthy donor subjects and one myeloma patient. Isolated T cells were activated and transduced with a viral vector encoding an anti-BCMA CAR. The CAR contained an scFv antigen-binding domain specific for BCMA having a V$_H$ domain and a V$_L$ domain with amino acid sequences set forth in SEQ ID NOS: 24 and 25, respectively, a spacer, a spacer having an amino acid sequence set forth in SEQ ID NO:31, a CD28 transmembrane region, a 4-1BB costimulatory signaling region and a CD3-zeta derived intracellular signaling domain. The nucleic acid construct encoding the CAR also included a truncated receptor sequence for use as a transduction marker, separated from the CAR sequence by a self-cleaving T2A sequence.

1. Cytolytic Activity

Anti-BCMA CAR-T cells generated as described in this Example above were cultured at 37° C. with either OPM2 or RPMI-8226 target cells at an effector to target (E:T) ratio of 0.3:1. The target cells were labeled with NucLight Red (NLR), to permit tracking of target cells by microscopy. Cultures were incubated in the absence of LY3039478 or in the presence of LY3039478 at concentrations of 0.1 nM, 1 nM, 10 nM, 100 nM, 1000 nM, 10000 nM or 100000 nM (the range covering the estimated human pharmacokinetic range is shown by the boxes in FIGS. 3A-3D). As a control, target cells were incubated with LY3039478 but without culture with CAR-T cells. Cytolytic activity was assessed by measuring the loss of viable target cells after about 150 hours, as determined by red fluorescent signal (using the IncuCyte® Live Cell Analysis System, Essen Bioscience). The area under the curve for killing observed during the culture period (~150 hours) was determined. Percent lysis (% killing) was determined by normalizing the AUC for killing to cultures incubated without the inhibitor.

Figure 2A:
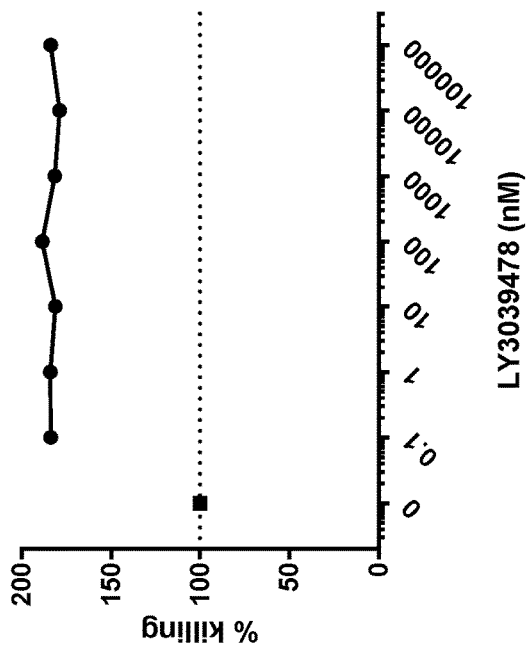
FIG. 2A and FIG. 2B show percent lysis (% killing) of OPM2 cells (FIG. 2A) or RPMI-8226 cells (FIG. 2B) co-cultured with anti-BCMA CAR-expressing T cells in the presence or absence of a representative of gamma secretase inhibitor (LY3039478) after about 150 hours of co-culture.
Figure 2B:
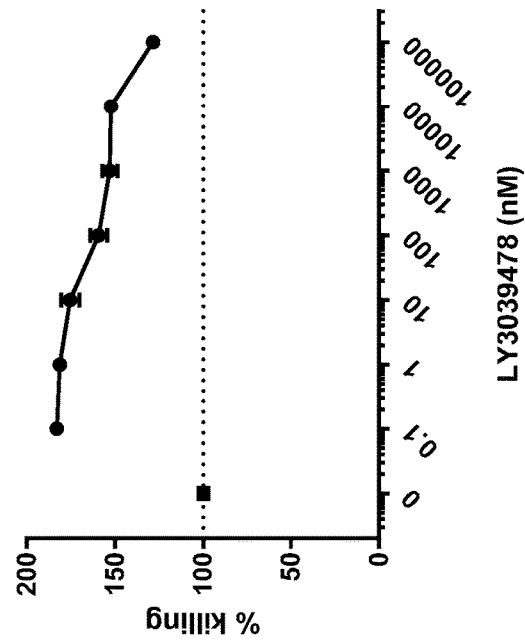

Assessment of CAR-T cells from the myeloma patient-derived donor are depicted in FIGS. 2A (OPM2) and 2B (RPMI-8226). As shown, LY3039478 increased the cytolytic activity of anti-BCMA CAR T cells at all concentrations tested in both cell lines, although the magnitude of the effect across tested inhibitor concentrations was cell-line dependent. No detrimental effects on CAR T cell function in this assay were observed at 100 µM LY3039478, which is 300 times above the calculated Cmax observed in patients. No differences were observed in target survival in the presence of LY3039478 alone without CAR-T cells. Similar results were observed at an E:T ratio of 1:1. CAR-T cells derived from the other donors that were incubated with LY3039478 also showed an increase in CAR-T function, although some donor to donor variability was observed. These results indicate that treatment in the presence of a gamma secretase inhibitor can increase surface BCMA expressing and anti-BCMA CAR T cell cytolytic function.

Figure 2C:
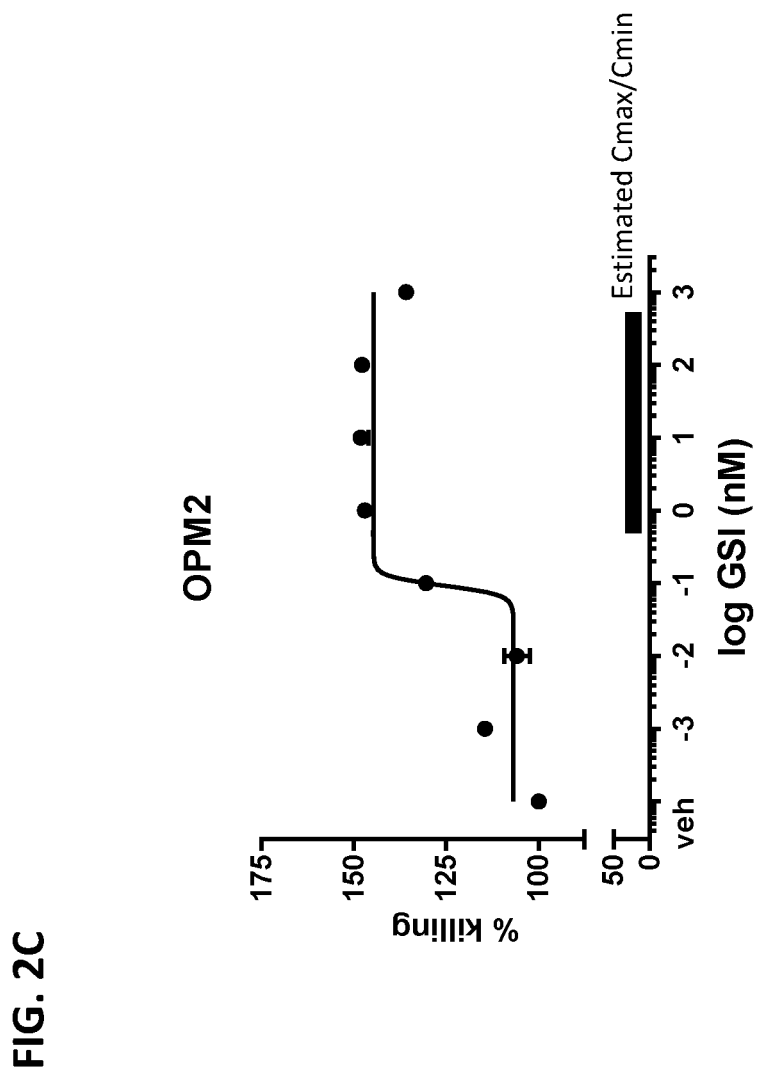
FIG. 2C shows percent lysis (% killing) of OPM2 cells co-cultured with anti-BCMA CAR-expressing T cells in the presence or absence of a representative gamma secretase inhibitor (LY3039478). The bar near the X-axis suggests the estimated $C_{max}$ and $C_{min}$ for the inhibitor.

A similar study was carried out to further assess the effects of different concentrations of LY3039478, including concentrations within the estimated Cmax/Cmin for the inhibitor, on the cytolytic function of anti-BCMA CAR-T cells against OPM2 target cells. Results in FIG. 2C from one exemplary donor showed that LY3039478 was capable of increasing anti-BCMA CAR-T killing of BCMA-expressing target cells with an IC50 of 0.1-0.25 nM.

2. Cytokine Production

The production of cytokines by anti-BCMA CAR-T cells in the presence or absence of LY3039478 was assessed by monitoring cytokine levels in the supernatants of co-cultures of CAR-T cells with BCMA-expressing target cells. CAR-T cells generated as described in this Example above were cultured with either OPM2 or RPMI-8226 target cells in the absence of LY3039478 or in the presence of LY3039478 at concentrations of 0.1 nM, 1 nM, 10 nM, 100 nM, 1000 nM, 10000 nM or 100000 nM (the range covering the estimated human pharmacokinetic range is shown by the boxes in FIGS. 3A-3D). Culture supernatants were harvested after 24 hours, and IFNγ and IL-2 were measured from the culture supernatants.

The presence of LY3039478 increased the production of IFN-gamma (FIG. 3A and FIG. 3B) and IL-2 (FIGS. 3C and 3D) in supernatant of anti-BCMA CAR T cells co-cultured with BCMA-expressing target cells compared to co-cultures incubated in the absence of LY3039478. The magnitude of the effect differed between cell lines and, in some cases, the concentration of the inhibitor. Similar to effects on cytolytic function, the results indicated that combination with a gamma secretase inhibitor increases BCMA antigen availability for the anti-BCMA CAR-T cells, leading to increased effect of the CAR-T cells, including production of cytokines.

Figure 3A:
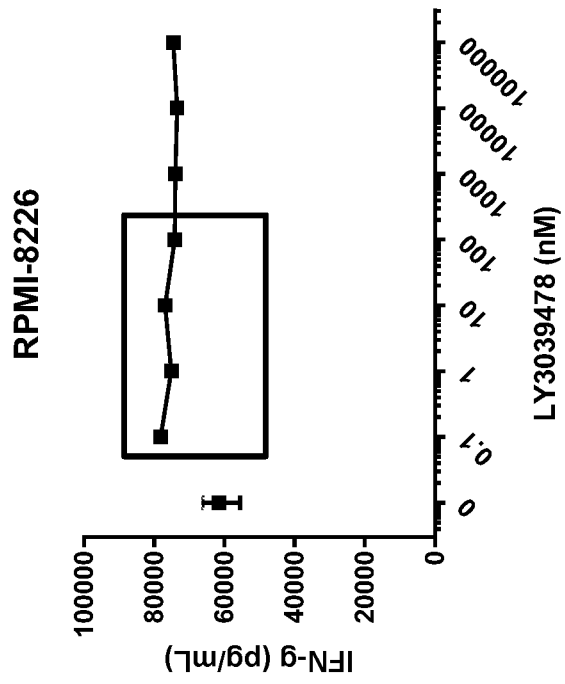
FIGS. 3A-3D show the production of IFN-gamma and IL-2 in the supernatant of anti-BCMA CAR-expressing T cells co-cultured with OPM2 (FIGS. 3A and 3C) or RPMI-8226 cells (FIGS. 3B and 3D) in the presence or absence of a representative of gamma secretase inhibitor (LY3039478) after 24 hours of co-culture.
Figure 3B:
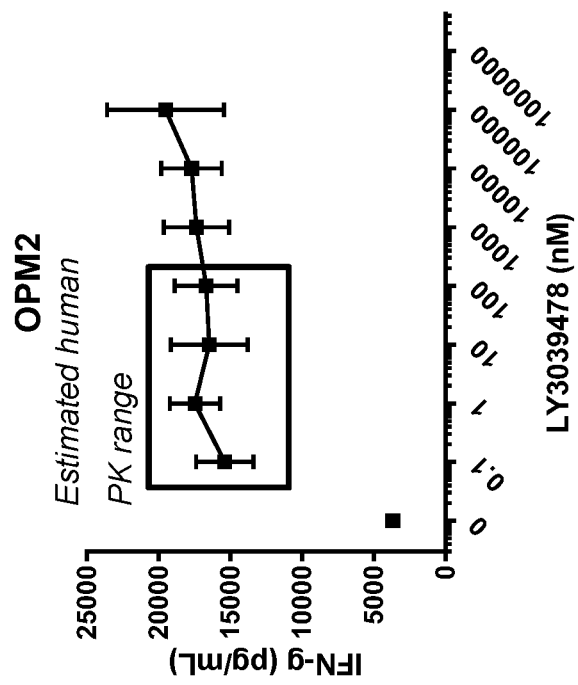
Figure 3D:
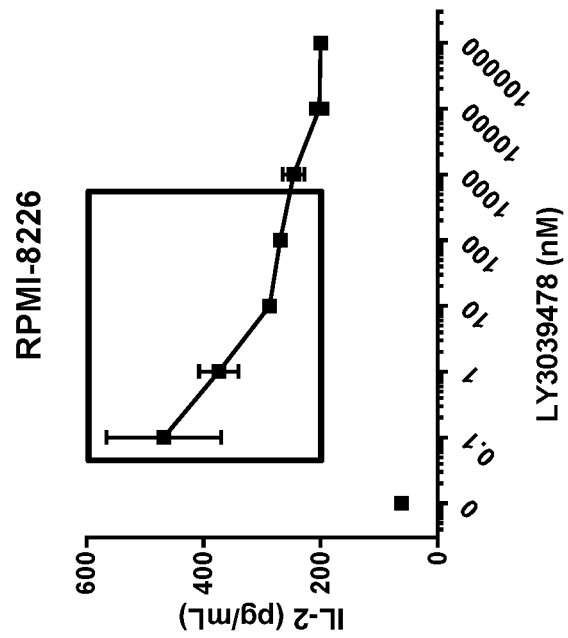
Figure 3C:
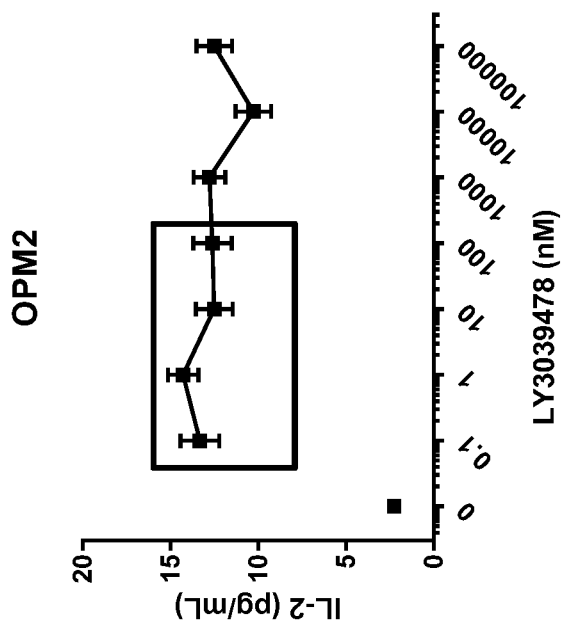
Figure 3E:
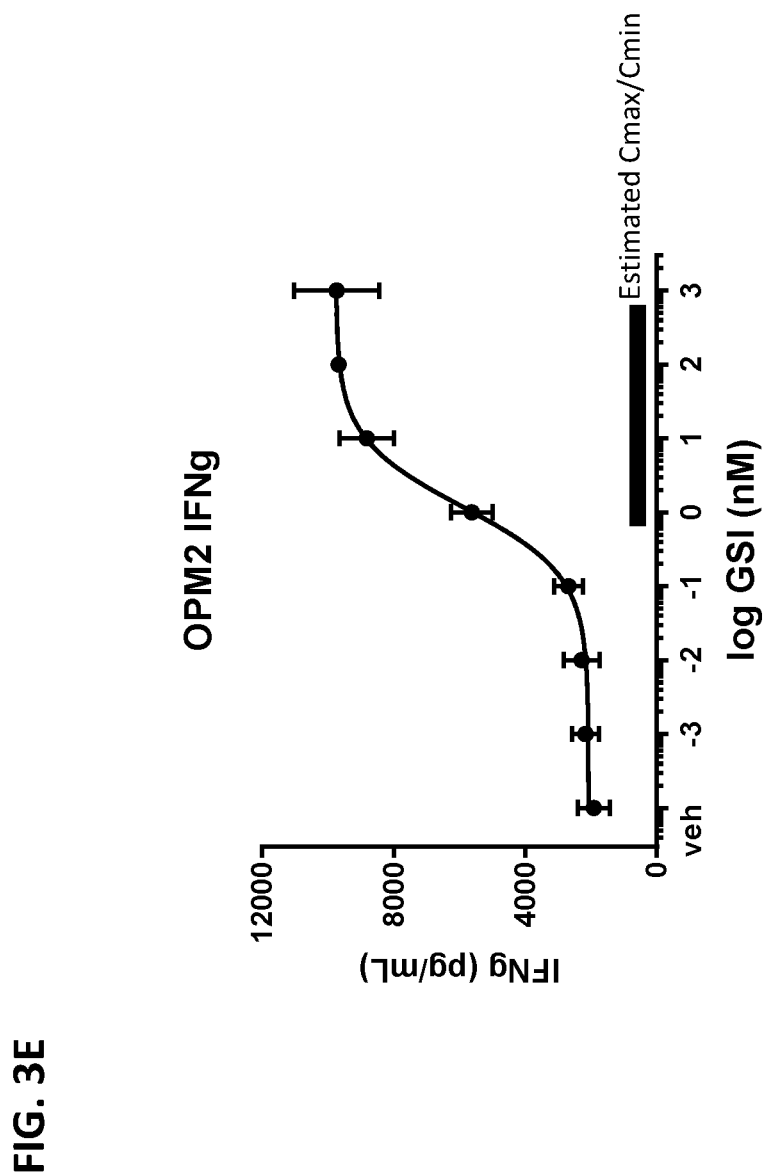
FIG. 3E shows the production of IFN-gamma in the supernatant of anti-BCMA CAR-expressing T cells co-cultured with OPM2 cells and different concentrations of a representative gamma secretase inhibitor (LY3039478). The bar near the X-axis suggests the estimated $C_{max}$ and $C_{min}$ for the inhibitor.

A similar study was carried out to further assess the effects of different concentrations of LY3039478, including concentrations within the estimated Cmax/Cmin for the inhibitor, on the ability of anti-BCMA CAR-T cells generated as described in this Example 2 above to produce cytokines following co-culture with OPM2 target cells. Results in FIG. 3E from one exemplary donor were consistent with an interpretation that LY3039478 was capable of increasing cytokine production (with an IC50 of 0.1-0.25 nM) by anti-BCMA CAR-T cells cultured with BCMA-expressing target cells.

Figure 4A:
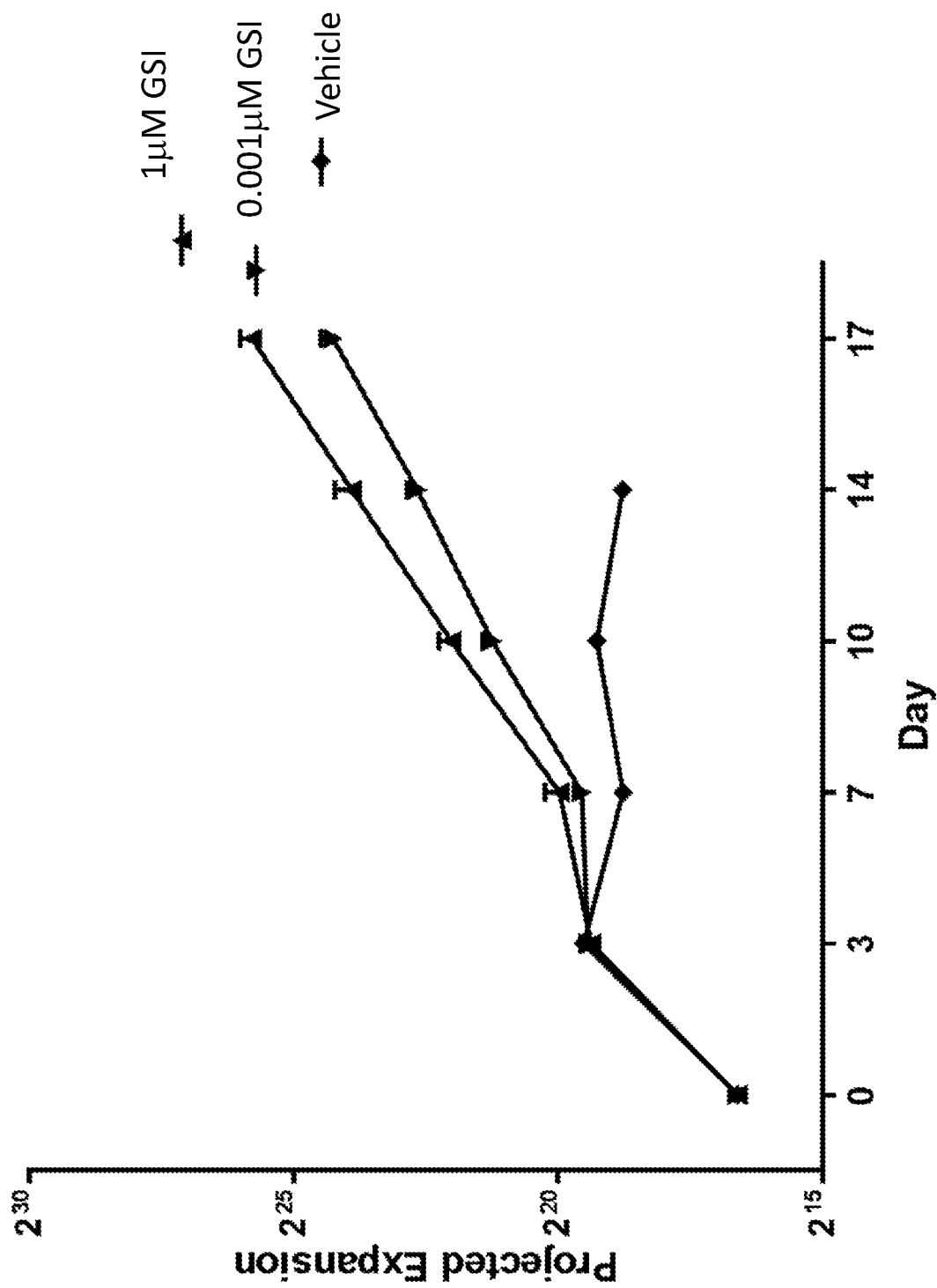
FIGS. 4A and 4B show the cell number of anti-BCMA CAR-expressing T cells originally obtained from a healthy donor (FIG. 4A) and a donor with multiple myeloma (FIG. 4B) after multiple rounds of stimulation with MM1S cells over a period of 10-17 days in the absence of a representative of gamma secretase inhibitor (LY3039478) (vehicle control, square) or in the presence of the inhibitor with a concentration of 1 µM (upward triangle) or 0.001 µM (downward triangle).

Example 3: Effect of Gamma Secretase Inhibitor on CAR-T Cell Expansion and Cytokine Production after Serial Restimulation The ability of CAR T cells to expand ex vivo following repeated rounds of antigen stimulation can correlate with in vivo function and/or capacity of the cells to persist in in vivo (e.g., following administration and initial activation in response to encounter with antigen) (Zhao et al. (2015) Cancer Cell, 28:415-28). To assess the effect of the exemplary gamma secretase inhibitor on CAR-T cell activity after serial restimulation, anti-BCMA CAR+ T cells were generated as described above in Example 2, and irradiated BCMA-expressing target cells (MM1S cells) were added at an effector-to-target (E:T) ratio of 1:2 in the presence of LY3039478 at two different concentrations, either 0.001 µM (a concentration around the IC50) or a higher concentration of 1.0 µM (approximately 3 times Cmax), or with vehicle only control. The assay was performed on a composition of anti-BCMA CAR+ T cells generated from T cells derived from a healthy donor or from a donor with multiple myeloma. Every 3-4 days, CAR-expressing T cells were harvested, counted and re-plated at the initial seeding density with fresh media containing new irradiated target cells at the same E:T ratio in the presence or absence of the same concentration of LY3039478. A total of 3-5 rounds of stimulation were carried out during a 10-14 day culture period. Effects of the inhibitor on T cell function were assessed by monitoring the cell number (FIGS. 4A and 4B) or cytokine production in harvested supernatant (FIG. 5A and FIG. 5B) at each round of stimulation.

Figure 4B:
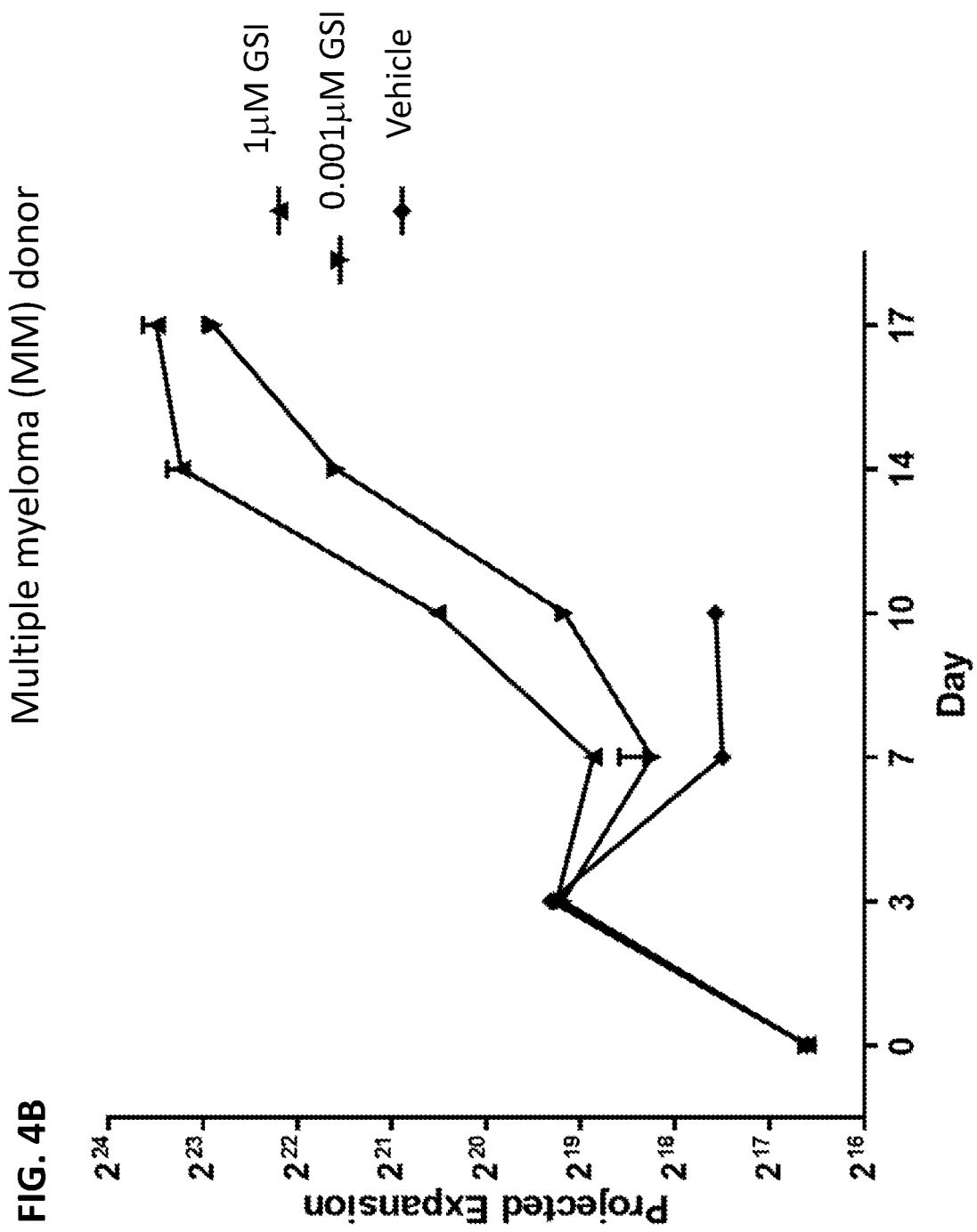

The number of CAR-T cells was determined at each round prior to re-plating for anti-BCMA CAR+ T cells derived from the healthy donor-derived cells (FIG. 4A) or the patient-derived cells (FIG. 4B). For anti-BCMA CAR+ T cells derived from both donors, increased expansion of anti-BCMA CAR T cells was observed over the period of 10-14 days when CAR-T cells were incubated in the presence of both concentrations of LY3039478 (0.001 µM and 1.0 µM). The results indicated that LY3039478 did not exhibit any detrimental effects on CAR-T cell function, even though it is a known inhibitor of the Notch signaling pathway, which is involved in T cell differentiation. The results were consistent with a conclusion that the exemplary gamma secretase inhibitor LY3039478 can promote continued CAR+ T cell expansion and/or survival following repeated encounter with cognate antigen.

The production of cytokines by anti-BCMA CAR-T cells upon restimulation with antigen-expressing cells in the presence or absence of LY3039478 was assessed after the first round of re-plating at day 4. Culture supernatants were harvested 24 hours after re-plating, and IFN-gamma, IL-2 and TNF-alpha were measured from the culture supernatants. Increased levels of IFN-gamma, IL-2 and TNF-alpha were observed for both concentration of LY3039478 (0.001 µM and 1.0 µM) in anti-BCMA CAR+ T cells derived from the healthy donor cells (FIG. 5A) or the patient donor cells (FIG. 5B).

Example 4: Assessment of Agents on Blocking Activity of Anti-BCMA CAR Activity

Polynucleotides encoding exemplary chimeric antigen receptors (CARs), each containing a human anti-BCMA scFv antigen-binding domain, were generated. Among the CARs were those containing anti-BCMA scFvs containing a $V_H$ and $V_L$ set forth in SEQ ID NOS: 22 and 23, respectively (referred to in this example as anti-BCMA.3 CAR), a $V_H$ and $V_L$ set forth in SEQ ID NOS: 24 and 25, respectively (referred to in this example as anti-BCMA.4 CAR), and a $V_H$ and $V_L$ set forth in SEQ ID NOS: 18 and 19, respectively (referred to in this example as anti-BCMA.1 CAR). The encoded CARS also were generated to contain an exemplary spacer set forth in SEQ ID NO:31, a human CD28 transmembrane domain, a human 4-1BB-derived intracellular co-signaling sequence, and a CD3-zeta derived intracellular signaling domain.

cDNA clones encoding such CARs, were linked to a downstream ribosomal skip element (such as T2A) followed by a truncated receptor-encoding sequence, and cloned into a lentiviral expression vector.

To generate anti-BCMA CAR-expressing T cells, T cells were isolated by immunoaffinity-based enrichment from leukapheresis samples from human donor subjects. Isolated T cells were activated and transduced with lentiviral vectors containing the respective polynucleotides encoding the anti-BCMA CARs and expanded; CD4+ and CD8+ T cells were stained and analyzed by flow cytometry to confirm transduction and expression of the anti-BCMA CARs. Various functions of anti-BCMA CAR-expressing cells were assessed following incubation with BCMA-expressing target cells and soluble BCMA.

To assess cytolytic activity, anti-BCMA CAR-expressing T cells were incubated with OPM2 target cells at an E:T ratio of 5:1 in the presence of soluble BCMA-Fc at 0, 0.3, 3, 30 or 300 ng/mL. Target cells were labeled with NucLight Red (NLR) to permit tracking of target cells by microscopy. Cytolytic activity was assessed by measuring the loss of viable target cells over a period of between 24 and 72 hours, as determined by red fluorescent signal (using the IncuCyte® Live Cell Analysis System, Essen Bioscience). Percent lysis (% Lysis) was normalized to the lysis that occurred in target cells incubated with mock T cells. Cytolytic activity of T cells expressing the anti-BCMA.1-containing CAR or anti-BCMA.3 CAR were substantially reduced in the presence of 3 ng/mL or more BCMA-Fc, however the cytolytic activity of cells expressing the anti-BCMA.4 CAR was not blocked by the presence of up to 300 ng/mL BCMA-Fc.

To assess cytokine production, anti-BCMA CAR-expressing T cells were incubated with OPM2 target cells at an E:T ratio of 5:1 in the presence of soluble BCMA-Fc at 0, 111, 333 and 1000 ng/mL. T cells not expressing a CAR (mock) also were assessed. Cytokine accumulation of IFN-γ, TNF-α and IL-2 in supernatant was assessed. Cytokine accumulation in cultures containing T cells expressing the anti-BCMA.1 CAR or anti-BCMA.3 CAR was substantially reduced in the presence of 111 ng/ml or more BCMA-Fc, however less reduction in cytokine accumulation was observed in cultures containing T cells expressing the anti-BCMA.4 CAR in the presence of soluble BCMA-Fc at all concentrations tested.

In another experiment, activity of the anti-BCMA.4 CAR-expressing T cells in the presence vs. absence of soluble BCMA was assessed. Anti-BCMA.4 CAR-expressing T cells were co-cultured with RPMI-8226 tumor cells, with recombinant BCMA-Fc, or with cell culture supernatant derived from NCI-H929 multiple myeloma cells (BCMA-secreting cell line, the supernatant containing soluble BCMA). Neither tumor-cell lysis nor cytokine production was affected by any of the concentrations of NCI-H929-derived soluble BCMA (up to 1000 ng/mL). Both tumor-cell lysis and cytokine production were only minimally decreased at similarly high physiological levels of recombinant BCMA.

Example 5: Administration of Gamma Secretase Inhibitor Compound LY3039478 and Anti-BCMA CAR+ T Cells In Vivo in an Animal Tumor Model A pharmacokinetics and pharmacodyamics study was carried out following oral administration of a single dose of LY3039478 (3 mg/kg) in a human multiple myeloma xenograft model. Specifically, NOD.Cg.PrkdescidIL2rgtm1 Wjl/SzJ (NSG) mice were injected subcutaneously (s.c.) with 1E+07 RPMI-8226 cells modified to express GFP and firefly luciferase (RPMI-8226 flluc) and tumors were allowed to grow. Thirty two (32) days after RPMI-8226 injection (day 0 of study), a single dose of 3 mg/kg LY3039478 was administered orally.

Figure 6:
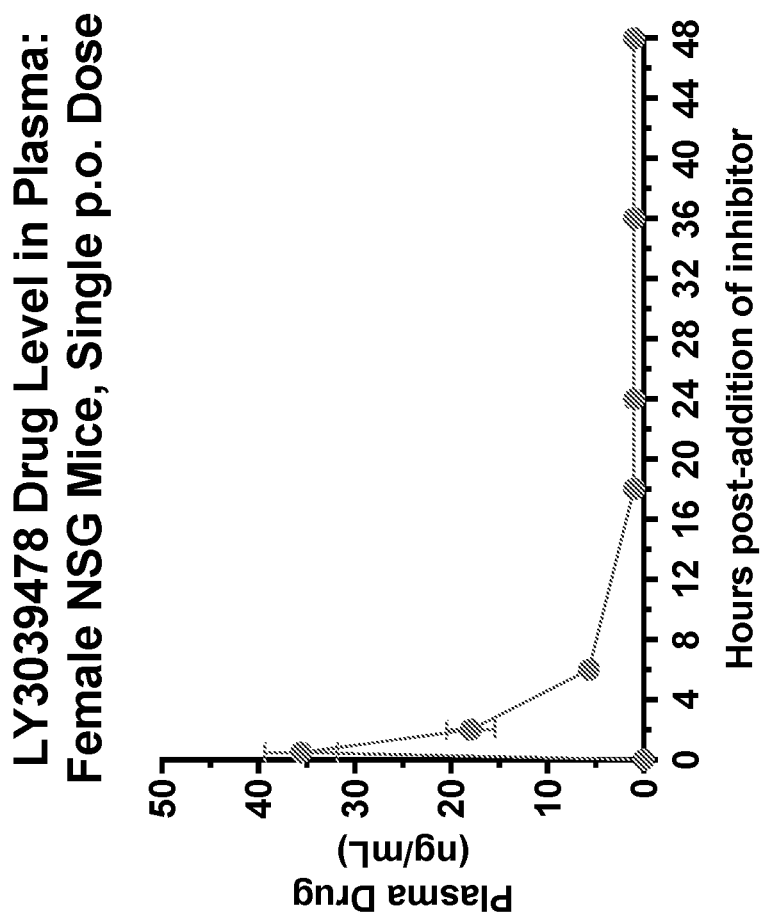
FIG. 6 shows plasma levels of gamma secretase inhibitor LY3039478 at different time points following oral administration of a single dose of LY3039478 (3 mg/kg).
Figure 7:
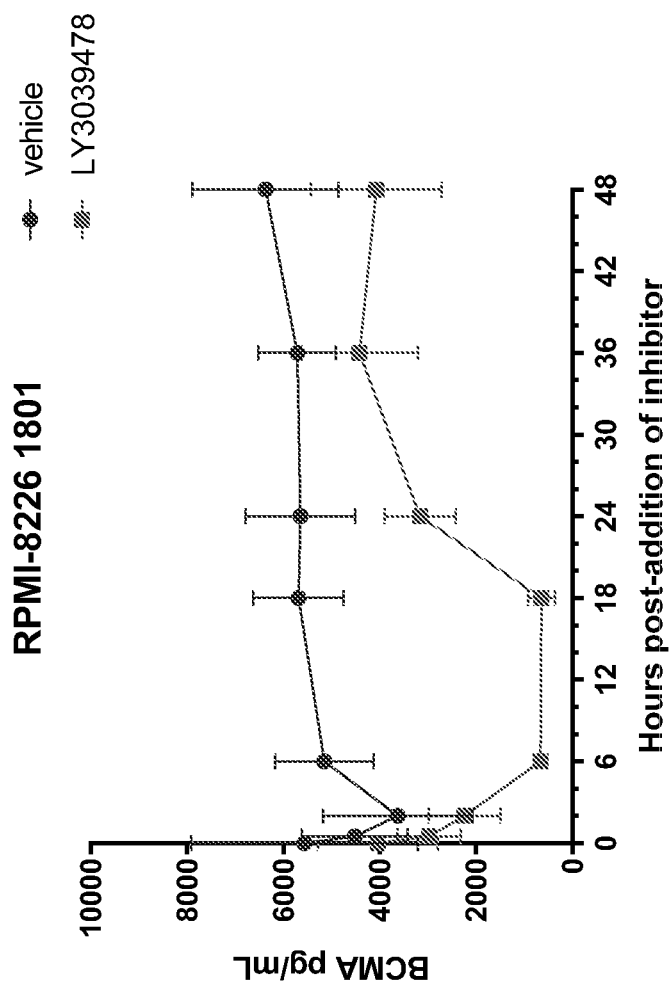
FIG. 7 shows plasma levels of BCMA over time following oral administration of a single dose of LY3039478 (3 mg/kg) in a mouse xenograft model for human multiple myeloma (RPMI-8226).
Figure 8:
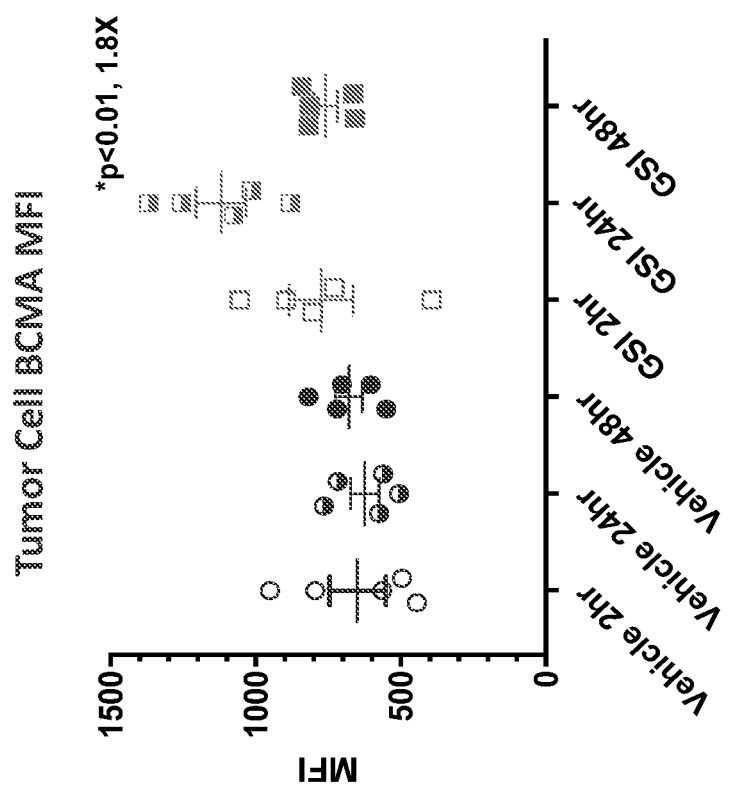
FIG. 8 shows surface BCMA expression, as assessed by flow cytometry, in subcutaneous tumor cells derived from a mouse xenograft model for human multiple myeloma (RPMI-8226) over time following oral administration of a single dose of LY3039478.

FIG. 6 depicts analysis of blood samples, taken at 0, 0.5, 2, 6, 18, 24, 36, and 48 hour post-administration, for plasma levels of the drug. FIG. 7 shows plasma BCMA levels over time in plasma samples taken at 0, 0.5, 2, 6, 18, 24, 36, and 48 hours post-administration in mice administered a single oral dose of LY3039478 (3 g/kg) or vehicle in this study. Tumor cells at 2 hours, 24 hours or 48 hours after administration of LY3039478 or vehicle control in the study were assessed for surface expression of BCMA. Mean fluorescence intensity (MFI) of surface BCMA, as assessed by flow cytometry, is shown in FIG. 8. Increased BCMA expression on tumors was confirmed with a dosing schedule of 0.1 mg/kg or 1 mg/kg administered two oral administrations of LY3039478 in an alternative multiple myeloma tumor cell model.

Anti-tumor effects following administration of anti-BCMA CAR T cells and a gamma secretase inhibitor compound, LY3039478, each, individually, and in combination, were assessed in a RPMI-8226 human multiple myeloma xenograft mouse model. The anti-BCMA CAR-expressing T cells were generated as described in Example 2.

NOD.Cg.PrkdescidIL2rgtm1 Wjl/SzJ (NSG) mice were injected subcutaneously (s.c.) with 1E+07 RPMI-8226 cells modified to express GFP and firefly luciferase (RPMI-8226 flluc), and tumor volume was allowed to increase over the course of 25 days, the 25th day being designated "day 0" in this study. Animals were divided into 8 groups, and each group received one of the following treatments: (1) vehicle only, (2) LY3039478 (3 mg/kg) only, (3) Mock T cells (not expressing the CAR) (3.00E+06 T cells per mouse) and vehicle, (4) Mock T cells (3.00E+06 T cells per mouse) and LY3039478 (3 mg/kg), (5) anti-BCMA CAR+ T cells (1.00E+06 CAR+ cells per mouse) and vehicle, (6) anti-BCMA CAR+ T cells (1.00E+06 CAR+ cells per mouse) and LY3039478 (3 mg/kg), (7) anti-BCMA CAR+ T cells (3.00E+06 CAR+ cells per mouse) and vehicle, or (8) anti-BCMA CAR+ T cells (3.00E+06 CAR+ cells per mouse) and LY3039478 (3 mg/kg). In each group, LY3039478 or vehicle was delivered by mouth (p.o.) at day-1 and at day zero (0) and every other day (e.o.d.) up to day 21. Where applicable, T cells were administered by a single intravenous (i.v.) injection on day 0.

Figure 9A:
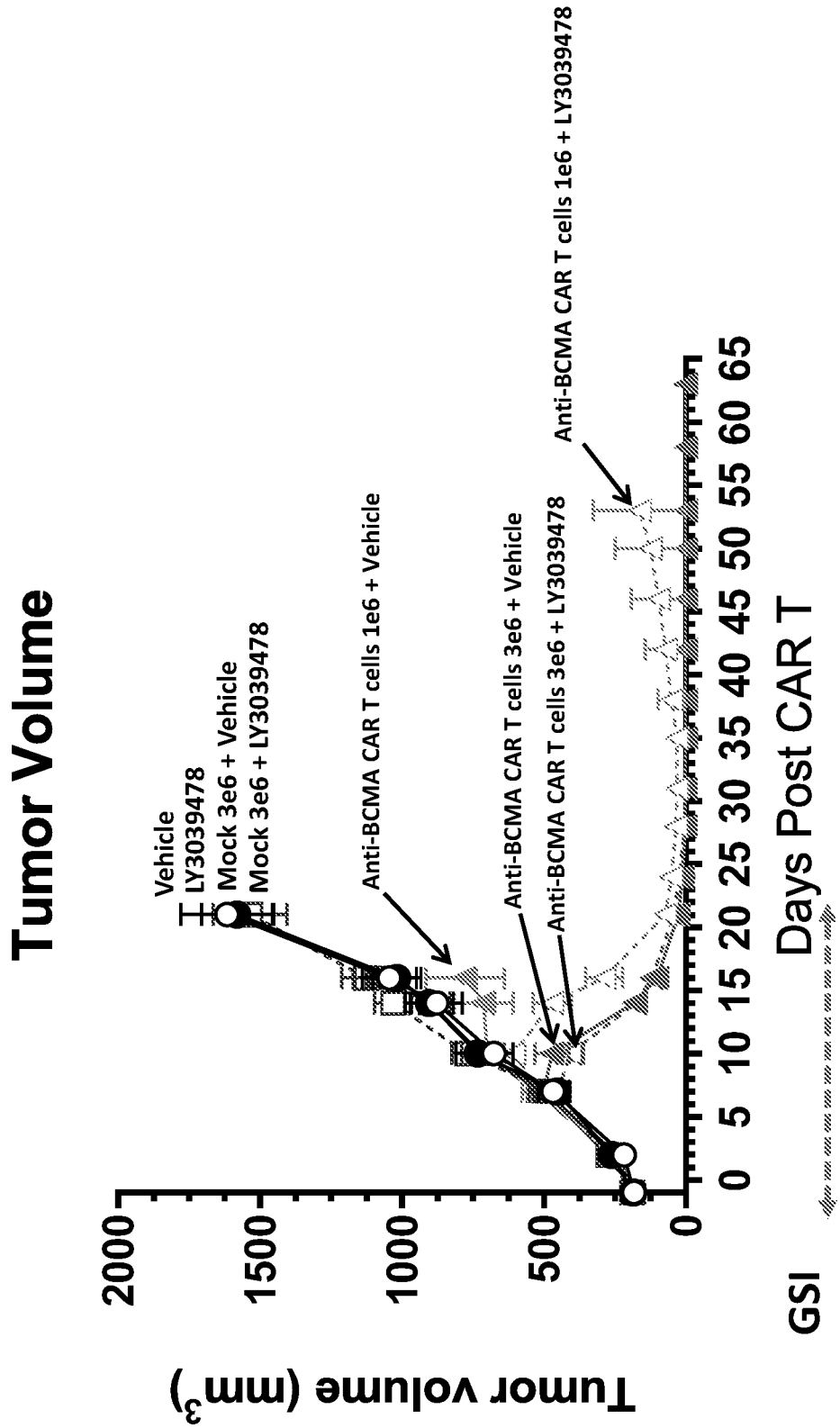
FIGS. 9A-9B show results from the study described in Example 5, assessing the impact of different treatments in a mouse xenograft model for human multiple myeloma.

Tumor volume was assessed twice weekly over the course of the study; results for different groups are shown in FIG. 9A. CAR+ T cells in blood and in tumor were assessed on days 7, 15, 21, and 28 by flow cytometry using antibodies specific for cell surface markers and a reagent specific to the anti-BCMA CAR. Animal survival was monitored throughout the study.

As shown in FIG. 9A, tumors continued to grow over the course of the study following adoptive transfer of negative control cells (Mock) or in mice not receiving treatment. In mice that had received the higher dose anti-BCMA CAR-expressing T cells, complete regression of tumor growth was observed by about 20 days post-CAR T cell transfer and was sustained throughout the remainder of the study; some reduction in tumor growth was observed in animals having received the lower dose of anti-BCMA CAR-expressing T cells and vehicle. In animals having received administration of LY3039478 in combination with the lower dose of anti-BCMA CAR-expressing cells, there was observed a substantial reduction in tumor growth compared to mice treated with the lower dose of anti-BCMA CAR-expressing cells and vehicle. LY3039478 administration was well-tolerated throughout the study as indicated by body weight and condition score.

Figure 9B:
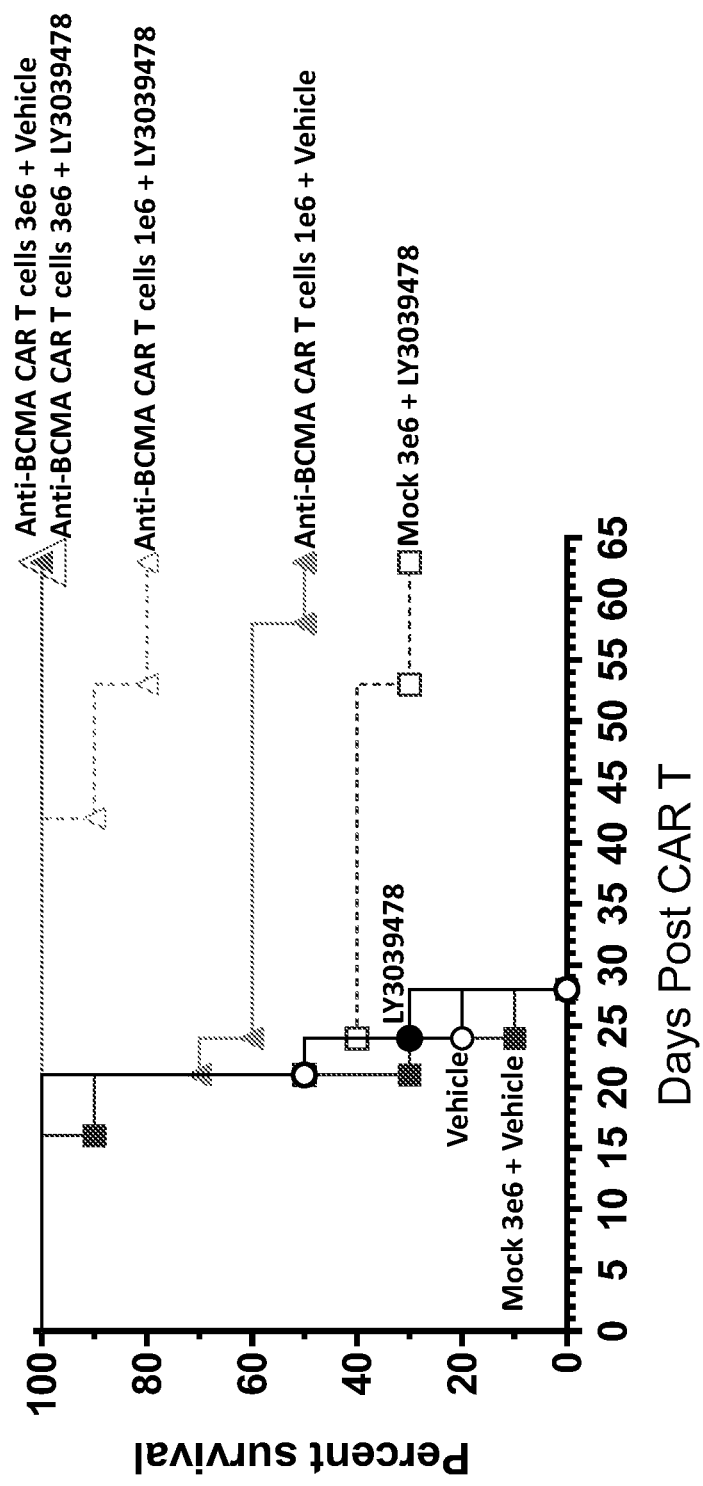

The percent survival of animals over the course of the study is shown in FIG. 9B. Administration of anti-BCMA CAR-expressing T cells was observed to result in increased survival. A further survival benefit was observed in mice treated with the combination of the lower dose anti-BCMA CAR-expressing T cells and the GSI, LY3039478, as compared to the group treated with the lower dose of CAR-T cells and vehicle.

TABLE E1

Survival across groups

| Group | Median Survival (days) | Number of deaths | Day 65 Survival % | Day 65 tumor free survival |
|---|---|---|---|---|
| Vehicle | 22.5 | 10 | 0 | NA |
| LY3039478 | 22.5 | 10 | 0 | NA |
| Mock + Vehicle | 21 | 10 | 0 | NA |
| Mock + LY3039478 | 22.5 | 7 | 30 | 2/3 |

TABLE E1-continued

Survival across groups

| Group | Median Survival (days) | Number of deaths | Day 65 Survival % | Day 65 tumor free survival |
|---|---|---|---|---|
| anti-BCMA CAR-expressing T cell 1e6 + Vehicle | 60.5 | 5 | 50 | 5/5 |
| anti-BCMA CAR-expressing T cell 1e6 + LY3039478 | Undef | 2 | 80 | 8/8 |
| anti-BCMA CAR-expressing T cell 3e6 + Vehicle | Undef | 0 | 100 | 10/10 |
| anti-BCMA CAR-expressing T cell 3e6 + LY3039478 | Undef | 0 | 100 | 10/10 |

Figure 10A:
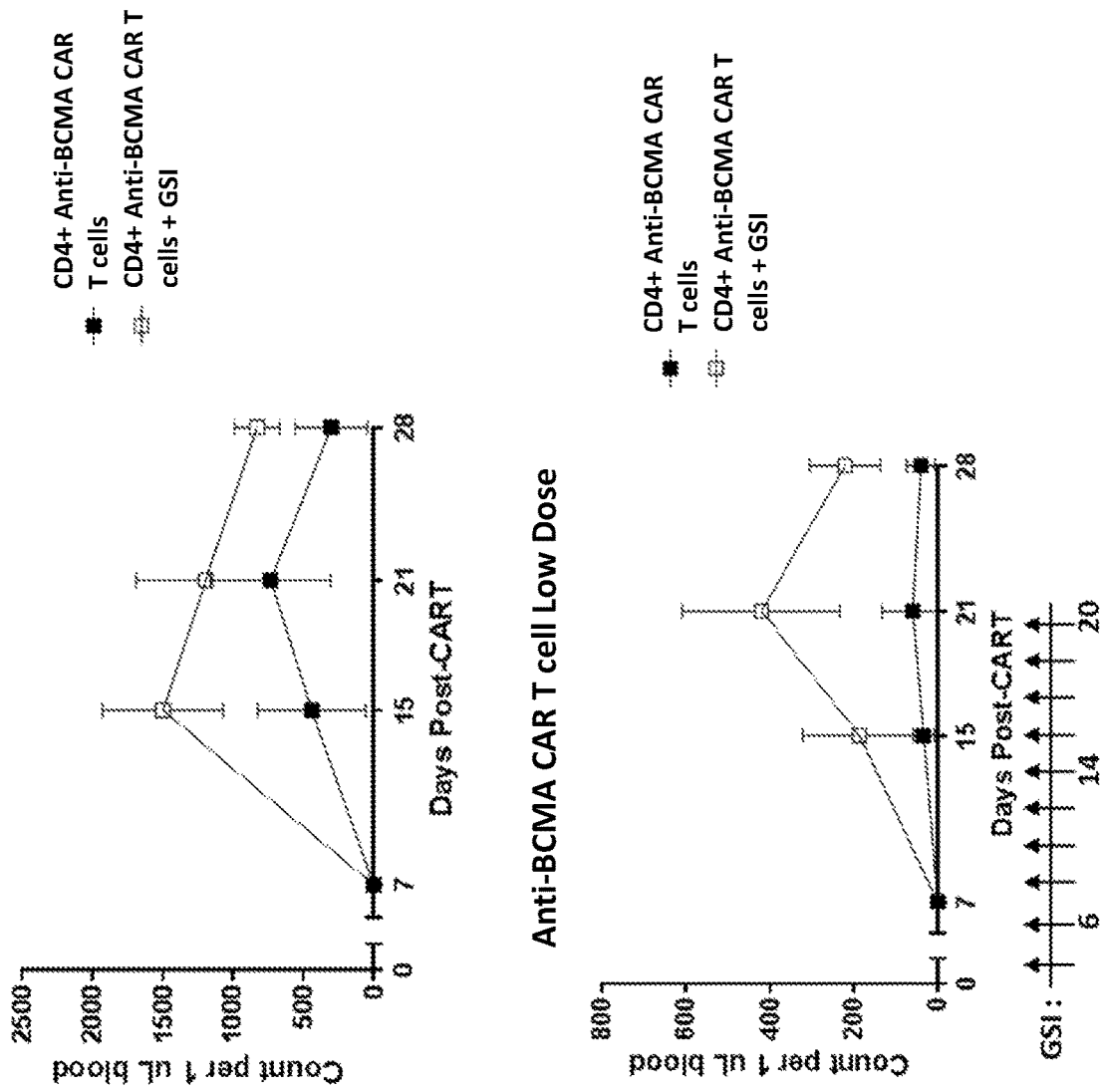
FIGS. 10A-10B show CD4+ CAR T+ and CD8+ CAR T+ peripheral blood counts over time (days) following CAR T injection (Days Post-CAR T injection) of animals of a human multiple myeloma xenograft mouse model treated under various conditions as described in Example 5.
Figure 10B:
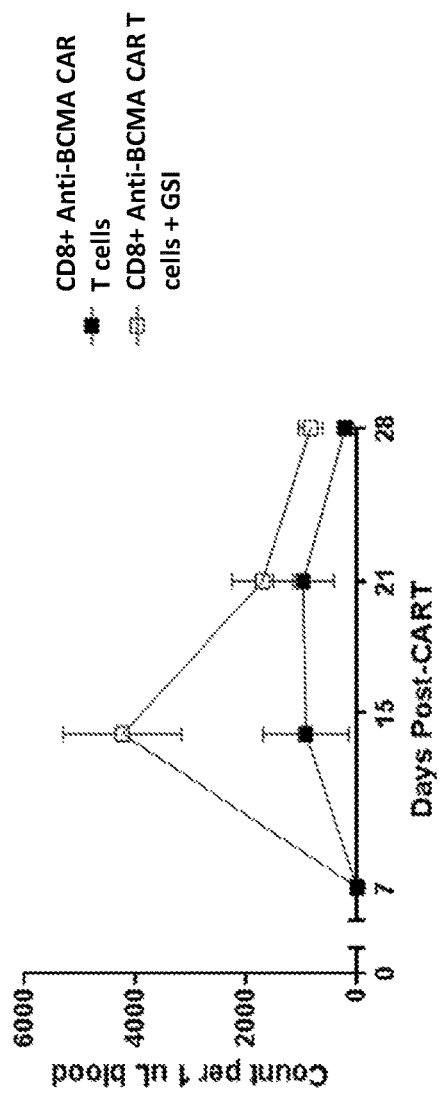
Figure 10B:
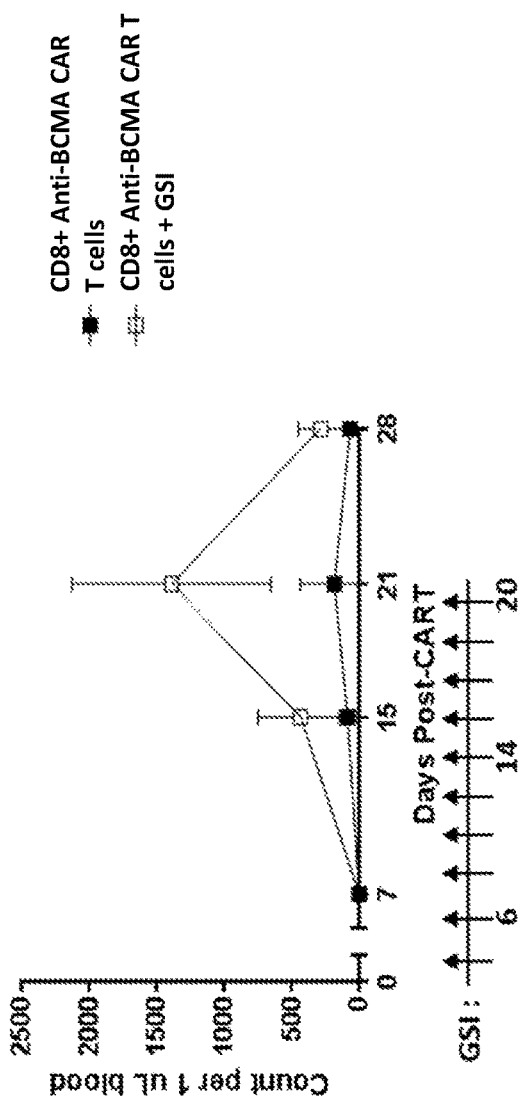

The presence of CAR+ T cells in the blood was monitored over the course of the study (from blood drawn on days 7, 14, 21 and 28 post CAR-T cell administration). White blood cells from blood samples were stained with various reagents to detect various markers on the surface of immune cells, including T cells, and expression of the CAR (including a reagent specific for the CAR and a reagent specific for a transduction marker encoded by the CAR vector). Results are shown in FIGS. 10A and 10B.

As shown, increased anti-BCMA CAR-expressing CD4+ T cells (FIG. 10A) and anti-BCMA CAR-expressing CD8+ T cells (FIG. 10B) counts were observed in the peripheral blood at Day 15, 21 and 28 following administration of either the higher or lower dose CAR-expressing T cells in combination with LY3039478 compared to its absence. In the presence of LY3039478, peak expansion was at about day 15 following administration of higher dose anti-BCMA CAR-expressing cells and was about day 21 following administration of lower dose anti-BCMA CAR-expressing T cells. No changes in peripheral blood count were observed for CD4+ or CD8+ T cells that did not express the anti-BCMA CAR when treated with or without LY3039478.

Figure 11:
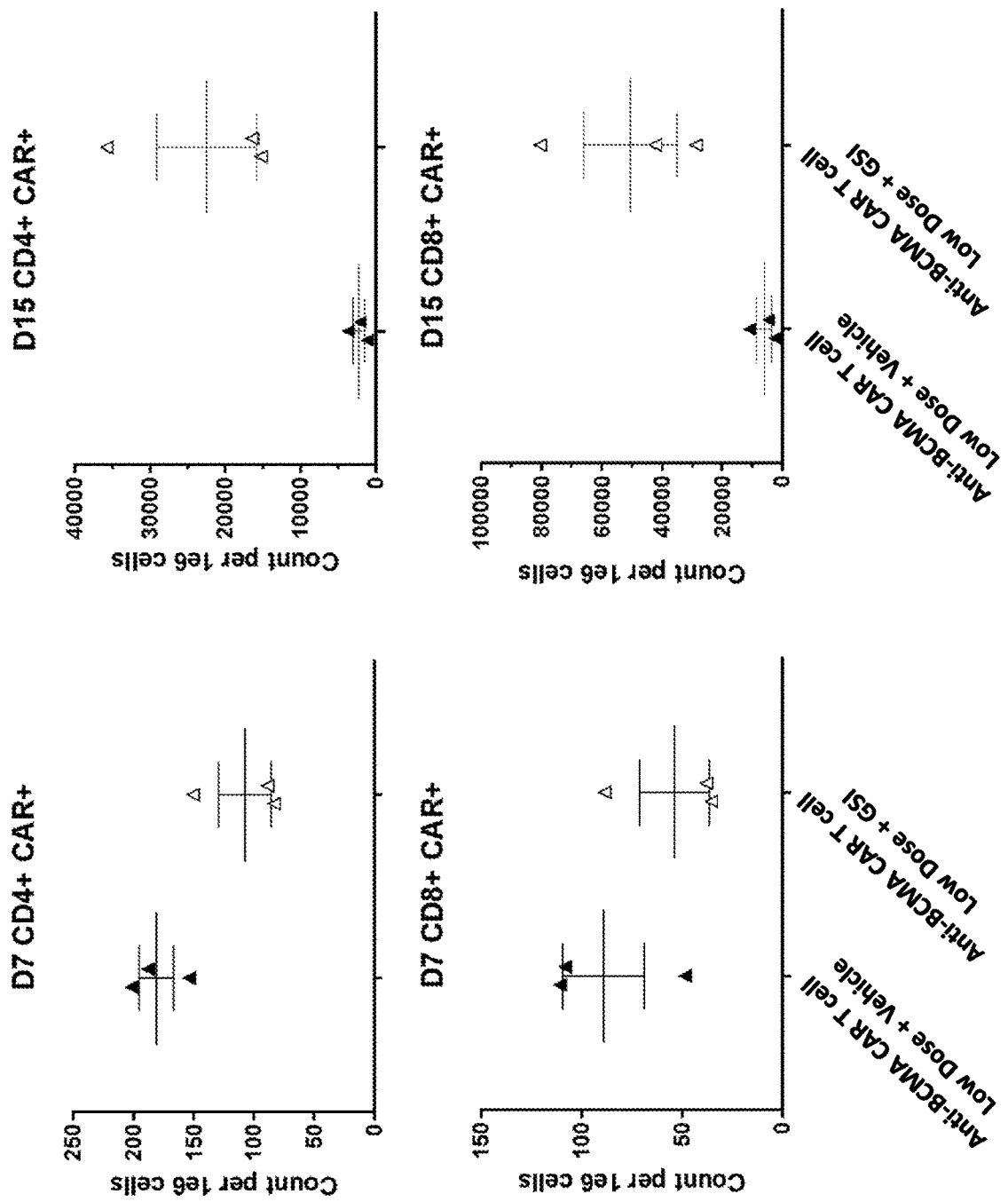
FIG. 11 shows CD4+(top) and CD8+(bottom) CAR+ T cell counts per 1×10$^6$ cells from satellite tumor digests taken on days 7 and 15 following low dose (1e6) CAR T injection in the study described in Example 5.
Figures 12A, 12B:
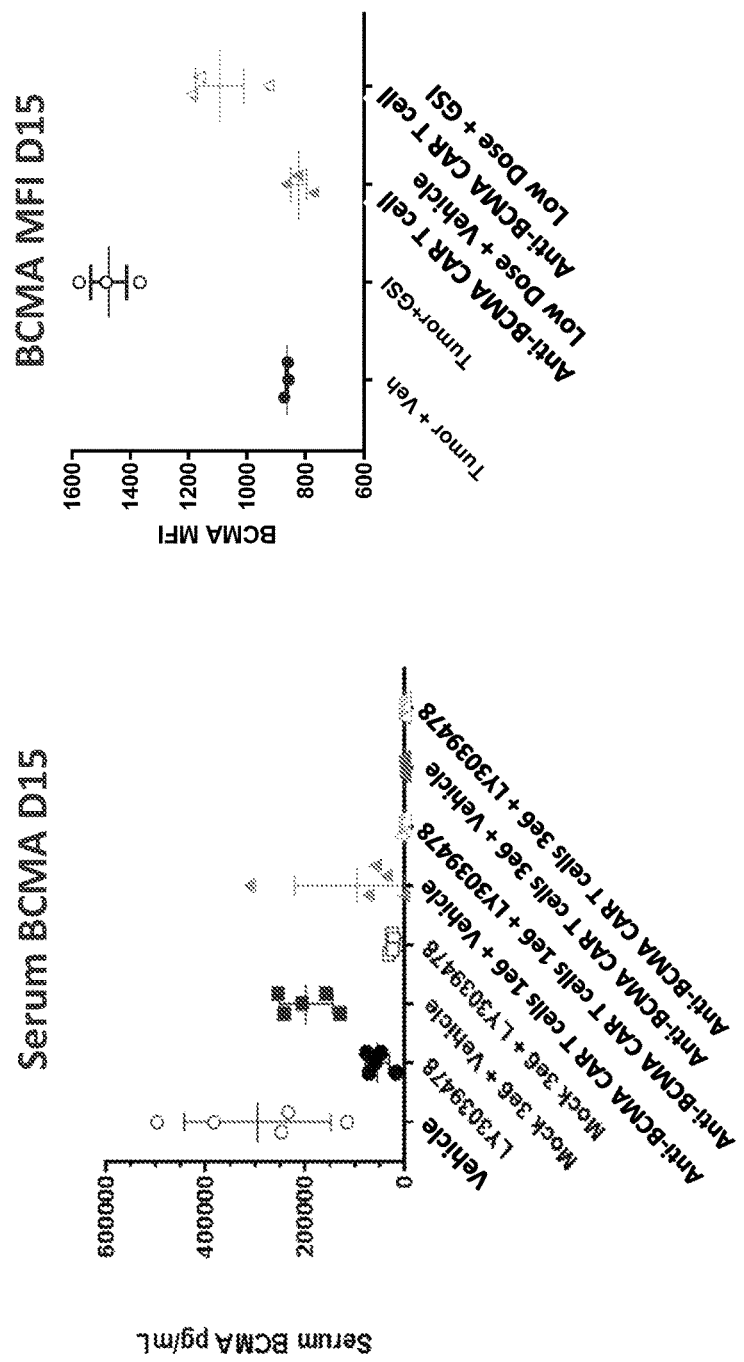
FIG. 12A shows serum levels of BCMA on days 7 and 15 following commencement of different treatment regimes as describe in Example 5.
FIG. 12B shows surface BCMA expression, as assessed by flow cytometry, from tumor digests taken on days 7 and 15 following anti-BCMA CAR T cell injection in mice from various treatment groups as described in Example 5.

Tumor digests were also analyzed to determine the number of CD4+ and CD8+ CAR+ T cells in tumors following the various treatment conditions. On days 7 and 15, satellite tumor digests from mice treated with lower dose anti-BCMA CAR+ T cells and LY3039478 showed a higher number of CD4+ and CD8+ CAR+ T cells per $1\times10^6$ cells compared to mice treated with lower dose anti-BCMA CAR+ T cells and vehicle (FIG. 11). Analysis of cells from tumor digests for surface BCMA expression by flow cytometry, as measured by mean fluorescence intensity (MFI), showed that the presence of LY3039478 increased surface BCMA MFI on RPMI-8226 tumor cells (FIG. 12B). Serum BCMA was also assessed according to treatment condition. FIG. 12A shows BCMA serum levels on days 7 and 15 for each treatment condition. These results are consistent with the ability of LY3039478 to reduce or prevent cleavage of surface BCMA.

These results are consistent with a finding that administration of LY3039478 in combination with the lower dose of anti-BCMA CAR T cells led to increased anti-tumor effects as compared to administration of the lower dose of anti-BCMA CAR-expressing T cells in combination with vehicle alone.

Example 6: Assessment of Anti-BCMA CAR+ T Cells Following Chronic Stimulation and Re-Challenge in the Presence of a Gamma Secretase Inhibitor Compound, LY3039478

The effect of a gamma secretase inhibitor compound, LY3039478, on the cytotoxicity of anti-BCMA CAR+ T cells after long-term CAR-specific stimulation was assessed. Anti-BCMA CAR+ T cell compositions, generated as described in Example 2 containing anti-BCMA CAR-expressing CD4+ and CD8+ T cells, were incubated with 50 μg/mL BCMA-Fc conjugated beads for 7 days, under conditions designed to functionally exhaust the CAR T cells.

The CAR-T cells then were re-challenged with antigen-expressing target cells in the presence or absence of LY3039478. Specifically, anti-BCMA CAR-expressing T cells were co-cultured with multiple myeloma cell lines RPMI-8226, OPM2, or MM1.S in the presence of 1 μM LY3039478 or DMSO vehicle control at an effector to target ratio of 0.3:1. To assess cytolytic activity, the target cells were labeled with NucLight Red (NLR) to permit tracking by fluorescent microscopy. Killing activity was assessed by measuring the loss of viable target cells over time, as determined by loss of fluorescent signal over time by kinetic fluorescence microscopy (using the INCUCYTE® Live Cell Analysis System, Essen Bioscience). Target fluorescence was monitored over time and was normalized to target cell count.

Figure 13A:
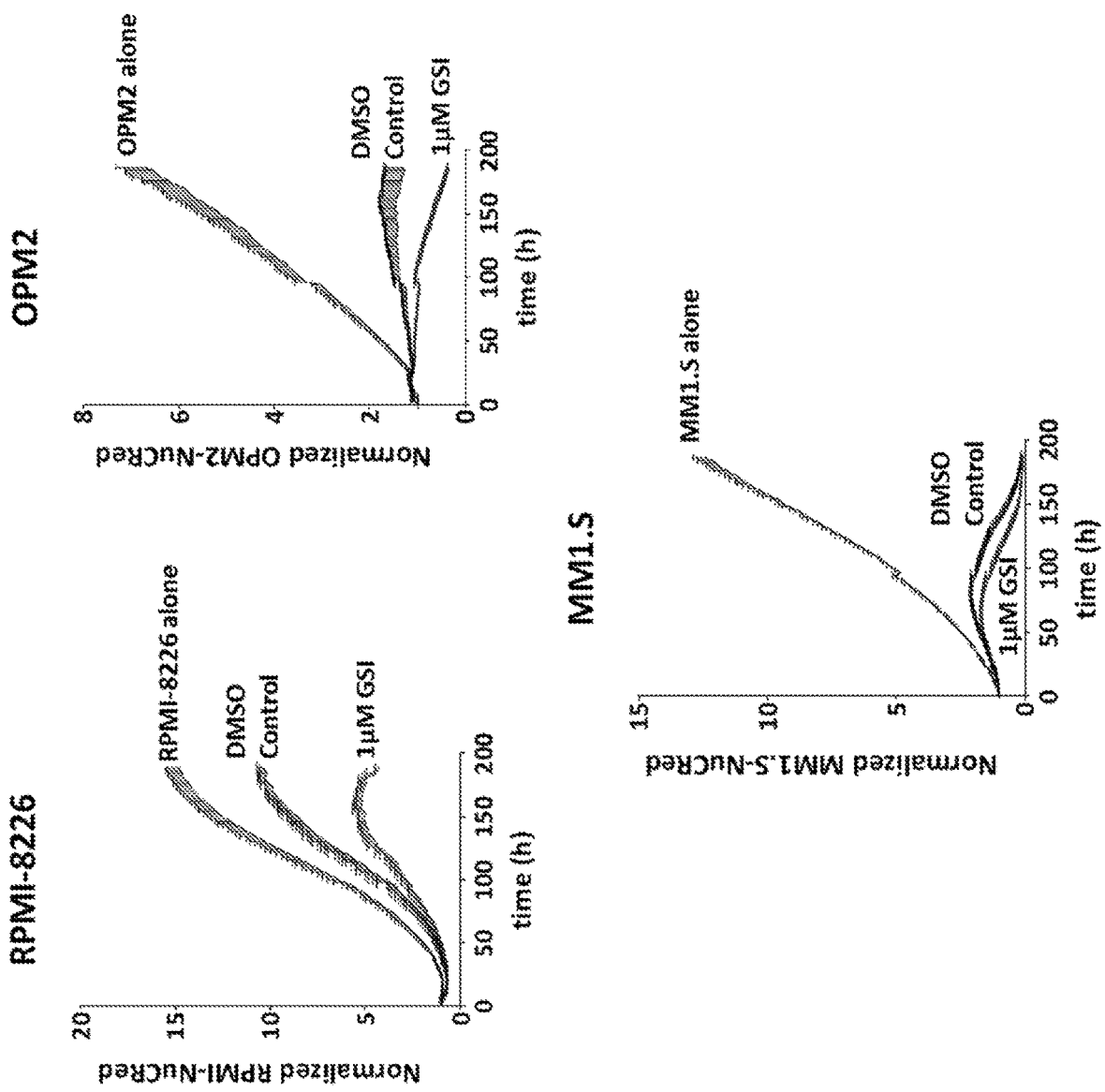
FIG. 13A shows RPMI-8226, OPM2, and MM1.S cell viability over time when treated with chronically stimulated anti-BCMA CAR+ T cells and DMSO (DMSO control) or the gamma secretase inhibitor compound LY3039478 (1 µM GSI), at an effector to target ratio of 0.3:1, or when untreated (RPMI, OPM2, or MM1.S alone).
Figure 13B:
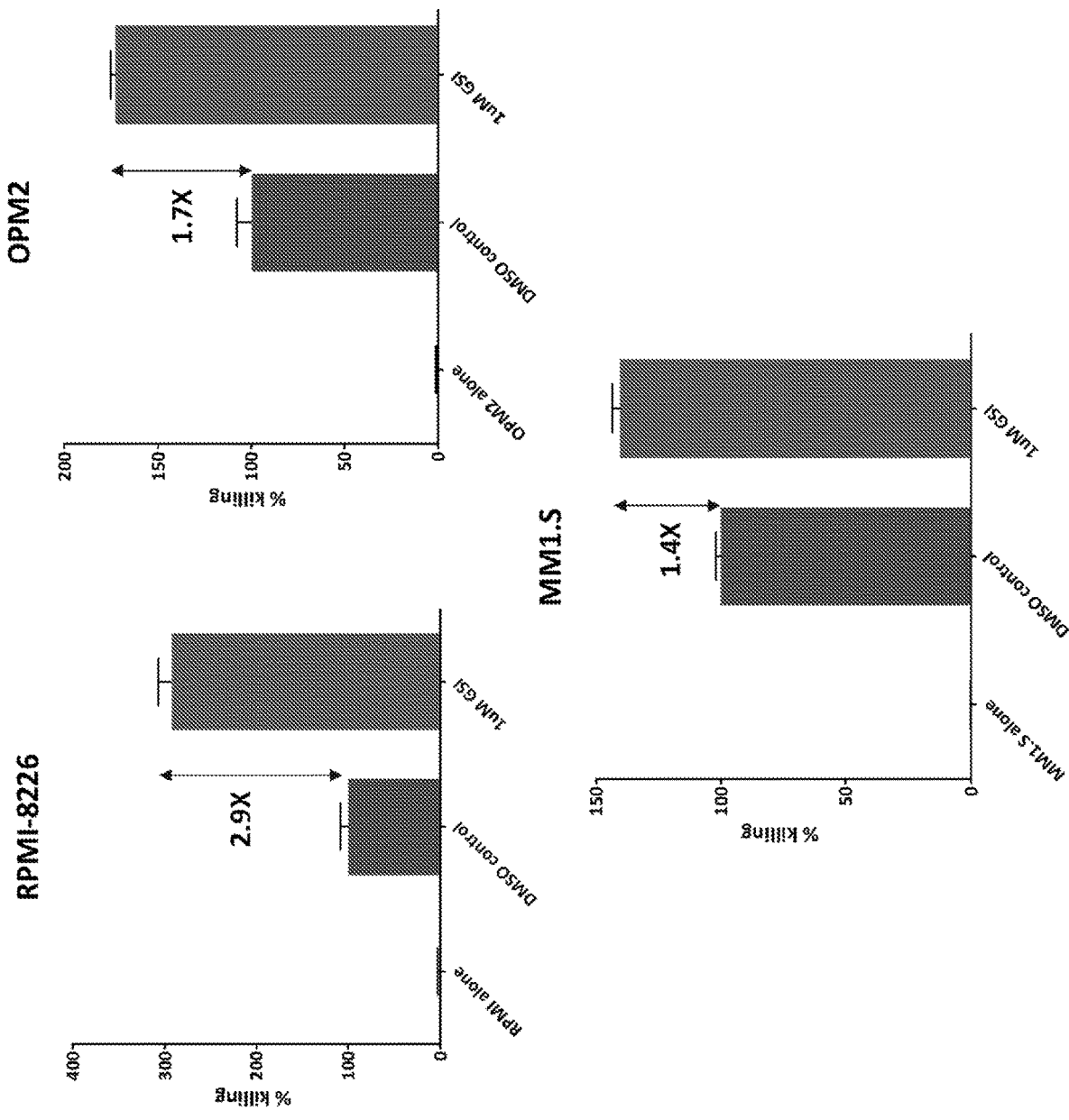
FIG. 13B shows the percentage of killing of RPMI-8226, OPM2, and MM1.S cells when treated with chronically stimulated anti-BCMA CAR+ T cells and DMSO (DMSO control) or LY3039478 (1 µM GSI), or when untreated (RPMI, OPM2, or MM1.S alone).

The results shown in FIG. 13A demonstrated that the presence of LY3039478 improved cytolytic activity of anti-BCMA CAR+ T cells that had been chronically stimulated. A killing index was determined as the inverse of the area under the curve (AUC) for target fluorescence over time, and was normalized relative to DMSO vehicle control. As shown in FIG. 13B, the degree of improvement on cell killing correlated to the density of BCMA antigen on the target cells (antigen density: RPMI-8226<OPM2<MM1.S).

Figure 13C:
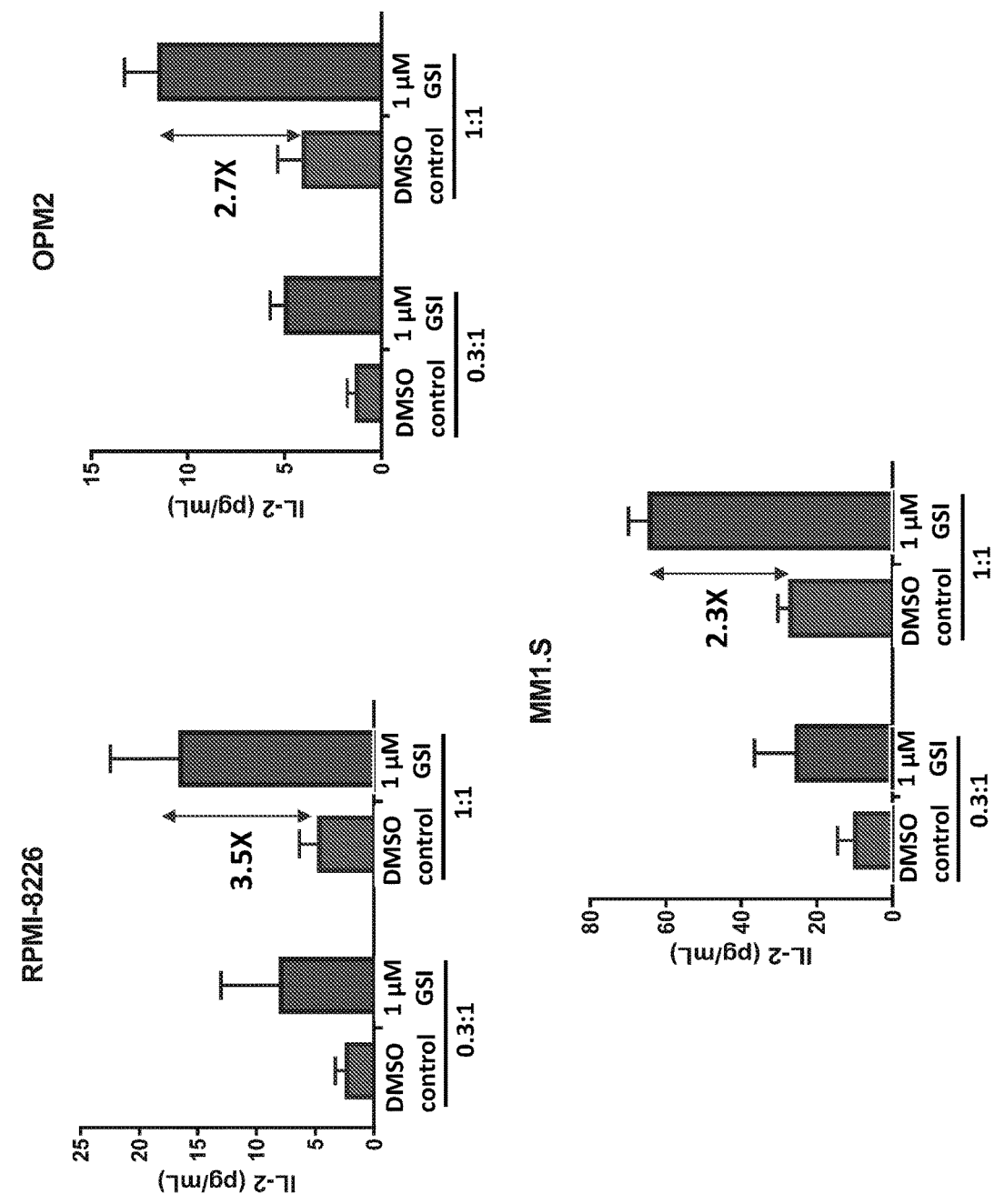
FIG. 13C shows supernatant IL-2 concentrations following 24 hour incubation of RPMI-8226, OPM2, and MM1.S cells with chronically stimulated anti-BCMA CAR+ T cells and LY3039478 (1 µM GSI) or DMSO (DMSO control) at effector to target ratios of 0.3:1 or 1:1.

Cell culture supernatant was harvested from co-cultures 24 hours after initiation of culture of anti-BCMA CAR-expressing T cells and target cells in the experiment above, or in a similar experiment but in which anti-BCMA CAR+ T cells and target cells were co-cultured at an E:T ratio of 1:1. The production of TNF-alpha, IFN-gamma and IL-2 in the harvested supernatant was measured using a Luminex Multiplex Assay. At both E:T ratios, the presence of the GSI LY3039478 improved function of the chronically stimulated anti-BCMA CAR-expressing T cells to produce cytokines (FIG. 13C). The degree of improvement in cytokine production also correlated to the density of BCMA antigen on the target cells.

Figure 14:
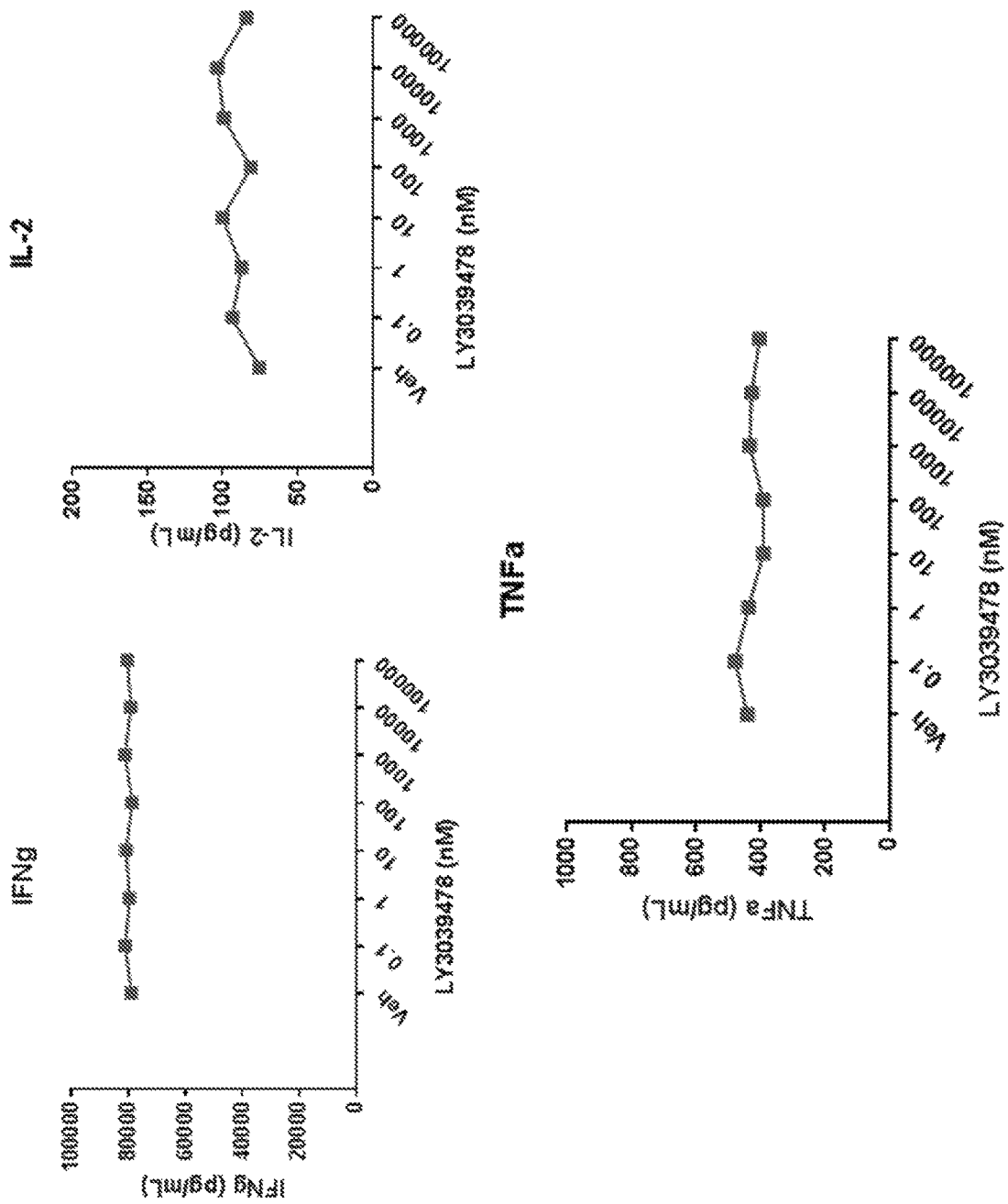
FIG. 14 shows IFNg, IL-2, and TNFa concentrations in supernatant following 24 hour incubation of anti-BCMA CAR+ T cells with BCMA-containing beads in different concentrations of gamma secretase inhibitor LY3039478 or DMSO (veh.).

Example 7: Assessment of Cytokine Production by Anti-BCMA CAR+ T Cells in the Presence or Absence of a Gamma Secretase Inhibitor Various parameters indicative of T cell function were assessed following incubation of anti-BCMA CAR+ T cells with BCMA-containing beads in the presence of different concentrations of the gamma secretase inhibitor, LY3039478, or vehicle (DMSO). Supernatant was harvested after 24 hours and production of TNF-alpha, IFN-gamma and IL-2 were measured using a Luminex Multiplex Assay. The results are shown in FIG. 14. The results were consistent with a conclusion that the presence of this GSI compound did not impact cytokine production, CAR+ T cell count, or viability.

Figure 15A:
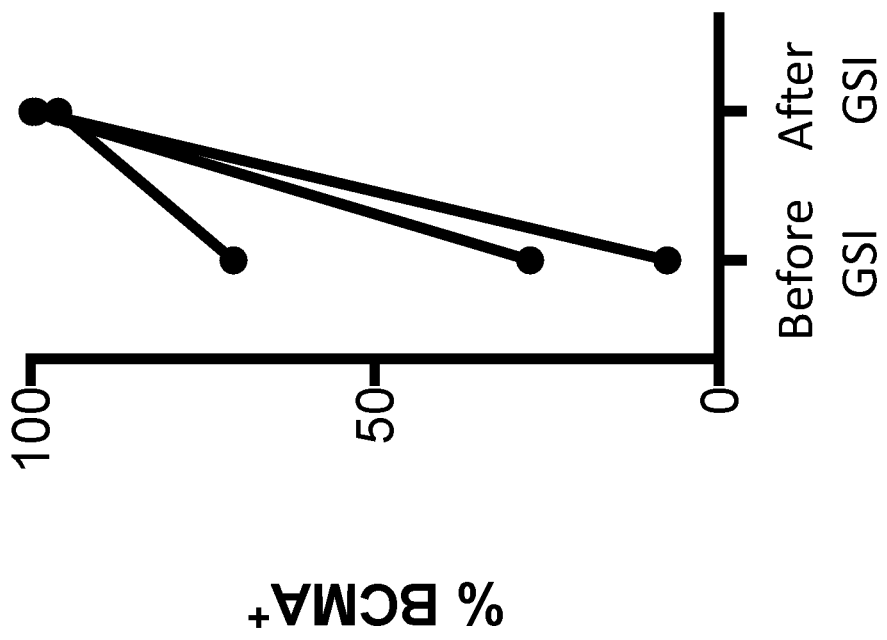
FIG. 15A shows BCMA antibody binding capacity (BCMA ABC) on the surface of cells in samples derived from multiple myeloma patients cells before (Before GSI) and after (After GSI) administration of three doses of the small molecule gamma secretase inhibitor (GSI) LY3039478 by mouth as described in Example 8.
Figure 15B:
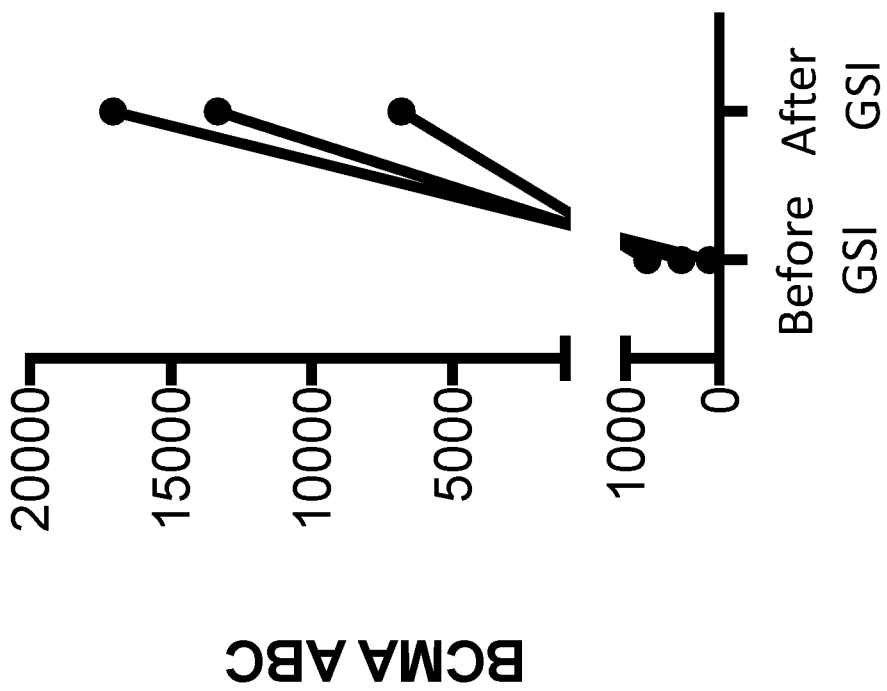
FIG. 15B shows the percentage of plasma cells in patient samples determined to have measurable surface BCMA expression, before (Before GSI) and after (After GSI) administration of three doses of the small molecule gamma secretase inhibitor (GSI) LY3039478 by mouth, as described in Example 8.

Example 8: Assessment of BCMA Surface Expression in Multiple Myeloma Cells in Patients Treated with Gamma Secretase Inhibitor Three human subjects having multiple myeloma were administered three 25 mg doses of the gamma secretase inhibitor (GSI) LY3039478 by mouth. The absolute B cell maturation antigen (BCMA) antibody binding capacity (ABC) on the surface of multiple myeloma cells was quantitated by flow cytometry performed on bone marrow aspirate specimens obtained from each of the patients prior to administration of the GSI, and immediately after the third oral GSI dose. A mean 66-fold increase in BCMA ABC was observed following GSI administration (FIG. 15A). Percentage of plasma cells in the patient samples that were determined to have measurable surface BCMA expression was observed to increase from 35% (mean) before GSI to 98.4% (mean) following the three oral doses (FIG. 15B).

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| SEQ ID NO. | SEQUENCE | DESCRIPTION |
|---|---|---|
| 1 | ESKYGPPCPPCP | spacer (IgG4hinge) (aa) Homo sapiens |
| 2 | GAATCTAAGTACGGACCGCCCTGCCCCCCTTGCCCT | spacer (IgG4hinge) (nt) Homo sapiens |
| 3 | ESKYGPPCPPCPGQPREPQVYTLPPSQEEMTKNQVSLTCLVKGFYPSDIAVEWE SNGQPENNYKTTPPVLDSDGSFFLYSRLTVDKSRWQEGNVFSCSVMHEALHNHY TQKSLSLSLGK | Hinge-CH3 spacer Homo sapiens |
| 4 | ESKYGPPCPPCPAPEFLGGPSVFLFPPKPKDTLMISRTPEVTCVVVDVSQEDPE VQFNWYVDGVEVHNAKTKPREEQFNSTYRVVSVLTVLHQDWLNGKEYKCKVSNK GLPSSIEKTISKAKGQPREPQVYTLPPSQEEMTKNQVSLTCLVKGFYPSDIAVE WESNGQPENNYKTTPPVLDSDGSFFLYSRLTVDKSRWQEGNVFSCSVMHEALHN HYTQKSLSLSLGK | Hinge-CH2—CH3 spacer Homo sapiens |
| 5 | RWPESPKAQASSVPTAQPQAEGSLAKATTAPATTRNTGRGGEEKKKEKEKEEQE ERETKTPECPSHTQPLGVYLLTPAVQDLWLRDKATFTCFVVGSDLKDAHLTWEV AGKVPTGGVEEGLLERHSNGSQSQHSRLTLPRSLWNAGTSVTCTLNHPSLPPQR LMALREPAAQAPVKLSLNLLASSDPPEAASWLLCEVSGFSPPNILLMWLEDQRE VNTSGFAPARPPPQPGSTTFWAWSVLRVPAPPSPQPATYTCVVSHEDSRTLLNA SRSLEVSYVTDH | IgD-hinge-Fc Homo sapiens |
| 6 | LEGGGEGRGSLLTCGDVEENPGPR | T2A artificial |
| 7 | RKVCNGIGIGEFKDSLSINATNIKHFKNCTSISGDLHILPVAFRGDSFTHTPPL DPQELDILKTVKEITGFLLIQAWPENRTDLHAFENLEIIRGRTKQHGQFSLAVV SLNITSLGLRSLKEISDGDVIISGNKNLCYANTINWKKLFGTSGQKTKIISNRG ENSCKATGQVCHALCSPEGCWGPEPRDCVSCRNVSRGRECVDKCNLLEGEPREF VENSECIQCHPECLPQAMNITCTGRGPDNCIQCAHYIDGPHCVKTCPAGVMGEN NTLVWKYADAGHVCHLCHPNCTYGCTGPGLEGCPTNGPKIPSIATGMVGALLLL LVVALGIGLFM | tEGFR artificial |
| 8 | FWVLVVVGGVLACYSLLVTVAFIIFWV | CD28 (amino acids 153-179 of Accession No. P10747) Homo sapiens |
| 9 | IEVMYPPPYLDNEKSNGTIIHVKGKHLCPSPLFPGPSKPFWVLVVVGGVLACYS LLVTVAFIIFWV | CD28 (amino acids 114-179 of Accession No. P10747) Homo sapiens |
| 10 | RSKRSRLLHSDYMNMTPRRPGPTRKHYQPYAPPRDFAAYRS | CD28 (amino acids 180-220 of P10747) Homo sapiens |
| 11 | RSKRSRGGHSDYMNMTPRRPGPTRKHYQPYAPPRDFAAYRS | CD28 (LL to GG) Homo sapiens |

| SEQ ID NO. | SEQUENCE | DESCRIPTION |
|---|---|---|
| 12 | KRGRKKLLYIFKQPFMRPVQTTQEEDGCSCRFPEEEEGGCEL | 4-1BB (amino acids 214-255 of Q07011.1) *Homo sapiens* |
| 13 | RVKFSRSADAPAYQQGQNQLYNELNLGRREEYDVLDKRRGRDPEMGGKPRRKNP QEGLYNELQKDKMAEAYSEIGMKGERRRGKGHDGLYQGLSTATKDTYDALHMQA LPPR | CD3 zeta *Homo sapiens* |
| 14 | RVKFSRSAEPPAYQQGQNQLYNELNLGRREEYDVLDKRRGRDPEMGGKPRRKNP QEGLYNELQKDKMAEAYSEIGMKGERRRGKGHDGLYQGLSTATKDTYDALHMQA LPPR | CD3 zeta *Homo sapiens* |
| 15 | RVKFSRSADAPAYKQGQNQLYNELNLGRREEYDVLDKRRGRDPEMGGKPRRKNP QEGLYNELQKDKMAEAYSEIGMKGERRRGKGHDGLYQGLSTATKDTYDALHMQA LPPR | CD3 zeta *Homo sapiens* |
| 16 | PGGG-(SGGGG)5-P- wherein P is proline, G is glycine and S is serine | linker |
| 17 | GSADDAKKDAAKKDGKS | Linker |
| 18 | QIQLVQSGPELKKPGETVKISCKASGYTFTDYSINWVKRAPGKGLKWMGWINTE TREPAYAYDFRGRFAFSLETSASTAYLQINNLKYEDTATYFCALDYSYAMDYWG QGTSVTVSS | Variable heavy (VH) Anti-BCMA |
| 19 | DIVLTQSPPSLAMSLGKRATISCRASESVTILGSHLIHWYQQKPGQPPTLLIQL ASNVQTGVPARFSGSGSRTDFTLTIDPVEEDDVAVYYCLQSRTIPRTFGGGTKL EIK | Variable light (VL) Anti-BCMA |
| 20 | QIQLVQSGPDLKKPGETVKLSCKASGYTFTNFGMNWVKQAPGKGFKWMAWINTY TGESYFADDFKGRFAFSVETSATTAYLQINNLKTEDTATYFCARGEIYYGYDGG FAYWGQGTLVTVSA | Variable heavy (VH) Anti-BCMA |
| 21 | DVVMTQSHRFMSTSVGDRVSITCRASQDVNTAVSWYQQKPGQSPKLLIFSASYR YTGVPDRFTGSGSGADFTLTISSVQAEDLAVYYCQQHYSTPWTFGGGTKLDIK | Variable light (VL) Anti-BCMA |
| 22 | EVQLVQSGAEVKKPGESLKISCKGSGYSFTSYWIGWVRQMPGKGLEWMGIIYPG DSDTRYSPSFQGHVTISADKSISTAYLQWSSLKASDTAMYYCARYSGSFDNWGQ GTLVTVSS | Variable heavy (VH) Anti-BCMA |
| 23 | SYELTQPPSASGTPGQRVTMSCSGTSSNIGSHSVNWYQQLPGTAPKLLIYTNNQ RPSGVPDRFSGSKSGTSASLAISGLQSEDEADYYCAAWDGSLNGLVFGGGTKLT VLG | Variable light (VL) Anti-BCMA |
| 24 | EVQLVQSGAEMKKPGASLKLSCKASGYTFIDYYVYWMRQAPGQGLESMGWINPN SGGTNYAQKFQGRVTMTRDTSISTAYMELSRLRSDDTAMYYCARSQRDGYMDYW GQGTLVTVSS | Variable heavy (VH) Anti-BCMA |
| 25 | QSALTQPASVSASPGQSIAISCTGTSSDVGWYQQHPGKAPKLMIYEDSKRPSGV SNRFSGSKSGNTASLTISGLQAEDEADYYCSSNTRSSTLVFGGGTKLTVLG | Variable light (VL) Anti-BCMA |
| 26 | GGGGS | Linker |
| 27 | GGGS | Linker |
| 28 | GGGGSGGGGSGGGGS | Linker |
| 29 | GSTSGSGKPGSGEGSTKG | Linker |
| 30 | SRGGGGSGGGGSGGGGSLEMA | Linker |
| 31 | ESKYGPPCPPCPAPPVAGPSVFLFPPKPKDTLMISRTPEVTCVVVDVSQEDPEV QFNWYVDGVEVHNAKTKPREEQFQSTYRVVSVLTVLHQDWLNGKEYKCKVSNKG LPSSIEKTISKAKGQPREPQVYTLPPSQEEMTKNQVSLTCLVKGFYPSDIAVEW ESNGQPENNYKTTPPVLDSDGSFFLYSRLTVDKSRWQEGNVFSCSVMHEALHNH YTQKSLSLSLGK | Hinge-CH2—CH3 spacer *Homo sapiens* |
| 32 | EVQLVQSGAEVKKPGSSVKVSCKASGGTFSSYAISWVRQAPGQGLEWMGRIIPI LGIANYAQKFQGRVTMTEDTSTDTAYMELSSLRSEDTAVYYCARSGYSKSIVSY MDYWGQGTLVTVSS | Variable heavy (VH) Anti-BCMA |

-continued

| SEQ ID NO. | SEQUENCE | DESCRIPTION |
|---|---|---|
| 33 | LPVLTQPPSTSGTPGQRVTVSCSGSSSNIGSNVVFWYQQLPGTAPKLVIYRNNQ RPSGVPDRFSVSKSGTSASLAISGLRSEDEADYYCAAWDDSLSGYVFGTGTKVT VLG | Variable light (VL) Anti-BCMA |
| 34 | QVQLVQSGAEVKKPGSSVKVSCKASGGTFSSYAISWVRQAPGQGLEWMGRIIPI LGTANYAQKFQGRVTITADESTSTAYMELSSLRSEDTAVYYCARSGYGSYRWED SWGQGTLVTVSS | Variable heavy (VH) Anti-BCMA |
| 35 | QAVLTQPPSASGTPGQRVTISCSGSSSNIGSNYVFWYQQLPGTAPKLLIYSNNQ RPSGVPDRFSGSKSGTSASLAISGLRSEDEADYYCAAWDDSLSASYVFGTGTKV TVLG | Variable light (VL) Anti-BCMA |
| 36 | QVQLVQSGAEVKKPGASVKVSCKASGYTFTDYYMHWVRQAPGQRLEWMGWINPN SGGTNYAQKFQDRITVTRDTSSNTGYMELTRLRSDDTAVYYCARSPYSGVLDKW GQGTLVTVSS | Variable heavy (VH) Anti-BCMA |
| 37 | QSVLTQPPSVSGAPGQRVTISCTGSSSNIGAGFDVHWYQQLPGTAPKLLIYGNS NRPSGVPDRFSGSKSGTSASLAITGLQAEDEADYYCQSYDSSLSGYVFGTGTKV TVLG | Variable light (VL) Anti-BCMA |
| 38 | ASGGGGSGGRASGGGGS | Linker |
| 39 | MALPVTALLLPLALLLHAARP | CD8a signal peptide |
| 40 | METDTLLLWVLLLWVPGSTG | signal peptide |
| 41 | EVQLLESGGGLVQPGGSLRLSCAASGFTFSSYAMSWVRQAPGKGLEWVSAISGS GGSTYYADSVKGRFTISRDNSKNTLYLQMNSLRAEDTAVYYCARAEMGAVFDIW GQGTMVTVSS | Variable heavy (VH) Anti-BCMA |
| 42 | EIVLTQSPATLSLSPGERATLSCRASQSVSRYLAWYQQKPGQAPRLLIYDASNR ATGIPARFSGSGSGTDFTLTISSLEPEDFAVYYCQQRISWPFTGGGTKVEIK | Variable light (VL) Anti-BCMA |
| 43 | QVQLVESGGGVVQPGRSLRLSCAASGFTFSSYGMHWVRQAPGKGLEWVAVISYD GSNKYYADSVKGRFTISRDNSKNTLYLQMNSLRAEDTAVYYCARDGTYLGGLWY FDLWGRGTLVTVSS | Variable heavy (VH) Anti-BCMA |
| 44 | DIVMTQSPLSLPVTPGEPASISCRSSQSLLHSNGYNYLDWYLQKPGQSPQLLIY LGSNRASGVPDRFSGSGSGTDFTLKISRVEAEDVGVYYCMQGLGLPLTFGGGTK VEIK | Variable light (VL) Anti-BCMA |
| 45 | QVQLVQSGAEVKKPGASVKVSCKASGYTFTSYYMHWVRQAPGQGLEWMGIINPG GGSTSYAQKFQGRVTMTRDTSTSTVYMELSSLRSEDTAVYYCARESWPMDVWGQ GTTVTVSS | Variable heavy (VH) Anti-BCMA |
| 46 | EIVMTQSPATLSVSPGERATLSCRASQSVSSNLAWYQQKPGQAPRLLIYGASTR ATGIPARFSGSGSGTEFTLTISSLQSEDFAVYYCQQYAAYPTFGGGTKVEIK | Variable light (VL) Anti-BCMA |
| 47 | QLQLQESGPGLVKPSETLSLTCTVSGGSISSSSYYWGWIRQPPGKGLEWIGSIS YSGSTYYNPSLKSRVTISVDTSKNQFSLKLSSVTAADTAVYYCARGRGYATSLA FDIWGQGTMVTVSS | Variable heavy (VH) Anti-BCMA |
| 48 | EIVLTQSPATLSLSPGERATLSCRASQSVSSYLAWYQQKPGQAPRLLIYDASNR ATGIPARFSGSGSGTDFTLTISSLEPEDFAVYYCQQRHVWPPTFGGGTKVEIK | Variable light (VL) Anti-BCMA |
| 49 | EVQLVESGGGLVQPGGSLRLSCAASGFTFSSYSMNWVRQAPGKGLEWVSTISSS SSTIYYADSVKGRFTISRDNAKNSLYLQMNSLRAEDTAVYYCARGSQEHLIFDY WGQGTLVTVSS | Variable heavy (VH) Anti-BCMA |
| 50 | EIVLTQSPATLSLSPGERATLSCRASQSVSRYLAWYQQKPGQAPRLLIYDASNR ATGIPARFSGSGSGTDFTLTISSLEPEDFAVYYCQQRFYYPWTFGGGTKVEIK | Variable light (VL) Anti-BCMA |
| 51 | QVQLVESGGGVVQPGRSLRLSCAASGFTFSSYGMHWVRQAPGKGLEWVAVISYD GSNKYYADSVKGRFTISRDNSKNTLYLQMNSLRAEDTAVYYCARTDFWSGSPPG LDYWGQGTLVTVSS | Variable heavy (VH) Anti-BCMA |
| 52 | DIQLTQSPSSVSASVGDRVTITCRASQGISSWLAWYQQKPGKAPKLLIYGASSL QSGVPSRFSGSGSGTDFTLTISSLQPEDFATYYCQQIYTFPPFTGGGTKVEIK | Variable light (VL) Anti-BCMA |
| 53 | QVQLVQSGAEVKKPGSSVKVSCKASGGTFSSYAISWVRQAPGQGLEWMGGIIPI FGTANYAQKFQGRVTITADESTSTAYMELSSLRSEDTAVYYCARTPEYSSSIWH YYYGMDVWGQGTTVTVSS | Variable heavy (VH) Anti-BCMA |

| SEQ ID NO. | SEQUENCE | DESCRIPTION |
|---|---|---|
| 54 | DIVMTQSPDSLAVSLGERATINCKSSQSVLYSSNNKNYLAWYQQKPGQPPKLLI YWASTRESGVPDRFSGSGSGTDFTLTISSLQAEDVAVYYCQQFAHTPFTFGGGT KVEIK | Variable light (VL) Anti-BCMA |
| 55 | QVQLVESGGGVVQPGRSLRLSCAASGFTFSSYGMHWVRQAPGKGLEWVAVISYD GSNKYYADSVKGRFTISRDNSKNTLYLQMNSLRAEDTAVYYCVKGPLQEPPYDY GMDVWGQGTTVTVSS | Variable heavy (VH) Anti-BCMA |
| 56 | EIVMTQSPATLSVSPGERATLSCRASQSVSSNLAWYQQKPGQAPRLLIYSASTR ATGIPARFSGSGSGTEFTLTISSLQSEDFAVYYCQQHHVWPLTFGGGTKVEIK | Variable light (VL) Anti-BCMA |
| 57 | QVQLVQSGAEVKKPGSSVKVSCKASGGTFSSYAISWVRQAPGQGLEWMGRIIPI LGIANYAQKFQGRVTITADKSTSTAYMELSSLRSEDTAVYYCARGGYYSHDMWS EDWGQGTLVTVSS | Variable heavy (VH) Anti-BCMA |
| 58 | LPVLTQPPSASGTPGQRVTISCSGRSSNIGSNSVNWYRQLPGAAPKLLIYSNNQ RPPGVPVRFSGSKSGTSASLAISGLQSEDEATYYCATWDDNLNVHYVFGTGTKV TVLG | Variable light (VL) Anti-BCMA |
| 59 | QVQLVQSGSELKKPGASVKVSCKASGYTFTDYSINWVRQAPGQGLEWMGWINTE TREPAYAYDFRGRFVFSLDTSVSTAYLQISSLKAEDTAVYYCARDYSYAMDYWG QGTLVTVSS | Variable heavy (VH) Anti-BCMA |
| 60 | DIVLTQSPASLAVSLGERATINCRASESVSVIGAHLIHWYQQKPGQPPKLLIYL ASNLETGVPARFSGSGSGTDFTLTISSLQAEDAAIYYCLQSRIFPRTFGQGTKL EIK | Variable light (VL) Anti-BCMA |
| 61 | EVQLVESGGGLVQPGGSLRLSCAVSGFALSNHGMSWVRRAPGKGLEWVSGIVYS GSTYYAASVKGRFTISRDNSRNTLYLQMNSLRPEDTAIYYCSAHGGESDVWGQG TTVTVSS | Variable heavy (VH) Anti-BCMA |
| 62 | DIQLTQSPSSLSASVGDRVTITCRASQSISSYLNWYQQKPGKAPKLLIYAASSL QSGVPSRFSGSGSGTDFTLTISSLQPEDFATYYCQQSYSTPYTFGQGTKVEIK | Variable light (VL) Anti-BCMA |
| 63 | QVQLVESGGGLVQPGRSLRLSCAASGFTFSNYAMSWVRQAPGKGLGWVSGISRS GENTYYADSVKGRFTISRDNSKNTLYLQMNSLRDEDTAVYYCARSPAHYYGGMD VWGQGTTVTVSS | Variable heavy (VH) Anti-BCMA |
| 64 | DIVLTQSPGTLSLSPGERATLSCRASQSISSSFLAWYQQKPGQAPRLLIYGASR RATGIPDRFSGSGSGTDFTLTISRLEPEDSAVYYCQQYHSSPSWTFGQGTKLEI K | Variable light (VL) Anti-BCMA |
| 65 | QVQLVESGGGLVQPGGSLRLSCAVSGFALSNHGMSWVRRAPGKGLEWVSGIVYS GSTYYAASVKGRFTISRDNSRNTLYLQMNSLRPEDTAIYYCSAHGGESDVWGQG TTVTVSS | Variable heavy (VH) Anti-BCMA |
| 66 | DIRLTQSPSPLSASVGDRVTITCQASEDINKFLNWYHQTPGKAPKLLIYDASTL QTGVPSRFSGSGSGTDFTLTINSLQPEDIGTYYCQQYESLPLTFGGGTKVEIK | Variable light (VL) Anti-BCMA |
| 67 | EVQLVESGGGLVQPGGSLRLSCAVSGFALSNHGMSWVRRAPGKGLEWVSGIVYS GSTYYAASVKGRFTISRDNSRNTLYLQMNSLRPEDTAIYYCSAHGGESDVWGQG TTVTVSS | Variable heavy (VH) Anti-BCMA |
| 68 | EIVLTQSPGTLSLSPGERATLSCRASQSIGSSSLAWYQQKPGQAPRLLMYGASS RASGIPDRFSGSGSGTDFTLTISRLEPEDFAVYYCQQYAGSPPFTFGQGTKVEI K | Variable light (VL) Anti-BCMA |
| 69 | QIQLVQSGPELKKPGETVKISCKASGYTFRHYSMNWVKQAPGKGLKWMGRINTE SGVPIYADDFKGRFAFSVETSASTAYLVINNLKDEDTASYFCSNDYLYSLDFWG QGTALTVSS | Variable heavy (VH) Anti-BCMA |
| 70 | DIVLTQSPPSLAMSLGKRATISCRASESVTILGSHLIYWYQQKPGQPPTLLIQL ASNVQTGVPARFSGSGSRTDFTLTIDPVEEDDVAVYYCLQSRTIPRTFGGGTKL EIK | Variable light (VL) Anti-BCMA |
| 71 | QIQLVQSGPELKKPGETVKISCKASGYTFTHYSMNWVKQAPGKGLKWMGRINTE TGEPLYADDFKGRFAFSLETSASTAYLVINNLKNEDTATFFCSNDYLYSCDYWG QGTTLTVSS | Variable heavy (VH) Anti-BCMA |
| 72 | DIVLTQSPASLAMSLGKRATISCRASESVSVIGAHLIHWYQQKPGQPPKLLIYL ASNLETGVPARFSGSGSGTDFTLTIDPVEEDDVAIYSCLQSRIFPRTFGGGTKL EIK | Variable light (VL) Anti-BCMA |

| SEQ ID NO. | SEQUENCE | DESCRIPTION |
|---|---|---|
| 73 | QVQLVQSGAEVKKPGASVKVSCKASGYSFPDYYINWVRQAPGQGLEWMGWIYFA SGNSEYNQKFTGRVTMTRDTSINTAYMELSSLTSEDTAVYFCASLYDYDWYFDV WGQGTMVTVSS | Variable heavy (VH) Anti-BCMA |
| 74 | DIVMTQTPLSLSVTPGQPASISCKSSQSLVHSNGNTYLHWYLQKPGQSPQLLIY KVSNRFSGVPDRFSGSGSGTDFTLKISRVEAEDVGIYYCSQSSIYPWTFGQGTK LEIK | Variable light (VL) Anti-BCMA |
| 75 | QVQLVQSGAEVKKPGASVKVSCKASGYSFPDYYINWVRQAPGQGLEWMGWIYFA SGNSEYNQKFTGRVTMTRDTSSSTAYMELSSLRSEDTAVYFCASLYDYDWYFDV WGQGTMVTVSS | Variable heavy (VH) Anti-BCMA |
| 76 | DIVMTQTPLSLSVTPGEPASISCKSSQSLVHSNGNTYLHWYLQKPGQSPQLLIY KVSNRFSGVPDRFSGSGSGADFTLKISRVEAEDVGVYYCAETSHVPWTFGQGTK LEIK | Variable light (VL) Anti-BCMA |
| 77 | QVQLVESGGGLVQPGGSLRLSCEASGFTLDYYAIGWFRQAPGKEREGVICISRS DGSTYYADSVKGRFTISRDNAKKTVYLQMISLKPEDTAAYYCAAGADCSGYLRD YEFRGQGTQVTVSS | Anti-BCMA sdAb |
| 78 | IEVMYPPPYLDNEKSNGTIIHVKGKHLCPSPLFPGPSKP | CD28 spacer |
| 79 | IYIWAPLAGTCGVLLLSLVITLYCN | CD8a TM |
| 80 | LDNEKSNGTIIHVKGKHLCPSPLFPGPSKP | CD28 spacer (truncated) |
| 81 | PTTTPAPRPPTPAPTIASQPLSLRPEACRPAAGGAVHTRGLDFACD | CD8a hinge |
| 82 | TTTPAPRPPTPAPTIASQPLSLRPEACRPAAGGAVHTRGLDFACD | CD8a hinge |
| 83 | FVPVFLPAKPTTTPAPRPPTPAPTIASQPLSLRPEACRPAAGGAVHTRGLDFAC D | CD8a hinge |
| 84 | DTGLYICKVELMYPPPYYLGIGNGTQIYVIDPEPCPDSD | CTLA4 hinge |
| 85 | FLLWILAAVSSGLFFYSFLLTAVS | CTLA4 TM |
| 86 | QIKESLRAELRVTERRAEVPTAHPSPSPRPAGQFQTLV | PD-1 hinge |
| 87 | VGVVGGLLGSLVLLVWVLAVI | PD-1 TM |
| 88 | GLAVSTISSFFPPGYQ | Fc(gamma)RIIIa hinge |
| 89 | EPKSPDKTHTCPPCPAPPVAGPSVFLFPPKPKDTLMIARTPEVTCVVVDVSHED PEVKFNWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIA VEWESNGQPENNYKTTPPVLDSDGSFFLYSKLTVDKSRWQQGNVFSCSVMHEAL HNHYTQKSLSLSPGK | IgG1 hinge |
| 90 | EVQLLESGGGLVQPGGSLRLSCAASGFTFSSYAMSWVRQAPGKGLEWVSAISGS GGSTYYADSVKGRFTISRDNSKNTLYLQMNSLRAEDTAVYYCARAEMGAVFDIW GQGTMVTVSSGSTSGSGKPGSGEGSTKGEIVLTQSPATLSLSPGERATLSCRAS QSVSRYLAWYQQKPGQAPRLLIYDASNRATGIPARFSGSGSGTDFTLTISSLEP EDFAVYYCQQRISWPFTFGGGTKVEIKRAAALDNEKSNGTIIHVKGKHLCPSPL FPGPSKPFWVLVVVGGVLACYSLLVTVAFIIFWVRSKRSRLLHSDYMNMTPRRP GPTRKHYQPYAPPRDFAAYRSRVKFSRSADAPAYQQGQNQLYNELNLGRREEYD VLDKRRGRDPEMGGKPRRKNPQEGLYNELQKDKMAEAYSEIGMKGERRRGKGHD GLYQGLSTATKDTYDALHMQALPPR | anti-BCMA CAR |
| 91 | EIVLTQSPATLSLSPGERATLSCRASQSVSRYLAWYQQKPGQAPRLLIYDASNR ATGIPARFSGSGSGTDFTLTISSLEPEDFAVYYCQQRISWPFTFGGGTKVEIKR GSTSGSGKPGSGEGSTKGEVQLLESGGGLVQPGGSLRLSCAASGFTFSSYAMSW VRQAPGKGLEWVSAISGSGGSTYYADSVKGRFTISRDNSKNTLYLQMNSLRAED TAVYYCARAEMGAVFDIWGQGTMVTVSSAAALDNEKSNGTIIHVKGKHLCPSPL FPGPSKPFWVLVVVGGVLACYSLLVTVAFIIFWVRSKRSRLLHSDYMNMTPRRP GPTRKHYQPYAPPRDFAAYRSRVKFSRSADAPAYQQGQNQLYNELNLGRREEYD VLDKRRGRDPEMGGKPRRKNPQEGLYNELQKDKMAEAYSEIGMKGERRRGKGHD GLYQGLSTATKDTYDALHMQALPPR | anti-BCMA CAR |
| 92 | QVQLVESGGGVVQPGRSLRLSCAASGFTFSSYGMHWVRQAPGKGLEWVAVISYD GSNKYYADSVKGRFTISRDNSKNTLYLQMNSLRAEDTAVYYCARDGTYLGGLWY FDLWGRGTLVTVSSGSTSGSGKPGSGEGSTKGDIVMTQSPLSLPVTPGEPASIS | anti-BCMA CAR |

| SEQ ID NO. | SEQUENCE | DESCRIPTION |
|---|---|---|
|  | CRSSQSLLHSNGYNYLDWYLQKPGQSPQLLIYLGSNRASGVPDRFSGSGSGTDF<br>TLKISRVEAEDVGVYYCMQGLGLPLTFGGGTKVEIKRAAALDNEKSNGTIIHVK<br>GKHLCPSPLFPGPSKPFWVLVVVGGVLACYSLLVTVAFIIFWVRSKRSRLLHSD<br>YMNMTPRRPGPTRKHYQPYAPPRDFAAYRSRVKFSRSADAPAYQQGQNQLYNEL<br>NLGRREEYDVLDKRRGRDPEMGGKPRRKNPQEGLYNELQKDKMAEAYSEIGMKG<br>ERRRGKGHDGLYQGLSTATKDTYDALHMQALPPR |  |
| 93 | DIVMTQSPLSLPVTPGEPASISCRSSQSLLHSNGYNYLDWYLQKPGQSPQLLIY<br>LGSNRASGVPDRFSGSGSGTDFTLKISRVEAEDVGVYYCMQGLGLPLTFGGGTK<br>VEIKRGSTSGSGKPGSGEGSTKGQVQLVESGGGVVQPGRSLRLSCAASGFTFSS<br>YGMHWVRQAPGKGLEWVAVISYDGSNKYYADSVKGRFTISRDNSKNTLYLQMNS<br>LRAEDTAVYYCARDGTYLGGLWYFDLWGRGTLVTVSSAAALDNEKSNGTIIHVK<br>GKHLCPSPLFPGPSKPFWVLVVVGGVLACYSLLVTVAFIIFWVRSKRSRLLHSD<br>YMNMTPRRPGPTRKHYQPYAPPRDFAAYRSRVKFSRSADAPAYQQGQNQLYNEL<br>NLGRREEYDVLDKRRGRDPEMGGKPRRKNPQEGLYNELQKDKMAEAYSEIGMKG<br>ERRRGKGHDGLYQGLSTATKDTYDALHMQALPPR | anti-BCMA CAR |
| 94 | QVQLVQSGAEVKKPGASVKVSCKASGYTFTSYYMHWVRQAPGQGLEWMGIINPG<br>GGSTSYAQKFQGRVTMTRDTSTSTVYMELSSLRSEDTAVYYCARESWPMDVWGQ<br>GTTVTVSSGSTSGSGKPGSGEGSTKGEIVMTQSPATLSVSPGERATLSCRASQS<br>VSSNLAWYQQKPGQAPRLLIYGASTRATGIPARFSGSGSGTEFTLTISSLQSED<br>FAVYYCQQYAAYPTFGGGTKVEIKRAAALDNEKSNGTIIHVKGKHLCPSPLFPG<br>PSKPFWVLVVVGGVLACYSLLVTVAFIIFWVRSKRSRLLHSDYMNMTPRRPGPT<br>RKHYQPYAPPRDFAAYRSRVKFSRSADAPAYQQGQNQLYNELNLGRREEYDVLD<br>KRRGRDPEMGGKPRRKNPQEGLYNELQKDKMAEAYSEIGMKGERRRGKGHDGLY<br>QGLSTATKDTYDALHMQALPPR | anti-BCMA CAR |
| 95 | EIVMTQSPATLSVSPGERATLSCRASQSVSSNLAWYQQKPGQAPRLLIYGASTR<br>ATGIPARFSGSGSGTEFTLTISSLQSEDFAVYYCQQYAAYPTFGGGTKVEIKRG<br>STSGSGKPGSGEGSTKGQVQLVQSGAEVKKPGASVKVSCKASGYTFTSYYMHWV<br>RQAPGQGLEWMGIINPGGGSTSYAQKFQGRVTMTRDTSTSTVYMELSSLRSEDT<br>AVYYCARESWPMDVWGQGTTVTVSSAAALDNEKSNGTIIHVKGKHLCPSPLFPG<br>PSKPFWVLVVVGGVLACYSLLVTVAFIIFWVRSKRSRLLHSDYMNMTPRRPGPT<br>RKHYQPYAPPRDFAAYRSRVKFSRSADAPAYQQGQNQLYNELNLGRREEYDVLD<br>KRRGRDPEMGGKPRRKNPQEGLYNELQKDKMAEAYSEIGMKGERRRGKGHDGLY<br>QGLSTATKDTYDALHMQALPPR | anti-BCMA CAR |
| 96 | QLQLQESGPGLVKPSETLSLTCTVSGGSISSSSYYWGWIRQPPGKGLEWIGSIS<br>YSGSTYYNPSLKSRVTISVDTSKNQFSLKLSSVTAADTAVYYCARGRGYATSLA<br>FDIWGQGTMVTVSSGSTSGSGKPGSGEGSTKGEIVLTQSPATLSLSPGERATLS<br>CRASQSVSSYLAWYQQKPGQAPRLLIYDASNRATGIPARFSGSGSGTDFTLTIS<br>SLEPEDFAVYYCQQRHVWPPTFGGGTKVEIKRAAALDNEKSNGTIIHVKGKHLC<br>PSPLFPGPSKPFWVLVVVGGVLACYSLLVTVAFIIFWVRSKRSRLLHSDYMNMT<br>PRRPGPTRKHYQPYAPPRDFAAYRSRVKFSRSADAPAYQQGQNQLYNELNLGRR<br>EEYDVLDKRRGRDPEMGGKPRRKNPQEGLYNELQKDKMAEAYSEIGMKGERRRG<br>KGHDGLYQGLSTATKDTYDALHMQALPPR | anti-BCMA CAR |
| 97 | EIVLTQSPATLSLSPGERATLSCRASQSVSSYLAWYQQKPGQAPRLLIYDASNR<br>ATGIPARFSGSGSGTDFTLTISSLEPEDFAVYYCQQRHVWPPTFGGGTKVEIKR<br>GSTSGSGKPGSGEGSTKGQLQLQESGPGLVKPSETLSLTCTVSGGSISSSSYYW<br>GWIRQPPGKGLEWIGSISYSGSTYYNPSLKSRVTISVDTSKNQFSLKLSSVTAA<br>DTAVYYCARGRGYATSLAFDIWGQGTMVTVSSAAALDNEKSNGTIIHVKGKHLC<br>PSPLFPGPSKPFWVLVVVGGVLACYSLLVTVAFIIFWVRSKRSRLLHSDYMNMT<br>PRRPGPTRKHYQPYAPPRDFAAYRSRVKFSRSADAPAYQQGQNQLYNELNLGRR<br>EEYDVLDKRRGRDPEMGGKPRRKNPQEGLYNELQKDKMAEAYSEIGMKGERRRG<br>KGHDGLYQGLSTATKDTYDALHMQALPPR | anti-BCMA CAR |
| 98 | EVQLVESGGGLVQPGGSLRLSCAASGFTFSSYSMNWVRQAPGKGLEWVSTISSS<br>SSTIYYADSVKGRFTISRDNAKNSLYLQMNSLRAEDTAVYYCARGSQEHLIFDY<br>WGQGTLVTVSSGSTSGSGKPGSGEGSTKGEIVLTQSPATLSLSPGERATLSCRA<br>SQSVSRYLAWYQQKPGQAPRLLIYDASNRATGIPARFSGSGSGTDFTLTISSLE<br>PEDFAVYYCQQRFYYPWTFGGGTKVEIKRAAALDNEKSNGTIIHVKGKHLCPSP<br>LFPGPSKPFWVLVVVGGVLACYSLLVTVAFIIFWVRSKRSRLLHSDYMNMTPRR<br>PGPTRKHYQPYAPPRDFAAYRSRVKFSRSADAPAYQQGQNQLYNELNLGRREEY<br>DVLDKRRGRDPEMGGKPRRKNPQEGLYNELQKDKMAEAYSEIGMKGERRRGKGH<br>DGLYQGLSTATKDTYDALHMQALPPR | anti-BCMA CAR |
| 99 | EIVLTQSPATLSLSPGERATLSCRASQSVSRYLAWYQQKPGQAPRLLIYDASNR<br>ATGIPARFSGSGSGTDFTLTISSLEPEDFAVYYCQQRFYYPWTFGGGTKVEIKR<br>GSTSGSGKPGSGEGSTKGEVQLVESGGGLVQPGGSLRLSCAASGFTFSSYSMNW<br>VRQAPGKGLEWVSTISSSSTIYYADSVKGRFTISRDNAKNSLYLQMNSLRAED<br>TAVYYCARGSQEHLIFDYWGQGTLVTVSSAAALDNEKSNGTIIHVKGKHLCPSP<br>LFPGPSKPFWVLVVVGGVLACYSLLVTVAFIIFWVRSKRSRLLHSDYMNMTPRR<br>PGPTRKHYQPYAPPRDFAAYRSRVKFSRSADAPAYQQGQNQLYNELNLGRREEY | anti-BCMA CAR |

| SEQ ID NO. | SEQUENCE | DESCRIPTION |
|---|---|---|
|  | DVLDKRRGRDPEMGGKPRRKNPQEGLYNELQKDKMAEAYSEIGMKGERRRGKGH DGLYQGLSTATKDTYDALHMQALPPR |  |
| 100 | QVQLVESGGGVVQPGRSLRLSCAASGFTFSSYGMHWVRQAPGKGLEWVAVISYD GSNKYYADSVKGRFTISRDNSKNTLYLQMNSLRAEDTAVYYCARTDFWSGSPPG LDYWGQGTLVTVSSGSTSGSGKPGSGEGSTKGDIQLTQSPSSVSASVGDRVTIT CRASQGISSWLAWYQQKPGKAPKLLIYGASSLQSGVPSRFSGSGSTDFTLTIS SLQPEDFATYYCQQIYTFPFTFGGGTKVEIKRAAALDNEKSNGTIIHVKGKHLC PSPLFPGPSKPFWVLVVVGGVLACYSLLVTVAFIIFWVRSKRSRLLHSDYMNMT PRRRPGPTRKHYQPYAPPRDFAAYRSRVKFSRSADAPAYQQGQNQLYNELNLGRR EEYDVLDKRRGRDPEMGGKPRRKNPQEGLYNELQKDKMAEAYSEIGMKGERRRG KGHDGLYQGLSTATKDIYDALHMQALPPR | anti-BCMA CAR |
| 101 | DIQLTQSPSSVSASVGDRVTITCRASQGISSWLAWYQQKPGKAPKLLIYGASSL QSGVPSRFSGSGSTDFTLTISSLQPEDFATYYCQQIYTFPFTFGGGTKVEIKR GSTSGSGKPGSGEGSTKGQVQLVESGGGVVQPGRSLRLSCAASGFTFSSYGMHW VRQAPGKGLEWVAVISYDGSNKYYADSVKGRFTISRDNSKNTLYLQMNSLRAED TAVYYCARTDFWSGSPPGLDYWGQGTLVTVSSAAALDNEKSNGTIIHVKGKHLC PSPLFPGPSKPFWVLVVVGGVLACYSLLVTVAFIIFWVRSKRSRLLHSDYMNMT PRRRPGPTRKHYQPYAPPRDFAAYRSRVKFSRSADAPAYQQGQNQLYNELNLGRR EEYDVLDKRRGRDPEMGGKPRRKNPQEGLYNELQKDKMAEAYSEIGMKGERRRG KGHDGLYQGLSTATKDIYDALHMQALPPR | anti-BCMA CAR |
| 102 | QVQLVQSGAEVKKPGSSVKVSCKASGGTFSSYAISWVRQAPGQGLEWMGGIIPI FGTANYAQKFQGRVTITADESTSTAYMELSSLRSEDTAVYYCARTPEYSSSIWH YYYGMDVWGQGTTVTVSSGSTSGSGKPGSGEGSTKGDIVMTQSPDSLAVSLGER ATINCKSSQSVLYSSNNKNYLAWYQQKPGQPPKLLIYWASTRESGVPDRFSGSG SGTDFTLTISSLQAEDVAVYYCQQFAHTPFTFGGGTKVEIKRAAALDNEKSNGT IIHVKGKHLCPSPLFPGPSKPFWVLVVVGGVLACYSLLVTVAFIIFWVRSKRSR LLHSDYMNMTPRRPGPTRKHYQPYAPPRDFAAYRSRVKFSRSADAPAYQQGQNQ LYNELNLGRREEYDVLDKRRGRDPEMGGKPRRKNPQEGLYNELQKDKMAEAYSE IGMKGERRRGKGHDGLYQGLSTATKDTYDALHMQALPPR | anti-BCMA CAR |
| 103 | DIVMTQSPDSLAVSLGERATINCKSSQSVLYSSNNKNYLAWYQQKPGQPPKLLI YWASTRESGVPDRFSGSGSGTDFTLTISSLQAEDVAVYYCQQFAHTPFTFGGGT KVEIKRGSTSGSGKPGSGEGSTKGQVQLVQSGAEVKKPGSSVKVSCKASGGTFS SYAISWVRQAPGQGLEWMGGIIPIFGTANYAQKFQGRVTITADESTSTAYMELS SLRSEDTAVYYCARTPEYSSSIWHYYYGMDVWGQGTTVTVSSAAALDNEKSNGT IIHVKGKHLCPSPLFPGPSKPFWVLVVVGGVLACYSLLVTVAFIIFWVRSKRSR LLHSDYMNMTPRRPGPTRKHYQPYAPPRDFAAYRSRVKFSRSADAPAYQQGQNQ LYNELNLGRREEYDVLDKRRGRDPEMGGKPRRKNPQEGLYNELQKDKMAEAYSE IGMKGERRRGKGHDGLYQGLSTATKDTYDALHMQALPPR | anti-BCMA CAR |
| 104 | QVQLVESGGGVVQPGRSLRLSCAASGFTFSSYGMHWVRQAPGKGLEWVAVISYD GSNKYYADSVKGRFTISRDNSKNTLYLQMNSLRAEDTAVYYCVKGPLQEPPYDY GMDVWGQGTTVTVSSGSTSGSGKPGSGEGSTKGEIVMTQSPATLSVSPGERATL SCRASQSVSSNLAWYQQKPGQAPRLLIYSASTRATGIPARFSGSGSGTEFTLTI SSLQSEDFAVYYCQQHHVWPLTFGGGTKVEIKRAAALDNEKSNGTIIHVKGKHL CPSPLFPGPSKPFWVLVVVGGVLACYSLLVTVAFIIFWVRSKRSRLLHSDYMNM TPRRPGPTRKHYQPYAPPRDFAAYRSRVKFSRSADAPAYQQGQNQLYNELNLGR REEYDVLDKRRGRDPEMGGKPRRKNPQEGLYNELQKDKMAEAYSEIGMKGERRR GKGHDGLYQGLSTATKDIYDALHMQALPPR | anti-BCMA CAR |
| 105 | EIVMTQSPATLSVSPGERATLSCRASQSVSSNLAWYQQKPGQAPRLLIYSASTR ATGIPARFSGSGSGTEFTLTISSLQSEDFAVYYCQQHHVWPLTFGGGTKVEIKR GSTSGSGKPGSGEGSTKGQVQLVESGGGVVQPGRSLRLSCAASGFTFSSYGMHW VRQAPGKGLEWVAVISYDGSNKYYADSVKGRFTISRDNSKNTLYLQMNSLRAED TAVYYCVKGPLQEPPYDYGMDVWGQGTTVTVSSAAALDNEKSNGTIIHVKGKHL CPSPLFPGPSKPFWVLVVVGGVLACYSLLVTVAFIIFWVRSKRSRLLHSDYMNM TPRRPGPTRKHYQPYAPPRDFAAYRSRVKFSRSADAPAYQQGQNQLYNELNLGR REEYDVLDKRRGRDPEMGGKPRRKNPQEGLYNELQKDKMAEAYSEIGMKGERRR GKGHDGLYQGLSTATKDIYDALHMQALPPR | anti-BCMA CAR |
| 106 | QSALTQPASVSASPGQSIAISCTGTSSDVGWYQQHPGKAPKLMIYEDSKRPSGV SNRFSGSKSGNTASLTISGLQAEDEADYYCSSNTRSSTLVFGGGTKLTVLGSRG GGGSGGGGSGGGGSLEMAEVQLVQSGAEMKKPGASLKLSCKASGYTFIDYYVYW MRQAPGQGLESMGWINPNSGGTNYAQKFQGRVTMTRDTSISTAYMELSRLRSDD TAMYYCARSQRDGYMDYWGQGTLVTVSSAAAIEVMPPPYLDNEKSNGTIIHVK GKHLCPSPLFPGPSKPFWVLVVVGGVLACYSLLVTVAFIIFWVRSKRSLLHSD YMNMTPRRPGPTRKHYQPYAPPRDFAAYRSRVKFSRSADAPAYQQGQNQLYNEL NLGRREEYDVLDKRRGRDPEMGGKPRRKNPQEGLYNELQKDKMAEAYSEIGMKG ERRRGKGHDGLYQGLSTATKDTYDALHMQALPPR | anti-BCMA CAR |

| SEQ ID NO. | SEQUENCE | DESCRIPTION |
|---|---|---|
| 107 | QSVLTQPPSVSGAPGQRVTISCTGSSSNIGAGFDVHWYQQLPGTAPKLLIYGNS<br>NRPSGVPDRFSGSKSGTSASLAITGLQAEDEADYYCQSYDSSLSGYVFGTGTKV<br>TVLGSRGGGGSGGGGSGGGGSLEMAQVQLVQSGAEVKKPGASVKVSCKASGYTF<br>TDYYMHWVRQAPGQRLEWMGWINPNSGGTNYAQKFQDRITVTRDTSSNTGYMEL<br>TRLRSDDTAVYYCARSPYSGVLDKWGQGTLVTVSSAAAIEVMYPPPYLDNEKSN<br>GTIIHVKGKHLCPSPLFPGPSKPFWVLVVVGGVLACYSLLVTVAFIIFWVRSKR<br>SRLLHSDYMNMTPRRPGPTRKHYQPYAPPRDFAAYRSRVKFSRSADAPAYQQGQ<br>NQLYNELNLGRREEYDVLDKRRGRDPEMGGKPRRKNPQEGLYNELQKDKMAEAY<br>SEIGMKGERRRGKGHDGLYQGLSTATKDTYDALHMQALPPR | anti-BCMA CAR |
| 108 | SYELTQPPSASGTPGQRVTMSCSGTSSNIGSHSVNWYQQLPGTAPKLLIYTNNQ<br>RPSGVPDRFSGSKSGTSASLAISGLQSEDEADYYCAAWDGSLNGLVFGGGTKLT<br>VLGSRGGGGSGGGGSGGGGSLEMAEVQLVQSGAEVKKPGESLKISCKGSGYSFT<br>SYWIGWVRQMPGKGLEWMGIIYPGDSDTRYSPSFQGHVTISADKSISTAYLQWS<br>SLKASDTAMYYCARYSGSFDNWGQGTLVTVSSAAAIEVMYPPPYLDNEKSNGTI<br>IHVKGKHLCPSPLFPGPSKPFWVLVVVGGVLACYSLLVTVAFIIFWVRSKRSRL<br>LHSDYMNMTPRRPGPTRKHYQPYAPPRDFAAYRSRVKFSRSADAPAYQQGQNQL<br>YNELNLGRREEYDVLDKRRGRDPEMGGKPRRKNPQEGLYNELQKDKMAEAYSEI<br>GMKGERRRGKGHDGLYQGLSTATKDTYDALHMQALPPR | anti-BCMA CAR |
| 109 | LPVLTQPPSASGTPGQRVTISCSGRSSNIGSNSVNWYRQLPGAAPKLLIYSNNQ<br>RPPGVPVRFSGSKSGTSASLAISGLQSEDEATYYCATWDDNLNVHYVFGTGTKV<br>TVLGSRGGGGSGGGGSGGGGSLEMAQVQLVQSGAEVKKPGSSVKVSCKASGGTF<br>SSYAISWVRQAPGQGLEWMGRIIPILGIANYAQKFQGRVTITADKSTSTAYMEL<br>SSLRSEDTAVYYCARGGYYSHDMWSEDWGQGTLVTVSSAAAIEVMYPPPYLDNE<br>KSNGTIIHVKGKHLCPSPLFPGPSKPFWVLVVVGGVLACYSLLVTVAFIIFWVR<br>SKRSRLLHSDYMNMTPRRPGPTRKHYQPYAPPRDFAAYRSRVKFSRSADAPAYQ<br>QGQNQLYNELNLGRREEYDVLDKRRGRDPEMGGKPRRKNPQEGLYNELQKDKMA<br>EAYSEIGMKGERRRGKGHDGLYQGLSTATKDTYDALHMQALPPR | anti-BCMA CAR |
| 110 | QAVLTQPPSASGTPGQRVTISCSGSSSNIGSNYVFWYQQLPGTAPKLLIYSNNQ<br>RPSGVPDRFSGSKSGTSASLAIGLRSEDEADYYCAAWDDSLSASYVFGTGTKV<br>TVLGSRGGGGSGGGGSGGGGSLEMAQVQLVQSGAEVKKPGSSVKVSCKASGGTF<br>SSYAISWVRQAPGQGLEWMGRIIPILGTANYAQKFQGRVTITADESTSTAYMEL<br>SSLRSEDTAVYYCARSGYGSYRWEDSWGQGTLVTVSSAAAIEVMYPPPYLDNEK<br>SNGTIIHVKGKHLCPSPLFPGPSKPFWVLVVVGGVLACYSLLVTVAFIIFWVRS<br>KRSRLLHSDYMNMTPRRPGPTRKHYQPYAPPRDFAAYRSRVKFSRSADAPAYQQ<br>GQNQLYNELNLGRREEYDVLDKRRGRDPEMGGKPRRKNPQEGLYNELQKDKMAE<br>AYSEIGMKGERRRGKGHDGLYQGLSTATKDTYDALHMQALPPR | anti-BCMA CAR |
| 111 | LPVLTQPPSASGTPGQRVTISCSGRSSNIGSNSVNWYRQLPGAAPKLLIYSNNQ<br>RPPGVPVRFSGSKSGTSASLAISGLQSEDEATYYCATWDDNLNVHYVFGTGTKV<br>TVLGSRGGGGSGGGGSGGGGSLEMAQVQLVQSGAEVKKPGSSVKVSCKASGGTF<br>SSYAISWVRQAPGQGLEWMGRIIPILGIANYAQKFQGRVTITADKSTSTAYMEL<br>SSLRSEDTAVYYCARGGYYSHDMWSEDWGQGTLVTVSSAAAPTTTPAPRPPTPA<br>PTIASQPLSLRPEACRPAAGGAVHTRGLDFACDIYIWAPLAGTCGVLLLSLVIT<br>LYCNKRGRKKLLYIFKQPFMRPVQTTQEEDGCSCRFPEEEEGGCELRVKFSRSA<br>EPPAYQQGQNQLYNELNLGRREEYDVLDKRRGRDPEMGGKPRRKNPQEGLYNEL<br>QKDKMAEAYSEIGMKGERRRGKGHDGLYQGLSTATKDTYDALHMQALPPR | anti-BCMA CAR |
| 112 | SYELTQPPSASGTPGQRVTMSCSGTSSNIGSHSVNWYQQLPGTAPKLLIYTNNQ<br>RPSGVPDRFSGSKSGTSASLAISGLQSEDEADYYCAAWDGSLNGLVFGGGTKLT<br>VLGSRGGGGSGGGGSGGGGSLEMAEVQLVQSGAEVKKPGESLKISCKGSGYSFT<br>SYWIGWVRQMPGKGLEWMGIIYPGDSDTRYSPSFQGHVTISADKSISTAYLQWS<br>SLKASDTAMYYCARYSGSFDNWGQGTLVTVSSAAAPTTTPAPRPPTPAPTIASQ<br>PLSLRPEACRPAAGGAVHTRGLDFACDIYIWAPLAGTCGVLLLSLVITLYCNKR<br>GRKKLLYIFKQPFMRPVQTTQEEDGCSCRFPEEEEGGCELRVKFSRSAEPPAYQ<br>QGQNQLYNELNLGRREEYDVLDKRRGRDPEMGGKPRRKNPQEGLYNELQKDKMA<br>EAYSEIGMKGERRRGKGHDGLYQGLSTATKDTYDALHMQALPPR | anti-BCMA CAR |
| 113 | QAVLTQPPSASGTPGQRVTISCSGSSSNIGSNYVFWYQQLPGTAPKLLIYSNNQ<br>RPSGVPDRFSGSKSGTSASLAIGLRSEDEADYYCAAWDDSLSASYVFGTGTKV<br>TVLGSRGGGGSGGGGSGGGGSLEMAQVQLVQSGAEVKKPGSSVKVSCKASGGTF<br>SSYAISWVRQAPGQGLEWMGRIIPILGTANYAQKFQGRVTITADESTSTAYMEL<br>SSLRSEDTAVYYCARSGYGSYRWEDSWGQGTLVTVSSAAAPTTTPAPRPPTPAP<br>TIASQPLSLRPEACRPAAGGAVHTRGLDFACDIYIWAPLAGTCGVLLLSLVIIL<br>YCNKRGRKKLLYIFKQPFMRPVQTTQEEDGCSCRFPEEEEGGCELRVKFSRSAE<br>PPAYQQGQNQLYNELNLGRREEYDVLDKRRGRDPEMGGKPRRKNPQEGLYNELQ<br>KDKMAEAYSEIGMKGERRRGKGHDGLYQGLSTATKDTYDALHMQALPPR | anti-BCMA CAR |
| 114 | QSVLTQPPSVSGAPGQRVTISCTGSSSNIGAGFDVHWYQQLPGTAPKLLIYGNS<br>NRPSGVPDRFSGSKSGTSASLAITGLQAEDEADYYCQSYDSSLSGYVFGTGTKV<br>TVLGSRGGGGSGGGGSGGGGSLEMAQVQLVQSGAEVKKPGASVKVSCKASGYTF | anti-BCMA CAR |

| SEQ ID NO. | SEQUENCE | DESCRIPTION |
|---|---|---|
|  | TDYYMHWVRQAPGQRLEWMGWINPNSGGTNYAQKFQDRITVTRDTSSNTGYMEL<br>TRLRSDDTAVYYCARSPYSGVLDKWGQGTLVTVSSAAAPTTTPAPRPPTPAPTI<br>ASQPLSLRPEACRPAAGGAVHTRGLDFACDIYIWAPLAGTCGVLLLSLVITLYC<br>NKRGRKKLLYIFKQPFMRPVQTTQEEDGCSCRFPEEEEGGCELRVKFSRSAEPP<br>AYQQGQNQLYNELNLGRREEYDVLDKRRGRDPEMGGKPRRKNPQEGLYNELQKD<br>KMAEAYSEIGMKGERRRGKGHDGLYQGLSTATKDTYDALHMQALPPR |  |
| 115 | QSALTQPASVSASPGQSIAISCTGTSSDVGWYQQHPGKAPKLMIYEDSKRPSGV<br>SNRFSGSKSGNTASLTISGLQAEDEADYYCSSNTRSSTLVFGGGTKLTVLGSRG<br>GGGSGGGGSGGGGSLEMAEVQLVQSGAEMKKPGASLKLSCKASGYTFIDYYVYW<br>MRQAPGQGLESMGWINPNSGGTNYAQKFQGRVTMTRDTSISTAYMELSRLRSDD<br>TAMYYCARSQRDGYMDYWGQGTLVTVSSAAAPTTTPAPRPPTPAPTIASQPLSL<br>RPEACRPAAGGAVHTRGLDFACDIYIWAPLAGTCGVLLLSLVITLYCNKGRKK<br>LLYIFKQPFMRPVQTTQEEDGCSCRFPEEEEGGCELRVKFSRSAEPPAYQQGQN<br>QLYNELNLGRREEYDVLDKRRGRDPEMGGKPRRKNPQEGLYNELQKDKMAEAYS<br>EIGMKGERRRGKGHDGLYQGLSTATKDTYDALHMQALPPR | anti-BCMA CAR |
| 116 | DIVLTQSPPSLAMSLGKRATISCRASESVTILGSHLIHWYQQKPGQPPTLLIQL<br>ASNVQTGVPARFSGSGSRTDFTLTIDPVEEDDVAVYYCLQSRTIPRTFGGGTKL<br>EIKGSTSGSGKPGSGEGSTKGQIQLVQSGPELKKPGETVKISCKASGYTFTDYS<br>INWVKRAPGKGLKWMGWINTETEREPAYAYDFRGRFAFSLETSASTAYLQINNL<br>YEDTATYFCALDYSYAMDYWGQGTSVTVSSAAATTTPAPRPPTPAPTIASQPLS<br>LRPEACRPAAGGAVHTRGLDFACDIYIWAPLAGTCGVLLLSLVITLYCKRGRKK<br>LLYIFKQPFMRPVQTTQEEDGCSCRFPEEEEGGCELRVKFSRSADAPAYQQGQN<br>QLYNELNLGRREEYDVLDKRRGRDPEMGGKPRRKNPQEGLYNELQKDKMAEAYS<br>EIGMKGERRRGKGHDGLYQGLSTATKDTYDALHMQALPPR | anti-BCMA CAR |
| 117 | DIVLTQSPASLAVSLGERATINCRASESVSVIGAHLIHWYQQKPGQPPKLLIYL<br>ASNLETGVPARFSGSGSGTDFTLTISSLQAEDAAIYYCLQSRIFPRTFGQGTKL<br>EIKGSTSGSGKPGSGEGSTKGQVQLVQSGSELKKPGASVKVSCKASGYTFTDYS<br>INWVRQAPGQGLEWMGWINTETEREPAYAYDFRGRFVFSLDTSVSTAYLQISSLK<br>AEDTAVYYCARDYSYAMDYWGQGTLVTVSSAAATTTPAPRPPTPAPTIASQPLS<br>LRPEACRPAAGGAVHTRGLDFACDIYIWAPLAGTCGVLLLSLVILYCKRGRKK<br>LLYIFKQPFMRPVQTTQEEDGCSCRFPEEEEGGCELRVKFSRSADAPAYQQGQN<br>QLYNELNLGRREEYDVLDKRRGRDPEMGGKPRRKNPQEGLYNELQKDKMAEAYS<br>EIGMKGERRRGKGHDGLYQGLSTATKDTYDALHMQALPPR | anti-BCMA CAR |
| 118 | DIVLTQSPASLAVSLGERATINCRASESVSVIGAHLIHWYQQKPGQPPKLLIYL<br>ASNLETGVPARFSGSGSGTDFTLTISSLQAEDAAIYYCLQSRIFPRTFGQGTKL<br>EIKGSTSGSGKPGSGEGSTKGQVQLVQSGSELKKPGASVKVSCKASGYTFTDYS<br>INWVRQAPGQGLEWMGWINTETEREPAYAYDFRGRFVFSLDTSVSTAYLQISSLK<br>AEDTAVYYCARDYSYAMDYWGQGTLVTVSSAAADTGLYICKVELMYPPPYYLGI<br>GNGTQIYVIDPEPCPDSDFLLWILAAVSSGLFFYSFLLTAVSKRGRKKLLYIFK<br>QPFMRPVQTTQEEDGCSCRFPEEEEGGCELRVKFSRSADAPAYQQGQNQLYNEL<br>NLGRREEYDVLDKRRGRDPEMGGKPRRKNPQEGLYNELQKDKMAEAYSEIGMKG<br>ERRRGKGHDGLYQGLSTATKDTYDALHMQALPPR | anti-BCMA CAR |
| 119 | DIVLTQSPASLAVSLGERATINCRASESVSVIGAHLIHWYQQKPGQPPKLLIYL<br>ASNLETGVPARFSGSGSGTDFTLTISSLQAEDAAIYYCLQSRIFPRTFGQGTKL<br>EIKGSTSGSGKPGSGEGSTKGQVQLVQSGSELKKPGASVKVSCKASGYTFTDYS<br>INWVRQAPGQGLEWMGWINTETEREPAYAYDFRGRFVFSLDTSVSTAYLQISSLK<br>AEDTAVYYCARDYSYAMDYWGQGTLVTVSSAAAQIKESLRAELRVTERRAEVPT<br>AHPSPSPRPAGQFQTLVVGVVGGLLGSLVLLVWVLAVICSKRGRKKLLYIFKQP<br>FMRPVQTTQEEDGCSCRFPEEEEGGCELRVKFSRSADAPAYQQGQNQLYNELNL<br>GRREEYDVLDKRRGRDPEMGGKPRRKNPQEGLYNELQKDKMAEAYSEIGMKGER<br>RRGKGHDGLYQGLSTATKDTYDALHMQALPPR | anti-BCMA CAR |
| 120 | EVQLVESGGGLVKPGGSLRLSCAASGFTFSDYYMSWIRQAPGKGLEWVSYISSS<br>GSTIYYADSVKGRFTISRDNAKNSLYLQMNSLRAEDTAVYYCAKVDGDYTEDYW<br>GQGTLVTVSSGGGGSGGGGSGGGGSQSALTQPASVSGSPGQSITISCTGSSSDV<br>GKYNLVSWYQQPPGKAPKLIIYDVNKRPSGVSNRFSGSKSGNTATLTISGLQGD<br>DEADYYCSSYGGSRSYVFGTGTKVTVLESKYGPPCPPCPAPPVAGPSVFLFPPK<br>PKDTLMISRTPEVTCVVVDVSQEDPEVQFNWYVDGVEVHNAKTKPREEQFQSTY<br>RVVSVLTVLHQDWLNGKEYKCKVSNKGLPSSIEKTISKAKGQPREPQVYTLPPS<br>QEEMTKNQVSLTCLVKGFYPSDIAVEWESNGQPENNYKTTPPVLDSDGSFFLYS<br>RLTVDKSRWQEGNVFSCSVMHEALHNHYTQKSLSLSLGKMFWVLVVVGGVLACY<br>SLLVTVAFIIFWVKRGRKKLLYIFKQPFMRPVQTTQEEDGCSCRFPEEEEGGCE<br>LRVKFSRSADAPAYQQGQNQLYNELNLGRREEYDVLDKRRGRDPEMGGKPRRKN<br>PQEGLYNELQKDKMAEAYSEIGMKGERRRGKGHDGLYQGLSTATKDTYDALHMQ<br>ALPPR | anti-BCMA CAR |
| 121 | EVQLVQSGGGLVQPGRSLRLSCTASGFTFGDYAMSWFKQAPGKGLEWVGFIRSK<br>AYGGTTEYAASVKGRFTISRDDSKSIAYLQMNSLKTEDTAVYYCAAWSAPTDYW<br>GQGTLVTVSSGGGGSGGGGSGGGGSDIQMTQSPAFLSASVGDRVTVTCRASQGI | anti-BCMA CAR |

| SEQ ID NO. | SEQUENCE | DESCRIPTION |
|---|---|---|
| | SNYLAWYQQKPGNAPRLLIYSASTLQSGVPSRFRGTGYGTEFSLTIDSLQPEDF<br>ATYYCQQSYTSRQTFGPGTRLDIKESKYGPPCPPCPAPPVAGPSVFLFPPKPKD<br>TLMISRTPEVTCVVVDVSQEDPEVQFNWYVDGVEVHNAKTKPREEQFQSTYRVV<br>SVLTVLHQDWLNGKEYKCKVSNKGLPSSIEKTISKAKGQPREPQVYTLPPSQEE<br>MTKNQVSLTCLVKGFYPSDIAVEWESNGQPENNYKTTPPVLDSDGSFFLYSRLT<br>VDKSRWQEGNVFSCSVMHEALHNHYTQKSLSLSLGKMFWVLVVVGGVLACYSLL<br>VTVAFIIFWVKRGRKKLLYIFKQPFMRPVQTTQEEDGCSCRFPEEEEGGCELRV<br>KFSRSADAPAYQQGQNQLYNELNLGRREEYDVLDKRRGRDPEMGGKPRRKNPQE<br>GLYNELQKDKMAEAYSEIGMKGERRRGKGHDGLYQGLSTATKDTYDALHMQALP<br>PR | |
| 122 | EVQLVESGGGLVKPGGSLRLSCAASGFTFSDYYMSWIRQAPGKGLEWVSYISSS<br>GSTIYYADSVKGRFTISRDNAKNSLYLQMNSLRAEDTAVYYCAKVDGPPSFDIW<br>GQGTMVTVSSGGGGSGGGGSGGGGSSYVLTQPPSVSVAPGQTARITCGANNIGS<br>KSVHWYQQKPGQAPMLVVYDDDDRPSGIPERFSGSNSGNTATLTISGVEAGDEA<br>DYFCHLWDRSRDHYVFGTGTKLTVLESKYGPPCPPCPAPPVAGPSVFLFPPKPK<br>DTLMISRTPEVTCVVVDVSQEDPEVQFNWYVDGVEVHNAKTKPREEQFQSTYRV<br>VSVLTVLHQDWLNGKEYKCKVSNKGLPSSIEKTISKAKGQPREPQVYTLPPSQE<br>EMTKNQVSLTCLVKGFYPSDIAVEWESNGQPENNYKTTPPVLDSDGSFFLYSRL<br>TVDKSRWQEGNVFSCSVMHEALHNHYTQKSLSLSLGKMFWVLVVVGGVLACYSL<br>LVTVAFIIFWVKRGRKKLLYIFKQPFMRPVQTTQEEDGCSCRFPEEEEGGCELR<br>VKFSRSADAPAYQQGQNQLYNELNLGRREEYDVLDKRRGRDPEMGGKPRRKNPQ<br>EGLYNELQKDKMAEAYSEIGMKGERRRGKGHDGLYQGLSTATKDTYDALHMQAL<br>PPR | anti-BCMA CAR |
| 123 | SYELTQPPSASGTPGQRVTMSCSGTSSNIGSHSVNWYQQLPGTAPKLLIYTNNQ<br>RPSGVPDRFSGSKSGTSASLAISGLQSEDEADYYCAAWDGSLNGLVFGGGTKLT<br>VLGSRGGGGSGGGGSGGGGSLEMAEVQLVQSGAEVKKPGESLKISCKGSGYSFT<br>SYWIGWVRQMPGKGLEWMGIIYPGDSDTRYSPSFQGHVTISADKSISTAYLQWS<br>SLKASDTAMYYCARYSGSFDNWGQGTLVTVSSESKYGPPCPPCPAPPVAGPSVF<br>LFPPKPKDTLMISRTPEVTCVVVDVSQEDPEVQFNWYVDGVEVHNAKTKPREEQ<br>FQSTYRVVSVLTVLHQDWLNGKEYKCKVSNKGLPSSIEKTISKAKGQPREPQVY<br>TLPPSQEEMTKNQVSLTCLVKGFYPSDIAVEWESNGQPENNYKTTPPVLDSDGS<br>FFLYSRLTVDKSRWQEGNVFSCSVMHEALHNHYTQKSLSLSLGKMFWVLVVVGG<br>VLACYSLLVTVAFIIFWVKRGRKKLLYIFKQPFMRPVQTTQEEDGCSCRFPEEE<br>EGGCELRVKFSRSADAPAYQQGQNQLYNELNLGRREEYDVLDKRRGRDPEMGGK<br>PRRKNPQEGLYNELQKDKMAEAYSEIGMKGERRRGKGHDGLYQGLSTATKDTYD<br>ALHMQALPPR | anti-BCMA CAR |
| 124 | QSALTQPASVSASPGQSIAISCTGTSSDVGWYQQHPGKAPKLMIYEDSKRPSGV<br>SNRFSGSKSGNTASLTISGLQAEDEADYYCSSNTRSSTLVFGGGTKLTVLGSRG<br>GGGSGGGGSGGGGSLEMAEVQLVQSGAEMKKPGASLKLSCKASGYTFIDYYVYW<br>MRQAPGQGLESMGWINPNSGGTNYAQKFQGRVTMTRDTSISTAYMELSRLRSDD<br>TAMYYCARSQRDGYMDWGQGTLVTVSSESKYGPPCPPCPAPPVAGPSVFLFPP<br>KPKDTLMISRTPEVTCVVVDVSQEDPEVQFNWYVDGVEVHNAKTKPREEQFQST<br>YRVVSVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGSFFLY<br>SRLTVDKSRWQEGNVFSCSVMHEALHNHYTQKSLSLSLGKMFWVLVVVGGVLAC<br>YSLLVTVAFIIFWVKRGRKKLLYIFKQPFMRPVQTTQEEDGCSCRFPEEEEGGC<br>ELRVKFSRSADAPAYQQGQNQLYNELNLGRREEYDVLDKRRGRDPEMGGKPRRK<br>NPQEGLYNELQKDKMAEAYSEIGMKGERRRGKGHDGLYQGLSTATKDTYDALHM<br>QALPPR | anti-BCMA CAR |
| 125 | QSALTQPASVSASPGQSIAISCTGTSSDVGWYQQHPGKAPKLMIYEDSKRPSGV<br>SNRFSGSKSGNTASLTISGLQAEDEADYYCSSNTRSSTLVFGGGTKLTVLGSRG<br>GGGSGGGGSGGGGSLEMAEVQLVQSGAEMKKPGASLKLSCKASGYTFIDYYVYW<br>MRQAPGQGLESMGWINPNSGGTNYAQKFQGRVTMTRDTSISTAYMELSRLRSDD<br>TAMYYCARSQRDGYMDWGQGTLVTVSSESKYGPPCPPCPAPPVAGPSVFLFPP<br>KPKDTLMISRTPEVTCVVVDVSQEDPEVQFNWYVDGVEVHNAKTKPREEQFQST<br>YRVVSVLTVLHQDWLNGKEYKCKVSNKGLPSSIEKTISKAKGQPREPQVYTLPP<br>SQEEMTKNQVSLTCLVKGFYPSDIAVEWESNGQPENNYKTTPPVLDSDGSFFLY<br>SRLTVDKSRWQEGNVFSCSVMHEALHNHYTQKSLSLSLGKMFWVLVVVGGVLAC<br>YSLLVTVAFIIFWVRSKRSRLLHSDYMNMTPRRPGPTRKHYQPYAPPRDFAAYR<br>SRVKFSRSADAPAYQQGQNQLYNELNLGRREEYDVLDKRRGRDPEMGGKPRRKN<br>PQEGLYNELQKDKMAEAYSEIGMKGERRRGKGHDGLYQGLSTATKDTYDALHMQ<br>ALPPR | anti-BCMA CAR |
| 126 | EVQLVESGGGLVQPGGSLRLSCAVSGFALSNHGMSWVRRAPGKGLEWVSGIVYS<br>GSTYYAASVKGRFTISRDNSRNTLYLQMNSLRPEDTAIYYCSAHGGESDVWGQG<br>TTVTVTVSSASGGGGSGGGRASGGGGSDIQLTQSPSSLSASVGDRVTITCRASQSIS<br>SYLNWYQQKPGKAPKLLIYAASSLQSGVPSRFSGSGSGTDFTLTISSLQPEDFA<br>TYYCQQSYSTPYTFGQGTKVEIKTTTPAPRPPTPAPTIASQPLSLRPEACRPAA<br>GGAVHTRGLDFACDIYIWAPLAGTCGVLLLSLVITLYCKRGRKKLLYIFKQPFM<br>RPVQTTQEEDGCSCRFPEEEEGGCELRVKFSRSADAPAYKQGQNQLYNELNLGR | anti-BCMA CAR |

| SEQ ID NO. | SEQUENCE | DESCRIPTION |
|---|---|---|
| | REEYDVLDKRRGRDPEMGGKPRRKNPQEGLYNELQKDKMAEAYSEIGMKGERRR GKGHDGLYQGLSTATKDTYDALHMQALPPR | |
| 127 | QVQLVESGGGLVQPGRSLRLSCAASGFTFSNYAMSWVRQAPGKGLGWVSGISRS GENTYYADSVKGRFTISRDNSKNTLYLQMNSLRDEDTAVYYCARSPAHYYGGMD VWGQGTTVTVSSASGGGGSGGRASGGGGSDIVLTQSPGTLSLSPGERATLSCRA SQSISSSFLAWYQQKPGQAPRLLIYGASRRATGIPDRFSGSGSGTDFTLTISRL EPEDSAVYYCQQYHSSPSWTFGQGTKLEIKTTTPAPRPPTPAPTIASQPLSLRP EACRPAAGGAVHTRGLDFACDIYIWAPLAGTCGVLLLSLVITLYCKRGRKKLLY IFKQPFMRPVQTTQEEDGCSCRFPEEEEGGCELRVKFSRSADAPAYKQGQNQLY NELNLGRREEYDVLDKRRGRDPEMGGKPRRKNPQEGLYNELQKDKMAEAYSEIG MKGERRRGKGHDGLYQGLSTATKDTYDALHMQALPPR | anti-BCMA CAR |
| 128 | QVQLVESGGGLVQPGGSLRLSCAVSGFALSNHGMSWVRRAPGKGLEWVSGIVYS GSTYYAASVKGRFTISRDNSRNTLYLQMNSLRPEDTAIYYCSAHGGESDVWGQG TTVTVSSASGGGGSGGRASGGGGSDIRLTQSPSPLSASVGDRVTITCQASEDIN KFLNWYHQTPGKAPKLLIYDASTLQTGVPSRFSGSGSGTDFTLTINSLQPEDIG TYYCQQYESLPLTFGGGTKVEIKTTTPAPRPPTPAPTIASQPLSLRPEACRPAA GGAVHTRGLDFACDIYIWAPLAGTCGVLLLSLVITLYCKRGRKKLLYIFKQPFM RPVQTTQEEDGCSCRFPEEEEGGCELRVKFSRSADAPAYKQGQNQLYNELNLGR REEYDVLDKRRGRDPEMGGKPRRKNPQEGLYNELQKDKMAEAYSEIGMKGERRR GKGHDGLYQGLSTATKDTYDALHMQALPPR | anti-BCMA CAR |
| 129 | EVQLVESGGGLVQPGGSLRLSCAVSGFALSNHGMSWVRRAPGKGLEWVSGIVYS GSTYYAASVKGRFTISRDNSRNTLYLQMNSLRPEDTAIYYCSAHGGESDVWGQG TTVTVSSASGGGGSGGRASGGGGSEIVLTQSPGTLSLSPGERATLSCRASQSIG SSSLAWYQQKPGQAPRLLMYGASSRASGIPDRFSGSGSGTDFTLTISRLEPEDF AVYYCQQYAGSPPFTFGQGTKVEIKTTTPAPRPPTPAPTIASQPLSLRPEACRP AAGGAVHTRGLDFACDIYIWAPLAGTCGVLLLSLVITLYCKRGRKKLLYIFKQP FMRPVQTTQEEDGCSCRFPEEEEGGCELRVKFSRSADAPAYKQGQNQLYNELNL GRREEYDVLDKRRGRDPEMGGKPRRKNPQEGLYNELQKDKMAEAYSEIGMKGER RRGKGHDGLYQGLSTATKDTYDALHMQALPPR | anti-BCMA CAR |
| 130 | QIQLVQSGPDLKKPGETVKLSCKASGYTFTNFGMNWVKQAPGKGFKWMAWINTY TGESYFADDFKGRFAFSVETSATTAYLQINNLKTEDTATYFCARGEIYYGYDGG FAYWGQGTLVTVSAGGGGSGGGGSGGGGSDVVMTQSHRFMSTSVGDRVSITCRA SQDVNTAVSWYQQKPGQSPKLLIFSASYRYTGVPDRFTGSGSGADFTLTISSVQ AEDLAVYYCQQHYSTPWTFGGGTKLDIKTTTPAPRPPTPAPTIASQPLSLRPEA CRPAAGGAVHTRGLDFACDIYIWAPLAGTCGVLLLSLVITLYCKRGRKKLLYIF KQPFMRPVQTTQEEDGCSCRFPEEEEGGCELRVKFSRSADAPAYKQGQNQLYNE LNLGRREEYDVLDKRRGRDPEMGGKPRRKNPQEGLYNELQKDKMAEAYSEIGMK GERRRGKGHDGLYQGLSTATKDTYDALHMQALPPR | anti-BCMA CAR |
| 131 | QIQLVQSGPELKKPGETVKISCKASGYTFTDYSINWVKRAPGKGLKWMGWINTE TREPAYAYDFRGRFAFSLETSASTAYLQINNLKYEDTATYFCALDYSYAMDYWG QGTSVTVSSGGGGSGGGGSGGGGSQIQLVQSGPELKKPGETVKISCKASGYTFT DYSINWVKRAPGKGLKWMGWINTETREPAYAYDFRGRFAFSLETSASTAYLQIN NLKYEDTATYFCALDYSYAMDYWGQGTSVTVSSTTTPAPRPPTPAPTIASQPLS LRPEACRPAAGGAVHTRGLDFACDIYIWAPLAGTCGVLLLSLVITLYCKRGRKK LLYIFKQPFMRPVQTTQEEDGCSCRFPEEEEGGCELRVKFSRSADAPAYKQGQN QLYNELNLGRREEYDVLDKRRGRDPEMGGKPRRKNPQEGLYNELQKDKMAEAYS EIGMKGERRRGKGHDGLYQGLSTATKDTYDALHMQALPPR | anti-BCMA CAR |
| 132 | QIQLVQSGPELKKPGETVKISCKASGYTFTDYSINWVKRAPGKGLKWMGWINTE TREPAYAYDFRGRFAFSLETSASTAYLQINNLKYEDTATYFCALDYSYAMDYWG QGTSVTVSSGGGGSGGGGSGGGGSDIVLTQSPASLAMSLGKRATISCRASESVS VIGAHLIHWYQQKPGQPPKLLIYLASNLETGVPARFSGSGSGTDFTLTDPVEE DDVAIYSCLQSRIFPRTFGGGTKLEIKTTTPAPRPPTPAPTIASQPLSLRPEAC RPAAGGAVHTRGLDFACDIYIWAPLAGTCGVLLLSLVITLYCKRGRKKLLYIFK QPFMRPVQTTQEEDGCSCRFPEEEEGGCELRVKFSRSADAPAYKQGQNQLYNEL NLGRREEYDVLDKRRGRDPEMGGKPRRKNPQEGLYNELQKDKMAEAYSEIGMKG ERRRGKGHDGLYQGLSTATKDTYDALHMQALPPR | anti-BCMA CAR |
| 133 | QIQLVQSGPELKKPGETVKISCKASGYTFRHYSMNWVKQAPGKGLKWMGRINTE SGVPIYADDFKGRFAFSVETSASTAYLVINNLKDEDTASYFCSNDYLYSLDFWG QGTALTVSSGGGGSGGGGSGGGGSDIVLTQPPSLAMSLGKRATISCRASESVT ILGSHLIYWYQQKPGQPPTLLIQLASNVQTGVPARFSGSGSRTDFTLTIDPVEE DDVAVYYCLQSRTIPRTFGGGTKLEIKTTTPAPRPPTPAPTIASQPLSLRPEAC RPAAGGAVHTRGLDFACDIYIWAPLAGTCGVLLLSLVITLYCKRGRKKLLYIFK QPFMRPVQTTQEEDGCSCRFPEEEEGGCELRVKFSRSADAPAYKQGQNQLYNEL NLGRREEYDVLDKRRGRDPEMGGKPRRKNPQEGLYNELQKDKMAEAYSEIGMKG ERRRGKGHDGLYQGLSTATKDTYDALHMQALPPR | anti-BCMA CAR |

| SEQ ID NO. | SEQUENCE | DESCRIPTION |
|---|---|---|
| 134 | QIQLVQSGPELKKPGETVKISCKASGYTFTHYSMNWVKQAPGKGLKWMGRINTE TGEPLYADDFKGRFAFSLETSASTAYLVINNLKNEDTATFFCSNDYLYSCDYWG QGTTLTVSSGGGGSGGGGSGGGGSDIVLTQSPPSLAMSLGKRATISCRASESVT ILGSHLIYWYQQKPGQPPTLLIQLASNVQTGVPARFSGSGSRTDFTLTIDPVEE DDVAVYYCLQSRTIPRTFGGGTKLEIKTTTPAPRPPTPAPTIASQPLSLRPEAC RPAAGGAVHTRGLDFACDIYIWAPLAGTCGVLLLSLVITLYCKRGRKKLLYIFK QPFMRPVQTTQEEDGCSCRFPEEEEGGCELRVKFSRSADAPAYKQGQNQLYNEL NLGRREEYDVLDKRRGRDPEMGGKPRRKNPQEGLYNELQKDKMAEAYSEIGMKG ERRRGKGHDGLYQGLSTATKDTYDALHMQALPPR | anti-BCMA CAR |
| 135 | DIVLTQSPPSLAMSLGKRATISCRASESVTILGSHLIHWYQQKPGQPPTLLIQL ASNVQTGVPARFSGSGSRTDFTLTIDPVEEDDVAVYYCLQSRTIPRTFGGGTKL EIKGSTSGSGKPGSGEGSTKGQIQLVQSGPELKKPGETVKISCKASGYTFTDYS INWVKRAPGKGLKWMGWINTETREPAYAYDFRGRFAFSLETSASTAYLQINNLK YEDTATYFCALDYSYAMDYWGQGTSVTVSSFVPVFLPAKPTTTPAPRPPTPAPT IASQPLSLRPEACRPAAGGAVHTRGLDFACDIYIWAPLAGTCGVLLLSLVITLY CNHRNRSKRSRLLHSDYMNMTPRRPGPTRKHYQPYAPPRDFAAYRSRVKFSRSA DAPAYQQGQNQLYNELNLGRREEYDVLDKRRGRDPEMGGKPRRKNPQEGLYNEL QKDKMAEAYSEIGMKGERRRGKGHDGLYQGLSTATKDTYDALHMQALPPR | anti-BCMA CAR |
| 136 | QVQLVQSGAEVKKPGASVKVSCKASGYSFPDYYINWVRQAPGQGLEWMGWIYFA SGNSEYNQKFTGRVTMTRDTSINTAYMELSSLTSEDTAVYFCASLYDYDWYFDV WGQGTMVTVSSGGGGSGGGGSGGGGSDIVMTQTPLSLSVTPGQPASISCKSSQS LVHSNGNTYLHWYLQKPGQSPQLLIYKVSNRFSGVPDRFSGSGSGTDFTLKISR VEAEDVGIYYCSQSSIYPWTFGQGTKLEIKGLAVSTISSFFPPGYQIYIWAPLA GTCGVLLLSLVITLYCKRGRKKLLYIFKQPFMRPVQTTQEEDGCSCRFPEEEEG GCELRVKFSRSADAPAYQQGQNQLYNELNLGRREEYDVLDKRRGRDPEMGGKPR RKNPQEGLYNELQKDKMAEAYSEIGMKGERRRGKGHDGLYQGLSTATKDTYDAL HMQALPPR | anti-BCMA CAR |
| 137 | QVQLVQSGAEVKKPGASVKVSCKASGYSFPDYYINWVRQAPGQGLEWMGWIYFA SGNSEYNQKFTGRVTMTRDTSINTAYMELSSLTSEDTAVYFCASLYDYDWYFDV WGQGTMVTVSSGGGGSGGGGSGGGGSDIVMTQTPLSLSVTPGQPASISCKSSQS LVHSNGNTYLHWYLQKPGQSPQLLIYKVSNRFSGVPDRFSGSGSGTDFTLKISR VEAEDVGIYYCSQSSIYPWTFGQGTKLEIKTTTPAPRPPTPAPTIASQPLSLRP EACRPAAGGAVHTRGLDFACDIYIWAPLAGTCGVLLLSLVITLYCKRGRKKLLY IFKQPFMRPVQTTQEEDGCSCRFPEEEEGGCELRVKFSRSADAPAYQQGQNQLY NELNLGRREEYDVLDKRRGRDPEMGGKPRRKNPQEGLYNELQKDKMAEAYSEIG MKGERRRGKGHDGLYQGLSTATKDTYDALHMQALPPR | anti-BCMA CAR |
| 138 | QVQLVQSGAEVKKPGASVKVSCKASGYSFPDYYINWVRQAPGQGLEWMGWIYFA SGNSEYNQKFTGRVTMTRDTSINTAYMELSSLTSEDTAVYFCASLYDYDWYFDV WGQGTMVTVSSGGGGSGGGGSGGGGSDIVMTQTPLSLSVTPGQPASISCKSSQS LVHSNGNTYLHWYLQKPGQSPQLLIYKVSNRFSGVPDRFSGSGSGTDFTLKISR VEAEDVGIYYCSQSSIYPWTFGQGTKLEIKEPKSPDKTHTCPPCPAPPVAGPSV FLFPPKPKDTLMIARTPEVTCVVVDVSHEDPEVKFNWYVDGVEVHNAKTKPREE QYNSTYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVLDSDG SFFLYSKLTVDKSRWQQGNVFSCSVMHEALHNHYTQKSLSLSPGKIYIWAPLAG TCGVLLLSLVITLYCKRGRKKLLYIFKQPFMRPVQTTQEEDGCSCRFPEEEEGG CELRVKFSRSADAPAYQQGQNQLYNELNLGRREEYDVLDKRRGRDPEMGGKPRR KNPQEGLYNELQKDKMAEAYSEIGMKGERRRGKGHDGLYQGLSTATKDTYDALH MQALPPR | anti-BCMA CAR |
| 139 | QVQLVQSGAEVKKPGASVKVSCKASGYSFPDYYINWVRQAPGQGLEWMGWIYFA SGNSEYNQKFTGRVTMTRDTSSSTAYMELSSLRSEDTAVYFCASLYDYDWYFDV WGQGTMVTVSSGGGGSGGGGSGGGGSDIVMTQTPLSLSVTPGEPASISCKSSQS LVHSNGNTYLHWYLQKPGQSPQLLIYKVSNRFSGVPDRFSGSGSGADFTLKISR VEAEDVGVYYCAETSHVPWTFGQGTKLEIKGLAVSTISSFFPPGYQIYIWAPLA GTCGVLLLSLVITLYCKRGRKKLLYIFKQPFMRPVQTTQEEDGCSCRFPEEEEG GCELRVKFSRSADAPAYQQGQNQLYNELNLGRREEYDVLDKRRGRDPEMGGKPR RKNPQEGLYNELQKDKMAEAYSEIGMKGERRRGKGHDGLYQGLSTATKDTYDAL HMQALPPR | anti-BCMA CAR |
| 140 | QVQLVQSGAEVKKPGASVKVSCKASGYSFPDYYINWVRQAPGQGLEWMGWIYFA SGNSEYNQKFTGRVTMTRDTSSSTAYMELSSLRSEDTAVYFCASLYDYDWYFDV WGQGTMVTVSSGGGGSGGGGSGGGGSDIVMTQTPLSLSVTPGEPASISCKSSQS LVHSNGNTYLHWYLQKPGQSPQLLIYKVSNRFSGVPDRFSGSGSGADFTLKISR VEAEDVGVYYCAETSHVPWTFGQGTKLEIKTTTPAPRPPTPAPTIASQPLSLRP EACRPAAGGAVHTRGLDFACDIYIWAPLAGTCGVLLLSLVITLYCKRGRKKLLY IFKQPFMRPVQTTQEEDGCSCRFPEEEEGGCELRVKFSRSADAPAYQQGQNQLY NELNLGRREEYDVLDKRRGRDPEMGGKPRRKNPQEGLYNELQKDKMAEAYSEIG MKGERRRGKGHDGLYQGLSTATKDTYDALHMQALPPR | anti-BCMA CAR |

| SEQ ID NO. | SEQUENCE | DESCRIPTION |
|---|---|---|
| 141 | QVQLVQSGAEVKKPGASVKVSCKASGYSFPDYYINWVRQAPGQGLEWMGWIYFA SGNSEYNQKFTGRVTMTRDTSSSTAYMELSSLRSEDTAVYFCASLYDYDWYFDV WGQGTMVTVSSGGGGSGGGGSGGGGSDIVMTQTPLSLSVTPGEPASISCKSSQS LVHSNGNTYLHWYLQKPGQSPQLLIYKVSNRFSGVPDRFSGSGSGADFTLKISR VEAEDVGVYYCAETSHVPWTFGQGTKLEIKEPKSPDKTHTCPPCPAPPVAGPSV FLFPPKPKDTLMIARTPEVTCVVVDVSHEDPEVKFNWYVDGVEVHNAKTKPREE QYNSTYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVLDSDG SFFLYSKLTVDKSRWQQGNVFSCSVMHEALHNHYTQKSLSLSPGKIYIWAPLAG TCGVLLLSLVITLYCKRGRKKLLYIFKQPFMRPVQTTQEEDGCSCRFPEEEEGG CELRVKFSRSADAPAYQQGQNQLYNELNLGRREEYDVLDKRRGRDPEMGGKPRR KNPQEGLYNELQKDKMAEAYSEIGMKGERRRGKGHDGLYQGLSTATKDTYDALH MQALPPR | anti-BCMA CAR |
| 142 | IYIWAPLAGTCGVLLLSLVITLYCNHRN | CD8a TM |
| 143 | IYIWAPLAGTCGVLLLSLVIT | CD8a TM |
| 144 | RAAA | linking peptide |
| 145 | EVQLVESGGGLVKPGGSLRLSCAASGFTFSDYYMSWIRQAPGKGLEWVSYISSS GSTIYYADSVKGRFTISRDNAKNSLYLQMNSLRAEDTAVYYCAKVDGDYTEDYW GQGTLVTVSS | Variable heavy (VH) Anti-BCMA |
| 146 | QSALTQPASVSGSPGQSITISCTGSSSDVGKYNLVSWYQQPPGKAPKIIYDVN KRPSGVSNRFSGSKSGNTATLTISGLQGDDEADYYCSSYGGSRSYVFGTGTKVT VL | Variable light (VL) Anti-BCMA VL |
| 147 | EVQLVQSGGGLVQPGRSLRLSCTASGFTFGDYAMSWFRQAPGKGLEWVGFIRSK AYGGTTEYAASVKGRFTISRDDSKSIAYLQMNSLKTEDTAVYYCAAWSAPTDYW GQGTLVTVSS | Variable heavy (VH) Anti-BCMA |
| 148 | DIQMTQSPAFLSASVGDRVTVTCRASQGISNYLAWYQQKPGNAPRLLIYSASTL QSGVPSRFRGTGYGTEFSLTIDSLQPEDFATYYCQQSYTSRQTFGPGTRLDIK | Variable light (VL) Anti-BCMA |
| 149 | EVQLVESGGGLVKPGGSLRLSCAASGFTFSDYYMSWIRQAPGKGLEWVSYISSS GSTIYYADSVKGRFTISRDNAKNSLYLQMNSLRAEDTAVYYCAKVDGPPSFDIW GQGTMVTVSS | Variable heavy (VH) Anti-BCMA |
| 150 | SYVLTQPPSVSVAPGQTARITCGANNIGSKSVHWYQQKPGQAPMLVVYDDDDRP SGIPERFSGSNSGNTATLTISGVEAGDEADYFCHLWDRSRDHYVFGTGTKLTVL | Variable light (VL) Anti-BCMA |
| 151 | EVQLVQSGAEVKKPGSSVKVSCKASGGTFSSYAISWVRQAPGQGLEWMGRIIPI LGIANYAQKFQGRVTMTEDTSTDTAYMELSSLRSEDTAVYYCARSGYSKSIVSY MDYWGQGTLVTVSS | Variable heavy (VH) Anti-BCMA |
| 152 | LPVLTQPPSTSGTPGQRVTVSCSGSSSNIGSNVVFWYQQLPGTAPKLVIYRNNQ RPSGVPDRFSVSKSGTSASLAISGLRSEDEADYYCAAWDDSLSGYVFGTGTKVT VLG | Variable light (VL) Anti-BCMA |
| 153 | MPLLLLLPLLWAGALA | CD33 Signal peptide |
| 154 | MALPVTALLLPLALLLHA | CD8 alpha signal peptide |
| 155 | atgcttctcctggtgacaagccttctgctctgtgagttaccacacccagcattc ctcctgatccca | GMCSFR alpha chain signal sequence |
| 156 | MLLLVTSLLLCELPHPAFLLIP | GMCSFR alpha chain signal sequence |
| 157 | Glu Val Val Val Lys Tyr Gly Pro Pro Cys Pro Pro Cys Pro | Exemplary IgG Hinge |
| 158 | X1PPX2P X1 is glycine, cysteine or arginine X2 is cysteine or threonine | Exemplary IgG Hinge |
| 159 | Glu Pro Lys Ser Cys Asp Lys Thr His Thr Cys Pro Pro Cys Pro | Exemplary IgG Hinge |

| SEQ ID NO. | SEQUENCE | DESCRIPTION |
|---|---|---|
| 160 | Glu Arg Lys Cys Cys Val Glu Cys Pro Pro Cys Pro | Exemplary IgG Hinge |
| 161 | ELKTPLGDTHTCPRCPEPKSCDTPPPCPRCPEPKSCDTPPPCPRCPEPKSCDTPPPCPRCP | Exemplary IgG Hinge |
| 162 | Glu Ser Lys Tyr Gly Pro Pro Cys Pro Ser Cys Pro | Exemplary IgG Hinge |
| 163 | Glu Ser Lys Tyr Gly Pro Pro Cys Pro Pro Cys Pro | Exemplary IgG Hinge |
| 164 | Tyr Gly Pro Pro Cys Pro Pro Cys Pro | Exemplary IgG Hinge |
| 165 | Lys Tyr Gly Pro Pro Cys Pro Pro Cys Pro | Exemplary IgG Hinge |
| 166 | MLLLVTSLLLCELPHPAFLLIPRKVCNGIGIGEFKDSLSINATNIKHFK NCTSISGDLHILPVAFRGDSFTHTPPLDPQELDILKTVKEITGFLLIQA WPENRTDLHAFENLEIIRGRTKQHGQFSLAVVSLNITSLGLRSLKEISD GDVIISGNKNLCYANTINWKKLFGTSGQKTKIISNRGENSCKATGQVCH ALCSPEGCWGPEPRDCVSCRNVSRGRECVDKCNLLEGEPREFVENSECI QCHPECLPQAMNITCTGRGPDNCIQCAHYIDGPHCVKTCPAGVMGENNT LVWKYADAGHVCHLCHPNCTYGCTGPGLEGCPTNGPKIPSIATGMVGAL LLLLVVALGIGLFM | tEGFR artificial |
| 167 | EGRGSLLTCGDVEENPGP | T2A artificial |
| 168 | GSGATNFSLLKQAGDVEENPGP | P2A |
| 169 | ATNFSLLKQAGDVEENPGP | P2A |
| 170 | QCTNYALLKLAGDVESNPGP | E2A |
| 171 | VKQTLNFDLLKLAGDVESNPGP | F2A |
| 172 | MLQMAGQCSQNEYFDSLLHACIPCQLRCSSNTPPLTCQRYCNASVTNSV KGTNAGGGGSPKSSDKTHTCPPCPAPEAEGAPSVFLFPPKPKDTLMISR TPEVTCVVVDVSHEDPEVKFNWYVDGVEVHNAKTKPREEQYNSTYRVVS VLTVLHQDWLNGKEYKCKVSNKALPSSIEKTISKAKGQPREPQVYTLPP SRDELTKNQVSLTCLVKGFYPSDIAVEWESNGQPENNYKTTPPVLDSDG SFFLYSKLTVDKSRWQQGNVFSCSVMHEALHNHYTQKSLSLSPGK | BCMA-Fc fusion polypeptide |
| 173 | DYYVY | CDR-H1 |
| 174 | WINPNSGGTNYAQKFQG | CDR-H2 |
| 175 | SQRDGYMDY | CDR-H3 |
| 176 | GYTFIDY | CDR-H1 |
| 177 | NPNSGG | CDR-H2 |
| 178 | GYTFIDYYVY | CDR-H1 |
| 179 | WINPNSGGTN | CDR-H2 |
| 180 | GYTFIDYY | CDR-H1 |
| 181 | INPNSGGT | CDR-H2 |
| 182 | ARSQRDGYMDY | CDR-H3 |
| 183 | TGTSSDVG | CDR-L1 |
| 184 | EDSKRPS | CDR-L2 |
| 185 | SSNTRSSTLV | CDR-L3 |
| 186 | ISCTGTSSD | CDR-L1 |
| 187 | EDS | CDR-L2 |

| SEQ ID NO. | SEQUENCE | DESCRIPTION |
|---|---|---|
| 188 | QSALTQPASVSASPGQSIAISCTGTSSDVGWYQQHPGKAPKLMIYEDSK RPSGVSNRFSGSKSGNTASLTISGLQAEDEADYYCSSNTRSSTLVFGGG TKLTVLGSRGGGGSGGGGSGGGGSLEMAEVQLVQSGAEMKKPGASLKLS CKASGYTFIDYYVYWMRQAPGQGLESMGWINPNSGGTNYAQKFQGRVTM TRDTSISTAYMELSRLRSDDTAMYYCARSQRDGYMDYWGQGTLVTVSS | anti-BCMA scFv |

What is claimed:

1. A method of treatment, the method comprising:
   (a) administering a T cell therapy to a subject having multiple myeloma, the cell therapy comprising a dose of T cells expressing a recombinant receptor, wherein the recombinant receptor specifically binds to BCMA; and
   (b) administering to the subject a compound of the structure:

Compound 1

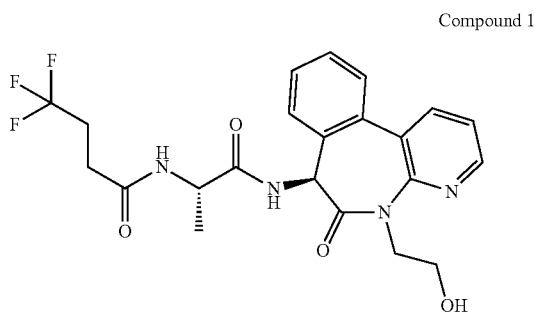 [SMILES: C[C@H](NC(=O)CCC(F)(F)F)C(=O)N[C@@H]1C(=O)N(CCO)c2ncccc2-c2ccccc21]

or a stereoisomer thereof, or a pharmaceutically acceptable salt or hydrate of either of the foregoing.

2. The method of claim 1, wherein the initiation of administration of the compound is prior to, concurrently with or subsequently to initiation of administration of the cell therapy.

3. The method of claim 2, wherein the compound is administered prior to initiation of administration of the cell therapy.

4. The method of claim 1, wherein initiation of administration of the compound is within 72 hours, within 96 hours or within 1 week prior to the initiation of the administration of the cell therapy.

5. The method of claim 1, wherein the compound is administered subsequently to initiation of administration of the cell therapy.

6. The method of claim 1, wherein the recombinant receptor is a chimeric antigen receptor.

7. The method of claim 1, wherein the compound, stereoisomer, pharmaceutically acceptable salt or hydrate is administered orally.

8. The method of claim 1, wherein the compound, stereoisomer, pharmaceutically acceptable salt or hydrate is administered at least or is administered six times daily, five times daily, four times daily, three times daily, twice daily, once daily, every other day, three times a week, at least once a week, twice a week or only one time.

9. The method of claim 1, wherein the compound, stereoisomer, pharmaceutically acceptable salt or hydrate is administered once every other day.

10. The method of claim 1, wherein the compound, stereoisomer, pharmaceutically acceptable salt or hydrate is administered no more than once per day.

11. The method of claim 1, wherein the compound, stereoisomer, pharmaceutically acceptable salt or hydrate is administered once three times per week.

12. The method of claim 1, wherein the compound, stereoisomer, pharmaceutically acceptable salt or hydrate is administered on days 2, 4, 7, 9, 11, 14, 16, and 18 after initiation of the administration of the cell therapy.

13. The method of claim 1, wherein the compound, stereoisomer, pharmaceutically acceptable salt or hydrate is administered at an amount that is or is about 25 mg.

14. The method of claim 1, wherein the compound, stereoisomer, pharmaceutically acceptable salt or hydrate is administered at an amount that is or is about 50 mg.

15. The method of claim 1, wherein the multiple myeloma is a relapsed or treatment refractory multiple myeloma.

16. The method of claim 1, wherein the method further comprises, prior to said administration of the cell therapy, selecting a subject for the administration having a cancer that, or the cells of which, express CD138, surface CD38 or a surface plasma cell marker or are derived from plasma cells.

17. The method of claim 16, wherein the subject further comprises low expression of surface B cell maturation antigen (BCMA) and/or a level of expression of surface BCMA below a threshold level.

18. The method of claim 1, wherein the recombinant receptor is a chimeric antigen receptor comprising an antigen-binding domain that binds BCMA, wherein the antigen-binding domain comprises:
   a $V_H$ region comprising a CDRH1, a CDRH2 and a CDRH3 comprising the amino acid sequence of SEQ ID NOS: 173, 174 and 175, respectively and a $V_L$ region comprising a CDRL1, a CDRL2 and a CDRL3 comprising the amino acid sequence of SEQ ID NOS: 183, 184 and 185, respectively;
   a $V_H$ region comprising a CDRH1, a CDRH2 and a CDRH3 comprising the amino acid sequence of SEQ ID NOS: 176, 177 and 175, respectively and a $V_L$ region comprising a CDRL1, a CDRL2 and a CDRL3 comprising the amino acid sequence of SEQ ID NOS: 183, 184 and 185, respectively;
   a $V_H$ region comprising a CDRH1, a CDRH2 and a CDRH3 comprising the amino acid sequence of SEQ ID NOS: 178, 179 and 175, respectively and a $V_L$ region comprising a CDRL1, a CDRL2 and a CDRL3 comprising the amino acid sequence of SEQ ID NOS: 183, 184 and 185, respectively; or
   a $V_H$ region comprising a CDRH1, a CDRH2 and a CDRH3 comprising the amino acid sequence of SEQ ID NOS: 180, 181 and 182, respectively and a $V_L$ region comprising a CDRL1, a CDRL2 and a CDRL3 comprising the amino acid sequence of SEQ ID NOS: 186, 187 and 185, respectively.

19. The method of claim 1, wherein the antigen-binding domain comprises a $V_H$ region comprising an amino acid sequence having at least at or about 90% sequence identity to SEQ ID NO:24; and a $V_L$ region comprising an amino acid sequence having at least at or about 90%, sequence identity to SEQ ID NO:25.

20. The method of claim 1, wherein the antigen-binding domain comprises a $V_H$ region comprising the amino acid sequence set forth in SEQ ID NO:24; and a $V_L$ region comprising the amino acid sequence set forth in SEQ ID NO:25.

21. The method of claim 1, wherein the antigen-binding domain is an scFv comprising an amino acid sequence having at least at or about 90% sequence identity to SEQ ID NO:188.

22. The method of claim 21, wherein the antigen-binding domain is an scFv comprising the amino acid sequence set forth in SEQ ID NO:188.

23. The method of claim 1, wherein the dose of genetically engineered T cells comprises between at $2.5 \times 10^7$ CAR-expressing T cells and $1.2 \times 10^9$ CAR-expressing T cells, inclusive.

24. The method of claim 1, wherein the method further comprises administering a lymphodepleting chemotherapy prior to administration of the T cell therapy and/or wherein the subject has received a lymphodepleting chemotherapy prior to administration of the dose of T cells expressing a recombinant receptor.

25. The method of claim 24, wherein the lymphodepleting chemotherapy comprises administering fludarabine and/or cyclophosphamide to the subject.

26. The method of claim 1, wherein the recombinant receptor is a chimeric antigen receptor (CAR) comprising an antigen-binding domain that binds BCMA, the antigen-binding domain having:
    (a) a VH with an amino acid sequence set forth in SEQ ID NO: 18 and a VL with an amino acid sequence set forth in SEQ ID NO: 19;
    (b) a VH with an amino acid sequence set forth in SEQ ID NO: 20 and a VL with an amino acid sequence set forth in SEQ ID NO: 21;
    (c) a VH with an amino acid sequence set forth in SEQ ID NO: 22 and a VL with an amino acid sequence set forth in SEQ ID NO: 23;
    (d) a VH with an amino acid sequence set forth in SEQ ID NO: 24 and a VL with an amino acid sequence set forth in SEQ ID NO: 25;
    (e) a VH with an amino acid sequence set forth in SEQ ID NO: 32 and a VL with an amino acid sequence set forth in SEQ ID NO: 33;
    (f) a VH with an amino acid sequence set forth in SEQ ID NO: 34 and a VL with an amino acid sequence set forth in SEQ ID NO: 35;
    (g) a VH with an amino acid sequence set forth in SEQ ID NO: 36 and a VL with an amino acid sequence and a VL set forth in SEQ ID NO: 37;
    (h) a VH with an amino acid sequence set forth in SEQ ID NO: 41 and a VL with an amino acid sequence set forth in SEQ ID NO: 42;
    (i) a VH with an amino acid sequence set forth in SEQ ID NO: 43 and a VL with an amino acid sequence set forth in SEQ ID NO: 44;
    (j) a VH with an amino acid sequence set forth in SEQ ID NO: 45 and a VL with an amino acid sequence set forth in SEQ ID NO: 46;
    (k) a VH with an amino acid sequence set forth in SEQ ID NO: 47 and a VL with an amino acid sequence set forth in SEQ ID NO: 48;
    (l) a VH with an amino acid sequence set forth in SEQ ID NO: 49 and a VL with an amino acid sequence set forth in SEQ ID NO: 50;
    (m) a VH with an amino acid sequence set forth in SEQ ID NO: 51 and a VL with an amino acid sequence VL set forth in SEQ ID NO: 52;
    (n) a VH with an amino acid sequence set forth in SEQ ID NO: 53 and a VL with an amino acid sequence set forth in SEQ ID NO: 54;
    (o) a VH with an amino acid sequence set forth in SEQ ID NO: 55 and a VL with an amino acid sequence set forth in SEQ ID NO: 56;
    (p) a VH with an amino acid sequence set forth in SEQ ID NO: 57 and a VL with an amino acid sequence set forth in SEQ ID NO: 58;
    (q) a VH with an amino acid sequence set forth in SEQ ID NO: 59 and a VL with an amino acid sequence VL set forth in SEQ ID NO: 60;
    (r) a VH with an amino acid sequence set forth in SEQ ID NO: 61 and a VL with an amino acid sequence set forth in SEQ ID NO: 62;
    (s) a VH with an amino acid sequence set forth in SEQ ID NO: 63 and a VL with an amino acid sequence set forth in SEQ ID NO: 64;
    (t) a VH with an amino acid sequence set forth in SEQ ID NO: 65 and a VL with an amino acid sequence set forth in SEQ ID NO: 66;
    (u) a VH with an amino acid sequence set forth in SEQ ID NO: 67 and a VL with an amino acid sequence set forth in SEQ ID NO: 68;
    (v) a VH with an amino acid sequence set forth in SEQ ID NO: 69 and a VL with an amino acid sequence set forth in SEQ ID NO: 70;
    (w) a VH with an amino acid sequence set forth in SEQ ID NO: 71 and a VL with an amino acid sequence set forth in SEQ ID NO: 72;
    (x) a VH with an amino acid sequence set forth in SEQ ID NO: 73 and a VL with an amino acid sequence set forth in SEQ ID NO: 74;
    (y) a VH with an amino acid sequence set forth in SEQ ID NO: 75 and a VL with an amino acid sequence set forth in SEQ ID NO: 76;
    (z) a VH with an amino acid sequence set forth in SEQ ID NO: 145 and a VL with an amino acid sequence set forth in SEQ ID NO: 146;
    (aa) a VH with an amino acid sequence set forth in SEQ ID NO: 147 and a VL with an amino acid sequence set forth in SEQ ID NO: 148;
    (bb) a VH with an amino acid sequence set forth in SEQ ID NO: 149 and a VL with an amino acid sequence set forth in SEQ ID NO: 150; or
    (cc) a VH with an amino acid sequence set forth in SEQ ID NO: 151 and a VL with an amino acid sequence in SEQ ID NO: 152.

27. The method of claim 1, wherein the recombinant receptor is a chimeric antigen receptor (CAR) comprising an antigen-binding domain that binds BCMA, wherein the antigen-binding domain comprises the VH region set forth in SEQ ID NO: 18 and the VL region set forth in SEQ ID NO:19.

28. The method of claim 1, wherein the CAR comprises a sequence as set forth in any one of SEQ ID NOS: 90-141 or a sequence of amino acids that exhibits at least 90%, at least 91%, at least 92%, at least 93%, at least 94%, at least 95%, at least 96%, at least 97%, at least 98%, or at least 99% sequence identity to any one of SEQ ID NOS: 90-141.

29. The method of claim 1, wherein the CAR comprises a sequence as set forth in SEQ ID NO: 116 or a sequence of amino acids that exhibits at least 90%, at least 95%, at least 96%, at least 97%, at least 98%, or at least 99% sequence identity to any one of SEQ ID NO: 116.

30. The method of claim 1, wherein the CAR comprises a sequence as set forth in SEQ ID NO: 124 or a sequence of amino acids that exhibits at least 90%, at least 95%, at least 96%, at least 97%, at least 98%, or at least 99% sequence identity to any one of SEQ ID NO: 124.

31. The method of claim 1, wherein the antigen-binding domain comprises a $V_H$ region comprising an amino acid sequence having at least at or about 90% sequence identity to SEQ ID NO: 18; and a $V_L$ region comprising an amino acid sequence having at least at or about 90%, sequence identity to SEQ ID NO:19.

32. The method of claim 1, wherein the compound, stereoisomer, pharmaceutically acceptable salt or hydrate is administered at an amount of 10 mg to 100 mg.

\* \* \* \* \*